(12) United States Patent
Lee et al.

(10) Patent No.: US 12,390,266 B2
(45) Date of Patent: Aug. 19, 2025

(54) END TOOL OF SURGICAL INSTRUMENT AND ELECTROCAUTERIZATION SURGICAL INSTRUMENT COMPRISING SAME

(71) Applicant: LIVSMED INC., Seongnam-si (KR)

(72) Inventors: Jung Joo Lee, Seongnam-si (KR); Hee Jin Kim, Seongnam-si (KR); Dong Kyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/897,979

(22) Filed: Sep. 26, 2024

(65) Prior Publication Data

US 2025/0017644 A1    Jan. 16, 2025

Related U.S. Application Data

(63) Continuation of application No. PCT/KR2023/007038, filed on May 23, 2023.

(30) Foreign Application Priority Data

May 23, 2022   (KR) .................. 10-2022-0063142
Mar. 3, 2023   (KR) .................. 10-2023-0028804

(51) Int. Cl.
  *A61B 18/14*   (2006.01)
  *A61B 17/29*   (2006.01)
  *A61B 18/00*   (2006.01)

(52) U.S. Cl.
  CPC .. *A61B 18/1442* (2013.01); *A61B 2017/2903* (2013.01); *A61B 2017/2929* (2013.01); *A61B 2018/00208* (2013.01); *A61B 2018/00595* (2013.01); *A61B 2018/1455* (2013.01)

(58) Field of Classification Search
  CPC .... A61B 17/07207; A61B 2017/00367; A61B 2017/07271; A61B 2017/07278; A61B 2017/2903; A61B 2017/291; A61B 2017/2927; A61B 2017/2929; A61B 2017/2936; A61B 2017/2937; A61B 2017/2939; A61B 34/30; A61B 34/71; A61B 18/1442; A61B 18/1455
  See application file for complete search history.

(56) References Cited

U.S. PATENT DOCUMENTS

| | | |
|---|---|---|
| 2009/0326530 A1 | 12/2009 | Orban, III et al. |
| 2016/0228171 A1* | 8/2016 | Boudreaux ............ A61B 18/00 |
| 2017/0252096 A1 | 9/2017 | Felder et al. |
| 2020/0038127 A1* | 2/2020 | Chaplin ............. A61B 17/0218 |
| 2020/0107894 A1* | 4/2020 | Wallace ............. A61B 17/3423 |
| 2021/0022819 A1 | 1/2021 | Duque et al. |
| 2021/0244430 A1 | 8/2021 | Lee et al. |

FOREIGN PATENT DOCUMENTS

| | | |
|---|---|---|
| JP | 2015-506724 A | 3/2015 |
| JP | 2019-530530 A | 10/2019 |
| KR | 10-2019-0112195 A | 10/2019 |
| KR | 10-2118721 B1 | 6/2020 |
| KR | 10-2153408 B1 | 9/2020 |
| WO | 2020/198372 A1 | 10/2020 |

* cited by examiner

*Primary Examiner* — Khadijeh A Vahdat
(74) *Attorney, Agent, or Firm* — Bridgeway IP Law Group, PLLC; Sang Ho Lee; Hyun Woo Shin

(57) ABSTRACT

Provided is a surgical instrument for electrocautery, and in particular, a surgical instrument for electrocautery installed on a robot arm or manually operable in order to be used in laparoscopic surgery or other various surgeries.

13 Claims, 224 Drawing Sheets

(a)

(b)

(a)

(b)

(a)

(b)

END TOOL OF SURGICAL INSTRUMENT AND ELECTROCAUTERIZATION SURGICAL INSTRUMENT COMPRISING SAME

CROSS-REFERENCE TO RELATED APPLICATION(S)

The instant application is a continuation application of international patent application No. PCT/KR2023/007038, filed on May 23, 2023, which claims priority to Korean Patent Application No. 10-2022-0063142, filed on May 23, 2022, and Korean Patent Application No. 10-2023-0028807, filed on Mar. 3, 2023, with the Korean Intellectual Property Office, the disclosures of which are incorporated herein in their entirety by reference.

TECHNICAL FIELD

One or more embodiments of the present disclosure relate to an end tool of a surgical instrument and a surgical instrument for electrocautery including the same, and in particular, to an end tool of a surgical instrument and a surgical instrument for electrocautery including the end tool that is capable of rotating in two or more directions and intuitively matching a movement of a manipulation portion, wherein the surgical instrument may be installed on a robot arm or manually operable in order to be used in laparoscopic surgery or other various surgeries.

BACKGROUND ART

Surgical operations in many cases require cutting and joining of body tissues including organs, muscular tissues, connective tissues, and blood vessels. Over the centuries, sharp blades and sutures have been used for cutting and joining. However, bleeding occurs when cutting body tissues, in particular, relatively highly vascularized tissue during surgical operation. Therefore, doctors require surgical instruments and methods to slow or reduce bleeding during surgical operations.

Recently, it has become possible to use an electric surgical instrument that uses electrical energy to perform certain surgical tasks. For example, regarding surgical instruments such as graspers, scissors, tweezers, blades, needles, and hooks, electric surgical instruments including one or more electrodes formed to receive electric energy have been developed. Electrical energy supplied through the electrodes may be used to coagulate, bond, or cut the patient's body tissues. In particular, when electrical energy is used, amputation and hemostasis may be performed at the same time.

Electric surgical instruments are typically classified into two types: monopolar and bipolar. In a monopolar electric surgical instrument, electrical energy of a specific polarity is supplied to one or more electrodes of the instrument. And electricity of different polarity is electrically connected to the patient. In a bipolar electric surgical instrument, one or more electrodes are electrically connected to a first polarity electrical energy source, and one or more electrodes are electrically connected to a second polarity electrical energy source opposite to the first polarity.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

DESCRIPTION OF EMBODIMENTS

Technical Problem

The present disclosure is directed to providing a surgical instrument for electrocautery including an end tool that is capable of rotating in two or more directions, and moving to intuitively match a movement of a manipulation portion, in a manually operable surgical instrument for electrocautery that is installed on a robot arm or manually operable for use in laparoscopic surgery or other various surgeries.

Solution to Problem

Second Embodiment of Surgical Instrument for Electrocautery-Forming X-Shaped Structure of First and Second Jaws FIG. 41 is a perspective view illustrating a surgical instrument for electrocautery according to a second embodiment of the present disclosure. FIGS. 42 to 47 are views illustrating an end tool of the surgical instrument for electrocautery of FIG. 41.

Referring to FIG. 41, an electric cauterization surgical instrument 10 according to the second embodiment of the present disclosure includes an end tool 700, a manipulation portion 200, a power transmission portion 300, and a connection portion 400.

The electric cauterization surgical instrument 10 according to the second embodiment of the present disclosure is different from the electric cauterization surgical instrument 10 according to the first embodiment in that the end tool 700 has a different configuration, and thus the configuration of the end tool 700 will be described in detail below.

The end tool 700 is formed on the other end portion of the connection portion 400, and performs necessary motions for surgery by being inserted into a surgical site. In an example of the end tool 700 described above, as illustrated in FIG. 41, a pair of jaws 703 for performing a grip motion may be used. However, the concept of the present disclosure is not limited thereto, and various devices for performing surgery may be used as the end tool 700. For example, a configuration of a cantilever cautery may also be used as the end tool 700. The end tool 700 is connected to the manipulation portion 200 by the power transmission portion 300, and receives a driving force of the manipulation portion 200 through the power transmission portion 300 to perform a motion necessary for surgery, such as gripping, cutting, suturing, or the like.

Here, the end tool 700 of the electric cauterization surgical instrument 10 according to the second embodiment of the present disclosure is formed to be rotatable in at least one direction, and for example, the end tool 700 may be formed to perform a pitch motion around a Y-axis of FIG. 41 and simultaneously perform a yaw motion and an actuation motion around a Z-axis of FIG. 41.

Referring to FIGS. 42 to 47, 55, and 56, the end tool 700 of the electric cauterization surgical instrument 10 according to the second embodiment of the present disclosure includes a first electrode 751, a second electrode 752, a pitch hub 750, an end tool hub 760, a plurality of rotation shafts 741, 743, and 744, and the like that are the same as those of the first embodiment in configuration and effect, and is different in that a jaw rotation shaft 701e, a tube through hole 701f, a jaw pulley coupling hole 701d, and a movable coupling hole 701c are formed in a first jaw 701, and a shaft pass-through portion 702e through which the rotation shaft 701e, which is a jaw rotation shaft formed in the first jaw 701, is able to pass, a movable coupling hole 702c, and a hole 702d, which is a jaw pulley coupling hole, are formed in a second jaw 702 that faces and is connectable to the first jaw 701.

FIG. 48 is a perspective view illustrating the end tool hub of the surgical instrument for electrocautery of FIG. 41. FIGS. 49 and 50 are cut-away perspective views of the end tool hub of FIG. 48. FIGS. 51 and 52 are perspective views illustrating the end tool hub of FIG. 48. FIG. 53 is a side view illustrating the end tool hub of FIG. 48 and a guide tube. FIG. 54 is a plan view illustrating the end tool hub of FIG. 48 and the guide tube.

Referring to FIGS. 48 to 54, the end tool hub 760 provided in the end tool 700 of the electric cauterization surgical instrument 10 of FIG. 41 has a predetermined radius of curvature on an inner circumferential surface thereof for gentle curved movement of the guide tube 670, and may include a yaw round portion 767 and a pitch round portion 766 formed in a curved shape.

In addition, a yaw slit 765 passing through the end tool hub 760 may be formed on a plane perpendicular to a first rotation shaft 741 to allow a guide tube 770, which is configured to guide a movement path of a blade 775 and the blade wire 307 connected to the blade 775, to stably move through the end tool hub 760.

In addition, a pitch slit 764, which is a separation space, may be formed between a first pitch pulley portion 763a and a second pitch pulley portion 763b facing each other so that the guide tube 670 may pass therethrough, thereby allowing the guide tube 770 to stably move through the pitch slit 764.

Referring to FIG. 51, in addition to the yaw slit 765 formed in the end tool hub 760, the yaw rotation shaft 741 may be divided into two parts and provided as a pair, and the guide tube 670 may move through a space formed between the divided pair of yaw rotation shafts 741.

Referring to FIGS. 51 to 54, the end tool hub 760 of the surgical instrument for electrocautery according to the second embodiment has the same configuration as the end tool hub 660 of the surgical instrument for electrocautery according to the first embodiment, and thus a detailed description thereof will be omitted in the overlapping range.

FIG. 55 is a perspective view illustrating the first jaw of the end tool of the surgical instrument for electrocautery of FIG. 41. FIG. 56 is a perspective view illustrating the second jaw of the end tool of the surgical instrument for electrocautery of FIG. 41.

Referring to FIG. 55, the first jaw 701 of the end tool 700 of the surgical instrument for electrocautery of FIG. 41 may include the jaw rotation shaft 701e, which has the tube through hole 701f formed therein and is formed to protrude, the movable coupling hole 701c, and the jaw pulley coupling hole 701d.

The first jaw 701 is formed entirely in an elongated bar shape, a path through which the blade 775 is movable is formed in the first jaw 701 at a distal end side (left side based on FIG. 55), and a pulley 711, which is a first jaw pulley, is coupled to the first jaw 701 at a proximal end side (right side based on FIG. 55) and formed to be rotatable around the rotation shaft 741.

Referring to FIG. 55, the movable coupling hole 701c and the jaw pulley coupling hole 701d may be formed in the first jaw 701 at the proximal end side. Here, the movable coupling hole 701c may be formed to have a predetermined curvature, and may be formed in an approximately elliptical shape.

A shaft coupling portion 711a formed on the first jaw pulley 711 may be fitted into the movable coupling hole 701c formed in the first jaw 701. Here, a short radius of the movable coupling hole 701c may be formed to be substantially the same as or slightly greater than a radius of the shaft coupling portion 711a.

Referring to FIG. 55, a long radius of the movable coupling hole 701c may be formed to be greater than the radius of the shaft coupling portion 711a. Thus, a path may be formed so that the shaft coupling portion 711a is movable therethrough to a certain degree in the movable coupling hole 701c in a state in which the shaft coupling portion 711a of the pulley 711 is fitted into the movable coupling hole 701c of the first jaw 701, This will be described in detail later.

Referring to FIG. 55, the jaw pulley coupling hole 701d formed in the first jaw 701 is formed in the form of a cylindrical hole, and a jaw coupling portion 711b of the pulley 711 may be fitted into the jaw pulley coupling hole 701d.

Here, a radius of the jaw pulley coupling hole 101d may be formed to be substantially the same as or relatively greater than a radius of the jaw coupling portion 711b. Thus, the jaw coupling portion 711b of the pulley 711 may be formed to be rotatably coupled to the jaw pulley coupling hole 701d of the first jaw 701. This will be described in more detail later.

Referring to FIG. 56, the second jaw 702 disposed to face the first jaw 701 may include the shaft pass-through portion 702e, the movable coupling hole 702c, and the jaw pulley coupling hole 702d. The second jaw 702 may be formed entirely in an elongated bar shape, the shaft pass-through portion 702e may be formed in the distal end, and the jaw pulley coupling hole 702d may be formed in the proximal end.

Referring to FIG. 59, the movable coupling hole 702c formed in the second jaw 702 may be formed to have a predetermined curvature and may be formed in an approximately elliptical shape. A shaft coupling portion 721a of a pulley 721 may be fitted into the movable coupling hole 702c. Here, a short radius of the movable coupling hole 702c may be formed to be substantially the same as or slightly greater than a radius of the shaft coupling portion 721a.

Meanwhile, a long radius of the movable coupling hole 702c may be formed to be relatively greater than the radius of the shaft coupling portion 721a. Thus, the shaft coupling portion 721a is formed to be movable to a certain degree in the movable coupling hole 702c in a state in which the shaft coupling portion 721a of the pulley 721 is fitted into the movable coupling hole 702c of the second jaw 702. This will be described in more detail later.

Meanwhile, the jaw pulley coupling hole 702d is formed in the form of a cylindrical hole, and a jaw coupling portion 721b of the pulley 721 may be fitted into the jaw pulley coupling hole 702d. Here, a radius of the jaw pulley coupling hole 702d may be formed to be substantially the same as or greater than a radius of the jaw coupling portion 721b. Thus, the jaw coupling portion 721b of the pulley 721 may be rotatably coupled to the jaw pulley coupling hole 702d of the second jaw 702.

Meanwhile, the shaft pass-through portion 702e may be formed in the second jaw 702 at the distal end side relative to the movable coupling hole 702c and the jaw pulley coupling hole 702d.

Referring to FIGS. 55 and 56, the shaft pass-through portion 702e formed in the second jaw 702 may be formed in a hole shape, and the jaw rotation shaft 701e formed in the first jaw 701 may be inserted through the shaft pass-through portion 702e.

Referring to FIG. 57, the pulley 711, which is a first jaw pulley, may include the shaft coupling portion 711a and the jaw coupling portion 711b. The pulley 711 is formed entirely in the shape of a rotatable disk and has one surface (lower surface based on FIG. 57) on which the shaft coupling portion 711a and the jaw coupling portion 711b may be formed to protrude to a certain degree.

As described above, the shaft coupling portion 711a of the pulley 711 may be fitted into the movable coupling hole 701c of the first jaw 701, and the jaw coupling portion 711b of the pulley 711 may be fitted into the jaw pulley coupling hole 701d of the first jaw 701. The pulley 711 may be formed to be rotatable with the rotation shaft 741, which is an end tool jaw pulley rotation shaft, as the center of rotation.

Meanwhile, the pulley 721, which is a second jaw pulley, may include the shaft coupling portion 721a and the jaw coupling portion 721b.

The second jaw pulley 721 is formed entirely in the form of a rotatable disk and has one surface on which the shaft coupling portion 721a and the jaw coupling portion 721b may be formed to protrude to a certain degree. As described above, the shaft coupling portion 712a of the pulley 712 may be fitted into the movable coupling hole 702c of the second jaw 702, and the jaw coupling portion 712b of the pulley 712 may be fitted into the jaw pulley coupling hole 702d of the second jaw 702. The pulley 721 may be formed to be rotatable with the rotation shaft 741, which is an end tool jaw pulley rotation shaft, as the center of rotation.

The coupling relationship between the components described above is as follows.

The rotation shaft 741, which is an end tool jaw pulley rotation shaft, is sequentially inserted through the shaft coupling portion 711a of the pulley 711, the movable coupling hole 701c of the first jaw 701, the movable coupling hole 702c of the second jaw 702, and the shaft coupling portion 721a of the pulley 721.

The rotation shaft 701e, which is a jaw rotation shaft, is inserted through the shaft pass-through portion 702e of the second jaw 702.

The shaft coupling portion 711a of the pulley 711 is fitted into the movable coupling hole 701c of the first jaw 701, and the jaw coupling portion 711b of the pulley 711 is fitted into the jaw pulley coupling hole 701d of the first jaw 701.

At this time, the jaw pulley coupling hole 701d of the first jaw 701 and the jaw coupling portion 711b of the pulley 711 are axially coupled to each other so as to be rotatable, and the movable coupling hole 701c of the first jaw 701 and the shaft coupling portion 711a of the pulley 711 are movably coupled to each other.

The shaft coupling portion 721a of the pulley 721 is fitted into the movable coupling hole 702c of the second jaw 702, and the jaw coupling portion 721b of the pulley 721 is fitted into the jaw pulley coupling hole 702d of the second jaw 702.

At this time, the jaw pulley coupling hole 702d of the second jaw 702 and the jaw coupling portion 721b of the pulley 721 are axially coupled to each other to be rotatable, and the movable coupling hole 702c of the second jaw 702 and the shaft coupling portion 721a of the pulley 721 are movably coupled to each other.

Here, the pulley 711 and the pulley 721 rotate around the rotation shaft 741, which is an end tool jaw pulley rotation shaft. The first jaw 701 and the second jaw 702 rotate around the rotation shaft 701e, which is a jaw rotation shaft. That is, the pulley 711 and the first jaw 701 have different shafts of rotation. Similarly, the pulley 721 and the second jaw 702 have different shafts of rotation.

That is, the rotation angle of the first jaw 701 is limited to a certain degree by the movable coupling hole 701c, but is essentially rotated about the rotation shaft 701e, which is a jaw rotation shaft. Similarly, the rotation angle of the second jaw 702 is limited to a certain degree by the movable coupling hole 702c, but is essentially rotated around the rotation shaft 701c, which is a jaw rotation shaft.

Amplification of grip force due to the coupling relationship between the above-described components will be described.

FIG. 58 is a plan view illustrating an opening and closing motion of the first jaw of the end tool of the surgical instrument for electrocautery of FIG. 41. FIG. 59 is a plan view illustrating an opening and closing motion of the second jaw of the end tool of the surgical instrument for electrocautery of FIG. 41. FIG. 60 is a plan view illustrating an opening and closing motion of the first jaw and the second jaw of the end tool of the surgical instrument for electrocautery of FIG. 41.

Referring to FIGS. 58 to 60, in the electric cauterization surgical instrument 10 according to the second embodiment, the coupling structure of the first jaw 701 and the second jaw 702 forms an X-shaped structure, so that when the first jaw 701 and the second jaw 702 rotate in a direction of approaching each other (i.e. when the first jaw 701 and the second jaw 702 are closed), a grip force in a direction of closing the first jaw 701 and the second jaw 702 further increases. This will be described below in more detail.

As described above, in motions of the first jaw 701 and the second jaw 702 being opened and closed, there are two shafts that serve as the centers of rotation for the first jaw 701 and the second jaw 702.

That is, the first jaw 701 and the second jaw 702 perform an opening and closing motion around two shafts of the rotation shaft 741 and the rotation shaft 701e. In this case, the centers of rotation of the first jaw 701 and the second jaw 702 become the rotation shaft 701c, and the centers of rotation of rotation of the pulley 711 and the pulley 721 become the rotation shaft 741.

At this time, the rotation shaft 741 is a shaft whose position is relatively fixed, and the rotation shaft 701e is a shaft whose position is relatively moved linearly. In other words, when the pulley 711 and the pulley 721 rotate in a state in which the position of the rotation shaft 741 is fixed, the first jaw 701 and the second jaw 702 are opened/closed while the rotation shaft 701c, which is a rotation shaft of the first jaw 701 and the second jaw 702, is moved backward and forward. This will be described below in more detail.

In FIG. 58, r1 is a distance from the jaw coupling portion 711b of the pulley 711 to the shaft coupling portion 711a, and a length thereof is constant. Thus, a distance from the rotation shaft 741 inserted into the shaft coupling portion 711a to the jaw coupling portion 711b is also constant as r1.

Meanwhile, r2 of FIG. 58 is a distance from the jaw pulley coupling hole 701d of the first jaw 701 to the rotation shaft 701e that is a jaw rotation shaft, and a length thereof is constant. Thus, a distance from the jaw coupling portion 711b of the pulley 711 inserted into the jaw pulley coupling hole 701d to the jaw rotation shaft 701e is also constant as r2.

Referring to FIG. 58, the lengths of r1 and r2 remain constant. Accordingly, when the pulley 711 and the pulley 721 rotate in the directions of an arrow A1 of FIG. 58 and of an arrow A2 of FIG. 59, respectively, around the rotation shaft 741 to perform a closing motion, the first jaw 701 and the second jaw 702 rotate around the rotation shaft 701e as the angle between r1 and r2 changes while the lengths of r1 and r2 remain constant, and at this time, the rotation shaft 701e itself is also linearly moved (i.e., is moved forward/backward) by as much as an arrow C1 of FIG. 58 and an arrow C2 of FIG. 59.

That is, assuming that the position of the rotation shaft 741, which is an end tool jaw pulley rotation shaft, is fixed, when the first jaw 701 and the second jaw 702 are closed, a force is applied in a direction in which the rotation shaft 701e, which is a jaw rotation shaft, is moved forward (i.e., toward the distal end), and thus the grip force in the direction in which the first jaw 701 and the second jaw 702 are closed becomes larger.

In other words, since the lengths of r1 and r2 remain constant when the second jaw 702 rotates around the jaw rotation shaft 701e, when the pulley 721 rotates around the rotation shaft 741, the angle between r1 and r2 changes while the lengths of r1 and r2 remain constant. That is, the angle between r1 and r2 in a state in which the second jaw 702 is open as shown in FIG. 59A is relatively greater than the angle between r1 and r2 in a state in which the second jaw 702 is closed as shown in FIG. 59B.

Thus, when the second jaw 702 rotates from the open state to the close state, the angle between r1 and r2 changes, and a force is applied in a direction in which the jaw rotation shaft 701e passing through the shaft pass-through portion 702e formed in the second jaw 702 is moved forward.

In this case, since the rotation shaft 741 is a shaft whose position is relatively fixed, the jaw rotation shaft 701e is moved forward in the direction of the arrow C1 of FIG. 58 and the direction of an arrow C2 of FIG. 59, and the grip force is further increased in a direction in which the second jaw 702 is closed.

In other words, when the pulley 711 and the pulley 721 rotate around the rotation shaft 741, which is a shaft whose relative position is fixed, the angle between r1 and r2 changes while the distance between r1 and r2 remains constant. In addition, when the angle changes as described above, the first jaw 701 and the second jaw 702 push or pull the rotation shaft 701c, and thus the jaw rotation shaft 701e is moved forward or backward.

In this case, when the first jaw 701 and the second jaw 702 rotate in the direction of closing, the grip force is further increased as the rotation shaft 701e is moved forward in the directions of the arrow C1 of FIG. 58 and the arrow C2 of FIG. 59.

On the contrary, when the first jaw 701 and the second jaw 702 rotate in the direction of opening, the rotation shaft 701e is moved backward in directions opposite to the arrow C1 of FIG. 58 and the arrow C2 of FIG. 59.

With this configuration, the grip force becomes stronger when the first jaw 701 and the second jaw 702 are closed, thereby enabling a surgical operator to perform the actuation motion powerfully even with a small force.

That is, as shown in FIG. 60, as the first jaw 701 and the second jaw 702, which have an X-shaped structure, rotate relative to each other around the first rotation shaft 741 that is a fixed shaft, the rotation shaft 701e, which is a jaw rotation shaft, is moved forward toward the distal end of the end tool 700, so that the grip force may be amplified.

FIGS. 61 and 62 are plan views illustrating an opening and closing motion of the first jaw 701 and the second jaw 702 in response to an actuation motion of the end tool 700 of the surgical instrument for electrocautery of FIG. 41.

Referring to FIGS. 61 and 62, the first jaw 701 and the second jaw 702 are connected in an X-shaped structure, and the first jaw 701 and the second jaw 702 rotate relative to each other as the first jaw pulley 711 and the second jaw pulley 721 rotate with the fixed rotation shaft 741 as the center of rotation, enabling an actuation motion.

In the end tool 700 of the electric cauterization surgical instrument 10 according to the second embodiment of the present disclosure, as the first jaw 701 and the second jaw 702 rotate relative to each other, a grip force may be amplified when the jaw rotation shaft 701e is moved forward/backward, particularly forward.

Referring to FIG. 62, as the pulley 711 and the pulley 721 rotate in opposite directions with the first rotation shaft 741 as the central axis of rotation, the first jaw 701 and the second jaw 702, which are respectively connected to the pulley 711 and the pulley 721, rotate in opposite directions and move away from each other, and thus the end tool 700 may be in an open state.

Referring to FIGS. 61 to 65, it may be said that the tissue between the first jaw 701 and the second jaw 702 is cut as the cutting motion of FIGS. 63 to 65 is performed in a state in which the first jaw 701 and the second jaw 702 are closed as shown in FIG. 61.

Here, a first position shown in FIG. 63 may be defined as a state in which the blade 775 is drawn in toward a proximal end 705 of the end tool as much as possible. Alternatively, the first position may also be defined as a state in which the blade 775 is located adjacent to the pulley 711/pulley 712.

Meanwhile, a third position illustrated in FIG. 65 may be defined as a state in which the blade 775 is withdrawn toward a distal end 704 of the end tool 700 as much as possible. Alternatively, the third position may also be defined as a state in which the blade 775 is spaced away from the pulley 711/pulley 712 as much as possible.

First, as shown in FIG. 62, a tissue to be cut is located between the first jaw 701 and the second jaw 702 in a state in which the first jaw 701 and the second jaw 702 are opened, and then an actuation motion is performed to close the first jaw 701 and the second jaw 702 as shown in FIG. 61.

Next, as shown in FIG. 63, in a state in which the blade wire 307 and the blade 775 are located at the first position, currents of different polarities are applied to the first electrode 751 and the second electrode 752 to cauterize the tissue between the first jaw 701 and the second jaw 702. At this time, a generator (not shown) configured to supply power to the electrodes may itself perform monitoring of at least some of current, voltage, resistance, impedance, and temperature, and may stop supplying power when the cauterization is completed.

In the state in which the cauterization is completed as described above, when the blade wire 307 moves sequentially in the directions of an arrow A1 of FIG. 64 and an arrow A2 of FIG. 65, the blade 775 coupled to the blade wire 307 moves from the first position at the proximal end 705 of the end tool toward the third position at the distal end 704 of the end tool, reaching the positions in FIGS. 64 and 65 in turn.

As such, the blade 775 cuts the tissue located between the first jaw 701 and the second jaw 702 while moving in the X-axis direction.

However, it is to be understood that the linear motion of the blade 775 here does not mean a motion in a completely straight line, but rather means a motion of the blade 775 to the extent that the blade 775 is able to cut the tissue while achieving a linear motion when viewed as a whole, even though the motion is not in a completely straight line, for example, the middle part of the straight line is bent by a certain angle or there is a section having a gentle curvature in a certain section.

Meanwhile, in this state, when the blade wire 307 is pulled in the opposite direction, the blade 775 coupled to the blade wire 307 also returns to the first position.

According to the present disclosure, the multi-joint/multi-degree-of-freedom surgical instrument capable of pitch/yaw/actuation motions may also perform cauterizing and cutting motions.

Referring to FIGS. 66 and 67, views are illustrated in which a process of performing an opening and closing motion in a state in which the end tool 700 of the electric cauterization surgical instrument 10 of FIG. 41 is yaw-rotated by +90°.

Referring to FIG. 66, the pulley 711 and the pulley 721 that faces the pulley 711 may be rotated around the first rotation shaft 741 due to the wires of the power transmission portion 300 in the manipulation portion 200. In FIG. 66, when the pulley 711 and the pulley 721 rotate in opposite directions, the first jaw 701 and the second jaw 702 respectively coupled to the pulley 711 and the pulley 721 may rotate relative to each other in a direction of approaching each other to perform an actuation motion, and as shown in FIG. 67, the first jaw 701 and the second jaw 702 may be in a closed state.

FIGS. 66 and 67 are views illustrating a process of performing an opening and closing motion in a state in which the end tool of the surgical instrument for electro-cautery of FIG. 41 is yaw-rotated by −90°.

Referring to FIGS. 66 and 67, as the pulley 711 and the pulley 711 are yaw rotatable by −90° with the first rotation shaft 741 as the central axis of rotation, and the pulley 711 and the pulley 711 rotates in different directions, an actuation motion is possible in which the first jaw 701 and the second jaw 702 respectively connected to the pulley 711 and the pulley 721 move closer or further away from each other.

Referring to FIGS. 66 to 69, a blade assembly, specifically, the guide tube 770 is connected to the end tool 700 at the other end portion, which is opposite one end portion connected to the connection portion 400, and may be of constant length.

The guide tube 770 may be gently curved with a predetermined radius of curvature when the end tool 700, specifically, the first jaw 701 and the second jaw 702 rotate with the first rotation shaft 741 as the central axis of rotation, and may stably provide a movement path for the blade wire 307 to be movable between the distal end 704 and the proximal end 705 of the end tool 700.

FIGS. 70 and 71 are views illustrating a path of the guide tube 770 and a movement path of the blade 775 during a cutting motion in a state in which the end tool 700 of the surgical instrument for electrocautery of FIG. 41 is yaw-rotated by +90°.

Referring to FIGS. 70 and 71, the end tool 700 of the electric cauterization surgical instrument 10 according to the second embodiment of the present disclosure is formed such that the jaws 701 and 702 are able to perform a normal cutting motion even when the jaws are yaw-rotated by +90°.

Specifically, as the blade wire 307 emerges from the inside of the guide tube 770, and the blade 775 connected to the blade wire 307 moves in the direction of an arrow A, which is a direction from the proximal end 705 toward the distal end 704 of the end tool 700, a cutting motion may be performed.

FIGS. 72 and 73 are views illustrating a process of performing an opening and closing motion in a state in which the end tool of the surgical instrument for electro-cautery of FIG. 41 is pitch-rotated by −90°. FIGS. 74 and 75 are views illustrating a process of performing an opening and closing motion in a state in which the end tool of the surgical instrument for electrocautery of FIG. 41 is pitch-rotated by +90°. FIG. 76 is a view illustrating a path of the guide tube in a state in which the end tool of the surgical instrument for electrocautery of FIG. 41 is pitch-rotated by −90°. FIGS. 77 and 78 are views illustrating a path of the guide tube and a movement path of the blade during a cutting motion in a state in which the end tool of the surgical instrument for electrocautery of FIG. 41 is pitch-rotated by −90°. FIG. 79 is a perspective view illustrating the surgical instrument for electrocautery of FIG. 41 in a pitch-rotated and yaw-rotated state. FIGS. 80 to 82 are views illustrating the end tool of the surgical instrument for electrocautery of FIG. 41 performing a cutting motion in a state in which the end tool is pitch-rotated by −90° and simultaneously yaw-rotated by +90°.

FIGS. 74 and 75 are views illustrating a process of performing an opening and closing motion in a state in which the end tool 700 of the surgical instrument for electrocautery of FIG. 41 is pitch-rotated by +90°. FIG. 76 is a view illustrating a path of the guide tube 770 in a state in which the end tool 700 of the surgical instrument for electrocautery of FIG. 41 is pitch-rotated by −90°. FIGS. 77 and 78 are views illustrating a path of the guide tube and a movement path of the blade during a cutting motion in a state in which the end tool of the surgical instrument for electrocautery of FIG. 41 is pitch-rotated by −90°.

Referring to FIGS. 72 to 78, the end tool 700 of the electric cauterization surgical instrument 10 according to the second embodiment of the present disclosure is formed such that the jaws 701 and 702 are able to perform a cutting motion normally even when the jaws are pitch-rotated by −90° and +90°.

Meanwhile, FIG. 79 is a view illustrating a state in which the jaws are pitch-rotated by −90° and simultaneously yaw-rotated by +90°, and FIGS. 80 to 82 are views illustrating a state in which the end tool of the surgical instrument for electrocautery of FIG. 41 performs a cutting motion in a state in which the end tool is pitch-rotated by −90° and simultaneously yaw-rotated by +90°.

Referring to FIGS. 79 to 82, the end tool 700 of the electric cauterization surgical instrument 10 according to the second embodiment of the present disclosure is formed such that the jaws 701 and 702 are able to perform a cutting motion normally even when the jaws are pitch-rotated by −90° and simultaneously yaw-rotated by +90°.

Modified Example of Second Embodiment-Disposing Auxiliary Pulley on End Tool Hub Hereinafter, an end tool 700 of a surgical instrument according to a modified example of the second embodiment of the present disclosure will be described. Here, the end tool 700 of the surgical instrument according to the modified example of the second embodiment of the present disclosure is different from the end tool of the surgical instrument according to the second embodiment of the present disclosure described above in that the configuration of an end tool hub 760' and the configuration of auxiliary pulleys 712 and 722 are different. The configuration changed from the second embodiment as described above will be described in detail later.

FIGS. 83 to 85 are views illustrating the end tool of the surgical instrument for electrocautery according to the modified example of the second embodiment of the present disclosure.

Referring to FIGS. 83 to 85, the end tool 700 of the modified example of the second embodiment of the present disclosure includes a pair of jaws for performing a grip motion, specifically a first jaw 701 and a second jaw 702, and here, each of the first jaw 701 and the second jaw 702 or a component encompassing the first jaw 701 and the second jaw 702 may be referred to as a jaw 703.

The end tool 700 according to the modified example of the second embodiment may include a pulley 711, the pulley 712, a pulley 713, a pulley 714, a pulley 715, and a pulley 716 that are associated with a rotational motion of the first jaw 701. In addition, the end tool 700 may include a pulley 721, the pulley 722, a pulley 723, a pulley 724, a pulley 725, and a pulley 726 that are associated with a rotational motion of the second jaw 702.

Here, the pulleys facing each other are illustrated in the drawings as being formed parallel to each other, but the concept of the present disclosure is not limited thereto, and each of the pulleys may be variously formed with a position and a size suitable for the configuration of the end tool.

The end tool 700 according to the modified example of the second embodiment of the present disclosure may further include the pulley 712 and the pulley 722 as compared to the end tool 700 according to the second embodiment of the present disclosure illustrated with reference to FIG. 43.

Referring to FIGS. 84 and 85, the pulley 712 functions as an end tool first jaw auxiliary pulley, and the pulley 722 functions as an end tool second jaw auxiliary pulley, and these two components may collectively be referred to as end tool jaw auxiliary pulleys or simply auxiliary pulleys.

In detail, the pulley 712 and the pulley 722, which are end tool jaw auxiliary pulleys, may be additionally provided on one side of the pulley 711 and one side of the pulley 721, respectively. In other words, the pulley 712, which is an auxiliary pulley, may be disposed between the pulley 711 and the pulley 713/pulley 714. In addition, the pulley 722, which is an auxiliary pulley, may be disposed between the pulley 721 and the pulley 723/pulley 724.

The pulley 712 and the pulley 722 may be formed to be rotatable independently of each other around a second rotation shaft 742.

The pulley 712 and the pulley 722 may serve to increase rotation angles of the first jaw 701 and the second jaw 702, respectively, by coming into contact with a wire 305, which is a first jaw wire, and a wire 302, which is a second jaw wire, and changing the arrangement paths of the wire 305 and the wire 302 to a certain degree.

That is, when the auxiliary pulleys are not disposed, each of the first jaw 701 and the second jaw 702 may rotate only up to a right angle, but in the modified example of the second embodiment, by additionally providing the pulley 712 and the pulley 722, which are auxiliary pulleys, the effect of increasing the maximum rotation angle by a certain angle can be achieved.

This enables a motion in which two jaws of the end tool 700 have to be spread apart for an actuation motion in a state in which the two jaws are yaw-rotated together by 90° in the clockwise or counterclockwise direction.

In other words, a feature of increasing the range of yaw rotation in which an actuation motion is possible may be obtained through the pulley 712 and the pulley 722. This will be described below in more detail.

When the auxiliary pulleys are not disposed, since the first jaw wire 305 is fixedly coupled to the end tool first jaw pulley 711, and the second jaw wire 302 is fixedly coupled to the end tool second jaw pulley 721, each of the end tool first jaw pulley 711 and the end tool second jaw pulley 721 may rotate up to 90°.

In this case, when the actuation motion is performed in a state in which the first jaw 701 and the second jaw 702 are located at a 90° line, the first jaw 701 may be spread, but the second jaw 702 may not be rotated beyond 90°. Accordingly, when the first jaw 701 and the second jaw 702 perform a yaw motion over a certain angle, there was a problem that an actuation motion is not smoothly performed.

In order to address such a problem, in the electric cauterization surgical instrument 10 of the present disclosure, the pulley 712 and the pulley 722, which are auxiliary pulleys, are additionally disposed at one side of the pulley 711 and one side of the pulley 721, respectively. As described above, as the arrangement paths of the wire 305, which is a first jaw wire, and the wire 302, which is a second jaw wire, are changed to a certain degree by disposing the pulley 712 and the pulley 722, a tangential direction of the wires 305 and 302 is changed, and accordingly, a fastening member 324 for coupling the wire 302 and the pulley 721 is additionally rotatable by a certain angle.

That is, a fastening member 326, which is a coupling portion of the wire 302 and the pulley 721, is rotatable until being located on a common internal tangent of the pulley 721 and the pulley 722. Similarly, a fastening member 323, which is a coupling portion of the wire 305 and the pulley 711, is rotatable until being located on a common internal tangent of the pulley 711 and the pulley 712, so that the range of rotation may be increased.

In other words, due to the pulley 712 that is an auxiliary pulley, a wire 301 and a wire 305, which are two strands of the first jaw wire wound around the pulley 712, are disposed at one side with respect to a plane perpendicular to the Y-axis and passing through the X-axis. Simultaneously, due to the pulley 722, the wires 302 and 306, which are two strands of the second jaw wire wound around the pulley 721, are disposed at the other side with respect to the plane perpendicular to the Y-axis and passing through the X-axis.

In other words, the pulley 713 and the pulley 714 are disposed at one side with respect to the plane perpendicular to the Y-axis and passing through the X-axis, and the pulley 723 and the pulley 724 are disposed at the other side with respect to the plane perpendicular to the Y-axis and passing through the X-axis.

In other words, the wire 305 is located on the internal tangent of the pulley 711 and the pulley 712, and the rotation angle of the pulley 711 is increased due to the pulley 712. In addition, the wire 302 is located on the internal tangent of the pulley 721 and the pulley 722, and the rotation angle of the pulley 721 is increased due to the pulley 722.

According to the present disclosure, the rotation radii of the first jaw 701 and the second jaw 702 increase, so that an effect of increasing a yaw motion range in which a normal opening/closing actuation motion can be performed may be obtained.

Referring to FIG. 38, a first rotation shaft 741 and a second rotation shaft 742 may be inserted through the end tool hub 760' according to the modified example of the second embodiment of the present disclosure. Instead of respectively forming the first wire guide portion and the second wire guide portion on the surfaces of a first jaw pulley coupling portion 762a and a second jaw pulley coupling portion 762b facing each other as in the end tool hub 760 according to the second embodiment of the present disclosure, the pulley 712 and the pulley 722, which are configured as separate components from the end tool hub 760' and are able to be axially coupled to the second rotation shaft 742 that is inserted through the end tool hub 760', are additionally provided and allowed to function as auxiliary pulleys.

The second rotation shaft 742 inserted through the end tool hub 760' may include two shafts including a first sub-shaft and a second sub-shaft that face each other and are disposed to be spaced apart from each other by a certain distance. The second rotation shaft 742 is divided into two parts and spaced apart from each other by a certain distance, and thus a guide tube 770 may pass through the end tool hub 760' and a pitch hub 750 through between the two parts.

Referring to FIG. 83, the first rotation shaft 741, the second rotation shaft 742, a third rotation shaft 743, and a fourth rotation shaft 744 may be arranged sequentially from a distal end 704 toward a proximal end 705 of the end tool 700. Accordingly, starting from the distal end 704, the first rotation shaft 741 may be referred to as a first pin, the second rotation shaft 742 may be referred to as a second pin, the third rotation shaft 743 may be referred to as a third pin, and the fourth rotation shaft 744 may be referred to as a fourth pin.

As compared to the second embodiment, the end tool 700 of the modified example of the second embodiment of the present disclosure has the same configuration as the end tool 700 according to the second embodiment, except that the pulley 721 and the pulley 722, which are axially coupled to the end tool hub 760' by the second rotation shaft 742, are provided as separate components instead of being integrally formed with a body portion 761 in the end tool hub 760' and function as auxiliary pulleys, and thus a detailed description thereof will be omitted in the overlapping range.

Third Embodiment of Surgical Instrument for Electrocautery

FIG. 86 is a perspective view illustrating a surgical instrument for electrocautery according to a third embodiment of the present disclosure. FIGS. 87 to 92 are plan views illustrating an end tool of the surgical instrument for electrocautery of FIG. 86.

Referring to FIG. 86, an electric cauterization surgical instrument 10 according to the third embodiment of the present disclosure includes an end tool 800, a manipulation portion 200, a power transmission portion 300, and a connection portion 400.

As compared to the electric cauterization surgical instrument 10 according to the second embodiment, the electric cauterization surgical instrument 10 according to the third embodiment of the present disclosure is different from in a configuration of the end tool 800, specifically, a yaw hub 880, an actuation link 892, and the like, which will be described in detail below.

Referring to FIGS. 86 and 87, the end tool 800 according to the third embodiment of the present disclosure is formed at the other end of the connection portion 400, and performs necessary motions for surgery by being inserted into a surgical site. In an example of the end tool 800, as illustrated in FIG. 86, a pair of jaws 803 for performing a grip motion may be used.

However, the concept of the present disclosure is not limited thereto, and various devices for performing surgery may be used as the end tool 800. For example, a configuration of a cantilever cautery may also be used as the end tool 800.

The end tool 800 is connected to the manipulation portion 200 by the power transmission portion 300, and receives a driving force of the manipulation portion 200 through the power transmission portion 300 to perform a motion necessary for surgery, such as gripping, cutting, suturing, or the like.

Here, the end tool 800 of the electric cauterization surgical instrument 10 according to the third embodiment of the present disclosure is formed to be rotatable in at least one direction, and for example, the end tool 800 may be formed to perform a pitch motion around a Y-axis of FIG. 86 and simultaneously perform a yaw motion and an actuation motion around a Z-axis of FIG. 86.

End Tool According to Third Embodiment

Hereinafter, the end tool 800 of the electric cauterization surgical instrument 10 of FIG. 86 will be described in more detail.

FIG. 86 is a perspective view illustrating the surgical instrument for electrocautery according to the third embodiment of the present disclosure. FIGS. 87 to 92 are views illustrating the end tool of the surgical instrument for electrocautery of FIG. 86.

Here, FIG. 87 illustrates a state in which an end tool hub 860 and a pitch hub 850 are coupled, and FIG. 88 illustrates a state in which the end tool hub 860, the yaw hub 880, and the pitch hub 850 are removed. FIG. 89 illustrates a state in which the yaw hub 880 and the end tool hub 860 are connected to the end tool, and FIG. 90 illustrates a state in which a first jaw 801 and a second jaw 802 are removed. Meanwhile, FIG. 91 is a view mainly illustrating wires, and FIG. 92 is a view mainly illustrating pulleys.

Referring to FIGS. 87, 88, 91, and 92, the end tool 800 according to the third embodiment of the present disclosure may include a pair of jaws for performing a grip motion, that is, the first jaw 801 and the second jaw 802. Here, each of the first jaw 801 and the second jaw 802, or a component encompassing the first jaw 801 and the second jaw 802 may be referred to as the jaw 803.

In addition, the end tool 800 may include a pulley 891, a pulley 813, a pulley 814, a pulley 815, and a pulley 816, which are associated with a rotational motion of the first jaw 801. In addition, the end tool 800 may include a pulley 881, a pulley 823, a pulley 824, a pulley 825, and a pulley 826, which are associated with a rotational motion of the second jaw 802.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Referring to FIG. 87, the end tool 800 of the third embodiment of the present disclosure may include the end tool hub 860, the pitch hub 850, and the yaw hub 880.

A first rotation shaft 841, which will be described later, may be inserted through the end tool hub 860, and the end tool hub 860 may internally accommodate at least some of the pulley 891 and the pulley 881, which are axially coupled to the first rotation shaft 841.

The end tool hub 860 according to the third embodiment of the present disclosure is the same as the end tool hubs 660 and 760 according to the first and third embodiments, and thus a detailed description thereof will be omitted in the overlapping range.

Referring to FIG. 87, the pitch hub 850 may have a third rotation shaft 843 and a fourth rotation shaft 844, which will be described later, inserted therethrough, and may be axially coupled to a first pitch pulley portion 863a and a second pitch pulley portion 863b of the end tool hub 860 by the third rotation shaft 843. Accordingly, the end tool hub 860 may be formed to be rotatable around the third rotation shaft 843 with respect to the pitch hub 850.

In addition, the pitch hub 850 may internally accommodate at least some of the pulley 813, the pulley 814, the pulley 823, and the pulley 824 that are axially coupled to the third rotation shaft 843. In addition, the pitch hub 850 may internally accommodate at least some of the pulley 815, the pulley 816, the pulley 825, and the pulley 826 that are axially coupled to the fourth rotation shaft 844.

One end portion of the pitch hub 850 is connected to the end tool hub 860, and the other end portion of the pitch hub 850 is connected to the connection portion 400.

Referring to FIG. 87, the first rotation shaft 841 may function as an end tool jaw pulley rotation shaft, the third rotation shaft 843 may function as an end tool pitch rotation shaft, and the fourth rotation shaft 844 may function as an end tool pitch auxiliary rotation shaft of the end tool 100.

Here, each of the rotation shafts may be divided into two parts, and the respective divided rotation shafts may be spaced apart from each other. Each of the rotation shafts is formed by being divided into two parts as described above to allow a guide tube 870 to pass through the end tool hub 860 and the pitch hub 850.

That is, the guide tube 870 may pass between a first sub-shaft and a second sub-shaft of each of the rotation shafts. This will be described in more detail later. Here, the first sub-shaft and the second sub-shaft may be disposed on the same axis or may be disposed to be offset to a certain degree.

Meanwhile, it is illustrated in the drawings that each of the rotation shafts is formed by being divided into two parts, but the concept of the present disclosure is not limited thereto. That is, each of the rotation shafts is formed to be curved in the middle such that an escape path for the guide tube 870 is formed.

Referring to FIGS. 87 and 88, an actuation rotation shaft 845 may be further provided in the end tool 800 according to the third embodiment of the present disclosure. In detail, the actuation rotation shaft 845 may be provided in a coupling portion of the first jaw 801 and the second jaw 802, and the second jaw 802 rotates around the actuation rotation shaft 845 while the first jaw 801 is fixed, thereby performing an actuation motion. Here, the actuation rotation shaft 845 may be disposed closer to a distal end 804 than the first rotation shaft 841 is.

Here, in the end tool 800 of the third embodiment of the present disclosure, the first rotation shaft 841, which is a yaw rotation shaft, and the actuation rotation shaft 845 are provided separately rather than as the same shaft.

That is, by forming the first rotation shaft 841, which is a rotation shaft of the pulley 881/pulley 891 that are jaw pulleys and a rotation shaft of a yaw motion, and the actuation rotation shaft 845, which is a rotation shaft of the second jaw 802 with respect to the first jaw 801 and a rotation shaft of an actuation motion, to be spaced apart from each other by a certain distance, a space in which the guide tube 870 and the blade wire 307 accommodated therein can be gently bent may be secured. This actuation rotation shaft 845 will be described in more detail later.

The pulley 891 functions as an end tool first jaw pulley, and the pulley 881 functions as an end tool second jaw pulley. The pulley 891 may also be referred to as a first jaw pulley, and the pulley 881 may also be referred to as a second jaw pulley, and these two components may collectively be referred to as end tool jaw pulleys or simply jaw pulleys.

The pulley 891 and the pulley 881, which are end tool jaw pulleys, are formed to face each other, and are formed to be rotatable independently of each other around the first rotation shaft 841 which is an end tool jaw pulley rotation shaft.

In this case, the pulley 891 and the pulley 881 are formed to be spaced apart from each other by a certain distance, and a blade assembly may be accommodated therebetween.

In other words, the blade assembly including the guide tube 870 may be disposed between the pulley 891 and the pulley 881.

Meanwhile, the end tool 800 of the third embodiment of the present disclosure may further include components such as a first electrode 851, a second electrode 852, the guide tube 870, and a blade 875 in order to perform a cauterizing motion and a cutting motion.

Here, components related to the driving of the blade, such as the guide tube 870 and the blade 875, may be collectively referred to as a blade assembly. In one modified example of the present disclosure, by disposing the blade assembly including the blade 875 between the pulley 891, which is a first jaw pulley, and the pulley 881, which a second jaw pulley, the end tool 800 is able to perform the cutting motion using the blade in addition to the pitch and yaw motions. Components for performing a cauterizing motion and a cutting motion in the present embodiment are substantially the same as those described in the first and second embodiments, and thus a detailed description thereof will be omitted herein.

The electric cauterization surgical instrument 10 according to the third embodiment of the present disclosure may include a wire 301, a wire 302, the wire 303, the wire 304, a wire 305, a wire 306, and a blade wire 307, as in the first embodiment of the present disclosure.

(Jaw-Link-Pulley Connection Structure)

Hereinafter, a jaw-link-pulley connection structure in the end tool 800 according to the third embodiment of the present disclosure will be described in more detail.

Referring to FIGS. 87 to 101, the end tool 800 of the third embodiment of the present disclosure includes the first jaw 801, the second jaw 802, the yaw hub 880, an actuation link 592, the first jaw pulley 891, and the second jaw pulley 881. Hereinafter, the pulley 891 is referred to as the first jaw pulley 891, and the pulley 881 is referred to as the second jaw pulley 881.

Referring to FIGS. 97 to 100, the first jaw pulley 891 may be formed as a kind of multi-layered pulley. In other words, the first jaw pulley 891 may be formed in a form in which two pulleys are combined, and two grooves may be formed on an outer circumferential surface of the first jaw pulley 891.

In detail, a first coupling portion 891a may be formed on one surface of the first jaw pulley 891, and a second coupling portion 891b may be formed in the shape of a groove on the other surface opposite to the one surface on which the first coupling portion 891a is formed.

Here, the positions of the first coupling portion 891a and the second coupling portion 891b are positions allowing the wire 301 and the wire 305 to overlap each other. In other words, the first coupling portion 891a and the second coupling portion 891b may be formed so that at least some of the wire 302 and the wire 306 wound around the first jaw pulley 891 overlap each other.

In other words, the first coupling portion 891a and the second coupling portion 891b are asymmetrically disposed when viewed on an XY plane, so that the first coupling portion 891a and the second coupling portion 891b are disposed to be biased in any one region of the second jaw pulley 891.

In other words, the first coupling portion 891a may be formed at a position at which the wire 301 may be wound around the outer circumferential surface of the first jaw pulley 891 such that the central angle is an angle between 90° and 360°. Similarly, the second coupling portion 891b may be formed at a position at which the wire 305 may be wound around the outer circumferential surface of the second jaw pulley 891 such that the central angle is an angle between 90° and 360°.

In addition, one end portion of the wire 301 is coupled to a fastening member 334a, which may be coupled to the first coupling portion 891a of the first jaw pulley 891. One end portion of the wire 305 is coupled to a fastening member 334b, which may be coupled to the second coupling portion 891b of the first jaw pulley 891.

When the wire 301 is referred to as a first jaw wire R and the wire 305 is referred to as a first jaw wire L, the first coupling portion 891a to which the first jaw wire R(301) is coupled is formed on a side opposite to one side to which the first jaw wire R(301) is input, so that a rotation angle of the first jaw pulley 891 is increased by increasing the length of the first jaw wire R(305) wound around the first jaw pulley 891.

Also, the second coupling portion 891b to which the first jaw wire L(302) is coupled is formed on one side opposite to the other side to which the first jaw wire L(302) is input, so that the rotation angle of the first jaw pulley 891 may be increased by increasing the length of the first jaw wire L(302) wound around the first jaw pulley 891.

A rotation radius of the second jaw pulley 891 may be increased due to the first coupling portion 891a and the second coupling portion 891b. In addition, by increasing the length of the wire 301/wire 305 wound around the first jaw pulley 891 as described above, a long stroke of the actuation link 892 may be secured. This will be described in more detail later. Referring to FIG. 90, the yaw hub 880 is located between the first and second jaws 801 and 802 and the first and second jaw pulleys 891 and 881, and may include a yaw hub body 882.

The first jaw pulley 891 may be formed at one end portion of the yaw hub 880. A guide slit 883 may be formed on the other end portion of the yaw hub 880 in a longitudinal direction. A guide pin 893 formed to protrude from the actuation link 892 to be described later may be fitted into the guide slit 883.

Referring to FIGS. 90 and 93, a through hole through which the actuation rotation shaft 845 is inserted may be formed in the yaw hub 880 at one side of the guide slit 883. Referring to FIG. 93, the second jaw pulley 881 is integrally formed on one side of the yaw hub 880, but the present disclosure is not limited thereto, and various modifications are possible.

Although not shown in the drawings, it is also possible that the second jaw pulley 881 and the yaw hub 880 are each formed as a separate member, and the second jaw pulley 881 may be fixedly coupled to the yaw hub 880, specifically, the yaw hub body 882.

In addition, two divided first rotation shafts 841 may be inserted through the first jaw pulley 891 and the second jaw pulley 881, respectively.

Since the second jaw pulley 881 is integrally formed with or fixedly coupled to the yaw hub 880 as described above, the yaw hub 880 does not rotate with respect to the second jaw pulley 881, and when the second jaw pulley 881 rotates around the first rotation shaft 841, the yaw hub 580 may also rotate around the first rotation shaft 841 together with the second jaw pulley 881.

Referring to FIGS. 90 and 91, the actuation rotation shaft 845 may be disposed on the yaw hub 880. The actuation rotation shaft 845 may be divided into two parts, which may be disposed to be spaced apart from each other by a certain distance, and the guide tube 870, the blade wire 307 accommodated in the guide tube 870, and the blade 875 may pass through a space formed between the two divided actuation rotation shafts 845.

Referring to FIG. 90, the yaw hub 880, specifically, a guide slit 883 formed in the yaw hub body 882 may be formed to extend in a longitudinal direction between the actuation rotation shaft 845 and the yaw rotation shaft 841.

Referring to FIG. 90, the guide slit 883 may be formed to have the same width in the longitudinal direction, and the guide pin 893 formed to protrude from the actuation link 892 is movable, specifically, linearly movable in the guide slit 883.

Referring to FIG. 93, on the other side of the yaw hub 880 opposite to one side thereof on which the second jaw pulley 881 is formed, an actuation pulley coupling portion 885 may be formed to protrude so as to be coupled to the first jaw pulley 891.

The actuation pulley coupling portion 885 may share a central axis with the yaw rotation shaft 841. However, the present disclosure is not limited thereto, and various modifications are possible, including spacing apart and placing the actuation pulley coupling portion 885 and the yaw hub 880 side by side.

Referring to FIG. 101, the actuation link 892 may be formed to extend in a longitudinal direction. The actuation link 892 may include a link body 892a and a bending portion 892b. The link body 892a is a portion formed to extend in the longitudinal direction, and the bending portion 892b may be connected to the link body 892a with at least one bend.

Accordingly, one side of the actuation link 892 in which the bending portion 892b is located may be formed in a "U"-shape.

Referring to FIG. 101, a pin coupling hole (no reference number is assigned) may be formed in one surface of the bending portion 892b that is disposed in parallel with the link body 892a to be spaced apart therefrom by a certain distance.

A pin coupling hole may also be formed in one surface of the link body 892a facing the bending portion 892b to correspond to the pin coupling hole of the bending portion 892b. The guide pin 893 may be coupled to the pin coupling hole. A plurality of guide pins 893 may be provided, and may be coupled to the pin coupling holes formed in the respective facing surfaces of the bending portion 892b and the link body 892a.

The plurality of guide pins 893 may be disposed to be spaced apart from each other by a certain distance, and one side region of the U-shaped actuation link 892 formed with the bending portion 892b and the link body 892a may provide a movement path so that the guide tube 870 can pass therethrough. Due to the 'U' shaped region formed by the bending portion 892b and the link body 892a, the movement path of the guide tube 870 moving inside the yaw hub 880 and the end tool hub 860 is not disturbed when the actuation link 892 linearly moves.

Referring to FIG. 101, a link through-hole 892c may be formed on the other side of the link body 892a opposite to one side to which the bending portion 892b is connected. A protrusion 891c formed on the first jaw pulley 891 may be axially coupled to and fitted into the link through-hole 892c.

Accordingly, when the first jaw pulley 891 rotates, the actuation link 892 moves while rotating around the protrusion 891c.

The guide pin 893 provided in the actuation link 892 is fitted into the guide slit 883 formed in the yaw hub 880 and is movable along the shape of the guide slit 883.

The guide pin 893 passing through the guide slit 883 may be fitted into each of slots 801a and 802a respectively formed in the first jaw 801 and the second jaw 802. The first jaw 801 and the second jaw 802 have an X-shaped structure, and the guide pin 893 may be fitted into the slot 801a formed in the first jaw 801 and the slot 801b formed in the second jaw 802 at the same time.

The first jaw 801 and the second jaw 802 may perform an actuation motion while moving away from or close to each other with the actuation rotation shaft 845 as the center of rotation.

Referring to FIGS. 102 to 104, when the first jaw pulley 891 rotates in an A1 direction, the actuation link 892 axially coupled to the protrusion 891c formed in the first jaw pulley 891 is moved in a B1 direction. Specifically, the guide pin 893 provided in the actuation link 892 is moved linearly along the guide slit 883 formed in the yaw hub 880, and the guide pin 893 is fitted into the slots 801a and 802a respectively formed in the first jaw 801 and the second jaw 802, so that the guide pin 893 pushes the first jaw 801 and the second jaw 802. Thus, as the actuation link 892 is moved, the first jaw 801 and the second jaw 802 may perform an actuation motion while rotating around the actuation rotation shaft 845 as the center of rotation.

Referring to FIG. 103, as the actuation link 892 is moved toward the distal end, the first jaw 801 and the second jaw 802 may perform an actuation motion in C1 directions around the actuation rotation shaft 845 along the C1 directions.

Referring to FIG. 104, when the guide pin 893 is moved as much as possible toward the distal end in the slots 801a and 802a respectively formed in the first jaw 801 and the second jaw 802, the first jaw 801 and the second jaw 802 may be further spread apart in C2 directions.

In addition, the first jaw pulley 891 is formed in a multi-layered structure, and the first jaw wires 301 and 305 are wound so that the first jaw wires 301 and 305 overlap in different layers, and as a result, the length of the winding on the first jaw pulley 891 can be increased, and the rotation angle of the first jaw pulley 891 can be increased.

FIGS. 105 to 108 are perspective views illustrating an actuation motion of the end tool of the surgical instrument for electrocautery of FIG. 86. The guide pin 893 provided in the actuation link 892 is movable along the slots 801a and 802a respectively formed in the first jaw 801 and the second jaw 802, and accordingly, the first jaw 801 and the second jaw 802 may perform an actuation motion with the actuation rotation shaft 845 as the central axis of rotation.

FIGS. 109 to 111 are partial cross-sectional views illustrating an operation of the blade of the end tool of the surgical instrument for electrocautery of FIG. 86. The operation of the blade 875 is the same as those of the first and second embodiments, and thus a detailed description thereof will be omitted in the overlapping range.

FIGS. 112 and 113 are bottom views illustrating a process of performing an opening and closing motion in a state in which the end tool of the surgical instrument for electrocautery of FIG. 86 is yaw-rotated by +90°.

The guide slit 883 formed in the yaw hub 880 may be formed in a straight line direction, and the actuation rotation shaft 845 may be disposed along a longitudinal central axis of the guide slit 883.

The slots 801a and 802a respectively formed in the first jaw 801 and the second jaw 802 may be formed to be inclined at a certain angle with the longitudinal central axis of the guide slit 883 formed in the yaw hub 880.

This causes the first jaw 801 and second jaw 803 to spread apart from each other as shown in FIG. 113 when the actuation link 892, specifically the guide pin 893 that is moved by receiving power from the first jaw pulley 891, is moved forward toward the actuation rotation shaft 845 while the actuation rotation shaft 845 remains fixed.

Referring to FIGS. 114 and 115, the first jaw pulley 891 rotates in a state in which the end tool of the surgical instrument for electrocautery of FIG. 86 is yaw-rotated by +90°, and the guide pin 893 provided in the actuation link 892 connected to the first jaw pulley 891 is moved through the guide slit 883 formed in the yaw hub 880 and the slots 801a and 802a respectively formed in the first jaw 801 and the second jaw 802, so that an actuation motion can be performed even in a yaw rotated state.

Referring to FIGS. 116 to 125, there is room for problems when the guide tube 870 is in contact with the actuation link 892 while the end tool 800 is yaw-rotated, but the actuation link 892 of the present disclosure includes the link body 892a and the bending portion 892b connected thereto, which form a "U" shape, to prevent the contact with the guide tube 870, allowing the blade wire 307 and the guide tube 870 to move stably with respect to yaw, pitch, and actuation motions of the end tool 800.

Referring to FIGS. 126 to 136, the end tool 800 of the electric cauterization surgical instrument 10 according to the third embodiment of the present disclosure is formed such that the jaws 801 and 802 are able to perform a cutting motion normally even when the jaws arc pitch-rotated and simultaneously yaw-rotated.

Here, in the end tool 800 of the third embodiment of the present disclosure, a pin/slot-type structure is employed to secure a grip force in the actuation motion.

In detail, in the pin/slot-type structure, the actuation link 892 must move a longer distance to rotate the first jaw 801 by the same amount (that is, the actuation link 892 needs to have a long stroke). In addition, in order for the actuation link 590 to move a longer distance, the first jaw pulley 891 should rotate further. In other words, when the first jaw pulley 891 rotates further to rotate the first jaw 801 by the same amount, a greater force may be applied to the first jaw 801 by as much as the first jaw pulley 891 rotates further, so that a grip force in the actuation motion may be amplified.

In addition, in order to rotate the first jaw pulley 891 further as described above, the first jaw pulley 891 is formed in a multi-layered structure as described above to make the lengths of the wires 301 and 305 wound around the first jaw pulley 891 to be longer, thereby securing a long stroke of the actuation link 892.

Modified Example of Third Embodiment-Disposing Auxiliary Pulley on End Tool Hub

Hereinafter, an end tool 800 of a surgical instrument according to a modified example of the third embodiment of the present disclosure will be described. Here, the end tool 300 of the surgical instrument according to the modified example of the third embodiment of the present disclosure is different from the end tool of the surgical instrument according to the third embodiment of the present disclosure described above in that the configuration of an end tool hub 860' and the configuration of auxiliary pulleys 812 and 822 are different. The configuration changed from the third embodiment as described above will be described in detail later.

FIGS. 137 to 139 are views illustrating the end tool of the surgical instrument for electrocautery according to the modified example of the third embodiment of the present disclosure.

Referring to FIGS. 137 and 138, the end tool 800 of the modified example of the third embodiment of the present disclosure includes a pair of jaws for performing a grip motion, specifically a first jaw 801 and a second jaw 802, and here, each of the first jaw 801 and the second jaw 802 or a component encompassing the first jaw 801 and the second jaw 802 may be referred to as a jaw 803.

The end tool 800 according to the modified example of the third embodiment may include a pulley 811, the pulley 812, a pulley 813, a pulley 814, a pulley 815, and a pulley 816 that are associated with a rotational motion of the first jaw 801. In addition, the end tool 800 may include a pulley 821, the pulley 822, a pulley 823, a pulley 824, a pulley 825, and a pulley 826 that are associated with a rotational motion of the second jaw 802.

Here, the pulleys facing each other are illustrated in the drawings as being formed parallel to each other, but the concept of the present disclosure is not limited thereto, and each of the pulleys may be variously formed with a position and a size suitable for the configuration of the end tool.

The end tool 800 according to the modified example of the third embodiment of the present disclosure may further include the pulley 812 and the pulley 822 as compared to the end tool 800 according to the third embodiment of the present disclosure illustrated with reference to FIG. 86.

Referring to FIGS. 137 to 139, the pulley 812 functions as an end tool first jaw auxiliary pulley, and the pulley 822 functions as an end tool second jaw auxiliary pulley, and these two components may collectively be referred to as end tool jaw auxiliary pulleys or simply auxiliary pulleys.

In detail, the pulley 812 and the pulley 822, which are end tool jaw auxiliary pulleys, may be additionally provided on one side of the pulley 811 and one side of the pulley 821, respectively. In other words, the pulley 812, which is an auxiliary pulley, may be disposed between the pulley 811 and the pulley 813/pulley 814. In addition, the pulley 822, which is an auxiliary pulley, may be disposed between the pulley 821 and the pulley 823/pulley 824.

The pulley 812 and the pulley 822 may be formed to be rotatable independently of each other around a second rotation shaft 842.

The pulley 812 and the pulley 822 may serve to increase rotation angles of the first jaw 801 and the second jaw 802, respectively, by coming into contact with a wire 305, which is a first jaw wire, and a wire 302, which is a second jaw wire, and changing the arrangement paths of the wire 305 and the wire 302 to a certain degree.

That is, when the auxiliary pulleys are not disposed, each of the first jaw 801 and the second jaw 802 may rotate only up to a right angle, but in the modified example of the third embodiment, by additionally providing the pulley 812 and the pulley 822, which are auxiliary pulleys, the effect of increasing the maximum rotation angle by a certain angle can be achieved.

This enables a motion in which two jaws of the end tool 800 have to be spread apart for an actuation motion in a state in which the two jaws are yaw-rotated together by 90° in the clockwise or counterclockwise direction.

In other words, a feature of increasing the range of yaw rotation in which an actuation motion is possible may be obtained through the pulley 812 and the pulley 822. This will be described below in more detail.

When the auxiliary pulleys are not disposed, since the first jaw wire 305 is fixedly coupled to the end tool first jaw pulley 811, and the second jaw wire 302 is fixedly coupled to the end tool second jaw pulley 821, each of the end tool first jaw pulley 811 and the end tool second jaw pulley 821 may rotate up to 90°.

In this case, when the actuation motion is performed in a state in which the first jaw 801 and the second jaw 802 are located at a 90° line, the first jaw 801 may be spread, but the second jaw 802 may not be rotated beyond 90°. Accordingly, when the first jaw 801 and the second jaw 802 perform a yaw motion over a certain angle, there was a problem that an actuation motion is not smoothly performed.

In order to address such a problem, in the electric cauterization surgical instrument 10 of the present disclosure, the pulley 812 and the pulley 822, which are auxiliary pulleys, are additionally disposed at one side of the pulley 811 and one side of the pulley 821, respectively. As described above, as the arrangement paths of the wire 305, which is a first jaw wire, and the wire 302, which is a second jaw wire, are changed to a certain degree by disposing the pulley 812 and the pulley 822, a tangential direction of the wires 305 and 302 is changed, and accordingly, a fastening member 324 for coupling the wire 302 and the pulley 821 is additionally rotatable by a certain angle.

That is, a fastening member 326, which is a coupling portion of the wire 302 and the pulley 821, is rotatable until being located on a common internal tangent of the pulley 821 and the pulley 822. Similarly, a fastening member 323, which is a coupling portion of the wire 305 and the pulley 811, is rotatable until being located on a common internal tangent of the pulley 811 and the pulley 812, so that the range of rotation may be increased.

In other words, due to the pulley 812 that is an auxiliary pulley, the wires 301 and 305, which are two strands of the first jaw wire wound around the pulley 812, are disposed at one side with respect to a plane perpendicular to the Y-axis and passing through the X-axis. Simultaneously, due to the pulley 822, the wires 302 and 306, which are two strands of the second jaw wire wound around the pulley 821, are disposed at the other side with respect to the plane perpendicular to the Y-axis and passing through the X-axis.

In other words, the pulley 813 and the pulley 814 are disposed at one side with respect to the plane perpendicular to the Y-axis and passing through the X-axis, and the pulley 823 and the pulley 824 are disposed at the other side with respect to the plane perpendicular to the Y-axis and passing through the X-axis.

In other words, the wire 305 is located on the internal tangent of the pulley 811 and the pulley 812, and the rotation angle of the pulley 811 is increased due to the pulley 812. In addition, the wire 302 is located on the internal tangent of the pulley 821 and the pulley 822, and the rotation angle of the pulley 821 is increased due to the pulley 822.

According to the present disclosure, the rotation radii of the first jaw 801 and the second jaw 802 increase, so that an effect of increasing a yaw motion range in which a normal opening/closing actuation motion can be performed may be obtained.

As compared to the third embodiment, the end tool 800 of the modified example of the third embodiment of the present disclosure has the same configuration as the end tool 800 according to the third embodiment, except that the pulley 821 and the pulley 822, which are axially coupled to the end tool hub 860' by the second rotation shaft 842, are provided as separate components instead of being integrally formed with a body portion 861 in the end tool hub 860' and function as auxiliary pulleys, and thus a detailed description thereof will be omitted in the overlapping range

Fourth Embodiment of Surgical Instrument for Electrocautery

FIG. 140 is a perspective view illustrating a surgical instrument for electrocautery according to a fourth embodiment of the present disclosure. FIGS. 141 to 146 are views illustrating an end tool of the surgical instrument for electrocautery of FIG. 140. FIG. 147 is a perspective view illustrating an end tool hub of the surgical instrument for electrocautery of FIG. 140. FIGS. 148 and 149 are cut-away perspective views of the end tool hub of FIG. 147. FIGS. 150 and 151 are perspective views illustrating the end tool hub of FIG. 147. FIG. 152 is a side view illustrating the end tool hub of FIG. 147 and a guide tube. FIG. 153 is a plan view illustrating the end tool hub of FIG. 147 and the guide tube. FIG. 154 is a perspective view illustrating an actuation hub of the surgical instrument for electrocautery of FIG. 140. FIG. 155 is a cut-away perspective view of the actuation hub of FIG. 154. FIG. 156 is an exploded perspective view illustrating the end tool of the surgical instrument for electrocautery of FIG. 140. FIG. 157 is a perspective view illustrating a first jaw of the end tool of the surgical instrument for electrocautery of FIG. 140. FIG. 158 is a perspective view illustrating a second jaw of the end tool of the surgical instrument for electrocautery of FIG. 140. FIG. 159 is a perspective view illustrating a first jaw pulley of the surgical instrument for electrocautery of FIG. 140. FIG. 160 is a plan view illustrating an opening and closing motion of the first jaw of the end tool of the surgical instrument for electrocautery of FIG. 140. FIG. 161 is a plan view illustrating an opening and closing motion of the second jaw of the end tool of the surgical instrument for electrocautery of FIG. 140. FIG. 162 is a plan view illustrating an opening and closing motion of the first jaw and the second jaw of the end tool of the surgical instrument for electrocautery of FIG. 140.

Referring to FIGS. 140 to 162 and the like, an electric cauterization surgical instrument 10 according to the fourth embodiment of the present disclosure includes an end tool 1100, a manipulation portion 200, a power transmission portion 300, and a connection portion 400.

Here, the connection portion 400 is formed in the shape of a hollow shaft, and one or more wires and electric wires may be accommodated therein. The manipulation portion 200 is coupled to one end portion of the connection portion 400, the end tool 1100 is coupled to the other end portion thereof, and the connection portion 400 may serve to connect the manipulation portion 200 and the end tool 1100. Here, the connection portion 400 of the electric cauterization surgical instrument 10 according to the fourth embodiment of the present disclosure includes a straight portion 401 and a bent portion 402, wherein the straight portion 401 is formed at a side coupled to the end tool 1100, and the bent portion 402 is formed at a side to which the manipulation portion 200 is coupled. As such, since the end portion of the connection portion 400 at the side of the manipulation portion 200 is formed to be bent, a pitch manipulation portion 201, a yaw manipulation portion 202, and an actuation manipulation portion 203 may be formed along an extension line of the end tool 1100 or adjacent to the extension line. In other words, it may be said that the pitch manipulation portion 201 and the yaw manipulation portion 202 are at least partially accommodated in a concave portion formed by the bent portion 402. Due to the above-described shape of the bent portion 402, the shapes and motions of the manipulation portion 200 and the end tool 1100 may be further intuitively matched with each other.

Meanwhile, a plane on which the bent portion 402 is formed may be substantially the same as a pitch plane, that is, an XZ plane of FIG. 140. As such, as the bent portion 402 is formed on substantially the same plane as the XZ plane, interference with the manipulation portion may be reduced. Of course, for intuitive motions of the end tool and the manipulation portion, any form other than the XZ plane may be possible.

Meanwhile, a connector 410 may be formed on the bent portion 402. The connector 410 may be connected to an external power supply (not shown), and the connector 410 may be connected to a jaw 1103 through electric wires 411 and 412 to transfer electrical energy supplied from the external power supply (not shown) to the jaw 1103. Here, the connector 410 may be of a bipolar-type having two electrodes, or the connector 410 may be of a monopolar type having one electrode.

The manipulation portion 200 is formed at the one end portion of the connection portion 400 and provided as an interface to be directly controlled by a medical doctor, for example, a tongs shape, a stick shape, a lever shape, or the like, and when the medical doctor controls the manipulation portion 200, the end tool 1100, which is connected to the interface and inserted into the body of a surgical patient, performs a certain motion, thereby performing surgery. Here, the manipulation portion 200 is illustrated in FIG. 140 as being formed in a handle shape that is rotatable while the finger is inserted therein, the concept of the present disclosure is not limited thereto, and various types of manipulation portions that are connected to the end tool 1100 and manipulate the end tool 1100 may be possible.

The end tool 1100 is formed on the other end portion of the connection portion 400, and performs necessary motions for surgery by being inserted into a surgical site. In an example of the end tool 1100 described above, as shown in FIG. 140, a pair of jaws 1103 for performing a grip motion may be used. However, the concept of the present disclosure is not limited thereto, and various devices for performing surgery may be used as the end tool 1100. For example, a configuration of a cantilever cautery may also be used as the end tool. The end tool 1100 is connected to the manipulation portion 200 by the power transmission portion 300, and receives a driving force of the manipulation portion 200 through the power transmission portion 300 to perform a motion necessary for surgery, such as gripping, cutting, suturing, or the like.

Here, the end tool 1100 of the electric cauterization surgical instrument 10 according to the fourth embodiment of the present disclosure is formed to be rotatable in at least one direction, for example, the end tool 1100 may perform a pitch motion around a Y-axis of FIG. 140 and simultaneously perform a yaw motion and an actuation motion around a Z-axis of FIG. 140.

The power transmission portion 300 may connect the manipulation portion 200 to the end tool 1100, transmit the driving force of the manipulation portion 200 to the end tool 1100, and include a plurality of wires, pulleys, links, sections, gears, or the like.

The end tool 1100, the manipulation portion 200, the power transmission portion 300, and the like of the electric cauterization surgical instrument 10 of FIG. 140 will be described in detail later.

(Power Transmission Portion)

Hereinafter, the power transmission portion 300 of the electric cauterization surgical instrument 10 of FIG. 140 will be described in more detail.

Referring to FIGS. 140 to 146 and the like, the power transmission portion 300 of the electric cauterization surgical instrument 10 according to an embodiment of the present disclosure may include a wire 301, a wire 302, a wire 303, a wire 304, a wire 305, a wire 306, and a blade wire 307.

Here, the wire 301 and the wire 305 may be paired to serve as first jaw wires. The wire 302 and the wire 306 may be paired to serve as second jaw wires. Here, the components encompassing the wires 301 and 305, which are first jaw wires, and the wires 302 and 306, which are second jaw wires, may be referred to as jaw wires. In addition, the wires 303 and 304 may be paired to serve as pitch wires.

In addition, the power transmission portion 300 of the electric cauterization surgical instrument 10 according to an embodiment of the present disclosure may include a fastening member 321, a fastening member 322, a fastening member 323, a fastening member 324, a fastening member 326, and a fastening member 327 that are coupled to respective end portions of the wires to respectively couple the wires and the pulleys. Here, each of the fastening members may have various shapes as necessary, such as a ball shape, a tube shape, and the like.

Here, at the end tool 1100 side, the fastening member 321/fastening member 322 may serve as pitch wire-end tool fastening members, the fastening member 323 may serve as a first jaw wire-end tool fastening member, and the fastening member 326 may serve as a second jaw wire-end tool fastening member.

Further, at the manipulation portion 200 side, the fastening member 324 may serve as a first jaw wire-manipulation portion fastening member, and the fastening member 327 may serve as a second jaw wire-manipulation portion fastening member. In addition, although not shown in the drawings, a pitch wire-manipulation portion fastening member and a blade wire-manipulation portion fastening member may be further formed at the manipulation portion 200 side.

The coupling relationship between the wires, the fastening members, and the respectively pulleys will be described in detail as follows.

First, the wires 301 and 305, which are first jaw wires, may be a single wire. The fastening member 323, which is a first jaw wire-end tool fastening member, is inserted at an intermediate point of the first jaw wire, which is a single wire, and the fastening member 323 is crimped and fixed, and then, both strands of the first jaw wire centered on the fastening member 323 may be referred to as the wire 301 and the wire 305, respectively.

Alternatively, the wires 301 and 305, which are first jaw wires, may also be formed as separate wires, and connected by the fastening member 323.

In addition, by coupling the fastening member 323 to a pulley 1111, the wires 301 and 305 may be fixedly coupled to the pulley 1111. This allows the pulley 1111 to rotate as the wires 301 and 305 are pulled and released.

Meanwhile, the first jaw wire-manipulation portion fastening member 324 may be coupled to the other end portions of the wires 301 and 305, which are opposite to one end portions to which the fastening member 323 is fastened.

In addition, by coupling the first jaw wire-manipulation portion fastening member 324 to a pulley 211, the wires 301 and 305 may be fixedly coupled to the pulley 211. As a result, when the pulley 211 is rotated by a motor or human power, the wire 301 and the wire 305 are pulled and released, allowing the pulley 1111 of the end tool 1100 to rotate.

In the same manner, the wire 302 and the wire 306, which are second jaw wires, are coupled to each of the fastening member 326, which is a second jaw wire-end tool fastening member, and the second jaw wire-manipulation portion fastening member 327. In addition, the fastening member 326 is coupled to a pulley 1121, and the second jaw wire-manipulation portion fastening member is coupled to a pulley 220. As a result, when the pulley 220 is rotated by a motor or a human force, the pulley 1121 of the end tool 1100 may be rotated as the wire 302 and the wire 306 are pulled and released.

In the same manner, the wire 304, which is a pitch wire, is coupled to the fastening member 321, which is a pitch wire-end tool fastening member, and the pitch wire-manipulation portion fastening member (not shown). In addition, the wire 303, which is a pitch wire, is coupled to a fastening member 322, which is a pitch wire-end tool fastening member, and the pitch wire-manipulation portion fastening member (not shown).

In addition, the fastening member 321 is coupled to a first pitch pulley portion 1163a of an end tool hub 1160, the fastening member 322 is coupled to a second pitch pulley portion 1163b of the end tool hub 1160, and the pitch wire-manipulation portion fastening member (not shown) is coupled to a pulley 231. As a result, when the pulley 231 is rotated by a motor or human force, the wire 303 and the wire 304 are pulled and released, allowing the end tool hub 1160 of the end tool 1100 to rotate.

Meanwhile, one end portion of the blade wire 307 is coupled to a blade 1175 to be described later, and the other end portion thereof is coupled to a blade manipulation portion 260 of the manipulation portion 200. By the manipulation of the blade manipulation portion 260, a cutting motion may be performed as the blade wire 307 is moved from a proximal end 1105 toward a distal end 1104 of the end tool 1100, or the blade wire 307 may return from the distal end 1104 toward the proximal end 1105 of the end tool 1100.

At this time, at least a part of the blade wire 307 may be accommodated in a guide tube 1170 to be described later. Accordingly, when the guide tube 1170 is bent in response to a pitch motion or yaw motion of the end tool 1100, the blade wire 307 accommodated therein may also be bent together with the guide tube 1170. The guide tube 1170 will be described in more detail later.

In addition, the blade wire 307 is formed in a longitudinal direction of the connection portion 400 to be linearly movable in the connection portion 400. In addition, since one end portion of the blade wire 307 is coupled to the blade 1175, when the blade wire 307 is linearly moved in the longitudinal direction of the connection portion 400, the blade 1175 connected thereto is also linearly moved. That is, when the blade wire 307 is linearly moved in the longitudinal direction of the connection portion 400, a cutting motion is performed as the blade 1175 connected thereto is moved toward the distal end 1104 or the proximal end 1105 of the end tool 1100. This will be described in more detail later.

(End Tool)

Hereinafter, the end tool 1100 of the electric cauterization surgical instrument 10 of FIG. 140 will be described in more detail.

FIG. 140 is a perspective view illustrating the surgical instrument for electrocautery according to the fourth embodiment of the present disclosure. FIGS. 141 to 146 are views illustrating the end tool of the surgical instrument for electrocautery of FIG. 140.

Here, FIG. 141 illustrates a state in which the end tool hub 1160 and a pitch hub 1150 are coupled, and FIG. 142 illustrates a state in which the end tool hub 1160 and pitch hub 1150 are removed. FIG. 143 illustrates a state in which a first jaw 1101 and a second jaw 1102 are removed, and FIG. 144 illustrates a state in which the first jaw 1101, the second jaw 1102, the pulley 1111, the pulley 1121, and the like are removed. Meanwhile, FIG. 145 is a view mainly illustrating the wires, and FIG. 146 is a view mainly illustrating the pulleys.

Referring to FIGS. 140 to 162 and the like, the end tool 1100 of the fourth embodiment of the present disclosure includes a pair of jaws for performing a grip motion, that is, the first jaw 1101 and a second jaw 1102. Here, each of the first jaw 1101 and the second jaw 1102, or a component encompassing the first jaw 1101 and the second jaw 1102 may be referred to as the jaw 1103.

Further, the end tool 1100 may include the pulley 1111, a pulley 1113, a pulley 1114, a pulley 1115, and a pulley 1116 associated with a rotational motion of the first jaw 1101. In addition, the end tool 1100 may include the pulley 1121, a pulley 1123, a pulley 1124, a pulley 1125, and a pulley 1126, which are associated with a rotational motion of the second jaw 1102.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 1100 of the fourth embodiment of the present disclosure may include the end tool hub 1160 and the pitch hub 1150.

A first rotation shaft 1141 to be described later may be inserted through the end tool hub 1160, and the pulley 1111 and the pulley 1121 axially coupled to the first rotation shaft 1141 and at least some of the first jaw 1101 and the second jaw 1102 coupled to the pulley 1111 and the pulley 1121 may be accommodated inside the end tool hub 1160. Here, in an embodiment of the present disclosure, a wire guide portion 1168 serving as an auxiliary pulley is formed in the end tool hub 1160. That is, a first wire guide portion 1168*a* and a second wire guide portion 1168*b* for guiding paths of the wire 305 and the wire 302 may be formed in the end tool hub 1160. The wire guide portions 1168 of the end tool hub 1160 may serve as auxiliary pulleys (see 612 and 622 of FIG. 39) of the first embodiment and change the paths of the wires, and the first wire guide portion 1168*a* and the second wire guide portion 1168*b* of the end tool hub 1160 serving as auxiliary pulleys will be described in more detail later.

Meanwhile, the first pitch pulley portion 1163*a* and the second pitch pulley portion 1163*b*, which serve as end tool pitch pulleys, may be formed at one end portion of the end tool hub 1160. The wire 303 and the wire 304, which are pitch wires, are coupled to the first pitch pulley portion 1163*a* and the second pitch pulley portion 1163*b*, which serve as end tool pitch pulleys, and a pitch motion is performed while the end tool hub 1160 rotates around a third rotation shaft 1143.

The third rotation shaft 1143 and a fourth rotation shaft 1144 may be inserted through the pitch hub 1150, and the pitch hub 1150 may be axially coupled to the end tool hub 1160 by the third rotation shaft 1143. Accordingly, the end tool hub 1160 may be formed to be pitch-rotatable around the third rotation shaft 1143 with respect to the pitch hub 1150.

Further, the pitch hub 1150 may internally accommodate at least some of the pulley 1113, the pulley 1114, the pulley 1123, and the pulley 1124 that are axially coupled to the third rotation shaft 1143. Further, the pitch hub 1150 may internally accommodate at least some of the pulley 1115, the pulley 1116, the pulley 1125, and the pulley 1126 that are axially coupled to the fourth rotation shaft 1144.

One end portion of the pitch hub 1150 is connected to the end tool hub 1160, and the other end portion of the pitch hub 1150 is connected to the connection portion 400.

Here, the end tool 1100 of the fourth embodiment of the present disclosure may include the first rotation shaft 1141, the third rotation shaft 1143, and the fourth rotation shaft 1144. As described above, the first rotation shaft 1141 may be inserted through the end tool hub 1160, and the third rotation shaft 1143 and the fourth rotation shaft 1144 may be inserted through the pitch hub 1150.

The first rotation shaft 1141, the third rotation shaft 1143, and the fourth rotation shaft 1144 may be arranged sequentially from the distal end 1104 toward the proximal end 1105 of the end tool 1100. Accordingly, starting from the distal end 1104, the first rotation shaft 1141 may be referred to as a first pin, the third rotation shaft 1143 may be referred to as a third pin, and the fourth rotation shaft 1144 may be referred to as a fourth pin.

Here, the first rotation shaft 1141 may function as an end tool jaw pulley rotation shaft, the third rotation shaft 1143 may function as an end tool pitch rotation shaft, and the fourth rotation shaft 1144 may function as an end tool pitch auxiliary rotation shaft of the end tool 1100.

Here, each of the rotation shafts may include two shafts of a first sub-shaft and a second sub-shaft. Alternatively, it may be said that each of the rotation shafts is formed by being divided into two parts.

For example, the first rotation shaft 1141 may include two shafts of a first sub-shaft 1141*a* and a second sub-shaft 1141*b*. In addition, the third rotation shaft 1143 may include two shafts of a first sub-shaft 1143*a* and a second sub-shaft 1143*b*. The fourth rotation shaft 1144 may include two shafts of a first sub-shaft and a second sub-shaft.

Each of the rotation shafts is formed by being divided into two parts as described above to allow the guide tube 1170 to be described later to pass through the end tool hub 1160 and the pitch hub 1150. That is, the guide tube 1170 may pass between the first sub-shaft and the second sub-shaft of each of the rotation shafts. This will be described in more detail later. Here, the first sub-shaft and the second sub-shaft may be disposed on the same axis or may be disposed to be offset to a certain degree.

Meanwhile, it is illustrated in the drawings that each of the rotation shafts is formed by being divided into two parts, but the concept of the present disclosure is not limited thereto. That is, each of the rotation shafts is formed to be curved in the middle such that an escape path for the guide tube 1170 is formed.

Each of the rotation shafts 1141, 1143, and 1144 may be fitted into one or more pulleys, which will be described in detail below.

Meanwhile, the end tool 1100 may further include an actuation rotation shaft 1145. In detail, the first jaw 1101 and the second jaw 1102 may be axially coupled by the actuation rotation shaft 1145, and in this state, an actuation motion may be performed while the first jaw 1101 and the second jaw 1102 rotate around the actuation rotation shaft 1145. Here, the actuation rotation shaft 1145 may be disposed closer to the distal end 1104 than the first rotation shaft 1141 is.

Here, in the end tool 1100 of the fourth embodiment of the present disclosure, the first rotation shaft 1141, which is a yaw rotation shaft, and the actuation rotation shaft 1145 are provided separately rather than as the same shaft. That is, by forming the first rotation shaft 1141, which is a rotation shaft of the pulley 1111/pulley 1121 that are jaw pulleys and a rotation shaft of a yaw motion, and the actuation rotation shaft 1145, which is a rotation shaft of the second jaw 1102 with respect to the first jaw 1101 and a rotation shaft of an actuation motion, to be spaced apart from each other by a certain distance, a space in which the guide tube 1170 and the blade wire 307 accommodated therein can be gently bent may be secured. The actuation rotation shaft 1145 will be described in detail later.

The pulley 1111 functions as an end tool first jaw pulley, and the pulley 1121 functions as an end tool second jaw pulley. The pulley 1111 may also be referred to as a first jaw pulley, and the pulley 1121 may also be referred to as a second jaw pulley, and these two components may collectively be referred to as end tool jaw pulleys or simply jaw pulleys.

The pulley 1111 and the pulley 1121, which are end tool jaw pulleys, are formed to face each other, and are formed to be rotatable independently of each other around the first rotation shaft 1141 which is an end tool jaw pulley rotation shaft. In this case, the pulley 1111 and pulley 1121 are formed to be spaced apart by a certain distance, and a blade assembly accommodation portion may be accommodated therebetween. In addition, at least a part of a blade assembly to be described later may be disposed in the blade assembly accommodation portion. In other words, the blade assembly including the guide tube 1170 may be disposed between the pulley 1111 and the pulley 1121.

Here, since the pulley 1111 is connected to the first jaw 1101, when the pulley 1111 rotates around the first rotation shaft 1141, the first jaw 1101 may also rotate around the first rotation shaft 1141 together with the pulley 1111.

Meanwhile, since the pulley 1121 is connected to the second jaw 1102, when the pulley 1121 rotates around the first rotation shaft 1141, the second jaw 1102 connected to the pulley 1121 may rotate around the first rotation shaft 1141.

In addition, a yaw motion and an actuation motion of the end tool 1100 are performed in response to the rotation of the pulley 1111 and the pulley 1121. That is, when the pulley 1111 and the pulley 1121 rotate in the same direction around the first rotation shaft 1141, the yaw motion is performed as the first jaw 1101 and the second jaw 1102 rotate with the first rotation shaft 1141 as the center of rotation. Meanwhile, when the pulley 1111 and the pulley 1121 rotate in opposite directions around the first rotation shaft 1141, the actuation motion is performed as the first jaw 1101 and the second jaw 1102 rotate around the actuation rotation shaft 1145.

The pulley 1113 and the pulley 1114 function as end tool first jaw pitch main pulleys, and the pulley 1123 and the pulley 1124 function as end tool second jaw pitch main pulleys, and these two components may collectively be referred to as end tool jaw pitch main pulleys.

The pulley 1115 and the pulley 1116 function as end tool first jaw pitch sub-pulleys, and the pulley 1125 and the pulley 1126 function as end tool second jaw pitch sub-pulleys, and these two components collectively may be referred to as end tool jaw pitch sub-pulleys.

Hereinafter, components associated with the rotation of the pulley 1111 will be described.

The pulley 1113 and the pulley 1114 function as end tool first jaw pitch main pulleys. That is, the pulley 1113 and the pulley 1114 function as main rotation pulleys for a pitch motion of the first jaw 1101. Here, the wire 301, which is a first jaw wire, is wound around the pulley 1113, and the wire 305, which is a first jaw wire, is wound around the pulley 1114.

The pulley 1115 and the pulley 1116 function as end tool first jaw pitch sub-pulleys. That is, the pulley 1115 and the pulley 1116 function as sub-rotation pulleys for a pitch motion of the first jaw 1101. Here, the wire 301, which is a first jaw wire, is wound around the pulley 1115, and the wire 305, which is a first jaw wire, is wound around the pulley 1116.

Here, the pulley 1113 and the pulley 1114 are disposed on one side of the pulley 1111 to face each other. Here, the pulley 1113 and the pulley 1114 are formed to be rotatable independently of each other around the third rotation shaft 1143 that is an end tool pitch rotation shaft. In addition, the pulley 1115 and the pulley 1116 are disposed on one side of the pulley 1113 and one side of the pulley 1114, respectively, to face each other. Here, the pulley 1115 and the pulley 1116 are formed to be rotatable independently of each other around the fourth rotation shaft 1144 that is an end tool pitch auxiliary rotation shaft. Here, in the drawings, it is illustrated that the pulley 1113, the pulley 1115, the pulley 1114, and the pulley 1116 are all formed to be rotatable around a Y-axis direction, but the concept of the present disclosure is not limited thereto, and the rotation axes of the respective pulleys may be formed in various directions according to configurations thereof.

The wire 301, which is a first jaw wire, is sequentially wound to make contact with at least portions of the pulley 1115, the pulley 1113, and the pulley 1111. In addition, the wire 305 connected to the wire 301 by the fastening member 323 is sequentially wound to make contact with at least portions of the pulley 1111, the first wire guide portion 1168a of the end tool hub 1160, the pulley 1114, and the pulley 1116.

In other words, the wire 301 and the wire 305, which are the first jaw wire, are sequentially wound to make contact with at least portions of the pulley 1115, the pulley 1113, the pulley 1111, the first wire guide portion 1168a of the end tool hub 1160, the pulley 1114, and the pulley 1116, and the wire 301 and the wire 305 formed to move along the above pulleys while rotating the above pulleys.

Accordingly, when the wire 301 is pulled in the direction of an arrow 301 of FIG. 145, the fastening member 323 to which the wire 301 is coupled and the pulley 1111 coupled to the fastening member 323 are rotated in the counterclockwise direction. On the contrary, when the wire 305 is pulled in the direction of an arrow 305 of FIG. 145, the fastening member 323 to which the wire 305 is coupled and the pulley 1111 coupled to the fastening member 323 are rotated in the clockwise direction in the FIG. 145.

Next, components associated with the rotation of the pulley 1121 will be described.

The pulley 1123 and the pulley 1124 function as end tool second jaw pitch main pulleys. That is, the pulley 1123 and the pulley 1124 function as main rotation pulleys for a pitch motion of the second jaw 1102. Here, the wire 306, which is a second jaw wire, is wound around the pulley 1123, and the wire 302, which is a second jaw wire, is wound around the pulley 1124.

The pulley 1125 and the pulley 1126 function as end tool second jaw pitch sub-pulleys. That is, the pulley 1125 and the pulley 1126 function as sub-rotation pulleys for a pitch motion of the second jaw 1102. Here, the wire 306, which is a second jaw wire, is wound around the pulley 1125, and the wire 302, which is a second jaw wire, is wound around the pulley 1126.

Here, the pulley 1123 and the pulley 1124 are disposed on one side of the pulley 1121 to face each other. Here, the pulley 1123 and the pulley 1124 are formed to be rotatable independently of each other around the third rotation shaft 1143 that is an end tool pitch rotation shaft. In addition, the pulley 1125 and the pulley 1126 are disposed on one side of the pulley 1123 and one side of the pulley 1124, respectively, to face each other. Here, the pulley 1125 and the pulley 1126 are formed to be rotatable independently of each other around the fourth rotation shaft 1144 that is an end tool pitch auxiliary rotation shaft. Here, in the drawings, it is illustrated that all of the pulley 1123, the pulley 1125, the pulley 1124, and the pulley 1126 are formed to be rotatable around the Y-axis direction, but the concept of the present disclosure is not limited thereto, and the rotating axes of the respective pulleys may be formed in various directions according to configurations thereof.

The wire 306, which is a second jaw wire, is sequentially wound to make contact with at least portions of the pulley 1125, the pulley 1123, and the pulley 1121. In addition, the wire 302 connected to the wire 306 by the fastening member 326 is sequentially wound to make contact with at least portions of the pulley 1121, the second wire guide portion 1168b of the end tool hub 1160, the pulley 1124, and the pulley 1126.

In other words, the wire 306 and the wire 302, which are the second jaw wire, are sequentially wound to make contact with at least portions of the pulley 1125, the pulley 1123, the pulley 1121, the second wire guide portion 1168b of the end tool hub 1160, the pulley 1124, and the pulley 1126, and the wire 306 and the wire 302 are formed to move along the above pulleys while rotating the above pulleys.

Accordingly, when the wire 306 is pulled in the direction of an arrow 306 of FIG. 145, the fastening member 326 to which the wire 306 is coupled and the pulley 1121 coupled to the fastening member 326 are rotated in the clockwise direction in FIG. 145. On the contrary, when the wire 302 is pulled toward the arrow 302 of FIG. 145, the fastening member 326 coupled to the wire 302 and the pulley 1121 coupled to the fastening member 326 may rotate in the counterclockwise direction in FIG. 145.

Hereinafter, a pitch motion of the present disclosure will be described in more detail.

Meanwhile, when the wire 301 is pulled in the direction of the arrow 301 of FIG. 145, and simultaneously, the wire 305 is pulled in the direction of the arrow 305 of FIG. 145 (that is, when both strands of the first jaw wire are pulled), as shown in FIG. 144, since the wires 301 and 305 are wound around lower portions of the pulley 1113 and the pulley 1114 rotatable around the third rotation shaft 1143, which is an end tool pitch rotation shaft, the pulley 1111 to which the wires 301 and 305 are fixedly coupled and the end tool hub 1160 to which the pulley 1111 is coupled rotate as a whole in the counterclockwise direction around the third rotation shaft 1143, and as a result, the end tool 1100 may rotate downward to perform the pitch motion. At this time, since the second jaw 1102 and the wires 302 and 306 fixedly coupled thereto are wound around upper portions of the pulley 1123 and the pulley 1124 rotatable around the third rotation shaft 1143, the wires 302 and 306 are released in the opposite directions of the arrows 302 and 306, respectively.

On the contrary, when the wire 302 is pulled in the direction of the arrow 302 of FIG. 145, and simultaneously, the wire 306 is pulled in the direction of the arrow 306 of FIG. 145, as shown in FIG. 144, since the wires 302 and 306 are wound around the upper portions of the pulley 1123 and the pulley 1124 rotatable around the third rotation shaft 1143, which is an end tool pitch rotation shaft, the pulley 1121 to which the wires 302 and 306 are fixedly coupled and the end tool hub 1160 to which the pulley 1121 is coupled rotate as a whole in the clockwise direction around the third rotation shaft 1143, and as a result, the end tool 1100 may rotate upward to perform the pitch motion. At this time, since the first jaw 1101 and the wires 301 and 305 fixedly coupled thereto are wound around lower portions of the pulley 1113 and the pulley 1114 rotatable around the third rotation shaft 1143, the wires 302 and 306 are moved in the opposite directions of the arrows 301 and 305, respectively.

Meanwhile, the end tool hub 1160 of the end tool 1100 of the electric cauterization surgical instrument 10 of the present disclosure may further include the first pitch pulley portion 1163a and the second pitch pulley portion 1163b serving as end tool pitch pulleys, the manipulation portion 200 may further include the pulley 231 and a pulley 232, which are manipulation portion pitch pulleys, and the power transmission portion 300 may further include the wire 303 and the wire 304 which are pitch wires.

In detail, the end tool hub 1160 including the first pitch pulley portion 1163a and the second pitch pulley portion 1163b may be formed to be rotatable around the third rotation shaft 1143 that is an end tool pitch rotation shaft. In addition, the wires 303 and 304 may serve to connect the first and second pitch pulley portions 1163a and 1163b of the end tool 1100 and the pulleys 231 and 232 of the manipulation portion 200.

Thus, when the pulleys 231 and 232 of the manipulation portion 200 rotate, the rotation of the pulleys 231 and 232 is transmitted to the end tool hub 1160 of the end tool 1100 through the wires 303 and 304, causing the end tool hub 1160 to rotate as well, and as a result, the end tool 1100 performs a pitch motion while rotating.

That is, the electric cauterization surgical instrument 10 according to the fourth embodiment of the present disclosure includes the first and second pitch pulley portions 1163a and 1163b of the end tool 1100, the pulleys 231 and 232 of the manipulation portion 200, and the wires 303 and 304 of the power transmission portion 300 in order to transmit driving force for a pitch motion, and thus, the driving force for the pitch motion of the manipulation portion 200 is more completely transmitted to the end tool 1100, thereby improving operation reliability.

(Blade Wire and Guide Tube)

Hereinafter, the blade wire 307 and the guide tube 1170 of the present disclosure will be described in more detail.

The guide tube 1170 according to the present disclosure is formed to surround the blade wire 307 in a certain section, and at this time, the blade wire 307 is movable inside the guide tube 1170. In other words, in a state in which in which the blade wire 307 is inserted into the guide tube 1170, the blade wire 307 is movable relative to the guide tube 1170.

Here, the guide tube 1170 serves to guide the path of the blade wire 307 by preventing the blade wire 307 from being curved in an unintended direction when the blade wire 307 is pushed or pulled. A cutting motion may be smoothly performed by the guide tube 1170.

Meanwhile, one end portion of the guide tube 1170 may be fixedly coupled to an actuation hub 1190 to be described later. Here, the actuation hub 1190 may serve as a first coupling portion. In addition, the other end portion of the guide tube 1170 may be fixedly coupled to a second coupling portion (not shown) in the connection portion 400. Since both end portions of the guide tube 1170 are fixedly coupled to certain points (the first coupling portion and the second coupling portion) as described above, respectively, the entire length of the guide tube 1170 may remain constant. Accordingly, the length of the blade wire 307 inserted into the guide tube 1170 may also remain constant.

Meanwhile, the guide tube 1170 according to the present disclosure may be formed of a flexible material and formed to be bendable. Accordingly, when the end tool 1100 performs a yaw motion around the first rotation shaft 1141 or a pitch motion around the third rotation shaft 1143, the guide tube 1170 may be bent while being deformed in shape corresponding thereto. In addition, when the guide tube 1170 is bent, the blade wire 307 placed thereinside is also bent.

Here, although the length of the guide tube 1170 is constant, the relative position and distance of the first coupling portion (i.e., the actuation hub 1190) and the second coupling portion (not shown) may be changed as the end tool 1100 is pitch-rotated or yaw-rotated, and thus a space for the guide tube 1170 to move by the changed distance is required. To this end, a pitch slit 1164 and a yaw slit 1165 may be provided in the end tool hub 1160 to form spaces for movement of the guide tube 1170. Such a configuration of the end tool hub 1160 will be described in detail later.

Meanwhile, as described above, the blade wire 307 is inserted through the guide tube 1170, and the blade wire 307 is relatively movable inside the guide tube 1170 with respect to the guide tube 1170. That is, when the blade wire 307 is pulled in a state in which the guide tube 1170 is fixed, the blade 1175 connected to the blade wire 307 is moved toward the proximal end 1105, and when the blade wire 307 is pushed, the blade 1175 connected to the blade wire 307 is moved toward the distal end 1104.

This will be described below in more detail.

The most reliable way to perform a cutting motion using the blade 1175 is by pushing and pulling the blade 1175 with the blade wire 307. In addition, in order for the blade wire 307 to push and pull the blade 1175, the guide tube 1170 that can guide the path of the blade wire 307 should be provided. When the guide tube 1170 does not guide the path of the blade wire 307 (i.e., does not hold the blade wire 307), a phenomenon may occur in which cutting is not performed and a middle portion of the blade wire 307 is curved even when the blade wire 307 is pushed. Accordingly, in order to reliably perform the cutting motion using the blade 1175, the blade wire 307 and the guide tube 1170 should be essentially included.

However, when the blade wire 307 is used to drive a cutting motion, the cutting should be performed while pushing the blade wire 307, and in this case, in order for the blade wire 307 to receive a force, a relatively stiff (i.e., non-bendable) wire should be used for the blade wire 307. However, the stiff (i.e., non-bendable) wire may have a small bendable range and may be permanently deformed when a force equal to or greater than a certain degree is applied.

In other words, in the case of a stiff (i.e., non-bendable) wire, there is a minimum radius of curvature that may be bent and spread without permanent deformation. In other words, when the wire or the guide tube is curved below a specific radius of curvature, both the wire and the guide tube may undergo permanent deformation while being bent, thereby restricting the capacity to perform cutting while moving backward and forward. Thus, it is necessary to keep the blade wire 307 curved while having a gentle curvature.

Thus, in order to prevent the blade wire 307 from being rapidly bent while passing through the pulleys, a space, in which the blade wire 307 can be gently bent, is required between the jaw 1103 (i.e., the actuation rotation shaft 1145) and the end tool hub 1160 (i.e., the first rotation shaft 1141 that is a yaw shaft).

To this end, according to the present disclosure, the first rotation shaft 1141, which is a yaw rotation shaft, and the actuation rotation shaft 1145 are separately provided, and the first rotation shaft 1141 and the actuation rotation shaft 1145 are spaced apart from each other by a certain distance, thereby forming a space in which the blade wire 307 and the guide tube 1170 can be gently bent.

As described above, since the blade wire 307 and the guide tube 1170 need to be connected to the blade 1175 through the end tool hub 1160, and a space in which the blade wire 307 and the guide tube 1170 can be bent in the end tool hub 1160 is necessary, in the present disclosure, 1) spaces, through which the blade wire 307/the guide tube 1170 can pass and simultaneously are bendable, that is, the pitch slit 1164 and the yaw slit 1165, are formed in the end tool hub 1160, 2) each of the rotation shafts is formed by being divided into two parts, and 3) a pitch round portion 1166 and a yaw round portion 1167 are additionally formed to guide the bending of the blade wire 307 and the guide tube 1170.

In other words, when one end portion of the guide tube 1170 is fixed in the connection portion 400, and the other end portion thereof is moved while performing pitch and yaw motions, the guide tube 1170 is curved in a direction, in which the gentlest curvature (hereinafter, referred to as "maximum gentle curvature") can be achieved in response to a change in a distance between both end portions thereof. As such, by achieving the maximum gentle curvature of the natural state, the motion of the blade wire 307 is smooth and the permanent deformation does not occur.

Thus, in order to secure the maximum gentle curvature, the pitch slit 1164 and the yaw slit 1165 are formed on the path of the guide tube 1170, and furthermore, the pitch round portion 1166 and the yaw round portion 1167 may be additionally formed in the end tool hub 1160. Accordingly, the guide tube 1170 may have such a shape that is the most similar to the maximum gentle curvature (although not having the maximum gentle curvature).

Hereinafter, the end tool hub 1160 will be described in more detail.

(End Tool Hub)

FIG. 147 is a perspective view illustrating the end tool hub of the surgical instrument for electrocautery of FIG. 140. FIGS. 148 and 149 are cut-away perspective views of the end tool hub of FIG. 147. FIGS. 150 and 151 are perspective views illustrating the end tool hub of FIG. 147. FIG. 152 is a side view illustrating the end tool hub of FIG. 147 and the guide tube. FIG. 153 is a plan view illustrating the end tool hub of FIG. 147 and the guide tube.

Referring to FIGS. 147 to 153, the end tool hub 1160 includes a body portion 1161, a first jaw pulley coupling portion 1162a, a second jaw pulley coupling portion 1162b, the first pitch pulley portion 1163a, the second pitch pulley portion 1163b, the pitch slit 1164, the yaw slit 1165, the pitch round portion 1166, the yaw round portion 1167, and the wire guide portion 1168. In addition, the wire guide portion 1168 includes the first wire guide portion 1168a and the second wire guide portion 1168b.

The first jaw pulley coupling portion 1162a and the second jaw pulley coupling portion 1162b may be formed in the end tool hub 1160 at the distal end side. Here, the first jaw pulley coupling portion 1162a and the second jaw pulley coupling portion 1162b are formed to face each other, and the pulley 1111 and the pulley 1121 are accommodated therein. Here, the first jaw pulley coupling portion 1162a and the second jaw pulley coupling portion 1162b may be formed to be approximately parallel to a plane perpendicular to the first rotation shaft 1141 that is a yaw rotation shaft.

The first jaw pulley coupling portion 1162a and the second jaw pulley coupling portion 1162b are connected by the body portion 1161. That is, the first jaw pulley coupling portion 1162a and the second jaw pulley coupling portion 1162b, which are parallel to each other, are coupled by the body portion 1161 formed in a direction approximately perpendicular to the first jaw pulley coupling portion 1162a and the second jaw pulley coupling portion 1162b, so that the first jaw pulley coupling portion 1162a, the second jaw pulley coupling portion 1162b, and the body portion 1161 form an approximately U-shape, in which the pulley 1111 and the pulley 1121 are accommodated.

In other words, it may be said that the first jaw pulley coupling portion 1162a and the second jaw pulley coupling portion 1162b are formed to extend in the X-axis direction from the body portion 1161.

Here, the pulley 1111, which is a first jaw pulley, is disposed close to the first jaw pulley coupling portion 1162a of the end tool hub 1160, and the pulley 1121, which is a second jaw pulley, is disposed close to the second jaw pulley coupling portion 1162b of the end tool hub 1160, and thus the yaw slit 1165 may be formed between the first jaw pulley coupling portion 1162a and the second jaw pulley coupling portion 1162b. In addition, at least a part of the blade assembly to be described later may be disposed in the yaw slit 1165. In other words, it may be said that at least a part of the guide tube 1170 of the blade assembly may be disposed between the first jaw pulley coupling portion 1162a and the second jaw pulley coupling portion 1162b. As such, by disposing the blade assembly including the guide tube 1170 between the pulley 1111, which is a first jaw pulley, and the pulley 1121, which is a second jaw pulley, the end tool 1100 is able to perform the cutting motion using the blade 1175 in addition to the pitch and yaw motions. This will be described in more detail later.

Meanwhile, a through hole is formed in the first jaw pulley coupling portion 1162a such that the first rotation shaft 1141 passes through the first jaw pulley coupling portion 1162a and the pulley 1111 and axially couples the first jaw pulley coupling portion 1162a and the pulley 1111. In addition, a through hole is formed in the second jaw pulley coupling portion 1162b such that the first rotation shaft 1141 passes through the second jaw pulley coupling portion 1162b and the pulley 1121 and axially couples the second jaw pulley coupling portion 1162b and the pulley 1121.

Here, as described above, the first rotation shaft 1141, which is a yaw rotation shaft, may be formed by being divided into two parts of the first sub-shaft 1141a and the second sub-shaft 1141b, and the guide tube 1170 may pass between the first sub-shaft 1141a and the second sub-shaft 1141b of the first rotation shaft 1141.

In addition, the yaw slit 1165 may be formed between the first jaw pulley coupling portion 1162a and the second jaw pulley coupling portion 1162b. Since the yaw slit 1165 is formed in the end tool hub 1160 as described above, the guide tube 1170 may pass through the inside of the end tool hub 1160.

In other words, the first rotation shaft 1141 is vertically separated into two parts without passing through the end tool hub 1160, and the yaw slit 1165 may be formed on a plane perpendicular to the first rotation shaft 1141 in the vicinity of the first rotation shaft 1141. Accordingly, the guide tube 1170 is movable (i.e., movable left and right) in the yaw slit 1165 while passing through the vicinity of the first rotation shaft 1141.

Meanwhile, the yaw round portion 1167 may be further formed in the body portion 1161. The yaw round portion 1167 may be formed to be rounded so as to have a predetermined curvature. In detail, when viewed from a plane perpendicular to the first rotation shaft 1141 that is a yaw rotation shaft, the yaw round portion 1167 may be formed to be rounded so as to have a predetermined curvature. For example, the yaw round portion 1167 may be formed in a fan shape, and may be formed along a path in which the guide tube 1170 is bent on an XY plane. The yaw round portion 1167 as described above may serve to guide the path of the guide tube 1170 when the end tool 1100 yaw-rotates.

The wire guide portion 1168, which guides a path of the wire passing through the inside of the end tool hub 1160, is formed at one side of the body portion 1161. Here, the wire guide portion 1168 includes the first wire guide portion 1168a and the second wire guide portion 1168b. Here, the first wire guide portion 1168a may be formed on an inner side surface of the first jaw pulley coupling portion 1162a. In addition, the second wire guide portion 1168b may be formed on an inner side surface of the second jaw pulley coupling portion 1162b.

Here, the wire guide portion 1168 may be formed in a cylindrical shape with a cross section that is approximately semi-circular. In addition, the semi-circular portion may be disposed to protrude toward the pulley 1111 and the pulley 1121. In other words, it may be said that the wire guide portion 1168 is formed to protrude toward a space formed by the first jaw pulley coupling portion 1162a, the second jaw pulley coupling portion 1162b, and the body portion 1161. In other words, it may be said that, in the wire guide portion 1168, a region adjacent to the first jaw pulley coupling portion 1162a and the second jaw pulley coupling portion 1162b is formed to have a cross section that is curved with a predetermined curvature.

Alternatively, in other words, it may be also said that the wire guide portion 1168 functions as a kind of pulley member, which guides the paths of the wire 305 and the wire 302 by winding the wire 305 and the wire 302 around an outer circumferential surface thereof. However, here, the wire guide portion 1168 is not a member that rotates around a certain shaft as the original meaning pulley does, and it may be said that the wire guide portion 1168 is formed to be fixed as a portion of the end tool hub 1160 and performs some similar functions of a pulley by winding a wire therearound.

Here, the wire guide portion 1168 is illustrated in the drawing as being formed in a cylindrical shape with a cross section that is approximately semi-circular. That is, at least a part of the cross section of the wire guide portion 1168 on the XY plane is illustrated as having a certain arc shape. However, the concept of the present disclosure is not limited thereto, and the cross section may have a predetermined curvature like an oval or a parabola, or a corner of a polygonal column is rounded to a certain degree, so that the cross section may have various shapes and sizes suitable for guiding the paths of the wire 305 and the wire 302.

Here, a guide groove for guiding the paths of the wire 305 and the wire 302 well may be further formed in a portion of the wire guide portion 1168, which is in contact with the wire 305 and the wire 302. The guide groove may be formed in the form of a groove recessed to a certain degree from a protruding surface of the wire guide portion 1168.

Here, although the guide groove is illustrated in the drawing as being formed in the entire arc surface of the wire guide portion 1168, the concept of the present disclosure is not limited thereto, and the guide groove may be formed only in a portion of the arc surface of the wire guide portion 1168 as necessary.

As described above, by further forming the guide groove in the wire guide portion 1168, unnecessary friction between the wires is reduced, so that durability of the wires may be improved.

The first pitch pulley portion 1163*a* and the second pitch pulley portion 1163*b*, which serve as end tool pitch pulleys, may be formed on the end tool hub 1160 at the proximal end side. Here, the first pitch pulley portion 1163*a* and the second pitch pulley portion 1163*b* may be formed to face each other. Here, the first pitch pulley portion 1163*a* and the second pitch pulley portion 1163*b* may be formed to be approximately parallel to a plane perpendicular to the third rotation shaft 1143, which is a pitch rotation shaft.

In detail, one end portion of the end tool hub 1160 is formed in a disk shape similar to a pulley, and grooves around which a wire may be wound may be formed on an outer circumferential surface of the one end portion, thereby forming the first pitch pulley portion 1163*a* and the second pitch pulley portion 1163*b* The wire 303 and the wire 304 described above are coupled to the first pitch pulley portion 1163*a* and the second pitch pulley portion 1163*b*, which serve as end tool pitch pulleys, and a pitch motion is performed while the end tool hub 1160 rotates around the third rotation shaft 1143.

Meanwhile, although not shown in the drawings, the pitch pulley may be formed as a separate member from the end tool hub 1160 and coupled to the end tool hub 1160.

The first pitch pulley portion 1163*a* and the second pitch pulley portion 1163*b* may be connected by the body portion 1161. That is, the first pitch pulley portion 1163*a* and the second pitch pulley portion 1163*b*, which are parallel to each other, are coupled by the body portion 1161 formed in a direction approximately perpendicular to the first pitch pulley portion 1163*a* and the second pitch pulley portion 1163*b*, and thus the first pitch pulley portion 1163*a*, the second pitch pulley portion 1163*b*, and the body portion 1161 may form an approximately U-shape.

In other words, it may be said that the first pitch pulley portion 1163*a* and the second pitch pulley portion 1163*b* are formed to extend from the body portion 1161 in the X-axis direction.

Meanwhile, a through hole is formed in the first pitch pulley portion 1163*a* so that the third rotation shaft 1143 may pass through the first pitch pulley portion 1163*a*. In addition, a through hole is formed in the second pitch pulley portion 1163*b* so that the third rotation shaft 1143 may pass through the second pitch pulley portion 1163*b*.

In this case, as described above, the third rotation shaft 1143, which is a pitch rotation shaft, may be formed by being divided into two parts of the first sub-shaft 1143*a* and the second sub-shaft 1143*b*, and the guide tube 1170 may pass between the first sub-shaft 1143*a* and the second sub-shaft 1143*b* of the third rotation shaft 1143.

The pitch slit 1164 may be formed between the first pitch pulley portion 1163*a* and the second pitch pulley portion 1163*b*. Since the pitch slit 1164 is formed in the end tool hub 1160 as described above, the guide tube 1170 may pass through the inside of the end tool hub 1160.

In other words, the third rotation shaft 1143 is horizontally separated into two parts without passing through the end tool hub 1160, and the pitch slit 1164 may be formed on a plane perpendicular to the third rotation shaft 1143 in the vicinity of the third rotation shaft 1143. Accordingly, the guide tube 1170 is movable (movable up and down) in the pitch slit 1164 while passing through the vicinity of the third rotation shaft 1143.

Meanwhile, the pitch round portion 1166 may be further formed in the body portion 1161. The pitch round portion 1166 may be formed to be rounded to have a predetermined curvature. In detail, when viewed from a plane perpendicular to the third rotation shaft 1143, which is a pitch rotation shaft, the pitch round portion 1166 may be formed to be rounded to have a predetermined curvature. For example, the pitch round portion 1166 may be formed in a fan shape, and formed along a path in which the guide tube 1170 is bent on the XZ plane. The pitch round portion 1166 as described above may serve to guide the path of the guide tube 1170 when the end tool 1100 pitch-rotates.

Here, the pitch slit 1164 and the yaw slit 1165 may be formed to be connected to each other. Accordingly, the guide tube 1170 and the blade wire 307 located therein may be disposed to completely pass through the inside of the end tool hub 1160. In addition, the blade 1175 coupled to one end portion of the blade wire 307 may linearly reciprocate inside the first jaw 1101 and the second jaw 1102.

As described above, since the blade wire 307 and the guide tube 1170 need to be connected to the blade 1175 through the end tool hub 1160, and a space in which the blade wire 307 and the guide tube 1170 can be bent in the end tool hub 1160 is necessary, in the present disclosure, 1) spaces, through which the blade wire 307/the guide tube 1170 can pass and simultaneously are bendable, that is, the pitch slit 1164 and the yaw slit 1165, are formed in the end tool hub 1160, 2) the rotation shafts are formed by being divided into two parts, and 3) the pitch round portion 1166 and the yaw round portion 1167 are additionally formed to guide the bending of the blade wire 307/the guide tube 1170.

Hereinafter, the role and function of the wire guide portion 1168 will be described in more detail.

The wire guide portion 1168 may be in contact with the wire 305 and the wire 302 and may change the arrangement path of the wire 305 and the wire 302 to a certain degree to serve to increase a rotation radius of each of the first jaw 1101 and the second jaw 1102.

That is, when the auxiliary pulleys are not disposed, each of the pulley 1111, which is a first jaw pulley, and the pulley 1121, which is a second jaw pulley, may rotate up to a right angle, but in the fourth embodiment of the present disclosure, by additionally providing the wire guide portion 1168 in the end tool hub 1160, the maximum rotation angle of each pulley may be increased.

This enables a motion in which two jaws of the end tool 1100 have to be spread apart for an actuation motion in a state in which the two jaws are yaw-rotated together by 90°.

In other words, the range of yaw rotation in which an actuation motion is possible may be increased through the configuration of the wire guide portion 1168 of the end tool hub 1160. In other words, the range of yaw rotation in which an actuation motion is possible may be increased through the configuration of the wire guide portion 1168 of the end tool hub 1160.

Furthermore, by forming the wire guide portion 1168 in the end tool hub 1160, which already exists, without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also, the length of the end tool is shortened by as much as the size of the auxiliary pulley, so that the length of the end tool is shortened during a pitch motion. Accordingly, a surgical motion may be more easily performed in a narrow space.

This will be described below in more detail.

In the end tool 1100 of the surgical instrument according to the fourth embodiment of the present disclosure, the arrangement path of the wires may be changed without a separate structure by forming the wire guide portion 1168 capable of changing the path of the wire on an inner side wall of the end tool hub 1160. As described above, as the arrangement path of the wire 305 and the wire 302 is changed to a certain degree by forming the wire guide portion 1168 in the end tool hub 1160, a tangential direction of the wire 305 and the wire 302 is changed, and accordingly, rotation angles of the fastening member 323 and the fastening member 326 that couple respective wires and pulleys may be increased.

That is, the fastening member 326 that couples the wire 302 and the pulley 1121 is rotatable until being located on a common internal tangent of the pulley 1121 and the wire guide portion 1168. Similarly, the fastening member (see 323 of FIG. 6) that couples the wire 305 and the pulley 1111 is rotatable until being located on a common internal tangent of the pulley 1111 and the wire guide portion 1168, so that a rotation angle of the fastening member (see 323 of FIG. 6) may be increased.

In other words, the wire 301 and the wire 305 wound around the pulley 1111 by the wire guide portion 1168 are disposed on one side with respect to a plane perpendicular to the Y-axis and passing through the X-axis. Simultaneously, the wire 302 and the wire 306 wound around the pulley 1121 by the wire guide portion 1168 are disposed on the other side with respect to the plane perpendicular to the Y-axis and passing through the X-axis.

In other words, the pulley 1113 and the pulley 1114 are disposed at one side with respect to the plane perpendicular to the Y-axis and passing through the X-axis, and the pulley 1123 and the pulley 1124 are disposed at the other side with respect to the plane perpendicular to the Y-axis and passing through the X-axis.

In other words, the wire 305 is located on the internal tangent of the pulley 1111 and the wire guide portion 1168, and a rotation angle of the pulley 1111 is increased due to the wire guide portion 1168. In addition, the wire 302 is located on the internal tangent of the pulley 1121 and the wire guide portion 1168, and the rotation angle of the pulley 1121 is increased due to the wire guide portion 1168.

In the present embodiment in which an auxiliary pulley is not formed and the wire guide portion 1168 capable of changing the path of a wire is formed on the inner side wall of the end tool hub 1160, the length of the end tool of the surgical instrument may be shortened as compared to the surgical instrument of the first embodiment in which a separate auxiliary pulley is formed. Since the length of the end tool is shortened as described above, a surgical operator may easily manipulate a surgical instrument, and a side effect of surgery may be reduced when the surgery is performed in a narrow surgical space in the human body.

According to the present disclosure as described above, the rotation radii of the pulley 1111, which is a first jaw pulley, and the pulley 1121, which is a second jaw pulley, increase, so that a yaw motion range in which a normal opening/closing actuation motion and a normal cutting motion can be performed may be increased.

(Actuation Hub)

FIGS. 154A and 154B are a perspective view and a cut-away perspective view illustrating an actuation hub of the surgical instrument for electrocautery of FIG. 147 of FIG. 140. FIG. 155 is a view illustrating a state in which the guide tube, the blade wire, and the blade are mounted on the actuation hub illustrated in the cut-away perspective view of FIG. 154. FIG. 156 is an exploded perspective view illustrating the end tool of the surgical instrument for electrocautery of FIG. 140.

Referring to FIGS. 154 to 156, the actuation hub 1190 may be formed in the form of a box having a hollow therein. In addition, the actuation hub 1190 is coupled to each of the first jaw 1101 and the second jaw 1102. In detail, the actuation hub 1190 is axially coupled to the first jaw 1101 by a first actuation rotation shaft 1145*a*. In addition, the actuation hub 1190 is axially coupled to the second jaw 1102 by a second actuation rotation shaft 1145*b*. In this case, the first actuation rotation shaft 1145*a* and the second actuation rotation shaft 1145*b* may be disposed on the same line in a Z-axis direction.

In addition, a tube seating portion 1190*a* may be formed inside the actuation hub 1190, and one end portion of the guide tube 1170 may be fixedly coupled to the tube seating portion 1190*a*.

Meanwhile, a blade accommodation portion 1190*b* may be formed inside the actuation hub 1190, and the blade 1175 may be accommodated in the blade accommodation portion 1190*b*.

In addition, a wire through-hole 1190*c* may be formed between the tube seating portion 1190*a* and the blade accommodation portion 1190*b* inside the actuation hub 1190.

That is, the tube seating portion 1190*a*, the wire through-hole 1190*c*, and the blade accommodation portion 1190*b* are sequentially formed inside the actuation hub 1190, and the blade wire 307 may pass through the inside of the actuation hub 1190 to be connected to the blade 1175.

As described above, by providing the actuation hub 1190 to which the guide tube 1170 is coupled between the first jaw 1101 and the second jaw 1102, the guide tube 1170 may not be curved, or the angle at which the guide tube 1170 is curved may be reduced, even when the first jaw 1101 or the second jaw 1102 rotates around the first rotation shaft 1141 or the actuation rotation shaft 1145.

In detail, in a case in which the guide tube 1170 is directly coupled to the first jaw 1101 or the second jaw 1102, when the first jaw 1101 or the second jaw 1102 rotates, one end portion of the guide tube 1170 also rotates together with the first jaw 1101 or the second jaw 1102, causing the guide tube 1170 to be curved.

On the other hand, in a case in which the guide tube 1170 is coupled to the actuation hub 1190, which is independent of the rotation of the jaw 1103, as in the present embodiment, even when the first jaw 1101 or the second jaw 1102 rotates, the guide tube 1170 may not be curved, or the angle at which the guide tube 1170 is curved may be reduced even when the guide tube 1170 is curved.

That is, by changing the direct connection between the guide tube 1170 and the jaw 1103 by the actuation hub 1190 to an indirect connection, the degree to which the guide tube 1170 is curved by the rotation of the jaw 1103 may be reduced.

(First and Second Jaws and Actuation Motion)

Hereinafter, a coupling structure of the first jaw 1101 and the second jaw 1102 of the end tool 1100 of the surgical instrument 10 of FIG. 140 will be described in more detail.

Referring to FIGS. 157 to 162 and the like, the first jaw 1101 includes a movable coupling hole 1101c, a jaw pulley coupling hole 1101d, and a shaft pass-through portion 1101c.

The first jaw 1101 is formed entirely in an elongated bar shape, and formed to be rotatable together with the pulley 1111 by being coupled to the pulley 1111 at one end portion thereof.

Meanwhile, the movable coupling hole 1101c, the jaw pulley coupling hole 1101d, and the shaft pass-through portion 1101e may be formed in the first jaw 1101 at a side coupled to the pulley 1111, that is, at the proximal end side.

Here, the movable coupling hole 1101c may be formed to have a predetermined curvature, and may be formed in an approximately elliptical shape. A shaft coupling portion 1111a of the pulley 1111, which will be described later, may be fitted into the movable coupling hole 1101c. Here, a short radius of the movable coupling hole 1101c may be formed to be substantially the same as or slightly greater than a radius of the shaft coupling portion 1111a. Meanwhile, a long radius of the movable coupling hole 1101c may be formed to be greater than the radius of the shaft coupling portion 1111a. Thus, in a state in which the shaft coupling portion 1111a of the pulley 1111 is fitted into the movable coupling hole 1101c of the first jaw 1101, the shaft coupling portion 1111a is movable to a certain degree in the movable coupling hole 1101c. This will be described in more detail below.

Meanwhile, the jaw pulley coupling hole 1101d is formed in the form of a cylindrical hole, and a jaw coupling portion 1111b of the pulley 1111, which will be described later, may be fitted into the jaw pulley coupling hole 1101d. Here, a radius of the jaw pulley coupling hole 1101d may be formed to be substantially the same as or slightly greater than a radius of the jaw coupling portion 1111b. Thus, the jaw coupling portion 1111b of the pulley 1111 may be formed to be rotatably coupled to the jaw pulley coupling hole 1101d of the first jaw 1101. This will be described in more detail below.

Meanwhile, the shaft pass-through portion 1101e may be formed in the first jaw 1101 at the distal end side relative to the movable coupling hole 1101c and the jaw pulley coupling hole 1101d. The shaft pass-through portion 1101e may be formed in the form of a hole, and the actuation rotation shaft 1145, which is a jaw rotation shaft, may be inserted through the shaft pass-through portion 1101c.

The second jaw 1102 includes a movable coupling hole 1102c, a jaw pulley coupling hole 1102d, and a shaft pass-through portion 1102c.

The second jaw 1102 is formed entirely in an elongated bar shape, and formed to be rotatable together with the pulley 1121 by being coupled to the pulley 1121 at one end portion thereof.

Meanwhile, the movable coupling hole 1102c, the jaw pulley coupling hole 1102d, and the shaft pass-through portion 1102e may be formed in the second jaw 1102 at a side coupled to the pulley 1111, that is, at the proximal end side.

Here, the movable coupling hole 1102c may be formed to have a predetermined curvature, and may be formed in an approximately elliptical shape. A shaft coupling portion 1121a of the pulley 1121, which will be described later, may be fitted into the movable coupling hole 1102c. Here, a short radius of the movable coupling hole 1102c may be formed to be substantially the same as or slightly greater than a radius of the shaft coupling portion 1121a. Meanwhile, a long radius of the movable coupling hole 1102c may be formed to be greater than the radius of the shaft coupling portion 1121a. Thus, in a state in which the shaft coupling portion 1121a of the pulley 1121 is fitted into the movable coupling hole 1102c of the second jaw 1102, the shaft coupling portion 1121a is movable to a certain degree in the movable coupling hole 1102c. This will be described in more detail below.

Meanwhile, the jaw pulley coupling hole 1102d is formed in the form of a cylindrical hole, and a jaw coupling portion 1121b of the pulley 1121, which will be described later, may be fitted into the jaw pulley coupling hole 1102d. Here, a radius of the jaw pulley coupling hole 1102d may be formed to be substantially the same as or slightly greater than a radius of the jaw coupling portion 1121b. Thus, the jaw coupling portion 1121b of the pulley 1121 may be formed to be rotatably coupled to the jaw pulley coupling hole 1102d of the second jaw 1102. This will be described in more detail below.

Meanwhile, the shaft pass-through portion 1102e may be formed in the second jaw 1102 at the distal end side relative to the movable coupling hole 1102c and the jaw pulley coupling hole 1102d. The shaft pass-through portion 1102e may be formed in the form of a hole, and the actuation rotation shaft 1145, which is a jaw rotation shaft, may be inserted through the shaft pass-through portion 1102c.

The pulley 1111, which is a first jaw pulley, may include the shaft coupling portion 1111a and the jaw coupling portion 1111b. The pulley 1111 is formed entirely in the form of a rotatable disk, and the shaft coupling portion 1111a and the jaw coupling portion 1111b may be formed to protrude to a certain degree from one surface of the pulley 1111. As described above, the shaft coupling portion 1111a of the pulley 1111 may be fitted into the movable coupling hole 1101c of the first jaw 1101, and the jaw coupling portion 1111b of the pulley 1111 may be fitted into the jaw pulley coupling hole 1101d of the first jaw 1101. The pulley 1111 may be formed to be rotatable with the first rotation shaft 1141, which is an end tool jaw pulley rotation shaft, as the center of rotation.

Meanwhile, the pulley 1121, which is a second jaw pulley, may include the shaft coupling portion 1121a and the jaw coupling portion 1121b. The pulley 1121 is formed entirely in the form of a rotatable disk, and the shaft coupling portion 1121a and the jaw coupling portion 1121b may be formed to protrude to a certain degree from one surface of the pulley 1121. As described above, the shaft coupling portion 1112a of the pulley 1112 may be inserted into the movable coupling hole 1102c of the second jaw 1102, and the jaw coupling portion 1112b of the pulley 1112 may be inserted into the jaw pulley coupling hole 1102d of the second jaw 1102. The pulley 1121 may be formed to be rotatable with the first rotation shaft 1141, which is an end tool jaw pulley rotation shaft, as the center of rotation.

The coupling relationship between the components described above is as follows.

The first rotation shaft 1141, which is an end tool jaw pulley rotation shaft, is sequentially inserted through the shaft coupling portion 1111*a* of the pulley 1111, the movable coupling hole 1101*c* of the first jaw 1101, the movable coupling hole 1102*c* of the second jaw 1102, and the shaft coupling portion 1121*a* of the pulley 1121.

The first actuation rotation shaft 1145*a* is sequentially inserted through the shaft pass-through portion 1101*e* of the first jaw 1101 and the actuation hub 1190 The second actuation rotation shaft 1145*b* is sequentially inserted through the shaft pass-through portion 1102*e* of the second jaw 1102 and the actuation hub 1190.

The shaft coupling portion 1111*a* of the pulley 1111 is fitted into the movable coupling hole 1101*c* of the first jaw 1101, and the jaw coupling portion 1111*b* of the pulley 1111 is fitted into the jaw pulley coupling hole 1101*d* of the first jaw 1101.

At this time, the jaw pulley coupling hole 1101*d* of the first jaw 1101 and the jaw coupling portion 1111*b* of the pulley 1111 are axially coupled to each other so as to be rotatable, and the movable coupling hole 1101*c* of the first jaw 1101 and the shaft coupling portion 1111*a* of the pulley 1111 are movably coupled to each other (here, "movably coupled" means that the shaft coupling portion 1111*a* of the pulley 1111 is coupled so as to be movable to a certain degree in the movable coupling hole 1101*c* of the first jaw 1101).

The shaft coupling portion 1121*a* of the pulley 1121 is fitted into the movable coupling hole 1102*c* of the second jaw 1102, and the jaw coupling portion 1121*b* of the pulley 1121 is fitted into the jaw pulley coupling hole 1102*d* of the second jaw 1102.

At this time, the jaw pulley coupling hole 1102*d* of the second jaw 1101 and the jaw coupling portion 1121*b* of the pulley 1121 are axially coupled to each other to be rotatable, and the movable coupling hole 1102*c* of the second jaw 1102 and the shaft coupling portion 1121*a* of the pulley 1121 are movably coupled to each other.

Here, the pulley 1111 and the pulley 1121 rotate around the first rotation shaft 1141, which is an end tool jaw pulley rotation shaft. Meanwhile, the first jaw 1101 and the second jaw 1102 rotate around the actuation rotation shaft 1145, which is a jaw rotation shaft. That is, the pulley 1111 and the first jaw 1101 have different shafts of rotation. Similarly, the pulley 1121 and the second jaw 1102 have different shafts of rotation.

That is, the rotation angle of the first jaw 1101 is limited to a certain degree by the movable coupling hole 1101*c*, but the first jaw 1101 essentially rotates around the actuation rotation shaft 1145, which is a jaw rotation shaft. Similarly, the rotation angle of the second jaw 1102 is limited to a certain degree by the movable coupling hole 1102*c*, but the second jaw 1102 essentially rotates around the actuation rotation shaft 1145, which is a jaw rotation shaft.

Amplification of a grip force due to the coupling relationship between the above-described components will be described.

In the surgical instrument 110 according to an embodiment of the present disclosure, the coupling structure of the first jaw 1101 and the second jaw 1102 forms an X-shaped structure, and thus, when the first jaw 1101 and the second jaw 1102 rotate in a direction of approaching each other (i.e., when the first jaw 1101 and the second jaw 1102 are closed), the grip force is greater in a direction in which the first jaw 1101 and the second jaw 1102 are closed. This will be described below in more detail.

As described above, in motions of the first jaw 1101 and the second jaw 1102 being opened and closed, there are two shafts that serve as the centers of rotation for the first jaw 1101 and the second jaw 1102. That is, the first jaw 1101 and the second jaw 1102 perform the opening and closing motion around two shafts including the first rotation shaft 1141 and the actuation rotation shaft 1145. At this time, the centers of rotation of the first jaw 1101 and the second jaw 1102 become the actuation rotation shaft 1145, and the centers of rotation of rotation of the pulley 1111 and the pulley 1121 become the first rotation shaft 1141. At this time, the first rotation shaft 1141 is a shaft whose position is relatively fixed, and the actuation rotation shaft 1145 is a shaft whose position is relatively moved linearly. In other words, when the pulley 1111 and the pulley 1121 rotate in a state in which the position of the first rotation shaft 1141 is fixed, the first jaw 1101 and the second jaw 1102 are opened/closed while the actuation rotation shaft 1145, which is a rotation shaft of the first jaw 1101 and the second jaw 1102, is moved backward and forward. This will be described below in more detail.

In FIG. 161, r1 is a distance from the jaw coupling portion 1121*b* of the pulley 1121 to the shaft coupling portion 1121*a*, and a length thereof is constant. Thus, a distance from the first rotation shaft 1141 inserted into the shaft coupling portion 1121*a* to the jaw coupling portion 1121*b* is also constant as r1.

Meanwhile, r2 of FIG. 161 is a distance from the jaw pulley coupling hole 1102*d* of the second jaw 1102 to the shaft pass-through portion 1102*e*, and a length thereof is constant. Thus, a distance from the jaw coupling portion 1121*b* of the pulley 1121 inserted into the jaw pulley coupling hole 1102*d* to the rotation shaft 1145 inserted into the shaft pass-through portion 1102*e* is also constant as r2.

That is, the lengths of r1 and r2 remain constant. Accordingly, when the pulley 1111 and the pulley 1121 rotate in the directions of an arrow B1 of FIG. 160 and an arrow B2 of FIG. 161, respectively, around the first rotation shaft 1141 to perform a closing motion, the first jaw 1101 and the second jaw 1102 rotate around the actuation rotation shaft 1145 as the angle between r1 and r2 changes while the lengths of r1 and r2 remain constant, and at this time, the actuation rotation shaft 1145 itself is also linearly moved (i.e., is moved forward/backward) by as much as an arrow C1 of FIG. 160 and an arrow C2 of FIG. 161.

That is, assuming that the position of the first rotation shaft 1141, which is an end tool jaw pulley rotation shaft, is fixed, when the first jaw 1101 and the second jaw 1102 are closed, a force is applied in a direction in which the actuation rotation shaft 1145, which is a jaw rotation shaft, is moved forward (i.e., toward the distal end), and thus the grip force in the direction in which the first jaw 1101 and the second jaw 1102 are closed becomes larger.

In other words, since the lengths of r1 and r2 remain constant when the second jaw 1102 rotates around the actuation rotation shaft 1145, when the pulley 1121 rotates around the first rotation shaft 1141, the angle between r1 and r2 changes while the lengths of r1 and r2 remain constant. That is, $\theta_2$, which is the angle between r1 and r2 in a state in which the second jaw 1102 is open as shown in FIG. 161A, is greater than $\theta_1$, which is the angle between r1 and r2 in a state in which the second jaw 1102 is closed as shown in FIG. 161B.

Thus, when the second jaw 1102 rotates from the open state to the close state, the angle between r1 and r2 changes, and a force is applied in a direction in which the actuation rotation shaft 1145 is moved forward.

In this case, since the first rotation shaft 1141 is a shaft whose position is relatively fixed, the actuation rotation shaft 1145 is moved forward in the direction of the arrow C1 of FIG. 160 and the direction of the arrow C2 of FIG. 161, and the grip force is further increased in a direction in which the second jaw 1102 is closed.

In other words, when the pulley 1111 and the pulley 1121 rotate around the first rotation shaft 1141, which is a shaft whose relative position is fixed, the angle θ between r1 and r2 changes while the distance between r1 and r2 remains constant. In addition, when the angle θ changes as described above, the first jaw 1101 and the second jaw 1102 push or pull the actuation rotation shaft 1145, and thus the actuation rotation shaft 1145 is moved forward or backward. In this case, when the first jaw 1101 and the second jaw 1102 are rotated in the direction of closing, the grip force is further increased as the actuation rotation shaft 1145 is moved forward in the directions of the arrow C1 of FIG. 160 and the arrow C2 of FIG. 161. On the contrary, when the first jaw 1101 and the second jaw 1102 are rotated in the direction of opening, the actuation rotation shaft 1145 is moved backward in directions opposite to the arrow C1 of FIG. 160 and the arrow C2 of FIG. 161.

With this configuration, the grip force becomes stronger when the first jaw 1101 and the second jaw 1102 are closed, thereby enabling a surgical operator to perform the actuation motion powerfully even with a small force.

(Components Associated with Cautery and Cutting)

Subsequently, referring to FIGS. 140 to 162 and the like, the end tool 1100 of the fourth embodiment of the present disclosure may include the first jaw 1101, the second jaw 1102, a first electrode 1151, a second electrode 1152, the guide tube 1170, and the blade 1175 in order to perform cauterizing and cutting motions.

Here, components related to the driving of the blade, such as the guide tube 1170 and the blade 1175, may be collectively referred to as a blade assembly. In an embodiment of the present disclosure, by disposing the blade assembly including the guide tube 1170 and the blade 1175 between the pulley 1111, which is a first jaw pulley, and the pulley 1121, which a second jaw pulley, the end tool 1100 is able to perform the cutting motion using the blade 1175 in addition to the pitch and yaw motions. This will be described in more detail.

As described above, the first jaw 1101 is connected to the first jaw pulley 1111 and rotates around the first rotation shaft 1141 together with the first jaw pulley 1111 when the first jaw pulley 1111 rotates around the first rotation shaft 1141.

Meanwhile, the first electrode 1151 may be formed on a surface of the first jaw 1101 facing the second jaw 1102. In addition, the second electrode 1152 may be formed on a surface of the second jaw 1102 facing the first jaw 1101.

At this time, a slit 1151a may be formed in the first electrode 1151, and the blade 1175 may move along the slit 1151a. In addition, a slit 1152a may be formed in the second electrode 1152, and the blade 1175 may move along the slit 1152a.

Meanwhile, although not shown in the drawings, a spacer (not shown) may be formed between the first jaw 1101 and the first electrode 1151, and a spacer (not shown) may be formed between the second jaw 1102 and the second electrode 1152. The spacer (not shown) may include an insulating material such as ceramic. Alternatively, the first jaw 1101 and the second jaw 1102 may themselves be made of a nonconductor such that the first electrode 1151 and the second electrode 1152 may be maintained to be insulated from each other without a separate insulator until the first electrode 1151 and the second electrode 1152 are in contact with each other.

Meanwhile, although not shown in the drawings, one or more sensors (not shown) may be further formed on at least one of the first jaw 1101 or the second jaw 1102. The sensor (not shown) may be formed to measure at least some of current, voltage, resistance, impedance, and temperature during the cautery by locating tissue between the first jaw 1101 and the second jaw 1102 and passing a current through the first electrode 1151 and the second electrode 1152.

Alternatively, instead of providing a separate sensor, monitoring and controlling of at least some of current, voltage, resistance, impedance, and temperature may be directly performed by a generator (not illustrated) which supplies power to the electrodes.

An edge portion formed sharply and configured to cut tissue may be formed in one region of the blade 1175. The tissue disposed between the first jaw 1101 and the second jaw 1102 may be cut as at least a part of the blade 1175 moves between the distal end 1104 and the proximal end 1105 of the end tool 1100.

Here, the guide tube 1170 and the blade 1175 disposed between the pulley 1111 and the pulley 1121 are provided in the end tool 1100 of the electric cauterization surgical instrument 10 according to an embodiment of the present disclosure. In addition, by providing the guide tube 1170 and the blade 1175, a multi-joint/multi-degree-of-freedom surgical instrument capable of pitch/yaw/actuation motions may also perform cauterizing and cutting motions. This will be described below in more detail.

So far, various types of surgical instruments for electrocautery have been developed. Among the various types of surgical instruments for electrocautery, a blood vessel resection device called "Advanced Energy Device" or "Vessel Sealer" has a sensing function added to the existing bipolar cautery method, so that power of different polarities may be supplied to two electrodes, and after denaturing a vessel with the heat generated therefrom for hemostasis, the stanched part may be cut with a blade. At this time, the impedance of the tissue (or blood vessel) while the current is flowing is measured to determine whether the cauterization is completed, and when the cauterization is completed, the current supply is automatically stopped, and the tissue is cut with the blade.

In the case of such a bipolar-type blood vessel resection device, it is essential to have a blade to cut the tissue after cauterization, and the end tool needs to be equipped with a mechanism for facilitating a linear motion of the blade, and thus joint movements such as pitch/yaw movements are not possible in most cases.

Meanwhile, there have been attempts to implement joint movements using flexible joints with multiple nodes connected in the bipolar-type blood vessel resection device, but in this case, a rotation angle is limited and it is difficult to achieve accurate motion control of the end tool.

On the other hand, in the case of a method that utilizes vibration of ultrasonic waves to perform hemostasis and cutting, it is not feasible to provide joints due to the physical properties of ultrasonic waves.

To address these problems, the end tool 1100 of the electric cauterization surgical instrument 10 according to an embodiment of the present disclosure includes the guide tube 1170 disposed between the pulley 1111 and the pulley 1121, and the blade 1175 that moves between a first position and a second position in response to the movement of the blade wire 307 disposed inside the guide tube 1170. In addition, by providing the guide tube 1170 and the blade 1175 as described above, pitch/yaw/actuation motions may also be performed using a pulley/wire in a bipolar-type surgical instrument for cauterizing and cutting tissue.

FIG. 163 is a view illustrating a state in which the end tool of the surgical instrument for electrocautery of FIG. 140 is closed, and FIG. 164 is a view illustrating a state in which the end tool of the surgical instrument for electrocautery of FIG. 140 is opened. In addition, FIG. 165 is a view illustrating a state in which the blade wire 307 and the blade 1175 are located at a first position, FIG. 166 is a view illustrating a state in which the blade wire 307 and the blade 1175 are located at a second position, and FIG. 167 is a view illustrating a state in which the blade wire 307 and the blade 1175 are located at a third position.

Referring to FIGS. 163 to 167, it may be said that the tissue between the first jaw 1101 and the second jaw 1102 is cut as the cutting motion of FIGS. 165 to 167 is performed in a state in which the first jaw 1101 and the second jaw 1102 are closed as shown in FIG. 163.

Here, the first position illustrated in FIG. 165 may be defined as a state in which the blade 1175 is drawn in toward the proximal end 1105 of the end tool 1100 as much as possible. Alternatively, the first position may be defined as a state in which the blade 1175 is located adjacent to the pulley 1111/pulley 1121.

Meanwhile, the third position illustrated in FIG. 167 may be defined as a state in which the blade 1175 is withdrawn toward the distal end 1104 of the end tool 1100 as much as possible. Alternatively, the third position may be defined as a state in which the blade 1175 is spaced away from the pulley 1111/pulley 1121 as much as possible.

First, as shown in FIG. 164, a tissue to be cut is located between the first jaw 1101 and the second jaw 1102 in a state in which the first jaw 1101 and the second jaw 1102 are opened, and then an actuation motion is performed to close the first jaw 1101 and the second jaw 1102 as shown in FIG. 163.

Next, as shown in FIG. 165, in a state in which the blade wire 307 and the blade 1175 are located at the first position, currents of different polarities are applied to the first electrode 1151 and the second electrode 1152 to cauterize the tissue between the first jaw 1101 and the second jaw 1102. At this time, a generator (not shown) configured to supply power to the electrodes may itself perform monitoring of at least some of current, voltage, resistance, impedance, and temperature, and may stop supplying power when the cauterization is completed.

In the state in which the cautery is completed as described above, when the blade wire 307 moves sequentially in the directions of an arrow A1 of FIG. 155 and an arrow A2 of FIG. 167, the blade 1175 coupled to the blade wire 307 moves from the first position at the proximal end 1105 of the end tool 1100 toward the third position at the distal end 1104 of the end tool 1100, reaching the positions in FIGS. 166 and 167 in turn.

As such, the blade 1175 cuts the tissue between the first jaw 1101 and the second jaw 1102 while moving in the X-axis direction.

However, it is to be understood that the linear motion of the blade 1175 here does not mean a motion in a completely straight line, but rather means a motion of the blade 1175 to the extent that the blade 1175 is able to cut the tissue while achieving a linear motion when viewed as a whole, even though the motion is not in a completely straight line, for example, the middle part of the straight line is bent by a certain angle or there is a section having a gentle curvature in a certain section.

Meanwhile, in this state, when the blade wire 307 is pulled in the opposite direction, the blade 1175 coupled to the blade wire 307 also returns to the first position.

According to the present disclosure, the multi-joint/multi-degree-of-freedom surgical instrument capable of pitch/yaw/actuation motions may also perform cauterizing and cutting motions.

(Manipulation Portion)

FIGS. 216 and 217 are perspective views illustrating the manipulation portion 200 of the surgical instrument of FIG. 140. FIG. 218 is a diagram schematically illustrating only the pulleys and the wires constituting the joint of the surgical instrument for electrocautery of FIG. 140.

With reference to FIGS. 140 to 162 and FIGS. 216 to 218, the manipulation portion 200 of the electric cauterization surgical instrument 10 according to the fourth embodiment may include the first handle 204 which a user may hold, the actuation manipulation portion 203 configured to control the actuation motion of the end tool 1100, the yaw manipulation portion 202 configured to control the yaw motion of the end tool 1100, and the pitch manipulation portion 201 configured to control the pitch motion of the end tool 1100. FIGS. 216 and 217 illustrate components only associated with the pitch/yaw/actuation motions of the electric cauterization surgical instrument 10.

In addition, the manipulation portion 200 of the electric cauterization surgical instrument 10 may further include a blade manipulation portion 260 performing cutting by controlling the movement of the blade 171 of the end tool 1100, and a cautery manipulation portion 270 performing cautery by supplying electrical energy to the first electrode 1151 and the second electrode 1152 of the end tool 1100.

The manipulation portion 200 may include a pulley 210, a pulley 211, a pulley 212, a pulley 213, a pulley 214, a pulley 215, a pulley 216, a pulley 217, and a pulley 218, which are associated with the rotational motion of the first jaw 1101. In addition, the manipulation portion 200 may include a pulley 220, a pulley 221, a pulley 222, a pulley 223, a pulley 224, a pulley 225, a pulley 226, a pulley 227, and a pulley 228, which are associated with the rotational motion of the second jaw 1102. In one embodiment, the manipulation portion 200 may include a pulley 231, a pulley 232, a pulley 233, and a pulley 234, which are associated with the pitch motion. The manipulation portion 200 may include a pulley 235 which is an intermediate pulley arranged in some positions of the bent portion 402 of the connection portion 400.

Here, the drawings illustrate that the pulleys facing each other are arranged in parallel with each other; however, the technical concepts of the present disclosure are not limited thereto, and each pulley may be formed in various positions and sizes suitable for the configuration of the manipulation portion 200.

In addition, the manipulation portion 200 of the fourth embodiment may include a rotation shaft 241, a rotation shaft 242, a rotation shaft 243, a rotation shaft 244, a rotation shaft 245, and a rotation shaft 246. Here, the rotation shaft 241 may function as a manipulation portion first jaw actuation rotation shaft, and the rotation shaft 242 may function as a manipulation portion second jaw actuation rotation shaft. In addition, the rotation shaft 243 may function as a manipulation portion yaw main rotation shaft, and the rotation shaft 244 may function as a manipulation portion yaw subsidiary rotation shaft. The rotation shaft 245 may function as a manipulation portion pitch subsidiary rotation shaft, and the rotation shaft 246 may function as a manipulation portion pitch main rotation shaft.

The rotation shaft 241, the rotation shaft 242, the rotation shaft 243, the rotation shaft 244, the rotation shaft 245, and the rotation shaft 246 may be sequentially arranged in a direction towards a proximal end 206 from a distal end 205.

One or more pulleys may be fit into each of the rotation shafts 241, 242, 243, 244, 245, and 246 which will be described in detail below.

The pulley 210 may function as a manipulation portion first jaw actuation pulley, the pulley 220 may function as a manipulation portion second jaw actuation pulley, and these components may be collectively referred to as a manipulation portion actuation pulley.

The pulley 211 and the pulley 212 may function as a manipulation portion first jaw yaw main pulley, the pulley 221 and the pulley 222 may function as a manipulation portion second jaw yaw main pulley, and these two components may collectively be referred to as a manipulation portion yaw main pulley.

The pulley 213 and the pulley 214 may function as a manipulation portion first jaw yaw subsidiary pulley, the pulley 223 and the pulley 224 may function as a manipulation portion second jaw yaw subsidiary pulley, and these two components may collectively be referred to as a manipulation portion yaw subsidiary pulley.

The pulley 215 and the pulley 216 may function as a manipulation portion first jaw pitch subsidiary pulley, the pulley 225 and the pulley 226 may function as a manipulation portion second jaw pitch subsidiary pulley, and these two components may collectively be referred to as a manipulation portion pitch subsidiary pulley.

The pulley 217 and the pulley 218 may function as a manipulation portion first jaw pitch main pulley, the pulley 227 and the pulley 228 may function as a manipulation portion second jaw pitch main pulley, and these two components may collectively be referred to as a manipulation portion pitch main pulley.

The pulley 231 and the pulley 232 may function as a manipulation portion pitch wire main pulley, and the pulley 233 and the pulley 234 may function as a manipulation portion pitch wire subsidiary pulley.

The components may be classified from the viewpoint of the manipulation portion in connection with each motion (i.e., pitch/yaw/actuation) as follows.

The pitch manipulation portion 201 controlling the pitch motion of the end tool 1100 may include a pulley 215, a pulley 216, a pulley 217, a pulley 218, a pulley 225, a pulley 226, a pulley 227, a pulley 228, a pulley 231, a pulley 232, and a pulley 234. In addition, the pitch manipulation portion 201 may include the rotation shaft 245 and the rotation shaft 246. In one embodiment, the pitch manipulation portion 201 may further include a pitch frame 208.

The yaw manipulation portion 202 controlling the yaw motion of the end tool 1100 may include a pulley 211, a pulley 212, a pulley 213, a pulley 214, a pulley 221, a pulley 222, a pulley 223, and a pulley 224. In addition, the yaw manipulation portion 202 may include the rotation shaft 243 and the rotation shaft 244. In one embodiment, the yaw manipulation portion 202 may further include a yaw frame 207.

The actuation manipulation portion 203 controlling the actuation motion of the end tool 1100 may include the pulley 210, the pulley 220, the rotation shaft 241, and the rotation shaft 242. In one embodiment, the actuation manipulation portion 203 may further include a first actuation manipulation portion 251 and a second actuation manipulation portion 256.

Hereinafter, each component of the manipulation portion 200 will be described in more detail.

The first handle 204 may be held by a user, and more particularly, a user may hold the first handle 204 by wrapping it with his or her hand. The actuation manipulation portion 203 and the yaw manipulation portion 202 may be formed on the first handle 204, and the pitch manipulation portion 201 may be formed on one side of the yaw manipulation portion 202. In addition, another end of the pitch manipulation portion 201 may be connected to the bent portion 402 of the connection portion 400.

The actuation manipulation portion 203 may include the first actuation manipulation portion 251 and the second actuation manipulation portion 256. The first actuation manipulation portion 251 may include the rotation shaft 241, the pulley 210, a first actuation extension portion 252, and a first actuation gear 253. The second actuation manipulation portion 256 may include the rotation shaft 242, the pulley 220, a second actuation extension portion 257, and a second actuation gear 258. Here, ends of the first actuation extension portion 252 and the second actuation extension portion 257 may be formed in the shape of a hand ring, and may operate as a second handle.

The rotation shaft 241 and the rotation shaft 242, which are the actuation rotation shaft, may be formed to have a certain angle with the XY plane on which the connection portion 400 is formed. For example, the rotation shaft 241 and the rotation shaft 242 may be formed in a direction parallel with the Z-axis, and when the pitch manipulation portion 201 or the yaw manipulation portion 203 rotates, a coordinate system of the actuation manipulation portion 203 may be changed relatively. However, the technical ides of the present disclosure are not limited thereto, and by an ergonomic design, the rotation shaft 241 and the rotation shaft 242 may be formed in various directions suitable for a hand structure of a user holding the actuation manipulation portion 203.

The pulley 210, the first actuation extension portion 252, and the first actuation gear 253 may be fixedly coupled to each other and rotatable together around the rotation shaft 241. Here, the pulley 210 may include one pulley or two pulleys fixedly coupled to each other.

Likewise, the pulley 220, the second actuation extension portion 257, and the second actuation gear 258 may be fixedly coupled to each other and rotatable together around the rotation shaft 242. Here, the pulley 220 may include one pulley or two pulleys fixedly coupled to each other.

The first actuation gear 253 and the second actuation gear 258 may be formed to engage with each other, and when either one of them rotates in one direction, the other one may rotate concurrently in the opposite direction.

The yaw manipulation portion 202 may include the rotation shaft 243, the pulley 211 and the pulley 212, which are the manipulation portion first jaw yaw main pulley, the pulley 211 and the pulley 212, which are the manipulation portion second jaw yaw main pulley, and the yaw frame 207. In addition, the yaw manipulation portion 202 may further include the pulley 213 and the pulley 214, which are the manipulation portion first jaw yaw subsidiary pulley and arranged on one side of the pulley 211 and the pulley 212, and the pulley 223 and the pulley 224, which are the manipulation portion second jaw yaw subsidiary pulley and arranged on one side of the pulley 221 and the pulley 222.

Here, the pulley 213, the pulley 214, the pulley 223, and the pulley 224 may be coupled to the pitch frame 208 to be described later.

The drawings illustrate that the yaw manipulation portion 202 includes the pulley 211, the pulley 212, the pulley 221, and the pulley 222, and as the pulley 211 faces the pulley 212 and the pulley 221 faces the pulley 222, two pulleys may be rotatable independently of each other; however the technical concepts of the present disclosure are not limited thereto. That is, one or more pulleys having the same diameter or different diameters may be provided according to the configuration of the yaw manipulation portion 202.

More specifically, on the first handle 204, the rotation shaft 243, which is the manipulation portion yaw main rotation shaft, may be formed on one side of the actuation manipulation portion 203. In this case, the first handle 204 may be formed to be rotatable around the rotation shaft 243.

Here, the rotation shaft 243 may be formed to have a certain angle with the XY plane on which the connection portion 400 is formed. For example, the rotation shaft 243 may be formed in a direction parallel with the Z-axis, and when the pitch manipulation portion 201 rotates, the coordinate system of the rotation shaft 243 may be changed relatively as described above. However, the technical ides of the present disclosure are not limited thereto, and by an ergonomic design, the rotation shaft 243 may be formed in various directions suitable for a hand structure of a user holding the manipulation portion 200.

The pulley 211, the pulley 212, the pulley 221, and the pulley 222 may be coupled to the rotation shaft 243 to be rotatable around the rotation shaft 243. In addition, the wire 301 or the wire 305, which is the first jaw wire, may be wound around the pulley 211 and the pulley 212, and the wire 302 or the wire 306, which is the second jaw wire, may be wound around the pulley 221 and the pulley 222. At this time, as the pulley 211 faces the pulley 212, and the pulley 221 faces the pulley 222, there may be two pulleys which are rotatable independently. Accordingly, as the wire wound inward and the wire wound outward may be respectively wound around separate pulleys, the pulleys may operate without interfering with each other.

The yaw frame 207 may rigidly connect the first handle 204, the rotation shaft 241, the rotation shaft 242, and the rotation shaft 243, and accordingly, the first handle 204, the yaw manipulation portion 202, and the actuation manipulation portion 203 may yaw-rotate around the rotation shaft 243 in an integrated manner.

The pitch manipulation portion 201 may include the rotation shaft 246, the pulley 217 and the pulley 218, which are the manipulation portion first jaw pitch main pulley, the pulley 227 and the pulley 228, which are the manipulation portion second jaw pitch main pulley, and the pitch frame 208. In addition, the pitch manipulation portion 201 may further include the rotation shaft 245, the pulley 215 and the pulley 216, which are the manipulation portion first jaw pitch subsidiary pulley and arranged on one side of the pulley 217 and the pulley 218, and the pulley 225 and the pulley 226, which are the manipulation portion second jaw pitch subsidiary pulley and arranged on one side of the pulley 227 and pulley 228. The pitch manipulation portion 201 may be connected to the bent portion 402 of the connection portion 400 through the rotation shaft 246.

More specifically, the pitch frame 208 may be a base frame of the pitch manipulation portion 201, and one end of the pitch frame 208 may be rotatably coupled to the rotation shaft 243. That is, the yaw frame 207 may be formed to be rotatable around the rotation shaft 243 with respect to the pitch frame 208.

As described above, the yaw frame 207 may connect the first handle 204, the rotation shaft 243, the rotation shaft 241, and the rotation shaft 242, and as the yaw frame 207 is axially coupled to the pitch frame 208, when the pitch frame 208 pitch-rotates around the rotation shaft 246, the yaw frame 207, the first handle 204, the rotation shaft 241, the rotation shaft 242, and the rotation shaft 243, which are connected to the pitch frame 208, may also pitch rotate. That is, when the pitch manipulation portion 201 rotates around the rotation shaft 246, the actuation manipulation portion 203 and the yaw manipulation portion 202 may be rotated together with the pitch manipulation portion 201. In other words, when the user pitch-rotates the first handle 204 around the rotation shaft 246, the actuation manipulation portion 203, the yaw manipulation portion 202, and the pitch manipulation portion 201 may also move together with the first handle 204.

The pulley 217, the pulley 218, the pulley 227, and the pulley 228 may be coupled to the rotation shaft 246 so that they are rotatable around the rotation shaft 246 of the pitch frame 208.

Here, the pulley 217 and the pulley 218 may face each other and rotate independently. Accordingly, as the wire wound inward and the wire wound outward may be respectively wound around separate pulleys, the pulleys may operate without interfering with each other. Likewise, the pulley 227 and the pulley 228 may face each other and rotate independently. Accordingly, as the wire wound inward and the wire wound outward may be respectively wound around separate pulleys, the pulleys may operate without interfering with each other.

Next, the motions of the wire 303 and the wire 304 which are the pitch wire are described below.

In the end tool 1100, the pulley 1131, which is the end tool pitch pulley, may be fixedly coupled to the end tool hub 1180, and in the manipulation portion 200, the pulley 231 and the pulley 232, which are the manipulation portion pitch pulley, may be fixedly coupled to the pitch frame 208. These pulleys may be connected to each other by the wire 303 and the wire 304, which are the pitch wire, to facilitate the pitch motion of the end tool 1100 according to the pitch manipulation of the manipulation portion 200. Here, the wire 303 may be fixedly coupled to the pitch frame 208 via the pulley 231 and the pulley 233, and the wire 304 may be fixedly coupled to the pitch frame 208 via the pulley 232 and the pulley 234. That is, the pitch frame 208, the pulley 231, and the pulley 232 may rotate together around the rotation shaft 246 by the pitch rotation of the manipulation portion 200. As a result, the wire 303 and the wire 304 may also move, and separately from the pitch motion of the end tool 1100 by the wire 301, the wire 302, the wire 305, and the wire 306, which are the jaw wire, additional pitch rotation power may be transmitted.

The connection relation among the first handle 204, the pitch manipulation portion 201, the yaw manipulation portion 202, and the actuation manipulation portion 203 is described below. On the first handle 204, the rotation shaft 241, the rotation shaft 242, the rotation shaft 243, the rotation shaft 244, the rotation shaft 245, and the rotation shaft 246 may be formed. At this time, as the rotation shaft 241 and the rotation shaft 242 are directly formed on the first handle 204, the first handle 204 and the actuation manipulation portion 203 may be directly connected to each other. As the rotation shaft 243 is directly formed on the first handle 204, the first handle 204 and the yaw manipulation portion 202 may be directly connected to each other. As the pitch manipulation portion 201 is arranged on one side of the yaw manipulation portion 202 and connected to the yaw manipulation portion 202, the pitch manipulation portion 201 may not be directly connected to the first handle 204 and the pitch manipulation portion 201 and the first handle 204 may be indirectly connected to each other through the yaw manipulation portion 202.

With reference to the drawings, in the electric cauterization surgical instrument 10 according to the first embodiment, the pitch manipulation portion 201 and the end tool 1100 may be formed on the same or parallel axis (i.e., the X-axis). That is, the rotation shaft 246 of the pitch manipulation portion 201 may be formed at one end of the bent portion 402 of the connection portion 400, and the end tool 1100 may be formed at the other end of the connection portion 400.

In addition, one or more intermediate pulleys 235 changing or guiding a path of the wires may be arranged in some positions of the connection portion 400, in particular, in positions on the bent portion 402. At least a part of the wires may be wound around the intermediate pulleys 235 to guide the path of the wires so that the wires are arranged along the bent shape of the bent portion 402.

Here, the drawings illustrate that the connection portion 400 includes the bent portion 402 and thus is formed in a curved manner with a certain curvature; however, the technical concepts of the present disclosure are not limited thereto, and the connection portion 400 may be formed straightly, if necessary, or curved in one or more points. Even in such cases, the pitch manipulation portion 201 and the end tool 1100 may be formed on the substantially same or parallel axis. In addition, although FIG. 3 illustrates that the pitch manipulation portion 201 and the end tool 1100 are respectively formed on an axis parallel with the X-axis, the technical concepts of the present disclosure are not limited thereto, and the pitch manipulation portion 201 and the end tool 1100 may be formed on different axes.

(Actuation Motion, Yaw Motion, Pitch Motion)

Actuation motion, yaw motion, and pitch motion in this embodiment will be described as follows.

First, the actuation motion is as follows.

When a user puts the index finger in a hand ring formed at the first actuation extension 252, puts the thumb in a hand ring formed at the second actuation extension 257, and rotates the first actuation extension 252 and the second actuation extension 257 using any one of or both the fingers, the pulley 210 and the first actuation gear 253 fixedly coupled to the first actuation extension 252 rotate around the rotation shaft 241, and the pulley 220 and the second actuation gear 258 fixedly coupled to the second actuation extension 257 rotate around the rotation shaft 242. At this time, the pulley 210 and the pulley 220 rotate in opposite directions, and thus the wire 301 and the wire 305 each having one end fixedly coupled to and wound around the pulley 210 and the wire 302 and the wire 306 each having one end fixedly coupled to and wound around the pulley 220 move in opposite directions as well. This rotational force is transmitted to an end tool 1100 through a power transmission portion 300, two jaws 1103 of the end tool 1100 perform the actuation motion.

Here, the actuation motion refers to an action of opening or closing the jaws 1102 while the two jaws 1102 rotate in opposite directions to each other, as described above. In other words, when the actuation extensions 252 and 257 of the actuation manipulation portion 203 are rotated in directions toward each other, the first jaw 1101 rotates counterclockwise and the second jaw 1102 rotates clockwise, and thus the end tool 1100 is closed. Conversely, when the actuation extensions 252 and 257 of the actuation manipulation portion 203 are rotated in directions away from each other, the first jaw 1101 rotates clockwise and the second jaw 1102 rotates counterclockwise, and thus the end tool 1100 is opened.

In this embodiment, for the above-described actuation manipulation, the first actuation extension 252 and the second actuation extension 257 were provided to constitute a second handle, and two fingers were gripped to enable manipulation. However, unlike the above, the actuation manipulation portion 203 for actuation manipulation to open and close the two jaws of the end tool 1100 with each other may be configured differently so that, for example, two actuation pulleys (the pulley 210 and the pulley 220) operate opposite to each other by one actuation rotating portion.

Next, the yaw motion is as follows.

When the user rotates a first handle 204 around a rotation shaft 243 while holding the first handle 204, the actuation manipulation portion 203 and the yaw manipulation portion 202 yaw-rotates around the rotation shaft 243. In other words, when the pulley 210 of the first actuation manipulation portion 251 to which the wire 301 and the wire 305 are fixedly coupled rotates about the rotation shaft 243, the wire 301 and the wire 305 respectively wound around the pulley 211 and the pulley 212 move. Likewise, when the pulley 220 of the second actuation manipulation portion 256 to which the wire 302 and the wire 306 are fixedly coupled rotates about the rotation shaft 243, the wire 302 and the wire 306 respectively wound around the pulley 221 and the pulley 222 move. At this time, the wire 301 and the wire 305 connected to the first jaw 1101 and the wire 302 and the wire 306 connected to the second jaw 1102 are respectively wound around the pulley 211 and the pulley 212 and the pulley 221 and the pulley 222, such that the first jaw 1101 and the second jaw 1102 rotate in the same direction during a yaw rotation. And, this rotational force is transmitted to the end tool 1100 through the power transmission portion 300, the two jaws 1103 of the end tool 1100 performs the yaw motion that rotates in the same direction.

At this time, since the yaw frame 207 connects the first handle 204, the rotation shaft 241, the rotation shaft 242, and the rotation shaft 243, the first handle 204, the yaw manipulation portion 202, and the actuation manipulation portion 203 rotate together around the rotation shaft 243.

Next, the pitch motion is as follows.

When the user rotates a first handle 204 around a rotation shaft 246 while holding the first handle 204, the actuation manipulation portion 203, the yaw manipulation portion 202, and the pitch manipulation portion 201 make pitch rotation around the rotation shaft 243. In other words, when the pulley 210 of the first actuation manipulation portion 251 to which the wire 301 and the wire 305 are fixedly coupled rotates about the rotation shaft 246, the wire 301 and the wire 305 respectively wound around the pulley 217 and the pulley 218 move. Likewise, when the pulley 220 of the second actuation manipulation portion 256 to which the wire 302 and the wire 306 are fixedly coupled rotates about the rotation shaft 246, the wire 302 and the wire 306 respectively wound around the pulley 227 and the pulley 228 move. Here, as described above with reference to FIG. 5, the wire 301, the wire 305, the wire 302, and the wire 306, which are jaw wires, are wound around the pulley 217, the pulley 218, the pulley 227, and the pulley 228, which are manipulation portion pitch main pulleys, such that the wire 301 and wire 305, which are first jaw wires, move in the same direction and the wire 302 and the wire 306, which are second jaw wires, move in the same direction to enable pitch rotation of the first jaw 1101 and the second jaw 1102. And, this rotational force is transmitted to an end tool 1100 through a power transmission portion 300, two jaws 1103 of the end tool 1100 perform the pitch motion.

At this time, the pitch frame 208 is connected to the yaw frame 207 and the yaw frame 207 connects the first handle 204, the rotation shaft 241, the rotation shaft 242, and the rotation shaft 243. Therefore, when the pitch frame 208 rotates around the rotation shaft 246, the yaw frame 207 connected to the pitch frame 208, the first handle 204, the rotation shaft 241, the rotation shaft 242, and the rotation shaft 243 rotate together. That is, when a pitch manipulation portion 201 rotates around the rotation shaft 246, the actuation manipulation portion 203 and the yaw manipulation portion 202 are rotated together with the pitch manipulation portion 201.

In summary, in an electric cauterization surgical instrument 10 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 1100 is induced. Furthermore, auxiliary pulleys may be formed on one side of each pulley, and the wire may not be wound several times on one pulley by these auxiliary pulleys.

FIG. 218 is a schematic view of only the configuration of pulleys and wires constituting joints of the electric cauterization surgical instrument 10 according to an embodiment of the present disclosure shown in FIG. 140. In FIG. 218, intermediate pulleys that are for changing paths of wires and are not associated with joint motions are omitted.

Referring to FIG. 218, the manipulation portion 200 may include the pulley 210, the pulley 211, the pulley 212, the pulley 213, the pulley 214, the pulley 215, the pulley 216, the pulley 217, and the pulley 218 that are associated with the rotational motion of the first jaw 1101.

Also, the manipulation portion 200 may include the pulley 220, the pulley 221, the pulley 222, the pulley 223, the pulley 224, the pulley 225, the pulley 226, the pulley 227, and the pulley 228 associated with the rotational motion of the second jaw 1102. (The arrangement and the configuration of pulleys in the manipulation portion 200 are the same as the arrangement and the configuration of the pulleys in the end tool 1100 in principle, and thus some of the reference numerals thereof will be omitted in the drawings.)

The pulley 211 and the pulley 212 and the pulley 221 and the pulley 222 may be formed to be rotatable independently of each other around the same axis, that is, the rotation shaft 243. At this time, the pulley 211 and the pulley 212 may be formed to face the pulley 221 and the pulley 222, respectively, thereby forming two independently rotatable pulleys.

The pulley 213 and the pulley 214 and the pulley 223 and the pulley 224 may be formed to be rotatable independently of each other around the same axis, that is, the rotation shaft 244. At this time, the pulley 213 and the pulley 214 may be formed to face each other as two independently rotatable pulleys, and, in this case, the two pulleys may be formed to have different diameters. Likewise, the pulley 223 and the pulley 224 may be formed to face each other as two independently rotatable pulleys, and, in this case, the two pulleys may be formed to have different diameters.

The pulley 215 and the pulley 216 and the pulley 225 and the pulley 226 may be formed to be rotatable independently of each other around the same axis, that is, the rotation shaft 245. In this case, the pulley 215 and the pulley 216 may be formed to have different diameters. Also, the pulley 225 and the pulley 226 may be formed to have different diameters.

The pulley 217 and the pulley 218 and the pulley 227 and the pulley 228 may be formed to be rotatable independently of each other around the same axis, that is, the rotation shaft 246.

The wire 301 sequentially passes through the pulley 217, the pulley 215, the pulley 213, and the pulley 211 of the manipulation portion 200, is wound around the pulley 210, and then is coupled to the pulley 210 by a fastening member 324. Meanwhile, the wire 305 sequentially passes through the pulley 218, the pulley 216, the pulley 214, and the pulley 212 of the manipulation portion 200 and is coupled to the pulley 210 by the fastening member 324. Therefore, as the pulley 210 rotates, the wire 301 and the wire 305 are wound around or unwound from the pulley 210, and thus the first jaw 1101 rotates.

The wire 306 sequentially passes through the pulley 227, the pulley 225, the pulley 223, and the pulley 221 of the manipulation portion 200, is wound around the pulley 220, and then is coupled to the pulley 220 by a fastening member 327. Meanwhile, the wire 302 sequentially passes through the pulley 228, the pulley 226, the pulley 224, and the pulley 222 of the manipulation portion 200 and is coupled to the pulley 220 by the fastening member 327. Therefore, as the pulley 220 rotates, the wire 302 and the wire 306 are wound around or unwound from the pulley 220, and thus the second jaw 1102 rotates.

(Conceptual Diagram of Pulleys and Wires)

FIGS. 220 and 221 are diagrams illustrating a configuration of pulleys and wires, which are associated with an actuation motion and a yaw motion of the electric cauterization surgical instrument 10 according to an embodiment of the present disclosure illustrated in FIG. 140, in detail for each of the first jaw and the second jaw. FIG. 220 is a diagram illustrating only pulleys and wires related to the second jaw, and FIG. 221 is a diagram illustrating only pulleys and wires related to the first jaw. In addition, FIG. 219 is a perspective view illustrating a yaw motion of the surgical instrument shown in FIG. 140. Here, in FIG. 219, components associated with a cutting motion are omitted.

First, a wire operation in an actuation motion will be described.

Referring to FIG. 221, when the first actuation extension 252 rotates around the rotation shaft 241 in the direction of an arrow OPA1, the pulley 210 connected to the first actuation extension 252 is rotated, and the wire 301 and the wire 305 wound around the pulley 210 are moved in directions W1a and W1b, respectively, and as a result, the first jaw 1101 of the end tool 1100 is rotated in the direction of an arrow EPA1.

Referring to FIG. 220, when the second actuation extension 257 rotates around the rotation shaft 242 in the direction of an arrow OPA2, the pulley 220 connected to the second actuation extension 257 is rotated, and thus both strands of the wires 302 and 306 wound around the pulley 220 are moved in directions W2a and W2b, respectively, and as a result, the second jaw 1102 of the end tool 1100 is rotated in the direction of an arrow EPA2. Accordingly, when a user manipulates the first actuation extension 252 and the second actuation extension 257 in directions close to each other, a motion of the first jaw 1101 and the second jaw 1102 of the end tool being close to each other is performed.

Next, a wire operation in a yaw motion will be described.

First, since the rotation shaft 243 is connected to the rotation shafts 241 and 242 by the yaw frame (see 207 of FIG. 216), the rotation shaft 243 and the rotation shafts 241 and 242 are integrally rotated together.

Referring to FIG. 221, when the first handle 204 rotates around the rotation shaft 243 in the direction of an arrow OPY1, the pulley 210 and the pulleys 211 and 212 and the wires 301 and 305 wound therearound are rotated as a whole around the rotation shaft 243, and as a result, the wires 301 and 305 wound around the pulleys 211 and 212 are moved in the directions W1a and W1b, respectively, which in turn causes the first jaw 1101 of the end tool 1100 to rotate in the direction of an arrow EPY1.

Referring to FIG. 220, when the first handle 204 rotates around the rotation shaft 243 in the direction of an arrow OPY2, the pulley 220 and the pulleys 221 and 222 and the wires 302 and 306 wound therearound are rotated as a whole around the rotation shaft 243, and as a result, the wires 302 and 306 wound around the pulleys 221 and 222 are respectively moved in a direction opposite to the direction W1a and a direction opposite to the direction W1b, which in turn causes the first jaw 1101 of the end tool 1100 to rotate in the direction of an arrow EPY2.

FIGS. 223 and 224 are diagrams illustrating a configuration of pulleys and wires, which are associated with a pitch motion of the electric cauterization surgical instrument 10 according to an embodiment of the present disclosure illustrated in FIG. 140, in detail for each of the first jaw and the second jaw. FIG. 223 is a diagram illustrating only pulleys and wires related to the second jaw, and FIG. 224 is a diagram illustrating only pulleys and wires related to the first jaw. As shown in FIG. 140 and elsewhere herein, there are two pulleys related to the pitch motion, and both strands of each wire are wound in the same path, which is illustrated with one line in FIG. 223. In addition, FIG. 222 is a perspective view illustrating a pitch motion of the surgical instrument of FIG. 140. Here, in FIG. 222, components associated with a cutting motion are omitted.

Referring to FIG. 223, when the first handle 204 rotates around the rotation shaft 246 in the direction of an arrow OPP1, the pulley 210, the pulley 215, the pulley 217, and the like, and the wire 301 and the like wound therearound are rotated as a whole around the rotation shaft 246. At this time, since the wires 301 and 305, which are first jaw wires, are wound around upper portions of the pulley 217 and the pulley 218, the wires 301 and 305 are moved in the direction of an arrow W1. As a result, the first jaw 1101 of the end tool 1100 rotates in the direction of an arrow EPP1.

Referring to FIG. 224, when the first handle 204 rotates around the rotation shaft 246 in the direction of an arrow OPP2, the pulley 220, the pulley 225, the pulley 227, and the like, and the wire 302 and the like wound therearound are rotated as a whole around the rotation shaft 246. At this time, since the wires 302 and 306, which are second jaw wires, are wound around lower portions of the pulley 227 and the pulley 228, the wires 302 and 306 are moved in the direction of an arrow W2. As a result, the second jaw 1102 of the end tool 1100 rotates in the direction of an arrow EPP2.

Thus, the actuation, yaw, and pitch manipulations are manipulatable independent of each other.

As described with reference to FIG. 140, the actuation manipulation portion 203, the yaw manipulation portion 202, and the pitch manipulation portion 201 are configured such that the respective rotation shafts are located at the rear thereof to be identical to the joint configuration of the end tool, so that a user may intuitively perform matching manipulations.

In particular, in the electric cauterization surgical instrument 10 according to an embodiment of the present disclosure, the pulleys are formed on respective joint points (an actuation joint, a yaw joint, and a pitch joint), the wires (the first jaw wire or the second jaw wire) are formed to be wound around the pulleys, the rotational manipulations (actuation rotation, yaw rotation, and pitch rotation) of the manipulation portion cause the movement of each wire, which in turn induces the desired motion of the end tool 1100. Furthermore, the auxiliary pulleys may be formed on one side of the respective pulleys, and these auxiliary pulleys may prevent the wire from being wound around one pulley multiple times, so that the wires wound around the pulley do not come into contact with each other, and paths of the wire being wound around the pulley and the wire being released from the pulley are safely formed, so that safety and efficiency in the transmission of driving force of a wire may be improved.

Meanwhile, as described above, the yaw manipulation portion 202 and the actuation manipulation portion 203 are directly formed on the first handle 204. Thus, when the first handle 204 rotates around the rotation shaft 246, the yaw manipulation portion 202 and the actuation manipulation portion 203 are also rotated together with the first handle 204. Accordingly, the coordinate systems of the yaw manipulation portion 202 and the actuation manipulation portion 203 are not fixed, but are continuously changed relative to the rotation of the first handle 204. That is, in FIG. 140 or the like, the yaw manipulation portion 202 and the actuation manipulation portion 203 are illustrated as being parallel to the Z-axis. However, when the first handle 204 is rotated, the yaw manipulation portion 202 and the actuation manipulation portion 203 are not parallel to the Z-axis any longer. That is, the coordinate systems of the yaw manipulation portion 202 and the actuation manipulation portion 203 are changed according to the rotation of the first handle 204. However, in the present specification, for convenience of description, unless described otherwise, the coordinate systems of the yaw manipulation portion 202 and the actuation manipulation portion 203 are described on the basis of a state in which the first handle 204 is located perpendicular to the connection portion 400 as illustrated in FIG. 2.

(Pitch, Yaw, and Cutting Motions of End Tool)

FIGS. 168 and 169 are views illustrating a process of performing an opening and closing motion in a state in which the end tool of the surgical instrument for electrocautery of FIG. 140 is yaw-rotated by +90°. In addition, FIGS. 170 and 171 are views illustrating a process of performing an opening and closing motion in a state in which the end tool of the surgical instrument for electrocautery of FIG. 140 is yaw-rotated by −90°.

As shown in FIGS. 168 to 171, the end tool of the surgical instrument for electrocautery according to the fourth embodiment of the present disclosure is formed to be able to normally perform an opening and closing motion, that is, an actuation motion even in a state in which the jaws are yaw-rotated by +90° or −90°.

FIGS. 172 and 173 are views illustrating a process of performing a cutting motion in a state in which the end tool of the surgical instrument for electrocautery of FIG. 140 is yaw-rotated by +90°.

As shown in FIGS. 172 and 173, the end tool of the surgical instrument for electrocautery according to the fourth embodiment of the present disclosure is formed to be able to normally perform a cutting motion even in a state in which the jaws are yaw-rotated by +90°.

FIGS. 174 and 175 are views illustrating a process of performing an opening and closing motion in a state in which the end tool of the surgical instrument for electrocautery of FIG. 140 is pitch-rotated by +90°. FIGS. 176 and 177 are views illustrating a process of performing an opening and closing motion in a state in which the end tool of the surgical instrument for electrocautery of FIG. 140 is pitch-rotated by −90°. In addition, FIG. 178 is a cut-away perspective view of the end tool of the surgical instrument for electrocautery of FIG. 176. In addition, FIGS. 179 and 180 are views illustrating a process of performing a cutting motion in a state in which the end tool of the surgical instrument for electrocautery of FIG. 140 is pitch-rotated by −90°.

As shown in FIGS. 174 to 180, the end tool of the surgical instrument for electrocautery according to the fourth embodiment of the present disclosure is formed to be able to normally perform a cutting motion even in a state in which the jaws are pitch-rotated by −90°.

Meanwhile, FIG. 181 is a view illustrating a state in which the jaws are pitch-rotated by −90° and simultaneously yaw-rotated by +90°, and FIGS. 182, 183, and 184 are perspective views illustrating a cutting motion of the end tool of the surgical instrument for electrocautery of FIG. 140 and illustrate a state of performing a cutting motion while the jaws are pitch-rotated by −90° and simultaneously yaw-rotated by +90°.

As shown in FIGS. 181 to 184, the end tool of the surgical instrument for electrocautery according to the fourth embodiment of the present disclosure is formed to be able to normally perform a cutting motion even in a state in which the jaws are pitch-rotated by −90° and simultaneously yaw-rotated by +90°.

First Modified Example of Fourth Embodiment

Hereinafter, an end tool 1200 of a surgical instrument according to a first modified example of the fourth embodiment of the present disclosure will be described. Here, the end tool 1200 of the surgical instrument according to the first modified example of the fourth embodiment of the present disclosure is different from the end tool (see 1100 in FIG. 140 or the like) of the surgical instrument according to the fourth embodiment of the present disclosure described above in that the configuration of an actuation hub 1290 is different. The configuration changed from the fourth embodiment as described above will be described in detail later.

FIGS. 185 and 186 are perspective views illustrating the end tool of the surgical instrument for electrocautery according to the first modified example of the fourth embodiment of the present disclosure. FIGS. 187 and 188 are plan views illustrating the end tool of the surgical instrument for electrocautery according to the first modified example of the fourth embodiment of the present disclosure. FIGS. 189 and 190 are views illustrating an actuation hub of the surgical instrument for electrocautery according to the first modified example of the fourth embodiment of the present disclosure.

Referring to FIGS. 185 to 190, the end tool 1200 of the first modified example of the fourth embodiment of the present disclosure includes a pair of jaws for performing a grip motion, that is, a first jaw 1201 and a second jaw 1202, and herein, each of the first jaw 1201 and the second jaw 1202 or a component encompassing the first jaw 1201 and the second jaw 1202 may be referred to as a jaw 1203.

Meanwhile, the end tool 1200 includes a plurality of pulleys including a pulley 1211, a pulley 1213, and a pulley 1214 that are associated with a rotational motion of the first jaw 1201. Meanwhile, the end tool 1200 includes a plurality of pulleys including a pulley 1221 associated with a rotational motion of the second jaw 1202.

In addition, the end tool 1200 of the first modified example of the fourth embodiment of the present disclosure may include a rotation shaft 1241, a rotation shaft 1243, and a rotation shaft 1244. Here, the rotation shaft 1241 may be inserted through an end tool hub 1260, and the rotation shaft 1243 and the rotation shaft 1244 may be inserted through a pitch hub 1250. The rotation shaft 1241, the rotation shaft 1243, and the rotation shaft 1244 may be arranged sequentially from a distal end 1204 toward a proximal end 1205 of the end tool 1200.

Further, the end tool 1200 of the first modified example of the fourth embodiment of the present disclosure may include the end tool hub 1260 and the pitch hub 1250.

The rotation shaft 1241 is inserted through the end tool hub 1260, and the pulley 1211 and the pulley 1221, which are axially coupled to the rotation shaft 1241, and at least some of the first jaw 1201 and the second jaw 1202 coupled the pulley 1211 and the pulley 1221 may be accommodated inside the end tool hub 1260.

Meanwhile, a first pitch pulley portion 1263a and a second pitch pulley portion 1263b, which serve as end tool pitch pulleys, may be formed at one end portion of the end tool hub 1260. A wire (see 303 of FIG. 146) and a wire 304 (see 304 of FIG. 146) are coupled to the first pitch pulley portion 1263a and the second pitch pulley portion 1263b, which serve as end tool pitch pulleys, and a pitch motion is performed while the end tool hub 1260 rotates around the rotation shaft 1243.

The rotation shaft 1243 and the rotation shaft 1244 may be inserted through the pitch hub 1250, and the pitch hub 1250 may be axially coupled to the end tool hub 1260 by the rotation shaft 1243. Accordingly, the end tool hub 1260 may be formed to be pitch-rotatable around the rotation shaft 1243 with respect to the pitch hub 1250.

Meanwhile, the end tool 1200 of the fourth embodiment of the present disclosure may further include components such as a first electrode 1251, a second electrode 1252, a guide tube 1271, and a blade 1275 in order to perform a cauterizing motion and a cutting motion. Here, components related to the driving of the blade, such as the guide tube 1271 and the blade 1275, may be collectively referred to as a blade assembly. Components for performing a cauterizing motion and a cutting motion in the present embodiment are substantially the same as those described in the fourth embodiment, and thus a detailed description thereof will be omitted herein.

The surgical instrument for electrocautery according to the first modified example of the fourth embodiment of the present disclosure may include a wire 301, a wire 302, a wire 303, a wire 304, a wire 305, a wire 306, and a blade wire 307, as in the fourth embodiment of the present disclosure described with reference to FIG. 140 or the like.

Hereinafter, the actuation hub 1290 of the first modified example of the fourth embodiment of the present disclosure will be described in more detail.

Referring to FIGS. 185 to 190, the actuation hub 1290 may be formed in the form of a box having a hollow therein. Here, a first coupling hole 1290a is formed in any one surface of the actuation hub 1290, specifically, a surface coming into contact with the first jaw 1201, and a second coupling hole 1290*b* may be formed in the other surface of the actuation hub 1290, specifically, a surface coming into contact with the second jaw 1202.

In this case, the first coupling hole 1290*a* may be formed to be offset to a certain degree in one direction from the center line in the X-axis direction. In addition, the second coupling hole 1290*b* may be formed by being offset to a certain degree in another one direction from the center line in the X-axis direction.

In other words, it may be said that the first coupling hole 1290*a* and the second coupling hole 1290*b* are not on the same line in the Z-axis direction but are formed to be offset to a certain degree.

In addition, the actuation hub 1290 is coupled to each of the first jaw 1201 and the second jaw 1202. In detail, a first actuation rotation shaft 1291 is inserted through the first jaw 1201 and the first coupling hole 1290*a* of the actuation hub 1290, so that the actuation hub 1290 and the first jaw 1201 are axially coupled. Further, a second actuation rotation shaft 1292 is inserted through the second jaw 1202 and the second coupling hole 1290B of the actuation hub 1290, so that the actuation hub 1290 and the second jaw 1202 are axially coupled.

Meanwhile, as described with reference to FIG. 154 or the like, a tube seating portion, a wire through-hole, and a blade accommodation portion are sequentially formed inside the actuation hub 1290, and the blade wire 307 may pass through the inside of the actuation hub 1290 to be connected to the blade 1275.

As described above, by providing the actuation hub 1290 to which the guide tube 1270 is coupled between the first jaw 1201 and the second jaw 1202, the guide tube 1270 may not be curved, or the angle at which the guide tube 1270 is curved may be reduced, even when the first jaw 1201 or the second jaw 1202 rotates around the first rotation shaft 1241 or the actuation rotation shaft 1245.

In detail, in a case in which the guide tube 1270 is directly coupled to the first jaw 1201 or the second jaw 1202, when the first jaw 1201 or the second jaw 1202 rotates, one end portion of the guide tube 1270 also rotates together with the first jaw 1201 or the second jaw 1202, causing the guide tube 1270 to be curved.

On the other hand, in a case in which the guide tube 1270 is coupled to the actuation hub 1290, which is independent of the rotation of the jaw 1203, as in the present embodiment, even when the first jaw 1201 or the second jaw 1202 rotates, the guide tube 1270 may not be curved, or the angle at which the guide tube 1270 is curved may be reduced even when the guide tube 1270 is curved.

That is, by changing the direct connection between the guide tube 1270 and the jaw 1203 by the actuation hub 1290 to an indirect connection, the degree to which the guide tube 1270 is curved by the rotation of the jaw 1203 may be reduced.

In particular, in the end tool 1200 of the first modified example of the fourth embodiment of the present disclosure, when the actuation hub 1290 is coupled to the first jaw 1201 and the second jaw 1202, the first actuation rotation shaft 1291 and the second actuation rotation shaft 1292 are not on the same line in the Z-axis direction but are offset from each other to a certain degree. Thus, when the first jaw 1201 and the second jaw 1202 perform an actuation motion, the first actuation rotation shaft 1291 and the second actuation rotation shaft 1292 form a kind of two-point support, thereby obtaining an effect of more stably performing an actuation motion.

Second Modified Example of Fourth Embodiment

Hereinafter, an end tool 1300 of a surgical instrument according to a second modified example of the fourth embodiment of the present disclosure will be described. Here, the end tool 1300 of the surgical instrument according to the second modified example of the fourth embodiment of the present disclosure is different from the end tool (see 1100 in FIG. 140 or the like) of the surgical instrument according to the fourth embodiment of the present disclosure described above in that the configuration of an actuation hub 1390 is different. The configuration changed from the fourth embodiment as described above will be described in detail later.

FIGS. 191 to 196 are views illustrating the end tool of the surgical instrument for electrocautery according to the second modified example of the fourth embodiment of the present disclosure. FIGS. 197 and 198 are views illustrating an actuation hub of the end tool of the surgical instrument for electrocautery of FIG. 191. FIG. 199 is a perspective view illustrating a second jaw pulley of the end tool of the surgical instrument for electrocautery of FIG. 191. FIGS. 200 and 201 are views illustrating the end tool of the surgical instrument for electrocautery of FIG. 191.

Referring to FIGS. 191 to 201, the end tool 1300 of the second modified example of the fourth embodiment of the present disclosure includes a pair of jaws for performing a grip motion, that is, a first jaw 1301 and a second jaw 1302, and herein, each of the first jaw 1301 and the second jaw 1302 or a component encompassing the first jaw 1301 and the second jaw 1302 may be referred to as a jaw 1303.

Meanwhile, the end tool 1300 includes a plurality of pulleys including a pulley 1311, a pulley 1313, and a pulley 1314 associated with a rotational motion of a first jaw 1301. Meanwhile, the end tool 1300 includes a plurality of pulleys including a pulley 1321 associated with a rotational motion of the second jaw 1302.

In addition, the end tool 1300 of the second modified example of the fourth embodiment of the present disclosure may include a rotation shaft 1341, a rotation shaft 1343, and a rotation shaft 1344. Here, the rotation shaft 1341 may be inserted through an end tool hub 1360, and the rotation shaft 1343 and the rotation shaft 1344 may be inserted through a pitch hub 1350.

In addition, the end tool 1300 of the second modified example of the fourth embodiment of the present disclosure may include the end tool hub 1360 and the pitch hub 1350.

Meanwhile, the end tool 1300 of the second modified example of the fourth embodiment of the present disclosure may further include components such as a first electrode 1351, a second electrode 1352, a guide tube 1371, and a blade 1375 in order to perform a cauterizing motion and a cutting motion.

The surgical instrument for electrocautery according to the second modified example of the fourth embodiment of the present disclosure may include a wire 301, a wire 302, a wire 303, a wire 304, a wire 305, a wire 306, and a blade wire 307, as in the fourth embodiment of the present disclosure described with reference to FIG. 140 or the like.

Since components of the present modified example described above are substantially the same as the components described in the fourth embodiment, a detailed description thereof will be omitted herein.

Hereinafter, the actuation hub 1390 of the second modified example of the fourth embodiment of the present disclosure will be described in more detail.

Referring to FIGS. 191 to 201, the actuation hub 1390 may be formed in the form of a box having a hollow therein.

Here, a first coupling hole 1390*a* is formed in any one surface of the actuation hub 1390, specifically, a surface coming into contact with the first jaw 1301, and a second coupling hole 1390*b* may be formed in the other surface of the actuation hub 1390, specifically, a surface coming into contact with the second jaw 1302.

In this case, the first coupling hole 1390*a* may be formed to be offset to a certain degree in one direction from the center line in the X-axis direction. In addition, the second coupling hole 1390*b* may be formed by being offset to a certain degree in another one direction from the center line in the X-axis direction.

In other words, it may be said that the first coupling hole 1390*a* and the second coupling hole 1390*b* are not on the same line in the Z-axis direction but are formed to be offset to a certain degree.

In addition, the actuation hub 1390 is coupled to each of the first jaw 1301 and the second jaw 1302. In detail, a first actuation rotation shaft 1391 is inserted through the first jaw 1301 and the first coupling hole 1390*a* of the actuation hub 1390, so that the actuation hub 1390 and the first jaw 1301 are axially coupled. Further, a second actuation rotation shaft 1392 is inserted through the second jaw 1302 and the second coupling hole 1390*b* of the actuation hub 1390, so that the actuation hub 1390 and the second jaw 1302 are axially coupled.

Meanwhile, as described with reference to FIG. 154 or the like, a tube seating portion, a wire through-hole, and a blade accommodation portion are sequentially formed inside the actuation hub 1390, and the blade wire 307 may pass through the inside of the actuation hub 1390 to be connected to the blade 1375.

In addition, a guide slit 1390*c* may be formed in any one surface of the actuation hub 1390 or in both surfaces thereof in a longitudinal direction thereof (i.e., the X-axis direction). In addition, a slit coupling portion 1321*c* formed on the pulley 1321 may be fitted into the guide slit 1390*c*, so that a linear movement of the pulley 1321 in the X-axis direction may be guided by the guide slit 1390*c*.

In detail, a shaft coupling portion 1321*a*, a jaw coupling portion 1321*b*, and the slit coupling portion 1321*c* may be formed on the pulley 1321. Here, the shaft coupling portion 1321*a* and the jaw coupling portion 1321*b* may be formed in the same manner as described in the fourth embodiment or the like. The slit coupling portion 1321*c* may be formed to protrude to a certain degree further from the shaft coupling portion 1321*a*. The above-described slit coupling portion 1321*c* is fitted into the guide slit 1390*c* of the actuation hub 1390.

Meanwhile, although not shown in the drawings, a slit coupling portion (not shown) may also be formed in the pulley 1311.

As described above, by providing the actuation hub 1390 to which the guide tube 1370 is coupled between the first jaw 1301 and the second jaw 1302, the guide tube 1370 may not be curved, or the angle at which the guide tube 1370 is curved may be reduced, even when the first jaw 1301 or the second jaw 1302 rotates around the first rotation shaft 1341 or the actuation rotation shaft 1345.

In detail, in a case in which the guide tube 1370 is directly coupled to the first jaw 1301 or the second jaw 1302, when the first jaw 1301 or the second jaw 1302 rotates, one end portion of the guide tube 1370 also rotates together with the first jaw 1301 or the second jaw 1302, causing the guide tube 1370 to be curved.

On the other hand, in a case in which the guide tube 1370 is coupled to the actuation hub 1390, which is independent of the rotation of the jaw 1303, as in the present embodiment, even when the first jaw 1301 or the second jaw 1302 rotates, the guide tube 1370 may not be curved, or the angle at which the guide tube 1370 is curved may be reduced even when the guide tube 1370 is curved.

That is, by changing the direct connection between the guide tube 1370 and the jaw 1303 by the actuation hub 1390 to an indirect connection, the degree to which the guide tube 1370 is curved by the rotation of the jaw 1303 may be reduced.

In particular, in the end tool 1300 of the second modified example of the fourth embodiment of the present disclosure, when the actuation hub 1390 is coupled to the first jaw 1301 and the second jaw 1302, the first actuation rotation shaft 1391 and the second actuation rotation shaft 1392 are not on the same line in the Z-axis direction but are offset to a certain degree. Thus, when the first jaw 1301 and the second jaw 1302 perform an actuation motion, the first actuation rotation shaft 1391 and the second actuation rotation shaft 1392 form a kind of two point support, thereby obtaining an effect of more stably performing an actuation motion.

In addition, in the end tool 1300 of the second modified example of the fourth embodiment of the present disclosure, the slit coupling portion 1321*c* formed on the pulley 1321 is fitted into the guide slit 1390*c* of the actuation hub 1390 so that the linear movement of the pulley 1321 in the X-axis direction may be guided by the guide slit 1390*c*. That is, when the first jaw 1301 and the second jaw 1302 perform an actuation motion, the first jaw 1301 and the second jaw 1302 move along the guide slit 1390*c* of the actuation hub 1390, thereby obtaining an effect of more stably performing the actuation motion.

Third Modified Example of Fourth Embodiment

Hereinafter, an end tool 1400 of a surgical instrument according to a third modified example of the fourth embodiment of the present disclosure will be described. Here, the end tool 1400 of the surgical instrument according to the third modified example of the fourth embodiment of the present disclosure is different from the end tool (see 1100 in FIG. 140 or the like) of the surgical instrument according to the fourth embodiment of the present disclosure described above in that the configuration of an actuation hub 1490 is different. The configuration changed from the fourth embodiment as described above will be described in detail later.

FIGS. 202 to 205 are views illustrating the end tool of the surgical instrument for electrocautery according to the third modified example of the fourth embodiment of the present disclosure. FIGS. 206 and 207 are views illustrating an actuation hub of the end tool of the surgical instrument for electrocautery of FIG. 202. FIG. 208 is a perspective view illustrating a second jaw pulley of the end tool of the surgical instrument for electrocautery of FIG. 202.

Referring to FIGS. 202 to 208, the end tool 1400 of the third modified example of the fourth embodiment of the present disclosure includes a pair of jaws for performing a grip motion, that is, a first jaw 1401 and a second jaw 1402, and herein, each of the first jaw 1401 and the second jaw 1402 or a component encompassing the first jaw 1401 and the second jaw 1402 may be referred to as a jaw 1403.

Meanwhile, the end tool 1400 includes a plurality of pulleys including a pulley 1411, a pulley 1413, and a pulley 1414 that are associated with a rotational motion of the first jaw 1401. Meanwhile, the end tool 1400 includes a plurality of pulleys including a pulley 1421 associated with a rotational motion of the second jaw 1402.

In addition, the end tool 1400 of the third modified example of the fourth embodiment of the present disclosure may include a rotation shaft 1441, a rotation shaft 1443, and a rotation shaft 1444. Here, the rotation shaft 1441 may be inserted through an end tool hub 1460, and the rotation shaft 1443 and the rotation shaft 1444 may be inserted through a pitch hub 1450.

In addition, the end tool 1400 of the third modified example of the fourth embodiment of the present disclosure may include the end tool hub 1460 and the pitch hub 1450.

Meanwhile, the end tool 1400 of the third modified example of the fourth embodiment of the present disclosure may further include components such as a first electrode 1451, a second electrode 1452, a guide tube 1471, and a blade 1475 in order to perform a cauterizing motion and a cutting motion.

The surgical instrument for electrocautery according to the third modified example of the fourth embodiment of the present disclosure may include a wire 301, a wire 302, a wire 303, a wire 304, a wire 305, a wire 306, and a blade wire 307, as in the fourth embodiment of the present disclosure described with reference to FIG. 140 or the like.

Since components of the present modified example described above are substantially the same as the components described in the fourth embodiment, a detailed description thereof will be omitted herein.

Hereinafter, the actuation hub 1490 of the third modified example of the fourth embodiment of the present disclosure will be described in more detail.

Referring to FIGS. 202 to 208, the actuation hub 1490 may be formed in the form of a box having a hollow therein.

Here, a first coupling hole 1490*a* is formed in any one surface of the actuation hub 1490, specifically, a surface coming into contact with the first jaw 1401, and a second coupling hole 1490*b* may be formed in the other surface of the actuation hub 1490, specifically, a surface coming into contact with the second jaw 1402.

Here, the first coupling hole 1490*a* and the second coupling hole 1490*b* may be located on the same line in the Z-axis direction.

In addition, the actuation hub 1490 is coupled to each of the first jaw 1401 and the second jaw 1402. In detail, a first actuation rotation shaft 1491 is inserted through the first jaw 1401 and the first coupling hole 1490*a* of the actuation hub 1490, so that the actuation hub 1490 and the first jaw 1401 are axially coupled. Further, a second actuation rotation shaft 1492 is inserted through the second jaw 1402 and the second coupling hole 1490*b* of the actuation hub 1490, so that the actuation hub 1490 and the second jaw 1402 are axially coupled.

Meanwhile, as described with reference to FIG. 154 or the like, a tube seating portion, a wire through-hole, and a blade accommodation portion are sequentially formed inside the actuation hub 1490, and the blade wire 307 may pass through the inside of the actuation hub 1490 to be connected to the blade 1475.

In addition, a guide slit 1490*c* may be formed in any one surface of the actuation hub 1490 or in both surfaces thereof in a longitudinal direction thereof (i.e., the X-axis direction). In addition, a slit coupling portion 1421*c* formed on the pulley 1421 may be fitted into the guide slit 1490*c*, so that a linear movement of the pulley 1421 in the X-axis direction may be guided by the guide slit 1490*c*.

In detail, a shaft coupling portion 1421*a*, a jaw coupling portion 1421*b*, and the slit coupling portion 1421*c* may be formed on the pulley 1421. Here, the shaft coupling portion 1421*a* and the jaw coupling portion 1421*b* may be formed in the same manner as described in the fourth embodiment or the like. The slit coupling portion 1421*c* may be formed to protrude to a certain degree further from the shaft coupling portion 1421*a*. The above-described slit coupling portion 1421*c* is fitted into the guide slit 1490*c* of the actuation hub 1490.

Meanwhile, although not shown in the drawings, a slit coupling portion (not shown) may also be formed in the pulley 1411.

As described above, by providing the actuation hub 1490 to which the guide tube 1470 is coupled between the first jaw 1401 and the second jaw 1402, the guide tube 1470 may not be curved, or the angle at which the guide tube 1470 is curved may be reduced, even when the first jaw 1401 or the second jaw 1402 rotates around the first rotation shaft 1441 or the actuation rotation shaft 1445.

In detail, in a case in which the guide tube 1470 is directly coupled to the first jaw 1401 or the second jaw 1402, when the first jaw 1401 or the second jaw 1402 rotates, one end portion of the guide tube 1470 also rotates together with the first jaw 1401 or the second jaw 1402, causing the guide tube 1470 to be curved.

On the other hand, in a case in which the guide tube 1470 is coupled to the actuation hub 1490, which is independent of the rotation of the jaw 1403, as in the present embodiment, even when the first jaw 1401 or the second jaw 1402 rotates, the guide tube 1470 may not be curved, or the angle at which the guide tube 1470 is curved may be reduced even when the guide tube 1470 is curved.

That is, by changing the direct connection between the guide tube 1470 and the jaw 1403 by the actuation hub 1490 to an indirect connection, the degree to which the guide tube 1470 is curved by the rotation of the jaw 1403 may be reduced.

In addition, in the end tool 1400 of the third modified example of the fourth embodiment of the present disclosure, the slit coupling portion 1421*c* formed on the pulley 1421 is fitted into the guide slit 1490*c* of the actuation hub 1490 so that the linear movement of the pulley 1421 in the X-axis direction may be guided by the guide slit 1490*c*. That is, when the first jaw 1401 and the second jaw 1402 perform an actuation motion, the first jaw 1401 and the second jaw 1402 move along the guide slit 1490*c* of the actuation hub 1490, thereby obtaining an effect of more stably performing the actuation motion.

Fourth Modified Example of Fourth Embodiment

Hereinafter, an end tool 1500 of a surgical instrument according to a fourth modified example of the fourth embodiment of the present disclosure will be described. Here, the end tool 1500 of the surgical instrument according to the fourth modified example of the fourth embodiment of the present disclosure is different from the end tool (see 1100 in FIG. 140 or the like) of the surgical instrument according to the fourth embodiment of the present disclosure described above in that the configuration of an actuation hub 1590 is different. The configuration changed from the fourth embodiment as described above will be described in detail later.

FIGS. 209 to 213 are views illustrating the end tool of the surgical instrument for electrocautery according to the fourth modified example of the fourth embodiment of the present disclosure. FIGS. 214 and 215 are views illustrating an actuation hub of the end tool of the surgical instrument for electrocautery of FIG. 209.

Referring to FIGS. 209 to 215, the end tool 1500 of the fourth modified example of the fourth embodiment of the present disclosure includes a pair of jaws for performing a grip motion, that is, a first jaw 1501 and a second jaw 1502, and herein, each of the first jaw 1501 and the second jaw 1502 or a component encompassing the first jaw 1501 and the second jaw 1502 may be referred to as a jaw 1503.

Meanwhile, the end tool 1500 includes a plurality of pulleys including a pulley 1511 and a pulley 1513, and a pulley 1514 that are associated with a rotational motion of the first jaw 1501. Meanwhile, the end tool 1500 includes a plurality of pulleys including a pulley 1521 associated with a rotational motion of the second jaw 1502.

In addition, the end tool 1500 of the fourth modified example of the fourth embodiment of the present disclosure may include a rotation shaft 1541, a rotation shaft 1543, and a rotation shaft 1544. Here, the rotation shaft 1541 may be inserted through an end tool hub 1560, and the rotation shaft 1543 and the rotation shaft 1544 may be inserted through a pitch hub 1550. The rotation shaft 1541, the rotation shaft 1543, and the rotation shaft 1544 may be arranged sequentially from a distal end 1504 toward a proximal end 1505 of the end tool 1500.

In addition, the end tool 1500 of the fourth modified example of the fourth embodiment of the present disclosure may include the end tool hub 1560 and the pitch hub 1550.

The rotation shaft 1541 is inserted through the end tool hub 1560, and the pulley 1511 and the pulley 1521, which are axially coupled to the rotation shaft 1541, and at least some of the first jaw 1501 and the second jaw 1502 coupled the pulley 1511 and the pulley 1521 may be accommodated inside the end tool hub 1560.

Meanwhile, a first pitch pulley portion 1563a and a second pitch pulley portion 1563b, which serve as end tool pitch pulleys, may be formed at one end portion of the end tool hub 1560. A wire (see 303 of FIG. 146) and a wire 304 (see 304 of FIG. 146) are coupled to the first pitch pulley portion 1563a and the second pitch pulley portion 1563b, which serve as end tool pitch pulleys, and a pitch motion is performed while the end tool hub 1560 rotates around the rotation shaft 1543.

The rotation shaft 1543 and the rotation shaft 1544 may be inserted through the pitch hub 1550, and the pitch hub 1550 may be axially coupled to the end tool hub 1560 by the rotation shaft 1543. Accordingly, the end tool hub 1560 may be formed to be pitch-rotatable around the rotation shaft 1543 with respect to the pitch hub 1550.

Meanwhile, the end tool 1500 of the fourth modified example of the fourth embodiment of the present disclosure may further include components such as a first electrode 1551, a second electrode 1552, a guide tube 1571, and a blade 1575 in order to perform a cauterizing motion and a cutting motion. Here, components related to the driving of the blade, such as the guide tube 1571 and the blade 1575, may be collectively referred to as a blade assembly. Components for performing a cauterizing motion and a cutting motion in the present embodiment are substantially the same as those described in the fourth embodiment, and thus a detailed description thereof will be omitted herein.

The surgical instrument for electrocautery according to the fourth modified example of the fourth embodiment of the present disclosure may include a wire 301, a wire 302, a wire 303, a wire 304, a wire 305, a wire 306, and a blade wire 307, as in the fourth embodiment of the present disclosure described with reference to FIG. 140 or the like.

Hereinafter, the actuation hub 1590 of the fourth modified example of the fourth embodiment of the present disclosure will be described in more detail.

Referring to FIGS. 209 to 215, the actuation hub 1590 may be formed in the form of a box having a hollow therein. Here, a first coupling hole 1590a is formed in any one surface of the actuation hub 1590, specifically, a surface coming into contact with the first jaw 1501, and a second coupling hole 1590b may be formed in the other surface of the actuation hub 1590, specifically, a surface coming into contact with the second jaw 1502. Here, the first coupling hole 1590a and the second coupling hole 1590b may be disposed on the same line in the Z-axis direction.

In addition, the actuation hub 1590 is coupled to each of the first jaw 1501 and the second jaw 1502. In detail, a first actuation rotation shaft 1591 is inserted through the first jaw 1501 and the first coupling hole 1590a of the actuation hub 1590, so that the actuation hub 1590 and the first jaw 1501 are axially coupled. Further, a second actuation rotation shaft 1592 is inserted through the second jaw 1502 and the second coupling hole 1590b of the actuation hub 1590, so that the actuation hub 1590 and the second jaw 1502 are axially coupled.

Meanwhile, as described with reference to FIG. 154 or the like, a tube seating portion, a wire through-hole, and a blade accommodation portion are sequentially formed inside the actuation hub 1590, and the blade wire 307 may pass through the inside of the actuation hub 1590 to be connected to the blade 1575.

As described above, by providing the actuation hub 1590 to which the guide tube 1570 is coupled between the first jaw 1501 and the second jaw 1502, the guide tube 1570 may not be curved, or the angle at which the guide tube 1570 is curved may be reduced, even when the first jaw 1501 or the second jaw 1502 rotates around the first rotation shaft 1541 or the actuation rotation shaft 1545.

In detail, in a case in which the guide tube 1570 is directly coupled to the first jaw 1501 or the second jaw 1502, when the first jaw 1501 or the second jaw 1502 rotates, one end portion of the guide tube 1570 also rotates together with the first jaw 1501 or the second jaw 1502, causing the guide tube 1570 to be curved.

On the other hand, in a case in which the guide tube 1570 is coupled to the actuation hub 1590, which is independent of the rotation of the jaw 1503, as in the present embodiment, even when the first jaw 1501 or the second jaw 1502 rotates, the guide tube 1570 may not be curved, or the angle at which the guide tube 1570 is curved may be reduced even when the guide tube 1570 is curved.

That is, by changing the direct connection between the guide tube 1570 and the jaw 1503 by the actuation hub 1590 to an indirect connection, the degree to which the guide tube 1570 is curved by the rotation of the jaw 1503 may be reduced.

As such, the present disclosure has been described with reference to the embodiments described with reference to the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

Advantageous Effects of Disclosure

According to the present disclosure, a manipulation direction of a manipulation portion by an operator and an operating direction of an end tool are intuitively identical to each other, so that the operator's convenience can be improved, and the accuracy, reliability and speed of surgery can be improved.

MODE OF DISCLOSURE

Figure 1E:
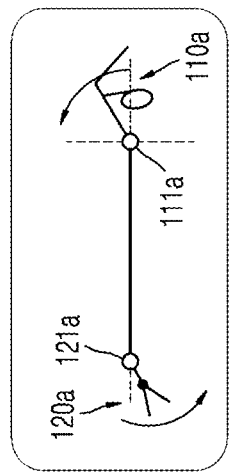
FIG. 1E is a conceptual diagram of a pitch motion of a surgical instrument according to the present disclosure.
Figure 1F:
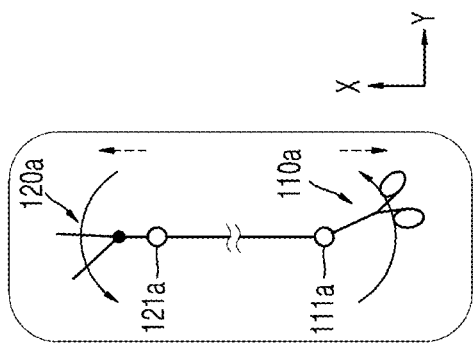
FIG. 1F is a conceptual diagram of a yaw motion thereof.
Figure 1C:
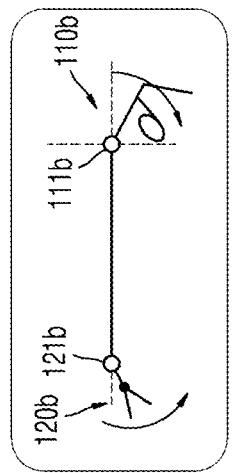
FIG. 1C is a conceptual diagram of a pitch motion of another conventional surgical instrument.
Figure 1D:
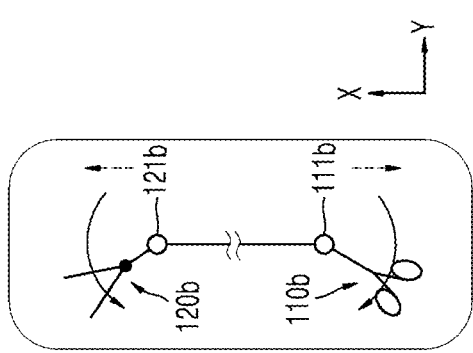
FIG. 1D is a conceptual diagram of a yaw motion thereof.
Figure 1A:
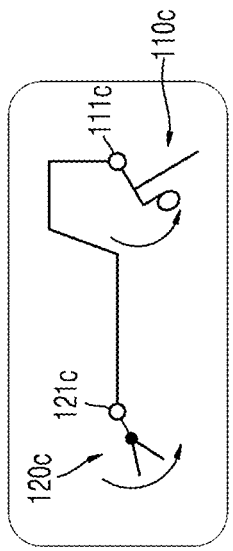
FIG. 1A is a conceptual diagram of a pitch motion of a conventional surgical instrument.
Figure 1B:
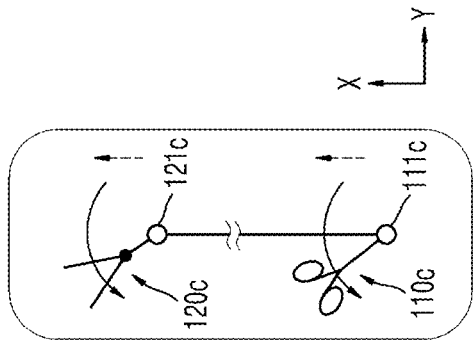
FIG. 1B is a conceptual diagram of a yaw motion thereof.

As the present disclosure allows for various changes and numerous embodiments, example embodiments will be illustrated in the drawings and described in detail. However, this is not intended to limit the present disclosure to particular modes of practice, and it is to be appreciated that all modifications, equivalents, and/or alternatives that do not depart from the spirit and technical scope are encompassed in the disclosure. In the description of embodiments, certain detailed explanations of the related art are omitted when they are deemed as unnecessarily obscuring the essence of the present disclosure.

While such terms as "first," "second," etc., may be used to describe various components, such components must not be limited by the above terms. The above terms are used only to distinguish one component from another.

The terms used in the present application are merely used to describe example embodiments, and are not intended to limit the present disclosure. As used herein, the singular forms "a," "an" and "the" are intended to include the plural forms as well, unless the context clearly indicates otherwise. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, embodiments of the present disclosure are described in detail with reference to the attached drawings. Like or corresponding reference numerals in the drawings denote like elements, and any redundant descriptions thereon will be omitted.

In addition, in describing various embodiments of the present disclosure, each embodiment does not have to be interpreted or practiced independently, and It should be understood that the technical concepts described in each embodiment may be interpreted or implemented in combination with other embodiments described individually.

In the surgical instrument for electrocautery according to the present disclosure, with respect to one or more motions from a pitch motion, a yaw motion, and an actuation motion, when a manipulation portion is rotated in one direction, an end tool may rotate in a direction intuitively the same as the manipulation direction of the manipulation portion.

(a) of FIG. 1 is a conceptual diagram of pitch motion of a conventional surgical instrument, and (b) of FIG. 1 is a conceptual diagram of yaw motion.

With reference to (a) of FIG. 1, in performing a pitch motion of a conventional surgical instrument, with an end tool 120a formed in front of a rotation center 121a of the end tool 120a and a manipulation portion 110a formed behind a rotation center 111a of the manipulation portion 110a, when the manipulation portion 110a is rotated in the clockwise direction, the end tool 120a may also be rotated in the clockwise direction, and when the manipulation portion 110a is rotated in the counterclockwise direction, the end tool 120a may also be rotated in the counterclockwise direction. With reference to (b) of FIG. 1, in performing a yaw motion of a conventional surgical instrument, with the end tool 120a formed in front of the rotation center 121a of the end tool 120a and the manipulation portion 110a formed behind the rotation center 111a of the manipulation portion 110a, when the manipulation portion 110a is rotated in the clockwise direction, the end tool 120a may also be rotated in the clockwise direction, and when the manipulation portion 110a is rotated in the counterclockwise direction, the end tool 120a may also be rotated in the counterclockwise direction. In this case, from the viewpoint of left and right sides of a user, when the user moves the manipulation portion 110a to the left, the end tool 120a may move to the right, and when the user moves the manipulation portion 110a to the right, the end tool 120a may move to the left. As a result, as the user manipulation direction is opposite to the end tool operation direction, the user may make a mistake, and have difficulty in manipulating the instrument.

(c) of FIG. 1 is a conceptual diagram of pitch motion of another conventional surgical instrument, and (d) of FIG. 1 is a conceptual diagram of yaw motion.

With reference to (c) of FIG. 1, some of the conventional surgical instruments may be formed in a mirror-symmetrical manner, and in performing a pitch motion, in a state where an end tool 120b is formed in front of a rotation center 121b of the end tool 120b, and a manipulation portion 110b is formed behind a rotation center 111b of the manipulation portion 110b, when the manipulation portion 110b is rotated in the clockwise direction, the end tool 120b may rotate in the counterclockwise direction, and when the manipulation portion 110b is rotated in the counterclockwise direction, the end tool 120b may rotate in the clockwise direction. In this case, from the viewpoint of rotation direction of the manipulation portion 110b and the end tool 120b, a rotation direction in which a user rotates the manipulation portion 110b may be opposite to a resulting rotation direction of the end tool 120b. Not only this may result in causing confusion about the manipulation direction to a user, but also movements of joints are not intuitive, which may lead to a mistake. In addition, with reference to (d) FIG. 1, in performing a yaw motion, in a state where the end tool 120b is formed in front of the rotation center 121b of the end tool 120b, and the manipulation portion 110b is formed behind the rotation center 111b of the manipulation portion 110b, when the manipulation portion 110b is rotated in the clockwise direction, the end tool 120b may rotate in the counterclockwise direction, and when the manipulation portion 110b is rotated in the counterclockwise direction, the end tool 120b may rotate in the clockwise direction. In this case, from the viewpoint of rotation direction of the manipulation portion 110b and the end tool 120b, a rotation direction in which a user rotates the manipulation portion 110b may be opposite to a resulting rotation direction of the end tool 120b. Not only this may result in causing confusion about the manipulation direction to a user, but also movements of joints are not intuitive, which may lead to a mistake. As such, in the pitch or yaw manipulation by a user of the conventional surgical instruments, there may be a discrepancy between the user manipulation direction and the operation direction of the end tool in terms of rotation direction or left and right direction. This is due to a configuration difference between the end tool and the manipulation portion in the joint configuration of the conventional surgical instruments. That is, the end tool may be formed in front of the rotation center of the end tool, whereas the manipulation portion may be formed behind the rotation center of the manipulation portion. To overcome such issue, in the surgical instrument according to an embodiment of the present disclosure shown in (c) and (f) of FIG. 1, an end tool 120c may be formed in front of a rotation center 121c of the end tool 120c, and a manipulation portion 110c may also be formed in front of a rotation center 111c of the manipulation portion 110c so that motions of the manipulation portion 110c and the end tool 120c are intuitively matched. In other words, unlike the existing examples of a configuration in which a manipulation portion approaches a user with respect to its joint (i.e., away from an end tool) as shown in (a), (b), (c), (d) of FIG. 1, in the surgical instrument according to an embodiment shown in (c) and (f) of FIG. 1, at least a part of the manipulation portion may become closer to the end tool than the joint of the manipulation portion in more than one moments during a manipulation process.

In other words, in the case of the conventional surgical instruments shown in (a), (b), (c), and (d) of FIG. 1, as the end tool may be formed in front of its rotation center whereas the manipulation portion may be formed behind its rotation center, the end tool of which front portion moves when its rear portion is fixed may move through a motion of the manipulation portion of which rear portion moves when its front portion is fixed, which is an intuitively unmatching structure. For this reason, a discrepancy in an aspect of left and right direction or an aspect of rotation direction in manipulation of a manipulation portion and motion of an end tool may occur, causing confusion to a user, and the manipulation of the manipulation portion may not be intuitively and quickly performed, which may lead to a mistake. On the contrary, in a surgical instrument according to an embodiment, as both of an end tool and a manipulation portion move based on rotation centers formed behind the end tool and the manipulation portion, respectively, structurally speaking, the motions thereof may intuitively match. In other words, as a moving portion of the end tool moves based on its rotation center formed therebehind, and similarly, a moving portion of the manipulation portion also moves based on its rotation center formed therebehind, structurally, the motions thereof may match intuitively. According to the foregoing, the user may intuitively and quickly control the direction of the end tool, and the possibility of causing a mistake may be significantly reduced. Hereinafter, a detailed mechanism enabling such function will be described.

First Embodiment of a Surgical Instrument for Electrocautery

Figure 2:
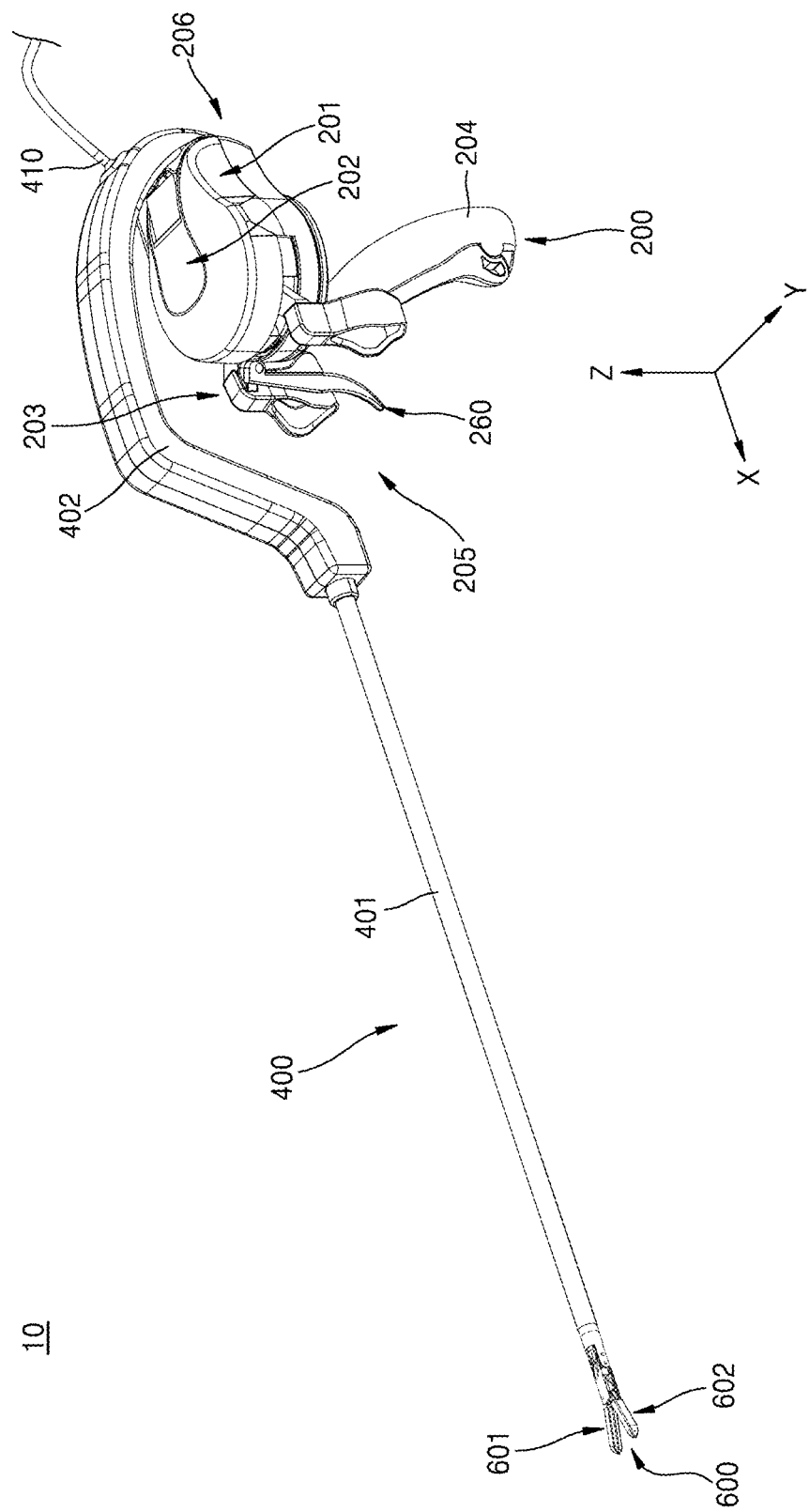
FIG. 2 is a perspective view illustrating a surgical instrument for electrocautery according to a first embodiment of the present disclosure.
Figure 5:
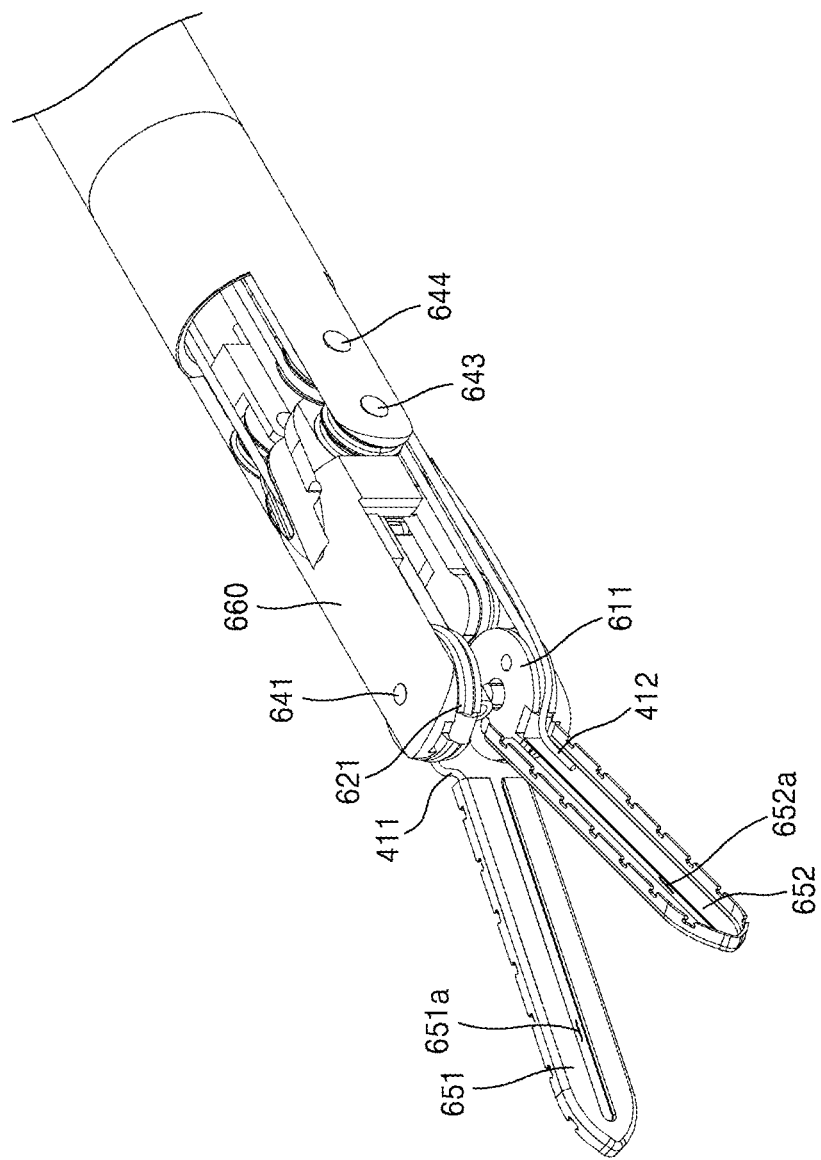
Figure 6:
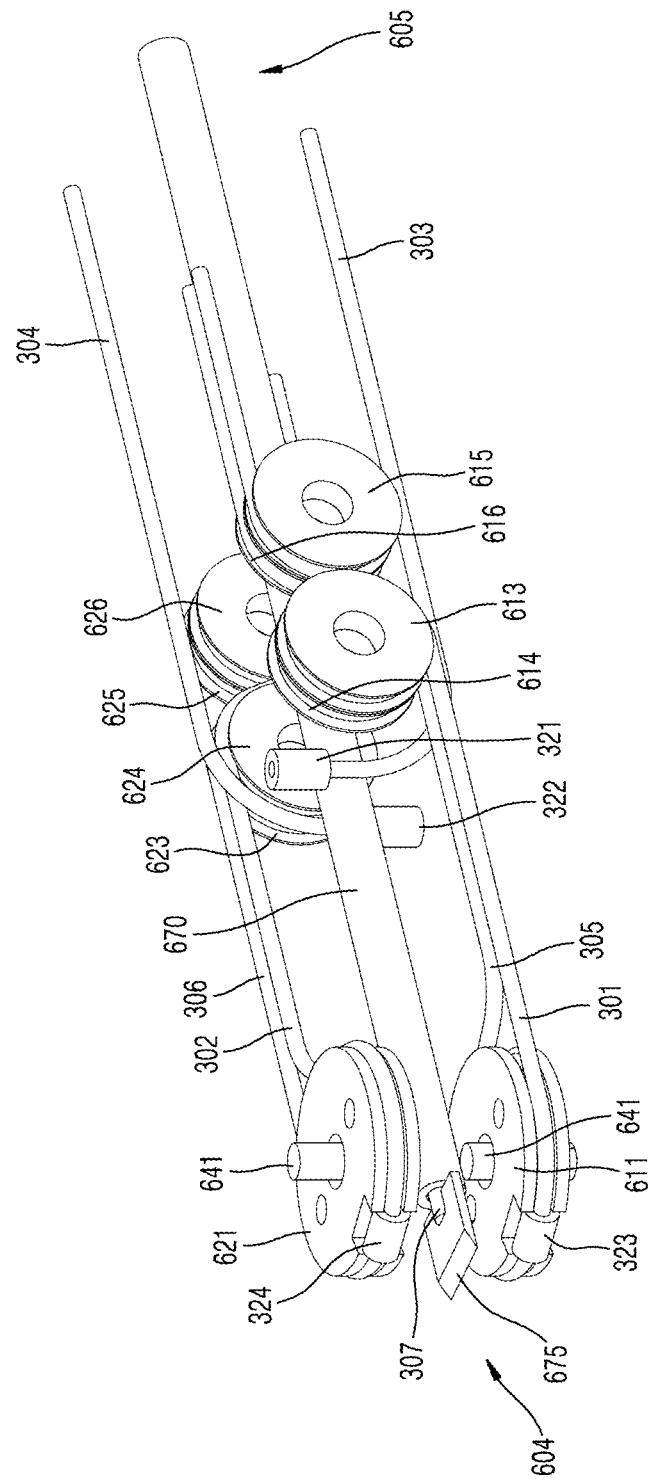
Figure 7:
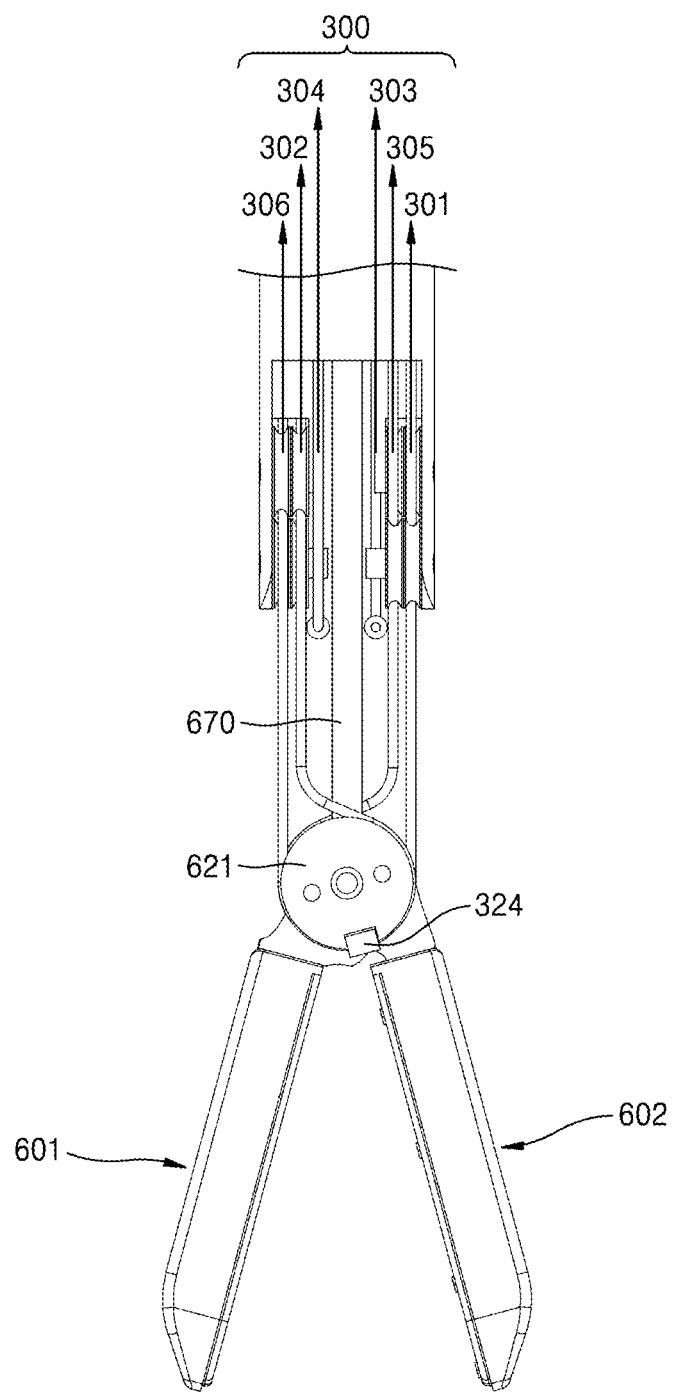
FIGS. 7 and 8 are plan views illustrating the end tool of the surgical instrument for electrocautery of FIG. 2.
Figure 8:
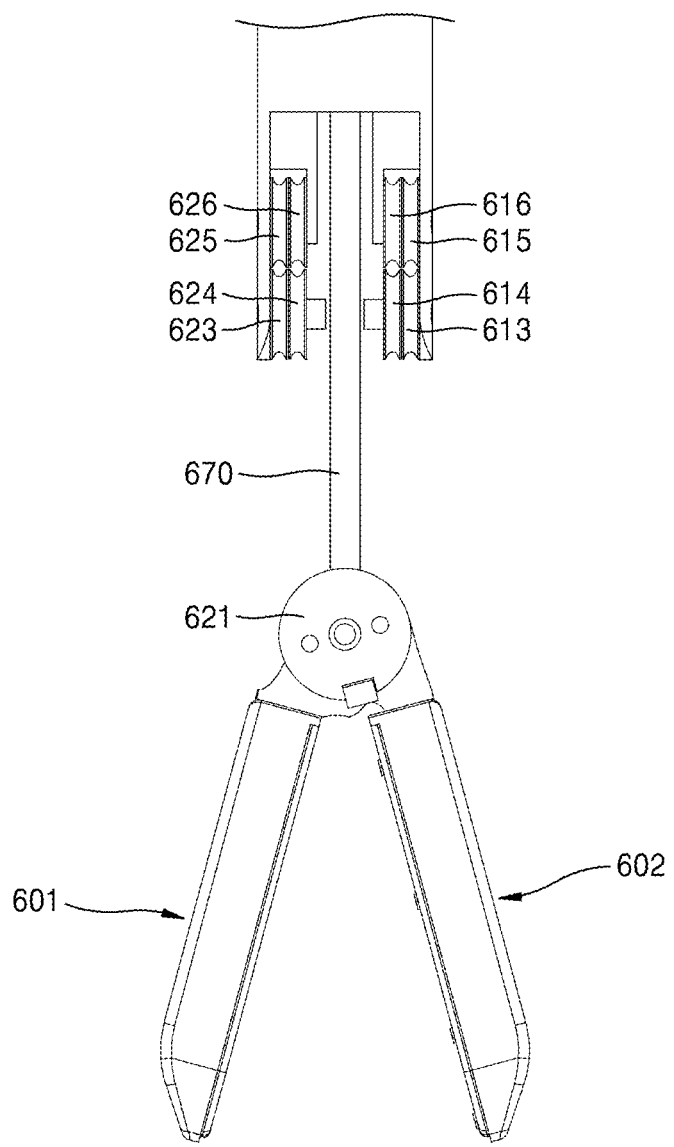
Figure 9:
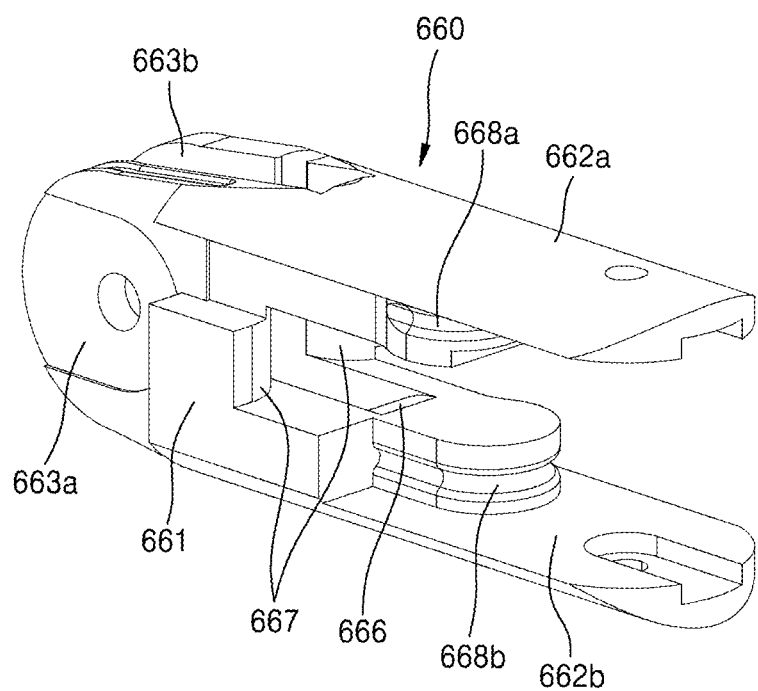
FIG. 9 is a perspective view illustrating an end tool hub of the surgical instrument for electrocautery of FIG. 2.
Figure 10:
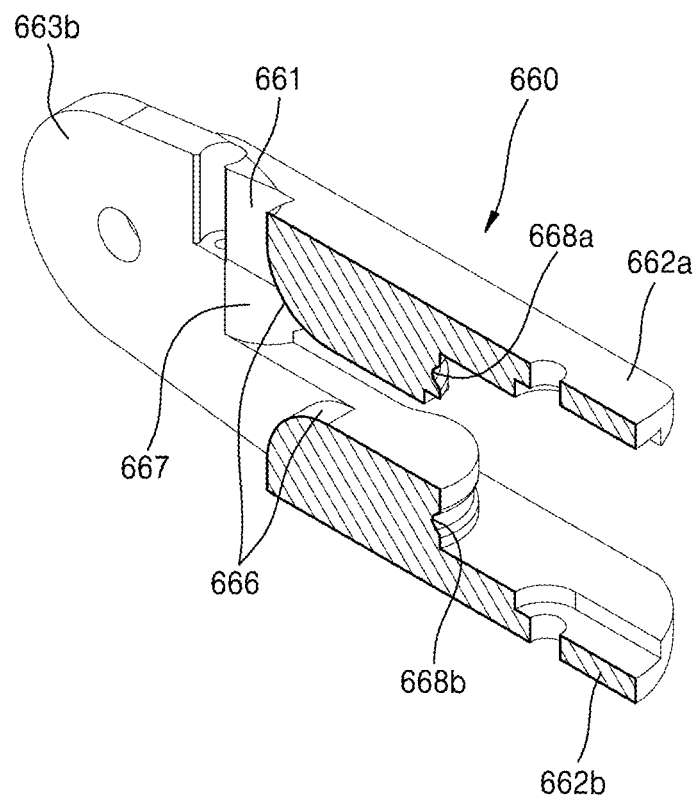
FIGS. 10 and 11 are cut-away perspective views of the end tool hub of FIG. 9.
Figure 11:
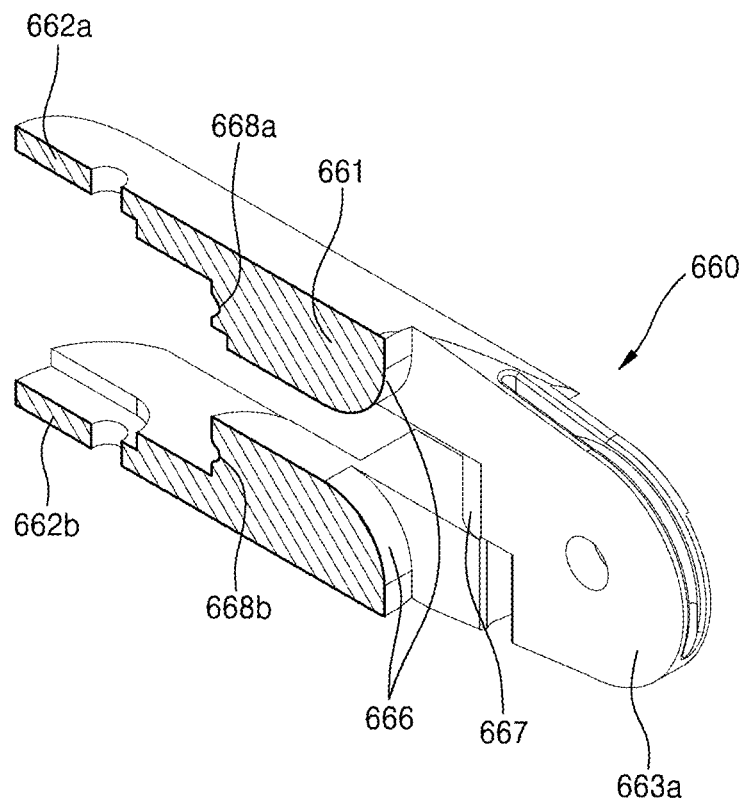
Figure 12:
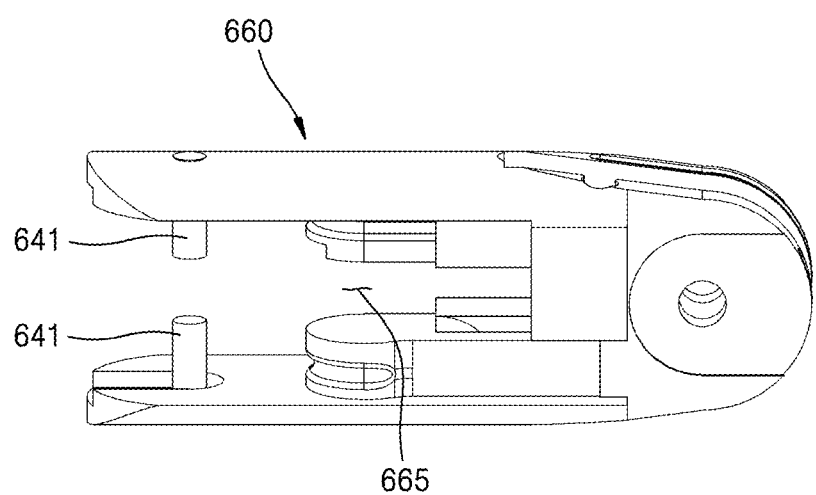
FIGS. 12 and 13 are perspective views illustrating the end tool hub of FIG. 9.
Figure 13:
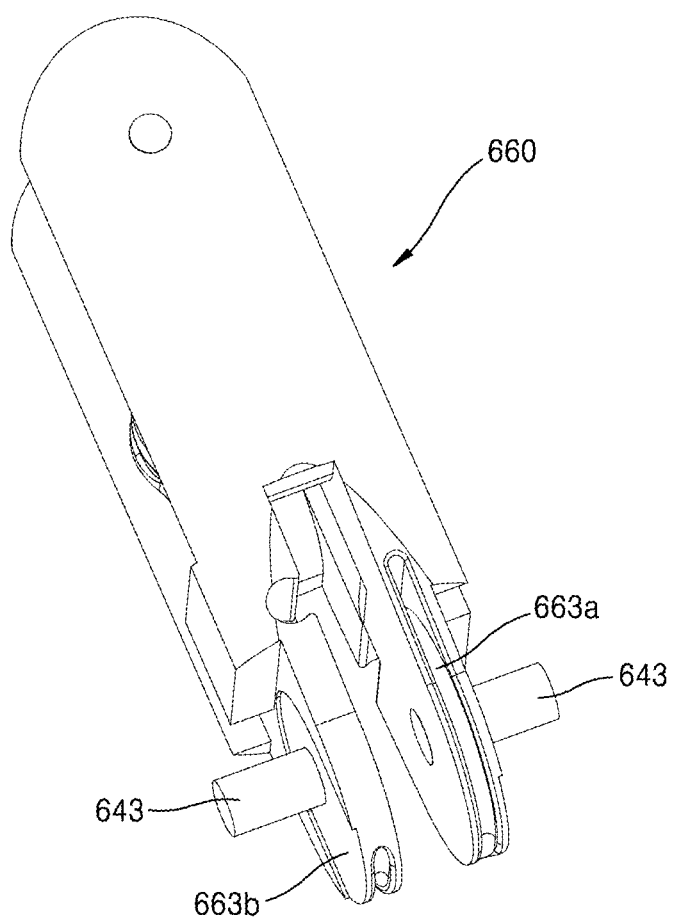
Figure 14:
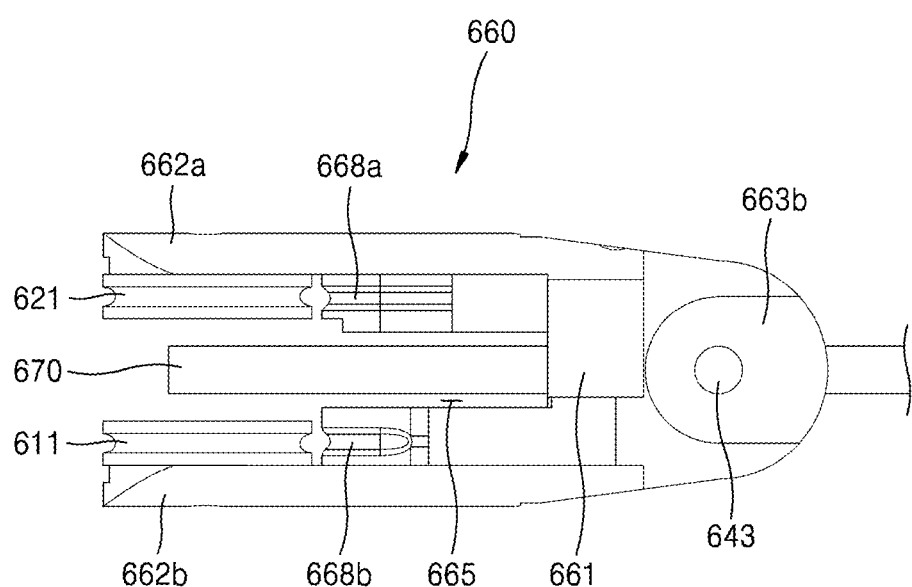
FIG. 14 is a side view illustrating the end tool hub of FIG. 9 and a guide tube.
Figure 15:
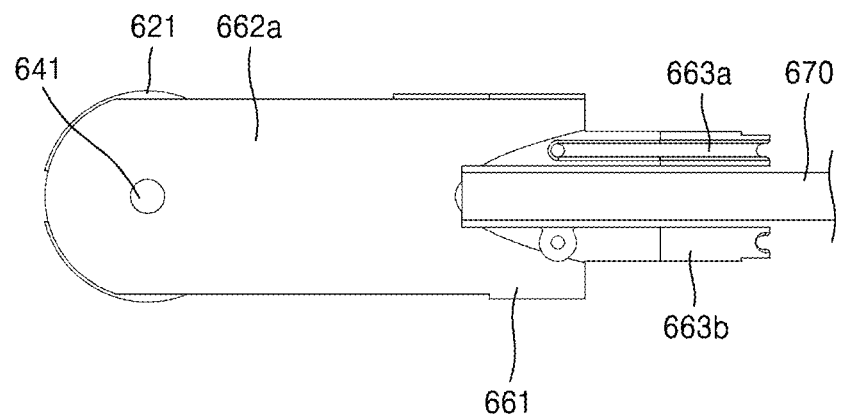
FIG. 15 is a plan view illustrating the end tool hub of FIG. 9 and the guide tube.
Figure 16:
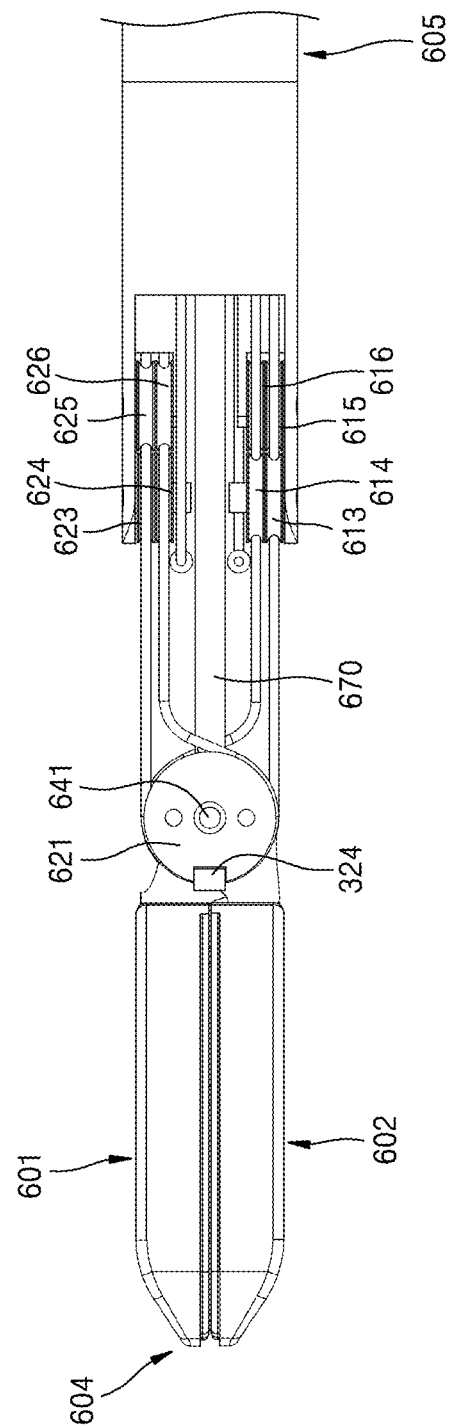
FIGS. 16 and 17 are plan views illustrating an opening and closing motion of the end tool of the surgical instrument for electrocautery of FIG. 2.
Figure 17:
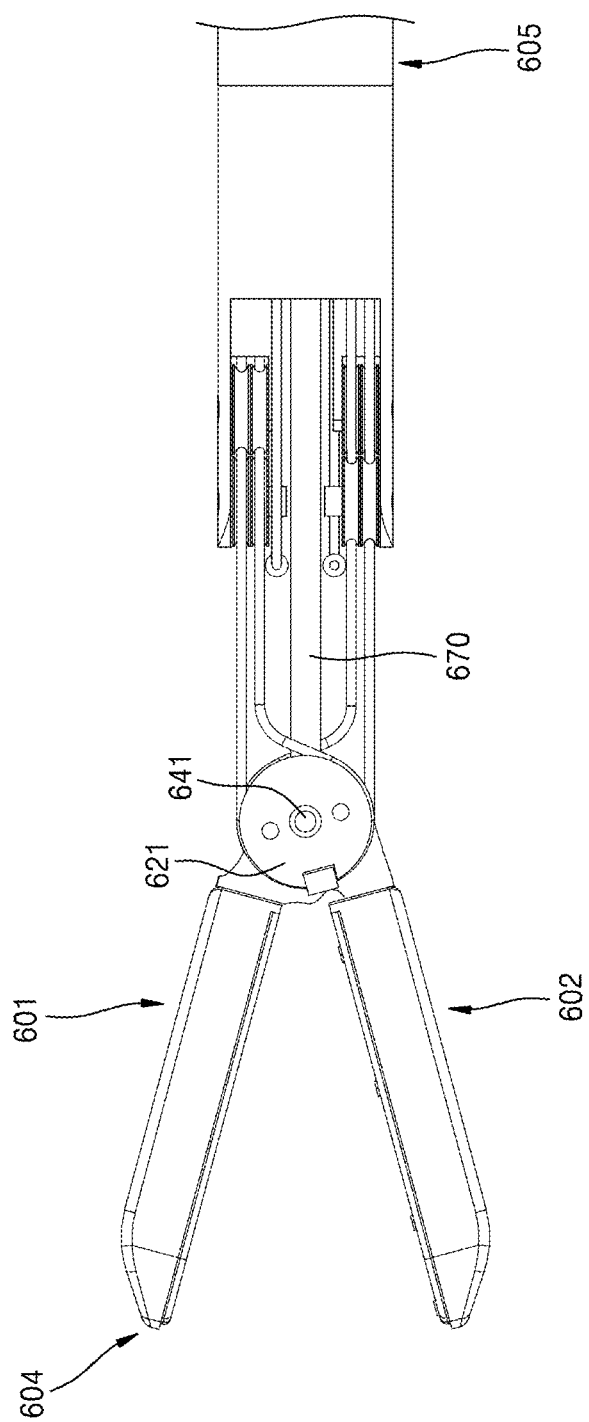

FIG. 2 is a perspective view illustrating a surgical instrument for electrocautery according to a first embodiment of the present disclosure. FIGS. 3, 4, 5, and 6 are perspective views illustrating an end tool of the surgical instrument for electrocautery of FIG. 2. FIGS. 7 and 8 are plan views illustrating the end tool of the surgical instrument for electrocautery of FIG. 2. FIG. 9 is a perspective view illustrating an end tool hub of the surgical instrument for electrocautery of FIG. 2. FIGS. 10 and 11 are cut-away perspective views of the end tool hub of FIG. 9. FIGS. 12 and 13 are perspective views illustrating the end tool hub of FIG. 9. FIG. 14 is a side view illustrating the end tool hub of FIG. 9 and a guide tube. FIG. 15 is a plan view illustrating the end tool hub of FIG. 9 and the guide tube. FIGS. 16 and 17 are plan views illustrating an opening and closing motion of the end tool of the surgical instrument for electrocautery of FIG. 2. First, with reference to FIG. 2, the electric cauterization surgical instrument 10 according to the first embodiment may include an end tool 600, a manipulation portion 200, a power transmission portion 300, and a connection portion 400.

Here, the connection portion 400 may be formed in the shape of a hollow shaft, and one or more wires and electric wires may be accommodated therein. As the manipulation portion 200 is coupled to one end of the connection portion 400, and the end tool 600 is coupled to the other end, the connection portion 400 may connect the manipulation portion 200 to the end tool 600. The connection portion 400 of the electric cauterization surgical instrument 10 according to the first embodiment may include a straight portion 401 and a curved portion 402. The straight portion 401 may be formed at a part of the connection portion 400 to which the end tool 600 is coupled, and the curved portion 402 may be formed at another part of the connection portion 400 to which the manipulation portion 200 is coupled. As such, as the end of the connection portion 400 coupled to the manipulation portion 200 is curved, a pitch manipulation portion 201, a yaw manipulation portion 202, and an actuation manipulation portion 203 may be arranged on an extension line of the end tool 600 or adjacent to the extension line of the end tool 600. In other words, at least a part of the pitch manipulation portion 201 and the yaw manipulation portion 202 may be accommodated in a concave portion formed by the curved portion 402. According to the shape of the curved portion 402 described above, the shape and motion of the manipulation portion 200 and the end tool 600 may match each other more intuitively.

Meanwhile, a plane on which the curved portion 402 is formed may be a pitch plane which is substantially the same as the XZ plane of FIG. 2. As such, as the curved portion 402 is formed on the plane substantially identical to the XZ plane, interference between the manipulation portions may be reduced. For intuitive operation of the end tool 600 and the manipulation portion 200, the plane may be configured otherwise in addition to the foregoing (i.e., the XZ plane).

Meanwhile, a connector 410 may be formed at the curved portion 402. The connector 410 may be connected to an external power supply (not illustrated), and the connector 410 may be connected to a jaw 603 through electric wires 411 and 412 to transfer electrical energy supplied from the external power supply (not illustrated) to the jaw 603. The connector 410 may be of a bipolar type having two electrodes, or the connector 410 may be of a monopolar type having one electrode.

The manipulation portion 200 may be formed at one end of the connection portion 400 and may include an interface which can be directly manipulated by a doctor, e.g., an interface in the shape of a pincer, a stick, a lever, etc. When the doctor manipulates the interface, the end tool 600, which is connected to the interface and inserted into the body of a patient, may be operated and perform a surgery. Here, although FIG. 2 illustrates that the manipulation portion 200 is formed in the shape of a handle which may be rotated while fingers are inserted, the present disclosure is not limited thereto, and various types of manipulation portions connected to the end tool 600 and manipulating the end tool 600 may be applicable.

The end tool 600 may be formed at the other end of the connection portion 400 and may be inserted into a body of a patient to perform operations required for a surgery. As an example of the end tool 600, a pair of jaws 603 for performing a grip motion may be used as illustrated in FIG. 2. However, the technical concepts of the present disclosure are not limited thereto, and various other surgical instruments may be used as the end tool 600. For example, a one-armed cautery may be used as the end tool 600. As the end tool 600 is connected to the manipulation portion 200 by the power transmission portion 300, the end tool 600 may receive driving power of the manipulation portion 200 through the power transmission portion 300 and perform motions required for a surgery, such as a grip motion, a cutting motion, a suturing motion, etc.

Here, the end tool 600 of the electric cauterization surgical instrument 10 according to the first embodiment may be formed to be rotatable in at least one direction, and for example, the end tool 600 may be formed to perform a yaw movement and an actuation movement around the Z-axis of FIG. 2 simultaneously with performing a pitch movement around the Y-axis of FIG. 2.

Each of the pitch, yaw, and actuation motions used in the present disclosure are defined as follows.

First, the pitch motion may refer to a motion that the end tool 600 rotates up and down with respect to a direction in which the connection portion 400 extends (i.e., the X-axis direction of FIG. 2), that is, a movement of rotating around the Y-axis of FIG. 2. In other words, the pitch motion may refer to a movement that the end tool 600 extending from the connection portion 400 in the direction in which the connection portion 400 extends (i.e., the X-axis direction in FIG. 2) rotates up and down around the Y-axis with respect to the connection portion 400.

Next, the yaw motion may refer to a motion that the end tool 600 rotates left and right with respect to the direction in which the connection portion 400 extends (i.e., the X-axis direction of FIG. 2), that is, a motion of rotating around the Z-axis of FIG. 2. In other words, the yaw motion may refer to a movement that the end tool 600 extending from the connection portion 400 in the direction in which the connection portion 400 extends (i.e., the X-axis direction in FIG. 2) rotates left and right around the Z-axis with respect to the connection portion 400. That is, the yaw motion means a movement that the two jaws 603 formed at the end tool 600 rotate around the Z-axis in the same direction.

The actuation motion may refer to a motion that the end tool 600 rotates around the same rotation shaft as in the yaw motion or a rotation shaft that is parallel to that in the yaw motion, or and two jaws 603 rotate in opposite directions by which the jaws 603 are closed together or opened up. That is, the actuation motion may refer to a movement that the two jaws 603 formed at the end tool 600 rotate in opposite directions around the Z-axis. In an embodiment, the actuation motion may refer to a motion in which, while one of the jaws is stopped, the other jaw rotates with respect to the jaw that is stopped. That is, the actuation motion may refer to a motion in which one jaw rotates with respect to the other jaw.

The power transmission portion 300 may transfer the driving power of the manipulation portion 200 to the end tool 600 by connecting the manipulation portion 200 to the end tool 600, and may include a plurality of wires, pulleys, links, joints, gears, etc.

The end tool 600, the manipulation portion 200, the power transmission portion 300, etc. of the electric cauterization surgical instrument 10 of FIG. 2 will be described in detail later.

(Intuitive Driving)

Hereinafter, the intuitive driving of the electric cauterization surgical instrument 10 of the present disclosure is described.

First, a user may hold with his or her palm and rotate a first handle 204 around the Y-axis to perform the pitch motion, and may rotate the first handle 204 around the Z-axis to perform the yaw motion. In addition, the user may insert his or her thumb and index finger into a first actuation extension portion and/or a second actuation extension portion formed in the shape of a handle at one end of the actuation manipulation portion 203 and manipulate the actuation manipulation portion 203 to perform the actuation motion.

In the electric cauterization surgical instrument 10 according to the first embodiment of the present disclosure, when the manipulation portion 200 rotates in one direction with respect to the connection portion 400, the end tool 600 may rotate in a direction intuitively the same as a manipulation direction of the manipulation portion 200. In other words, when the first handle 204 of the manipulation portion 200 rotates in one direction, the end tool 600 may also rotate in a direction intuitively the same as the aforementioned direction to perform a pitch motion or a yaw motion. Here, the intuitively the same direction may indicate that the moving direction of a finger of a user holding the manipulation portion 200 is substantially the same as the moving direction of an end portion of the end tool 600. The same direction may not be a perfectly matching direction on three-dimensional (3D) coordinates. For example, the sameness of the direction may be understood as a certain degree of sameness, with which, when the finger of the user moves to the left, the end portion of the end tool 600 may also move to the left, and when the finger of the user moves downwards, the end portion of the end tool 600 may also move downwards.

To this end, in the electric cauterization surgical instrument 10 according to the first embodiment, the manipulation portion 200 and the end tool 600 may be formed in the same direction with respect to a plane perpendicular to the extension axis (the X-axis) of the connection portion 400. That is, when seen based on the YZ plane of FIG. 2, the manipulation portion 200 may be formed to extend in the +X-axis direction, and at the same time, the end tool 600 may also be formed to extend in the +X-axis direction. In other words, the formation direction of the end tool 600 at one end of the connection portion 400 and the formation direction of the manipulation portion 200 at the other end of the connection portion 400 may be described as the same direction based on the YZ plane. Alternatively, the manipulation portion 200 may be formed in a direction proceeding away from a body of a user holding the manipulation portion 200, i.e., a direction towards the end tool 600. That is, in the first handle 204, the first actuation manipulation portion, and the second actuation manipulation portion, etc., which are held and moved by a user for the actuation motion, the yaw motion, and the pitch motion, the moving portions thereof for the respective motions may extend in the +X axis direction in comparison with the rotation centers of each joint for the respective motions. Based on the foregoing, the moving portion of the end tool 600 may extend in the +X axis direction in comparison with the rotation center of each joint for the respective motions, and the manipulation portion 200 may also be configured in the same manner. Then, as described above with reference to FIG. 1, the user manipulation direction may match the operation direction of the end tool in terms of rotation direction and left and right direction, which leads to intuitively matching manipulation.

More specifically, in the case of a conventional surgical instrument, as a direction in which the user manipulates the manipulation portion and an actual operation direction of the end tool are different and not intuitively the same, an operator may have difficulty in intuitive operation, and may need to use much time to become familiar with directing the end tool in a desired direction. In one embodiment, in some cases, a malfunction may occur, which can cause a damage to a patient.

To overcome such issue, in the electric cauterization surgical instrument 10 according to the first embodiment, the manipulation direction of the manipulation portion 200 may be intuitively identical to the operation direction of the end tool 600, and to this end, a portion of the manipulation portion 200 which actually moves for the actuation motion, the yaw motion, and the pitch motion may extend in the +X-axis direction in comparison with a rotation center of a joint for the respective motions as in the end tool 600.

Hereinafter, the end tool 600, the manipulation portion 200, the power transmission portion 300, etc. of the electric cauterization surgical instrument 10 of FIG. 2 will be described in more detail.

(Power Transmission Portion)

Hereinafter, the power transmission portion 300 of the electric cauterization surgical instrument 10 of FIG. 2 will be described in more detail. surgical instrument for electrocautery Referring to FIGS. 2 to 4, 6, 7, 19, 20, 26, 33, 36, and 37, the power transmission portion 300 of the electric cauterization surgical instrument 10 according to an embodiment of the present disclosure may include a wire 301, a wire 302, a wire 303, a wire 304, a wire 305, a wire 306, and a blade wire 307.

Here, the wires 301 and 305 may be paired to serve as first jaw wires. The wires 302 and 306 may be paired to serve as second jaw wires. Here, the components encompassing the wires 301 and 305, which are first jaw wires, and the wires 302 and 306, which are second jaw wires, may be referred to as jaw wires. In addition, the wires 303 and 304 may be paired to serve as pitch wires.

In addition, the power transmission portion 300 of the electric cauterization surgical instrument 10 according to an embodiment of the present disclosure may include a fastening member 321, a fastening member 322, a fastening member 323, and a fastening member 324 that are coupled to respective end portions of the wires to respectively couple the wires and the pulleys. Here, each of the fastening members may have various shapes as necessary, such as a ball shape, a tube shape, and the like.

Here, at the end tool 600 side, the fastening member 321/fastening member 322 may serve as pitch wire-end tool fastening members, the fastening member 323 may serve as a first jaw wire-end tool fastening member, and the fastening member 324 may serve as a second jaw wire-end tool fastening member.

In addition, although not shown in the drawings, the manipulation portion 200 may further include a fastening member configured to fasten the first jaw wire—the manipulation portion, and a fastening member configured to fasten the second jaw wire—the manipulation portion.

In addition, although not shown in the drawings, a pitch wire-manipulation portion fastening member and a blade wire-manipulation portion fastening member may be further formed at the manipulation portion 200 side.

The coupling relationship between the wires, the fastening members, and the respectively pulleys will be described in detail as follows.

First, the wires 301 and 305, which are first jaw wires, may be a single wire. The fastening member 323, which is a first jaw wire-end tool fastening member, is inserted at an intermediate point of the first jaw wire, which is a single wire, and the fastening member 323 is crimped and fixed, and then, both strands of the first jaw wire centered on the fastening member 323 may be referred to as the wire 301 and the wire 305, respectively.

Alternatively, the wires 301 and 305, which are first jaw wires, may also be formed as separate wires and connected by the fastening member 323.

In addition, by coupling the fastening member 323 to a pulley 611, the wires 301 and 305 may be fixedly coupled to the pulley 611. This allows the pulley 611 to rotate as the wires 301 and 305 are pulled and released.

Meanwhile, a first jaw wire-manipulation portion fastening member (not shown in the drawings) may be coupled to the other end portions of the wires 301 and 305, which are opposite to one end portions to which the fastening member 323 is fastened.

As a result, when a pulley of the manipulation portion 200 is rotated by a motor or a human force, the pulley 611 of the end tool 600 may be rotated as the wire 301 and the wire 305 are pulled and released.

In the same manner, the wire 302 and the wire 306, which are second jaw wires, are coupled to each of the fastening member 324, which is a second jaw wire-end tool fastening member, and a second jaw wire-manipulation portion fastening member (not shown in the drawings).

In addition, the fastening member 324 is coupled to a pulley 621, and the second jaw wire-manipulation portion fastening member is coupled to a pulley. As a result, when the pulley is rotated by a motor or a human force, the pulley 621 of the end tool may be rotated as the wire 302 and the wire 306 are pulled and released.

In the same manner, the wire 304, which is a pitch wire, is coupled to the fastening member 321, which is a pitch wire-end tool fastening member, and the pitch wire-manipulation portion fastening member (not shown). In addition, the wire 303, which is a pitch wire, is coupled to a fastening member 322, which is a pitch wire-end tool fastening member, and the pitch wire-manipulation portion fastening member (not shown).

In addition, the fastening member 321 is coupled to a first pitch pulley portion 663a of an end tool hub 660, the fastening member 322 is coupled to a second pitch pulley portion 663b of the end tool hub 660, and the pitch wire-manipulation portion fastening member (not shown) is coupled to a pulley provided in the manipulation portion 200. As a result, when the pulley provided in the manipulation portion 200 is rotated by a motor or a human force, the end tool hub 660 of the end tool 600 may be rotated as the wire 303 and the wire 304 are pulled and released.

Meanwhile, one end portion of the blade wire 307 is coupled to a blade 675 to be described later, and the other end portion thereof is coupled to a blade manipulation portion (not shown in the drawings) of the manipulation portion 200. By the manipulation of the blade manipulation portion, a cutting motion may be performed as the blade wire 307 is moved from a proximal end 605 toward a distal end 604 of the end tool, or the blade wire 307 may return from the distal end 604 toward the proximal end 605 of the end tool.

At this time, at least a part of the blade wire 307 may be accommodated in a guide tube 670 to be described later. Accordingly, when the guide tube 670 is bent in response to a pitch motion or yaw motion of the end tool 600, the blade wire 307 accommodated therein may also be bent together with the guide tube 670. The guide tube 670 will be described in more detail later.

In addition, the blade wire 307 is formed in a longitudinal direction of the connection portion 400 so as to be linearly movable in the connection portion 400. In addition, since one end portion of the blade wire 307 is coupled to the blade 675, when the blade wire 307 is linearly moved in the longitudinal direction of the connection portion 400, the blade 675 connected thereto is also linearly moved.

That is, when the blade wire 307 is linearly moved in the longitudinal direction of the connection portion 400, a cutting motion is performed as the blade 675 connected thereto is moved toward the distal end 604 or the proximal end 605 of the end tool 600. This will be described in more detail later.

(End Tool)

Hereinafter, the end tool 600 of the electric cauterization surgical instrument 10 of FIG. 2 will be described in more detail.

FIG. 2 is a perspective view illustrating the surgical instrument for electrocautery according to the first embodiment of the present disclosure. FIGS. 3, 4, 5, and 6 are perspective views illustrating the end tool of the surgical instrument for electrocautery of FIG. 2. FIGS. 7 and 8 are plan views illustrating the end tool of the surgical instrument for electrocautery of FIG. 2. FIG. 9 is a perspective view illustrating the end tool hub of the surgical instrument for electrocautery of FIG. 2. FIGS. 10 and 11 are cut-away perspective views of the end tool hub of FIG. 9. FIGS. 12 and 13 are perspective views illustrating the end tool hub of FIG. 9. FIG. 14 is a side view illustrating the end tool hub and the guide tube of FIG. 9. FIG. 15 is a plan view illustrating the end tool hub and the guide tube of FIG. 9. FIGS. 16 and 17 are plan views illustrating an opening and closing motion of the end tool of the surgical instrument for electrocautery of FIG. 2.

Figure 3:
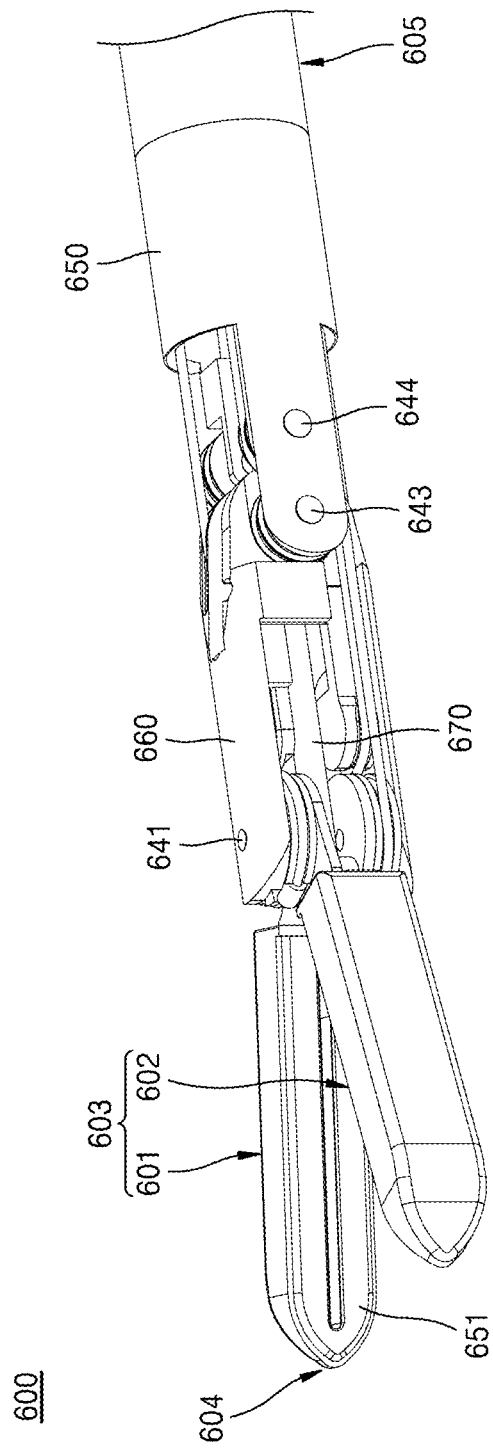
FIGS. 3, 4, 5, and 6 are perspective views illustrating an end tool of the surgical instrument for electrocautery of FIG. 2.
Figure 4:
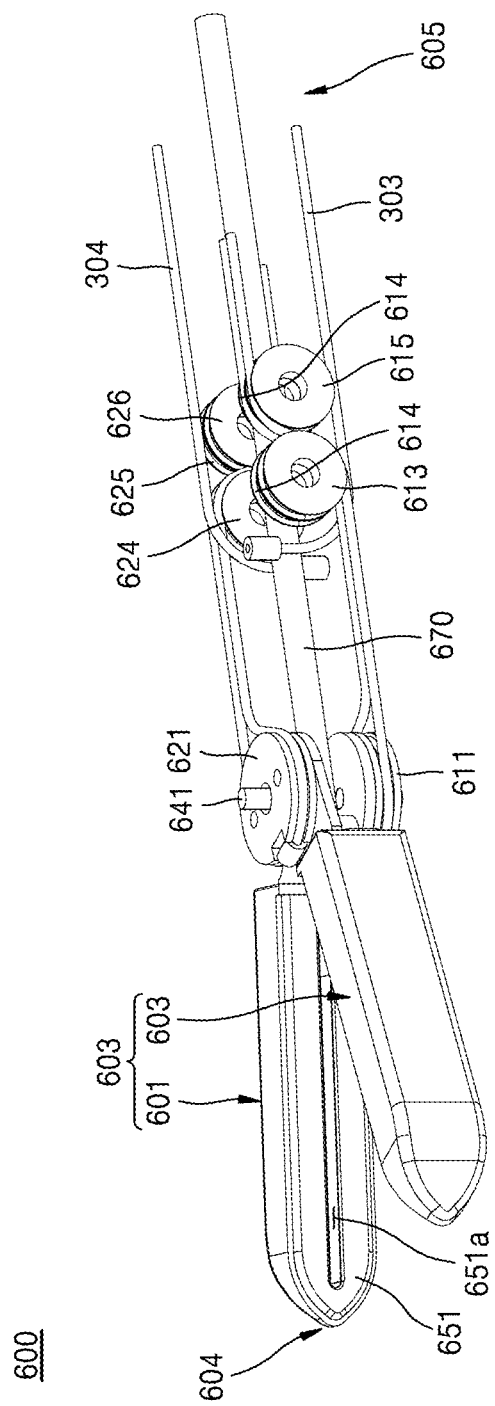

Here, FIG. 3 illustrates a state in which the end tool hub 660 and a pitch hub 650 are coupled, and FIG. 4 illustrates a state in which the end tool hub 660 and pitch hub 650 are removed. FIG. 5 illustrates a state in which a first jaw 601 and a second jaw 602 are removed, and FIG. 6 illustrates a state in which the first jaw 601, the second jaw 602, a first electrode 651, a second electrode 652, and the like are removed. Meanwhile, FIG. 7 is a view mainly illustrating the wires, and FIG. 8 is a view mainly illustrating the pulleys.

Referring to FIGS. 2 to 17 and the like, the end tool 600 according to the first embodiment of the present disclosure may include a pair of jaws 603 for performing a grip motion, that is, the first jaw 601 and the second jaw 602. Here, each of the first jaw 601 and the second jaw 602, or a component encompassing the first jaw 601 and the second jaw 602 may be referred to as the jaw 603.

In addition, the end tool may include the pulley 611, a pulley 613, a pulley 614, a pulley 615, and a pulley 616, which are associated with a rotational motion of the first jaw 601. In addition, the end tool may include the pulley 621, a pulley 623, a pulley 624, a pulley 625, and a pulley 626, which are associated with a rotational motion of the second jaw 602.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 600 of the first embodiment of the present disclosure may include the end tool hub 660 and the pitch hub 650.

Referring to FIG. 12, the end tool hub 660 may have a first rotation shaft 641 to be described later and a second rotation shaft 642 of a modified example of the first embodiment to be described later inserted therethrough, and may internally accommodate at least some of the pulley 611 and the pulley 621 that are axially coupled to the first rotation shaft 641. The end tool hub 660 will be described in more detail below.

Referring to FIG. 3, the pitch hub 650 may have a third rotation shaft 643 and a fourth rotation shaft 644, which will be described later, inserted therethrough, and may be axially coupled to a first pitch pulley portion 663a and a second pitch pulley portion 663b of the end tool hub 660 by the third rotation shaft 643. Accordingly, the end tool hub 660 may be formed to be rotatable around the third rotation shaft 643 with respect to the pitch hub 650.

In addition, the pitch hub 650 may internally accommodate at least some of the pulley 613, the pulley 614, the pulley 623, and the pulley 624 that are axially coupled to the third rotation shaft 643. Further, the pitch hub 650 may internally accommodate at least some of the pulley 615, the pulley 616, the pulley 625, and the pulley 626 that are axially coupled to the fourth rotation shaft 644.

One end portion of the pitch hub 650 is connected to the end tool hub 660, and the other end portion of the pitch hub 650 is connected to the connection portion 400.

Here, the end tool 600 of the first embodiment of the present disclosure may include the first rotation shaft 641, the third rotation shaft 643, and the fourth rotation shaft 644. As described above, the first rotation shaft 641 may be inserted through the end tool hub 660, and the third rotation shaft 643 and the fourth rotation shaft 644 may be inserted through the pitch hub 650.

Referring to FIG. 3, the first rotation shaft 641, the third rotation shaft 643, and the fourth rotation shaft 644 may be arranged sequentially from the distal end 604 toward the proximal end 605 of the end tool. Accordingly, starting from the distal end 604, the first rotation shaft 641 may be referred to as a first pin, the third rotation shaft 643 may be referred to as a third pin, and the fourth rotation shaft 644 may be referred to as a fourth pin.

The second rotation shaft 642 of the end tool 600 of the electric cauterization surgical instrument 10 according to the modified example of the first embodiment, which will be described later, may be inserted through the end tool hub 660 and may be referred to as a second pin.

Here, the first rotation shaft 641 may function as an end tool jaw pulley rotation shaft, the third rotation shaft 643 may function as an end tool pitch rotation shaft, and the fourth rotation shaft 644 may function as an end tool pitch auxiliary rotation shaft of the end tool.

Here, each of the rotation shafts may include two shafts of a first sub-shaft and a second sub-shaft. Alternatively, it may be said that each of the rotation shafts is formed by being divided into two parts.

For example, the first rotation shaft 641 may include two shafts of a first sub-shaft and a second sub-shaft, which face each other and are disposed to be spaced apart from each other by a certain distance. In addition, the third rotation shaft 643 may include two shafts of a first sub-shaft and a second sub-shaft, which face each other and are disposed to be spaced apart from each other by a certain distance. In addition, the fourth rotation shaft 644 may include two shafts of a first sub-shaft and a second sub-shaft, which face each other and are disposed to be spaced apart from each other by a certain distance.

Each of the rotation shafts is formed by being divided into two parts as described above to allow the guide tube 670 to be described later to pass through the end tool hub 660 and the pitch hub 650. That is, the guide tube 670 may pass between the first sub-shaft and the second sub-shaft of each of the rotation shafts.

This will be described in more detail later. Here, the first sub-shaft and the second sub-shaft may be formed such that longitudinal central axes thereof are disposed on the same axis or may be disposed to be offset to a certain degree.

Meanwhile, it is illustrated in the drawings that each of the rotation shafts is formed by being divided into two parts, but the concept of the present disclosure is not limited thereto. That is, each of the rotation shafts is formed to be curved in the middle such that an escape path for the guide tube 670 is formed.

Each of the rotation shafts 641, 642, and 644 may be fitted into one or more pulleys, which will be described in detail below.

Meanwhile, the first rotation shaft 641 provided in the end tool 600 may be an actuation rotation shaft. In detail, the first rotation shaft 641 may be provided in a coupling portion of the first jaw 601 and the second jaw 602, and may act as a yaw rotation shaft and an actuation rotation shaft.

That is, in the end tool 600 of the electric cauterization surgical instrument 10 according to the first embodiment of the present disclosure, a yaw rotation shaft and an actuation rotation shaft may be formed of the same rotation shaft, that is, the first rotation shaft 641.

In detail, the first rotation shaft 641, which is a yaw rotation shaft and an actuation rotation shaft, may be provided in the coupling portion of the first jaw 601 and the second jaw 602, and the first jaw 601 and the second jaw 602 may perform an actuation motion while rotating with the first rotation shaft 641 as the actuation rotation shaft.

Referring to FIGS. 4 to 7, the pulley 611 functions as an end tool first jaw pulley, and the pulley 621 functions as an end tool second jaw pulley. The pulley 611 may also be referred to as a first jaw pulley, and the pulley 621 may also be referred to as a second jaw pulley, and these two components may collectively be referred to as "end tool jaw pulleys" or simply "jaw pulleys."

The pulley 611 and the pulley 621, which are end tool jaw pulleys, are formed to face each other, and are formed to be rotatable independently of each other around the first rotation shaft 641, which is an end tool jaw pulley rotation shaft.

In this case, referring to FIG. 14, the pulley 611 and the pulley 621 are formed to be spaced apart from each other by a certain distance, and a blade assembly accommodation portion (no reference number is assigned) may be formed between the pulley 611 and the pulley 621. In addition, at least a part of the blade assembly (no reference number is assigned) to be described later may be disposed in the blade assembly accommodation portion. In other words, the blade assembly including the guide tube 670 may be disposed between the pulley 611 and the pulley 621.

In addition, a yaw motion and an actuation motion of the end tool are performed in response to the rotation of the pulley 611 and the pulley 621.

That is, when the pulley 611 and the pulley 621 rotate in the same direction around the first rotation shaft 641, the yaw motion is performed as the first jaw 601 and the second jaw 602 rotate with the first rotation shaft 641 as the central axis of rotation.

Meanwhile, when the pulley 611 and the pulley 621 rotate in opposite directions around the first rotation shaft 641, the actuation motion is performed in a state in which the first jaw 601 and the second jaw 602 rotate around the first rotation shaft 641, of which a central axis of rotation is shared by the yaw rotation shaft and the actuation rotation shaft.

Referring to FIGS. 4, 6, and 8, the pulley 613 and the pulley 614 function as end tool first jaw pitch main pulleys, and the pulley 623 and the pulley 624 function as end tool second jaw pitch main pulleys, and these two components may collectively be referred to as end tool jaw pitch main pulleys.

The pulley 615 and the pulley 616 function as end tool first jaw pitch sub-pulleys, and the pulley 625 and the pulley 626 function as end tool second jaw pitch sub-pulleys, and these two components may collectively be referred to as end tool jaw pitch sub-pulleys.

Hereinafter, components associated with the rotation of the pulley 611 will be described.

The pulley 613 and the pulley 614 function as end tool first jaw pitch main pulleys. That is, the pulley 613 and the pulley 614 may function as main rotation pulleys for the pitch motion of the first jaw 601. Here, the wire 301, which is a first jaw wire, is wound around the pulley 613, and the wire 305, which is a first jaw wire, is wound around the pulley 614.

The pulley 615 and the pulley 616 function as end tool first jaw pitch sub-pulleys. That is, the pulley 615 and the pulley 616 function as sub-rotation pulleys for the pitch motion of the first jaw 601. Here, the wire 301, which is a first jaw wire, is wound around the pulley 615, and the wire 305, which is a first jaw wire, is wound around the pulley 616.

Here, the pulley 613 and the pulley 614 are disposed on one side of the pulley 611 and the pulley 612 to face each other. Here, the pulley 613 and the pulley 614 are formed to be rotatable independently of each other around the third rotation shaft 643 that is an end tool pitch rotation shaft.

In addition, the pulley 615 and the pulley 616 are disposed on one side of the pulley 613 and one side of the pulley 614, respectively, to face each other. Here, the pulley 615 and the pulley 616 are formed to be rotatable independently of each other around the fourth rotation shaft 644 that is an end tool pitch auxiliary rotation shaft.

Here, in the drawings, it is illustrated that the pulley 613, the pulley 615, the pulley 614, and the pulley 616 are all formed to be rotatable around a Y-axis direction, but the concept of the present disclosure is not limited thereto, and the rotation shafts of the respective pulleys may be formed in various directions according to configurations thereof.

Referring to FIG. 6, the wire 301, which is a first jaw wire, is sequentially wound to make contact with at least portions of the pulley 615, the pulley 613, and the pulley 611. In addition, the wire 305 connected to the wire 301 by the fastening member 323 is sequentially wound to make contact with at least portions of the pulley 611, a first wire guide portion 668a of the end tool hub 680, the pulley 614, and the pulley 616.

In other words, the wire 301 and the wire 305, which are the first jaw wire, are sequentially wound to make contact with at least portions of the pulley 615, the pulley 613, the pulley 611, the first wire guide portion 668a of the end tool hub 680, the pulley 614, and the pulley 616, and the wire 301 and the wire 305 formed to move along the above pulleys while rotating the above pulleys.

Accordingly, referring to FIG. 7, when the wire 301 is pulled in a direction from the distal end 604 toward the proximal end 605 of the end tool 600 (upward direction from a lower side based on FIG. 7), the fastening member 323, to which the wire 301 is coupled, and the pulley 611 coupled to the fastening member 323 and disposed facing the pulley 621 rotate in a first direction (a counterclockwise direction based on FIG. 7).

On the contrary, when the wire 305 is pulled in the direction from the distal end 604 toward the proximal end 605 of the end tool 600 (upward direction from the lower side based on FIG. 7), the fastening member 323 to which the wire 305 is coupled and the pulley 611 coupled to the fastening member 323 are rotated in a second direction (a clockwise direction based on FIG. 7) opposite to the first direction.

Next, components associated with the rotation of the pulley 621 will be described.

The pulley 623 and the pulley 624 function as end tool second jaw pitch main pulleys. That is, the pulley 623 and the pulley 624 function as main rotation pulleys for a pitch motion of the second jaw 602. Here, the wire 306, which is a second jaw wire, is wound around the pulley 623, and the wire 302, which is a second jaw wire, is wound around the pulley 624.

Referring to FIG. 7, the pulley 625 and the pulley 626 function as end tool second jaw pitch sub-pulleys. That is, the pulley 625 and the pulley 626 function as sub-rotation pulleys for a pitch motion of the second jaw 602. Here, the wire 306, which is a second jaw wire, is wound around the pulley 625, and the wire 302, which is a second jaw wire, is wound around the pulley 626.

Here, the pulley 623 and the pulley 624 are disposed on one side of the pulley 621 to face each other. Here, the pulley 623 and the pulley 624 are formed to be rotatable independently of each other around the third rotation shaft 643 that is an end tool pitch rotation shaft. In addition, the pulley 625 and the pulley 626 are disposed on one side of the pulley 623 and one side of the pulley 624, respectively, to face each other.

Here, the pulley 625 and the pulley 626 are formed to be rotatable independently of each other around the fourth rotation shaft 644 that is an end tool pitch auxiliary rotation shaft. Here, in the drawings, it is illustrated that all of the pulley 623, the pulley 625, the pulley 624, and the pulley 626 are formed to be rotatable around the Y-axis direction, but the concept of the present disclosure is not limited thereto, and the rotation shafts of the respective pulleys may be formed in various directions according to configurations thereof.

The wire 306, which is a second jaw wire, is sequentially wound to make contact with at least portions of the pulley 625, the pulley 623, and the pulley 621. In addition, the wire 302 connected to the wire 306 by the fastening member 324 is sequentially wound to make contact with at least portions of the pulley 621, a second wire guide portion 668b of the end tool hub 680, the pulley 624, and the pulley 626.

In other words, the wire 306 and the wire 302, which are the second jaw wire, are sequentially wound to make contact with at least portions of the pulley 625, the pulley 623, the pulley 621, the second wire guide portion 668b of the end tool hub 680, the pulley 624, and the pulley 626, and the wire 306 and the wire 302 are formed to move along the above pulleys while rotating the above pulleys.

Accordingly, referring to FIG. 7, when the wire 306 is pulled in the direction from the distal end 604 toward the proximal end 605 of the end tool 600 (upward direction from the lower side based on FIG. 7), the fastening member 324, to which the wire 306 is coupled, and the pulley 621 coupled to the fastening member 324 and disposed facing the pulley 611 are rotated in the first direction (the clockwise direction based on FIG. 7).

On the contrary, when the wire 302 is pulled in the direction from the distal end 604 toward the proximal end 605 of the end tool 600 (upward direction from the lower side based on FIG. 7), the fastening member 324 to which the wire 302 is coupled and the pulley 621 coupled to the fastening member 324 are rotated in the second direction (the counterclockwise direction based on FIG. 7) opposite to the first direction.

Hereinafter, a pitch motion of the present disclosure will be described in more detail.

Meanwhile, when the wire 301 is pulled in the direction of an arrow 301 of FIG. 7, and simultaneously, the wire 305 is pulled in the direction of an arrow 305 of FIG. 7 (that is, when both strands of the first jaw wire are pulled), as shown in FIG. 6, since the wires 301 and 305 are wound around lower portions of the pulley 613 and the pulley 614 rotatable around the third rotation shaft 643, which is an end tool pitch rotation shaft, the pulley 611 to which the wires 301 and 305 are fixedly coupled and the end tool hub 660 to which the pulley 611 is coupled rotate as a whole in the counterclockwise direction around the third rotation shaft 643, and as a result, the end tool may rotate downward to perform the pitch motion.

At this time, since the second jaw 602 and the wires 302 and 306 fixedly coupled thereto are wound around upper portions of the pulley 623 and the pulley 624 rotatable around the third rotation shaft 643, the wires 302 and 306 are released in the opposite directions of the arrows 302 and 306, respectively.

On the contrary, when the wire 302 is pulled in the direction of an arrow 302 of FIG. 7, and simultaneously, the wire 306 is pulled in the direction of an arrow 306 of FIG. 7, as shown in FIG. 6, since the wires 302 and 306 are wound around the upper portions of the pulley 623 and the pulley 624 rotatable around the third rotation shaft 643, which is an end tool pitch rotation shaft, the pulley 621 to which the wires 302 and 306 are fixedly coupled and the end tool hub 660 to which the pulley 621 is coupled rotate as a whole in the clockwise direction around the third rotation shaft 643, and as a result, the end tool may rotate upward to perform the pitch motion.

At this time, since the first jaw 601 and the wires 301 and 305 fixedly coupled thereto are wound around lower portions of the pulley 613 and the pulley 614 rotatable around the third rotation shaft 643, the wires 302 and 306 are moved in the opposite directions of the arrows 301 and 305, respectively.

Meanwhile, the end tool hub 660 of the end tool 600 of the electric cauterization surgical instrument 10 of the present disclosure may further include the first pitch pulley portion 663a and the second pitch pulley portion 663b serving as end tool pitch pulleys, the manipulation portion 200 may further include a manipulation portion pitch pulley (not shown in the drawings), and the power transmission portion 300 may further include the wire 303 and the wire 304 which are pitch wires.

In detail, the end tool hub 660 including the first pitch pulley portion 663a and the second pitch pulley portion 663b may be formed to be rotatable around the third rotation shaft 643 which is an end tool pitch rotation shaft. In addition, the wire 303 and the wire 304 may serve to connect the first pitch pulley portion 663a and the second pitch pulley portion 663b of the end tool to the manipulation portion pitch pulley of the manipulation portion 200.

Thus, when the manipulation portion pitch pulley of the manipulation portion 200 rotates, the rotation of the manipulation portion pitch pulley is transmitted to the end tool hub 660 of the end tool 600 via the wire 303 and the wire 304 so that the end tool hub 660 rotates together with the manipulation portion pitch pulley, and as a result, the end tool 600 performs the pitch motion while rotating.

That is, the electric cauterization surgical instrument 10 according to the first embodiment of the present disclosure includes the first pitch pulley portion 663a and the second pitch pulley portion 663b of the end tool 600, the manipulation portion pitch pulley of the manipulation portion 200, and the wire 303 and the wire 304 of the power transmission portion 300 in order to transmit driving force for a pitch motion, and thus, the driving force for the pitch motion of the manipulation portion 200 is more completely transmitted to the end tool, thereby improving operation reliability.

(Blade Wire and Guide Tube)

Hereinafter, the blade assembly, specifically the blade wire 307 and the guide tube 670 of the present disclosure, will be described in more detail.

Referring to FIGS. 3, 4, and 6, the guide tube 670 according to the present disclosure is formed to surround the blade wire 307 in a certain section, and in this case, the blade wire 307 is movable inside the guide tube 670.

In other words, in a state in which the blade wire 307 is inserted into the guide tube 670, the blade wire 307 may move relative to the guide tube 670.

Here, the guide tube 670 has a certain degree of rigidity, and serves to guide the path of the blade wire 307 by preventing the blade wire 307 from being curved in an unintended direction when the blade wire 307 is pushed or pulled. A cutting motion on tissue may be smoothly performed by the guide tube 670.

Meanwhile, one end portion of the guide tube 670 may be fixedly coupled to the end tool hub 660 or a preset region (a first coupling portion) of the first jaw 601 or the second jaw 602, which will be described later. In addition, the other end portion of the guide tube 670 may be fixedly coupled to a second coupling portion (not shown) in the connection portion 400.

As described above, since both end portions of the guide tube 670 are fixedly coupled to certain points (the first coupling portion and the second coupling portion), respectively, the entire length of the guide tube 670 may remain constant. Accordingly, the length of the blade wire 307 inserted into the guide tube 670 may also remain constant.

In addition, the blade wire 307 may be prevented from moving in an unintended direction inside the end tool 600, which is caused by the blade wire 307 being able to move inside the guide tube 670.

Meanwhile, the guide tube 670 according to the present disclosure may be formed of a flexible material and formed to be bendable. Accordingly, when the end tool performs a yaw motion around the first rotation shaft 641 or a pitch motion around the third rotation shaft 643, the guide tube 670 may be bent while being deformed in shape corresponding thereto. In addition, when the guide tube 670 is bent, the blade wire 307 thereinside is also bent.

Here, although the length of the guide tube 670 is constant, the relative position and distance of the first coupling portion (not shown) and second coupling portion (not shown) may be changed as the end tool 600 is pitch-rotated or yaw-rotated, and thus a space for the guide tube 670 to move by the changed distance is required.

To this end, a pitch slit 664 and a yaw slit 665, which are separation spaces, may be provided in the end tool hub 660 to form spaces for movement of the guide tube 670. Such a configuration of the end tool hub 660 will be described in detail later.

Meanwhile, as described above, the blade wire 307 is inserted through the guide tube 670, and the blade wire 307 is relatively movable inside the guide tube 670 with respect to the guide tube 670. That is, in a state in which the guide tube 670 is fixed, when the blade wire 307 is pulled in a first direction (in a direction from left to right based on FIG. 6), the blade 675 connected to the blade wire 307 is moved toward the proximal end 605, and when the blade wire 307 is pushed in a second direction (in a direction from right to left based on in FIG. 6), the blade 675 connected to the blade wire 307 is moved toward the distal end 604.

This will be described below in more detail.

The most reliable way to perform a cutting motion using the blade 675 is by pushing and pulling the blade 675 with the blade wire 307. In addition, in order for the blade wire 307 to push and pull the blade 675, the guide tube 670 that can guide the path of the blade wire 307 should be provided.

When the guide tube 670 does not guide the path of the blade wire 307 (i.e., does not hold the blade wire 307), a phenomenon may occur in which cutting is not performed and a middle part of the blade wire 307 is curved even when the blade wire 307 is pushed. Accordingly, in order to reliably perform the cutting motion using the blade 675, the blade wire 307 and the guide tube 670 should be essentially included.

However, when the blade wire 307 is used to drive a cutting motion, the cutting should be performed while pushing the blade wire 307, and in this case, in order for the blade wire 307 to receive a force, a relatively stiff (i.e., non-bendable) wire should be used for the blade wire 307. However, the stiff (i.e., non-bendable) wire may have a small bendable range and may be permanently deformed when a force equal to or greater than a certain degree is applied.

In other words, in the case of a stiff (i.e., non-bendable) wire, there is a minimum radius of curvature that may be bent and spread without permanent deformation. In other words, when the wire or the guide tube is curved below a specific radius of curvature, both the wire and the guide tube may undergo permanent deformation while being bent, thereby restricting the capacity to perform cutting while moving backward and forward. Thus, it is necessary to keep the blade wire 307 curved while having a gentle curvature.

Accordingly, to prevent the blade wire 307 from being rapidly bent while passing through the pulleys, a space is needed in the end tool hub 660 to be described below in order to ensure that bending or shape changes in the guide tube 670, in which the blade wire 307 is accommodated, do not interfere with the end tool hub 660.

The blade wire 307 and the guide tube 670 need to be connected to the blade 675 through the end tool hub 660, and a space is needed in which the blade wire 307 and the guide tube 670 are bendable in the end tool hub 660, and thus, to this end, in the present disclosure, 1) the pitch slit 664 and the yaw slit 665 are formed in the end tool hub 660, wherein the pitch slit 664 and the yaw slit 665 correspond to a space in which the blade wire 307 and the guide tube 670 in which the blade wire 307 is accommodated can pass therethrough, and at the same time, are bendable, 2) each of the rotation shafts, specifically, the first rotation shaft 641, the third rotation shaft 643, and the fourth rotation shaft 644 is formed by being divided into two parts that are formed to face each other and to be spaced apart from each other by a certain distance, wherein the first rotation shaft 641 is a yaw rotation shaft and also is an actuation rotation shaft, the third rotation shaft 643 is a pitch rotation shaft, and the fourth rotation shaft 644 is an end tool pitch auxiliary rotation shaft of the end tool 600, and 3) a pitch round portion 666 and a yaw round portion 667 are additionally formed to guide the bending of the blade wire 307 and the guide tube 670.

In other words, when one end portion of the guide tube 670 is fixed in the connection portion 400, and the other end portion thereof is moved while performing pitch and yaw motions, the guide tube 670 is curved in a direction, in which the gentlest curvature (hereinafter, referred to as "maximum gentle curvature") can be achieved in response to a change in a distance between both end portions thereof. As such, by achieving the maximum gentle curvature of the natural state, the motion of the blade wire 307 is smooth and the permanent deformation does not occur.

Accordingly, in order to secure the maximum gentle curvature, the pitch slit 664 and the yaw slit 665 are formed on the path of the guide tube 670 and, furthermore, the pitch round portion 666 and the yaw round portion 667, each of which has a curved surface with a certain degree of curvature formed at each surface facing the guide tube 670, may be additionally formed in the end tool hub 660. Accordingly, the guide tube 670 may have such a shape that is the most similar to the maximum gentle curvature (although not having the maximum gentle curvature).

Hereinafter, the end tool hub 660 will be described.

(End Tool Hub)

Referring to FIGS. 9 to 15, the end tool hub 660 of the present disclosure may include a body portion 661, a first jaw pulley coupling portion 662a, a second jaw pulley coupling portion 662b, the first pitch pulley portion 663a, the second pitch pulley portion 663b, the pitch slit 664, the yaw slit 665, the pitch round portion 666, the yaw round portion 667, the first wire guide portion 668a, and the second wire guide portion 668b.

Referring to FIG. 9, the first jaw pulley coupling portion 662a and the second jaw pulley coupling portion 662b may be formed on the end tool hub at the distal end 604 side. The first jaw pulley coupling portion 662a and the second jaw pulley coupling portion 662b may be formed to face each other, and may respectively accommodate the end tool first jaw pulley 611 and the end tool second jaw pulley 612 therein.

Here, the first jaw pulley coupling portion 662a and the second jaw pulley coupling portion 662b may be formed to be approximately parallel to a plane perpendicular to the first rotation shaft 641 that is a yaw rotation shaft. However, the first jaw pulley coupling portion 662a and the second jaw pulley coupling portion 662b are not limited thereto, and may be disposed to face each other and formed at a certain angle with the plane perpendicular to the first rotation shaft 641, which is a yaw rotation shaft, in any technical concept in which the pulleys 611 and 612 may be accommodated.

Referring to FIGS. 9 and 10, the first jaw pulley coupling portion 662a and the second jaw pulley coupling portion 662b may be connected by the body portion 661. That is, the first jaw pulley coupling portion 662a and the second jaw pulley coupling portion 662b, which are parallel to each other, are coupled to each other by the body portion 661 formed in a direction approximately perpendicular thereto, so that the first jaw pulley coupling portion 662a, the second jaw pulley coupling portion 662b, and the body portion form an approximately "U" shape, in which each of the end tool first jaw pulley 611 and the end tool second jaw pulley 612 may be accommodated.

In other words, it may be said that the first jaw pulley coupling portion 662a and the second jaw pulley coupling portion 662b are formed to extend in the X-axis direction from the body portion 661.

Referring to FIGS. 9 and 12, a through hole (no reference number is assigned) is formed in the first jaw pulley coupling portion 662a to allow the first rotation shaft 641 to pass through and axially couple the first jaw pulley coupling portion 662a and the pulley 611, which is an end tool first jaw pulley.

In addition, similar to the first jaw pulley coupling portion 662a, a through hole (no reference number is assigned) is formed in the second jaw pulley coupling portion 662b to allow the first rotation shaft 641 to pass through and axially couple the second jaw pulley coupling portion 662b and the pulley 621, which is an end tool second jaw pulley.

Referring to FIG. 12, the first rotation shaft 641, which is a yaw rotation shaft, may be formed by being divided into two parts, and the two divided parts of the first rotation shaft 641 are connected to the through holes formed in the first jaw pulley coupling portion 662a and the second jaw pulley coupling portion 662b, respectively, and disposed to be spaced apart from each other by a certain distance.

As a result, a space is formed between the pair of first rotation shafts 641 that are connected to the facing first jaw pulley coupling portion 662a and second jaw pulley coupling portion 662b, respectively, and a space through which the guide tube 670 may pass may be formed between the pair of first rotation shafts 641.

In other words, by disposing the blade assembly including the guide tube 670 and the blade 675 between the pulley 611, which is a first jaw pulley, and the pulley 621, which is a second jaw pulley, the end tool 600 is able to perform the cutting motion using the blade 675 in addition to the pitch and yaw motions.

Referring to FIGS. 9 to 11, the first wire guide portion 668a may be formed on an inner side surface of the first jaw pulley coupling portion 662a, and the second wire guide portion 668b may be formed on an inner side surface of the second jaw pulley coupling portion 662b.

The first wire guide portion 668a and the second wire guide portion 668b may serve as auxiliary pulleys, and may increase a rotation angle of the end tool 600.

The wire guide portions, specifically the first wire guide portion 668a and the second wire guide portion 668b, are in contact with the wire 305 and the wire 302, respectively, to change the arrangement path of the wire 305 and the wire 302 to a certain degree, thereby increasing a rotation radius of each of the first jaw 601 and the second jaw 602.

That is, when the auxiliary pulleys are not disposed, each of the first jaw pulley 611 and the second jaw pulley 621 can be yaw-rotated up to a right angle, but by forming the first wire guide portion 668a and the second wire guide portion 668b formed on the end tool hub 660, the effect of increasing the maximum rotation angle of each pulley may be obtained.

This enables a motion in which the two jaws 601 and 602 of the end tool 600 should be spread for an actuation motion while yaw-rotated by 90°.

In other words, the range of yaw rotation in which an actuation motion is possible may be increased through the configuration of the wire guide portions 668a and 668b of the end tool hub 660. In other words, the range of yaw rotation in which an actuation motion is possible may be increased through the configuration of the wire guide portions 668a and 668b of the end tool hub 660.

Furthermore, by forming the wire guide portions 668a and 668b in the end tool hub 660, which already exists, without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also, the length of the end tool is shortened by as much as the size of the auxiliary pulley, so that the length of the end tool is shortened during a pitch motion. Accordingly, a surgical motion may be more easily performed in a narrow space.

According to the present disclosure as described above, the rotation radii of the pulley 611, which is a first jaw pulley, and the pulley 621, which is a second jaw pulley, increase, so that a yaw motion range in which a normal opening/closing actuation motion and a normal cutting motion can be performed may be increased.

The first wire guide portion 668a and the second wire guide portion 668b may be formed parallel to a plane perpendicular to the first rotation shaft 641 that is a yaw rotation shaft. However, the first wire guide portion 668a and the second wire guide portion 668b are not limited thereto, and may be formed to have a certain angle with a plane perpendicular to the first rotation shaft 641, which is a yaw rotation shaft, within the technical concept in which the first wire guide portion 668a and the second wire guide portion 668b are disposed to face each other.

The yaw slit 665 may be formed between the first jaw pulley coupling portion 662a and the second jaw pulley coupling portion 662b, and between the first wire guide portion 668a and the second wire guide portion 668b. Since the yaw slit 665 is formed in the end tool hub 660 as described above, the guide tube 670 may pass through the inside of the end tool hub 660.

In other words, a pair of divided first rotation shafts 641 are vertically separated from each other without passing through the end tool hub 660, and the yaw slit 665 is formed near the first rotation shaft 641 on a plane perpendicular to the first rotation shaft 641, thereby allowing the guide tube 670 to move in the yaw slit 665 while passing near the first rotation shaft 641.

Referring to FIGS. 9 and 10, a yaw round portion 667 may be formed on the body portion 661. The yaw round portion 667 may be formed to be rounded so as to have a certain degree of curvature. Specifically, when viewed from a plane perpendicular to the first rotation shaft 641, which is a yaw rotation shaft, the yaw round portion may be formed to have a predetermined curvature. The yaw round portion 667 as described above may serve to guide the path of the guide tube 670 when the end tool 600 yaw-rotates.

For example, the yaw round portion 667 may be formed in a fan shape, and may be formed along a path in which the guide tube 670 is bent on an XY plane. The yaw round portion 667 as described above may serve to guide the path of the guide tube 670 when the end tool 600 yaw-rotates.

The first pitch pulley portion 663a and the second pitch pulley portion 663b may be formed on the end tool hub 660 at the proximal end 605 side.

In detail, the proximal end 605 of the end tool hub 660 is formed in a disk shape similar to a pulley, and grooves around which a wire may be wound may be formed on an outer circumferential surface of the proximal end 605, thereby forming the first pitch pulley portion 663a and the second pitch pulley portion 663b.

The wire 303 and the wire 304 described above are coupled to the first pitch pulley portion 663a and the second pitch pulley portion 663b, which serve as end tool pitch pulleys, and a pitch motion is performed while the end tool hub 660 rotates around the third rotation shaft 643.

Meanwhile, although not shown in the drawings, various modifications are possible, e.g., the pitch pulley is formed as a separate member from the end tool hub 660 and coupled to the end tool hub 660.

The first pitch pulley portion 663a and the second pitch pulley portion 663b may be formed to face each other. Here, the first pitch pulley portion 663a and the second pitch pulley portion 663b may be formed to be approximately parallel to a plane perpendicular to the third rotation shaft 643, which is a pitch rotation shaft.

The first pitch pulley portion 663a and the second pitch pulley portion 663b may be connected by the body portion 661. That is, the first pitch pulley portion 663a and the second pitch pulley portion 663b, which are parallel to each other, are coupled by the body portion 661 formed in a direction approximately perpendicular to the first pitch pulley portion 663a and the second pitch pulley portion 663b, and thus the first pitch pulley portion 663a, the second pitch pulley portion 663b, and the body portion 661 may form an approximately U-shape.

In other words, the first pitch pulley portion 663a and the second pitch pulley portion 663b may be formed to extend side by side from the body portion 661 to face each other in the X-axis direction.

Meanwhile, a through hole (no reference number is assigned) is formed in the first pitch pulley portion 663a so that the third rotation shaft 643 may pass through and be connected to the first pitch pulley portion 663a. A through hole may be formed in the second pitch pulley portion 663b as in the first pitch pulley portion 663a, and the third rotation shaft 643 may pass through the second pitch pulley portion 663b.

At this time, the third rotation shaft 643, which is a pitch rotation shaft, may be divided into two parts and may be disposed to be spaced apart from each other, and the guide tube 670 may move while passing through a space formed between the pair of third rotation shafts 643.

Referring to FIG. 13, the pitch slit 664 may be formed between the first pitch pulley portion 663a and the second pitch pulley portion 663b. Since the pitch slit 664 is formed in the end tool hub 660 as described above, the guide tube 670 may pass through the inside of the end tool hub 660.

Meanwhile, the pitch round portion 666 may be further formed in the body portion 661. A curved surface may be formed on the pitch round portion 666 to have a predetermined curvature. In detail, when viewed from a plane perpendicular to the third rotation shaft 643, which is a pitch rotation shaft, the pitch round portion 666 may be formed to be rounded to have a predetermined curvature.

For example, the pitch round portion 666 may be formed in a fan shape, and may be formed along a path in which the guide tube 670 is bent on the XZ plane. The pitch round portion 666 as described above may serve to guide the path of the guide tube 670 when the end tool 600 pitch-rotates.

Accordingly, since the path of the guide tube 670 may be guided when the end tool 600 pitch-rotates, and the pitch round portion 666 having a predetermined curvature and formed to be rounded is formed on the inner side surface of the end tool hub 660 that may be in contact with the guide tube 670, a sudden path change of the guide tube 670 may be prevented, and the guide tube 670 and the blade wire 307 moving inside the guide tube 670 may be stably moved while having a gently curved path.

That is, the pitch round portion 666 may serve to guide the path of the guide tube 670 when the end tool 600 pitch-rotates.

Referring to FIG. 9, the pitch slit 664 and the yaw slit 665 may be formed to be connected to each other. That is, on an outer side with respect to a longitudinal central axis of the guide tube 670 located inside the end tool hub 660, the pitch slit 664 and the yaw slit 665 may be alternately formed along a circumferential direction of the end tool hub 660.

As a result, the guide tube 670 and the blade wire 307 located therein may be disposed to pass through the inside of the end tool hub 660. In addition, the blade 675 located at one end portion of the blade wire 307 may linearly reciprocate inside the first jaw 601 and the second jaw 602.

As described above, since the blade wire 307 and the guide tube 670 need to be connected to the blade 675 through the end tool hub 660, and a space is needed in which the blade wire 307 and the guide tube 670 are able to be bent in the end tool hub 660, in the present disclosure, 1) the pitch slit 664 and the yaw slit 665 are formed in the end tool hub 660, wherein the pitch slit 664 and the yaw slit 665 correspond to a space in which the blade wire 307/guide tube 670 can pass through the end tool hub 660 without interfering the end tool hub 660, and at the same time, are bendable, 2) each of the rotation shafts, specifically, the first rotation shaft 641 and the third rotation shaft 643 is formed by being divided into two parts, and 3) the pitch round portion 666 and the yaw round portion 667 are additionally formed to guide the bending of the blade wire 307 and the guide tube 670.

(Components Associated with Cautery and Cutting)

Referring to FIGS. 3 to 5, 18 to 20, 25, 26, 31 to 33, and 35 to 37, the end tool 600 of the first embodiment of the present disclosure may include the first jaw 601, the second jaw 602, the first electrode 651, the second electrode 652, the guide tube 670, and the blade 675 to perform cauterizing and cutting motions.

Here, components associated with the driving of the blade 675, such as the guide tube 670 and the blade 675, may be collectively referred to as a blade assembly. In an embodiment of the present disclosure, by disposing the blade assembly including the guide tube 670 and the blade 675 in the yaw slit 665 formed between the pulley 611, which is a first jaw pulley, and the pulley 621, which a second jaw pulley, the end tool 600 is able to perform the cutting motion using the blade 675 in addition to the pitch and yaw motions. This will be described in more detail.

As described above, the first jaw 601 is connected to the first jaw pulley 611, and rotates around the first rotation shaft 641 integrally with the first jaw pulley 611 when the first jaw pulley 611 rotates around the first rotation shaft 641.

Meanwhile, the first electrode 651 may be formed on a surface of the first jaw 601 facing the second jaw 602. In addition, the second electrode 652 may be formed on a surface of the second jaw 602 facing the first jaw 601.

Referring to FIG. 5, a slit 651*a* may be formed in the first electrode 651, and the blade 675 may move along the slit 651*a*. In addition, a slit 652*a* may be formed in the second electrode 652, and the blade 675 may move along the slit 652*a* in a preset direction.

In an optional embodiment, a spacer (not shown in the drawings) may be formed between the first jaw 601 and the first electrode 651, and a spacer may also be formed between the second jaw 602 and the second electrode 652. The spacer may include an insulating material such as ceramic. Alternatively, the first jaw 601 and the second jaw 602 may themselves be made of a nonconductor such that the first electrode 651 and the second electrode 652 may be maintained to be insulated from each other without a separate insulator until the first electrode 651 and the second electrode 652 are in contact with each other.

Meanwhile, although not shown in the drawings, one or more sensors (not shown) may be further formed on at least one of the first jaw 601 or the second jaw 602. The sensor (not shown) may be formed to measure at least some of current, voltage, resistance, impedance, and temperature during the cauterization by locating tissue between the first jaw 601 and the second jaw 602 and passing a current through the first electrode 651 and the second electrode 652.

Alternatively, instead of providing a separate sensor, monitoring and controlling of at least some of current, voltage, resistance, impedance, and temperature may be directly performed by a generator (not shown) which supplies power to the electrodes.

An edge portion formed sharply and configured to cut tissue may be formed in one region of the blade 675. The tissue disposed between the first jaw 601 and the second jaw 602 may be cut as at least a part of the blade 675 moves between the distal end 604 and the proximal end 605 of the end tool.

Here, the guide tube 670 and the blade 675 disposed between the pulley 611 and the pulley 621 are provided in the end tool 600 of an electric cauterization surgical instrument 10 according to an embodiment of the present disclosure.

In addition, by providing the guide tube 670 and the blade 675, a multi-joint/multi-degree-of-freedom surgical instrument capable of pitch/yaw/actuation motions may also perform cauterizing and cutting motions. This will be described below in more detail.

So far, various types of surgical instruments for electrocautery have been developed. Among the various types of surgical instruments for electrocautery, a blood vessel resection device called "Advanced Energy Device" or "Vessel Sealer" has a sensing function added to the existing bipolar cautery method, so that power of different polarities may be supplied to two electrodes, and after denaturing a vessel with the heat generated therefrom for hemostasis, the stanched part may be cut with a blade. At this time, the impedance of the tissue (or blood vessel) while the current is flowing is measured to determine whether the cauterization is completed, and when the cauterization is completed, the current supply is automatically stopped, and the tissue is cut with the blade.

In the case of such a bipolar-type blood vessel resection device, it is essential to have a blade to cut the tissue after cauterization, and the end tool needs to be equipped with a mechanism for facilitating a linear motion of the blade, and thus joint movements such as pitch/yaw movements are not possible in most cases.

Meanwhile, there have been attempts to implement joint movements using flexible joints with multiple nodes connected in the bipolar-type blood vessel resection device, but in this case, a rotation angle is limited and it is difficult to achieve accurate motion control of the end tool.

On the other hand, in the case of a method that utilizes vibration of ultrasonic waves to perform hemostasis and cutting, it is not feasible to provide joints due to the physical properties of ultrasonic waves.

To address these problems, the end tool 600 of the electric cauterization surgical instrument 10 according to an embodiment of the present disclosure includes the guide tube 670 disposed between the pulley 611 and the pulley 621, and the blade 675 that moves between a first position and a second position in response to the movement of the blade wire 307 disposed inside the guide tube 670. In addition, by providing the guide tube 670 and the blade 675 as described above, pitch/yaw/actuation motions may also be performed using a pulley/wire in a bipolar-type surgical instrument for cauterizing and cutting tissue.

FIG. 16 is a view illustrating the end tool 600 of the electric cauterization surgical instrument 10 of FIG. 2 in an open state, and FIG. 17 is a view illustrating the end tool 600 in a closed state. In addition, FIG. 18 is a view illustrating a state in which the blade wire 307 and the blade 675 connected to the blade wire 307 are located at the first position, FIG. 19 is a view illustrating a state in which the blade wire 307 and the blade 675 are located at the second position, and FIG. 20 is a view illustrating a state in which the blade wire 307 and the blade 675 are located at a third position.

Figure 18:
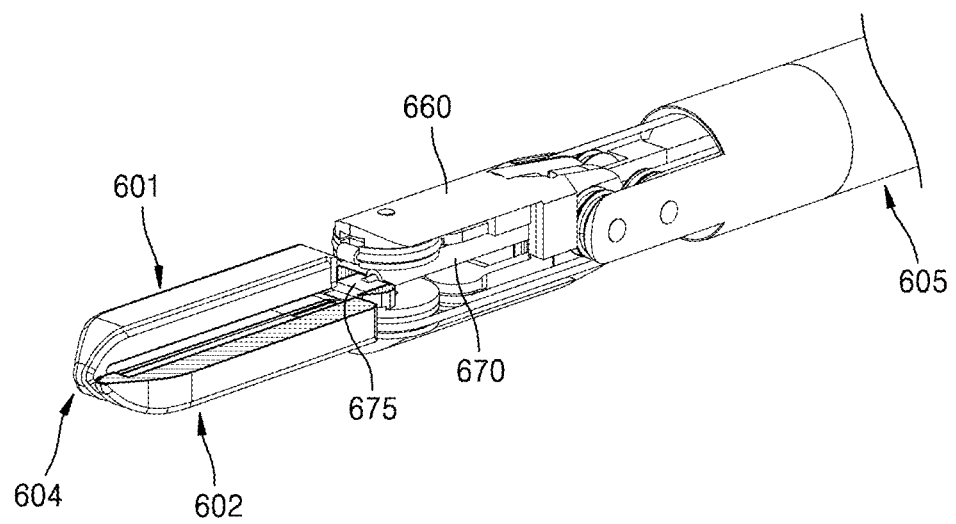
FIGS. 18 to 20 are partial cross-sectional views illustrating an operation of a blade of the end tool of the surgical instrument for electrocautery of FIG. 2.
Figure 19:
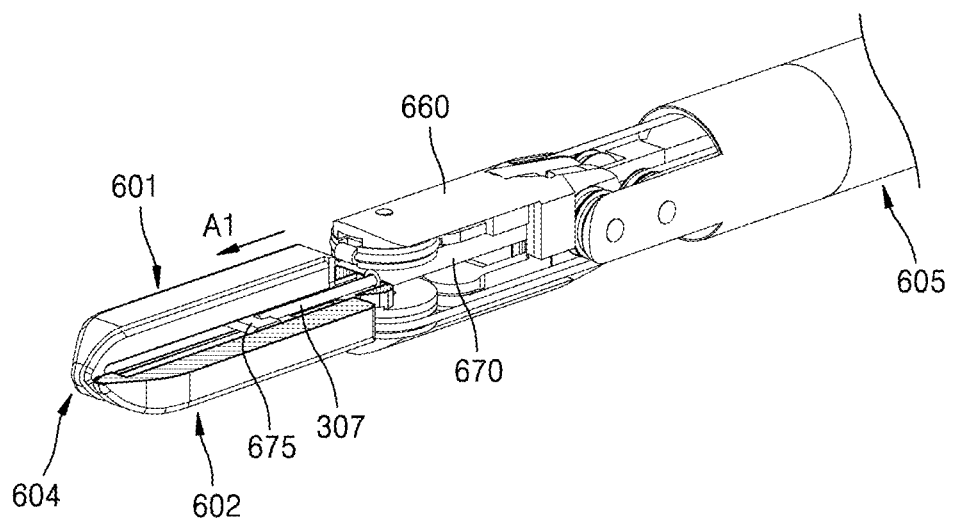
Figure 20:
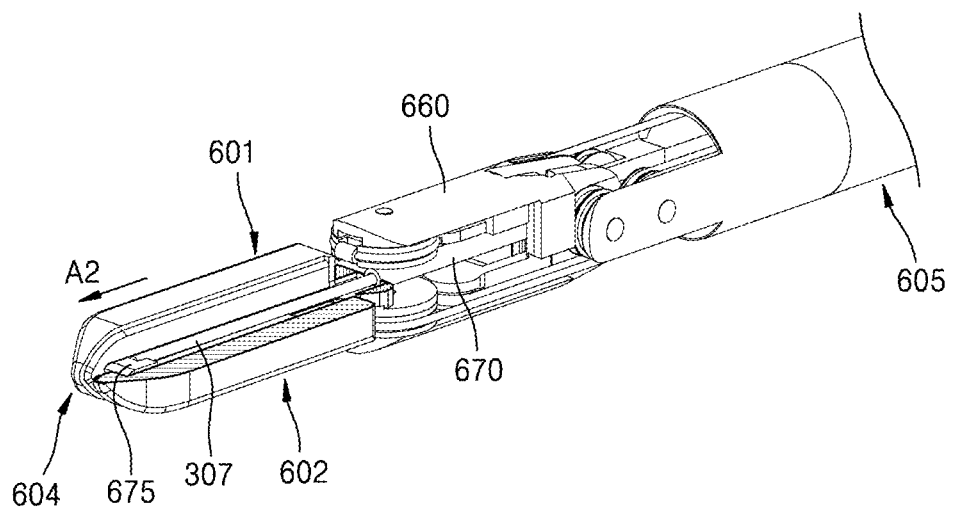

Referring to FIGS. 16 to 20, it may be said that the tissue between the first jaw 601 and the second jaw 602 is cut as the cutting motion of FIGS. 18 to 20 is performed in a state in which the first jaw 601 and the second jaw 602 are closed as shown in FIG. 16.

Here, the first position illustrated in FIG. 18 may be defined as a state in which the blade 675 is drawn in toward the proximal end 605 of the end tool as much as possible. Alternatively, the first position may also be defined as a state in which the blade 675 is located adjacent to the pulley 611/pulley 612.

Meanwhile, the third position illustrated in FIG. 20 may be defined as a state in which the blade 675 is withdrawn toward the distal end 604 of the end tool 600 as much as possible. Alternatively, the third position may also be defined as a state in which the blade 675 is spaced away from the pulley 611/pulley 612 as much as possible.

First, as shown in FIG. 17, a tissue to be cut is located between the first jaw 601 and the second jaw 602 in a state in which the first jaw 601 and the second jaw 602 are opened, and then an actuation motion is performed to close the first jaw 601 and the second jaw 602 as shown in FIG. 16.

Next, as shown in FIG. 18, in a state in which the blade wire 307 and the blade 675 are located at the first position, currents of different polarities are applied to the first electrode 651 and the second electrode 652 to cauterize the tissue between the first jaw 601 and the second jaw 602. At this time, a generator (not shown) configured to supply power to the electrodes may itself perform monitoring of at least some of current, voltage, resistance, impedance, and temperature, and may stop supplying power when the cauterization is completed.

In the state in which the cauterization is completed as described above, when the blade wire 307 moves sequentially in the directions of an arrow A1 of FIG. 19 and an arrow A2 of FIG. 20, the blade 675 coupled to the blade wire 307 moves from the first position at the proximal end 605 of the end tool toward the third position at the distal end 604 of the end tool, reaching the positions in FIGS. 19 and 20 in turn.

As such, the blade 675 cuts the tissue located between the first jaw 601 and the second jaw 602 while moving in the X-axis direction.

However, it is to be understood that the linear motion of the blade 675 here does not mean a motion in a completely straight line, but rather means a motion of the blade 675 to the extent that the blade 675 is able to cut the tissue while achieving a linear motion when viewed as a whole, even though the motion is not in a completely straight line, for example, the middle part of the straight line is bent by a certain angle or there is a section having a gentle curvature in a certain section.

Meanwhile, in this state, when the blade wire 307 is pulled in the opposite direction, the blade 675 coupled to the blade wire 307 also returns to the first position.

According to the present disclosure, the multi-joint/multi-degree-of-freedom surgical instrument capable of pitch/yaw/actuation motions may also perform cauterizing and cutting motions.

(Pitch, Yaw, Actuation, and Cutting Motions of End Tool)

FIGS. 16 and 17 are plan views illustrating an opening and closing motion of the end tool of the surgical instrument for electrocautery of FIG. 2. The first jaw 601 may be coupled to the pulley 611 and the second jaw 602 may be coupled to the pulley 621.

The pulley 611 functions as an end tool first jaw pulley, and the pulley 621 functions as an end tool second jaw pulley. The pulley 611 may also be referred to as a first jaw pulley, and the pulley 621 may also be referred to as a second jaw pulley, and these two components may collectively be referred to as end tool jaw pulleys or simply jaw pulleys.

The pulley 611 and the pulley 621, which are end tool jaw pulleys, are formed to face each other, and are formed to be rotatable independently of each other around the first rotation shaft 641 which is an end tool jaw pulley rotation shaft. In this case, the pulley 611 and the pulley 621 are formed to be spaced apart from each other by a certain distance, and the blade assembly, specifically the guide tube 670 accommodating the blade wire 307 therein may be disposed therebetween.

That is, at least a part of the blade assembly (no reference number is assigned) may be disposed between the pulley 611 and the pulley 621, and the blade assembly including the guide tube 670 may be disposed between the pulley 611 and the pulley 621.

Referring to FIGS. 16 and 17, when the pulley 621 rotates around the first rotation shaft 641, the second jaw 602 may also rotate around the first rotation shaft 641 together with the pulley 621.

Meanwhile, the pulley 611 is connected to the first jaw 601, and when the pulley 611 rotates around the first rotation shaft 641, the first jaw 601 connected to the pulley 611 may rotate around the first rotation shaft 641.

In the end tool 600 of the electric cauterization surgical instrument 10 according to an embodiment of the present disclosure, the first rotation shaft 641, which is a yaw rotation shaft, may function as an actuation rotation shaft.

That is, a yaw motion may be performed when the pulley 611 and the pulley 621, which are connected to the first jaw 601 and the second jaw 602, respectively, rotate in the same direction with the first rotation shaft 641, which is a yaw rotation shaft and an actuation rotation shaft, as the center of rotation, and an actuation motion may be performed when the pulley 611 and the pulley 621 rotate in different directions.

Referring to FIG. 17, as the pulley 611 and the pulley 621 rotate in opposite directions with the first rotation shaft 641 as the central axis of rotation, the first jaw 601 and second jaw 602, which are connected to the pulley 611 and the pulley 621, respectively, rotate in opposite directions and move away from each other, and thus the end tool 600 may be in an open state.

Figure 21:
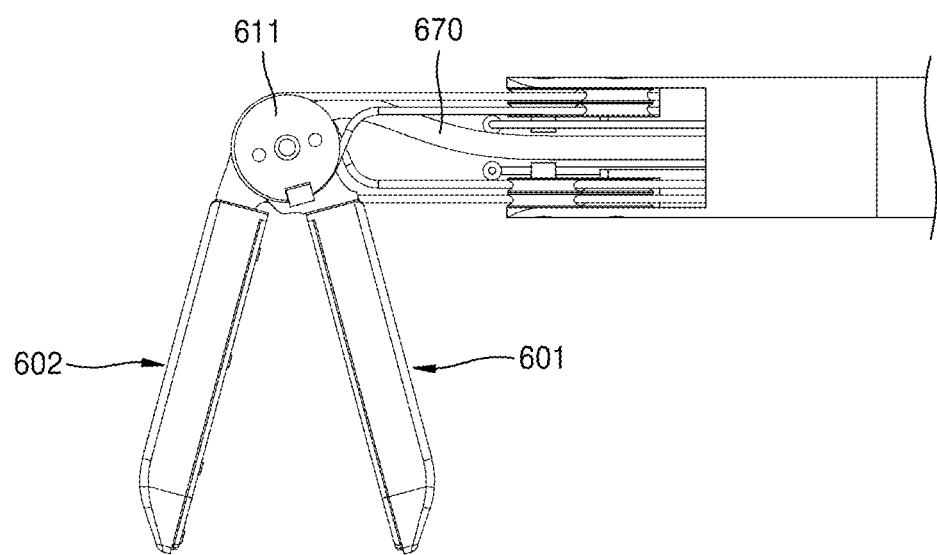
FIGS. 21 and 22 are bottom views illustrating a process of performing an opening and closing motion in a state in which the end tool of the surgical instrument for electrocautery of FIG. 2 is yaw-rotated by −90°.
Figure 22:
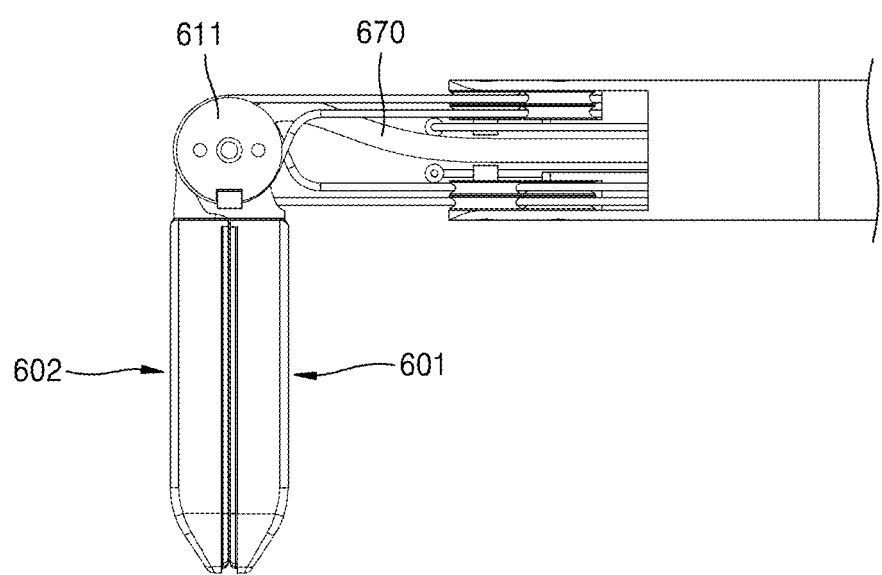

Referring to FIGS. 21 and 22, bottom views are illustrated in which a process of performing an opening and closing motion in a state in which the end tool 600 of the electric cauterization surgical instrument 10 of FIG. 2 is yaw-rotated by −90°.

In FIG. 21, the pulley 611 and the pulley 621 that faces the pulley 611 may rotate around the first rotation shaft 641 through the power transmission portion 300 in the manipulation portion 200. In FIG. 21, when the pulley 611 and the pulley 621 rotate in opposite directions, the first jaw 601 and the second jaw 602 respectively coupled to the pulley 611 and the pulley 621 may rotate relative to each other in a direction of approaching each other to perform an actuation motion, and as shown in FIG. 22, the first jaw 601 and the second jaw 602 may be in a closed state.

Figure 23:
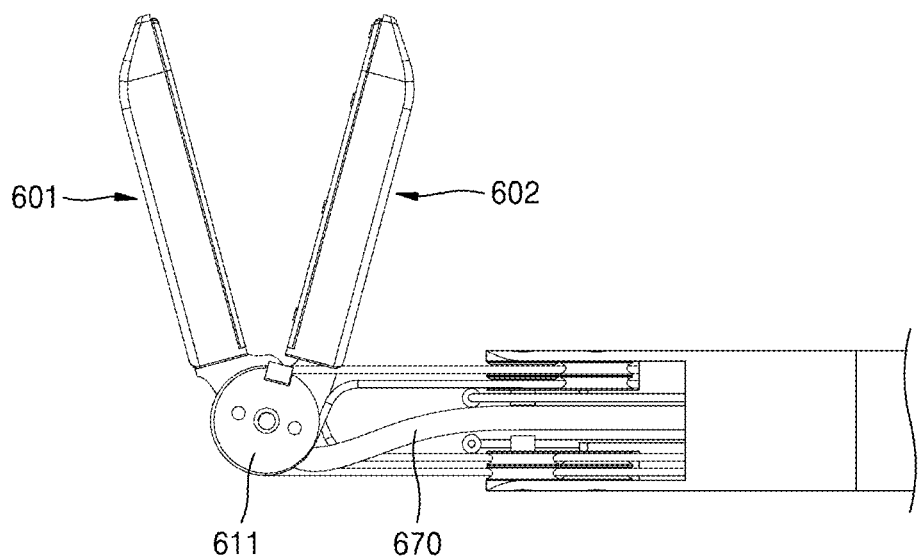
FIGS. 23 and 24 are bottom views illustrating a process of performing an opening and closing motion in a state in which the end tool of the surgical instrument for electrocautery of FIG. 2 is yaw-rotated by +90°.
Figure 24:
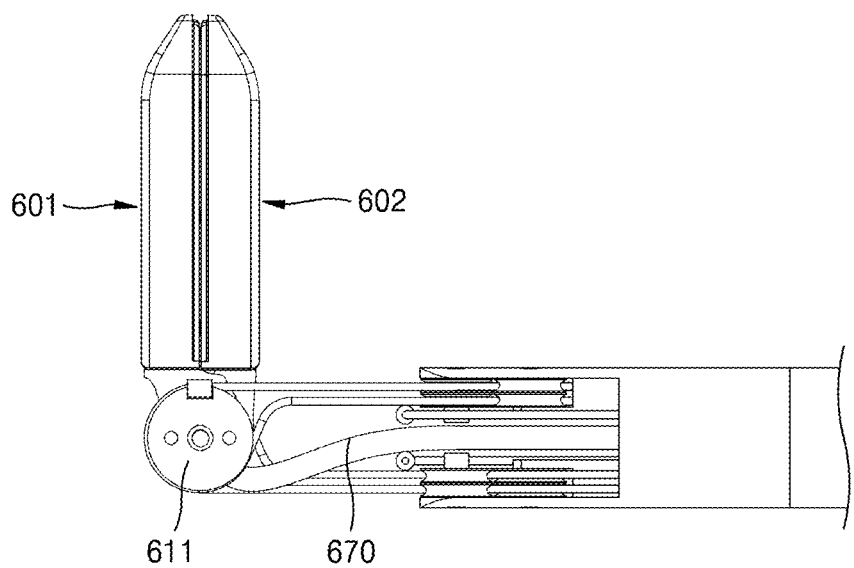

FIGS. 23 and 24 are bottom views illustrating a process of performing an opening and closing motion in a state in which the end tool of the surgical instrument for electrocautery of FIG. 2 is yaw-rotated by +90°. Referring to FIGS.

23 and 24, as the pulley 611 and the pulley 611 are yaw rotatable by +90° with the first rotation shaft 641 as the central axis of rotation, and the pulley 611 and the pulley 611 rotates in different directions, an actuation motion is possible in which the first jaw 601 and the second jaw 602 respectively connected to the pulley 611 and the pulley 621 move closer or further away from each other.

Referring to FIGS. 21 to 24, the blade assembly, specifically, the guide tube 670 is connected to the end tool 600 at the other end portion, which is opposite one end portion connected to the connection portion 400, and may be of constant length.

The guide tube 670 may be gently curved with a predetermined radius of curvature when the end tool 600, specifically, the first jaw 601 and the second jaw 602 rotate with the first rotation shaft 641 as the central axis of rotation, and may stably provide a movement path for the blade wire 307 to be movable between the distal end 604 and the proximal end 605 of the end tool 600.

Figure 25:
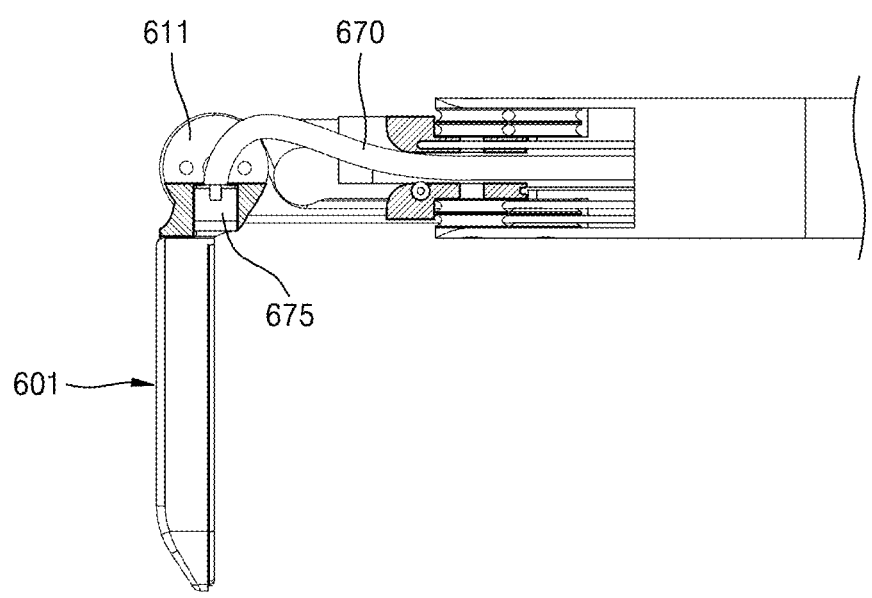
FIGS. 25 and 26 are views illustrating a path of the guide tube and a movement path of the blade during a cutting motion in a state in which the end tool of the surgical instrument for electrocautery of FIG. 2 is yaw-rotated by +90°.
Figure 26:
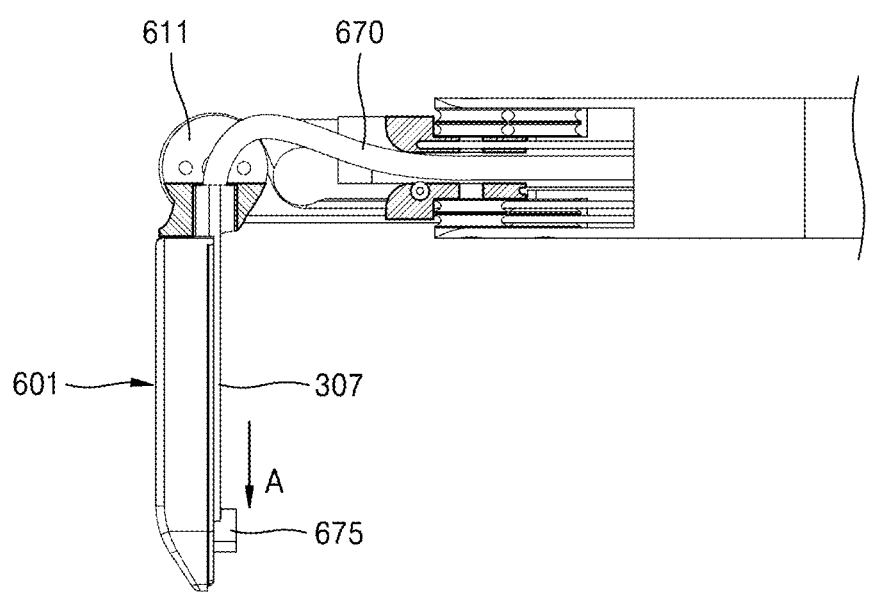

FIGS. 25 and 26 are views illustrating a path of the guide tube 670 and a movement path of the blade 675 during a cutting motion in a state in which the end tool 600 of the surgical instrument for electrocautery of FIG. 2 is yaw-rotated by +90°.

Referring to FIGS. 25 and 26, the end tool 600 of the electric cauterization surgical instrument 10 according to the first embodiment of the present disclosure is formed such that the jaws 601 and 602 are able to perform a normal cutting motion even when the jaws are yaw-rotated by +90°.

Specifically, as the blade wire 307 emerges from the inside of the guide tube 670, and the blade 675 connected to the blade wire 307 moves in the direction of an arrow A, which is a direction from the proximal end 605 toward the distal end 604 of the end tool 600, a cutting motion may be performed.

Figure 27:
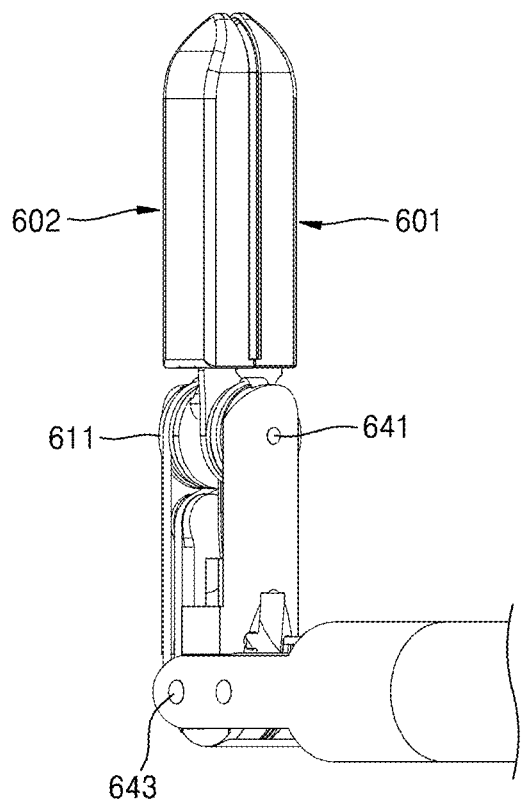
FIGS. 27 and 28 are views illustrating a process of performing an opening and closing motion in a state in which the end tool of the surgical instrument for electrocautery of FIG. 2 is pitch-rotated by −90°.
Figure 28:
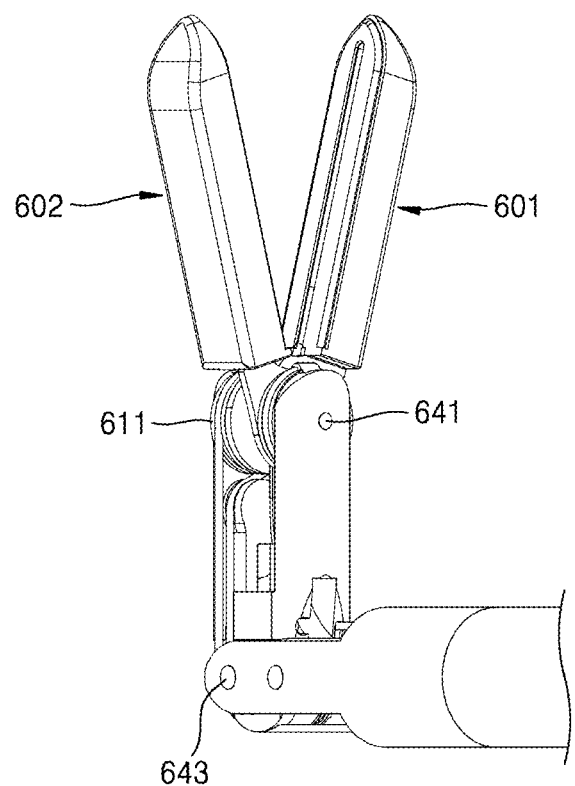
Figure 29:
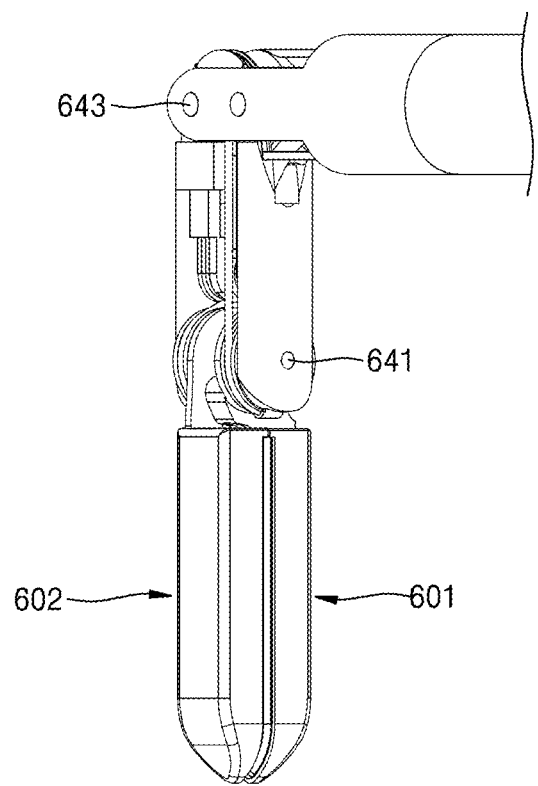
FIGS. 29 and 30 are views illustrating a process of performing an opening and closing motion in a state in which the end tool of the surgical instrument for electrocautery of FIG. 2 is pitch-rotated by +90°.
Figure 30:
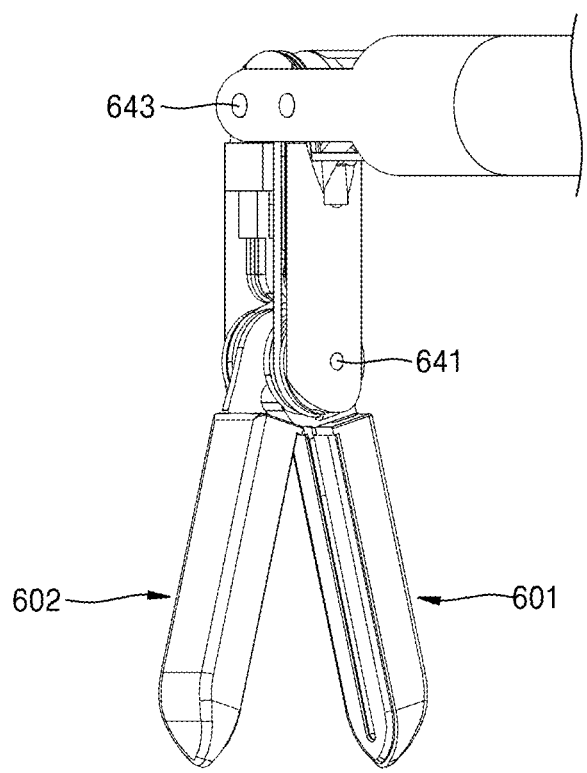
Figure 31:
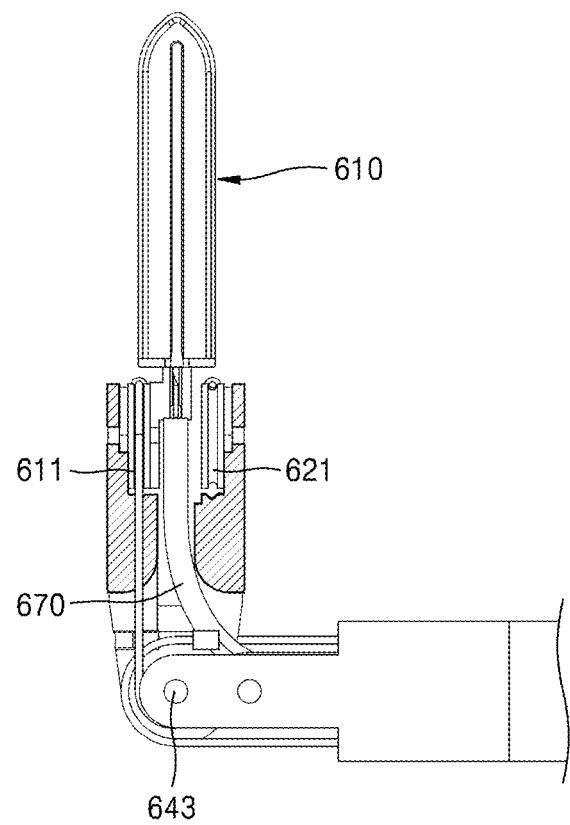
FIG. 31 is a view illustrating a path of the guide tube in a state in which the end tool of the surgical instrument for electrocautery of FIG. 2 is pitch-rotated by −90°.
Figure 32:
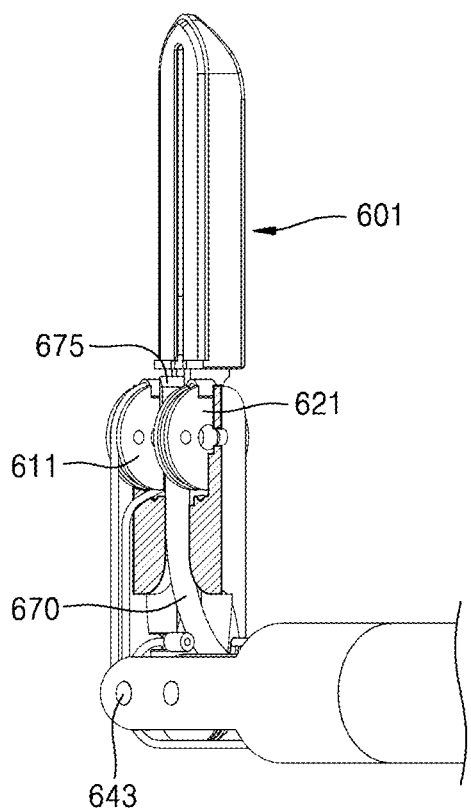
FIGS. 32 and 33 are views illustrating a path of the guide tube and a movement path of the blade during a cutting motion in a state in which the end tool of the surgical instrument for electrocautery of FIG. 2 is pitch-rotated by −90°.
Figure 33:
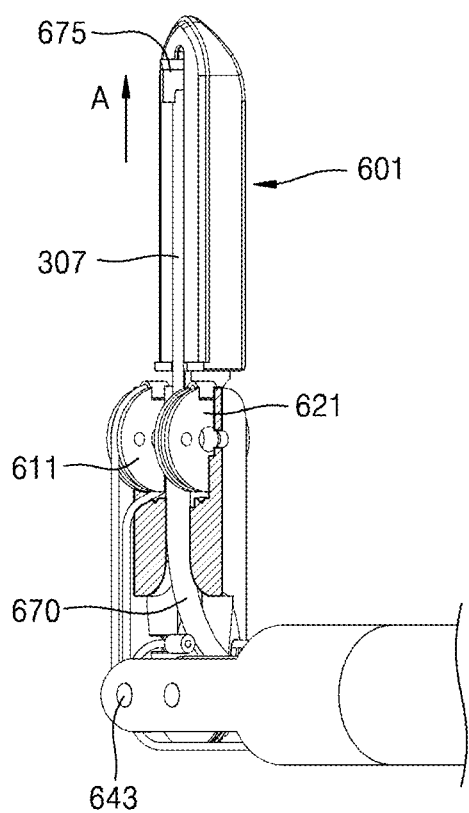

FIGS. 27 and 28 are views illustrating a process of performing an opening and closing motion in a state in which the end tool of the surgical instrument for electrocautery of FIG. 2 is pitch-rotated by −90°. FIGS. 29 and 30 are views illustrating a process of performing an opening and closing motion in a state in which the end tool of the surgical instrument for electrocautery of FIG. 2 is pitch-rotated by +90°. FIG. 31 is a view illustrating a path of the guide tube in a state in which the end tool of the surgical instrument for electrocautery of FIG. 2 is pitch-rotated by −90°. FIGS. 32 and 33 are views illustrating a path of the guide tube and a movement path of the blade during a cutting motion in a state in which the end tool of the surgical instrument for electrocautery of FIG. 2 is pitch-rotated by −90°.

Referring to FIGS. 27 to 33, the end tool 600 of the electric cauterization surgical instrument 10 according to the first embodiment of the present disclosure is formed such that the jaws 601 and 602 are able to perform a cutting motion normally even when the jaws are pitch-rotated by −90° and +90°.

Figure 34:
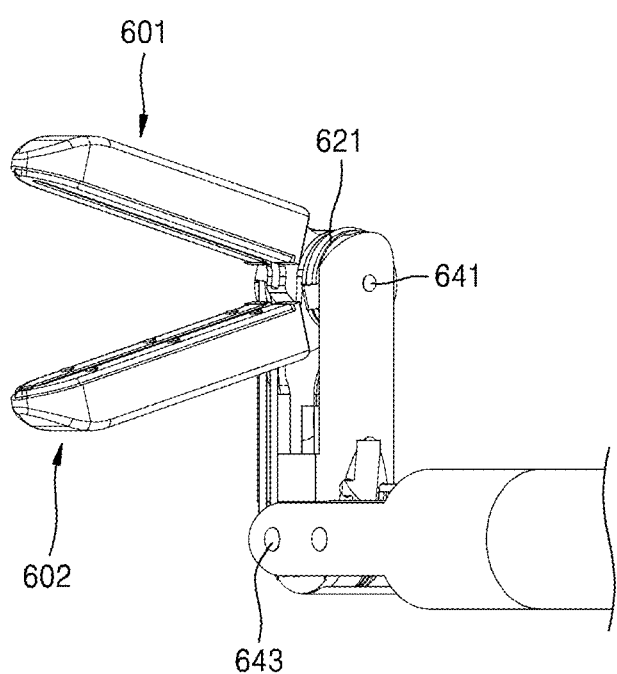
FIG. 34 is a perspective view illustrating the surgical instrument for electrocautery of FIG. 2 in a pitch-rotated and yaw-rotated state.
Figure 35:
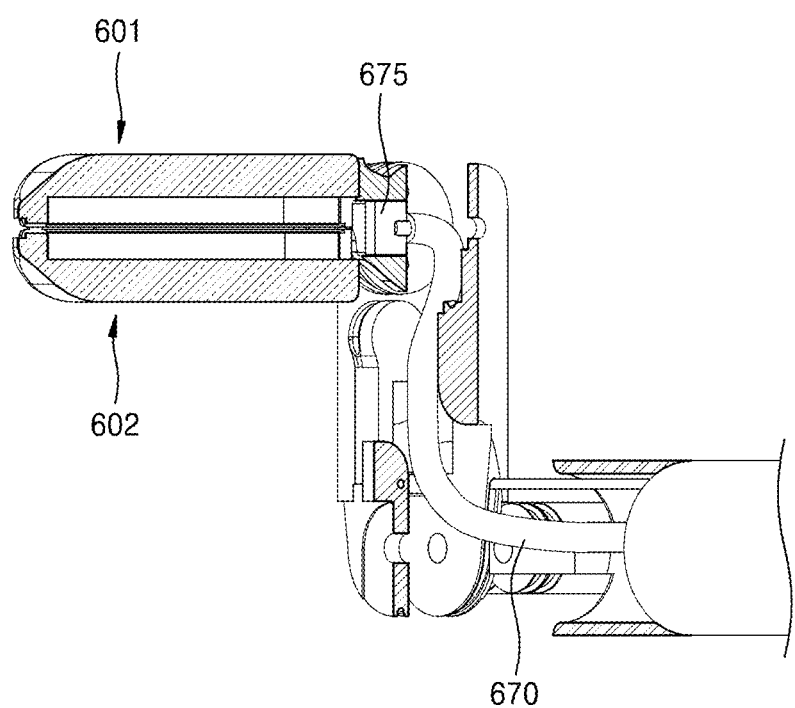
FIGS. 35 to 37 are views illustrating the end tool of the surgical instrument for electrocautery of FIG. 2 performing a cutting motion in a state in which the end tool is pitch-rotated by −90° and simultaneously yaw-rotated by +90°.
Figure 36:
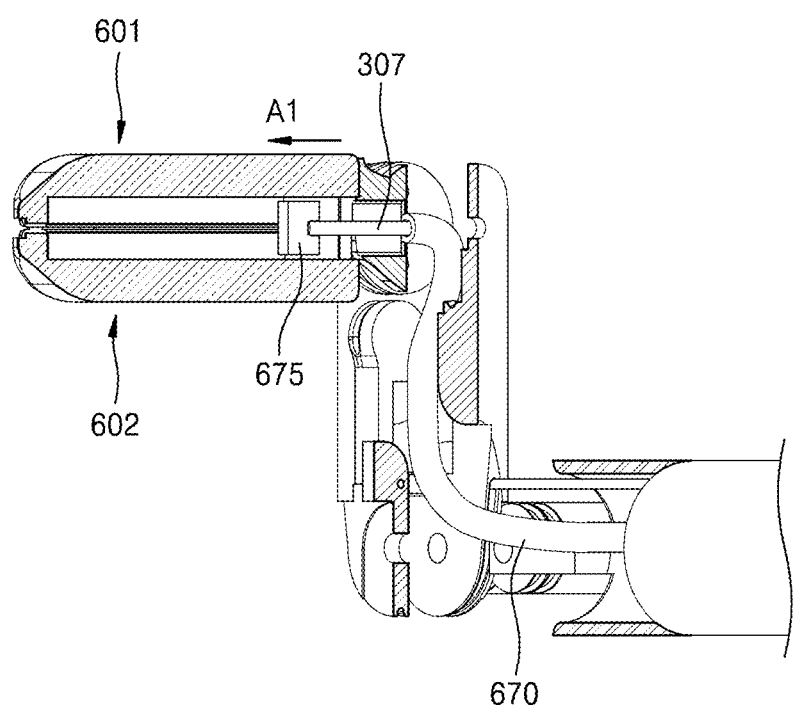
Figure 37:
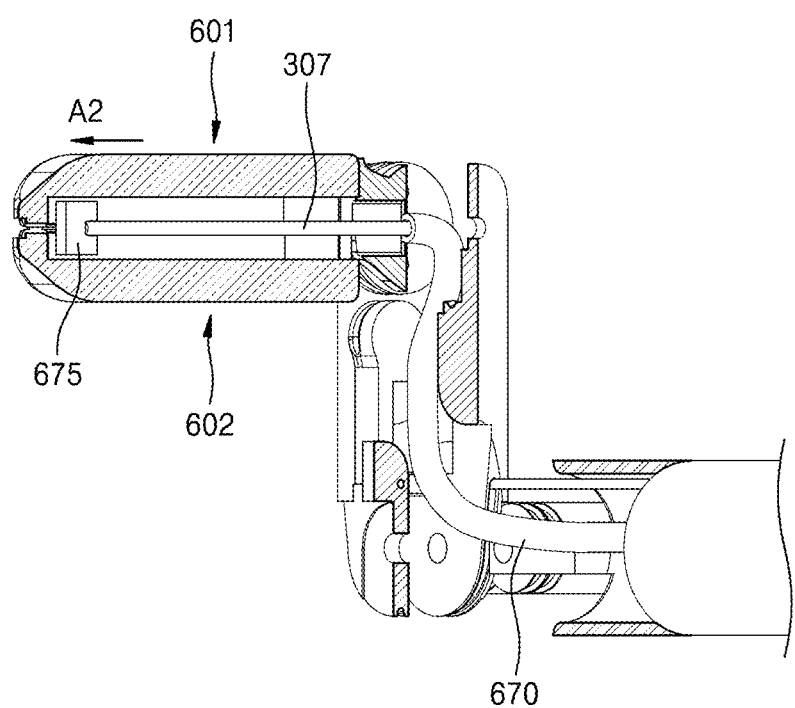

Meanwhile, FIG. 34 is a view illustrating a state in which the jaws are pitch-rotated by −90° and simultaneously yaw-rotated by +90°, and FIGS. 35 to 37 are views illustrating the end tool of the surgical instrument for electrocautery of FIG. 2 performing a cutting motion in a state in which the end tool is pitch-rotated by −90° and simultaneously yaw-rotated by +90°.

Referring to FIGS. 34 to 37, the end tool 600 of the electric cauterization surgical instrument 10 according to the first embodiment of the present disclosure is formed such that the jaws 601 and 602 are able to perform a cutting motion normally even when the jaws are pitch-rotated by −90° and simultaneously yaw-rotated by +90°.

Modified Example of First Embodiment-Disposing Auxiliary Pulley on End Tool Hub

Hereinafter, an end tool 600 of a surgical instrument according to a modified example of the first embodiment of the present disclosure will be described. Here, the end tool 600 of the surgical instrument according to the modified example of the first embodiment of the present disclosure is different from the end tool of the surgical instrument according to the first embodiment of the present disclosure described above in that the configuration of an end tool hub 660' and the configuration of auxiliary pulleys 612 and 622 are different. The configuration changed from the first embodiment as described above will be described in detail later.

Figure 38:
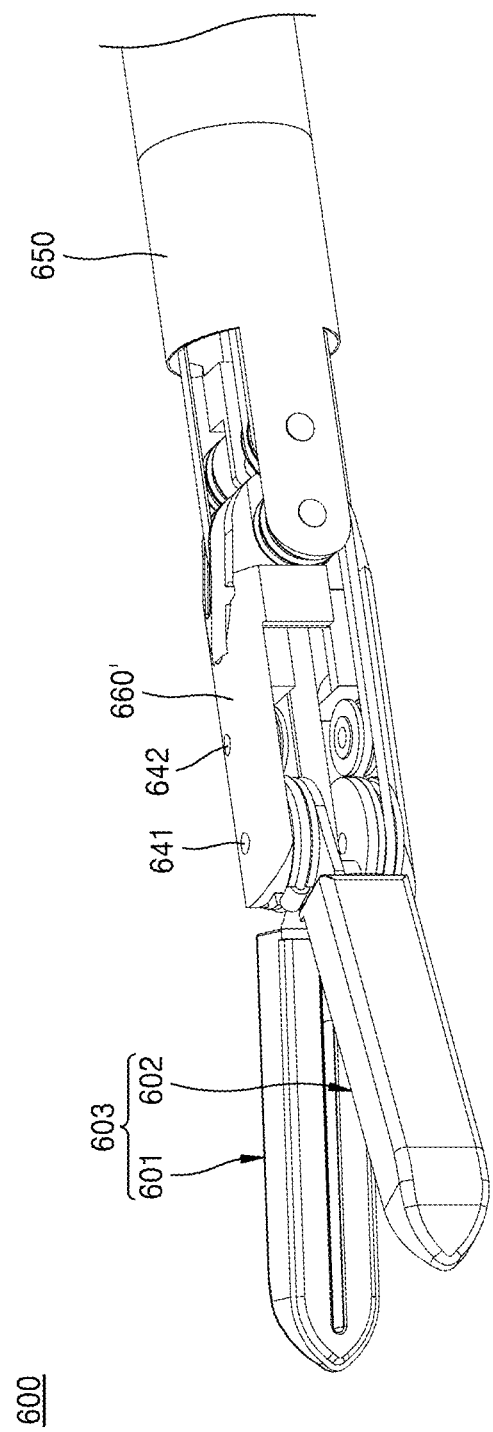
FIGS. 38 to 40 are views illustrating an end tool of a surgical instrument for electrocautery according to a modified example of the first embodiment of the present disclosure.
Figure 39:
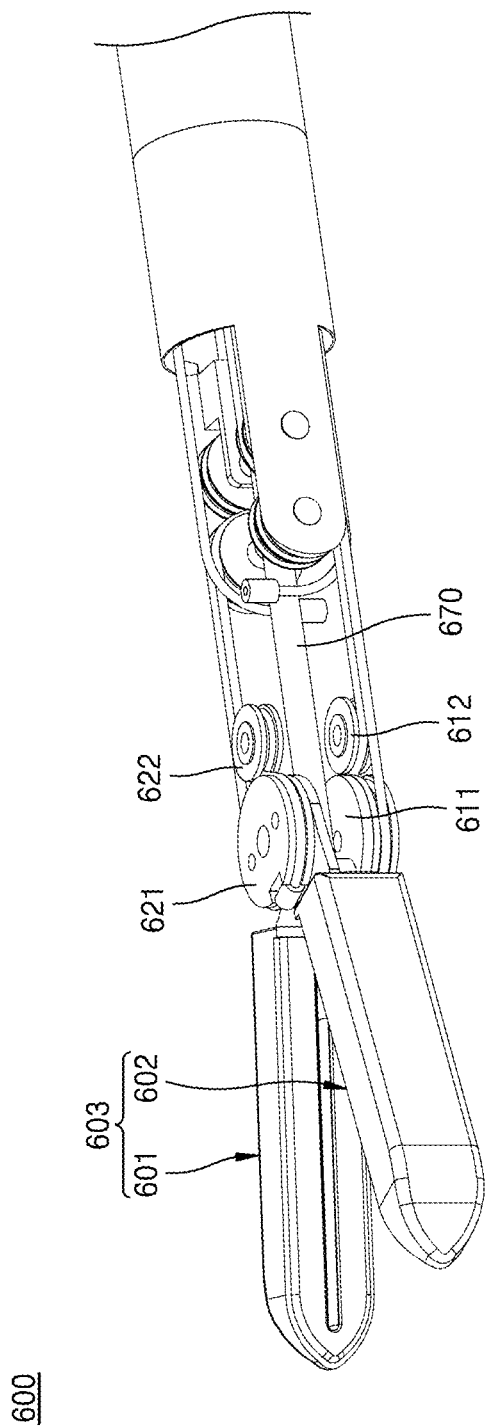
Figure 40:
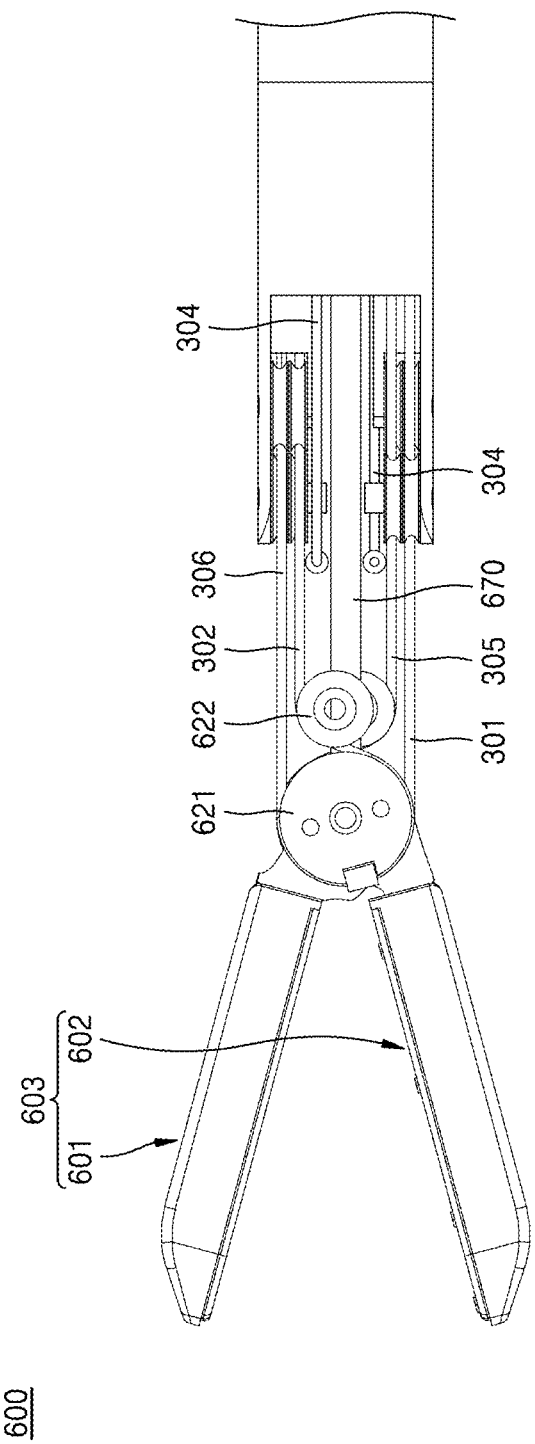

FIGS. 38 to 40 are views illustrating the end tool of the surgical instrument for electrocautery according to the modified example of the first embodiment of the present disclosure.

Referring to FIGS. 38 to 40, the end tool 600 of the modified example of the first embodiment of the present disclosure includes a pair of jaws for performing a grip motion, specifically a first jaw 601 and a second jaw 602, and here, each of the first jaw 601 and the second jaw 602 or a component encompassing the first jaw 601 and the second jaw 602 may be referred to as a jaw 603.

The end tool 600 according to the modified example of the first embodiment may include a pulley 611, the pulley 612, a pulley 613, a pulley 614, a pulley 615, and a pulley 616 that are associated with a rotational motion of the first jaw 601. In addition, the end tool 600 may include a pulley 621, the pulley 622, a pulley 623, a pulley 624, a pulley 625, and a pulley 626 that are associated with a rotational motion of the second jaw 602.

Here, the pulleys facing each other are illustrated in the drawings as being formed parallel to each other, but the concept of the present disclosure is not limited thereto, and each of the pulleys may be variously formed with a position and a size suitable for the configuration of the end tool.

The end tool 600 according to the modified example of the first embodiment of the present disclosure may further include the pulley 612 and the pulley 622 as compared to the end tool 600 according to the first embodiment of the present disclosure illustrated with reference to FIG. 6.

Referring to FIGS. 39 and 40, the pulley 612 functions as an end tool first jaw auxiliary pulley, and the pulley 622 functions as an end tool second jaw auxiliary pulley, and these two components may collectively be referred to as end tool jaw auxiliary pulleys or simply auxiliary pulleys.

In detail, the pulley 612 and the pulley 622, which are end tool jaw auxiliary pulleys, may be additionally provided on one side of the pulley 611 and one side of the pulley 621, respectively. In other words, the pulley 612, which is an auxiliary pulley, may be disposed between the pulley 611 and the pulley 613/pulley 614. In addition, the pulley 622, which is an auxiliary pulley, may be disposed between the pulley 621 and the pulley 623/pulley 624.

The pulley 612 and the pulley 622 may be formed to be rotatable independently of each other around the second rotation shaft 642.

The pulley 612 and the pulley 622 may serve to increase rotation angles of the first jaw 601 and the second jaw 602, respectively, by coming into contact with the wire 305, which is a first jaw wire, and the wire 302, which is a second jaw wire, and changing the arrangement paths of the wire 305 and the wire 302 to a certain degree.

That is, when the auxiliary pulleys are not disposed, each of the first jaw 601 and the second jaw 602 may rotate only up to a right angle, but in the modified example of the first embodiment, by additionally providing the pulley 612 and the pulley 622, which are auxiliary pulleys, the effect of increasing the maximum rotation angle by a certain angle can be achieved.

This enables a motion in which two jaws of the end tool 600 have to be spread apart for an actuation motion in a state in which the two jaws are yaw-rotated together by 90° in the clockwise or counterclockwise direction.

In other words, a feature of increasing the range of yaw rotation in which an actuation motion is possible may be obtained through the pulley 612 and the pulley 622. This will be described below in more detail.

When the auxiliary pulleys are not disposed, since the first jaw wire 305 is fixedly coupled to the end tool first jaw pulley 611, and the second jaw wire 302 is fixedly coupled to the end tool second jaw pulley 621, each of the end tool first jaw pulley 611 and the end tool second jaw pulley 621 may rotate up to 90°.

In this case, when the actuation motion is performed in a state in which the first jaw 601 and the second jaw 602 are located at a 90° line, the first jaw 601 may be spread, but the second jaw 602 may not be rotated beyond 90°. Accordingly, when the first jaw 601 and the second jaw 602 perform a yaw motion over a certain angle, there was a problem that an actuation motion is not smoothly performed.

In order to address such a problem, in the electric cauterization surgical instrument 10 of the present disclosure, the pulley 612 and the pulley 622, which are auxiliary pulleys, are additionally disposed at one side of the pulley 611 and one side of the pulley 621, respectively. As described above, as the arrangement paths of the wire 305, which is a first jaw wire, and the wire 302, which is a second jaw wire, are changed to a certain degree by disposing the pulley 612 and the pulley 622, a tangential direction of the wires 305 and 302 is changed, and accordingly, a fastening member 324 for coupling the wire 302 and the pulley 621 is additionally rotatable by a certain angle.

That is, a fastening member 326, which is a coupling portion of the wire 302 and the pulley 621, is rotatable until being located on a common internal tangent of the pulley 621 and the pulley 622. Similarly, a fastening member 323, which is a coupling portion of the wire 305 and the pulley 611, is rotatable until being located on a common internal tangent of the pulley 611 and the pulley 612, so that the range of rotation may be increased.

In other words, due to the pulley 612 that is an auxiliary pulley, the wires 301 and 305, which are two strands of the first jaw wire wound around the pulley 612, are disposed at one side with respect to a plane perpendicular to the Y-axis and passing through the X-axis. Simultaneously, due to the pulley 622, the wires 302 and 306, which are two strands of the second jaw wire wound around the pulley 621, are disposed at the other side with respect to the plane perpendicular to the Y-axis and passing through the X-axis.

In other words, the pulley 613 and the pulley 614 are disposed at one side with respect to the plane perpendicular to the Y-axis and passing through the X-axis, and the pulley 623 and the pulley 624 are disposed at the other side with respect to the plane perpendicular to the Y-axis and passing through the X-axis.

In other words, the wire 305 is located on the internal tangent of the pulley 611 and the pulley 612, and the rotation angle of the pulley 611 is increased due to the pulley 612. In addition, the wire 302 is located on the internal tangent of the pulley 621 and the pulley 622, and the rotation angle of the pulley 621 is increased due to the pulley 622.

According to the present disclosure, the rotation radii of the first jaw 601 and the second jaw 602 increase, so that an effect of increasing a yaw motion range in which a normal opening/closing actuation motion can be performed may be obtained.

Referring to FIG. 38, a first rotation shaft 641 and a second rotation shaft 642 may be inserted through the end tool hub 660' according to the modified example of the first embodiment of the present disclosure. Instead of respectively forming the first wire guide portion and the second wire guide portion on the surfaces of the first jaw pulley coupling portion 662a and the second jaw pulley coupling portion 662b facing each other as in the end tool hub 660 according to the first embodiment of the present disclosure, the pulley 612 and the pulley 622, which are configured as separate components from the end tool hub 660' and are able to be axially coupled to the second rotation shaft 642 that is inserted through the end tool hub 660', are additionally provided and allowed to function as auxiliary pulleys.

The second rotation shaft 642 inserted through the end tool hub 660' may include two shafts including a first sub-shaft and a second sub-shaft that face each other and are disposed to be spaced apart from each other by a certain distance. The second rotation shaft is divided into two parts and spaced apart from each other by a certain distance, and thus the guide tube 670 may pass through the end tool hub 660' and the pitch hub 650 through between the two parts.

Referring to FIG. 38, the first rotation shaft 641, the second rotation shaft 642, a third rotation shaft 643, and a fourth rotation shaft 644 may be arranged sequentially from a distal end 604 toward a proximal end 605 of the end tool 600. Accordingly, starting from the distal end 604, the first rotation shaft 641 may be referred to as a first pin, the second rotation shaft 642 may be referred to as a second pin, the third rotation shaft 643 may be referred to as a third pin, and the fourth rotation shaft 644 may be referred to as a fourth pin.

As compared to the first embodiment, the end tool 600 of the modified example of the first embodiment of the present disclosure has the same configuration as the end tool 600 according to the first embodiment, except that the pulley 621 and the pulley 622, which are axially coupled to the end tool hub 660' by the second rotation shaft 642, are provided as separate components instead of being integrally formed with a body portion 661 in the end tool hub 660' and function as auxiliary pulleys, and thus a detailed description thereof will be omitted in the overlapping range.

Figure 41:
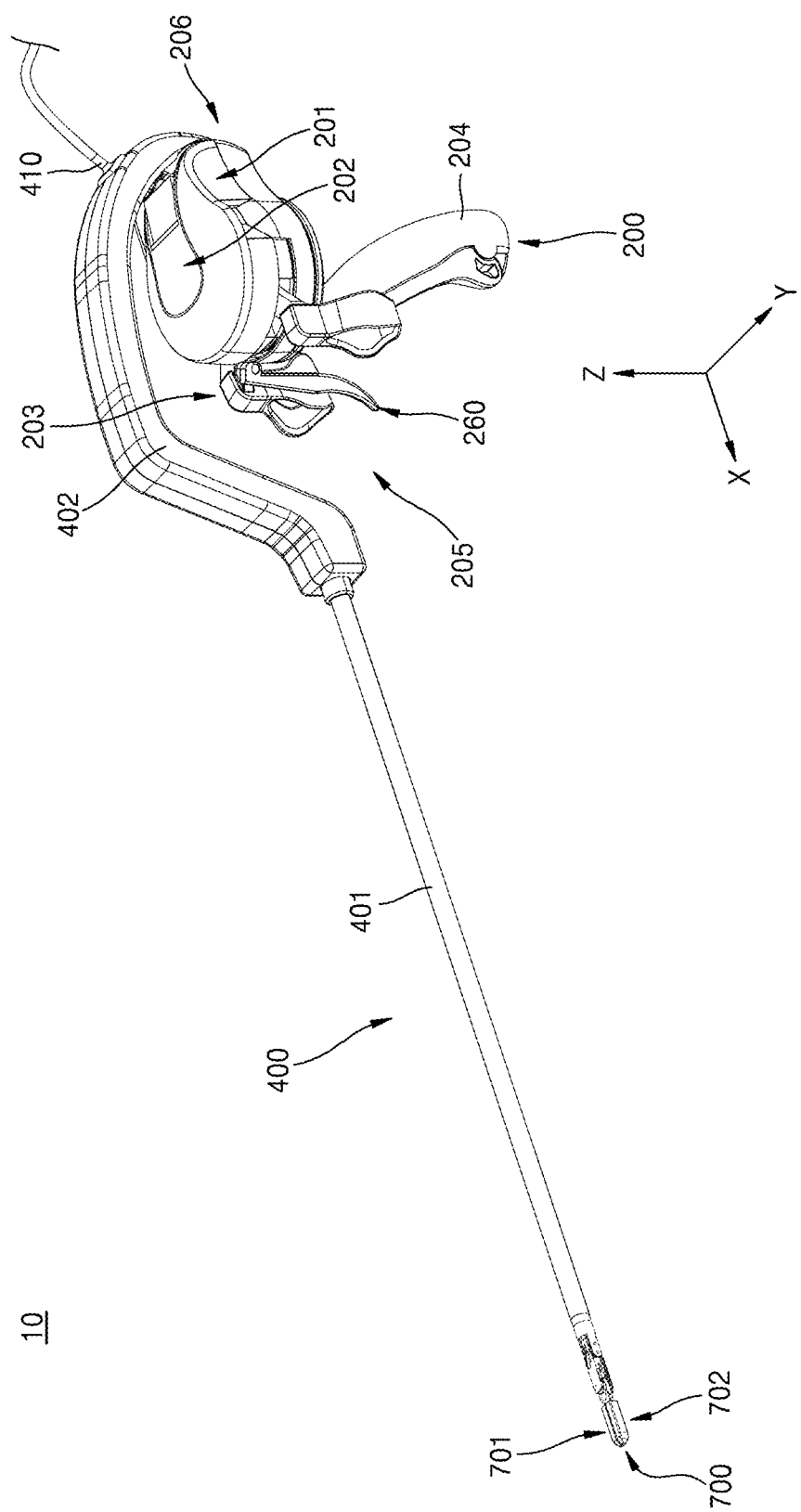
FIG. 41 is a perspective view illustrating a surgical instrument for electrocautery according to a second embodiment of the present disclosure.
Figure 42:
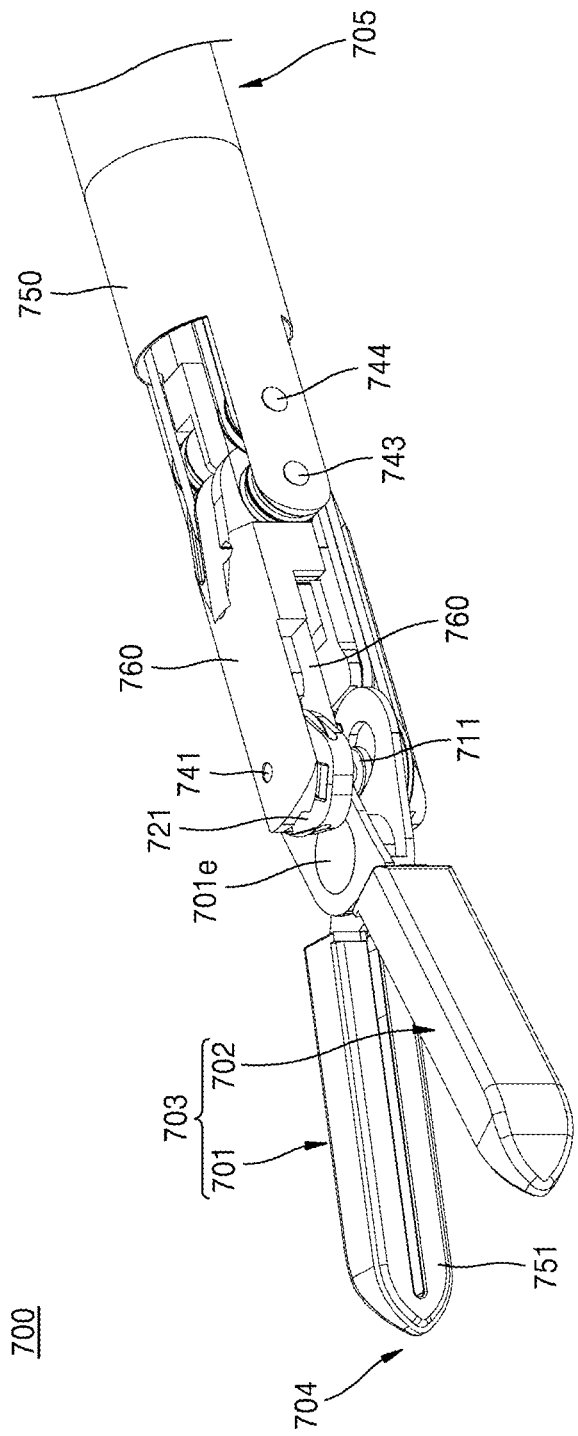
FIGS. 42 to 47 are views illustrating an end tool of the surgical instrument for electrocautery of FIG. 41.

Second Embodiment of Surgical Instrument for Electrocautery-Forming X-Shaped Structure of First and Second Jaws FIG. 41 is a perspective view illustrating a surgical instrument for electrocautery according to a second embodiment of the present disclosure. FIGS. 42 to 47 are views illustrating an end tool of the surgical instrument for electrocautery of FIG. 41.

Referring to FIG. 41, an electric cauterization surgical instrument 10 according to the second embodiment of the present disclosure includes an end tool 700, a manipulation portion 200, a power transmission portion 300, and a connection portion 400.

The electric cauterization surgical instrument 10 according to the second embodiment of the present disclosure is different from the electric cauterization surgical instrument 10 according to the first embodiment in that the end tool 700 has a different configuration, and thus the configuration of the end tool 700 will be described in detail below.

The end tool 700 is formed on the other end portion of the connection portion 400, and performs necessary motions for surgery by being inserted into a surgical site. In an example of the end tool 700 described above, as illustrated in FIG. 41, a pair of jaws 703 for performing a grip motion may be used.

However, the concept of the present disclosure is not limited thereto, and various devices for performing surgery may be used as the end tool 700. For example, a configuration of a cantilever cautery may also be used as the end tool 700. The end tool 700 is connected to the manipulation portion 200 by the power transmission portion 300, and receives a driving force of the manipulation portion 200 through the power transmission portion 300 to perform a motion necessary for surgery, such as gripping, cutting, suturing, or the like.

Here, the end tool 700 of the electric cauterization surgical instrument 10 according to the second embodiment of the present disclosure is formed to be rotatable in at least one direction, and for example, the end tool 700 may be formed to perform a pitch motion around a Y-axis of FIG. 41 and simultaneously perform a yaw motion and an actuation motion around a Z-axis of FIG. 41.

Referring to FIGS. 42 to 47, 55, and 56, the end tool 700 of the electric cauterization surgical instrument 10 according to the second embodiment of the present disclosure includes a first electrode 751, a second electrode 752, a pitch hub 750, an end tool hub 760, a plurality of rotation shafts 741, 743, and 744, and the like that are the same as those of the first embodiment in configuration and effect, and is different in that a jaw rotation shaft 701c, a tube through hole 701f, a jaw pulley coupling hole 701d, and a movable coupling hole 701c are formed in a first jaw 701, and a shaft pass-through portion 702e through which the rotation shaft 701c, which is a jaw rotation shaft formed in the first jaw 701, is able to pass, a movable coupling hole 702c, and a hole 702d, which is a jaw pulley coupling hole, are formed in a second jaw 702 that faces and is connectable to the first jaw 701.

Figure 48:
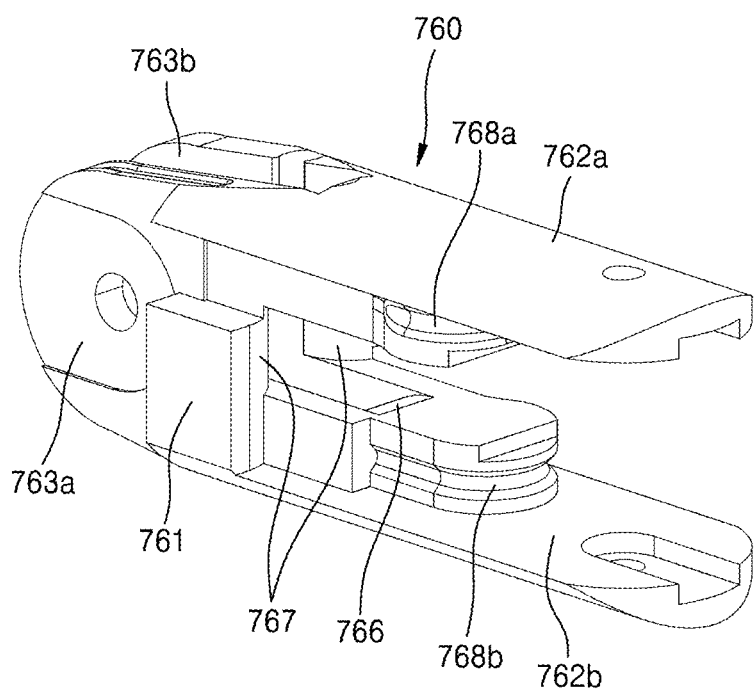
FIG. 48 is a perspective view illustrating an end tool hub of the surgical instrument for electrocautery of FIG. 41.
Figure 49:
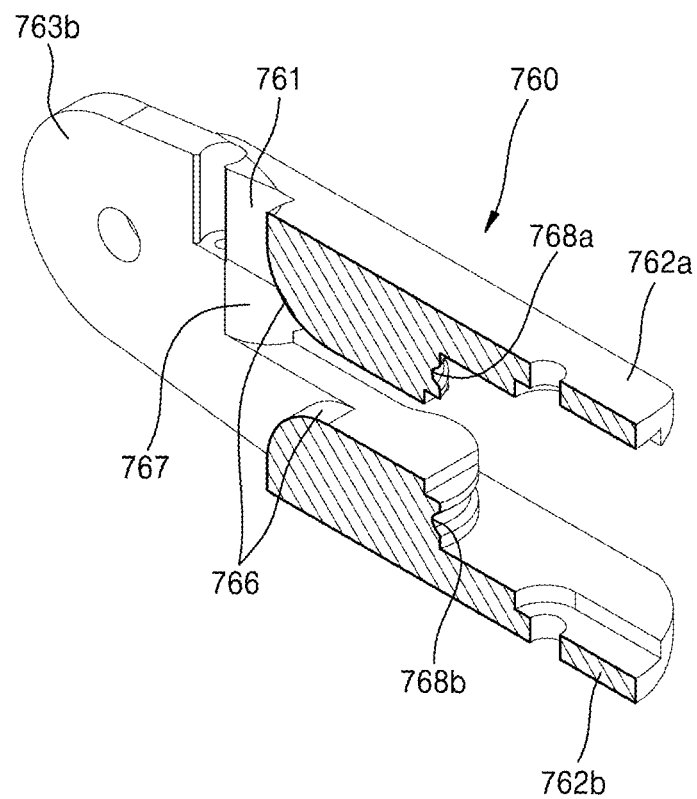
FIGS. 49 and 50 are cut-away perspective views of the end tool hub of FIG. 48.
Figure 50:
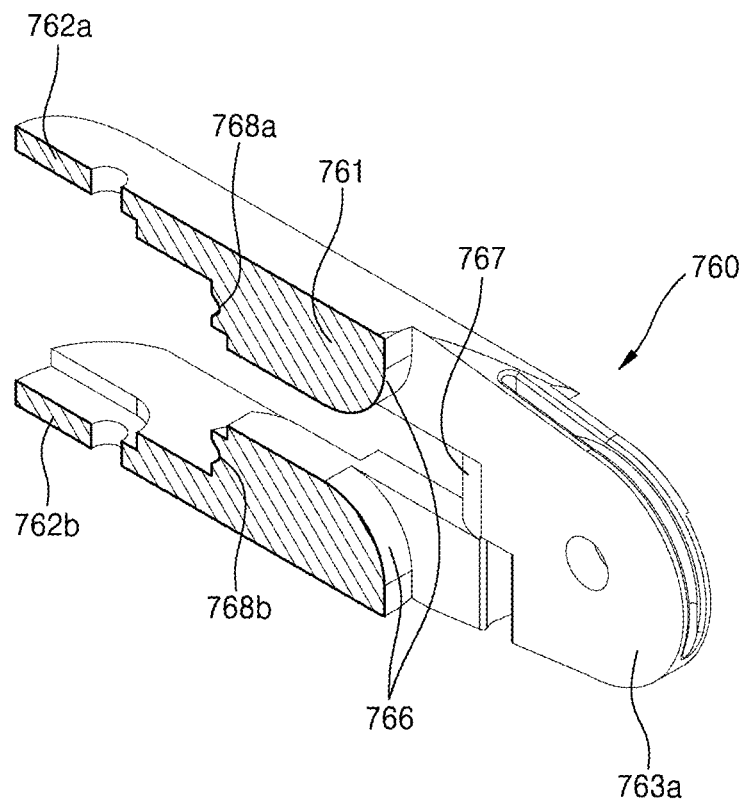
Figure 51:
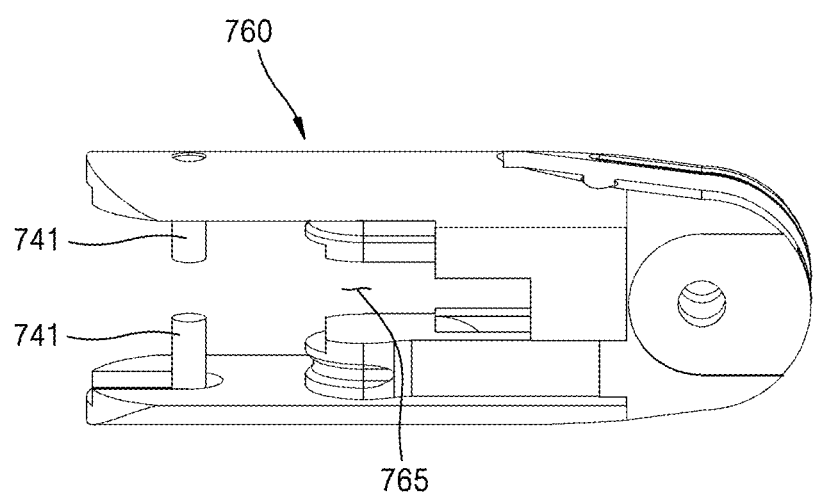
FIGS. 51 and 52 are perspective views illustrating the end tool hub of FIG. 48.
Figure 52:
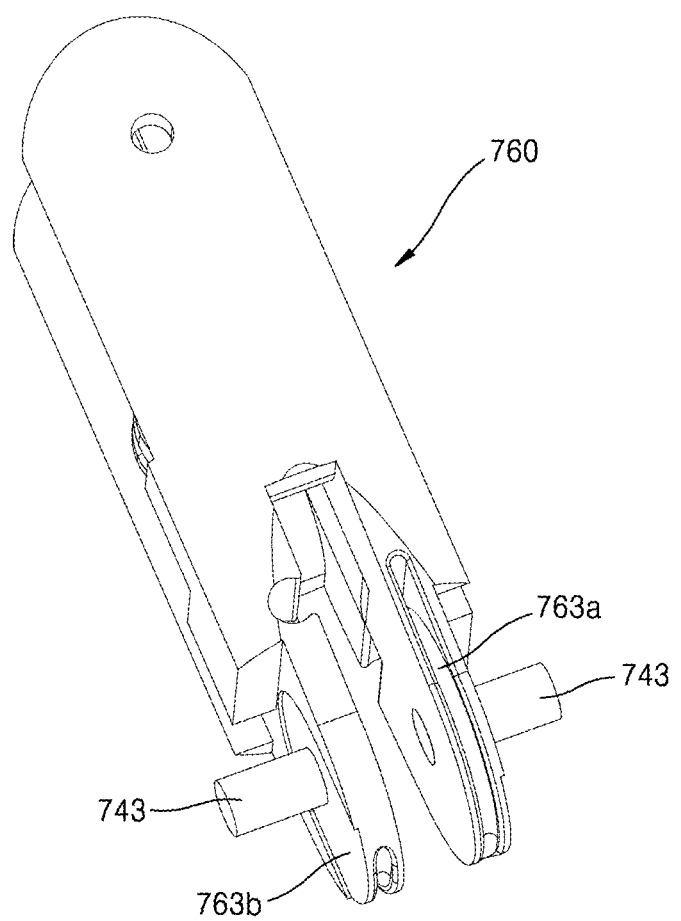
Figure 53:
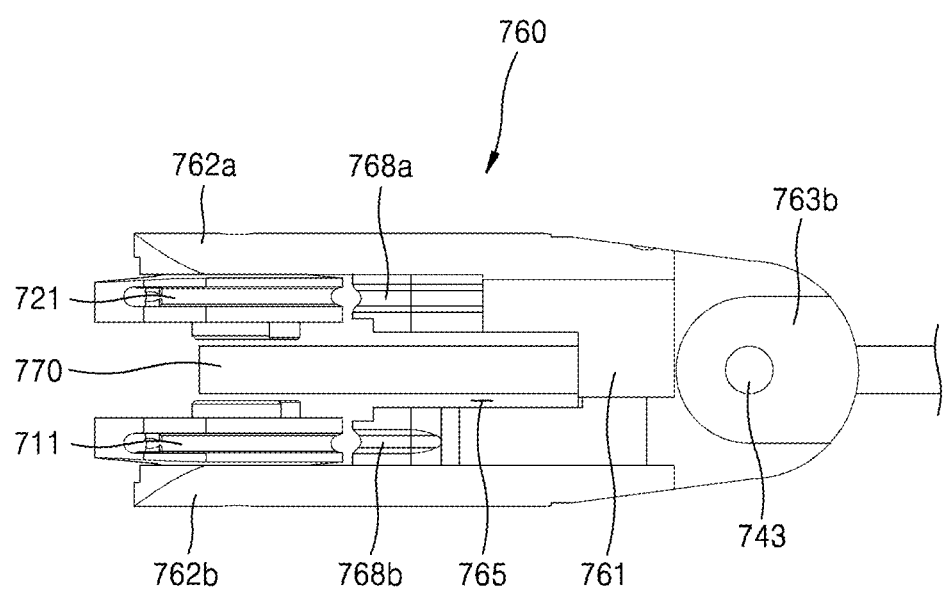
FIG. 53 is a side view illustrating the end tool hub of FIG. 48 and a guide tube.
Figure 54:
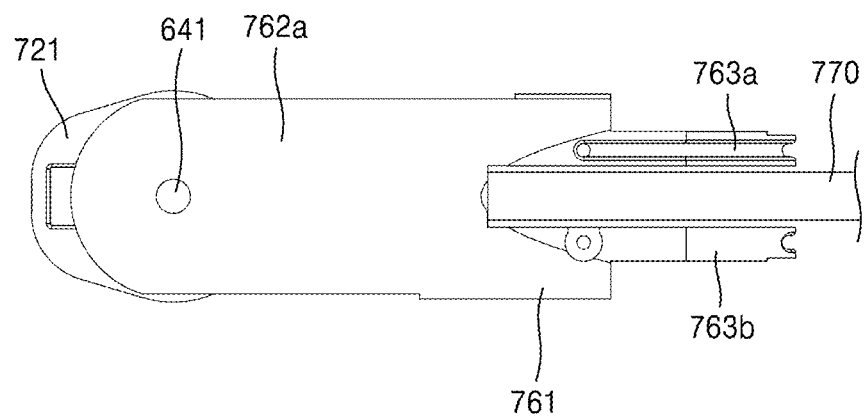
FIG. 54 is a plan view illustrating the end tool hub of FIG. 48 and the guide tube.

FIG. 48 is a perspective view illustrating the end tool hub of the surgical instrument for electrocautery of FIG. 41. FIGS. 49 and 50 are cut-away perspective views of the end tool hub of FIG. 48. FIGS. 51 and 52 are perspective views illustrating the end tool hub of FIG. 48. FIG. 53 is a side view illustrating the end tool hub of FIG. 48 and a guide tube. FIG. 54 is a plan view illustrating the end tool hub of FIG. 48 and the guide tube.

Referring to FIGS. 48 to 54, the end tool hub 760 provided in the end tool 700 of the electric cauterization surgical instrument 10 of FIG. 41 has a predetermined radius of curvature on an inner circumferential surface thereof for gentle curved movement of the guide tube 670, and may include a yaw round portion 767 and a pitch round portion 766 formed in a curved shape.

In addition, a yaw slit 765 passing through the end tool hub 760 may be formed on a plane perpendicular to a first rotation shaft 741 to allow a guide tube 770, which is configured to guide a movement path of a blade 775 and the blade wire 307 connected to the blade 775, to stably move through the end tool hub 760.

In addition, a pitch slit 764, which is a separation space, may be formed between a first pitch pulley portion 763a and a second pitch pulley portion 763b facing each other so that the guide tube 670 may pass therethrough, thereby allowing the guide tube 770 to stably move through the pitch slit 764.

Referring to FIG. 51, in addition to the yaw slit 765 formed in the end tool hub 760, the yaw rotation shaft 741 may be divided into two parts and provided as a pair, and the guide tube 670 may move through a space formed between the divided pair of yaw rotation shafts 741.

Referring to FIGS. 51 to 54, the end tool hub 760 of the surgical instrument for electrocautery according to the second embodiment has the same configuration as the end tool hub 660 of the surgical instrument for electrocautery according to the first embodiment, and thus a detailed description thereof will be omitted in the overlapping range.

Figure 55:
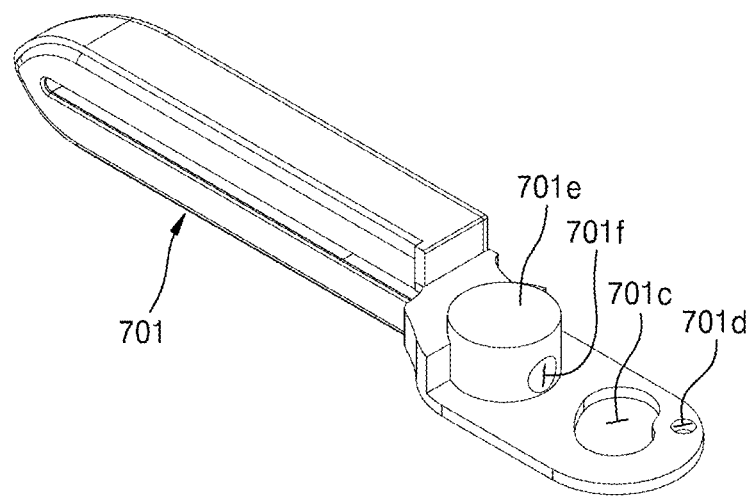
FIG. 55 is a perspective view illustrating a first jaw of the end tool of the surgical instrument for electrocautery of FIG. 41.
Figure 56:
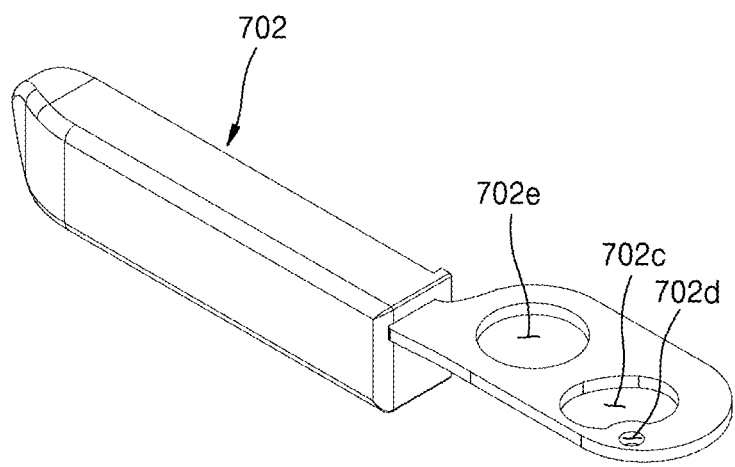
FIG. 56 is a perspective view illustrating a second jaw of the end tool of the surgical instrument for electrocautery of FIG. 41.

FIG. 55 is a perspective view illustrating the first jaw of the end tool of the surgical instrument for electrocautery of FIG. 41. FIG. 56 is a perspective view illustrating the second jaw of the end tool of the surgical instrument for electrocautery of FIG. 41.

Referring to FIG. 55, the first jaw 701 of the end tool 700 of the surgical instrument for electrocautery of FIG. 41 may include the jaw rotation shaft 701e, which has the tube through hole 701f formed therein and is formed to protrude, the movable coupling hole 701c, and the jaw pulley coupling hole 701d.

The first jaw 701 is formed entirely in an elongated bar shape, a path through which the blade 775 is movable is formed in the first jaw 701 at a distal end side (left side based on FIG. 55), and a pulley 711, which is a first jaw pulley, is coupled to the first jaw 701 at a proximal end side (right side based on FIG. 55) and formed to be rotatable around the rotation shaft 741.

Referring to FIG. 55, the movable coupling hole 701c and the jaw pulley coupling hole 701d may be formed in the first jaw 701 at the proximal end side. Here, the movable coupling hole 701c may be formed to have a predetermined curvature, and may be formed in an approximately elliptical shape.

A shaft coupling portion 711a formed on the first jaw pulley 711 may be fitted into the movable coupling hole 701c formed in the first jaw 701. Here, a short radius of the movable coupling hole 701c may be formed to be substantially the same as or slightly greater than a radius of the shaft coupling portion 711a.

Referring to FIG. 55, a long radius of the movable coupling hole 701c may be formed to be greater than the radius of the shaft coupling portion 711a. Thus, a path may be formed so that the shaft coupling portion 711a is movable therethrough to a certain degree in the movable coupling hole 701c in a state in which the shaft coupling portion 711a of the pulley 711 is fitted into the movable coupling hole 701c of the first jaw 701, This will be described in detail later.

Referring to FIG. 55, the jaw pulley coupling hole 701d formed in the first jaw 701 is formed in the form of a cylindrical hole, and a jaw coupling portion 711b of the pulley 711 may be fitted into the jaw pulley coupling hole 701d.

Here, a radius of the jaw pulley coupling hole 101d may be formed to be substantially the same as or relatively greater than a radius of the jaw coupling portion 711b. Thus, the jaw coupling portion 711b of the pulley 711 may be formed to be rotatably coupled to the jaw pulley coupling hole 701d of the first jaw 701. This will be described in more detail later.

Referring to FIG. 56, the second jaw 702 disposed to face the first jaw 701 may include the shaft pass-through portion 702e, the movable coupling hole 702c, and the jaw pulley coupling hole 702d. The second jaw 702 may be formed entirely in an elongated bar shape, the shaft pass-through portion 702e may be formed in the distal end, and the jaw pulley coupling hole 702d may be formed in the proximal end.

Figure 59:
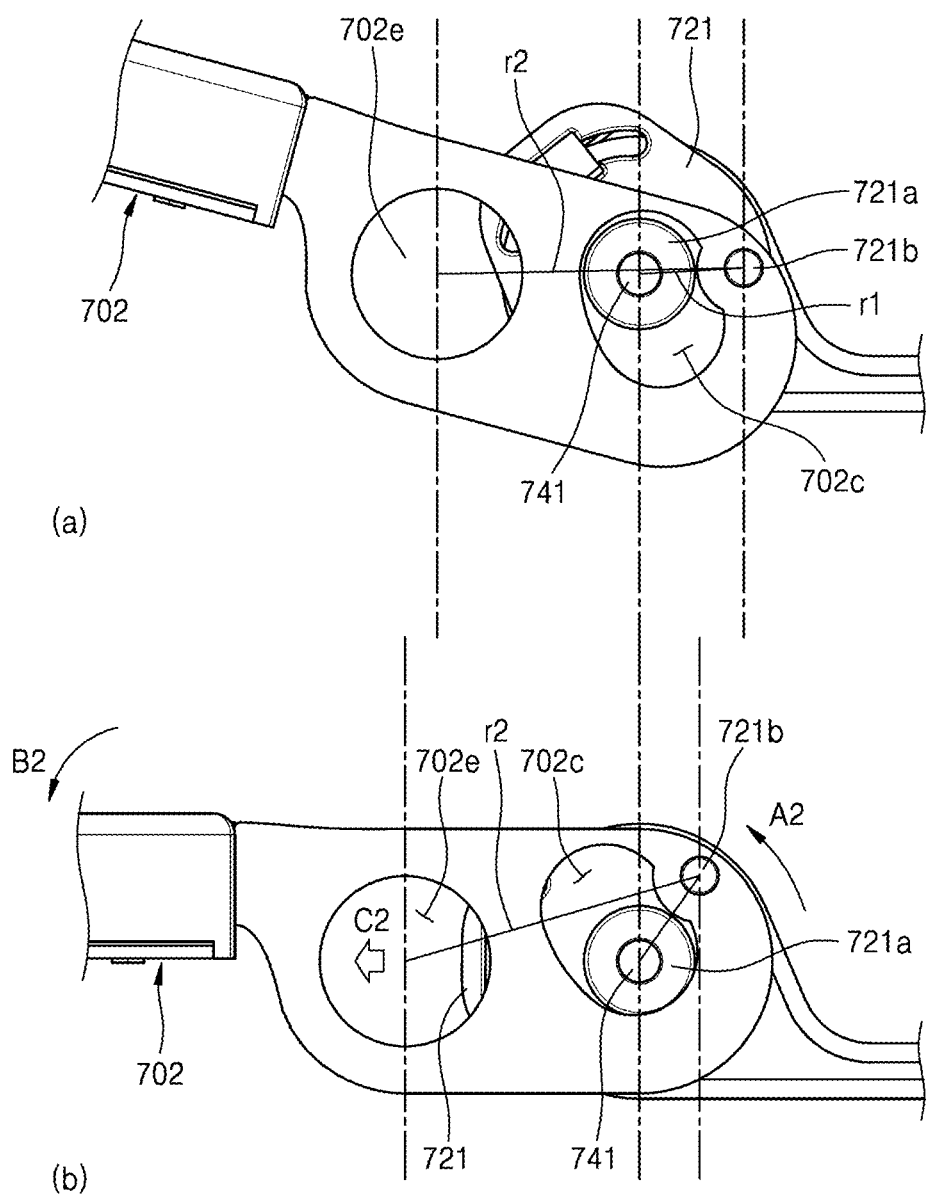
FIG. 59 is a plan view illustrating an opening and closing motion of the second jaw of the end tool of the surgical instrument for electrocautery of FIG. 41.

Referring to FIG. 59, the movable coupling hole 702c formed in the second jaw 702 may be formed to have a predetermined curvature and may be formed in an approximately elliptical shape. A shaft coupling portion 721a of a pulley 721 may be fitted into the movable coupling hole 702c. Here, a short radius of the movable coupling hole 702c may be formed to be substantially the same as or slightly greater than a radius of the shaft coupling portion 721a.

Meanwhile, a long radius of the movable coupling hole 702c may be formed to be relatively greater than the radius of the shaft coupling portion 721a. Thus, the shaft coupling portion 721a is formed to be movable to a certain degree in the movable coupling hole 702c in a state in which the shaft coupling portion 721a of the pulley 721 is fitted into the movable coupling hole 702c of the second jaw 702. This will be described in more detail later.

Meanwhile, the jaw pulley coupling hole 702d is formed in the form of a cylindrical hole, and a jaw coupling portion 721b of the pulley 721 may be fitted into the jaw pulley coupling hole 702d. Here, a radius of the jaw pulley coupling hole 702d may be formed to be substantially the same as or greater than a radius of the jaw coupling portion 721b. Thus, the jaw coupling portion 721b of the pulley 721 may be rotatably coupled to the jaw pulley coupling hole 702d of the second jaw 702.

Meanwhile, the shaft pass-through portion 702e may be formed in the second jaw 702 at the distal end side relative to the movable coupling hole 702c and the jaw pulley coupling hole 702d.

Referring to FIGS. 55 and 56, the shaft pass-through portion 702e formed in the second jaw 702 may be formed in a hole shape, and the jaw rotation shaft 701e formed in the first jaw 701 may be inserted through the shaft pass-through portion 702c.

Figure 57:
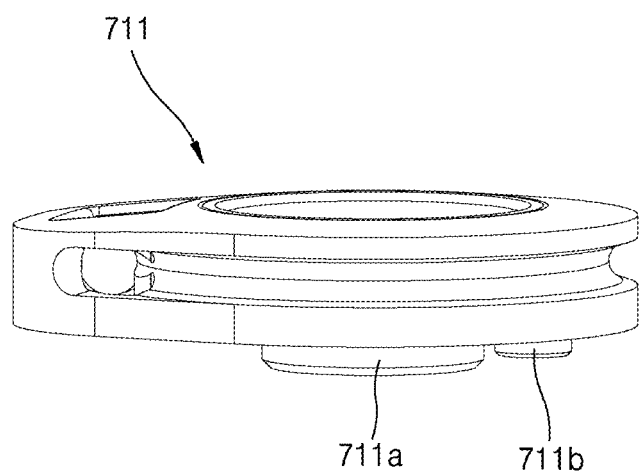
FIG. 57 is a perspective view illustrating a first jaw pulley of the end tool of the surgical instrument for electrocautery of FIG. 41.

Referring to FIG. 57, the pulley 711, which is a first jaw pulley, may include the shaft coupling portion 71 la and the jaw coupling portion 711b. The pulley 711 is formed entirely in the shape of a rotatable disk and has one surface (lower surface based on FIG. 57) on which the shaft coupling portion 711a and the jaw coupling portion 711b may be formed to protrude to a certain degree.

As described above, the shaft coupling portion 711a of the pulley 711 may be fitted into the movable coupling hole 701c of the first jaw 701, and the jaw coupling portion 711b of the pulley 711 may be fitted into the jaw pulley coupling hole 701d of the first jaw 701. The pulley 711 may be formed to be rotatable with the rotation shaft 741, which is an end tool jaw pulley rotation shaft, as the center of rotation.

Meanwhile, the pulley 721, which is a second jaw pulley, may include the shaft coupling portion 721a and the jaw coupling portion 721b.

The second jaw pulley 721 is formed entirely in the form of a rotatable disk and has one surface on which the shaft coupling portion 721a and the jaw coupling portion 721b may be formed to protrude to a certain degree. As described above, the shaft coupling portion 712a of the pulley 712 may be fitted into the movable coupling hole 702c of the second jaw 702, and the jaw coupling portion 712b of the pulley 712 may be fitted into the jaw pulley coupling hole 702d of the second jaw 702. The pulley 721 may be formed to be rotatable with the rotation shaft 741, which is an end tool jaw pulley rotation shaft, as the center of rotation.

The coupling relationship between the components described above is as follows.

The rotation shaft 741, which is an end tool jaw pulley rotation shaft, is sequentially inserted through the shaft coupling portion 711a of the pulley 711, the movable coupling hole 701c of the first jaw 701, the movable coupling hole 702c of the second jaw 702, and the shaft coupling portion 721a of the pulley 721.

The rotation shaft 701e, which is a jaw rotation shaft, is inserted through the shaft pass-through portion 702e of the second jaw 702.

The shaft coupling portion 711a of the pulley 711 is fitted into the movable coupling hole 701c of the first jaw 701, and the jaw coupling portion 711b of the pulley 711 is fitted into the jaw pulley coupling hole 701d of the first jaw 701.

At this time, the jaw pulley coupling hole 701d of the first jaw 701 and the jaw coupling portion 711b of the pulley 711 are axially coupled to each other so as to be rotatable, and the movable coupling hole 701c of the first jaw 701 and the shaft coupling portion 711a of the pulley 711 are movably coupled to each other.

The shaft coupling portion 721a of the pulley 721 is fitted into the movable coupling hole 702c of the second jaw 702, and the jaw coupling portion 721b of the pulley 721 is fitted into the jaw pulley coupling hole 702d of the second jaw 702.

At this time, the jaw pulley coupling hole 702d of the second jaw 702 and the jaw coupling portion 721b of the pulley 721 are axially coupled to each other to be rotatable, and the movable coupling hole 702c of the second jaw 702 and the shaft coupling portion 721a of the pulley 721 are movably coupled to each other.

Here, the pulley 711 and the pulley 721 rotate around the rotation shaft 741, which is an end tool jaw pulley rotation shaft. The first jaw 701 and the second jaw 702 rotate around the rotation shaft 701e, which is a jaw rotation shaft. That is, the pulley 711 and the first jaw 701 have different shafts of rotation. Similarly, the pulley 721 and the second jaw 702 have different shafts of rotation.

That is, the rotation angle of the first jaw 701 is limited to a certain degree by the movable coupling hole 701c, but is essentially rotated about the rotation shaft 701e, which is a jaw rotation shaft. Similarly, the rotation angle of the second jaw 702 is limited to a certain degree by the movable coupling hole 702c, but is essentially rotated around the rotation shaft 701e, which is a jaw rotation shaft.

Amplification of grip force due to the coupling relationship between the above-described components will be described.

Figure 58:
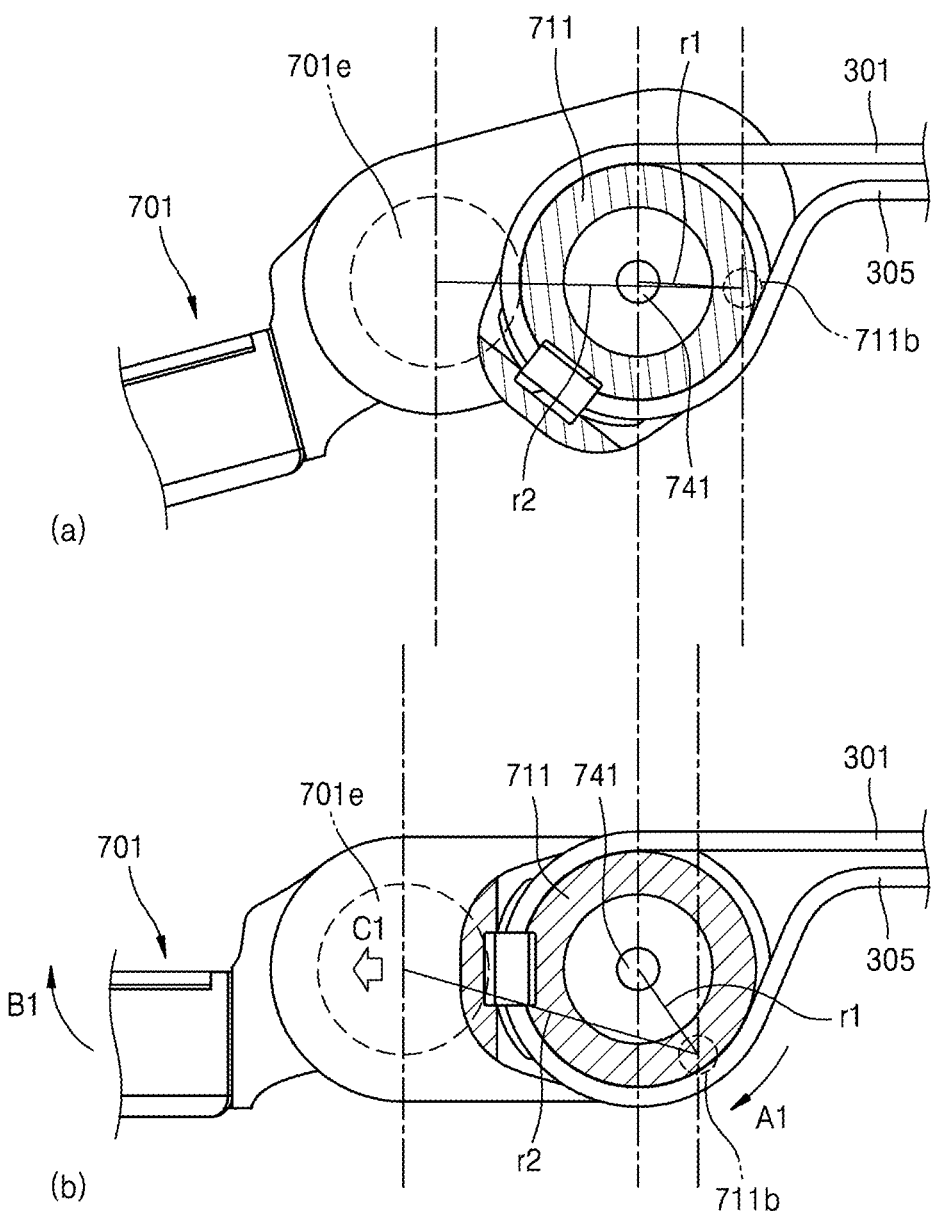
FIG. 58 is a plan view illustrating an opening and closing motion of the first jaw of the end tool of the surgical instrument for electrocautery of FIG. 41.
Figure 60:
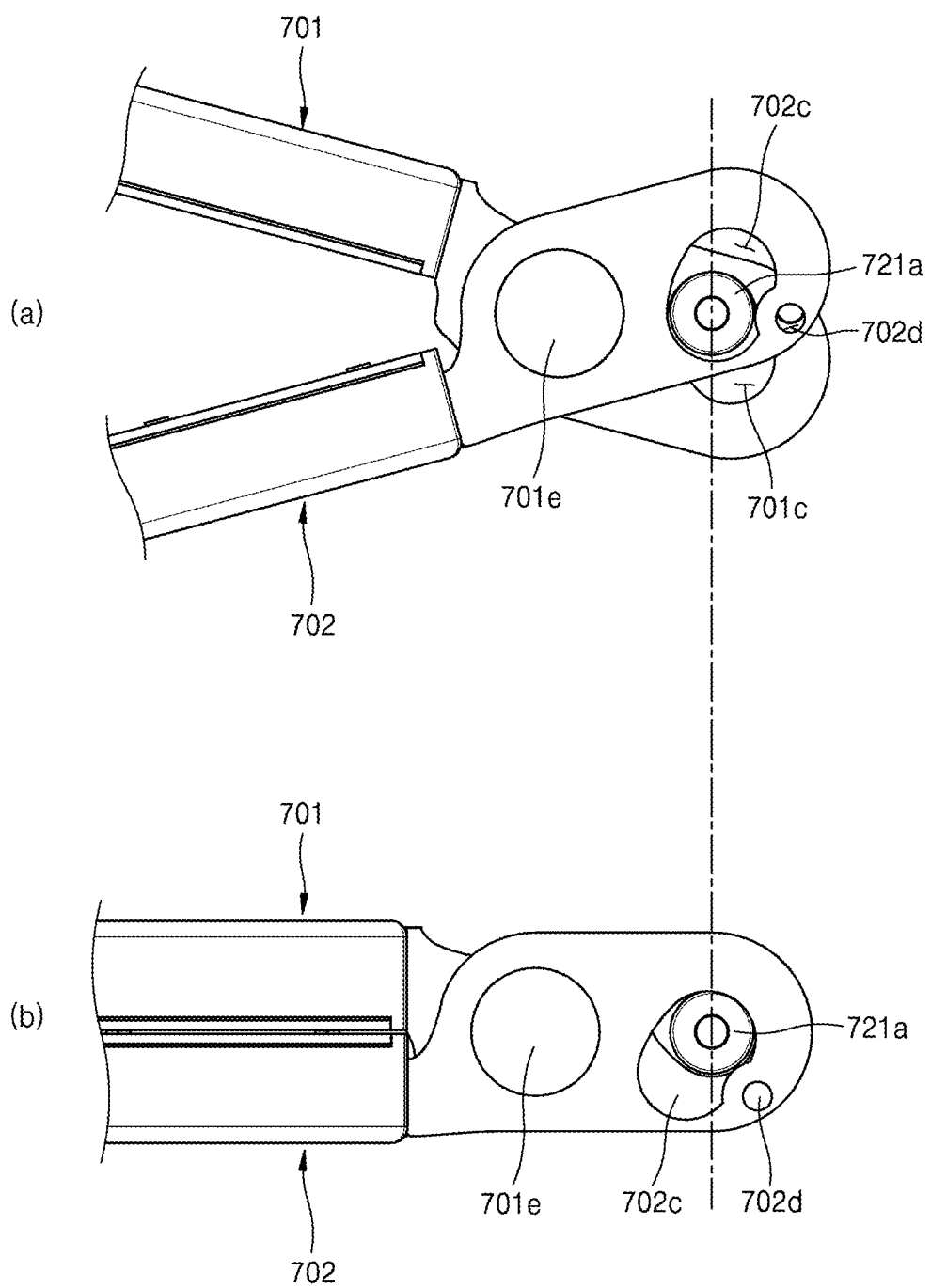
FIG. 60 is a plan view illustrating an opening and closing motion of the first jaw and the second jaw of the end tool of the surgical instrument for electrocautery of FIG. 41.

FIG. 58 is a plan view illustrating an opening and closing motion of the first jaw of the end tool of the surgical instrument for electrocautery of FIG. 41. FIG. 59 is a plan view illustrating an opening and closing motion of the second jaw of the end tool of the surgical instrument for electrocautery of FIG. 41. FIG. 60 is a plan view illustrating an opening and closing motion of the first jaw and the second jaw of the end tool of the surgical instrument for electrocautery of FIG. 41.

Referring to FIGS. 58 to 60, in the electric cauterization surgical instrument 10 according to the second embodiment, the coupling structure of the first jaw 701 and the second jaw 702 forms an X-shaped structure, so that when the first jaw 701 and the second jaw 702 rotate in a direction of approaching each other (i.e. when the first jaw 701 and the second jaw 702 are closed), a grip force in a direction of closing the first jaw 701 and the second jaw 702 further increases. This will be described below in more detail.

As described above, in motions of the first jaw 701 and the second jaw 702 being opened and closed, there are two shafts that serve as the centers of rotation for the first jaw 701 and the second jaw 702.

That is, the first jaw 701 and the second jaw 702 perform an opening and closing motion around two shafts of the rotation shaft 741 and the rotation shaft 701e. In this case, the centers of rotation of the first jaw 701 and the second jaw 702 become the rotation shaft 701e, and the centers of rotation of rotation of the pulley 711 and the pulley 721 become the rotation shaft 741.

At this time, the rotation shaft 741 is a shaft whose position is relatively fixed, and the rotation shaft 701e is a shaft whose position is relatively moved linearly. In other words, when the pulley 711 and the pulley 721 rotate in a state in which the position of the rotation shaft 741 is fixed, the first jaw 701 and the second jaw 702 are opened/closed while the rotation shaft 701e, which is a rotation shaft of the first jaw 701 and the second jaw 702, is moved backward and forward. This will be described below in more detail.

In FIG. 58, r1 is a distance from the jaw coupling portion 711b of the pulley 711 to the shaft coupling portion 711a, and a length thereof is constant. Thus, a distance from the rotation shaft 741 inserted into the shaft coupling portion 711a to the jaw coupling portion 711b is also constant as r1.

Meanwhile, r2 of FIG. 58 is a distance from the jaw pulley coupling hole 701d of the first jaw 701 to the rotation shaft 701e that is a jaw rotation shaft, and a length thereof is constant. Thus, a distance from the jaw coupling portion 711b of the pulley 711 inserted into the jaw pulley coupling hole 701d to the jaw rotation shaft 701e is also constant as r2.

Referring to FIG. 58, the lengths of r1 and r2 remain constant. Accordingly, when the pulley 711 and the pulley 721 rotate in the directions of an arrow A1 of FIG. 58 and of an arrow A2 of FIG. 59, respectively, around the rotation shaft 741 to perform a closing motion, the first jaw 701 and the second jaw 702 rotate around the rotation shaft 701e as the angle between r1 and r2 changes while the lengths of r1 and r2 remain constant, and at this time, the rotation shaft 701e itself is also linearly moved (i.e., is moved forward/backward) by as much as an arrow C1 of FIG. 58 and an arrow C2 of FIG. 59.

That is, assuming that the position of the rotation shaft 741, which is an end tool jaw pulley rotation shaft, is fixed, when the first jaw 701 and the second jaw 702 are closed, a force is applied in a direction in which the rotation shaft 701e, which is a jaw rotation shaft, is moved forward (i.e., toward the distal end), and thus the grip force in the direction in which the first jaw 701 and the second jaw 702 are closed becomes larger.

In other words, since the lengths of r1 and r2 remain constant when the second jaw 702 rotates around the jaw rotation shaft 701e, when the pulley 721 rotates around the rotation shaft 741, the angle between r1 and r2 changes while the lengths of r1 and r2 remain constant. That is, the angle between r1 and r2 in a state in which the second jaw 702 is open as shown in FIG. 59A is relatively greater than the angle between r1 and r2 in a state in which the second jaw 702 is closed as shown in FIG. 59B.

Thus, when the second jaw 702 rotates from the open state to the close state, the angle between r1 and r2 changes, and a force is applied in a direction in which the jaw rotation shaft 701e passing through the shaft pass-through portion 702e formed in the second jaw 702 is moved forward.

In this case, since the rotation shaft 741 is a shaft whose position is relatively fixed, the jaw rotation shaft 701e is moved forward in the direction of the arrow C1 of FIG. 58 and the direction of an arrow C2 of FIG. 59, and the grip force is further increased in a direction in which the second jaw 702 is closed.

In other words, when the pulley 711 and the pulley 721 rotate around the rotation shaft 741, which is a shaft whose relative position is fixed, the angle between r1 and r2 changes while the distance between r1 and r2 remains constant. In addition, when the angle changes as described above, the first jaw 701 and the second jaw 702 push or pull the rotation shaft 701e, and thus the jaw rotation shaft 701e is moved forward or backward.

In this case, when the first jaw 701 and the second jaw 702 rotate in the direction of closing, the grip force is further increased as the rotation shaft 701e is moved forward in the directions of the arrow C1 of FIG. 58 and the arrow C2 of FIG. 59.

On the contrary, when the first jaw 701 and the second jaw 702 rotate in the direction of opening, the rotation shaft 701e is moved backward in directions opposite to the arrow C1 of FIG. 58 and the arrow C2 of FIG. 59.

With this configuration, the grip force becomes stronger when the first jaw 701 and the second jaw 702 are closed, thereby enabling a surgical operator to perform the actuation motion powerfully even with a small force.

That is, as shown in FIG. 60, as the first jaw 701 and the second jaw 702, which have an X-shaped structure, rotate relative to each other around the first rotation shaft 741 that is a fixed shaft, the rotation shaft 701e, which is a jaw rotation shaft, is moved forward toward the distal end of the end tool 700, so that the grip force may be amplified.

Figure 61:
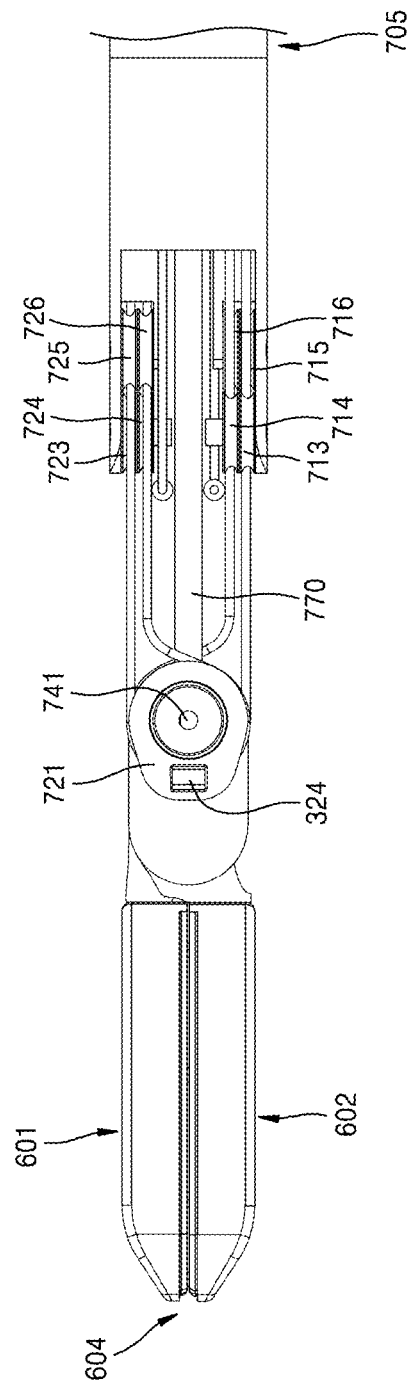
FIGS. 61 and 62 are plan views illustrating an opening and closing motion of the first jaw and the second jaw in response to an actuation motion of the end tool of the surgical instrument for electrocautery of FIG. 41.
Figure 62:
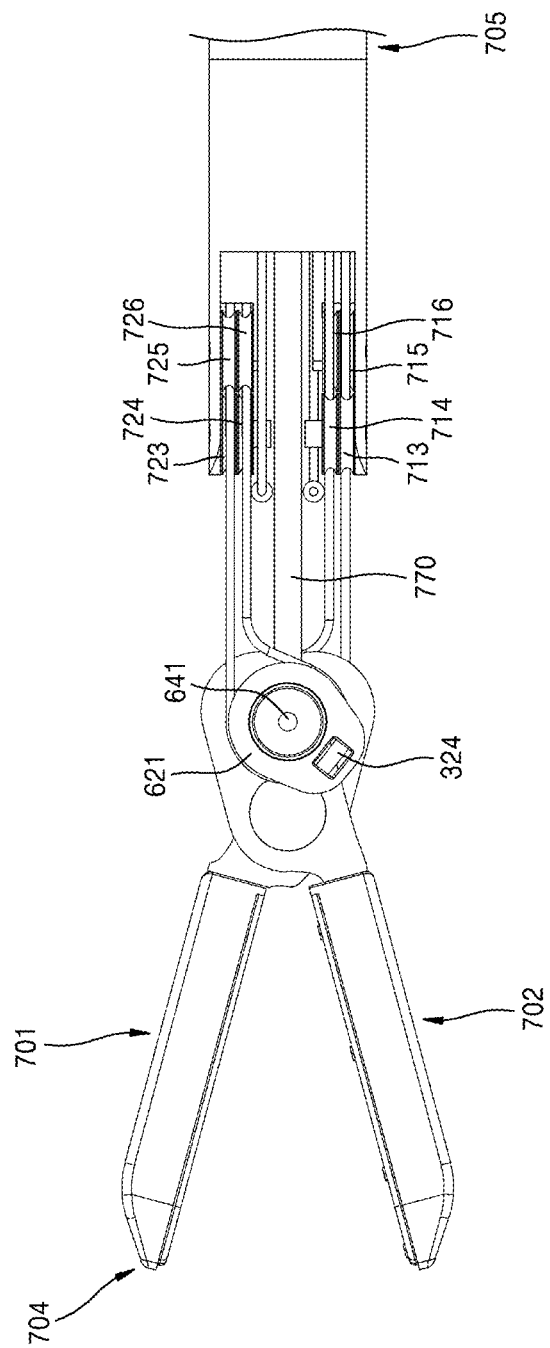

FIGS. 61 and 62 are plan views illustrating an opening and closing motion of the first jaw 701 and the second jaw 702 in response to an actuation motion of the end tool 700 of the surgical instrument for electrocautery of FIG. 41.

Referring to FIGS. 61 and 62, the first jaw 701 and the second jaw 702 are connected in an X-shaped structure, and the first jaw 701 and the second jaw 702 rotate relative to each other as the first jaw pulley 711 and the second jaw pulley 721 rotate with the fixed rotation shaft 741 as the center of rotation, enabling an actuation motion.

In the end tool 700 of the electric cauterization surgical instrument 10 according to the second embodiment of the present disclosure, as the first jaw 701 and the second jaw 702 rotate relative to each other, a grip force may be amplified when the jaw rotation shaft 70 1e is moved forward/backward, particularly forward.

Referring to FIG. 62, as the pulley 711 and the pulley 721 rotate in opposite directions with the first rotation shaft 741 as the central axis of rotation, the first jaw 701 and the second jaw 702, which are respectively connected to the pulley 711 and the pulley 721, rotate in opposite directions and move away from each other, and thus the end tool 700 may be in an open state.

Figure 63:
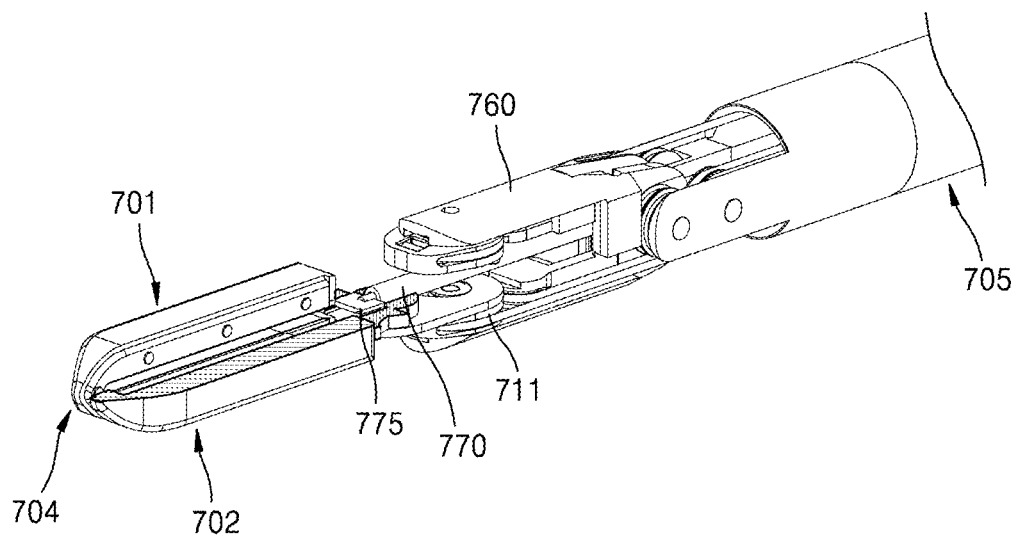
FIGS. 63 to 65 are partial cross-sectional view illustrating an operation of a blade of the end tool of the surgical instrument for electrocautery of FIG. 41.
Figure 64:
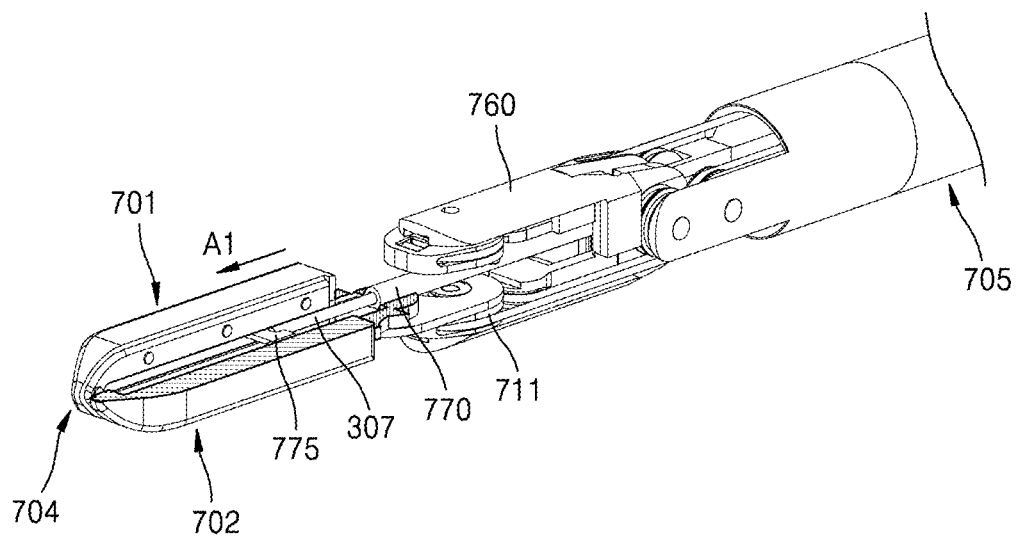
Figure 65:
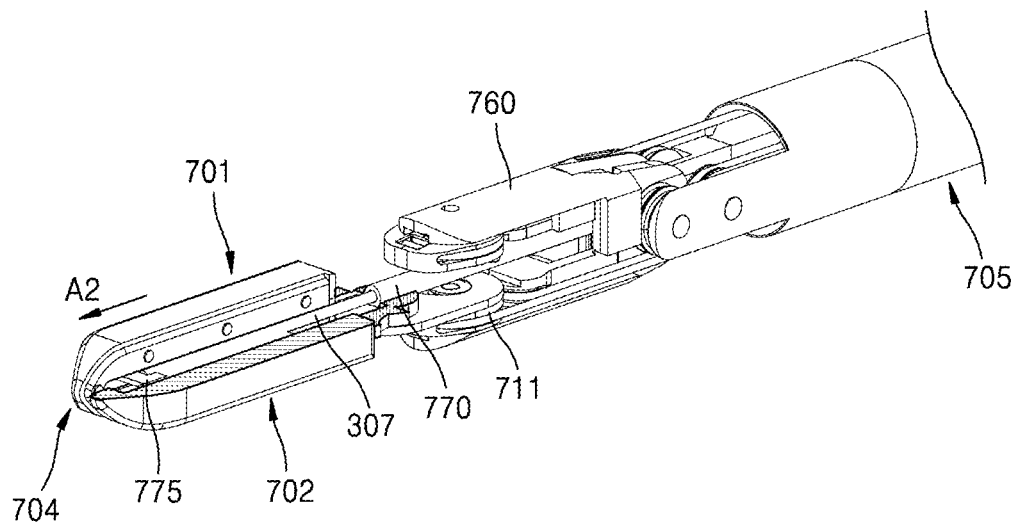

Referring to FIGS. 61 to 65, it may be said that the tissue between the first jaw 701 and the second jaw 702 is cut as the cutting motion of FIGS. 63 to 65 is performed in a state in which the first jaw 701 and the second jaw 702 are closed as shown in FIG. 61.

Here, a first position shown in FIG. 63 may be defined as a state in which the blade 775 is drawn in toward a proximal end 705 of the end tool as much as possible. Alternatively, the first position may also be defined as a state in which the blade 775 is located adjacent to the pulley 711/pulley 712.

Meanwhile, a third position illustrated in FIG. 65 may be defined as a state in which the blade 775 is withdrawn toward a distal end 704 of the end tool 700 as much as possible. Alternatively, the third position may also be defined as a state in which the blade 775 is spaced away from the pulley 711/pulley 712 as much as possible.

First, as shown in FIG. 62, a tissue to be cut is located between the first jaw 701 and the second jaw 702 in a state in which the first jaw 701 and the second jaw 702 are opened, and then an actuation motion is performed to close the first jaw 701 and the second jaw 702 as shown in FIG. 61.

Next, as shown in FIG. 63, in a state in which the blade wire 307 and the blade 775 are located at the first position, currents of different polarities are applied to the first electrode 751 and the second electrode 752 to cauterize the tissue between the first jaw 701 and the second jaw 702. At this time, a generator (not shown) configured to supply power to the electrodes may itself perform monitoring of at least some of current, voltage, resistance, impedance, and temperature, and may stop supplying power when the cauterization is completed.

In the state in which the cauterization is completed as described above, when the blade wire 307 moves sequentially in the directions of an arrow A1 of FIG. 64 and an arrow A2 of FIG. 65, the blade 775 coupled to the blade wire 307 moves from the first position at the proximal end 705 of the end tool toward the third position at the distal end 704 of the end tool, reaching the positions in FIGS. 64 and 65 in turn.

As such, the blade 775 cuts the tissue located between the first jaw 701 and the second jaw 702 while moving in the X-axis direction.

However, it is to be understood that the linear motion of the blade 775 here does not mean a motion in a completely straight line, but rather means a motion of the blade 775 to the extent that the blade 775 is able to cut the tissue while achieving a linear motion when viewed as a whole, even though the motion is not in a completely straight line, for example, the middle part of the straight line is bent by a certain angle or there is a section having a gentle curvature in a certain section.

Meanwhile, in this state, when the blade wire 307 is pulled in the opposite direction, the blade 775 coupled to the blade wire 307 also returns to the first position.

According to the present disclosure, the multi-joint/multi-degree-of-freedom surgical instrument capable of pitch/yaw/actuation motions may also perform cauterizing and cutting motions.

Figure 66:
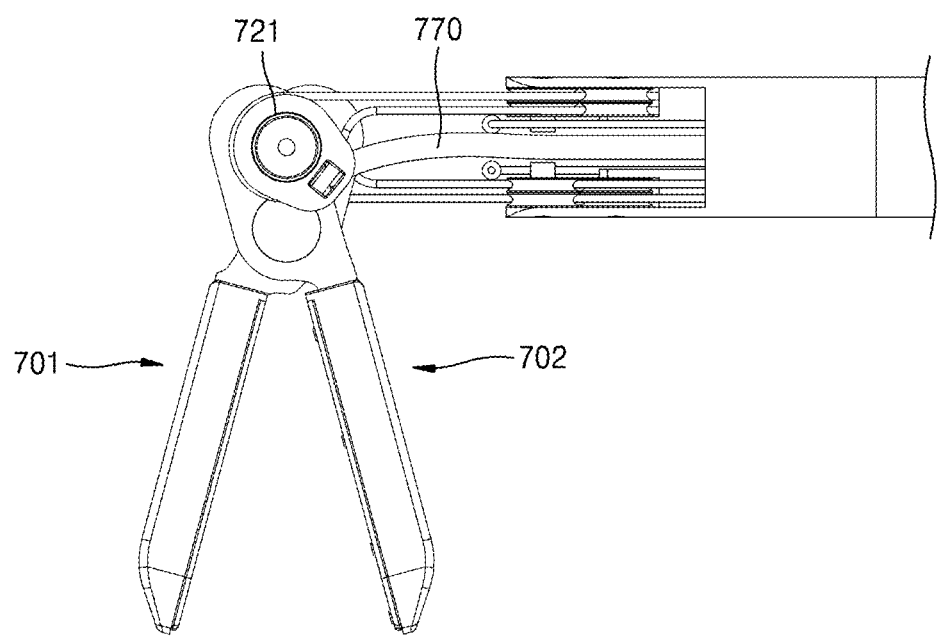
FIGS. 66 and 67 are views illustrating a process of performing an opening and closing motion in a state in which the end tool of the surgical instrument for electrocautery of FIG. 41 is yaw-rotated by +90°.
Figure 67:
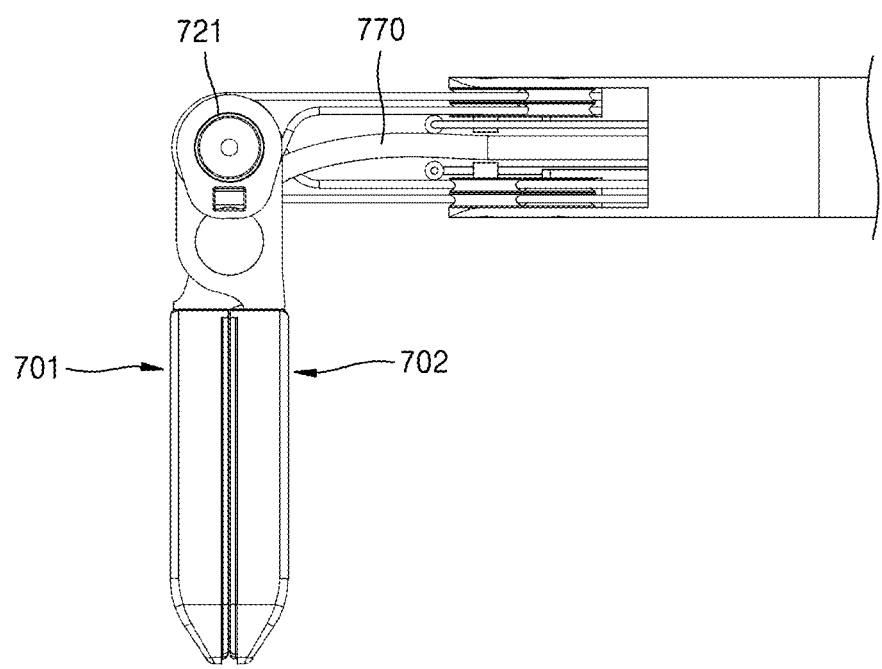
Figure 68:
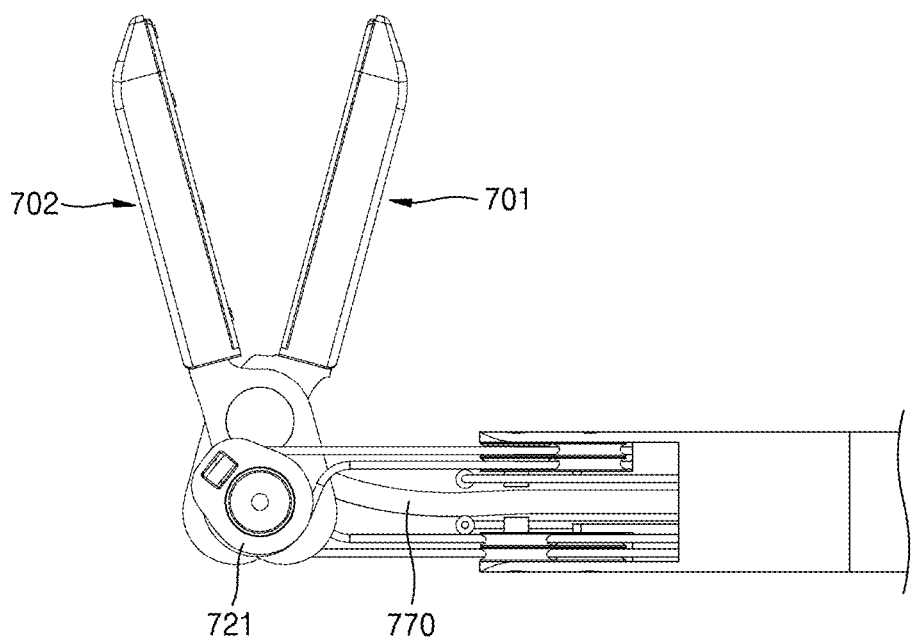
FIGS. 68 and 69 are views illustrating a process of performing an opening and closing motion in a state in which the end tool of the surgical instrument for electrocautery of FIG. 41 is yaw-rotated by −90°.
Figure 69:
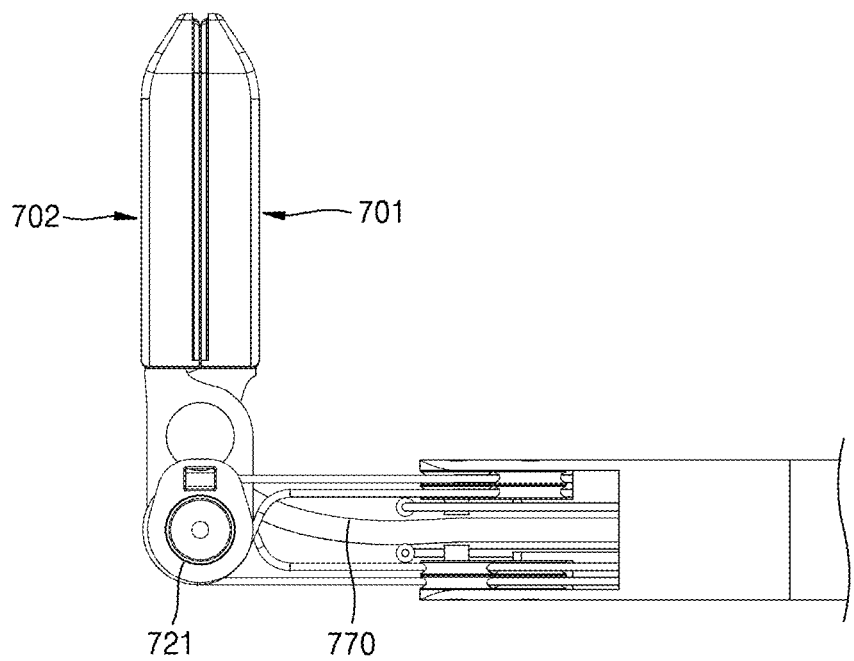

Referring to FIGS. 66 and 67, views are illustrated in which a process of performing an opening and closing motion in a state in which the end tool 700 of the electric cauterization surgical instrument 10 of FIG. 41 is yaw-rotated by +90°.

Referring to FIG. 66, the pulley 711 and the pulley 721 that faces the pulley 711 may be rotated around the first rotation shaft 741 due to the wires of the power transmission portion 300 in the manipulation portion 200. In FIG. 66, when the pulley 711 and the pulley 721 rotate in opposite directions, the first jaw 701 and the second jaw 702 respectively coupled to the pulley 711 and the pulley 721 may rotate relative to each other in a direction of approaching each other to perform an actuation motion, and as shown in FIG. 67, the first jaw 701 and the second jaw 702 may be in a closed state.

FIGS. 66 and 67 are views illustrating a process of performing an opening and closing motion in a state in which the end tool of the surgical instrument for electrocautery of FIG. 41 is yaw-rotated by −90°.

Referring to FIGS. 66 and 67, as the pulley 711 and the pulley 711 are yaw rotatable by −90° with the first rotation shaft 741 as the central axis of rotation, and the pulley 711 and the pulley 711 rotates in different directions, an actuation motion is possible in which the first jaw 701 and the second jaw 702 respectively connected to the pulley 711 and the pulley 721 move closer or further away from each other.

Referring to FIGS. 66 to 69, a blade assembly, specifically, the guide tube 770 is connected to the end tool 700 at the other end portion, which is opposite one end portion connected to the connection portion 400, and may be of constant length.

The guide tube 770 may be gently curved with a predetermined radius of curvature when the end tool 700, specifically, the first jaw 701 and the second jaw 702 rotate with the first rotation shaft 741 as the central axis of rotation, and may stably provide a movement path for the blade wire 307 to be movable between the distal end 704 and the proximal end 705 of the end tool 700.

Figure 70:
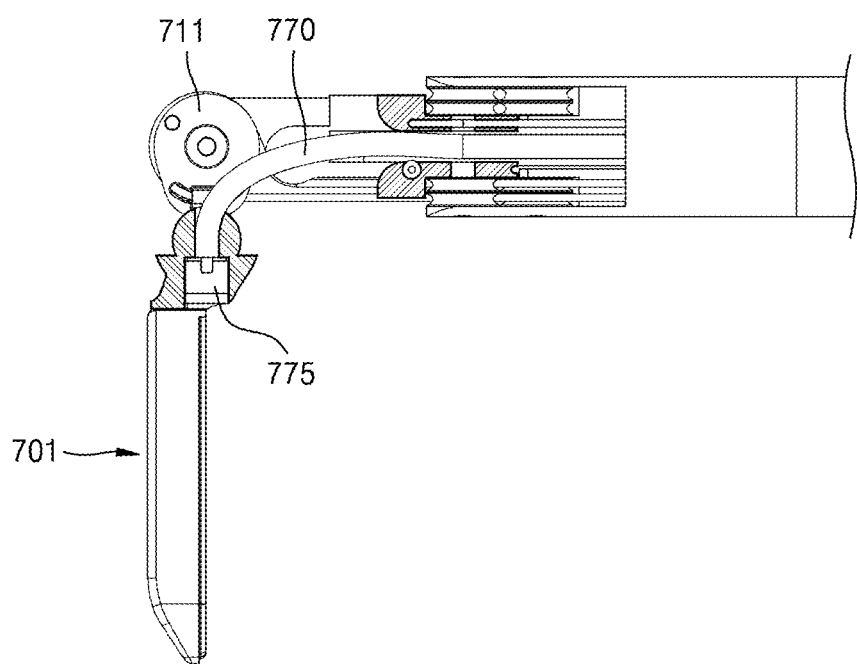
FIGS. 70 and 71 are views illustrating a path of the guide tube and a movement path of the blade during a cutting motion in a state in which the end tool of the surgical instrument for electrocautery of FIG. 41 is yaw-rotated by +90°.
Figure 71:
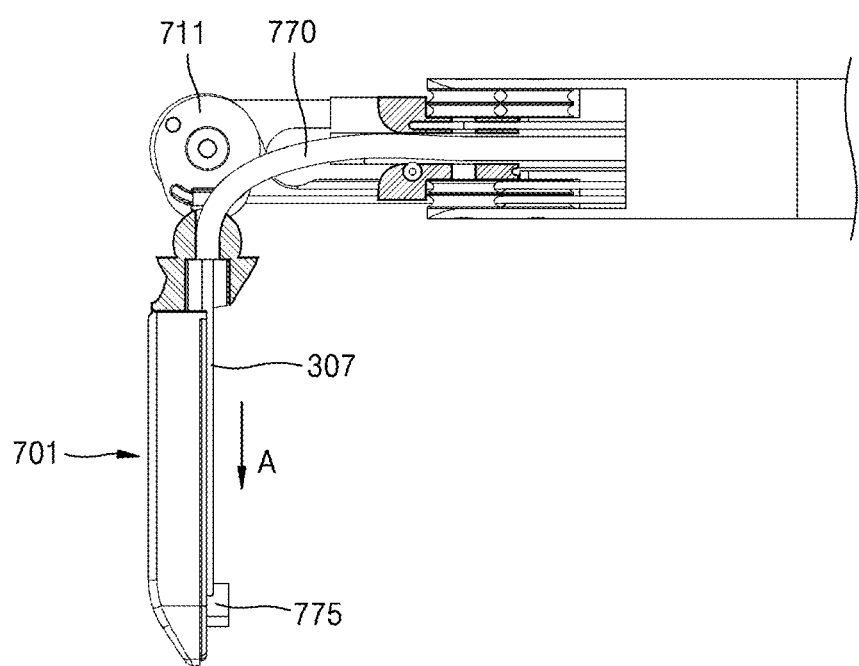

FIGS. 70 and 71 are views illustrating a path of the guide tube 770 and a movement path of the blade 775 during a cutting motion in a state in which the end tool 700 of the surgical instrument for electrocautery of FIG. 41 is yaw-rotated by +90°.

Referring to FIGS. 70 and 71, the end tool 700 of the electric cauterization surgical instrument 10 according to the second embodiment of the present disclosure is formed such that the jaws 701 and 702 are able to perform a normal cutting motion even when the jaws are yaw-rotated by +90°.

Specifically, as the blade wire 307 emerges from the inside of the guide tube 770, and the blade 775 connected to the blade wire 307 moves in the direction of an arrow A, which is a direction from the proximal end 705 toward the distal end 704 of the end tool 700, a cutting motion may be performed.

Figure 72:
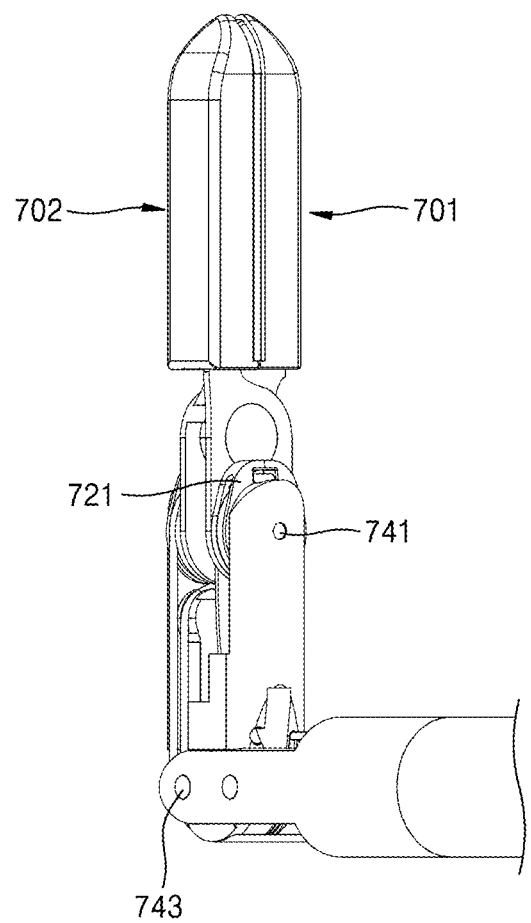
FIGS. 72 and 73 are views illustrating a process of performing an opening and closing motion in a state in which the end tool of the surgical instrument for electrocautery of FIG. 41 is pitch-rotated by −90°.
Figure 73:
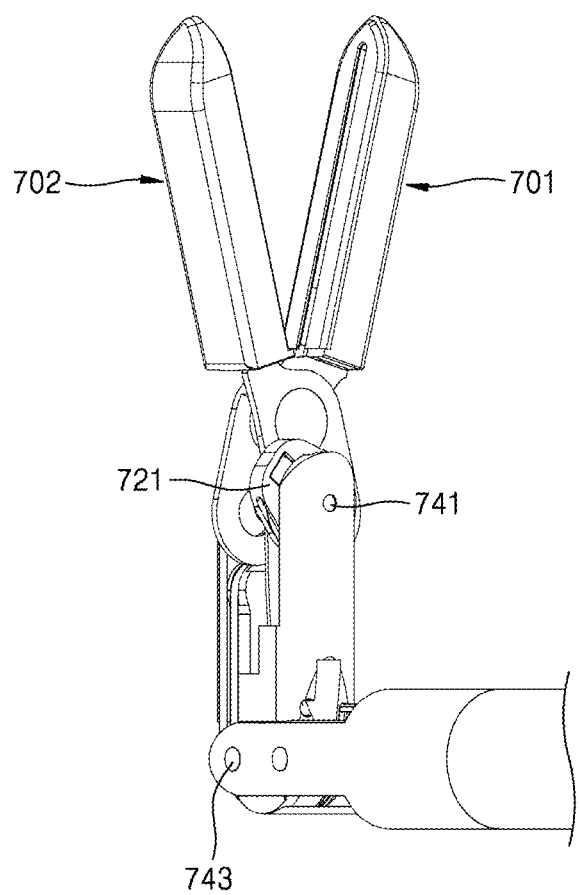
Figure 74:
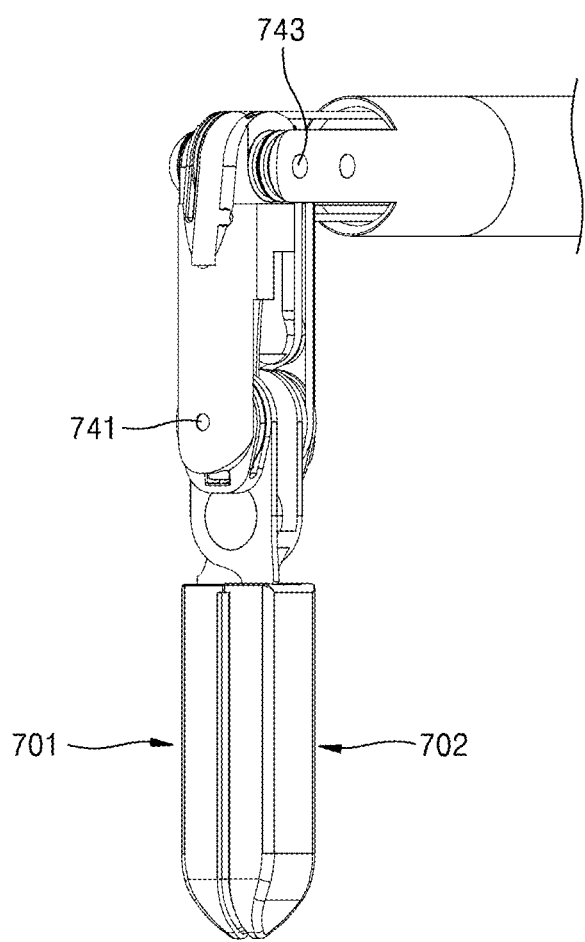
FIGS. 74 and 75 are views illustrating a process of performing an opening and closing motion in a state in which the end tool of the surgical instrument for electrocautery of FIG. 41 is pitch-rotated by +90°.
Figure 75:
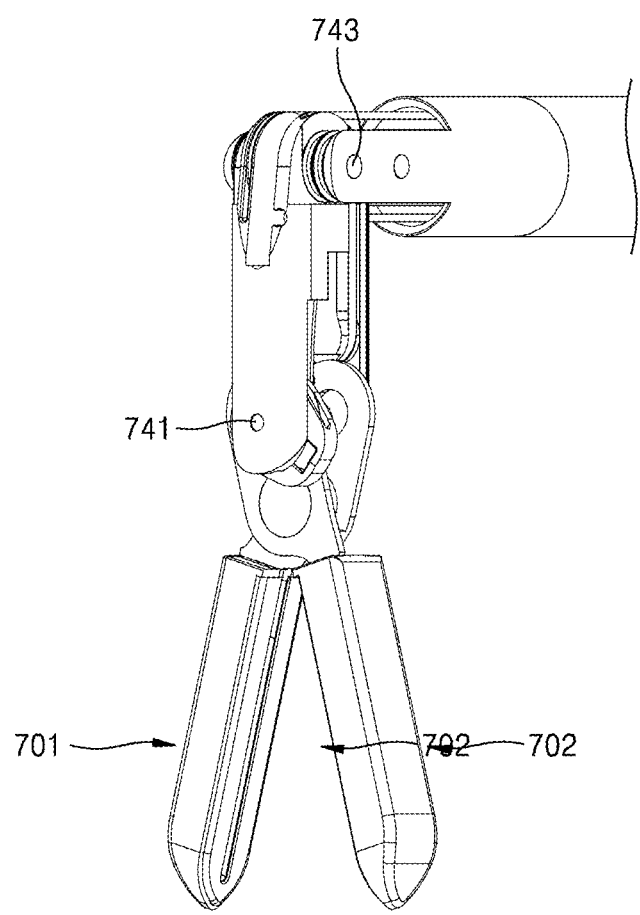
Figure 76:
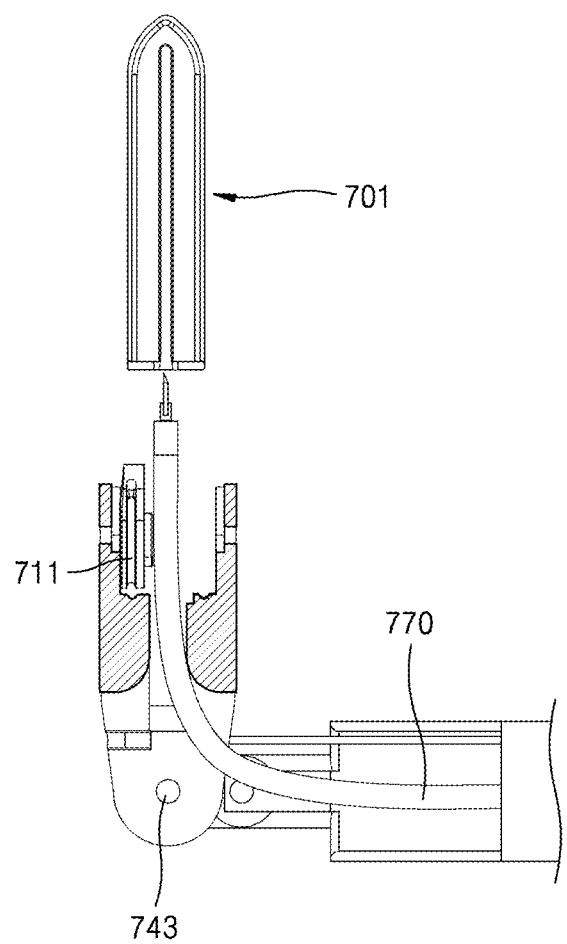
FIG. 76 is a view illustrating a path of the guide tube in a state in which the end tool of the surgical instrument for electrocautery of FIG. 41 is pitch-rotated by −90°.
Figure 77:
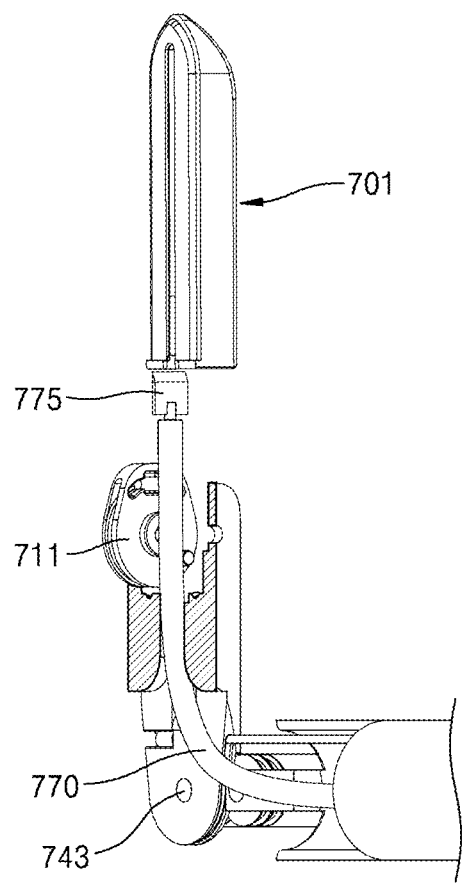
FIGS. 77 and 78 are views illustrating a path of the guide tube and a movement path of the blade during a cutting motion in a state in which the end tool of the surgical instrument for electrocautery of FIG. 41 is pitch-rotated by −90°.
Figure 78:
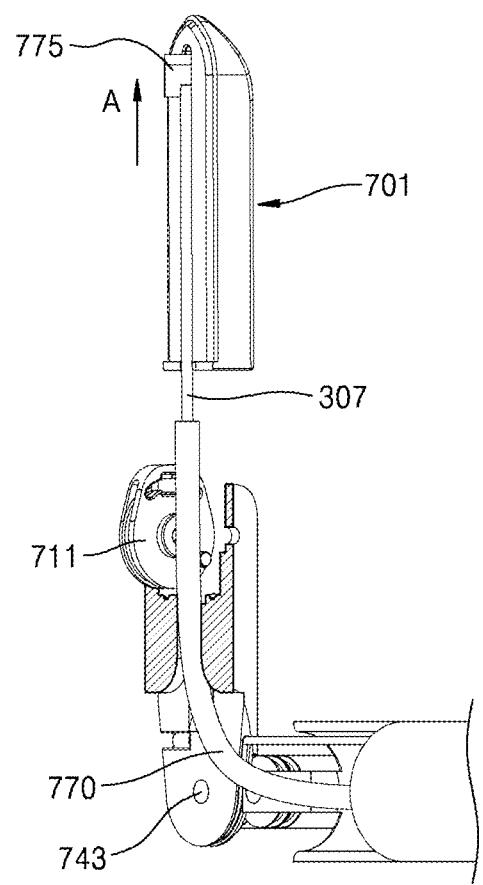
Figure 79:
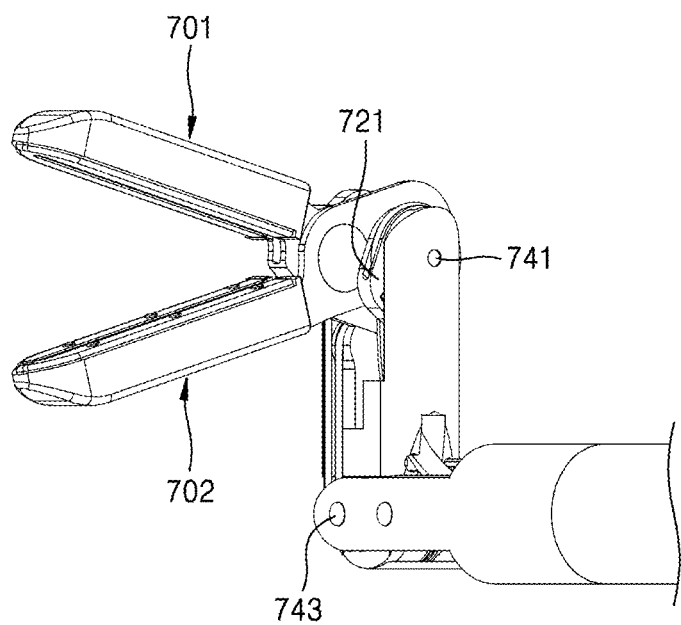
FIG. 79 is a perspective view illustrating the surgical instrument for electrocautery of FIG. 41 in a pitch-rotated and yaw-rotated state.
Figure 80:
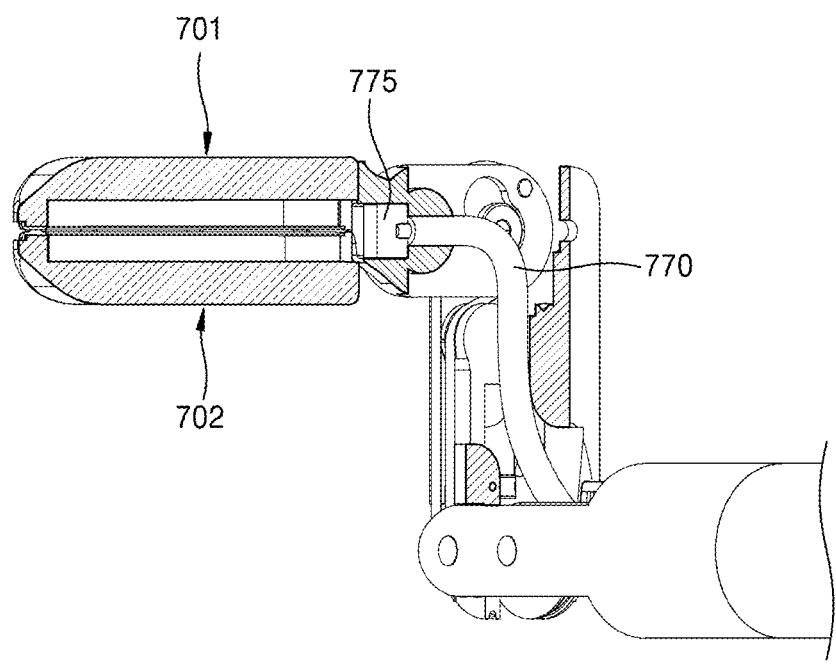
FIGS. 80 to 82 are views illustrating the end tool of the surgical instrument for electrocautery of FIG. 41 performing a cutting motion in a state in which the end tool is pitch-rotated by −90° and simultaneously yaw-rotated by +90°.
Figure 81:
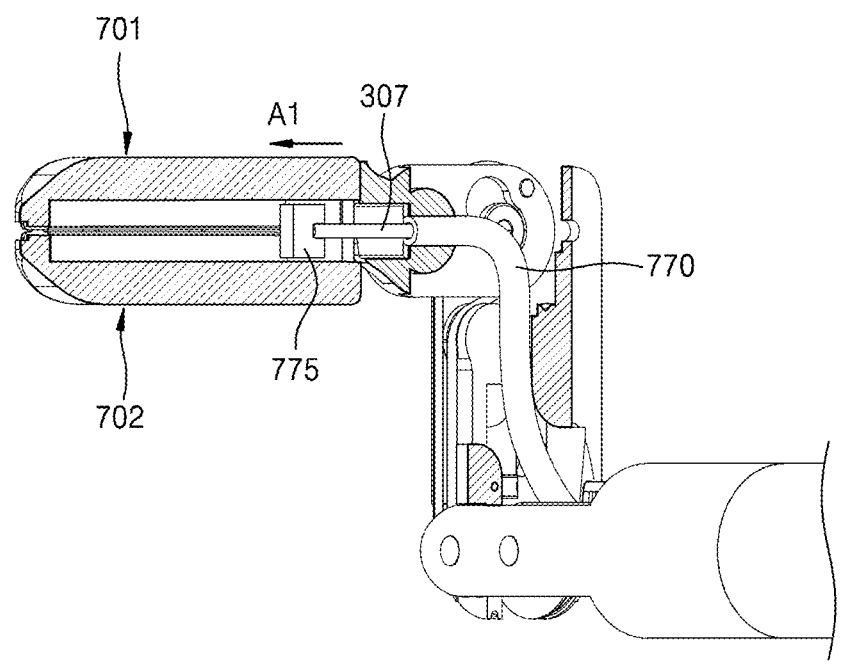
Figure 82:
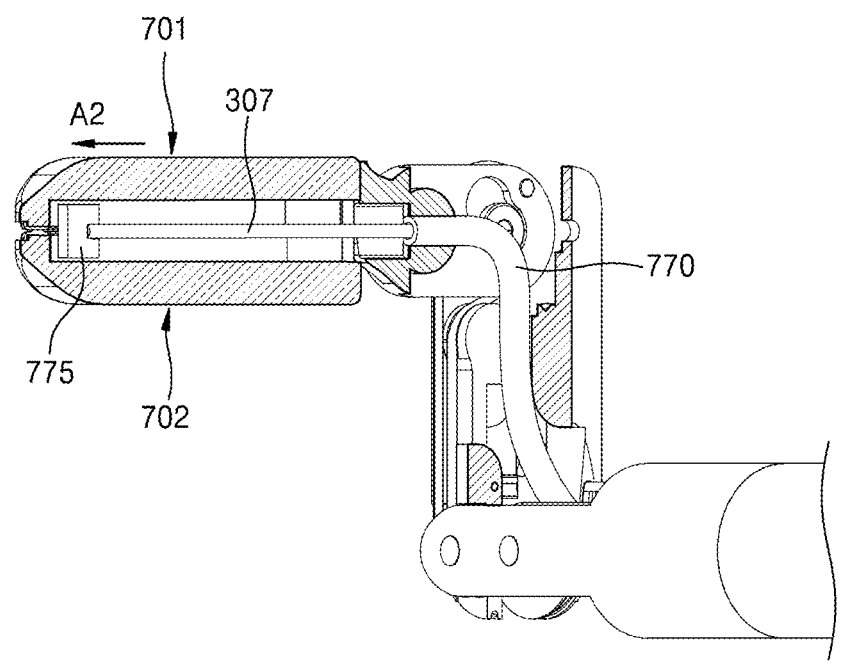

FIGS. 72 and 73 are views illustrating a process of performing an opening and closing motion in a state in which the end tool of the surgical instrument for electrocautery of FIG. 41 is pitch-rotated by −90°. FIGS. 74 and 75 are views illustrating a process of performing an opening and closing motion in a state in which the end tool of the surgical instrument for electrocautery of FIG. 41 is pitch-rotated by +90°. FIG. 76 is a view illustrating a path of the guide tube in a state in which the end tool of the surgical instrument for electrocautery of FIG. 41 is pitch-rotated by −90°. FIGS. 77 and 78 are views illustrating a path of the guide tube and a movement path of the blade during a cutting motion in a state in which the end tool of the surgical instrument for electrocautery of FIG. 41 is pitch-rotated by −90°. FIG. 79 is a perspective view illustrating the surgical instrument for electrocautery of FIG. 41 in a pitch-rotated and yaw-rotated state. FIGS. 80 to 82 are views illustrating the end tool of the surgical instrument for electrocautery of FIG. 41 performing a cutting motion in a state in which the end tool is pitch-rotated by −90° and simultaneously yaw-rotated by +90°.

FIGS. 74 and 75 are views illustrating a process of performing an opening and closing motion in a state in which the end tool 700 of the surgical instrument for electrocautery of FIG. 41 is pitch-rotated by +90°. FIG. 76 is a view illustrating a path of the guide tube 770 in a state in which the end tool 700 of the surgical instrument for electrocautery of FIG. 41 is pitch-rotated by −90°. FIGS. 77 and 78 are views illustrating a path of the guide tube and a movement path of the blade during a cutting motion in a state in which the end tool of the surgical instrument for electrocautery of FIG. 41 is pitch-rotated by −90°.

Referring to FIGS. 72 to 78, the end tool 700 of the electric cauterization surgical instrument 10 according to the second embodiment of the present disclosure is formed such that the jaws 701 and 702 are able to perform a cutting motion normally even when the jaws are pitch-rotated by −90° and +90°.

Meanwhile, FIG. 79 is a view illustrating a state in which the jaws are pitch-rotated by −90° and simultaneously yaw-rotated by +90°, and FIGS. 80 to 82 are views illustrating a state in which the end tool of the surgical instrument for electrocautery of FIG. 41 performs a cutting motion in a state in which the end tool is pitch-rotated by −90° and simultaneously yaw-rotated by +90°.

Referring to FIGS. 79 to 82, the end tool 700 of the electric cauterization surgical instrument 10 according to the second embodiment of the present disclosure is formed such that the jaws 701 and 702 are able to perform a cutting motion normally even when the jaws are pitch-rotated by −90° and simultaneously yaw-rotated by +90°.

Modified Example of Second Embodiment-Disposing Auxiliary Pulley on End Tool Hub Hereinafter, an end tool 700 of a surgical instrument according to a modified example of the second embodiment of the present disclosure will be described. Here, the end tool 700 of the surgical instrument according to the modified example of the second embodiment of the present disclosure is different from the end tool of the surgical instrument according to the second embodiment of the present disclosure described above in that the configuration of an end tool hub 760' and the configuration of auxiliary pulleys 712 and 722 are different. The configuration changed from the second embodiment as described above will be described in detail later.

Figure 83:
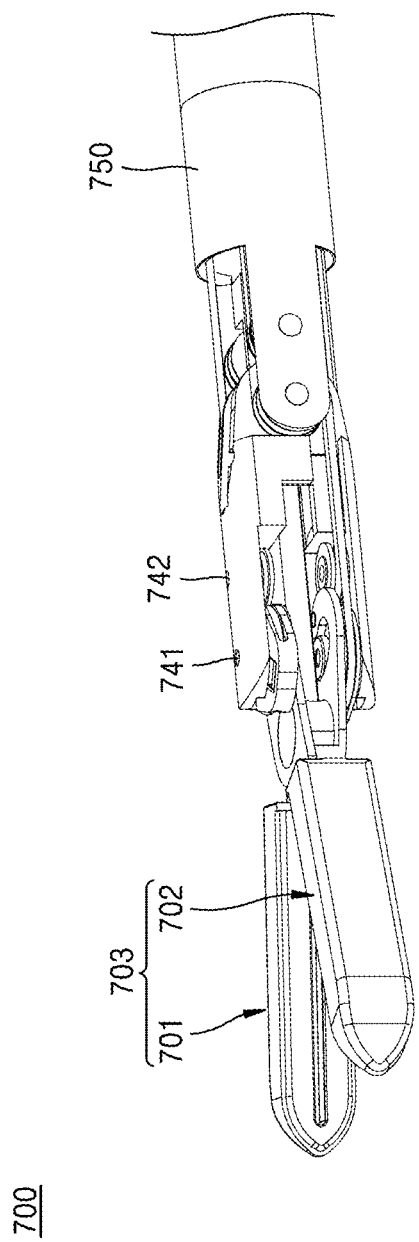
FIGS. 83 to 85 are views illustrating an end tool of a surgical instrument for electrocautery according to a modified example of the second embodiment of the present disclosure.
Figure 84:
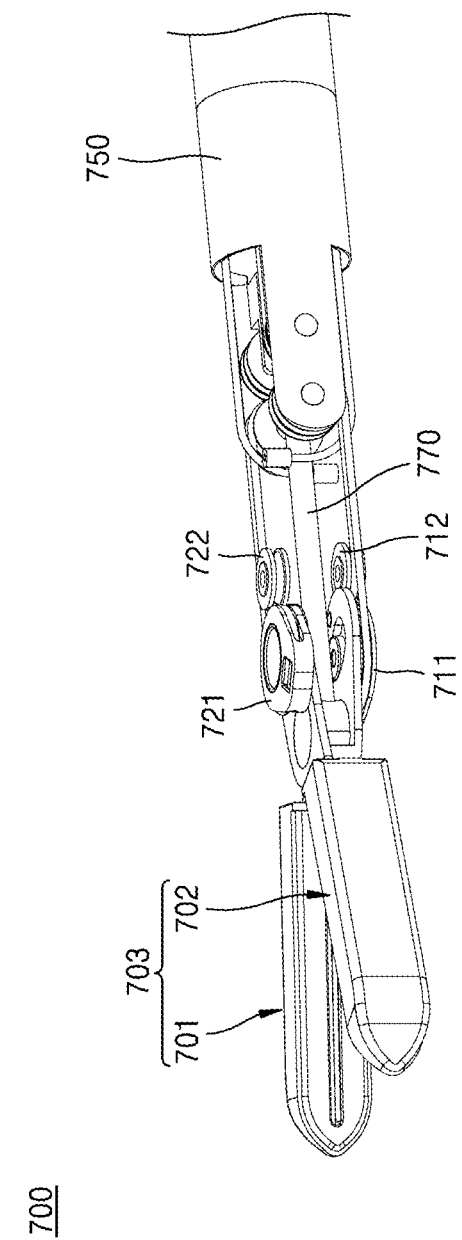
Figure 85:
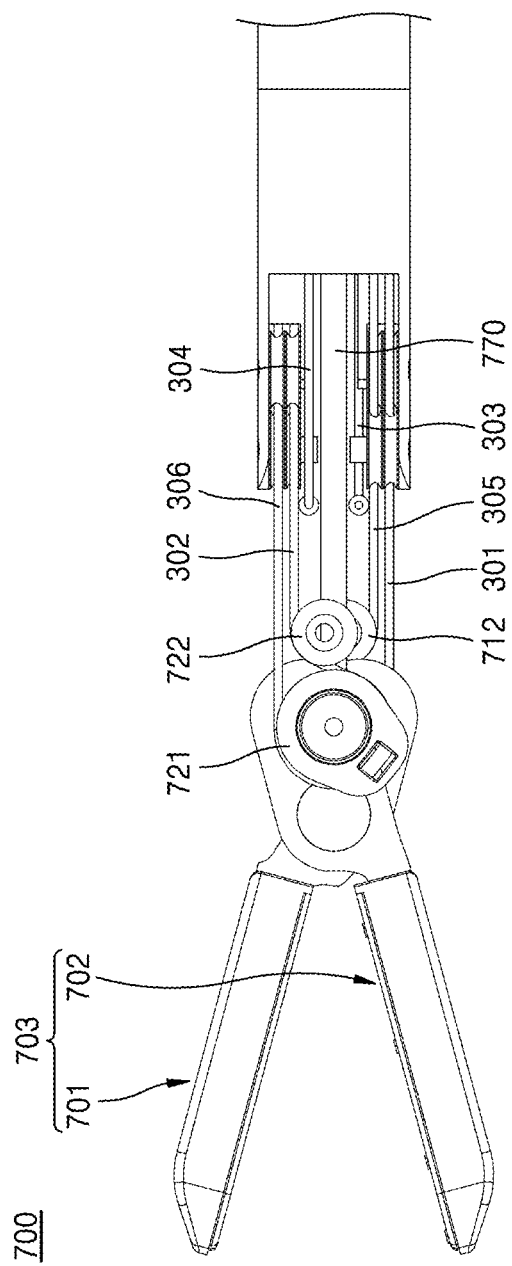

FIGS. 83 to 85 are views illustrating the end tool of the surgical instrument for electrocautery according to the modified example of the second embodiment of the present disclosure.

Referring to FIGS. 83 to 85, the end tool 700 of the modified example of the second embodiment of the present disclosure includes a pair of jaws for performing a grip motion, specifically a first jaw 701 and a second jaw 702, and here, each of the first jaw 701 and the second jaw 702 or a component encompassing the first jaw 701 and the second jaw 702 may be referred to as a jaw 703.

The end tool 700 according to the modified example of the second embodiment may include a pulley 711, the pulley 712, a pulley 713, a pulley 714, a pulley 715, and a pulley 716 that are associated with a rotational motion of the first jaw 701. In addition, the end tool 700 may include a pulley 721, the pulley 722, a pulley 723, a pulley 724, a pulley 725, and a pulley 726 that are associated with a rotational motion of the second jaw 702.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Figure 43:
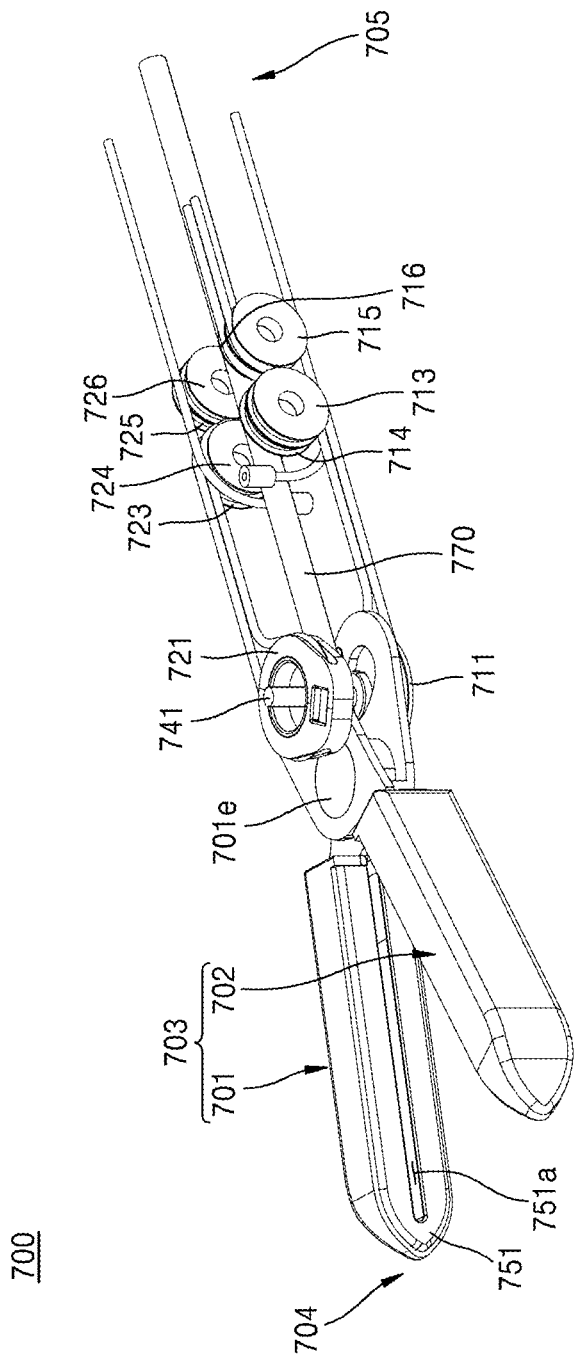
Figure 44:
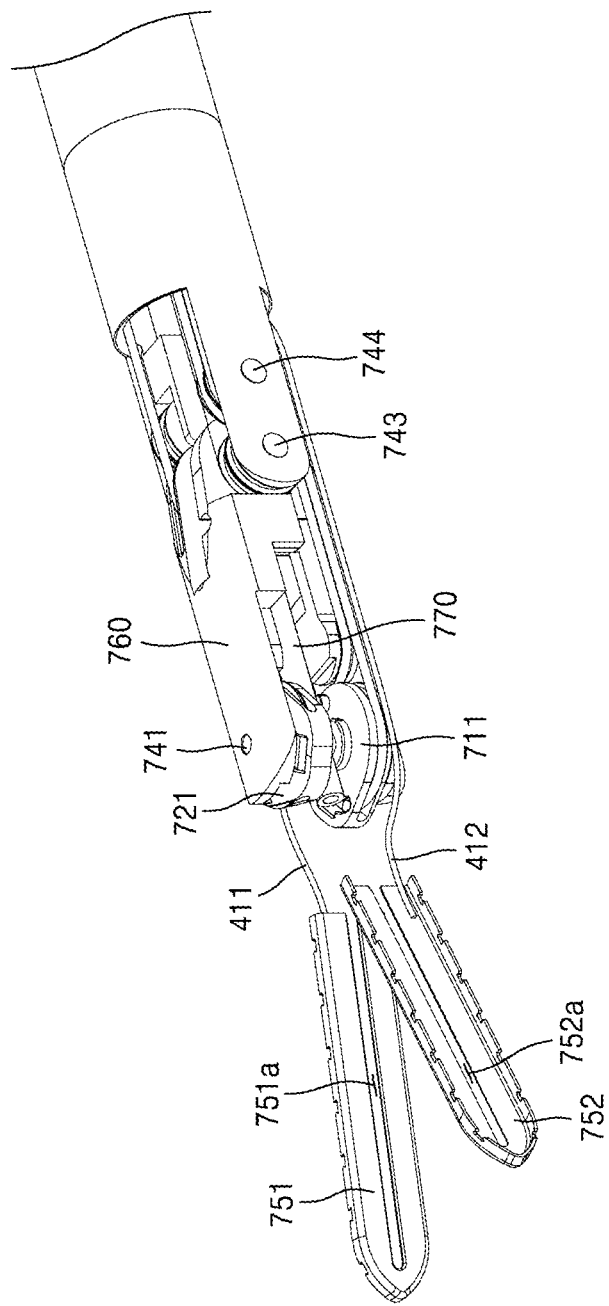
Figure 45:
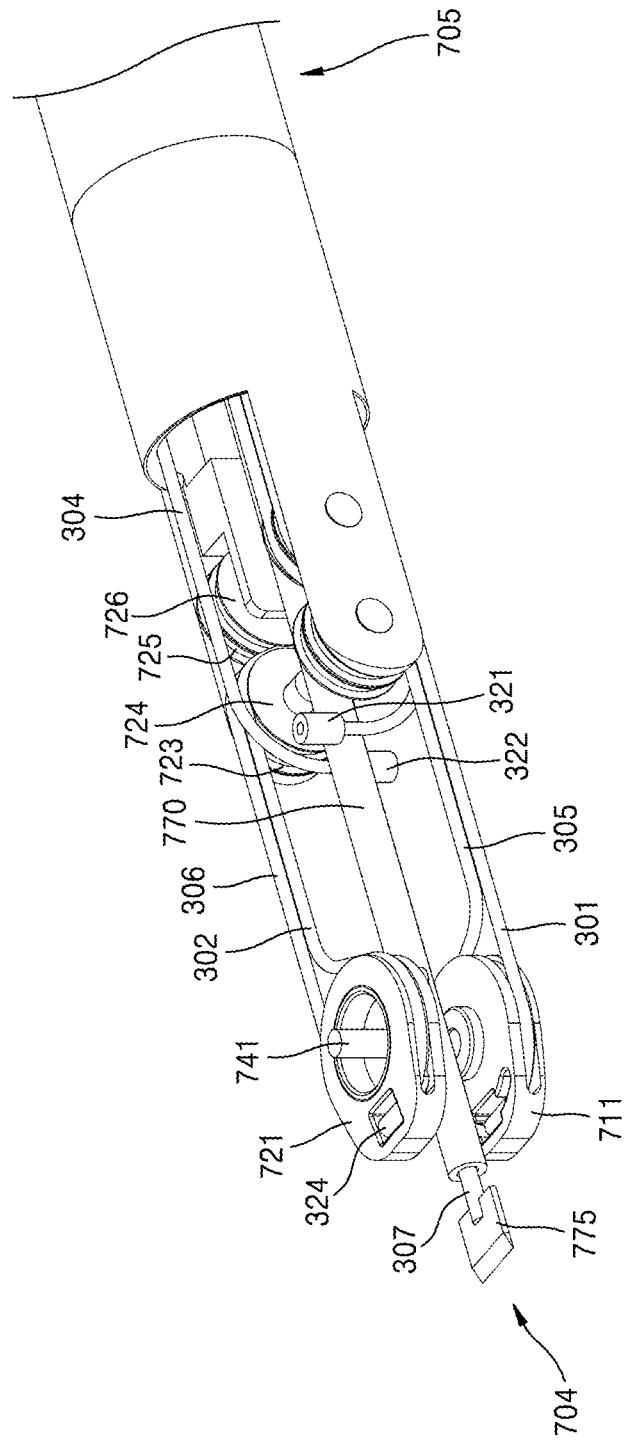
Figure 46:
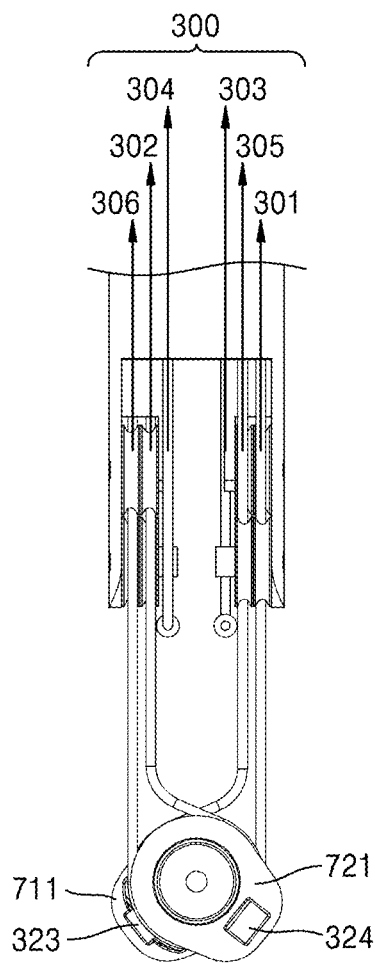
Figure 46:
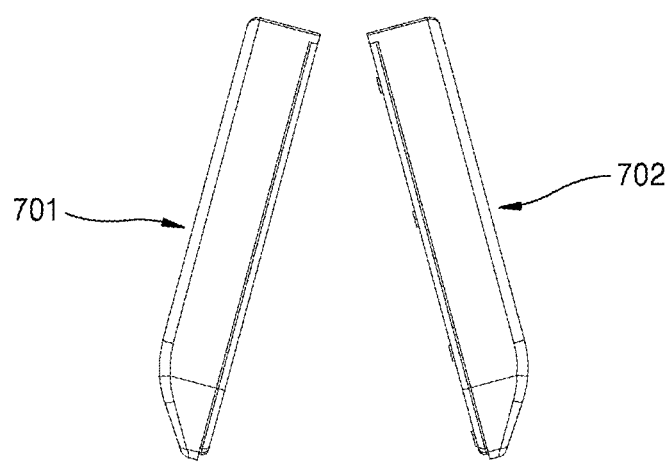
Figure 47:
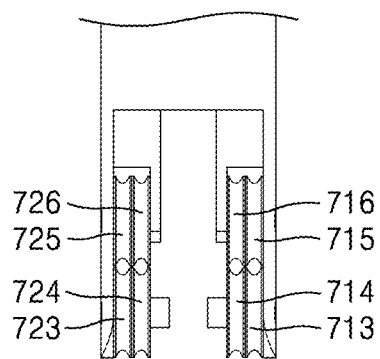
Figure 47:
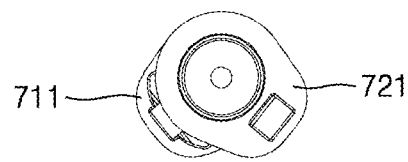
Figure 47:
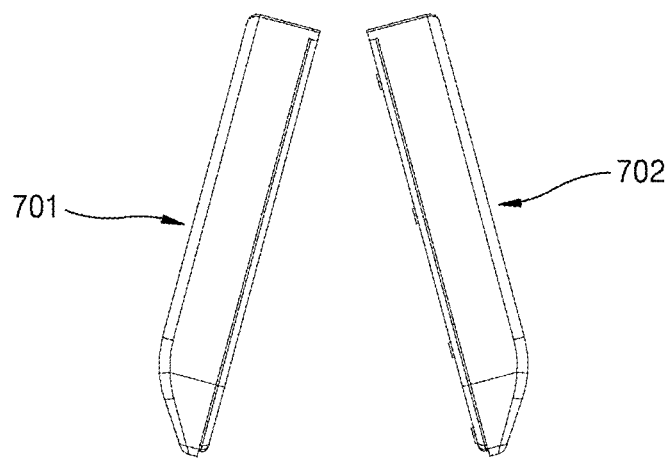

The end tool 700 according to the modified example of the second embodiment of the present disclosure may further include the pulley 712 and the pulley 722 as compared to the end tool 700 according to the second embodiment of the present disclosure illustrated with reference to FIG. 43.

Referring to FIGS. 84 and 85, the pulley 712 functions as an end tool first jaw auxiliary pulley, and the pulley 722 functions as an end tool second jaw auxiliary pulley, and these two components may collectively be referred to as end tool jaw auxiliary pulleys or simply auxiliary pulleys.

In detail, the pulley 712 and the pulley 722, which are end tool jaw auxiliary pulleys, may be additionally provided on one side of the pulley 711 and one side of the pulley 721, respectively. In other words, the pulley 712, which is an auxiliary pulley, may be disposed between the pulley 711 and the pulley 713/pulley 714. In addition, the pulley 722, which is an auxiliary pulley, may be disposed between the pulley 721 and the pulley 723/pulley 724.

The pulley 712 and the pulley 722 may be formed to be rotatable independently of each other around a second rotation shaft 742.

The pulley 712 and the pulley 722 may serve to increase rotation angles of the first jaw 701 and the second jaw 702, respectively, by coming into contact with a wire 305, which is a first jaw wire, and a wire 302, which is a second jaw wire, and changing the arrangement paths of the wire 305 and the wire 302 to a certain degree.

That is, when the auxiliary pulleys are not disposed, each of the first jaw 701 and the second jaw 702 may rotate only up to a right angle, but in the modified example of the second embodiment, by additionally providing the pulley 712 and the pulley 722, which are auxiliary pulleys, the effect of increasing the maximum rotation angle by a certain angle can be achieved.

This enables a motion in which two jaws of the end tool 700 have to be spread apart for an actuation motion in a state in which the two jaws are yaw-rotated together by 90° in the clockwise or counterclockwise direction.

In other words, a feature of increasing the range of yaw rotation in which an actuation motion is possible may be obtained through the pulley 712 and the pulley 722. This will be described below in more detail.

When the auxiliary pulleys are not disposed, since the first jaw wire 305 is fixedly coupled to the end tool first jaw pulley 711, and the second jaw wire 302 is fixedly coupled to the end tool second jaw pulley 721, each of the end tool first jaw pulley 711 and the end tool second jaw pulley 721 may rotate up to 90°.

In this case, when the actuation motion is performed in a state in which the first jaw 701 and the second jaw 702 are located at a 90° line, the first jaw 701 may be spread, but the second jaw 702 may not be rotated beyond 90°. Accordingly, when the first jaw 701 and the second jaw 702 perform a yaw motion over a certain angle, there was a problem that an actuation motion is not smoothly performed.

In order to address such a problem, in the electric cauterization surgical instrument 10 of the present disclosure, the pulley 712 and the pulley 722, which are auxiliary pulleys, are additionally disposed at one side of the pulley 711 and one side of the pulley 721, respectively. As described above, as the arrangement paths of the wire 305, which is a first jaw wire, and the wire 302, which is a second jaw wire, are changed to a certain degree by disposing the pulley 712 and the pulley 722, a tangential direction of the wires 305 and 302 is changed, and accordingly, a fastening member 324 for coupling the wire 302 and the pulley 721 is additionally rotatable by a certain angle.

That is, a fastening member 326, which is a coupling portion of the wire 302 and the pulley 721, is rotatable until being located on a common internal tangent of the pulley 721 and the pulley 722. Similarly, a fastening member 323, which is a coupling portion of the wire 305 and the pulley 711, is rotatable until being located on a common internal tangent of the pulley 711 and the pulley 712, so that the range of rotation may be increased.

In other words, due to the pulley 712 that is an auxiliary pulley, a wire 301 and a wire 305, which are two strands of the first jaw wire wound around the pulley 712, are disposed at one side with respect to a plane perpendicular to the Y-axis and passing through the X-axis. Simultaneously, due to the pulley 722, the wires 302 and 306, which are two strands of the second jaw wire wound around the pulley 721, are disposed at the other side with respect to the plane perpendicular to the Y-axis and passing through the X-axis.

In other words, the pulley 713 and the pulley 714 are disposed at one side with respect to the plane perpendicular to the Y-axis and passing through the X-axis, and the pulley 723 and the pulley 724 are disposed at the other side with respect to the plane perpendicular to the Y-axis and passing through the X-axis.

In other words, the wire 305 is located on the internal tangent of the pulley 711 and the pulley 712, and the rotation angle of the pulley 711 is increased due to the pulley 712. In addition, the wire 302 is located on the internal tangent of the pulley 721 and the pulley 722, and the rotation angle of the pulley 721 is increased due to the pulley 722.

According to the present disclosure, the rotation radii of the first jaw 701 and the second jaw 702 increase, so that an effect of increasing a yaw motion range in which a normal opening/closing actuation motion can be performed may be obtained.

Referring to FIG. 38, a first rotation shaft 741 and a second rotation shaft 742 may be inserted through the end tool hub 760' according to the modified example of the second embodiment of the present disclosure. Instead of respectively forming the first wire guide portion and the second wire guide portion on the surfaces of a first jaw pulley coupling portion 762a and a second jaw pulley coupling portion 762b facing each other as in the end tool hub 760 according to the second embodiment of the present disclosure, the pulley 712 and the pulley 722, which are configured as separate components from the end tool hub 760' and are able to be axially coupled to the second rotation shaft 742 that is inserted through the end tool hub 760', are additionally provided and allowed to function as auxiliary pulleys.

The second rotation shaft 742 inserted through the end tool hub 760' may include two shafts including a first sub-shaft and a second sub-shaft that face each other and are disposed to be spaced apart from each other by a certain distance. The second rotation shaft 742 is divided into two parts and spaced apart from each other by a certain distance, and thus a guide tube 770 may pass through the end tool hub 760' and a pitch hub 750 through between the two parts.

Referring to FIG. 83, the first rotation shaft 741, the second rotation shaft 742, a third rotation shaft 743, and a fourth rotation shaft 744 may be arranged sequentially from a distal end 704 toward a proximal end 705 of the end tool 700. Accordingly, starting from the distal end 704, the first rotation shaft 741 may be referred to as a first pin, the second rotation shaft 742 may be referred to as a second pin, the third rotation shaft 743 may be referred to as a third pin, and the fourth rotation shaft 744 may be referred to as a fourth pin.

As compared to the second embodiment, the end tool 700 of the modified example of the second embodiment of the present disclosure has the same configuration as the end tool 700 according to the second embodiment, except that the pulley 721 and the pulley 722, which are axially coupled to the end tool hub 760' by the second rotation shaft 742, are provided as separate components instead of being integrally formed with a body portion 761 in the end tool hub 760' and function as auxiliary pulleys, and thus a detailed description thereof will be omitted in the overlapping range.

Third Embodiment of Surgical Instrument for Electrocautery

Figure 86:
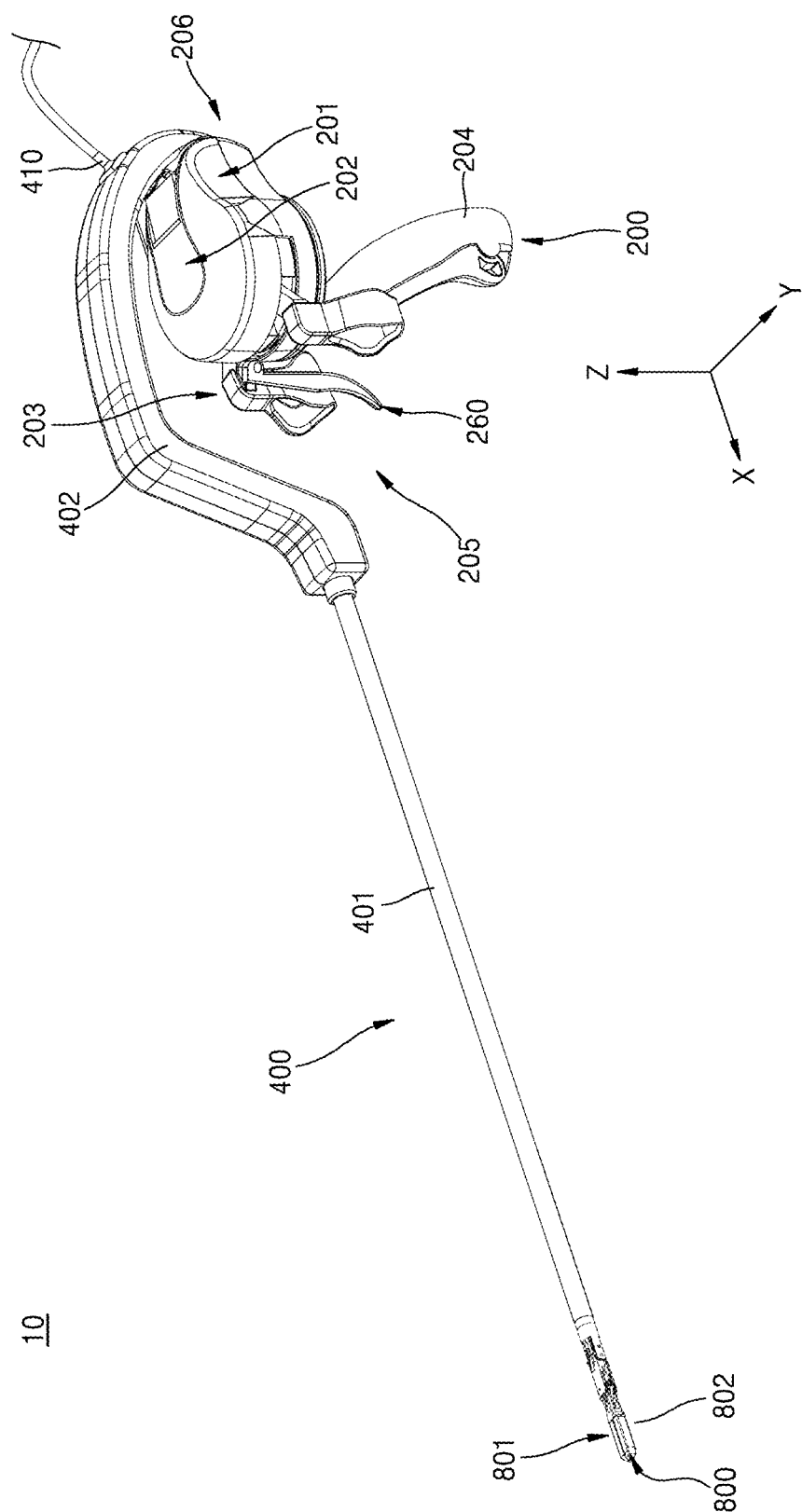
FIG. 86 is a perspective view illustrating a surgical instrument for electrocautery according to a third embodiment of the present disclosure.

FIG. 86 is a perspective view illustrating a surgical instrument for electrocautery according to a third embodiment of the present disclosure. FIGS. 87 to 92 are plan views illustrating an end tool of the surgical instrument for electrocautery of FIG. 86.

Referring to FIG. 86, an electric cauterization surgical instrument 10 according to the third embodiment of the present disclosure includes an end tool 800, a manipulation portion 200, a power transmission portion 300, and a connection portion 400.

As compared to the electric cauterization surgical instrument 10 according to the second embodiment, the electric cauterization surgical instrument 10 according to the third embodiment of the present disclosure is different from in a configuration of the end tool 800, specifically, a yaw hub 880, an actuation link 892, and the like, which will be described in detail below.

Figure 87:
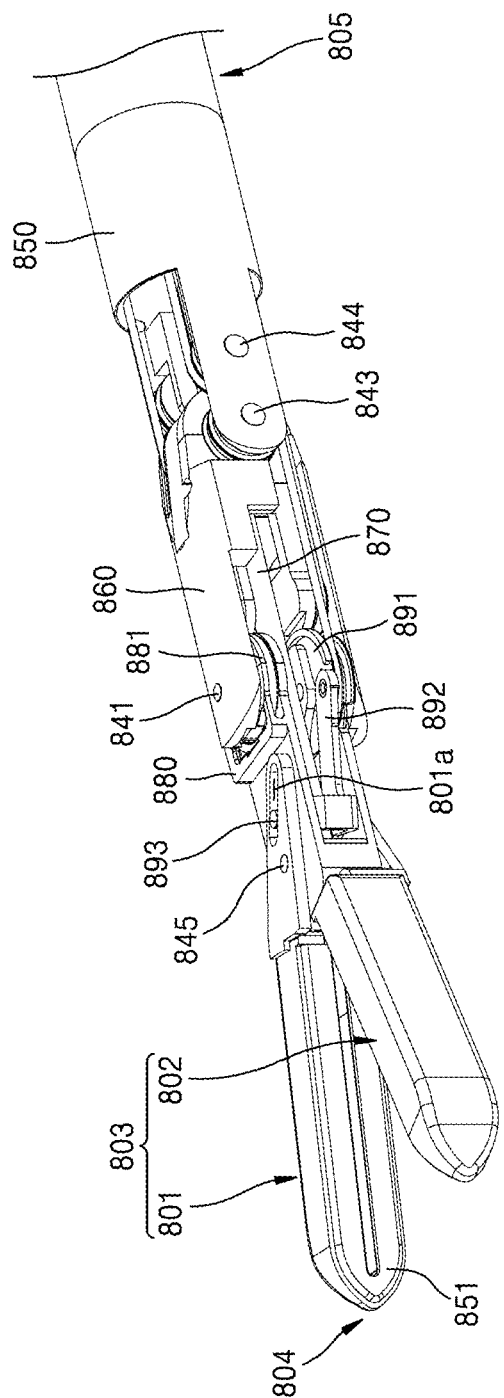
FIGS. 87 to 92 are views illustrating an end tool of the surgical instrument for electrocautery of FIG. 86.

Referring to FIGS. 86 and 87, the end tool 800 according to the third embodiment of the present disclosure is formed at the other end of the connection portion 400, and performs necessary motions for surgery by being inserted into a surgical site. In an example of the end tool 800, as illustrated in FIG. 86, a pair of jaws 803 for performing a grip motion may be used.

However, the concept of the present disclosure is not limited thereto, and various devices for performing surgery may be used as the end tool 800. For example, a configuration of a cantilever cautery may also be used as the end tool 800.

The end tool 800 is connected to the manipulation portion 200 by the power transmission portion 300, and receives a driving force of the manipulation portion 200 through the power transmission portion 300 to perform a motion necessary for surgery, such as gripping, cutting, suturing, or the like.

Here, the end tool 800 of the electric cauterization surgical instrument 10 according to the third embodiment of the present disclosure is formed to be rotatable in at least one direction, and for example, the end tool 800 may be formed to perform a pitch motion around a Y-axis of FIG. 86 and simultaneously perform a yaw motion and an actuation motion around a Z-axis of FIG. 86.

End Tool According to Third Embodiment

Hereinafter, the end tool 800 of the electric cauterization surgical instrument 10 of FIG. 86 will be described in more detail.

FIG. 86 is a perspective view illustrating the surgical instrument for electrocautery according to the third embodiment of the present disclosure. FIGS. 87 to 92 are views illustrating the end tool of the surgical instrument for electrocautery of FIG. 86.

Figure 88:
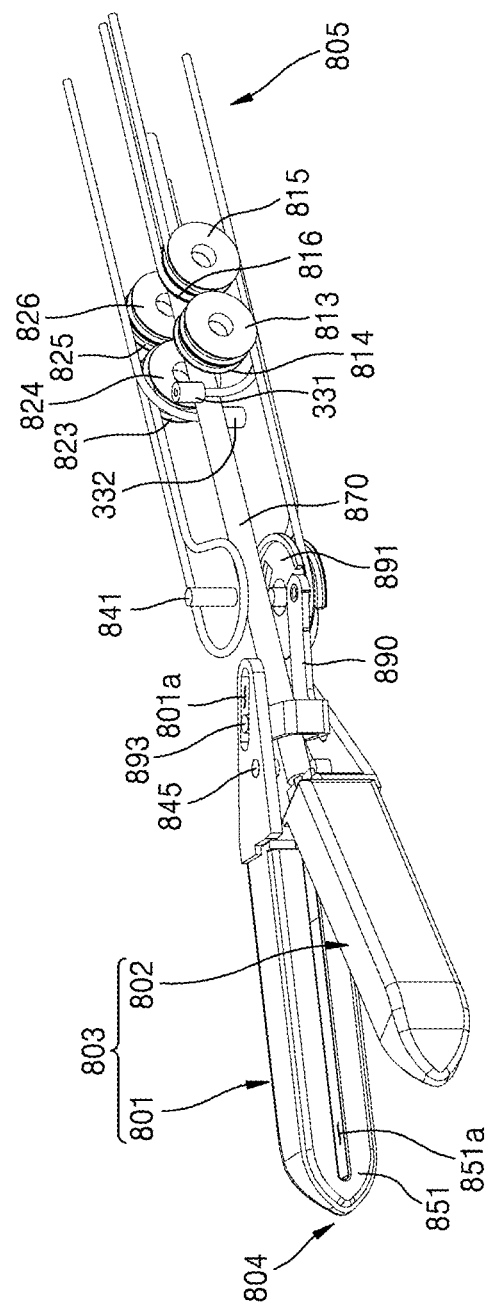
Figure 89:
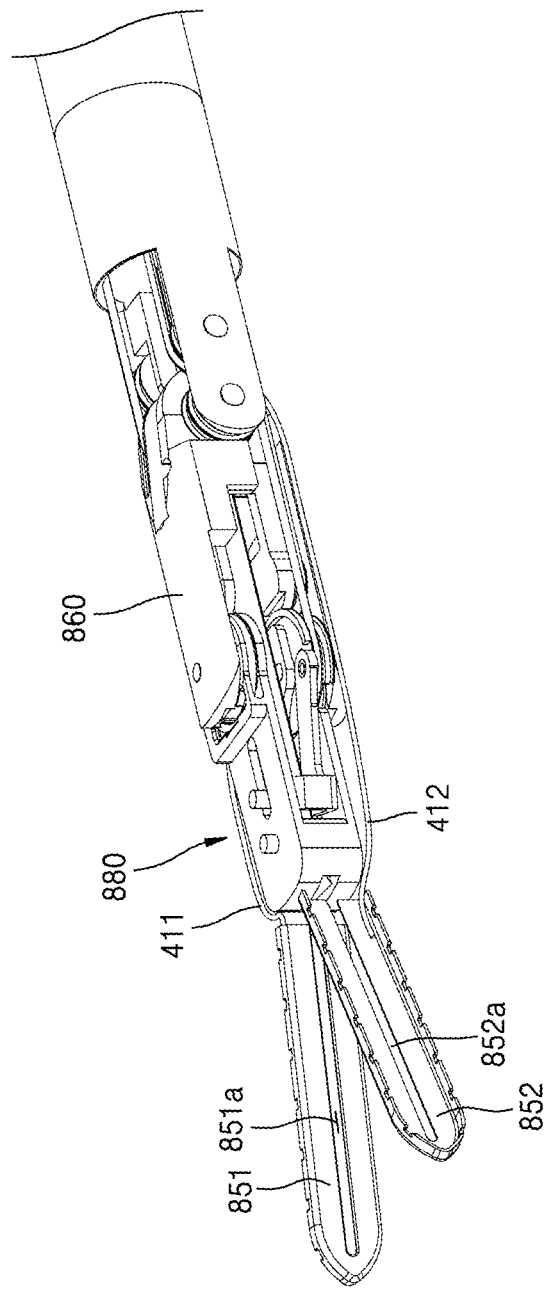
Figure 90:
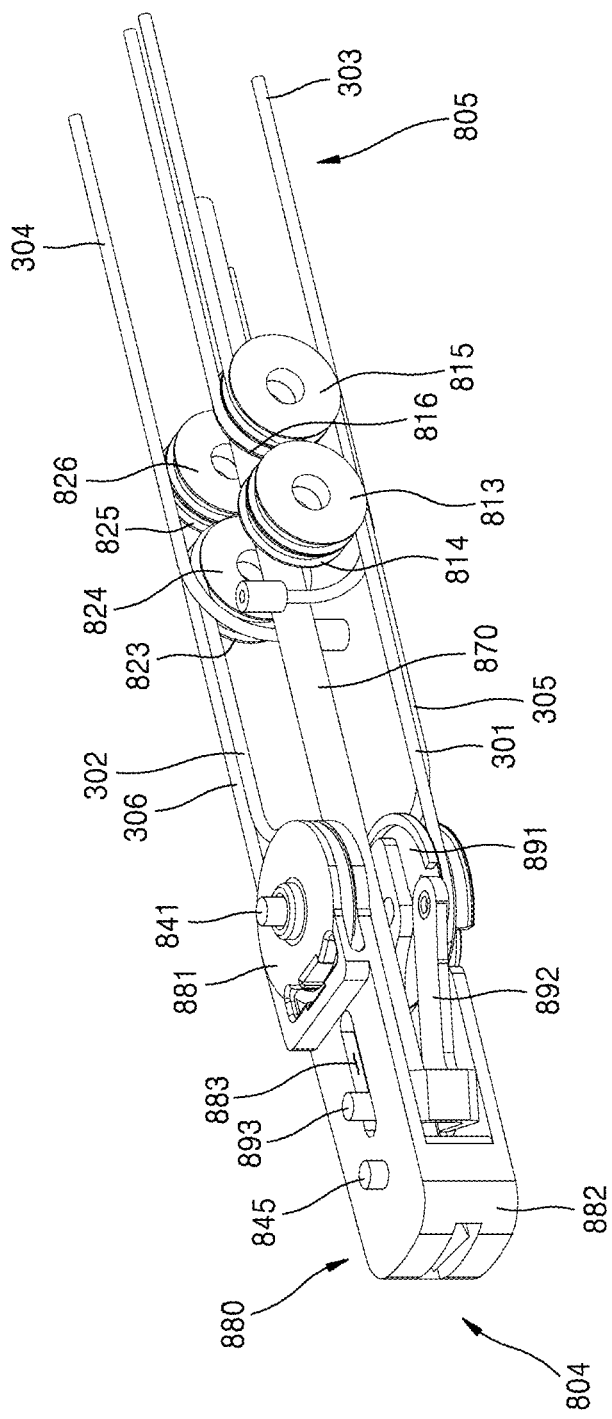
Figure 91:
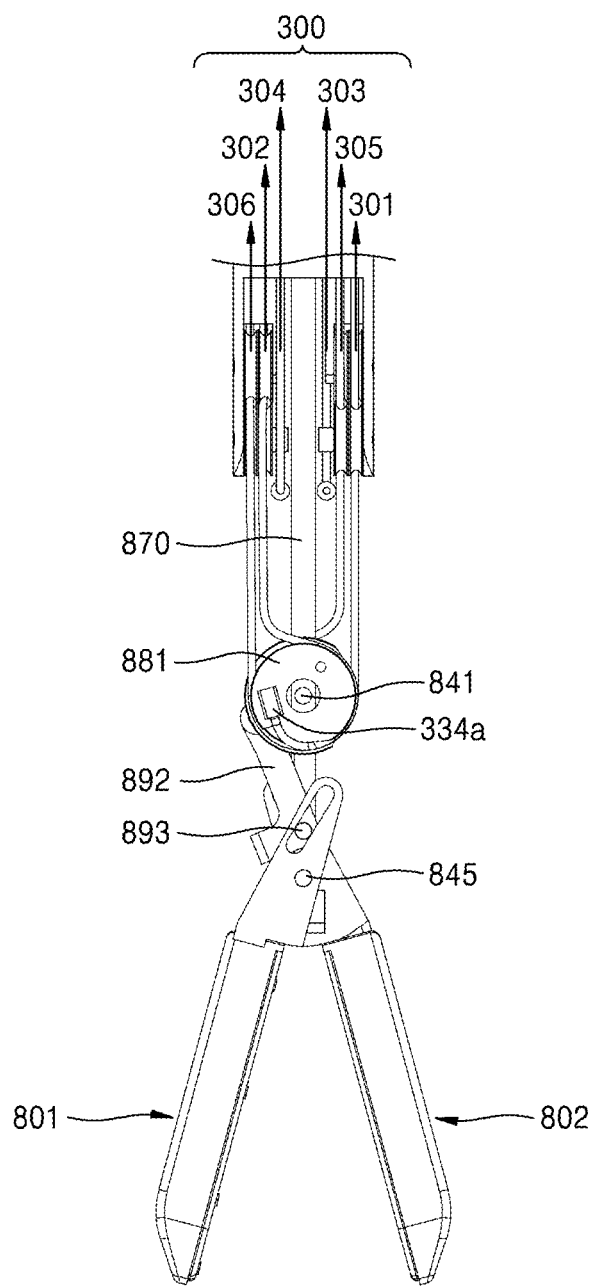
Figure 92:
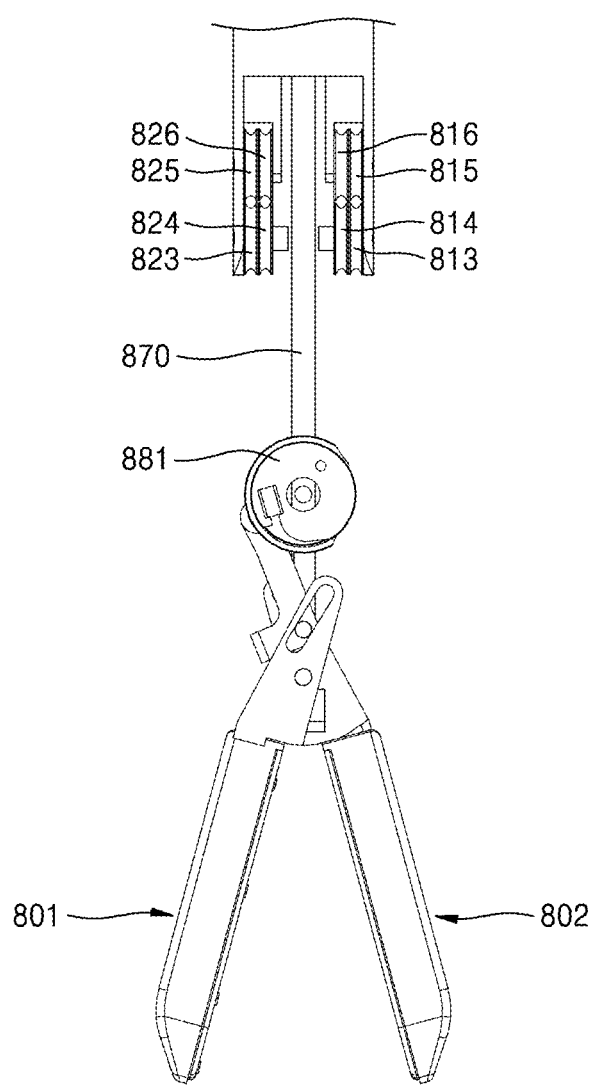

Here, FIG. 87 illustrates a state in which an end tool hub 860 and a pitch hub 850 are coupled, and FIG. 88 illustrates a state in which the end tool hub 860, the yaw hub 880, and the pitch hub 850 are removed. FIG. 89 illustrates a state in which the yaw hub 880 and the end tool hub 860 are connected to the end tool, and FIG. 90 illustrates a state in which a first jaw 801 and a second jaw 802 are removed. Meanwhile, FIG. 91 is a view mainly illustrating wires, and FIG. 92 is a view mainly illustrating pulleys.

Referring to FIGS. 87, 88, 91, and 92, the end tool 800 according to the third embodiment of the present disclosure may include a pair of jaws for performing a grip motion, that is, the first jaw 801 and the second jaw 802. Here, each of the first jaw 801 and the second jaw 802, or a component encompassing the first jaw 801 and the second jaw 802 may be referred to as the jaw 803.

In addition, the end tool 800 may include a pulley 891, a pulley 813, a pulley 814, a pulley 815, and a pulley 816, which are associated with a rotational motion of the first jaw 801. In addition, the end tool 800 may include a pulley 881, a pulley 823, a pulley 824, a pulley 825, and a pulley 826, which are associated with a rotational motion of the second jaw 802.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Referring to FIG. 87, the end tool 800 of the third embodiment of the present disclosure may include the end tool hub 860, the pitch hub 850, and the yaw hub 880.

A first rotation shaft 841, which will be described later, may be inserted through the end tool hub 860, and the end tool hub 860 may internally accommodate at least some of the pulley 891 and the pulley 881, which are axially coupled to the first rotation shaft 841.

The end tool hub 860 according to the third embodiment of the present disclosure is the same as the end tool hubs 660 and 760 according to the first and third embodiments, and thus a detailed description thereof will be omitted in the overlapping range.

Referring to FIG. 87, the pitch hub 850 may have a third rotation shaft 843 and a fourth rotation shaft 844, which will be described later, inserted therethrough, and may be axially coupled to a first pitch pulley portion 863a and a second pitch pulley portion 863b of the end tool hub 860 by the third rotation shaft 843. Accordingly, the end tool hub 860 may be formed to be rotatable around the third rotation shaft 843 with respect to the pitch hub 850.

In addition, the pitch hub 850 may internally accommodate at least some of the pulley 813, the pulley 814, the pulley 823, and the pulley 824 that are axially coupled to the third rotation shaft 843. In addition, the pitch hub 850 may internally accommodate at least some of the pulley 815, the pulley 816, the pulley 825, and the pulley 826 that are axially coupled to the fourth rotation shaft 844.

One end portion of the pitch hub 850 is connected to the end tool hub 860, and the other end portion of the pitch hub 850 is connected to the connection portion 400.

Referring to FIG. 87, the first rotation shaft 841 may function as an end tool jaw pulley rotation shaft, the third rotation shaft 843 may function as an end tool pitch rotation shaft, and the fourth rotation shaft 844 may function as an end tool pitch auxiliary rotation shaft of the end tool 100.

Here, each of the rotation shafts may be divided into two parts, and the respective divided rotation shafts may be spaced apart from each other. Each of the rotation shafts is formed by being divided into two parts as described above to allow a guide tube 870 to pass through the end tool hub 860 and the pitch hub 850.

That is, the guide tube 870 may pass between a first sub-shaft and a second sub-shaft of each of the rotation shafts. This will be described in more detail later. Here, the first sub-shaft and the second sub-shaft may be disposed on the same axis or may be disposed to be offset to a certain degree.

Meanwhile, it is illustrated in the drawings that each of the rotation shafts is formed by being divided into two parts, but the concept of the present disclosure is not limited thereto. That is, each of the rotation shafts is formed to be curved in the middle such that an escape path for the guide tube 870 is formed.

Referring to FIGS. 87 and 88, an actuation rotation shaft 845 may be further provided in the end tool 800 according to the third embodiment of the present disclosure. In detail, the actuation rotation shaft 845 may be provided in a coupling portion of the first jaw 801 and the second jaw 802, and the second jaw 802 rotates around the actuation rotation shaft 845 while the first jaw 801 is fixed, thereby performing an actuation motion. Here, the actuation rotation shaft 845 may be disposed closer to a distal end 804 than the first rotation shaft 841 is.

Here, in the end tool 800 of the third embodiment of the present disclosure, the first rotation shaft 841, which is a yaw rotation shaft, and the actuation rotation shaft 845 are provided separately rather than as the same shaft.

That is, by forming the first rotation shaft 841, which is a rotation shaft of the pulley 881/pulley 891 that are jaw pulleys and a rotation shaft of a yaw motion, and the actuation rotation shaft 845, which is a rotation shaft of the second jaw 802 with respect to the first jaw 801 and a rotation shaft of an actuation motion, to be spaced apart from each other by a certain distance, a space in which the guide tube 870 and the blade wire 307 accommodated therein can be gently bent may be secured. This actuation rotation shaft 845 will be described in more detail later.

The pulley 891 functions as an end tool first jaw pulley, and the pulley 881 functions as an end tool second jaw pulley. The pulley 891 may also be referred to as a first jaw pulley, and the pulley 881 may also be referred to as a second jaw pulley, and these two components may collectively be referred to as end tool jaw pulleys or simply jaw pulleys.

The pulley 891 and the pulley 881, which are end tool jaw pulleys, are formed to face each other, and are formed to be rotatable independently of each other around the first rotation shaft 841 which is an end tool jaw pulley rotation shaft.

In this case, the pulley 891 and the pulley 881 are formed to be spaced apart from each other by a certain distance, and a blade assembly may be accommodated therebetween.

In other words, the blade assembly including the guide tube 870 may be disposed between the pulley 891 and the pulley 881.

Meanwhile, the end tool 800 of the third embodiment of the present disclosure may further include components such as a first electrode 851, a second electrode 852, the guide tube 870, and a blade 875 in order to perform a cauterizing motion and a cutting motion.

Here, components related to the driving of the blade, such as the guide tube 870 and the blade 875, may be collectively referred to as a blade assembly. In one modified example of the present disclosure, by disposing the blade assembly including the blade 875 between the pulley 891, which is a first jaw pulley, and the pulley 881, which a second jaw pulley, the end tool 800 is able to perform the cutting motion using the blade in addition to the pitch and yaw motions. Components for performing a cauterizing motion and a cutting motion in the present embodiment are substantially the same as those described in the first and second embodiments, and thus a detailed description thereof will be omitted herein.

The electric cauterization surgical instrument 10 according to the third embodiment of the present disclosure may include a wire 301, a wire 302, the wire 303, the wire 304, a wire 305, a wire 306, and a blade wire 307, as in the first embodiment of the present disclosure.

(Jaw-Link-Pulley Connection Structure)

Hereinafter, a jaw-link-pulley connection structure in the end tool 800 according to the third embodiment of the present disclosure will be described in more detail.

Referring to FIGS. 87 to 101, the end tool 800 of the third embodiment of the present disclosure includes the first jaw 801, the second jaw 802, the yaw hub 880, an actuation link 592, the first jaw pulley 891, and the second jaw pulley 881. Hereinafter, the pulley 891 is referred to as the first jaw pulley 891, and the pulley 881 is referred to as the second jaw pulley 881.

Referring to FIGS. 97 to 100, the first jaw pulley 891 may be formed as a kind of multi-layered pulley. In other words, the first jaw pulley 891 may be formed in a form in which two pulleys are combined, and two grooves may be formed on an outer circumferential surface of the first jaw pulley 891.

In detail, a first coupling portion 891*a* may be formed on one surface of the first jaw pulley 891, and a second coupling portion 891*b* may be formed in the shape of a groove on the other surface opposite to the one surface on which the first coupling portion 891*a* is formed.

Here, the positions of the first coupling portion 891*a* and the second coupling portion 891*b* are positions allowing the wire 301 and the wire 305 to overlap each other. In other words, the first coupling portion 891*a* and the second coupling portion 891*b* may be formed so that at least some of the wire 302 and the wire 306 wound around the first jaw pulley 891 overlap each other.

In other words, the first coupling portion 891*a* and the second coupling portion 891*b* are asymmetrically disposed when viewed on an XY plane, so that the first coupling portion 891*a* and the second coupling portion 891*b* are disposed to be biased in any one region of the second jaw pulley 891.

In other words, the first coupling portion 891*a* may be formed at a position at which the wire 301 may be wound around the outer circumferential surface of the first jaw pulley 891 such that the central angle is an angle between 90° and 360°. Similarly, the second coupling portion 891*b* may be formed at a position at which the wire 305 may be wound around the outer circumferential surface of the second jaw pulley 891 such that the central angle is an angle between 90° and 360°.

In addition, one end portion of the wire 301 is coupled to a fastening member 334*a*, which may be coupled to the first coupling portion 891*a* of the first jaw pulley 891. One end portion of the wire 305 is coupled to a fastening member 334*b*, which may be coupled to the second coupling portion 891*b* of the first jaw pulley 891.

When the wire 301 is referred to as a first jaw wire R and the wire 305 is referred to as a first jaw wire L, the first coupling portion 891*a* to which the first jaw wire R(301) is coupled is formed on a side opposite to one side to which the first jaw wire R(301) is input, so that a rotation angle of the first jaw pulley 891 is increased by increasing the length of the first jaw wire R(305) wound around the first jaw pulley 891.

Also, the second coupling portion 891*b* to which the first jaw wire L(302) is coupled is formed on one side opposite to the other side to which the first jaw wire L(302) is input, so that the rotation angle of the first jaw pulley 891 may be increased by increasing the length of the first jaw wire L(302) wound around the first jaw pulley 891.

A rotation radius of the second jaw pulley 891 may be increased due to the first coupling portion 891*a* and the second coupling portion 891*b*. In addition, by increasing the length of the wire 301/wire 305 wound around the first jaw pulley 891 as described above, a long stroke of the actuation link 892 may be secured. This will be described in more detail later.

Referring to FIG. 90, the yaw hub 880 is located between the first and second jaws 801 and 802 and the first and second jaw pulleys 891 and 881, and may include a yaw hub body 882.

The first jaw pulley 891 may be formed at one end portion of the yaw hub 880. A guide slit 883 may be formed on the other end portion of the yaw hub 880 in a longitudinal direction. A guide pin 893 formed to protrude from the actuation link 892 to be described later may be fitted into the guide slit 883.

Figure 93:
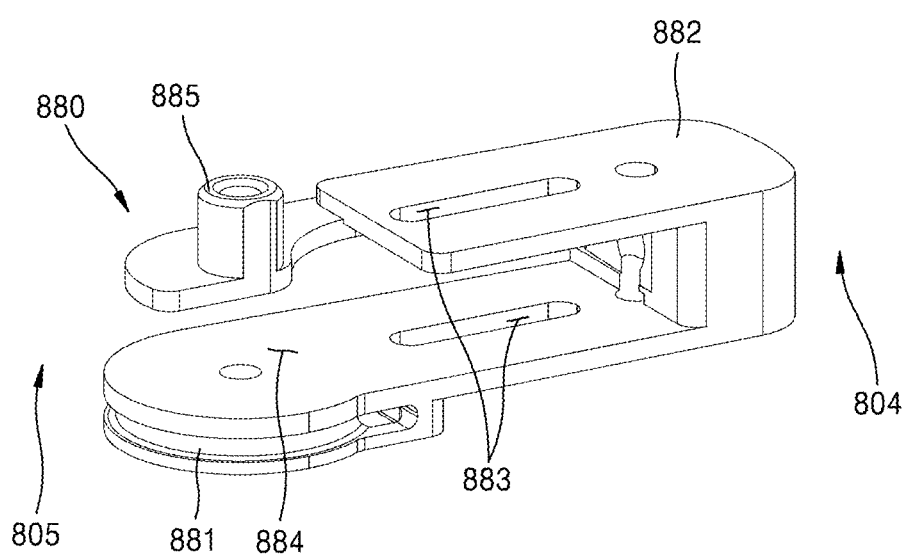
FIG. 93 is a perspective view illustrating a yaw hub of the end tool of the surgical instrument for electrocautery of FIG. 86.
Figure 94:
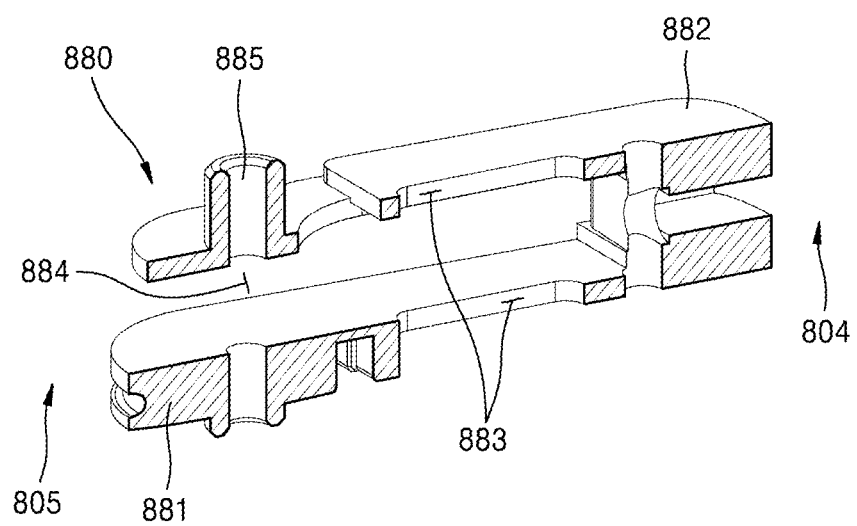
FIG. 94 is cut-away perspective view illustrating the yaw hub of the end tool of the surgical instrument for electrocautery of FIG. 86.
Figure 95:
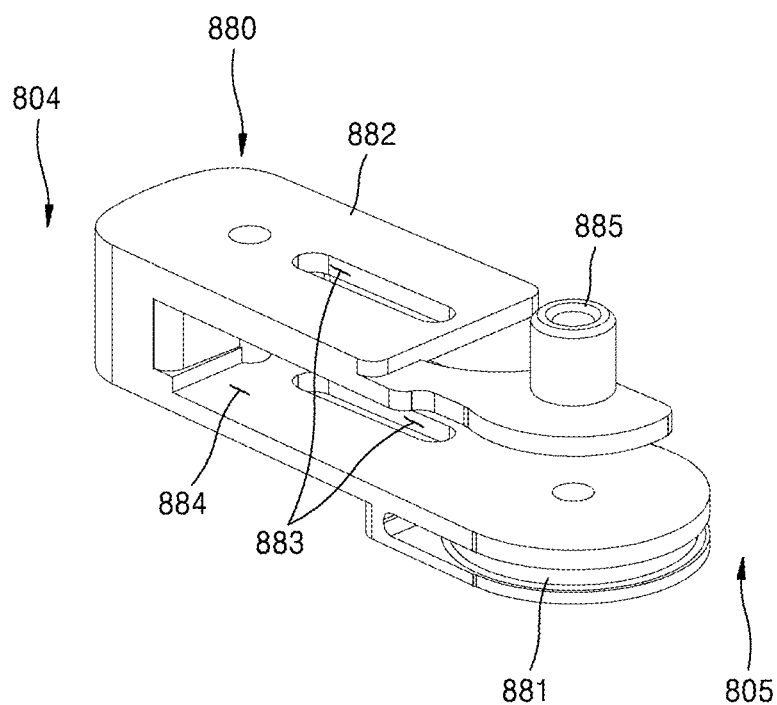
FIGS. 95 and 96 are perspective views illustrating the yaw hub of the end tool of the surgical instrument for electrocautery of FIG. 86.
Figure 96:
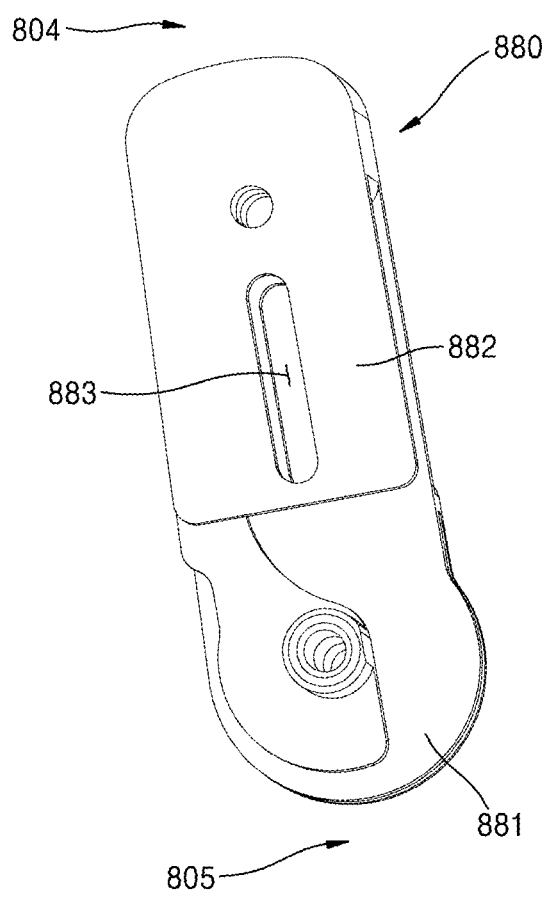
Figure 97:
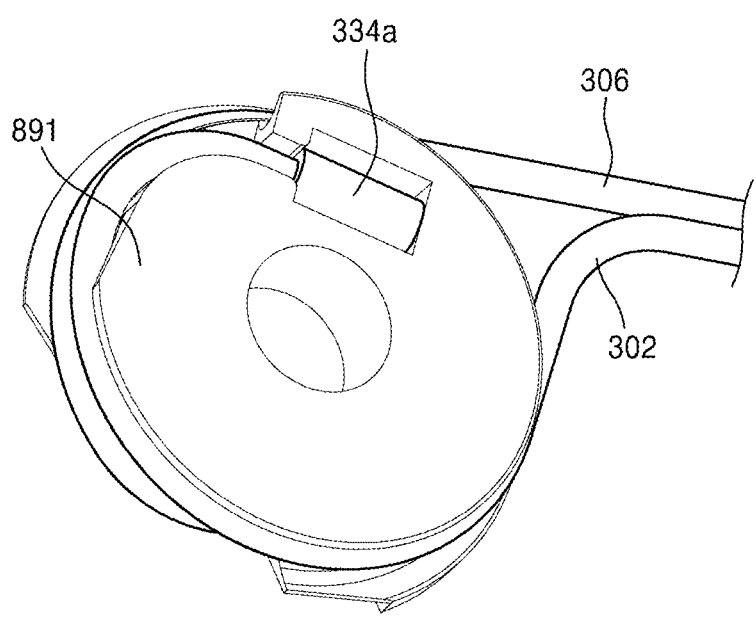
FIGS. 97 and 98 are perspective views illustrating an actuation pulley of the end tool of the surgical instrument for electrocautery of FIG. 86 and wires.
Figure 98:
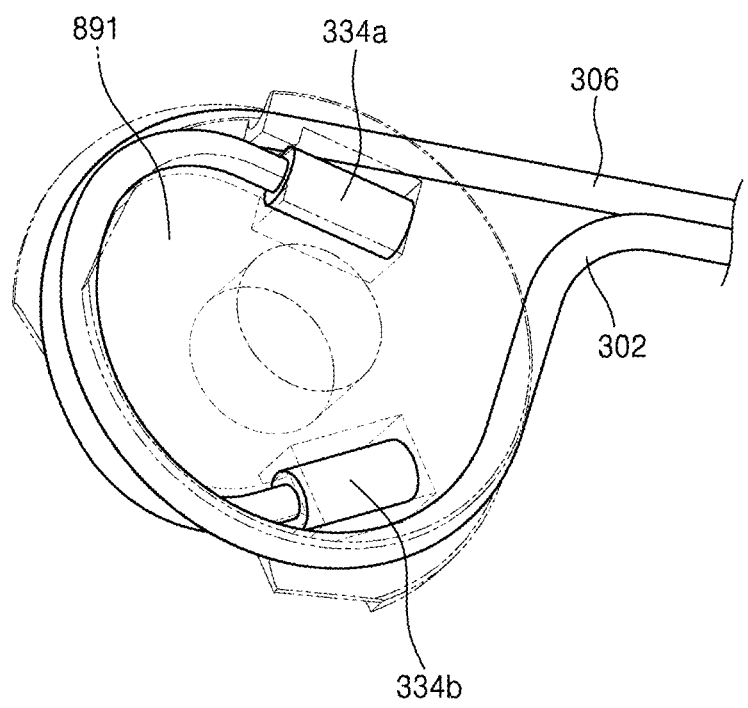
Figure 99:
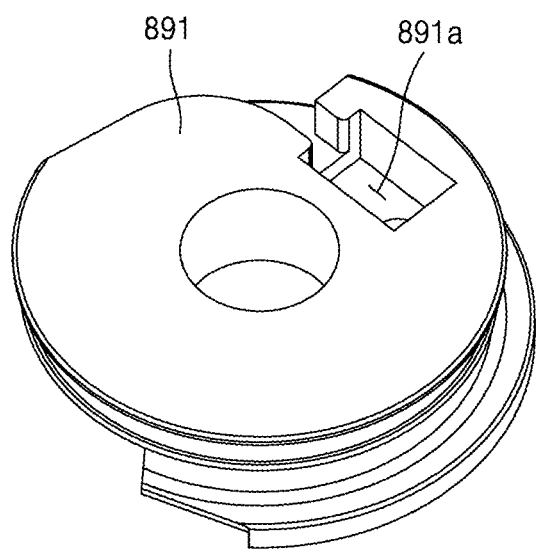
FIGS. 99 and 100 are perspective views illustrating the actuation pulley of the end tool of the surgical instrument for electrocautery of FIG. 86.
Figure 100:
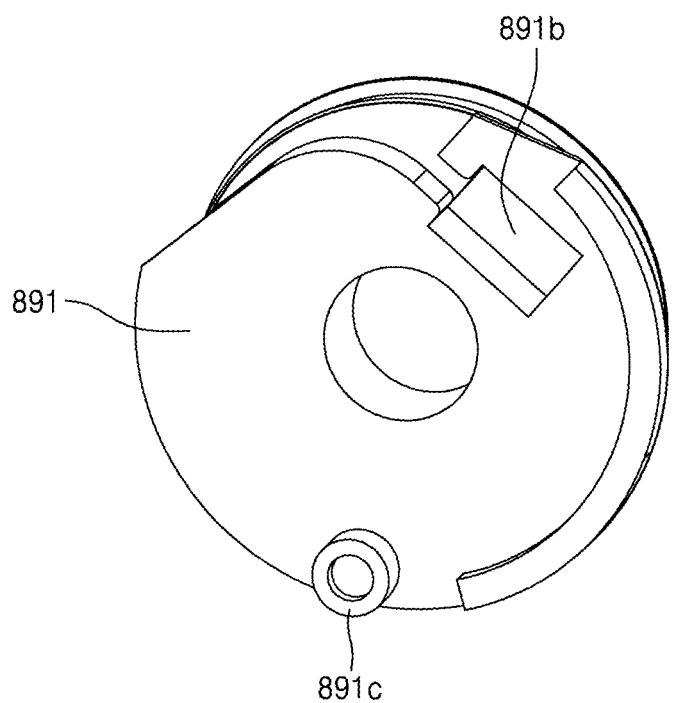

Referring to FIGS. 90 and 93, a through hole through which the actuation rotation shaft 845 is inserted may be formed in the yaw hub 880 at one side of the guide slit 883. Referring to FIG. 93, the second jaw pulley 881 is integrally formed on one side of the yaw hub 880, but the present disclosure is not limited thereto, and various modifications are possible.

Although not shown in the drawings, it is also possible that the second jaw pulley 881 and the yaw hub 880 are each formed as a separate member, and the second jaw pulley 881 may be fixedly coupled to the yaw hub 880, specifically, the yaw hub body 882.

In addition, two divided first rotation shafts 841 may be inserted through the first jaw pulley 891 and the second jaw pulley 881, respectively.

Since the second jaw pulley 881 is integrally formed with or fixedly coupled to the yaw hub 880 as described above, the yaw hub 880 does not rotate with respect to the second jaw pulley 881, and when the second jaw pulley 881 rotates around the first rotation shaft 841, the yaw hub 580 may also rotate around the first rotation shaft 841 together with the second jaw pulley 881.

Referring to FIGS. 90 and 91, the actuation rotation shaft 845 may be disposed on the yaw hub 880. The actuation rotation shaft 845 may be divided into two parts, which may be disposed to be spaced apart from each other by a certain distance, and the guide tube 870, the blade wire 307 accommodated in the guide tube 870, and the blade 875 may pass through a space formed between the two divided actuation rotation shafts 845.

Referring to FIG. 90, the yaw hub 880, specifically, a guide slit 883 formed in the yaw hub body 882 may be formed to extend in a longitudinal direction between the actuation rotation shaft 845 and the yaw rotation shaft 841.

Referring to FIG. 90, the guide slit 883 may be formed to have the same width in the longitudinal direction, and the guide pin 893 formed to protrude from the actuation link 892 is movable, specifically, linearly movable in the guide slit 883.

Referring to FIG. 93, on the other side of the yaw hub 880 opposite to one side thereof on which the second jaw pulley 881 is formed, an actuation pulley coupling portion 885 may be formed to protrude so as to be coupled to the first jaw pulley 891.

The actuation pulley coupling portion 885 may share a central axis with the yaw rotation shaft 841. However, the present disclosure is not limited thereto, and various modifications are possible, including spacing apart and placing the actuation pulley coupling portion 885 and the yaw hub 880 side by side.

Figure 101:
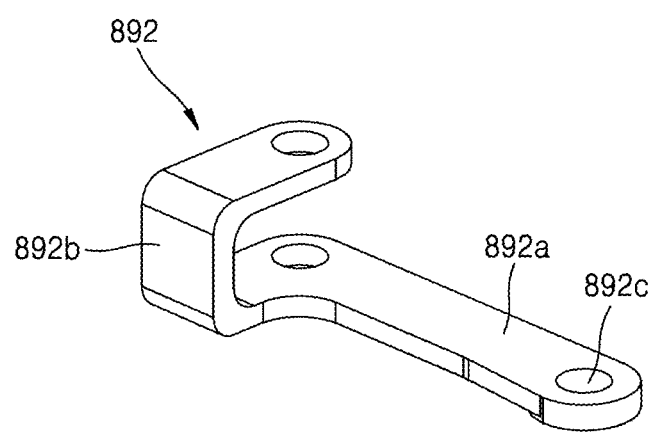
FIG. 101 is a perspective view illustrating an actuation link of the end tool of the surgical instrument for electrocautery of FIG. 86.

Referring to FIG. 101, the actuation link 892 may be formed to extend in a longitudinal direction. The actuation link 892 may include a link body 892a and a bending portion 892b. The link body 892a is a portion formed to extend in the longitudinal direction, and the bending portion 892b may be connected to the link body 892a with at least one bend.

Accordingly, one side of the actuation link 892 in which the bending portion 892b is located may be formed in a "U"-shape.

Referring to FIG. 101, a pin coupling hole (no reference number is assigned) may be formed in one surface of the bending portion 892b that is disposed in parallel with the link body 892a to be spaced apart therefrom by a certain distance.

A pin coupling hole may also be formed in one surface of the link body 892a facing the bending portion 892b to correspond to the pin coupling hole of the bending portion 892b. The guide pin 893 may be coupled to the pin coupling hole. A plurality of guide pins 893 may be provided, and may be coupled to the pin coupling holes formed in the respective facing surfaces of the bending portion 892b and the link body 892a.

The plurality of guide pins 893 may be disposed to be spaced apart from each other by a certain distance, and one side region of the U-shaped actuation link 892 formed with the bending portion 892b and the link body 892a may provide a movement path so that the guide tube 870 can pass therethrough. Due to the 'U' shaped region formed by the bending portion 892b and the link body 892a, the movement path of the guide tube 870 moving inside the yaw hub 880 and the end tool hub 860 is not disturbed when the actuation link 892 linearly moves.

Referring to FIG. 101, a link through-hole 892c may be formed on the other side of the link body 892a opposite to one side to which the bending portion 892b is connected. A protrusion 891c formed on the first jaw pulley 891 may be axially coupled to and fitted into the link through-hole 892c.

Accordingly, when the first jaw pulley 891 rotates, the actuation link 892 moves while rotating around the protrusion 891c.

The guide pin 893 provided in the actuation link 892 is fitted into the guide slit 883 formed in the yaw hub 880 and is movable along the shape of the guide slit 883.

The guide pin 893 passing through the guide slit 883 may be fitted into each of slots 801a and 802a respectively formed in the first jaw 801 and the second jaw 802. The first jaw 801 and the second jaw 802 have an X-shaped structure, and the guide pin 893 may be fitted into the slot 801a formed in the first jaw 801 and the slot 801b formed in the second jaw 802 at the same time.

The first jaw 801 and the second jaw 802 may perform an actuation motion while moving away from or close to each other with the actuation rotation shaft 845 as the center of rotation.

Figure 102:
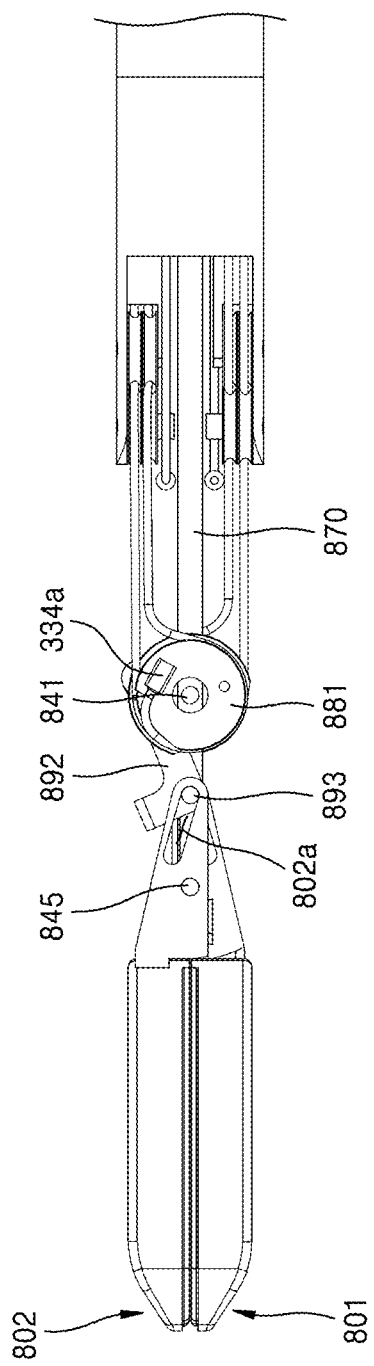
FIGS. 102 to 104 are views illustrating an opening and closing motion of a first jaw and a second jaw of the end tool of the surgical instrument for electrocautery of FIG. 86.
Figure 103:
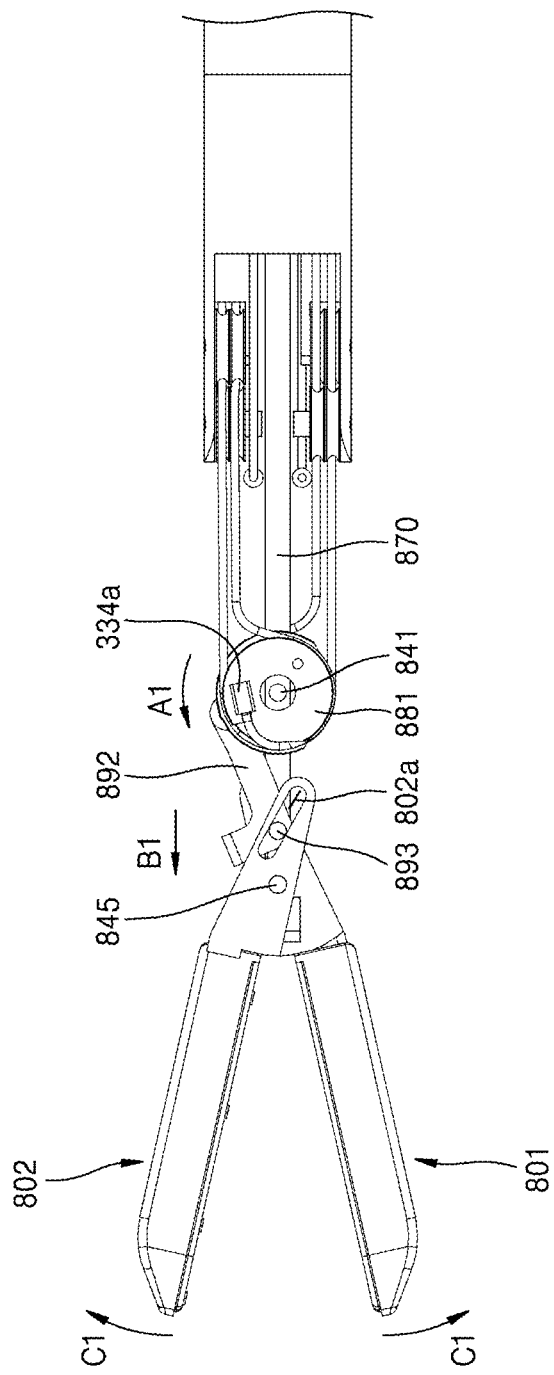
Figure 104:
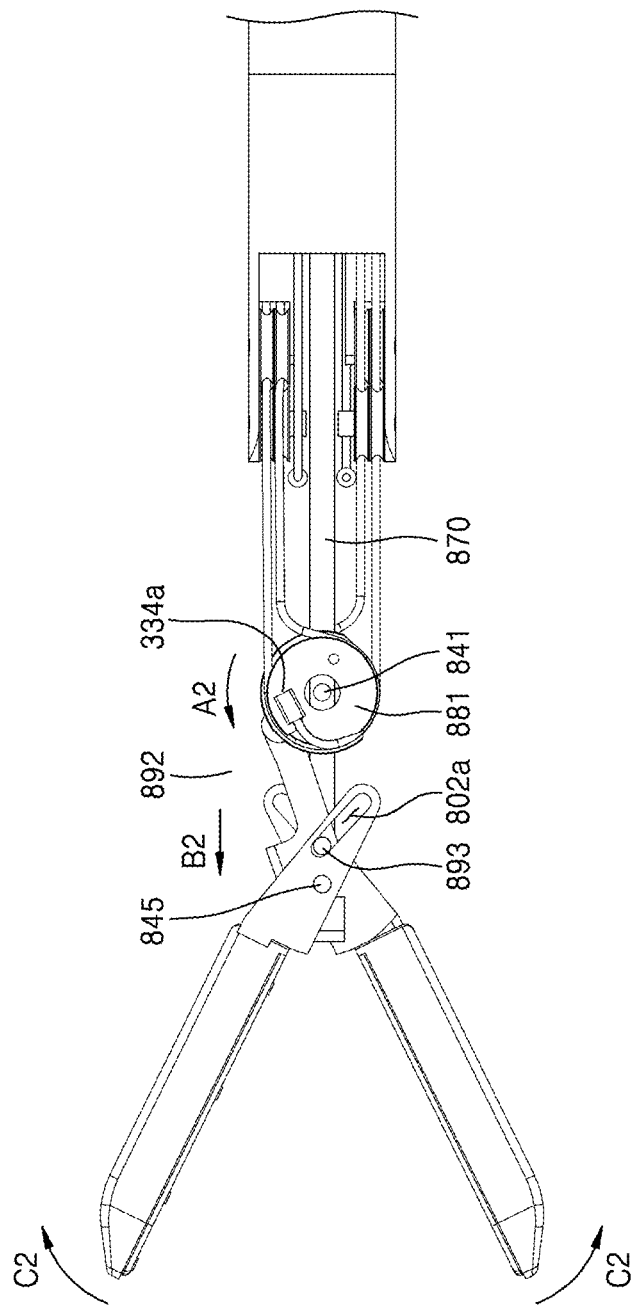
Figure 105:
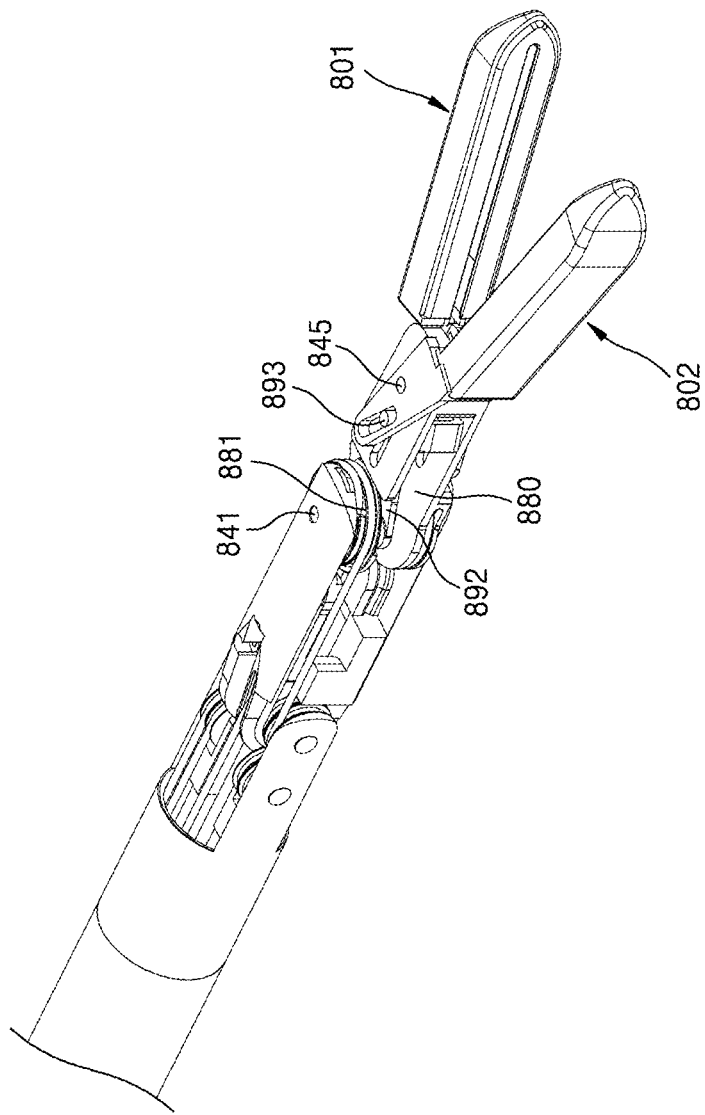
FIGS. 105 to 108 are perspective views illustrating an actuation motion of the end tool of the surgical instrument for electrocautery of FIG. 86.
Figure 106:
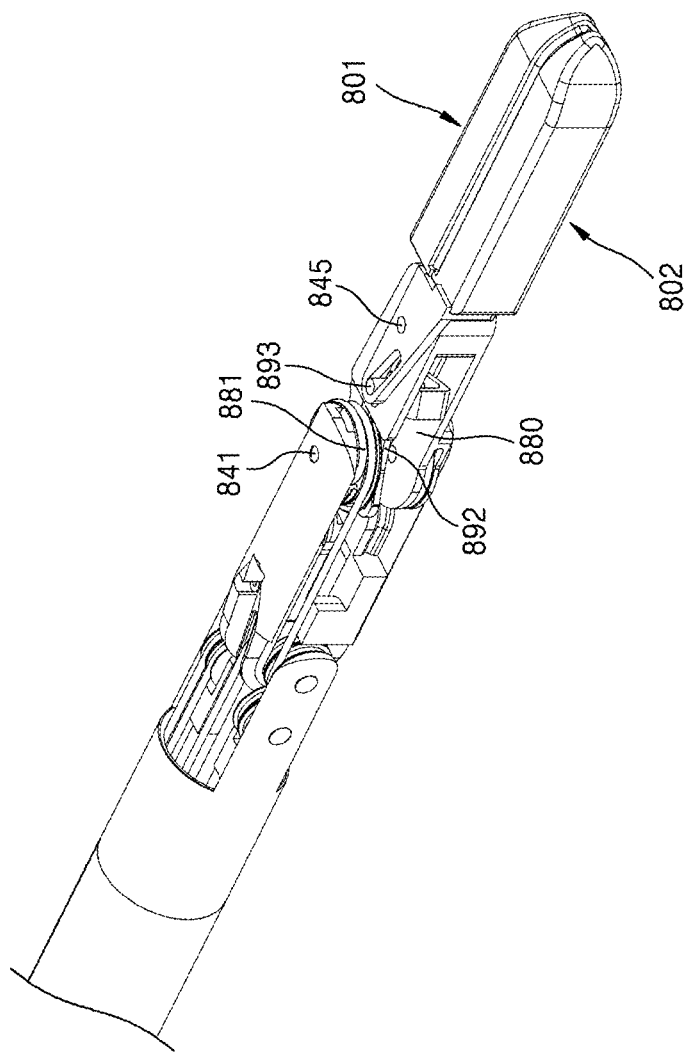
Figure 107:
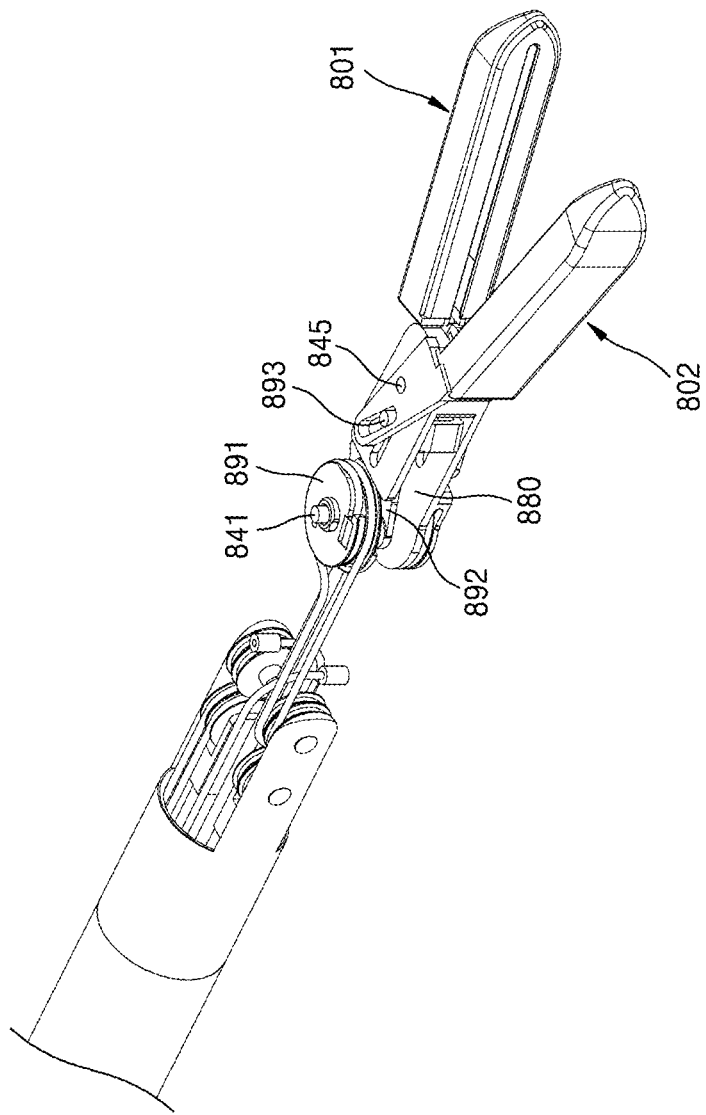
Figure 108:
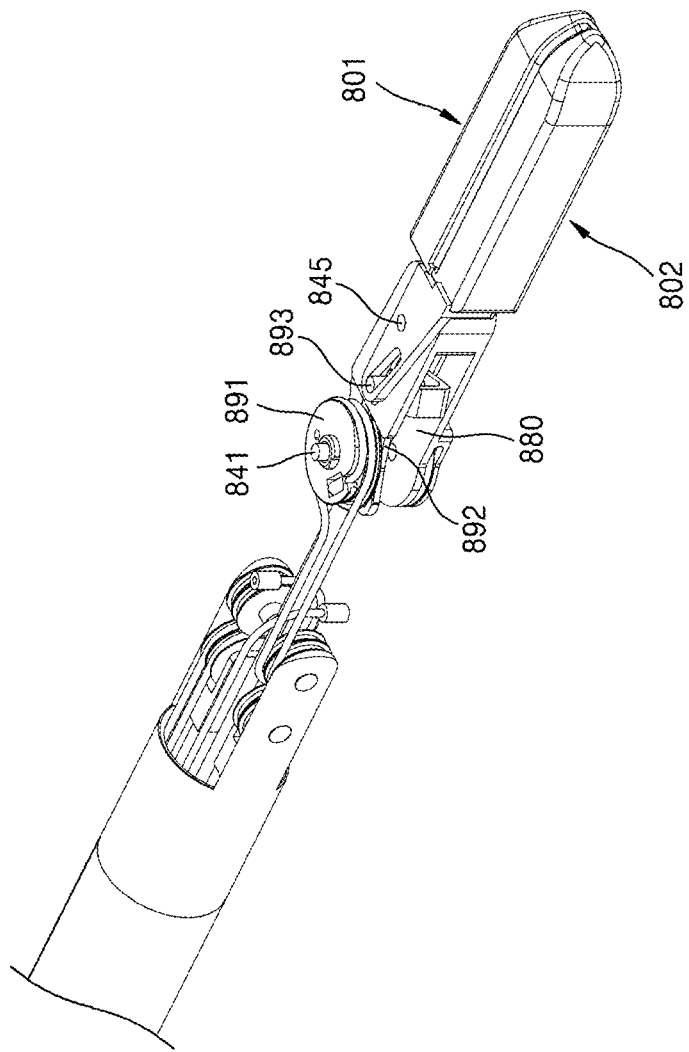

Referring to FIGS. 102 to 104, when the first jaw pulley 891 rotates in an A1 direction, the actuation link 892 axially coupled to the protrusion 891c formed in the first jaw pulley 891 is moved in a B1 direction. Specifically, the guide pin 893 provided in the actuation link 892 is moved linearly along the guide slit 883 formed in the yaw hub 880, and the guide pin 893 is fitted into the slots 801a and 802a respectively formed in the first jaw 801 and the second jaw 802, so that the guide pin 893 pushes the first jaw 801 and the second jaw 802. Thus, as the actuation link 892 is moved, the first jaw 801 and the second jaw 802 may perform an actuation motion while rotating around the actuation rotation shaft 845 as the center of rotation.

Referring to FIG. 103, as the actuation link 892 is moved toward the distal end, the first jaw 801 and the second jaw 802 may perform an actuation motion in C1 directions around the actuation rotation shaft 845 along the C1 directions.

Referring to FIG. 104, when the guide pin 893 is moved as much as possible toward the distal end in the slots 801a and 802a respectively formed in the first jaw 801 and the second jaw 802, the first jaw 801 and the second jaw 802 may be further spread apart in C2 directions.

In addition, the first jaw pulley 891 is formed in a multi-layered structure, and the first jaw wires 301 and 305 are wound so that the first jaw wires 301 and 305 overlap in different layers, and as a result, the length of the winding on the first jaw pulley 891 can be increased, and the rotation angle of the first jaw pulley 891 can be increased.

FIGS. 105 to 108 are perspective views illustrating an actuation motion of the end tool of the surgical instrument for electrocautery of FIG. 86. The guide pin 893 provided in the actuation link 892 is movable along the slots 801a and 802a respectively formed in the first jaw 801 and the second jaw 802, and accordingly, the first jaw 801 and the second jaw 802 may perform an actuation motion with the actuation rotation shaft 845 as the central axis of rotation.

Figure 109:
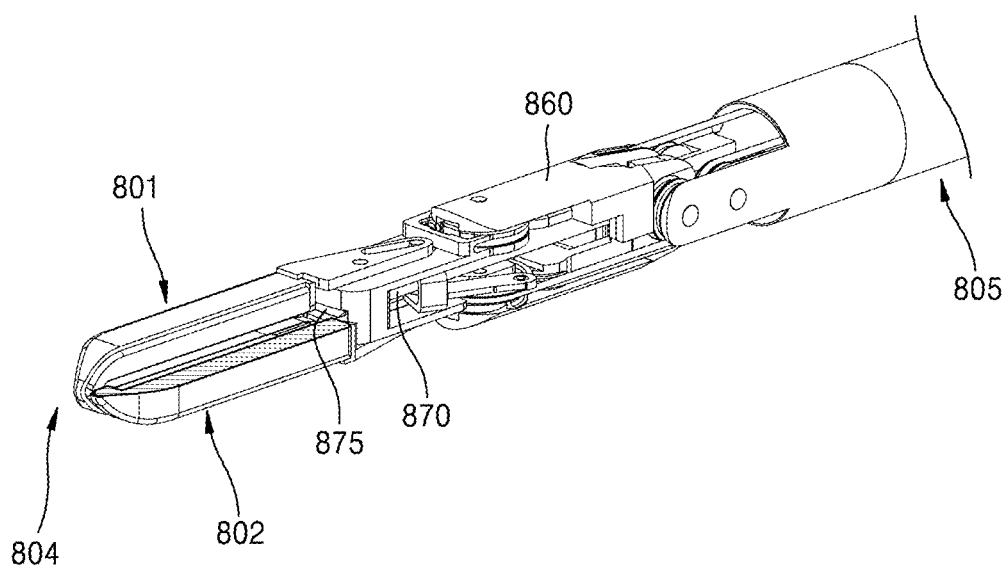
FIGS. 109 to 111 are partial cross-sectional views illustrating an operation of a blade of the end tool of the surgical instrument for electrocautery of FIG. 86.
Figure 110:
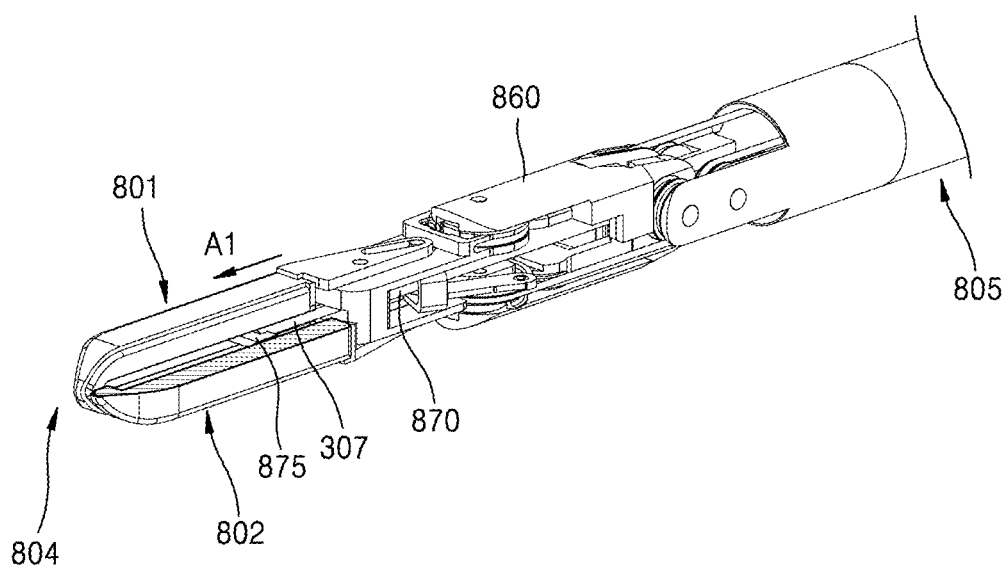
Figure 111:
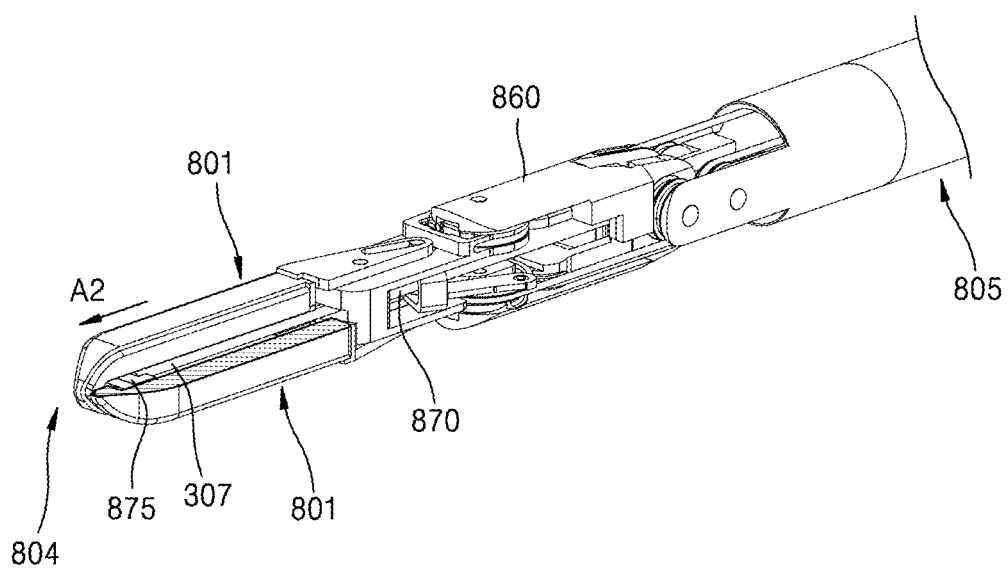

FIGS. 109 to 111 are partial cross-sectional views illustrating an operation of the blade of the end tool of the surgical instrument for electrocautery of FIG. 86. The operation of the blade 875 is the same as those of the first and second embodiments, and thus a detailed description thereof will be omitted in the overlapping range.

Figure 112:
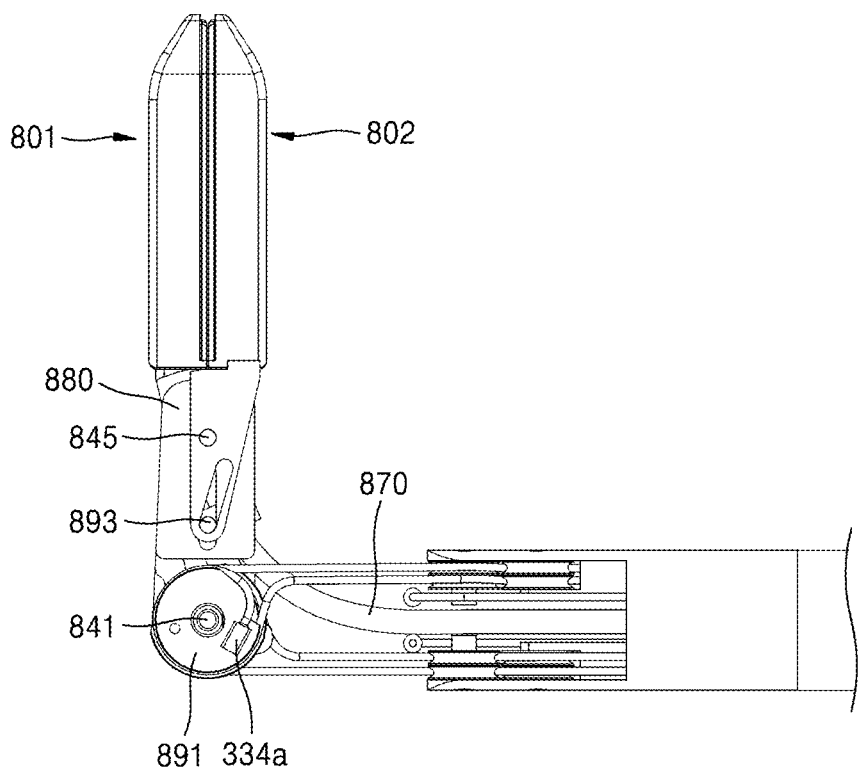
FIGS. 112 and 113 are bottom views illustrating a process of performing an opening and closing motion in a state in which the end tool of the surgical instrument for electrocautery of FIG. 86 is yaw-rotated by +90°.
Figure 113:
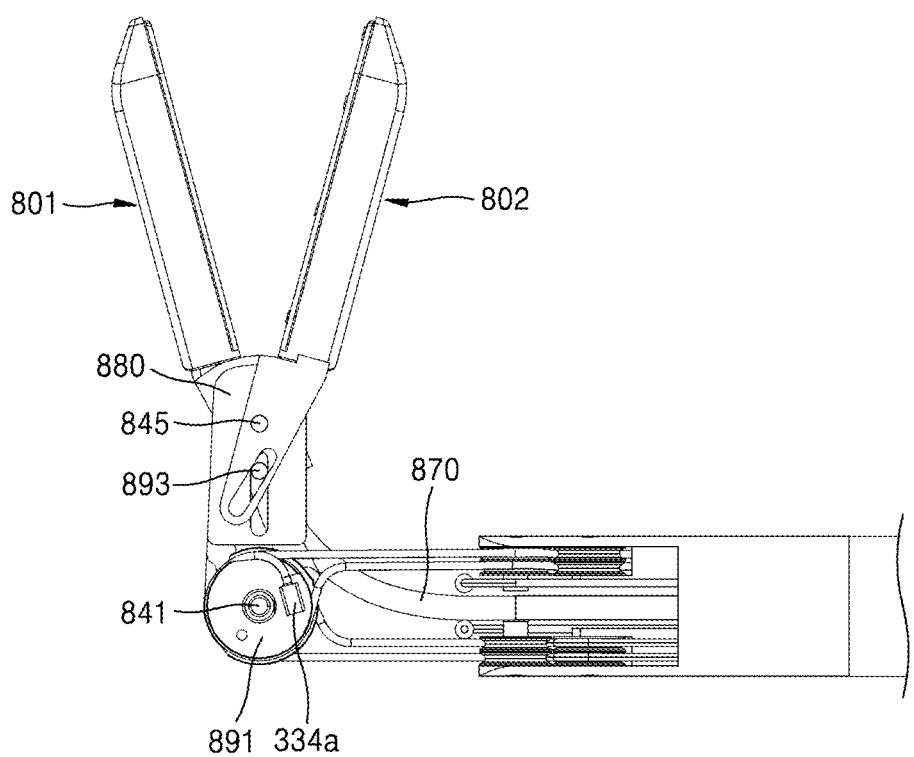

FIGS. 112 and 113 are bottom views illustrating a process of performing an opening and closing motion in a state in which the end tool of the surgical instrument for electrocautery of FIG. 86 is yaw-rotated by +90°.

The guide slit 883 formed in the yaw hub 880 may be formed in a straight line direction, and the actuation rotation shaft 845 may be disposed along a longitudinal central axis of the guide slit 883.

The slots 801a and 802a respectively formed in the first jaw 801 and the second jaw 802 may be formed to be inclined at a certain angle with the longitudinal central axis of the guide slit 883 formed in the yaw hub 880.

This causes the first jaw 801 and second jaw 803 to spread apart from each other as shown in FIG. 113 when the actuation link 892, specifically the guide pin 893 that is moved by receiving power from the first jaw pulley 891, is moved forward toward the actuation rotation shaft 845 while the actuation rotation shaft 845 remains fixed.

Figure 114:
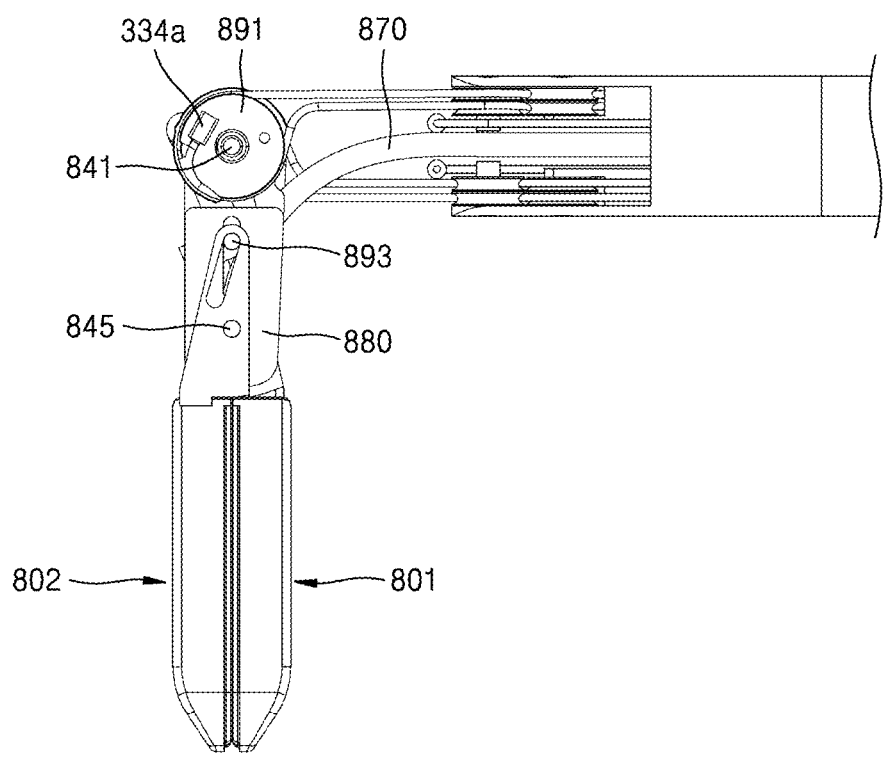
FIGS. 114 and 115 are bottom views illustrating a process of performing an opening and closing motion in a state in which the end tool of the surgical instrument for electrocautery of FIG. 86 is yaw-rotated by +90°.
Figure 115:
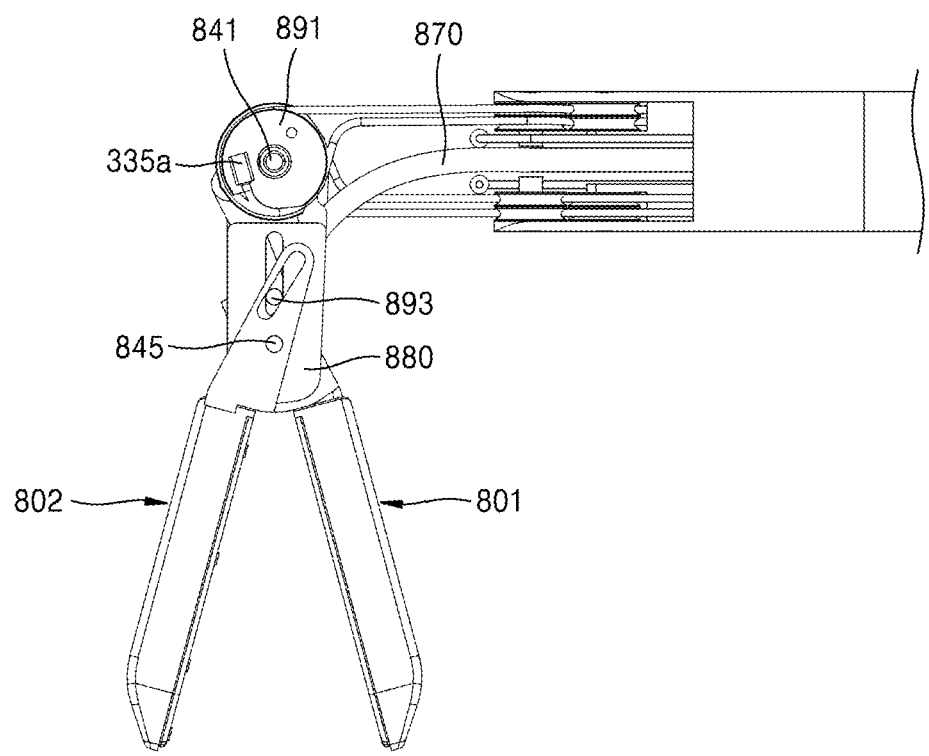
Figure 116:
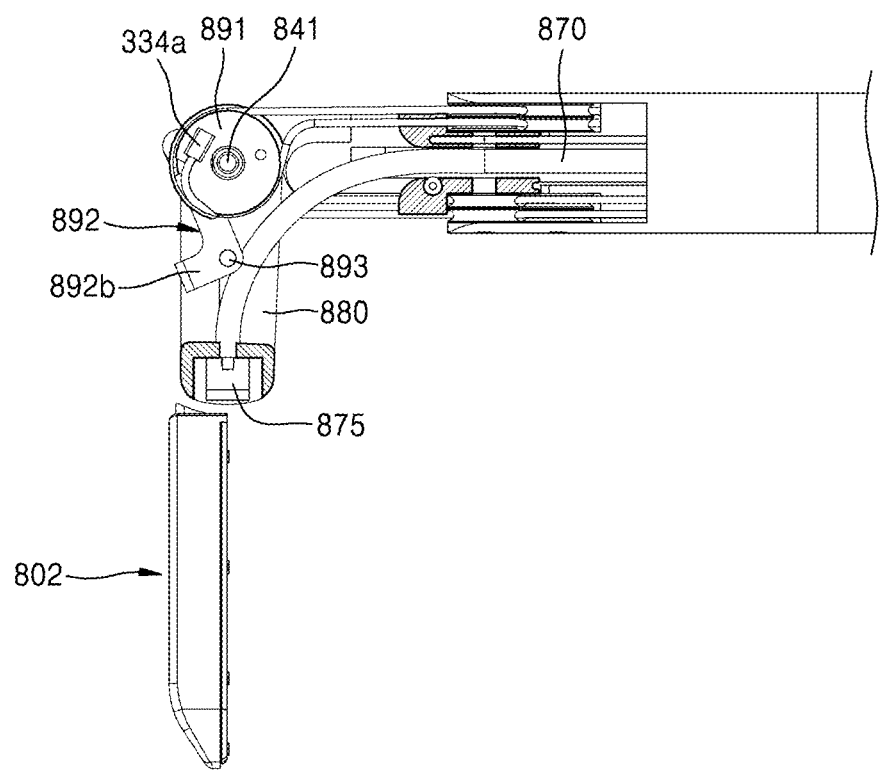
FIGS. 116 to 119 are views illustrating a path of a guide tube and a movement path of the blade during a cutting motion in a state in which the end tool of the surgical instrument for electrocautery of FIG. 86 is yaw-rotated by +90°.
Figure 117:
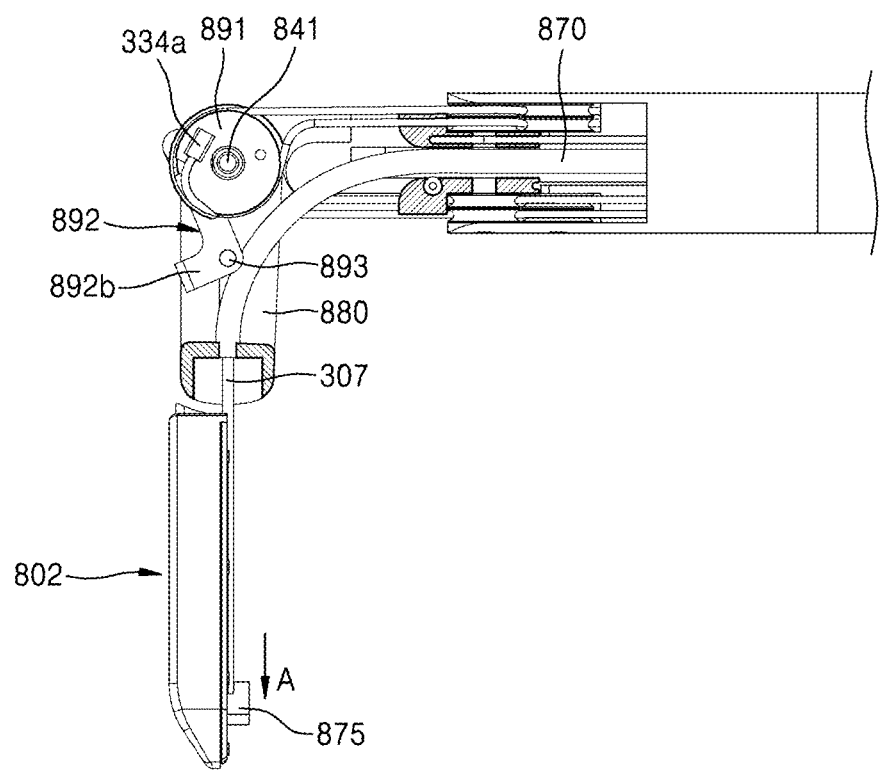
Figure 118:
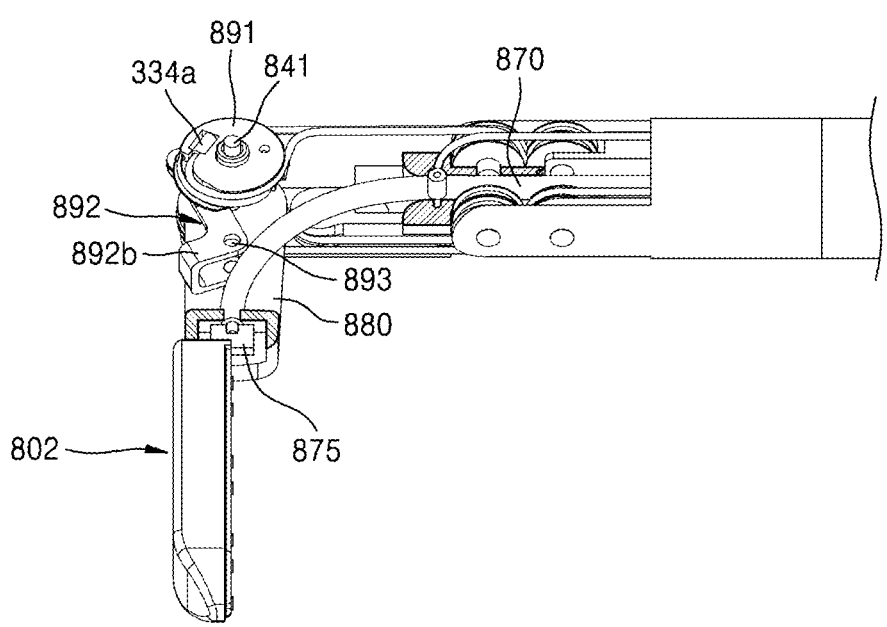
Figure 119:
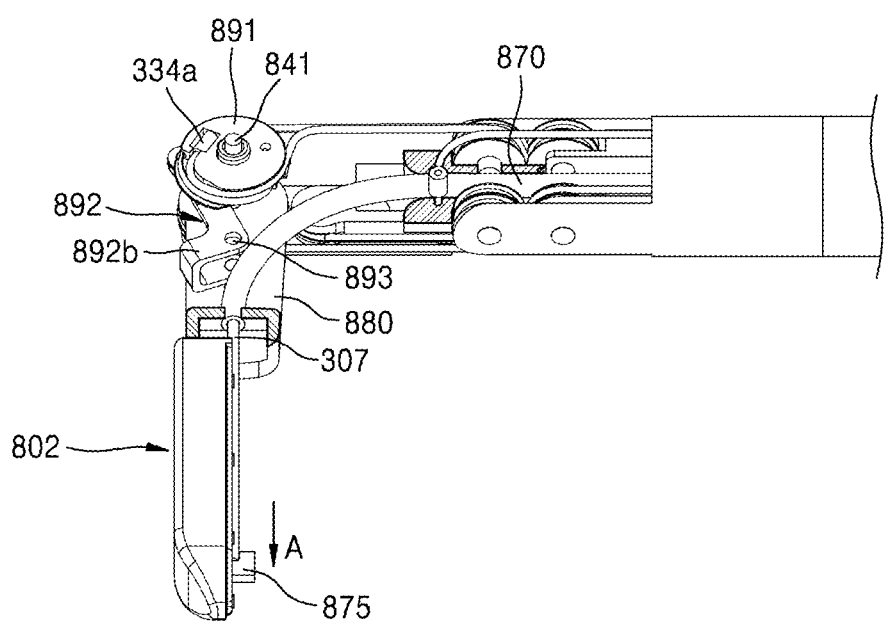
Figure 120:
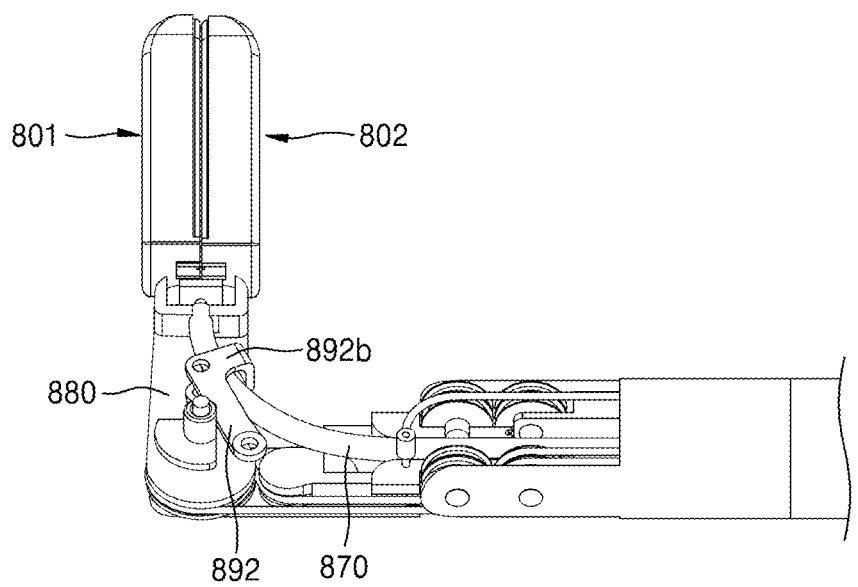
FIGS. 120 to 123 are views illustrating the actuation link and the guide tube in a state in which the end tool of the surgical instrument for electrocautery of FIG. 86 is yaw-rotated by +90°.
Figure 121:
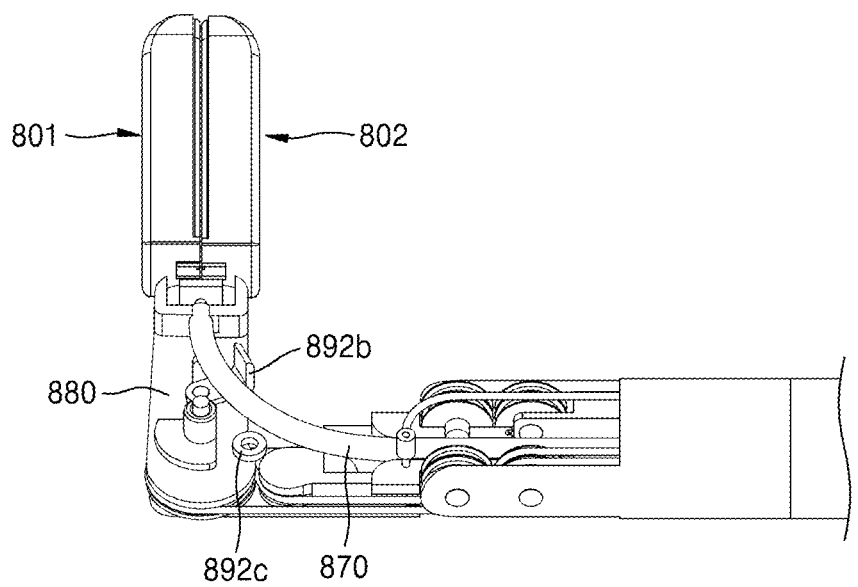
Figure 122:
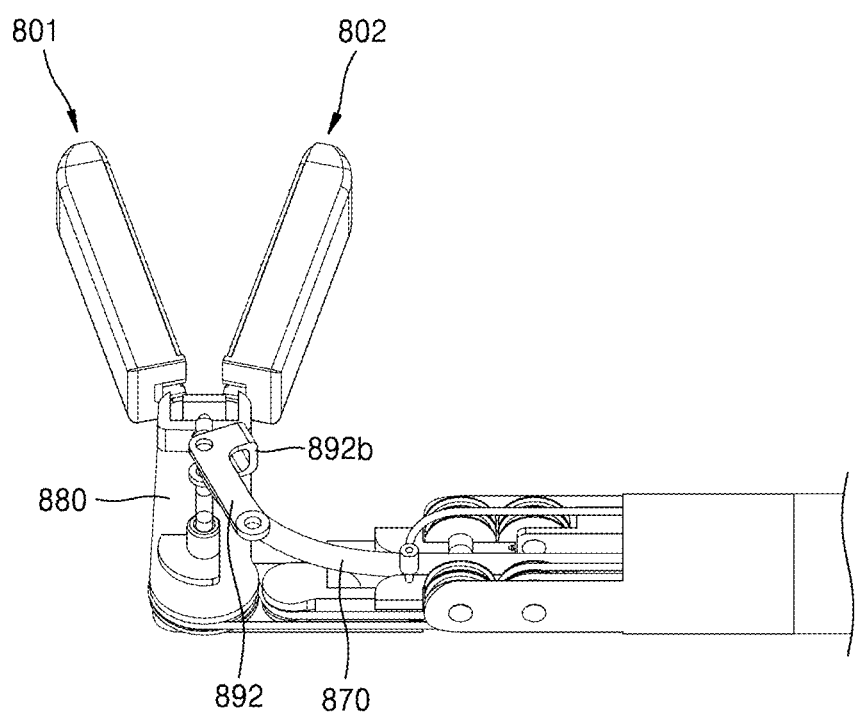
Figure 123:
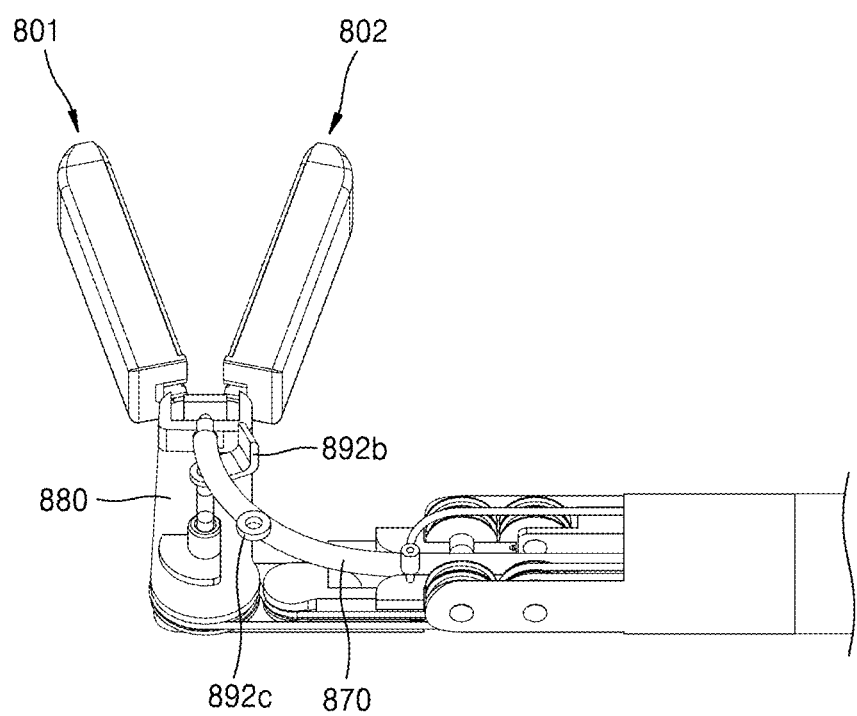
Figure 124:
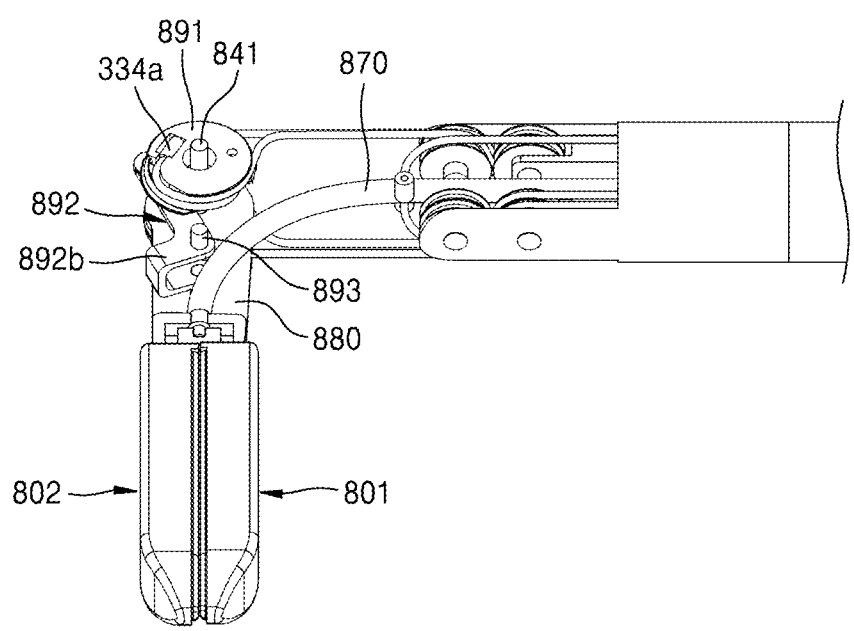
FIGS. 124 and 125 are views illustrating the actuation link and the guide tube in a state in which the end tool of the surgical instrument for electrocautery of FIG. 86 is yaw-rotated by +90°.
Figure 125:
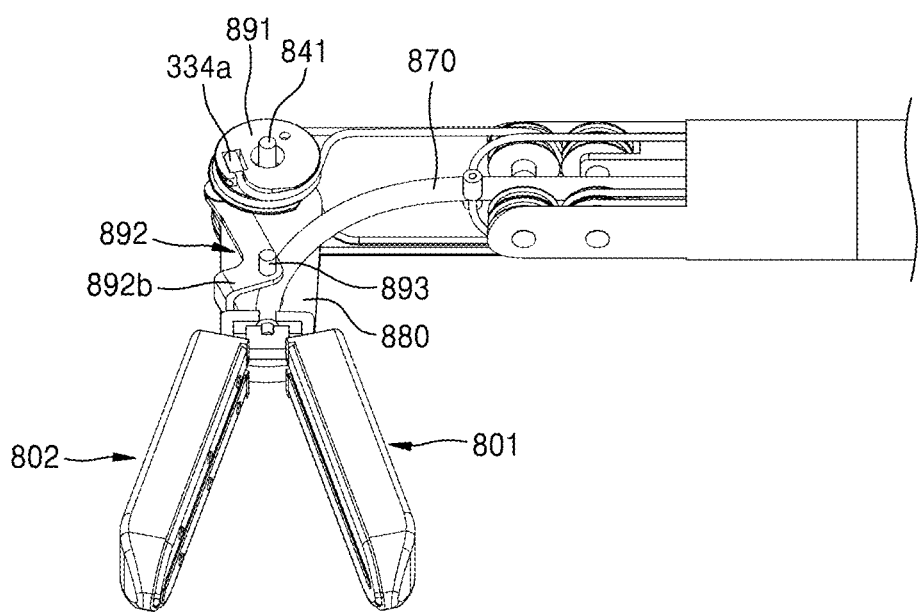
Figure 126:
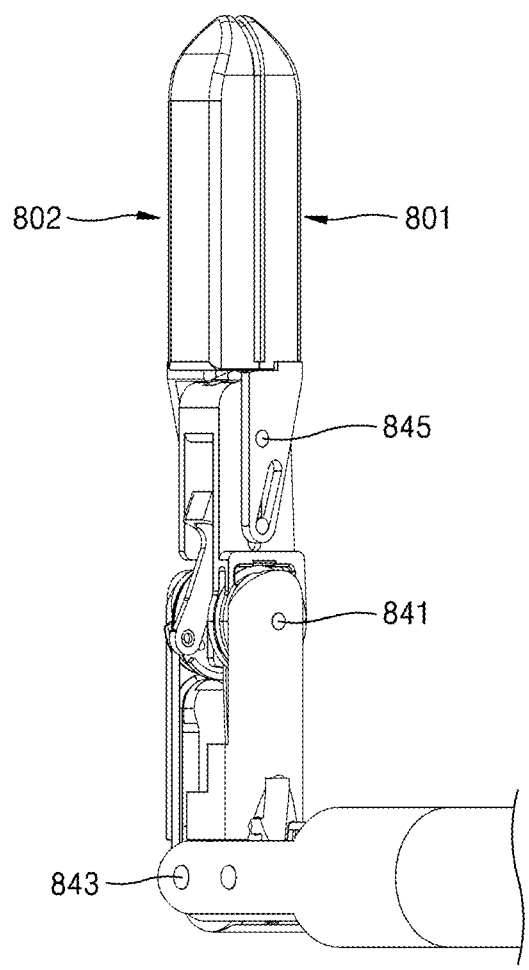
FIGS. 126 and 127 are views illustrating a process of performing an opening and closing motion in a state in which the end tool of the surgical instrument for electrocautery of FIG. 86 is pitch-rotated by −90°.
Figure 127:
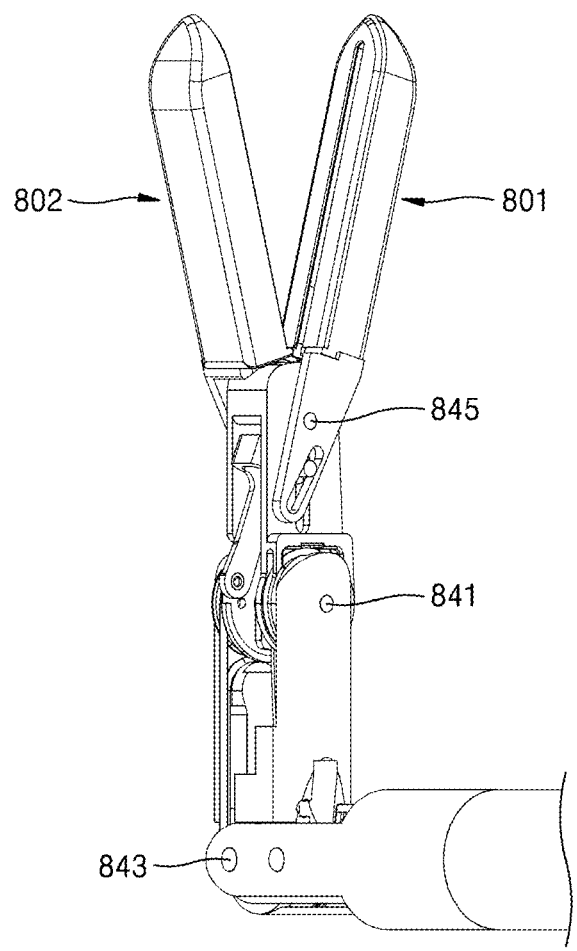
Figure 128:
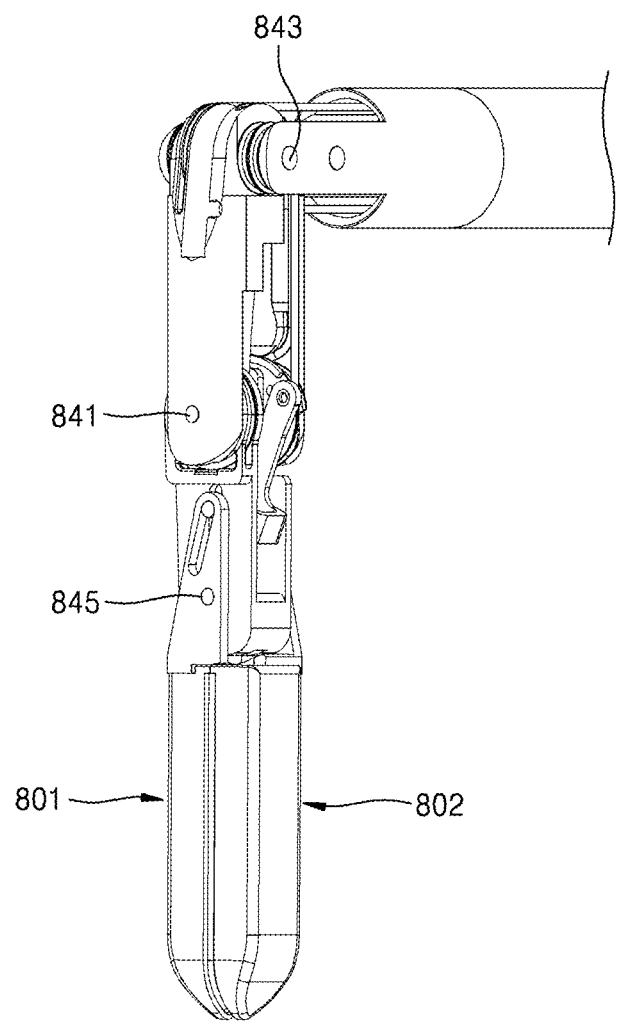
FIGS. 128 and 129 are views illustrating a process of performing an opening and closing motion in a state in which the end tool of the surgical instrument for electrocautery of FIG. 86 is pitch-rotated by +90°.
Figure 129:
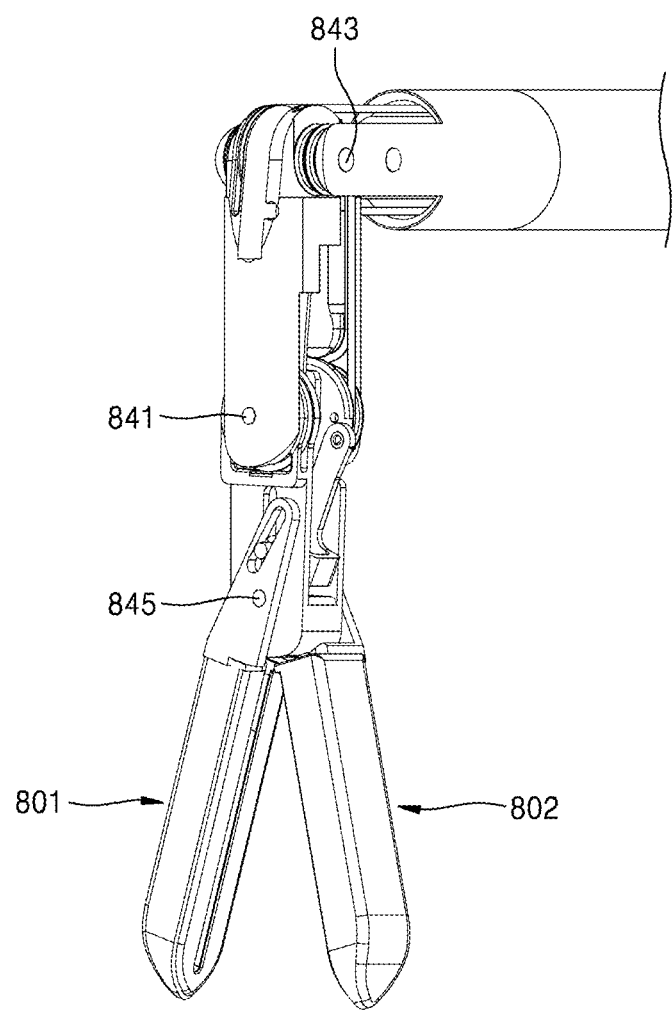
Figure 130:
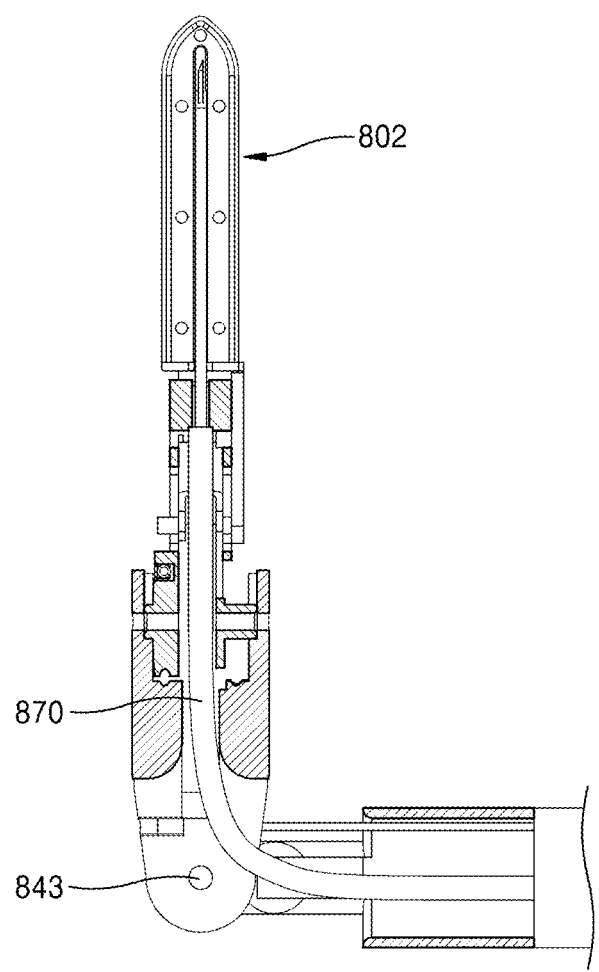
FIG. 130 is a view illustrating a path of the guide tube in a state in which the end tool of the surgical instrument for electrocautery of FIG. 86 is pitch-rotated by −90°.
Figure 131:
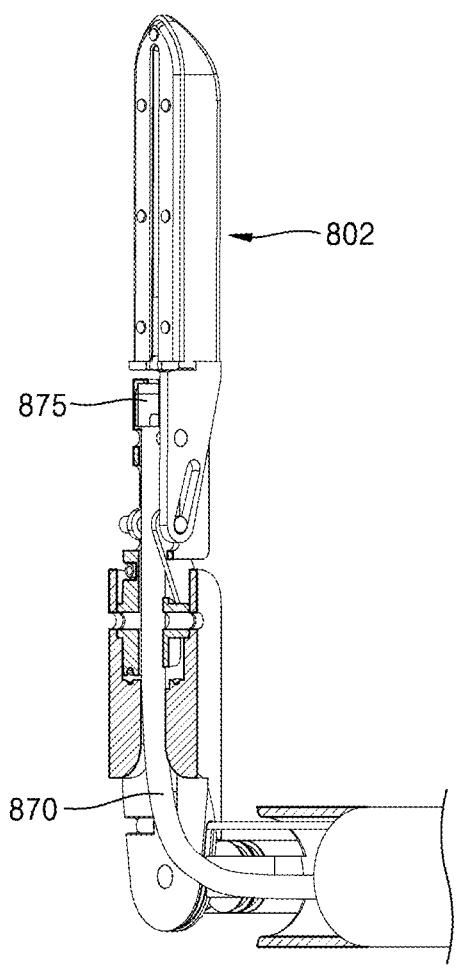
FIGS. 131 and 132 are views illustrating a path of the guide tube and a movement path of the blade during a cutting motion in a state in which the end tool of the surgical instrument for electrocautery of FIG. 86 is pitch-rotated by +90°.
Figure 132:
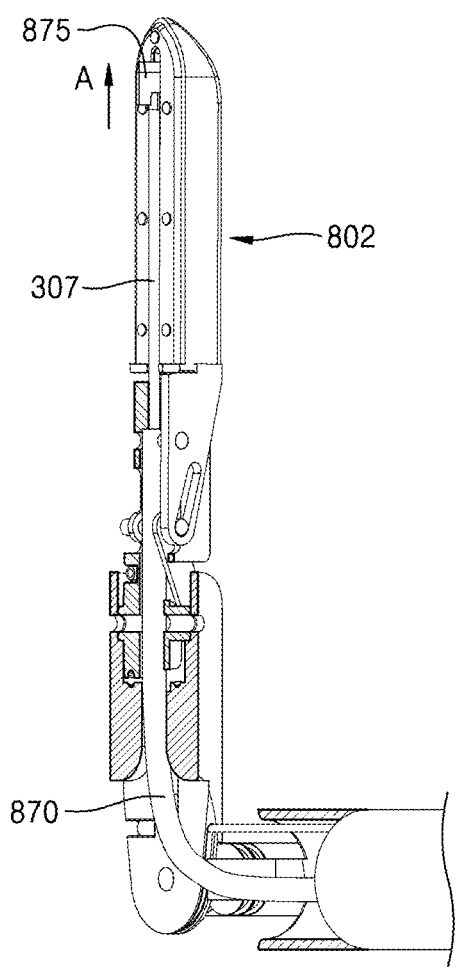
Figure 133:
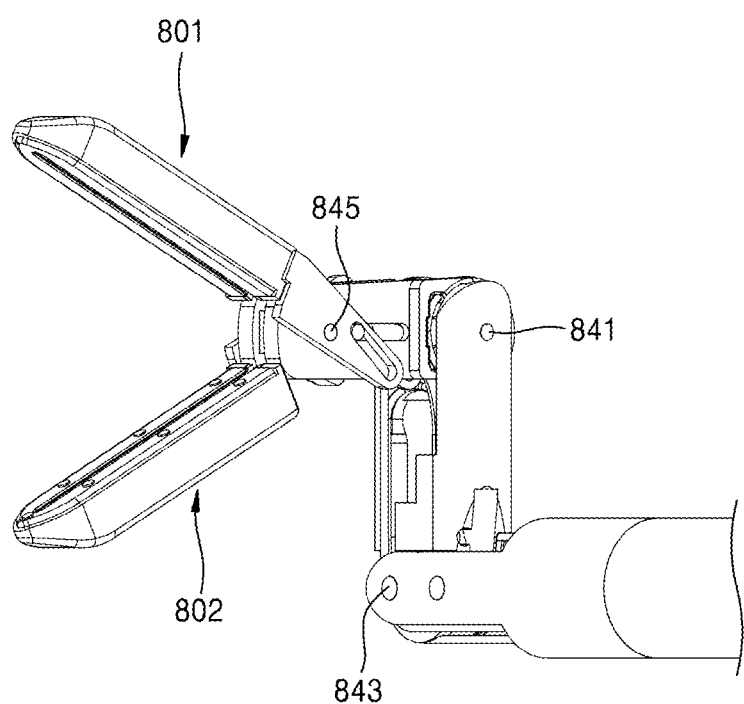
FIG. 133 is a perspective view illustrating the surgical instrument for electrocautery of FIG. 86 in a pitch-rotated and yaw-rotated state.
Figure 134:
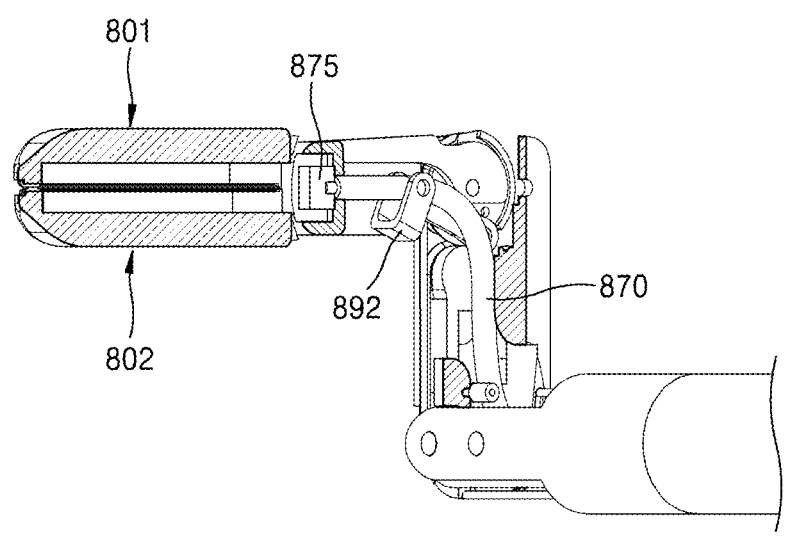
FIGS. 134 to 136 are views illustrating the end tool of the surgical instrument for electrocautery of FIG. 86 performing a cutting motion in a state in which the end tool is pitch-rotated by −90° and simultaneously yaw-rotated by +90°.
Figure 135:
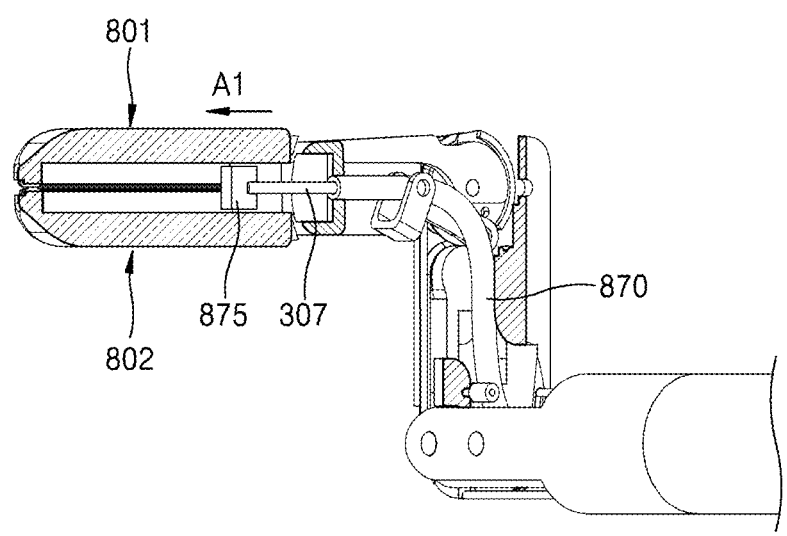
Figure 136:
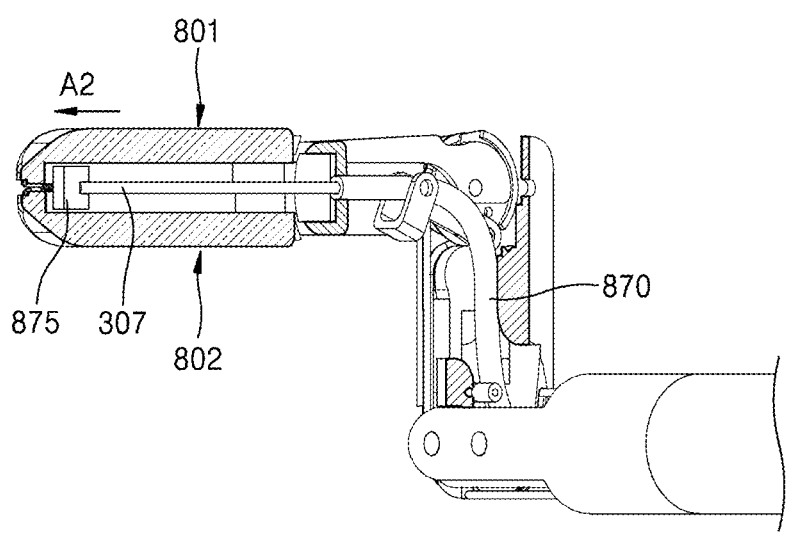

Referring to FIGS. 114 and 115, the first jaw pulley 891 rotates in a state in which the end tool of the surgical instrument for electrocautery of FIG. 86 is yaw-rotated by +90°, and the guide pin 893 provided in the actuation link 892 connected to the first jaw pulley 891 is moved through the guide slit 883 formed in the yaw hub 880 and the slots 801a and 802a respectively formed in the first jaw 801 and the second jaw 802, so that an actuation motion can be performed even in a yaw rotated state.

Referring to FIGS. 116 to 125, there is room for problems when the guide tube 870 is in contact with the actuation link 892 while the end tool 800 is yaw-rotated, but the actuation link 892 of the present disclosure includes the link body 892a and the bending portion 892b connected thereto, which form a "U" shape, to prevent the contact with the guide tube 870, allowing the blade wire 307 and the guide tube 870 to move stably with respect to yaw, pitch, and actuation motions of the end tool 800.

Referring to FIGS. 126 to 136, the end tool 800 of the electric cauterization surgical instrument 10 according to the third embodiment of the present disclosure is formed such that the jaws 801 and 802 are able to perform a cutting motion normally even when the jaws are pitch-rotated and simultaneously yaw-rotated.

Here, in the end tool 800 of the third embodiment of the present disclosure, a pin/slot-type structure is employed to secure a grip force in the actuation motion.

In detail, in the pin/slot-type structure, the actuation link 892 must move a longer distance to rotate the first jaw 801 by the same amount (that is, the actuation link 892 needs to have a long stroke). In addition, in order for the actuation link 590 to move a longer distance, the first jaw pulley 891 should rotate further. In other words, when the first jaw pulley 891 rotates further to rotate the first jaw 801 by the same amount, a greater force may be applied to the first jaw 801 by as much as the first jaw pulley 891 rotates further, so that a grip force in the actuation motion may be amplified.

In addition, in order to rotate the first jaw pulley 891 further as described above, the first jaw pulley 891 is formed in a multi-layered structure as described above to make the lengths of the wires 301 and 305 wound around the first jaw pulley 891 to be longer, thereby securing a long stroke of the actuation link 892.

Modified Example of Third Embodiment-Disposing Auxiliary Pulley on End Tool Hub Hereinafter, an end tool 800 of a surgical instrument according to a modified example of the third embodiment of the present disclosure will be described. Here, the end tool 300 of the surgical instrument according to the modified example of the third embodiment of the present disclosure is different from the end tool of the surgical instrument according to the third embodiment of the present disclosure described above in that the configuration of an end tool hub 860' and the configuration of auxiliary pulleys 812 and 822 are different. The configuration changed from the third embodiment as described above will be described in detail later.

Figure 137:
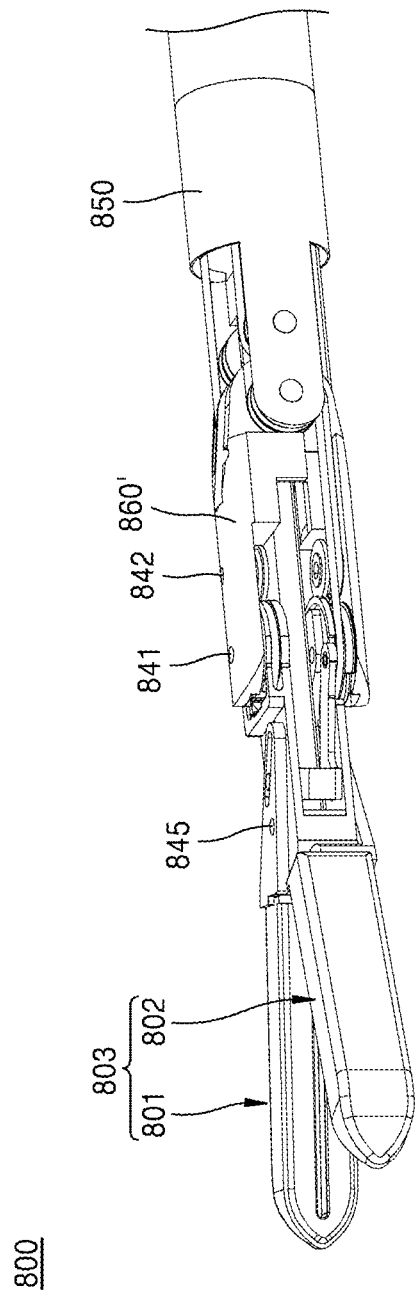
FIGS. 137 to 139 are views illustrating an end tool of a surgical instrument for electrocautery according to a modified example of the third embodiment of the present disclosure.
Figure 138:
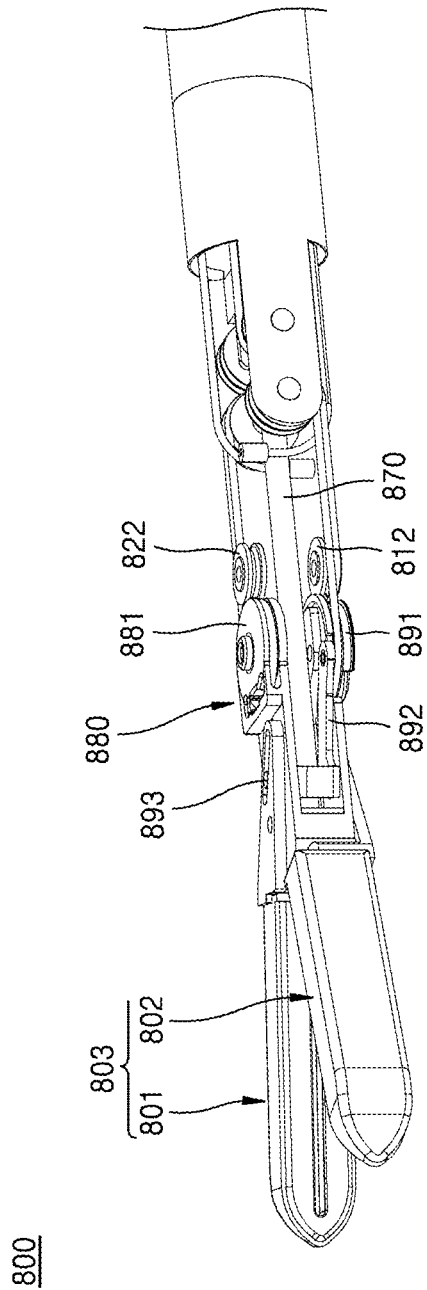
Figure 139:
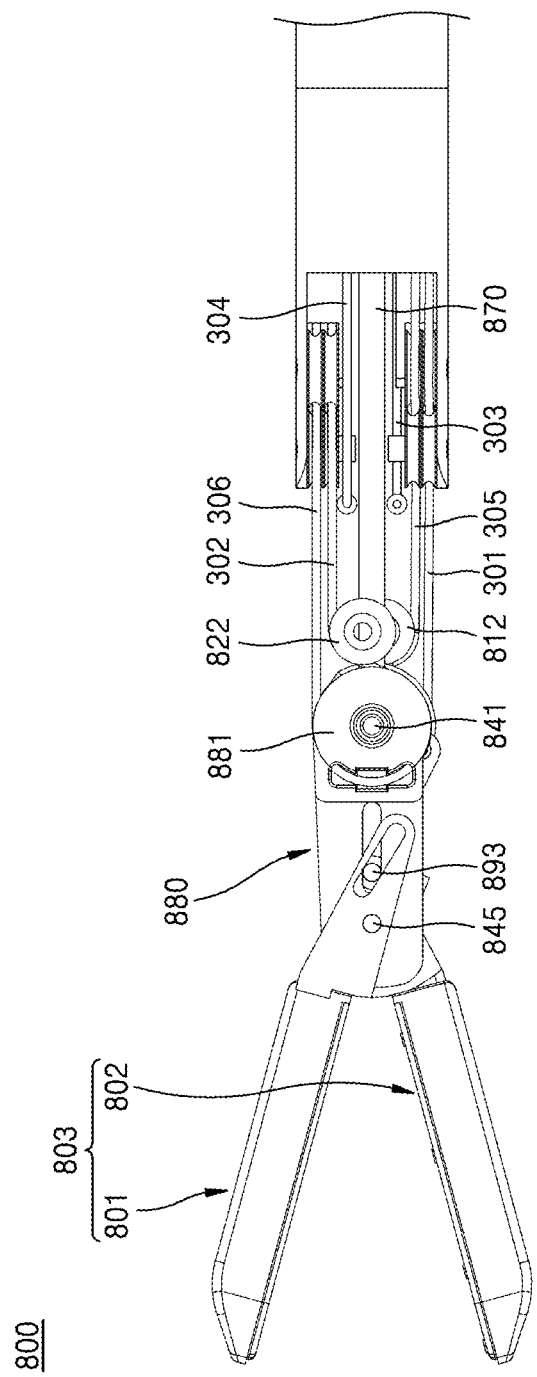

FIGS. 137 to 139 are views illustrating the end tool of the surgical instrument for electrocautery according to the modified example of the third embodiment of the present disclosure.

Referring to FIGS. 137 and 138, the end tool 800 of the modified example of the third embodiment of the present disclosure includes a pair of jaws for performing a grip motion, specifically a first jaw 801 and a second jaw 802, and here, each of the first jaw 801 and the second jaw 802 or a component encompassing the first jaw 801 and the second jaw 802 may be referred to as a jaw 803.

The end tool 800 according to the modified example of the third embodiment may include a pulley 811, the pulley 812, a pulley 813, a pulley 814, a pulley 815, and a pulley 816 that are associated with a rotational motion of the first jaw 801. In addition, the end tool 800 may include a pulley 821, the pulley 822, a pulley 823, a pulley 824, a pulley 825, and a pulley 826 that are associated with a rotational motion of the second jaw 802.

Here, the pulleys facing each other are illustrated in the drawings as being formed parallel to each other, but the concept of the present disclosure is not limited thereto, and each of the pulleys may be variously formed with a position and a size suitable for the configuration of the end tool.

The end tool 800 according to the modified example of the third embodiment of the present disclosure may further include the pulley 812 and the pulley 822 as compared to the end tool 800 according to the third embodiment of the present disclosure illustrated with reference to FIG. 86.

Referring to FIGS. 137 to 139, the pulley 812 functions as an end tool first jaw auxiliary pulley, and the pulley 822 functions as an end tool second jaw auxiliary pulley, and these two components may collectively be referred to as end tool jaw auxiliary pulleys or simply auxiliary pulleys.

In detail, the pulley 812 and the pulley 822, which are end tool jaw auxiliary pulleys, may be additionally provided on one side of the pulley 811 and one side of the pulley 821, respectively. In other words, the pulley 812, which is an auxiliary pulley, may be disposed between the pulley 811 and the pulley 813/pulley 814. In addition, the pulley 822, which is an auxiliary pulley, may be disposed between the pulley 821 and the pulley 823/pulley 824.

The pulley 812 and the pulley 822 may be formed to be rotatable independently of each other around a second rotation shaft 842.

The pulley 812 and the pulley 822 may serve to increase rotation angles of the first jaw 801 and the second jaw 802, respectively, by coming into contact with a wire 305, which is a first jaw wire, and a wire 302, which is a second jaw wire, and changing the arrangement paths of the wire 305 and the wire 302 to a certain degree.

That is, when the auxiliary pulleys are not disposed, each of the first jaw 801 and the second jaw 802 may rotate only up to a right angle, but in the modified example of the third embodiment, by additionally providing the pulley 812 and the pulley 822, which are auxiliary pulleys, the effect of increasing the maximum rotation angle by a certain angle can be achieved.

This enables a motion in which two jaws of the end tool 800 have to be spread apart for an actuation motion in a state in which the two jaws are yaw-rotated together by 90° in the clockwise or counterclockwise direction.

In other words, a feature of increasing the range of yaw rotation in which an actuation motion is possible may be obtained through the pulley 812 and the pulley 822. This will be described below in more detail.

When the auxiliary pulleys are not disposed, since the first jaw wire 305 is fixedly coupled to the end tool first jaw pulley 811, and the second jaw wire 302 is fixedly coupled to the end tool second jaw pulley 821, each of the end tool first jaw pulley 811 and the end tool second jaw pulley 821 may rotate up to 90°.

In this case, when the actuation motion is performed in a state in which the first jaw 801 and the second jaw 802 are located at a 90° line, the first jaw 801 may be spread, but the second jaw 802 may not be rotated beyond 90°. Accordingly, when the first jaw 801 and the second jaw 802 perform a yaw motion over a certain angle, there was a problem that an actuation motion is not smoothly performed.

In order to address such a problem, in the electric cauterization surgical instrument 10 of the present disclosure, the pulley 812 and the pulley 822, which are auxiliary pulleys, are additionally disposed at one side of the pulley 811 and one side of the pulley 821, respectively. As described above, as the arrangement paths of the wire 305, which is a first jaw wire, and the wire 302, which is a second jaw wire, are changed to a certain degree by disposing the pulley 812 and the pulley 822, a tangential direction of the wires 305 and 302 is changed, and accordingly, a fastening member 324 for coupling the wire 302 and the pulley 821 is additionally rotatable by a certain angle.

That is, a fastening member 326, which is a coupling portion of the wire 302 and the pulley 821, is rotatable until being located on a common internal tangent of the pulley 821 and the pulley 822. Similarly, a fastening member 323, which is a coupling portion of the wire 305 and the pulley 811, is rotatable until being located on a common internal tangent of the pulley 811 and the pulley 812, so that the range of rotation may be increased.

In other words, due to the pulley 812 that is an auxiliary pulley, the wires 301 and 305, which are two strands of the first jaw wire wound around the pulley 812, are disposed at one side with respect to a plane perpendicular to the Y-axis and passing through the X-axis. Simultaneously, due to the pulley 822, the wires 302 and 306, which are two strands of the second jaw wire wound around the pulley 821, are disposed at the other side with respect to the plane perpendicular to the Y-axis and passing through the X-axis.

In other words, the pulley 813 and the pulley 814 are disposed at one side with respect to the plane perpendicular to the Y-axis and passing through the X-axis, and the pulley 823 and the pulley 824 are disposed at the other side with respect to the plane perpendicular to the Y-axis and passing through the X-axis.

In other words, the wire 305 is located on the internal tangent of the pulley 811 and the pulley 812, and the rotation angle of the pulley 811 is increased due to the pulley 812. In addition, the wire 302 is located on the internal tangent of the pulley 821 and the pulley 822, and the rotation angle of the pulley 821 is increased due to the pulley 822.

According to the present disclosure, the rotation radii of the first jaw 801 and the second jaw 802 increase, so that an effect of increasing a yaw motion range in which a normal opening/closing actuation motion can be performed may be obtained.

Figure 140:
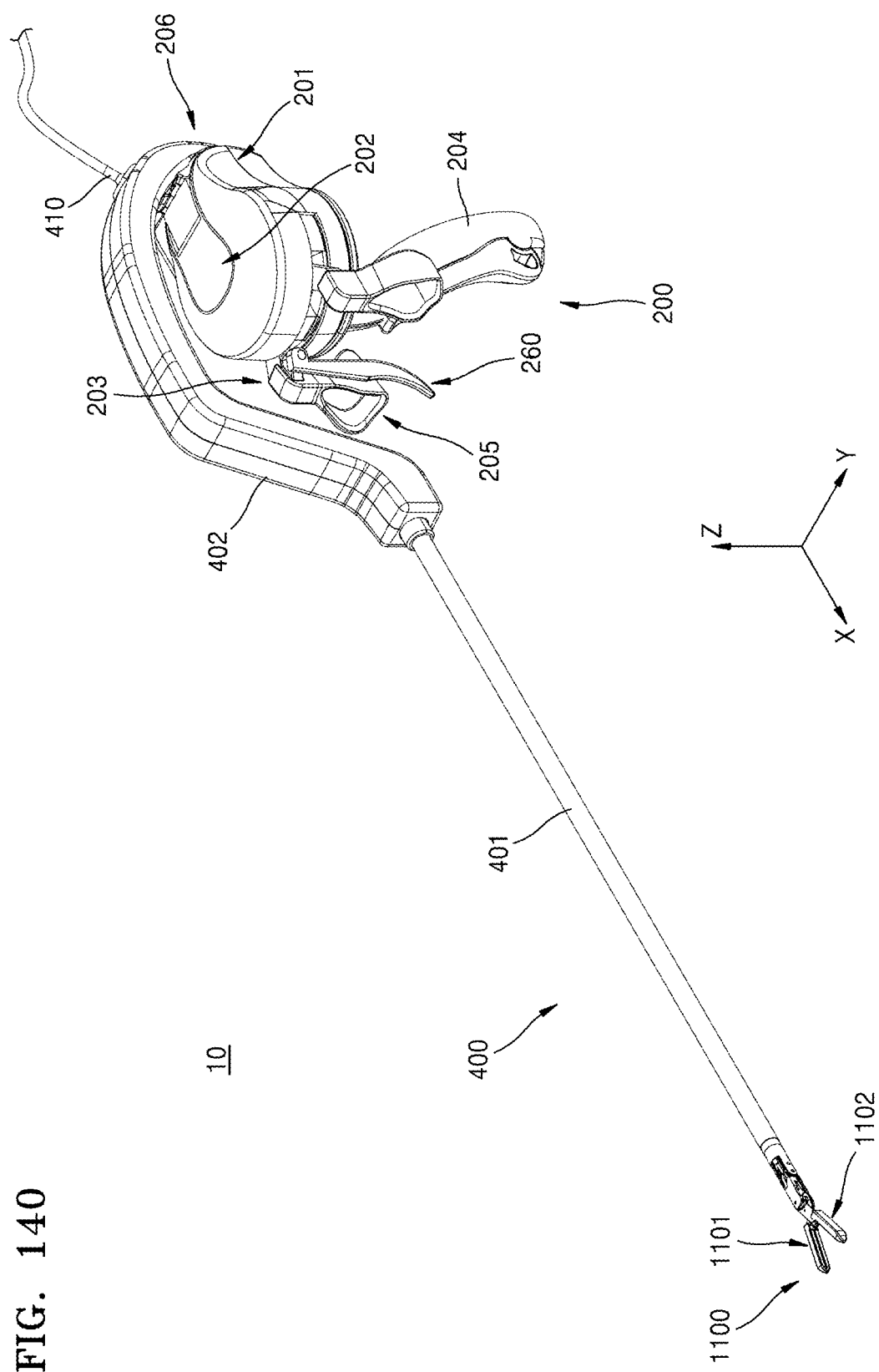
FIG. 140 is a perspective view illustrating a surgical instrument for electrocautery according to a fourth embodiment of the present disclosure.
Figure 145:
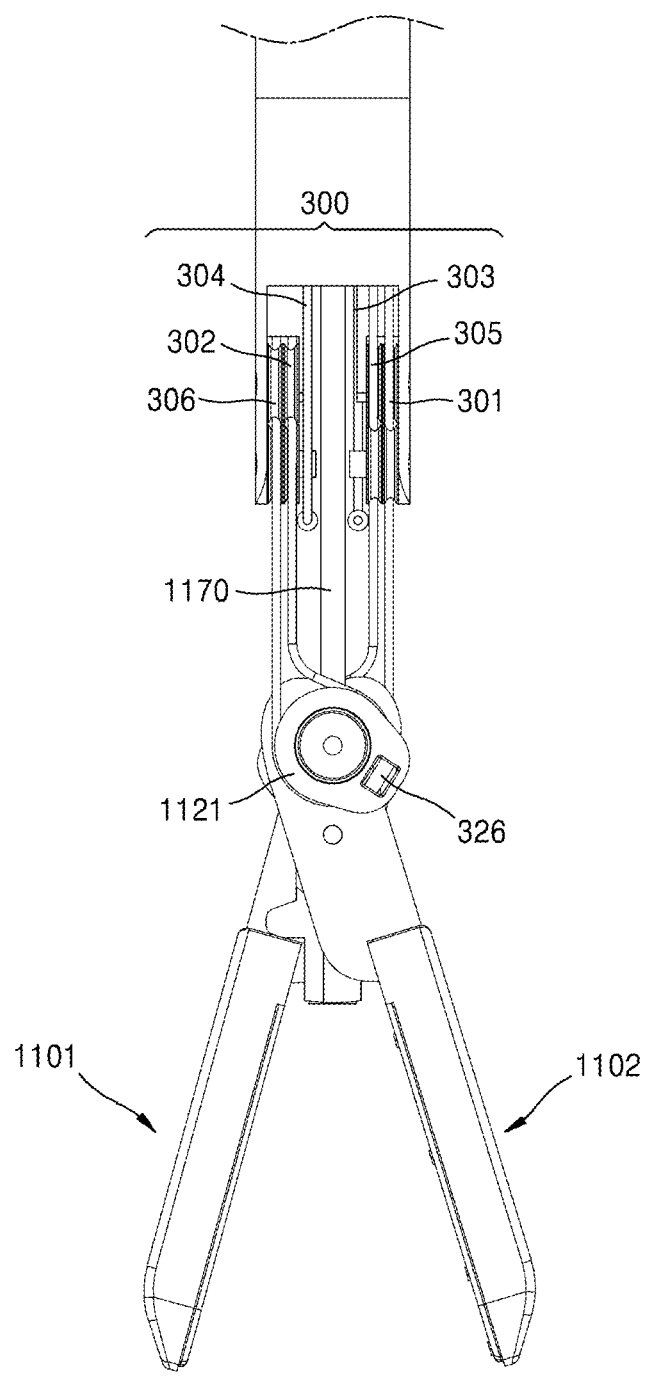
Figure 146:
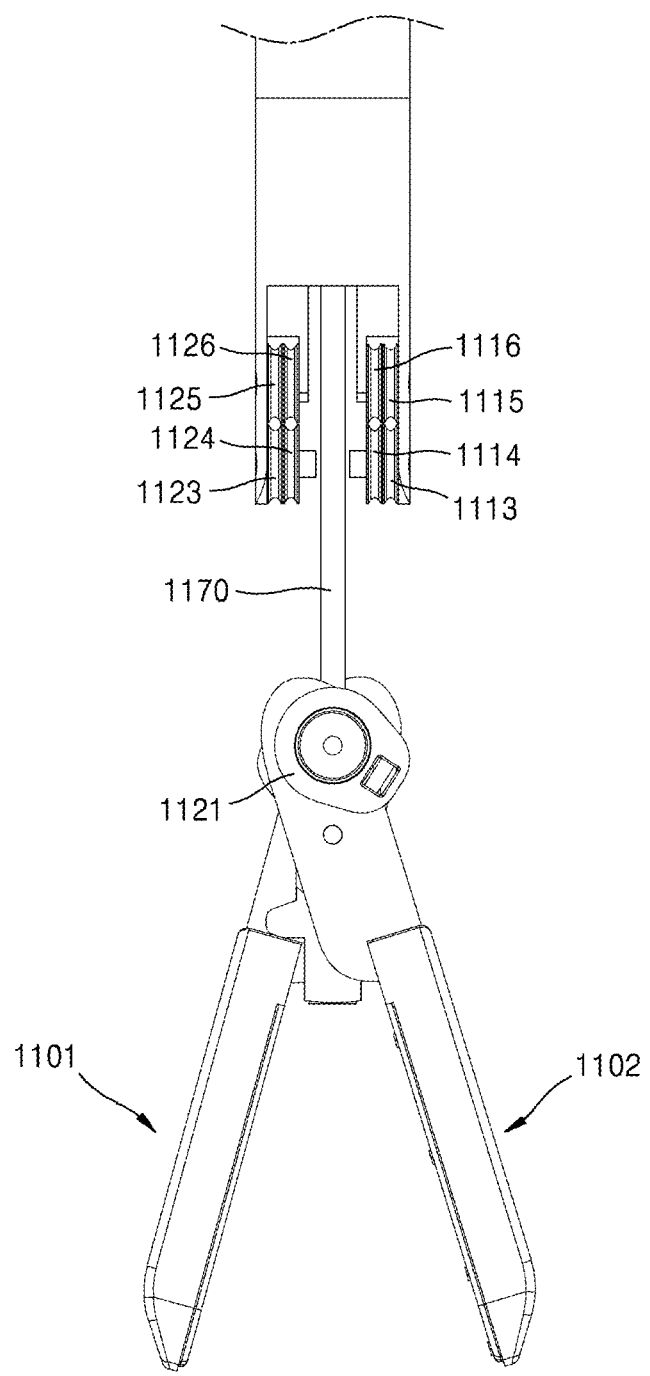
Figure 147:
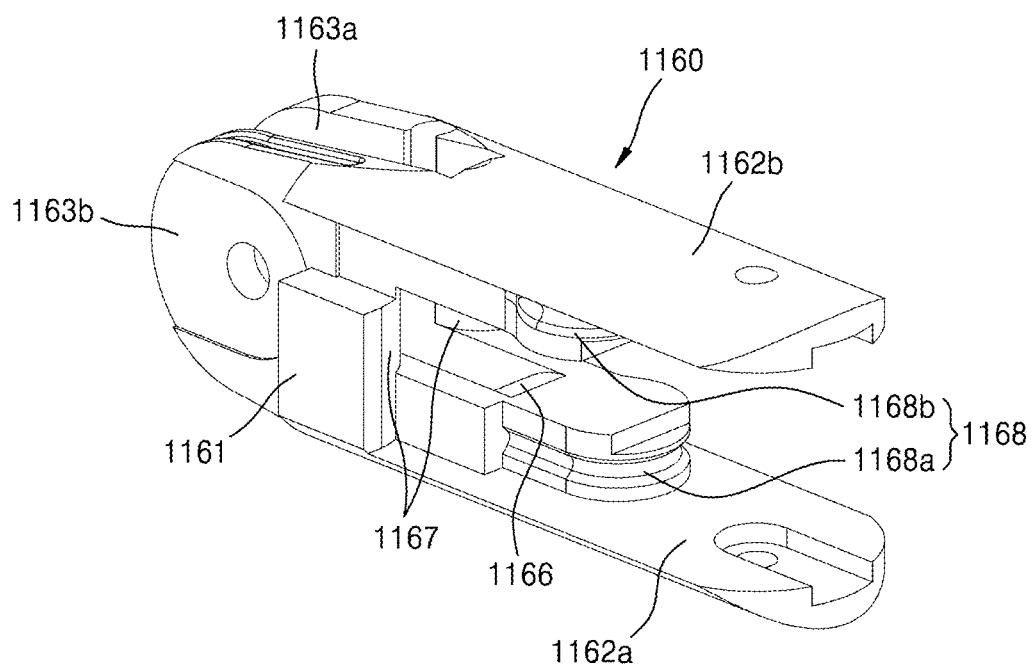
FIG. 147 is a perspective view illustrating an end tool hub of the surgical instrument for electrocautery of FIG. 140.
Figure 148:
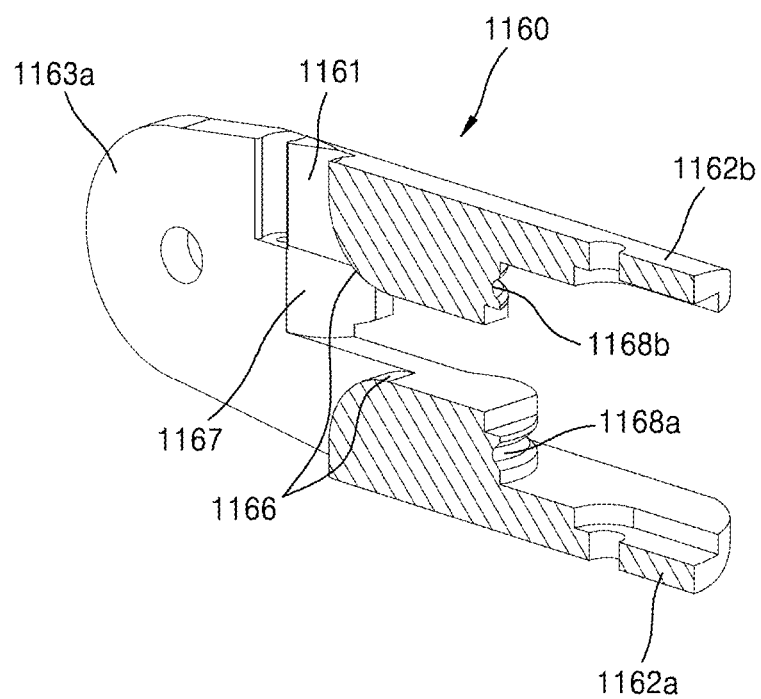
FIGS. 148 and 149 are cut-away perspective views of the end tool hub of FIG. 147.
Figure 149:
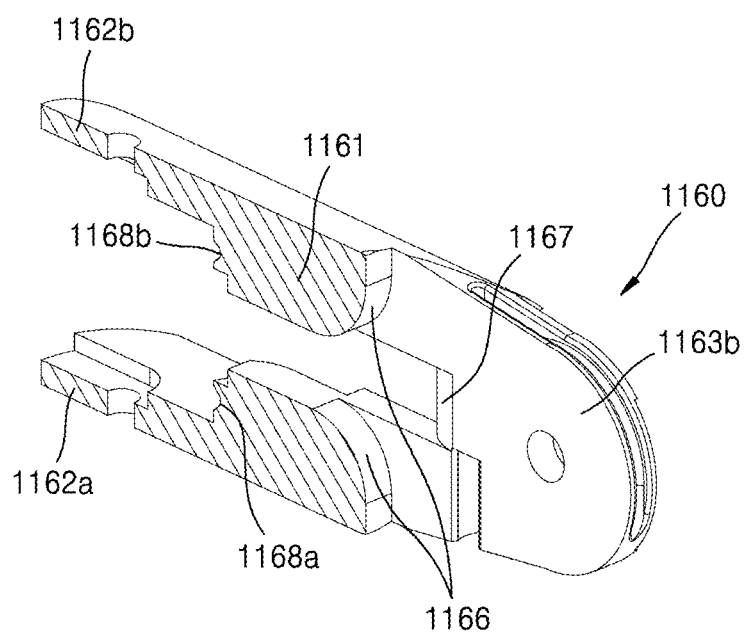
Figure 150:
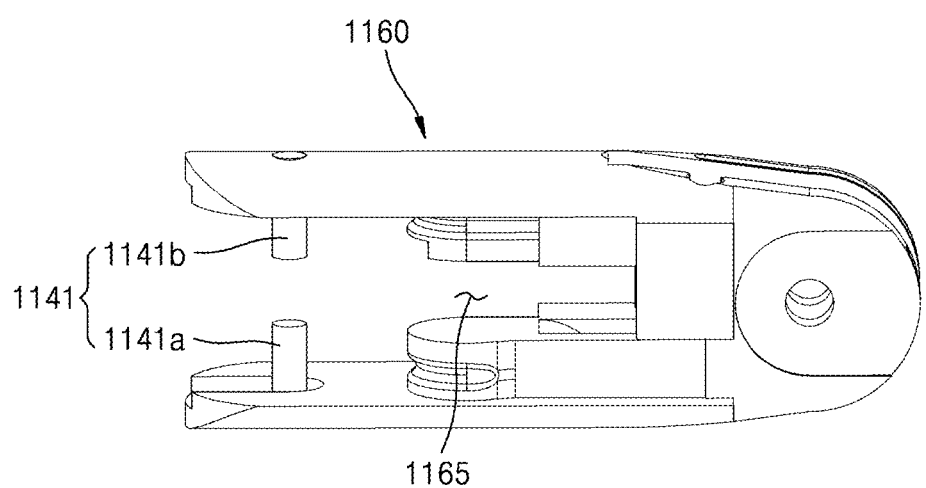
FIGS. 150 and 151 are perspective views illustrating the end tool hub of FIG. 147.
Figure 151:
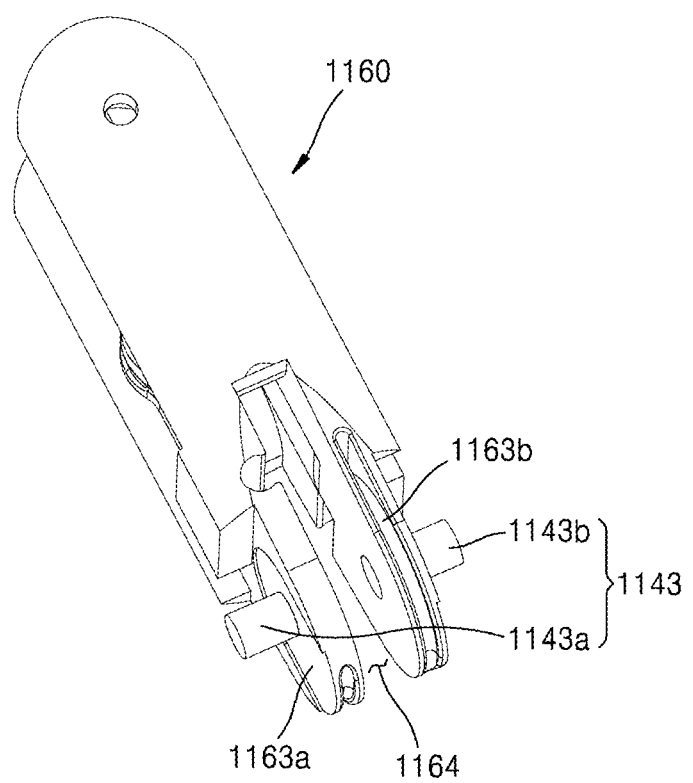
Figure 152:
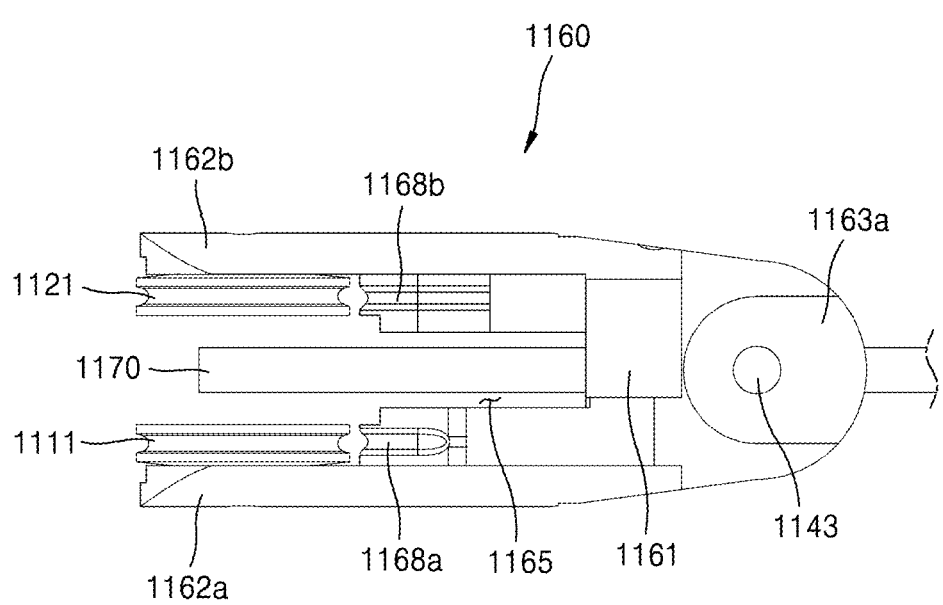
FIG. 152 is a side view illustrating the end tool hub of FIG. 147 and a guide tube.
Figure 153:
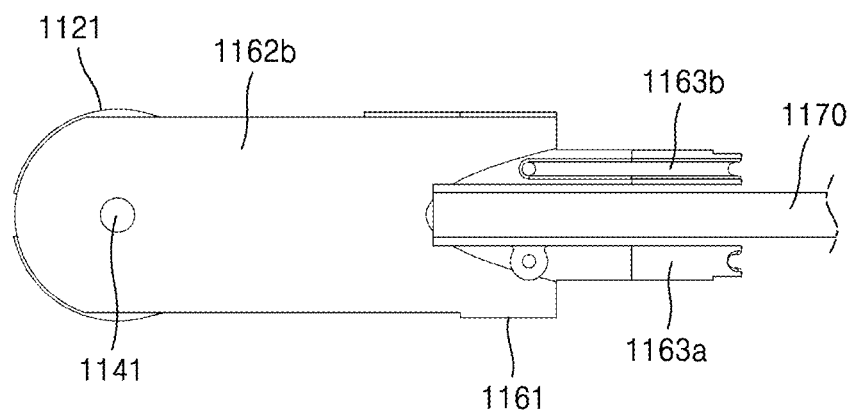
FIG. 153 is a plan view illustrating the end tool hub of FIG. 147 and the guide tube.
Figure 155:
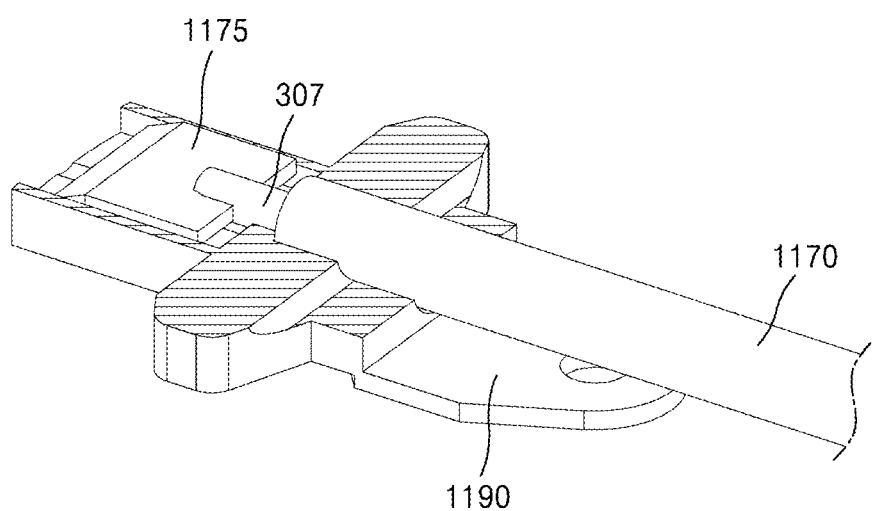
FIG. 155 is a view illustrating a state in which the guide tube, a blade wire, and a blade are mounted on the actuation hub illustrated in the cut-away perspective view of FIG. 154.
Figure 156:
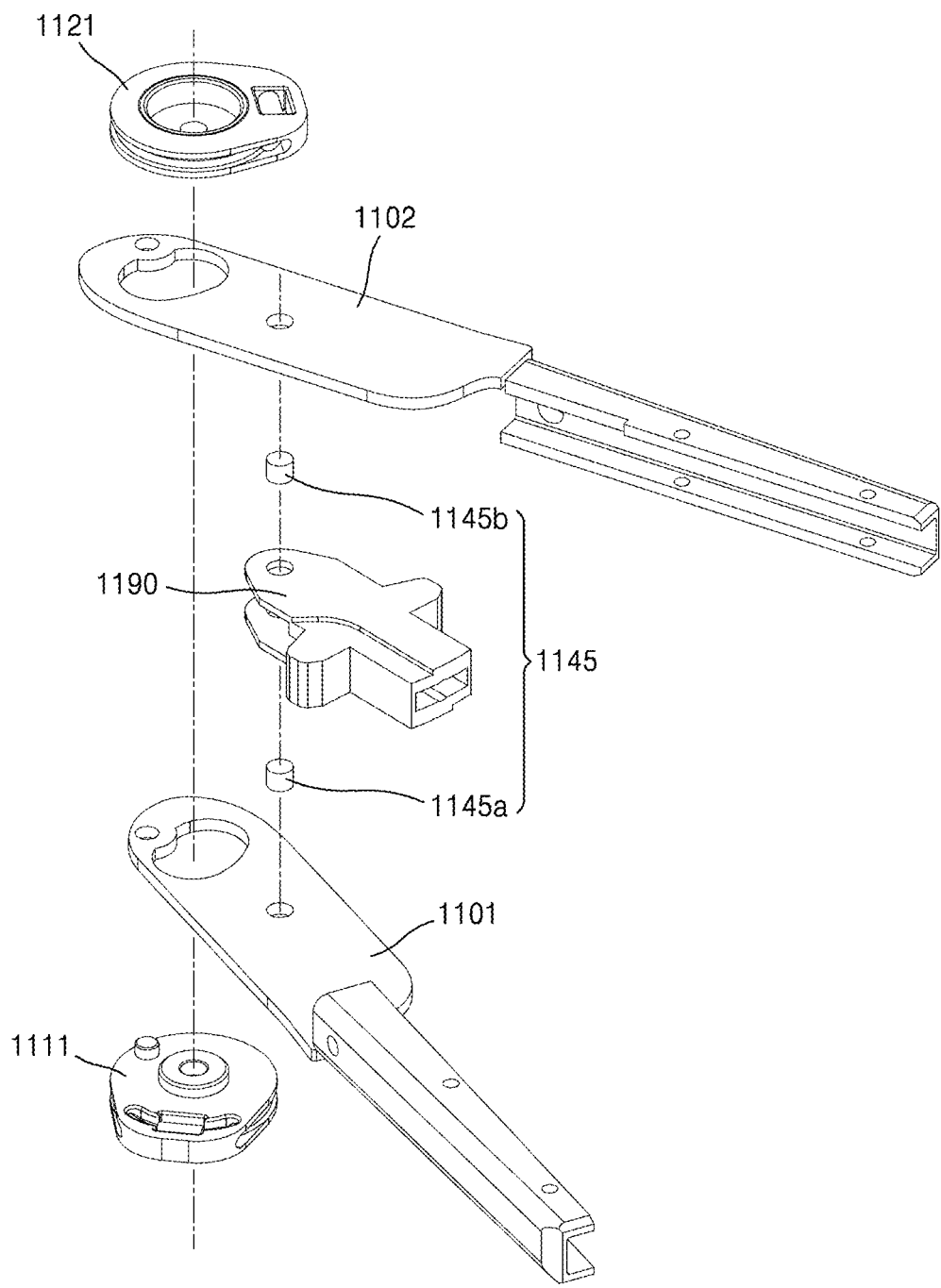
FIG. 156 is an exploded perspective view illustrating the end tool of the surgical instrument for electrocautery of FIG. 140.
Figure 157:
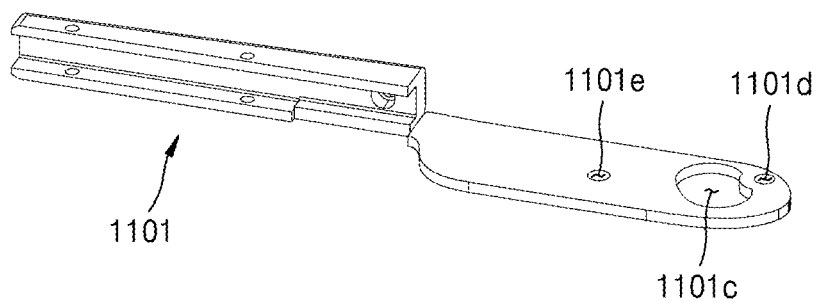
FIG. 157 is a perspective view illustrating a first jaw of the end tool of the surgical instrument for electrocautery of FIG. 140.
Figure 158:
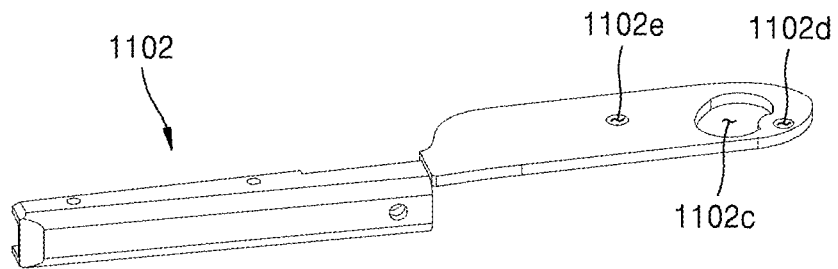
FIG. 158 is a perspective view illustrating a second jaw of the end tool of the surgical instrument for electrocautery of FIG. 140.
Figure 159:
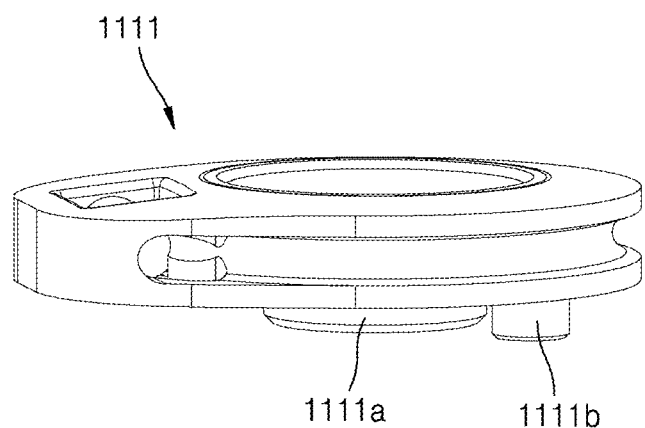
FIG. 159 is a perspective view illustrating a first jaw pulley of the surgical instrument for electrocautery of FIG. 140.
Figure 160:
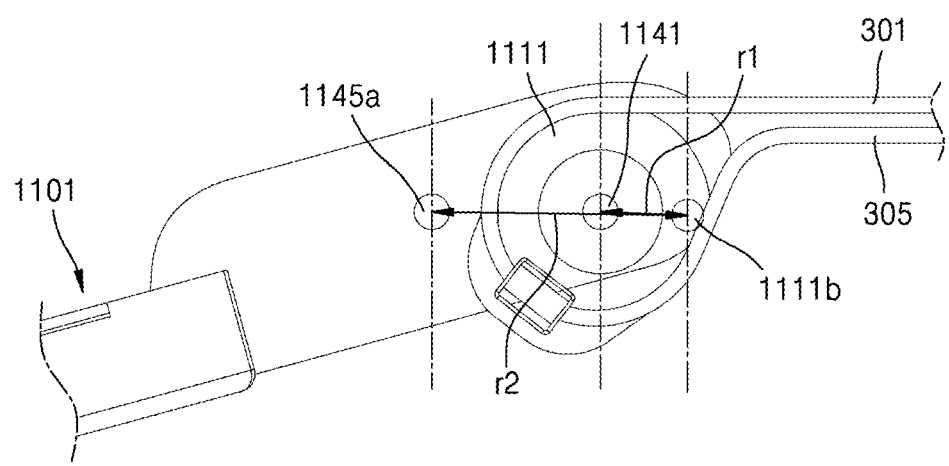
FIG. 160 is a plan view illustrating an opening and closing motion of the first jaw of the end tool of the surgical instrument for electrocautery of FIG. 140.
Figure 160:
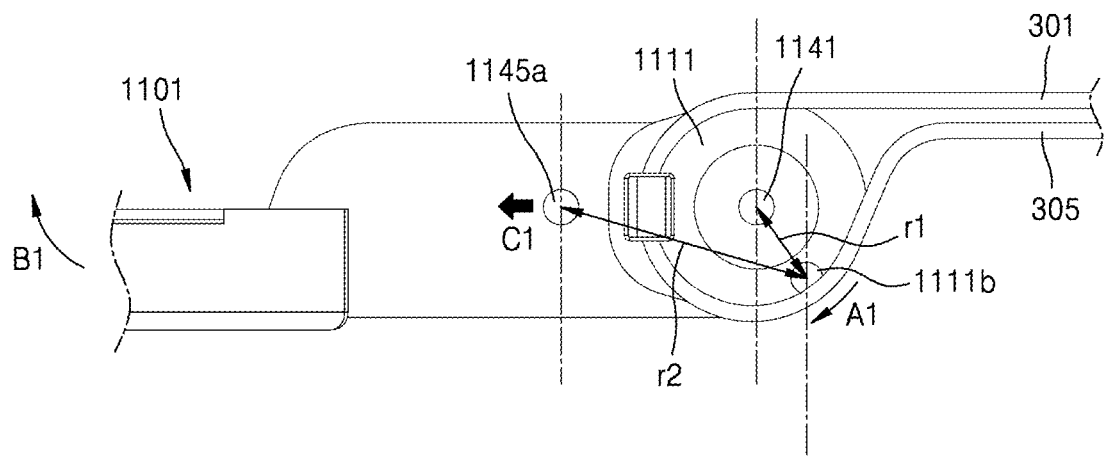
Figure 161:
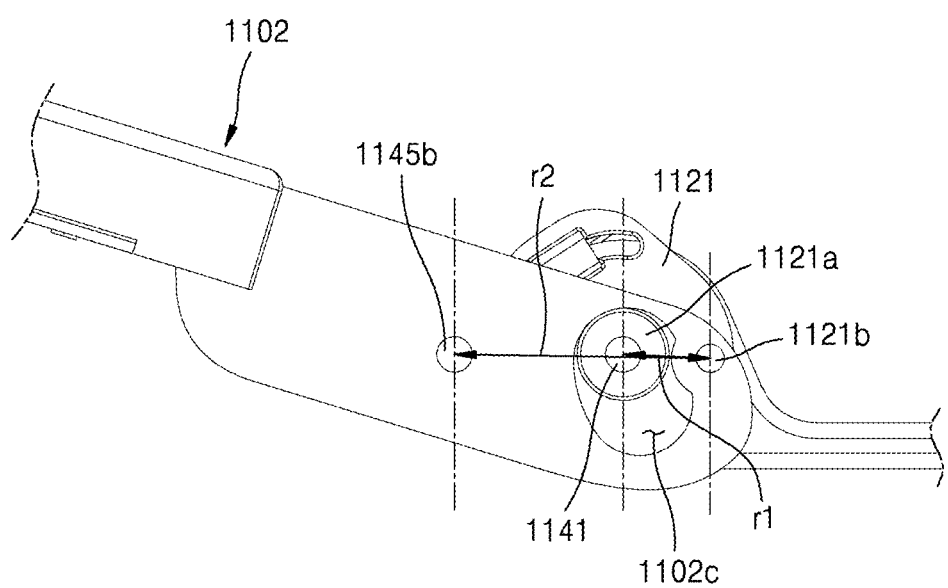
FIG. 161 is a plan view illustrating an opening and closing motion of the second jaw of the end tool of the surgical instrument for electrocautery of FIG. 140.
Figure 161:
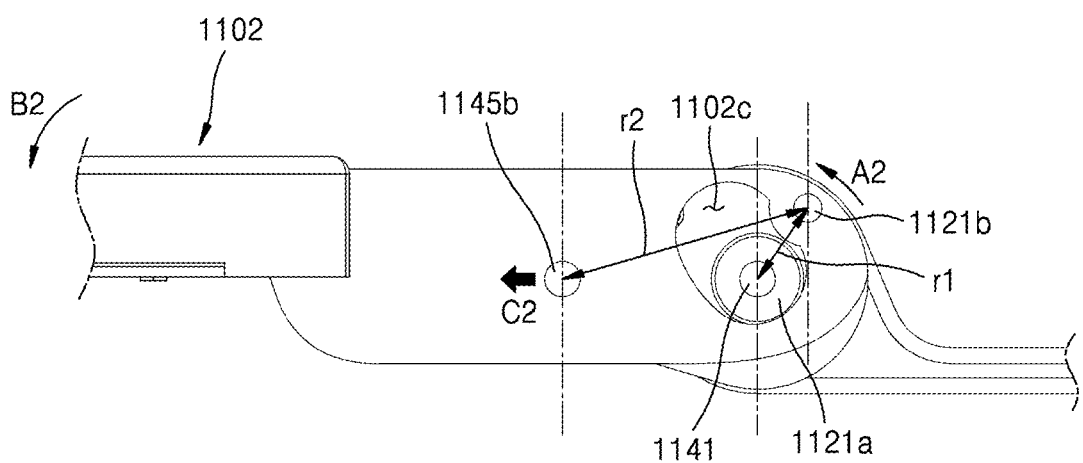
Figure 162:
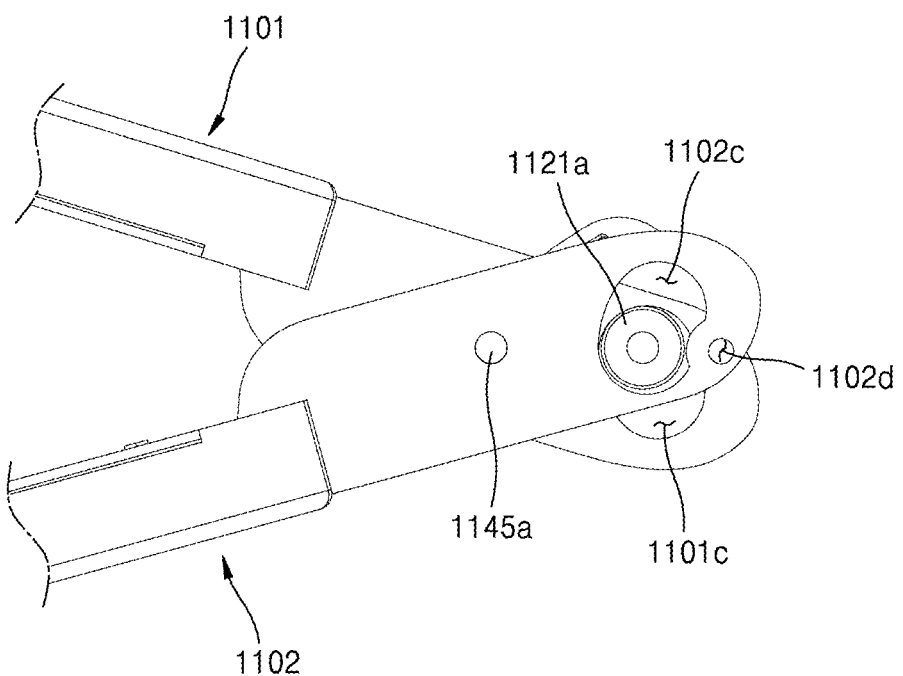
FIG. 162 is a plan view illustrating an opening and closing motion of the first jaw and the second jaw of the end tool of the surgical instrument for electrocautery of FIG. 140.
Figure 162:
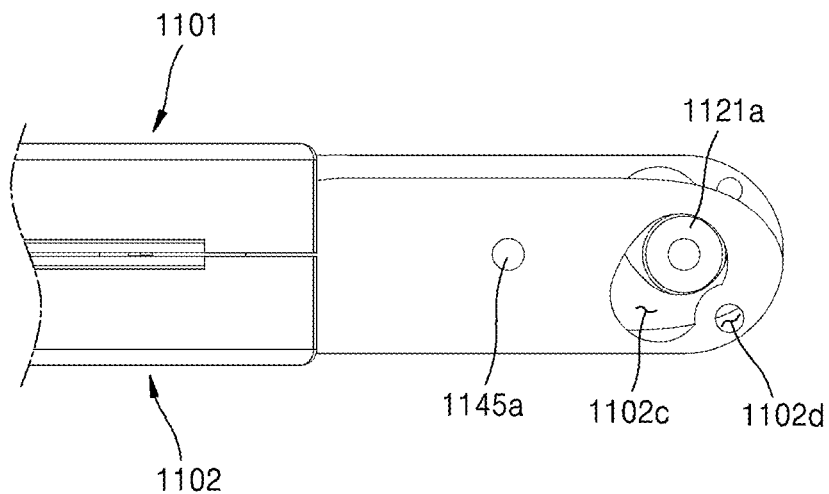

As compared to the third embodiment, the end tool 800 of the modified example of the third embodiment of the present disclosure has the same configuration as the end tool 800 according to the third embodiment, except that the pulley 821 and the pulley 822, which are axially coupled to the end tool hub 860' by the second rotation shaft 842, are provided as separate components instead of being integrally formed with a body portion 861 in the end tool hub 860' and function as auxiliary pulleys, and thus a detailed description thereof will be omitted in the overlapping range Fourth Embodiment of Surgical Instrument for Electrocautery FIG. 140 is a perspective view illustrating a surgical instrument for electrocautery according to a fourth embodiment of the present disclosure. FIGS. 141 to 146 are views illustrating an end tool of the surgical instrument for electrocautery of FIG. 140. FIG. 147 is a perspective view illustrating an end tool hub of the surgical instrument for electrocautery of FIG. 140. FIGS. 148 and 149 are cut-away perspective views of the end tool hub of FIG. 147. FIGS. 150 and 151 are perspective views illustrating the end tool hub of FIG. 147. FIG. 152 is a side view illustrating the end tool hub of FIG. 147 and a guide tube. FIG. 153 is a plan view illustrating the end tool hub of FIG. 147 and the guide tube. FIG. 154 is a perspective view illustrating an actuation hub of the surgical instrument for electrocautery of FIG. 140. FIG. 155 is a cut-away perspective view of the actuation hub of FIG. 154. FIG. 156 is an exploded perspective view illustrating the end tool of the surgical instrument for electrocautery of FIG. 140. FIG. 157 is a perspective view illustrating a first jaw of the end tool of the surgical instrument for electrocautery of FIG. 140. FIG. 158 is a perspective view illustrating a second jaw of the end tool of the surgical instrument for electrocautery of FIG. 140. FIG. 159 is a perspective view illustrating a first jaw pulley of the surgical instrument for electrocautery of FIG. 140. FIG. 160 is a plan view illustrating an opening and closing motion of the first jaw of the end tool of the surgical instrument for electrocautery of FIG. 140. FIG. 161 is a plan view illustrating an opening and closing motion of the second jaw of the end tool of the surgical instrument for electrocautery of FIG. 140. FIG. 162 is a plan view illustrating an opening and closing motion of the first jaw and the second jaw of the end tool of the surgical instrument for electrocautery of FIG. 140.

Referring to FIGS. 140 to 162 and the like, an electric cauterization surgical instrument 10 according to the fourth embodiment of the present disclosure includes an end tool 1100, a manipulation portion 200, a power transmission portion 300, and a connection portion 400.

Here, the connection portion 400 is formed in the shape of a hollow shaft, and one or more wires and electric wires may be accommodated therein. The manipulation portion 200 is coupled to one end portion of the connection portion 400, the end tool 1100 is coupled to the other end portion thereof, and the connection portion 400 may serve to connect the manipulation portion 200 and the end tool 1100. Here, the connection portion 400 of the electric cauterization surgical instrument 10 according to the fourth embodiment of the present disclosure includes a straight portion 401 and a bent portion 402, wherein the straight portion 401 is formed at a side coupled to the end tool 1100, and the bent portion 402 is formed at a side to which the manipulation portion 200 is coupled. As such, since the end portion of the connection portion 400 at the side of the manipulation portion 200 is formed to be bent, a pitch manipulation portion 201, a yaw manipulation portion 202, and an actuation manipulation portion 203 may be formed along an extension line of the end tool 1100 or adjacent to the extension line. In other words, it may be said that the pitch manipulation portion 201 and the yaw manipulation portion 202 are at least partially accommodated in a concave portion formed by the bent portion 402. Due to the above-described shape of the bent portion 402, the shapes and motions of the manipulation portion 200 and the end tool 1100 may be further intuitively matched with each other.

Meanwhile, a plane on which the bent portion 402 is formed may be substantially the same as a pitch plane, that is, an XZ plane of FIG. 140. As such, as the bent portion 402 is formed on substantially the same plane as the XZ plane, interference with the manipulation portion may be reduced. Of course, for intuitive motions of the end tool and the manipulation portion, any form other than the XZ plane may be possible.

Meanwhile, a connector 410 may be formed on the bent portion 402. The connector 410 may be connected to an external power supply (not shown), and the connector 410 may be connected to a jaw 1103 through electric wires 411 and 412 to transfer electrical energy supplied from the external power supply (not shown) to the jaw 1103. Here, the connector 410 may be of a bipolar-type having two electrodes, or the connector 410 may be of a monopolar type having one electrode.

The manipulation portion 200 is formed at the one end portion of the connection portion 400 and provided as an interface to be directly controlled by a medical doctor, for example, a tongs shape, a stick shape, a lever shape, or the like, and when the medical doctor controls the manipulation portion 200, the end tool 1100, which is connected to the interface and inserted into the body of a surgical patient, performs a certain motion, thereby performing surgery. Here, the manipulation portion 200 is illustrated in FIG. 140 as being formed in a handle shape that is rotatable while the finger is inserted therein, the concept of the present disclosure is not limited thereto, and various types of manipulation portions that are connected to the end tool 1100 and manipulate the end tool 1100 may be possible.

The end tool 1100 is formed on the other end portion of the connection portion 400, and performs necessary motions for surgery by being inserted into a surgical site. In an example of the end tool 1100 described above, as shown in FIG. 140, a pair of jaws 1103 for performing a grip motion may be used. However, the concept of the present disclosure is not limited thereto, and various devices for performing surgery may be used as the end tool 1100. For example, a configuration of a cantilever cautery may also be used as the end tool. The end tool 1100 is connected to the manipulation portion 200 by the power transmission portion 300, and receives a driving force of the manipulation portion 200 through the power transmission portion 300 to perform a motion necessary for surgery, such as gripping, cutting, suturing, or the like.

Here, the end tool 1100 of the electric cauterization surgical instrument 10 according to the fourth embodiment of the present disclosure is formed to be rotatable in at least one direction, for example, the end tool 1100 may perform a pitch motion around a Y-axis of FIG. 140 and simultaneously perform a yaw motion and an actuation motion around a Z-axis of FIG. 140.

The power transmission portion 300 may connect the manipulation portion 200 to the end tool 1100, transmit the driving force of the manipulation portion 200 to the end tool 1100, and include a plurality of wires, pulleys, links, sections, gears, or the like.

The end tool 1100, the manipulation portion 200, the power transmission portion 300, and the like of the electric cauterization surgical instrument 10 of FIG. 140 will be described in detail later.

(Power Transmission Portion)

Hereinafter, the power transmission portion 300 of the electric cauterization surgical instrument 10 of FIG. 140 will be described in more detail.

Referring to FIGS. 140 to 146 and the like, the power transmission portion 300 of the electric cauterization surgical instrument 10 according to an embodiment of the present disclosure may include a wire 301, a wire 302, a wire 303, a wire 304, a wire 305, a wire 306, and a blade wire 307.

Here, the wire 301 and the wire 305 may be paired to serve as first jaw wires. The wire 302 and the wire 306 may be paired to serve as second jaw wires. Here, the components encompassing the wires 301 and 305, which are first jaw wires, and the wires 302 and 306, which are second jaw wires, may be referred to as jaw wires. In addition, the wires 303 and 304 may be paired to serve as pitch wires.

In addition, the power transmission portion 300 of the electric cauterization surgical instrument 10 according to an embodiment of the present disclosure may include a fastening member 321, a fastening member 322, a fastening member 323, a fastening member 324, a fastening member 326, and a fastening member 327 that are coupled to respective end portions of the wires to respectively couple the wires and the pulleys. Here, each of the fastening members may have various shapes as necessary, such as a ball shape, a tube shape, and the like.

Here, at the end tool 1100 side, the fastening member 321/fastening member 322 may serve as pitch wire-end tool fastening members, the fastening member 323 may serve as a first jaw wire-end tool fastening member, and the fastening member 326 may serve as a second jaw wire-end tool fastening member.

Further, at the manipulation portion 200 side, the fastening member 324 may serve as a first jaw wire-manipulation portion fastening member, and the fastening member 327 may serve as a second jaw wire-manipulation portion fastening member. In addition, although not shown in the drawings, a pitch wire-manipulation portion fastening member and a blade wire-manipulation portion fastening member may be further formed at the manipulation portion 200 side.

The coupling relationship between the wires, the fastening members, and the respectively pulleys will be described in detail as follows.

First, the wires 301 and 305, which are first jaw wires, may be a single wire. The fastening member 323, which is a first jaw wire-end tool fastening member, is inserted at an intermediate point of the first jaw wire, which is a single wire, and the fastening member 323 is crimped and fixed, and then, both strands of the first jaw wire centered on the fastening member 323 may be referred to as the wire 301 and the wire 305, respectively.

Alternatively, the wires 301 and 305, which are first jaw wires, may also be formed as separate wires, and connected by the fastening member 323.

In addition, by coupling the fastening member 323 to a pulley 1111, the wires 301 and 305 may be fixedly coupled to the pulley 1111. This allows the pulley 1111 to rotate as the wires 301 and 305 are pulled and released.

Meanwhile, the first jaw wire-manipulation portion fastening member 324 may be coupled to the other end portions of the wires 301 and 305, which are opposite to one end portions to which the fastening member 323 is fastened.

In addition, by coupling the first jaw wire-manipulation portion fastening member 324 to a pulley 211, the wires 301 and 305 may be fixedly coupled to the pulley 211. As a result, when the pulley 211 is rotated by a motor or human power, the wire 301 and the wire 305 are pulled and released, allowing the pulley 1111 of the end tool 1100 to rotate.

In the same manner, the wire 302 and the wire 306, which are second jaw wires, are coupled to each of the fastening member 326, which is a second jaw wire-end tool fastening member, and the second jaw wire-manipulation portion fastening member 327. In addition, the fastening member 326 is coupled to a pulley 1121, and the second jaw wire-manipulation portion fastening member is coupled to a pulley 220. As a result, when the pulley 220 is rotated by a motor or a human force, the pulley 1121 of the end tool 1100 may be rotated as the wire 302 and the wire 306 are pulled and released.

In the same manner, the wire 304, which is a pitch wire, is coupled to the fastening member 321, which is a pitch wire-end tool fastening member, and the pitch wire-manipulation portion fastening member (not shown). In addition, the wire 303, which is a pitch wire, is coupled to a fastening member 322, which is a pitch wire-end tool fastening member, and the pitch wire-manipulation portion fastening member (not shown).

In addition, the fastening member 321 is coupled to a first pitch pulley portion 1163*a* of an end tool hub 1160, the fastening member 322 is coupled to a second pitch pulley portion 1163b of the end tool hub 1160, and the pitch wire-manipulation portion fastening member (not shown) is coupled to a pulley 231. As a result, when the pulley 231 is rotated by a motor or human force, the wire 303 and the wire 304 are pulled and released, allowing the end tool hub 1160 of the end tool 1100 to rotate.

Meanwhile, one end portion of the blade wire 307 is coupled to a blade 1175 to be described later, and the other end portion thereof is coupled to a blade manipulation portion 260 of the manipulation portion 200. By the manipulation of the blade manipulation portion 260, a cutting motion may be performed as the blade wire 307 is moved from a proximal end 1105 toward a distal end 1104 of the end tool 1100, or the blade wire 307 may return from the distal end 1104 toward the proximal end 1105 of the end tool 1100.

At this time, at least a part of the blade wire 307 may be accommodated in a guide tube 1170 to be described later. Accordingly, when the guide tube 1170 is bent in response to a pitch motion or yaw motion of the end tool 1100, the blade wire 307 accommodated therein may also be bent together with the guide tube 1170. The guide tube 1170 will be described in more detail later.

In addition, the blade wire 307 is formed in a longitudinal direction of the connection portion 400 to be linearly movable in the connection portion 400. In addition, since one end portion of the blade wire 307 is coupled to the blade 1175, when the blade wire 307 is linearly moved in the longitudinal direction of the connection portion 400, the blade 1175 connected thereto is also linearly moved. That is, when the blade wire 307 is linearly moved in the longitudinal direction of the connection portion 400, a cutting motion is performed as the blade 1175 connected thereto is moved toward the distal end 1104 or the proximal end 1105 of the end tool 1100. This will be described in more detail later.

(End Tool)

Hereinafter, the end tool 1100 of the electric cauterization surgical instrument 10 of FIG. 140 will be described in more detail.

FIG. 140 is a perspective view illustrating the surgical instrument for electrocautery according to the fourth embodiment of the present disclosure. FIGS. 141 to 146 are views illustrating the end tool of the surgical instrument for electrocautery of FIG. 140.

Figure 141:
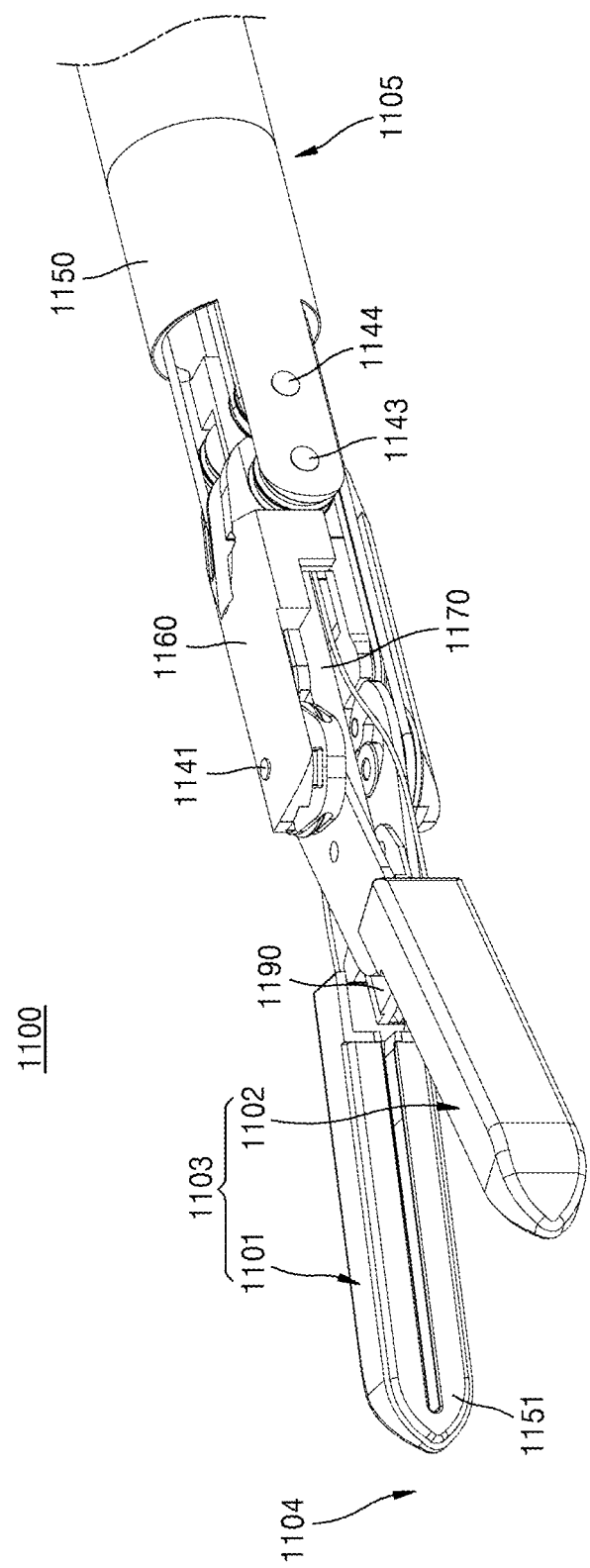
FIGS. 141 to 146 are views illustrating an end tool of the surgical instrument for electrocautery of FIG. 140.
Figure 142:
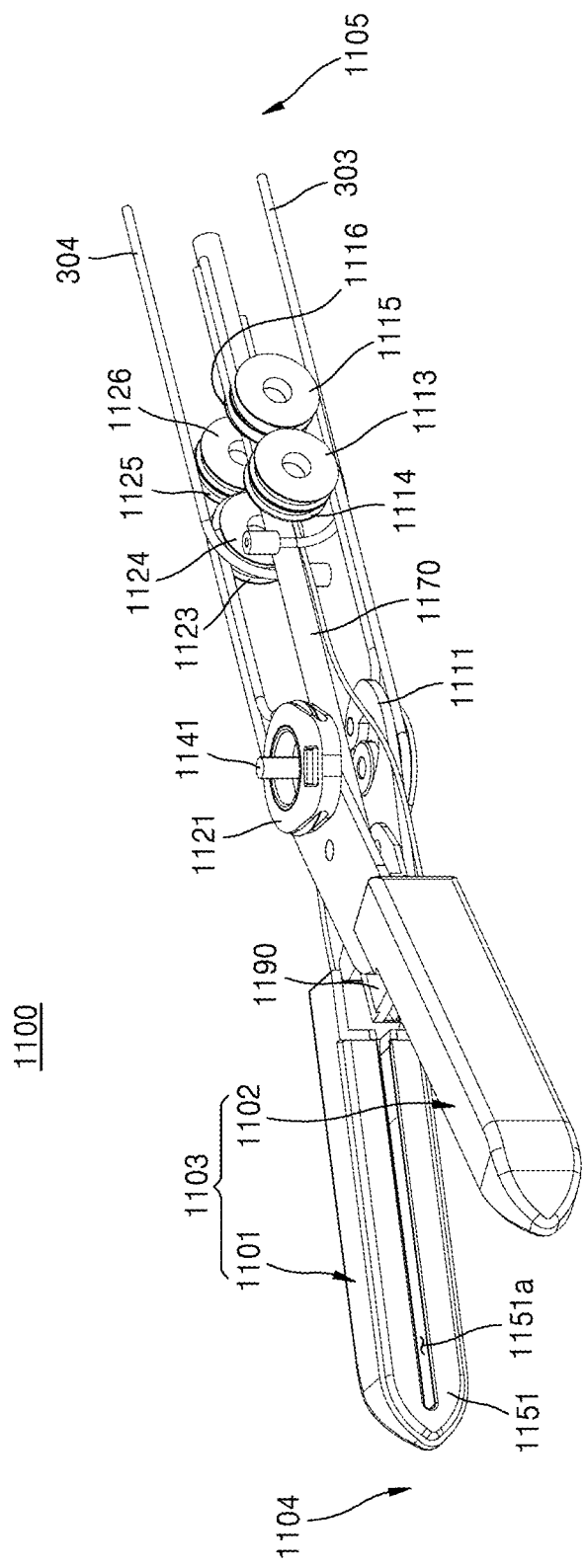
Figure 143:
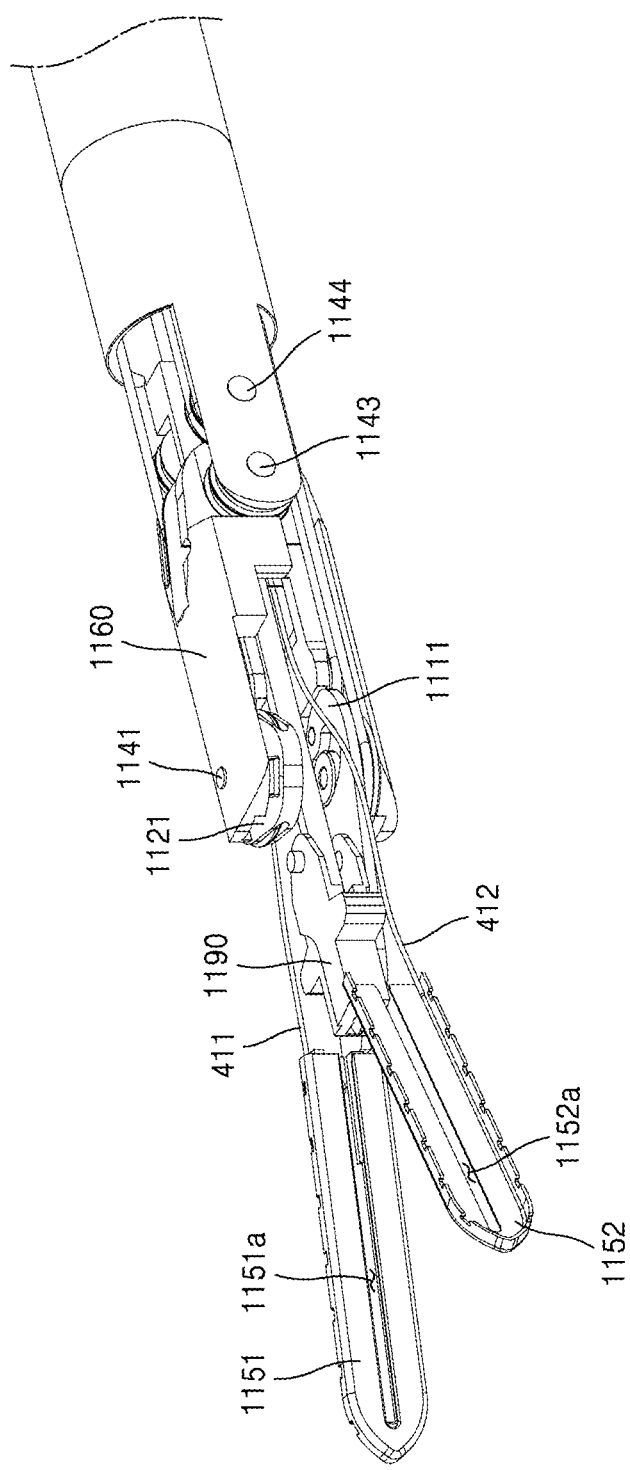
Figure 144:
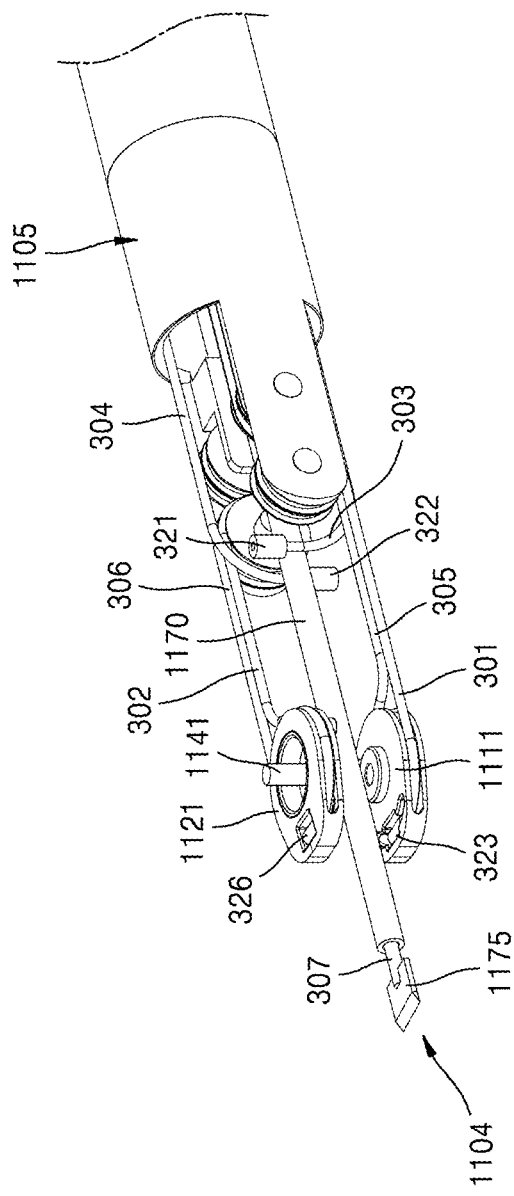

Here, FIG. 141 illustrates a state in which the end tool hub 1160 and a pitch hub 1150 are coupled, and FIG. 142 illustrates a state in which the end tool hub 1160 and pitch hub 1150 are removed. FIG. 143 illustrates a state in which a first jaw 1101 and a second jaw 1102 are removed, and FIG. 144 illustrates a state in which the first jaw 1101, the second jaw 1102, the pulley 1111, the pulley 1121, and the like are removed. Meanwhile, FIG. 145 is a view mainly illustrating the wires, and FIG. 146 is a view mainly illustrating the pulleys.

Referring to FIGS. 140 to 162 and the like, the end tool 1100 of the fourth embodiment of the present disclosure includes a pair of jaws for performing a grip motion, that is, the first jaw 1101 and a second jaw 1102. Here, each of the first jaw 1101 and the second jaw 1102, or a component encompassing the first jaw 1101 and the second jaw 1102 may be referred to as the jaw 1103.

Further, the end tool 1100 may include the pulley 1111, a pulley 1113, a pulley 1114, a pulley 1115, and a pulley 1116 associated with a rotational motion of the first jaw 1101. In addition, the end tool 1100 may include the pulley 1121, a pulley 1123, a pulley 1124, a pulley 1125, and a pulley 1126, which are associated with a rotational motion of the second jaw 1102.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 1100 of the fourth embodiment of the present disclosure may include the end tool hub 1160 and the pitch hub 1150.

A first rotation shaft 1141 to be described later may be inserted through the end tool hub 1160, and the pulley 1111 and the pulley 1121 axially coupled to the first rotation shaft 1141 and at least some of the first jaw 1101 and the second jaw 1102 coupled to the pulley 1111 and the pulley 1121 may be accommodated inside the end tool hub 1160. Here, in an embodiment of the present disclosure, a wire guide portion 1168 serving as an auxiliary pulley is formed in the end tool hub 1160. That is, a first wire guide portion 1168a and a second wire guide portion 1168b for guiding paths of the wire 305 and the wire 302 may be formed in the end tool hub 1160. The wire guide portions 1168 of the end tool hub 1160 may serve as auxiliary pulleys (see 612 and 622 of FIG. 39) of the first embodiment and change the paths of the wires, and the first wire guide portion 1168a and the second wire guide portion 1168b of the end tool hub 1160 serving as auxiliary pulleys will be described in more detail later.

Meanwhile, the first pitch pulley portion 1163a and the second pitch pulley portion 1163b, which serve as end tool pitch pulleys, may be formed at one end portion of the end tool hub 1160. The wire 303 and the wire 304, which are pitch wires, are coupled to the first pitch pulley portion 1163a and the second pitch pulley portion 1163b, which serve as end tool pitch pulleys, and a pitch motion is performed while the end tool hub 1160 rotates around a third rotation shaft 1143.

The third rotation shaft 1143 and a fourth rotation shaft 1144 may be inserted through the pitch hub 1150, and the pitch hub 1150 may be axially coupled to the end tool hub 1160 by the third rotation shaft 1143. Accordingly, the end tool hub 1160 may be formed to be pitch-rotatable around the third rotation shaft 1143 with respect to the pitch hub 1150.

Further, the pitch hub 1150 may internally accommodate at least some of the pulley 1113, the pulley 1114, the pulley 1123, and the pulley 1124 that are axially coupled to the third rotation shaft 1143. Further, the pitch hub 1150 may internally accommodate at least some of the pulley 1115, the pulley 1116, the pulley 1125, and the pulley 1126 that are axially coupled to the fourth rotation shaft 1144.

One end portion of the pitch hub 1150 is connected to the end tool hub 1160, and the other end portion of the pitch hub 1150 is connected to the connection portion 400.

Here, the end tool 1100 of the fourth embodiment of the present disclosure may include the first rotation shaft 1141, the third rotation shaft 1143, and the fourth rotation shaft 1144. As described above, the first rotation shaft 1141 may be inserted through the end tool hub 1160, and the third rotation shaft 1143 and the fourth rotation shaft 1144 may be inserted through the pitch hub 1150.

The first rotation shaft 1141, the third rotation shaft 1143, and the fourth rotation shaft 1144 may be arranged sequentially from the distal end 1104 toward the proximal end 1105 of the end tool 1100. Accordingly, starting from the distal end 1104, the first rotation shaft 1141 may be referred to as a first pin, the third rotation shaft 1143 may be referred to as a third pin, and the fourth rotation shaft 1144 may be referred to as a fourth pin.

Here, the first rotation shaft 1141 may function as an end tool jaw pulley rotation shaft, the third rotation shaft 1143 may function as an end tool pitch rotation shaft, and the fourth rotation shaft 1144 may function as an end tool pitch auxiliary rotation shaft of the end tool 1100.

Here, each of the rotation shafts may include two shafts of a first sub-shaft and a second sub-shaft. Alternatively, it may be said that each of the rotation shafts is formed by being divided into two parts.

For example, the first rotation shaft 1141 may include two shafts of a first sub-shaft 1141a and a second sub-shaft 1141b. In addition, the third rotation shaft 1143 may include two shafts of a first sub-shaft 1143a and a second sub-shaft 1143b. The fourth rotation shaft 1144 may include two shafts of a first sub-shaft and a second sub-shaft.

Each of the rotation shafts is formed by being divided into two parts as described above to allow the guide tube 1170 to be described later to pass through the end tool hub 1160 and the pitch hub 1150. That is, the guide tube 1170 may pass between the first sub-shaft and the second sub-shaft of each of the rotation shafts. This will be described in more detail later. Here, the first sub-shaft and the second sub-shaft may be disposed on the same axis or may be disposed to be offset to a certain degree.

Meanwhile, it is illustrated in the drawings that each of the rotation shafts is formed by being divided into two parts, but the concept of the present disclosure is not limited thereto. That is, each of the rotation shafts is formed to be curved in the middle such that an escape path for the guide tube 1170 is formed.

Each of the rotation shafts 1141, 1143, and 1144 may be fitted into one or more pulleys, which will be described in detail below.

Meanwhile, the end tool 1100 may further include an actuation rotation shaft 1145. In detail, the first jaw 1101 and the second jaw 1102 may be axially coupled by the actuation rotation shaft 1145, and in this state, an actuation motion may be performed while the first jaw 1101 and the second jaw 1102 rotate around the actuation rotation shaft 1145. Here, the actuation rotation shaft 1145 may be disposed closer to the distal end 1104 than the first rotation shaft 1141 is.

Here, in the end tool 1100 of the fourth embodiment of the present disclosure, the first rotation shaft 1141, which is a yaw rotation shaft, and the actuation rotation shaft 1145 are provided separately rather than as the same shaft. That is, by forming the first rotation shaft 1141, which is a rotation shaft of the pulley 1111/pulley 1121 that are jaw pulleys and a rotation shaft of a yaw motion, and the actuation rotation shaft 1145, which is a rotation shaft of the second jaw 1102 with respect to the first jaw 1101 and a rotation shaft of an actuation motion, to be spaced apart from each other by a certain distance, a space in which the guide tube 1170 and the blade wire 307 accommodated therein can be gently bent may be secured. The actuation rotation shaft 1145 will be described in detail later.

The pulley 1111 functions as an end tool first jaw pulley, and the pulley 1121 functions as an end tool second jaw pulley. The pulley 1111 may also be referred to as a first jaw pulley, and the pulley 1121 may also be referred to as a second jaw pulley, and these two components may collectively be referred to as end tool jaw pulleys or simply jaw pulleys.

The pulley 1111 and the pulley 1121, which are end tool jaw pulleys, are formed to face each other, and are formed to be rotatable independently of each other around the first rotation shaft 1141 which is an end tool jaw pulley rotation shaft. In this case, the pulley 1111 and pulley 1121 are formed to be spaced apart by a certain distance, and a blade assembly accommodation portion may be accommodated therebetween. In addition, at least a part of a blade assembly to be described later may be disposed in the blade assembly accommodation portion. In other words, the blade assembly including the guide tube 1170 may be disposed between the pulley 1111 and the pulley 1121.

Here, since the pulley 1111 is connected to the first jaw 1101, when the pulley 1111 rotates around the first rotation shaft 1141, the first jaw 1101 may also rotate around the first rotation shaft 1141 together with the pulley 1111.

Meanwhile, since the pulley 1121 is connected to the second jaw 1102, when the pulley 1121 rotates around the first rotation shaft 1141, the second jaw 1102 connected to the pulley 1121 may rotate around the first rotation shaft 1141.

In addition, a yaw motion and an actuation motion of the end tool 1100 are performed in response to the rotation of the pulley 1111 and the pulley 1121. That is, when the pulley 1111 and the pulley 1121 rotate in the same direction around the first rotation shaft 1141, the yaw motion is performed as the first jaw 1101 and the second jaw 1102 rotate with the first rotation shaft 1141 as the center of rotation. Meanwhile, when the pulley 1111 and the pulley 1121 rotate in opposite directions around the first rotation shaft 1141, the actuation motion is performed as the first jaw 1101 and the second jaw 1102 rotate around the actuation rotation shaft 1145.

The pulley 1113 and the pulley 1114 function as end tool first jaw pitch main pulleys, and the pulley 1123 and the pulley 1124 function as end tool second jaw pitch main pulleys, and these two components may collectively be referred to as end tool jaw pitch main pulleys.

The pulley 1115 and the pulley 1116 function as end tool first jaw pitch sub-pulleys, and the pulley 1125 and the pulley 1126 function as end tool second jaw pitch sub-pulleys, and these two components collectively may be referred to as end tool jaw pitch sub-pulleys.

Hereinafter, components associated with the rotation of the pulley 1111 will be described.

The pulley 1113 and the pulley 1114 function as end tool first jaw pitch main pulleys. That is, the pulley 1113 and the pulley 1114 function as main rotation pulleys for a pitch motion of the first jaw 1101. Here, the wire 301, which is a first jaw wire, is wound around the pulley 1113, and the wire 305, which is a first jaw wire, is wound around the pulley 1114.

The pulley 1115 and the pulley 1116 function as end tool first jaw pitch sub-pulleys. That is, the pulley 1115 and the pulley 1116 function as sub-rotation pulleys for a pitch motion of the first jaw 1101. Here, the wire 301, which is a first jaw wire, is wound around the pulley 1115, and the wire 305, which is a first jaw wire, is wound around the pulley 1116.

Here, the pulley 1113 and the pulley 1114 are disposed on one side of the pulley 1111 to face each other. Here, the pulley 1113 and the pulley 1114 are formed to be rotatable independently of each other around the third rotation shaft 1143 that is an end tool pitch rotation shaft. In addition, the pulley 1115 and the pulley 1116 are disposed on one side of the pulley 1113 and one side of the pulley 1114, respectively, to face each other. Here, the pulley 1115 and the pulley 1116 are formed to be rotatable independently of each other around the fourth rotation shaft 1144 that is an end tool pitch auxiliary rotation shaft. Here, in the drawings, it is illustrated that the pulley 1113, the pulley 1115, the pulley 1114, and the pulley 1116 are all formed to be rotatable around a Y-axis direction, but the concept of the present disclosure is not limited thereto, and the rotation axes of the respective pulleys may be formed in various directions according to configurations thereof.

The wire 301, which is a first jaw wire, is sequentially wound to make contact with at least portions of the pulley 1115, the pulley 1113, and the pulley 1111. In addition, the wire 305 connected to the wire 301 by the fastening member 323 is sequentially wound to make contact with at least portions of the pulley 1111, the first wire guide portion 1168*a* of the end tool hub 1160, the pulley 1114, and the pulley 1116.

In other words, the wire 301 and the wire 305, which are the first jaw wire, are sequentially wound to make contact with at least portions of the pulley 1115, the pulley 1113, the pulley 1111, the first wire guide portion 1168*a* of the end tool hub 1160, the pulley 1114, and the pulley 1116, and the wire 301 and the wire 305 formed to move along the above pulleys while rotating the above pulleys.

Accordingly, when the wire 301 is pulled in the direction of an arrow 301 of FIG. 145, the fastening member 323 to which the wire 301 is coupled and the pulley 1111 coupled to the fastening member 323 are rotated in the counterclockwise direction. On the contrary, when the wire 305 is pulled in the direction of an arrow 305 of FIG. 145, the fastening member 323 to which the wire 305 is coupled and the pulley 1111 coupled to the fastening member 323 are rotated in the clockwise direction in the FIG. 145.

Next, components associated with the rotation of the pulley 1121 will be described.

The pulley 1123 and the pulley 1124 function as end tool second jaw pitch main pulleys. That is, the pulley 1123 and the pulley 1124 function as main rotation pulleys for a pitch motion of the second jaw 1102. Here, the wire 306, which is a second jaw wire, is wound around the pulley 1123, and the wire 302, which is a second jaw wire, is wound around the pulley 1124.

The pulley 1125 and the pulley 1126 function as end tool second jaw pitch sub-pulleys. That is, the pulley 1125 and the pulley 1126 function as sub-rotation pulleys for a pitch motion of the second jaw 1102. Here, the wire 306, which is a second jaw wire, is wound around the pulley 1125, and the wire 302, which is a second jaw wire, is wound around the pulley 1126.

Here, the pulley 1123 and the pulley 1124 are disposed on one side of the pulley 1121 to face each other. Here, the pulley 1123 and the pulley 1124 are formed to be rotatable independently of each other around the third rotation shaft 1143 that is an end tool pitch rotation shaft. In addition, the pulley 1125 and the pulley 1126 are disposed on one side of the pulley 1123 and one side of the pulley 1124, respectively, to face each other. Here, the pulley 1125 and the pulley 1126 are formed to be rotatable independently of each other around the fourth rotation shaft 1144 that is an end tool pitch auxiliary rotation shaft. Here, in the drawings, it is illustrated that all of the pulley 1123, the pulley 1125, the pulley 1124, and the pulley 1126 are formed to be rotatable around the Y-axis direction, but the concept of the present disclosure is not limited thereto, and the rotating axes of the respective pulleys may be formed in various directions according to configurations thereof.

The wire 306, which is a second jaw wire, is sequentially wound to make contact with at least portions of the pulley 1125, the pulley 1123, and the pulley 1121. In addition, the wire 302 connected to the wire 306 by the fastening member 326 is sequentially wound to make contact with at least portions of the pulley 1121, the second wire guide portion 1168*b* of the end tool hub 1160, the pulley 1124, and the pulley 1126.

In other words, the wire 306 and the wire 302, which are the second jaw wire, are sequentially wound to make contact with at least portions of the pulley 1125, the pulley 1123, the pulley 1121, the second wire guide portion 1168*b* of the end tool hub 1160, the pulley 1124, and the pulley 1126, and the wire 306 and the wire 302 are formed to move along the above pulleys while rotating the above pulleys.

Accordingly, when the wire 306 is pulled in the direction of an arrow 306 of FIG. 145, the fastening member 326 to which the wire 306 is coupled and the pulley 1121 coupled to the fastening member 326 are rotated in the clockwise direction in FIG. 145. On the contrary, when the wire 302 is pulled toward the arrow 302 of FIG. 145, the fastening member 326 coupled to the wire 302 and the pulley 1121 coupled to the fastening member 326 may rotate in the counterclockwise direction in FIG. 145.

Hereinafter, a pitch motion of the present disclosure will be described in more detail.

Meanwhile, when the wire 301 is pulled in the direction of the arrow 301 of FIG. 145, and simultaneously, the wire 305 is pulled in the direction of the arrow 305 of FIG. 145 (that is, when both strands of the first jaw wire are pulled), as shown in FIG. 144, since the wires 301 and 305 are wound around lower portions of the pulley 1113 and the pulley 1114 rotatable around the third rotation shaft 1143, which is an end tool pitch rotation shaft, the pulley 1111 to which the wires 301 and 305 are fixedly coupled and the end tool hub 1160 to which the pulley 1111 is coupled rotate as a whole in the counterclockwise direction around the third rotation shaft 1143, and as a result, the end tool 1100 may rotate downward to perform the pitch motion. At this time, since the second jaw 1102 and the wires 302 and 306 fixedly coupled thereto are wound around upper portions of the pulley 1123 and the pulley 1124 rotatable around the third rotation shaft 1143, the wires 302 and 306 are released in the opposite directions of the arrows 302 and 306, respectively.

On the contrary, when the wire 302 is pulled in the direction of the arrow 302 of FIG. 145, and simultaneously, the wire 306 is pulled in the direction of the arrow 306 of FIG. 145, as shown in FIG. 144, since the wires 302 and 306 are wound around the upper portions of the pulley 1123 and the pulley 1124 rotatable around the third rotation shaft 1143, which is an end tool pitch rotation shaft, the pulley 1121 to which the wires 302 and 306 are fixedly coupled and the end tool hub 1160 to which the pulley 1121 is coupled rotate as a whole in the clockwise direction around the third rotation shaft 1143, and as a result, the end tool 1100 may rotate upward to perform the pitch motion. At this time, since the first jaw 1101 and the wires 301 and 305 fixedly coupled thereto are wound around lower portions of the pulley 1113 and the pulley 1114 rotatable around the third rotation shaft 1143, the wires 302 and 306 are moved in the opposite directions of the arrows 301 and 305, respectively.

Meanwhile, the end tool hub 1160 of the end tool 1100 of the electric cauterization surgical instrument 10 of the present disclosure may further include the first pitch pulley portion 1163*a* and the second pitch pulley portion 1163*b* serving as end tool pitch pulleys, the manipulation portion 200 may further include the pulley 231 and a pulley 232, which are manipulation portion pitch pulleys, and the power transmission portion 300 may further include the wire 303 and the wire 304 which are pitch wires.

In detail, the end tool hub 1160 including the first pitch pulley portion 1163a and the second pitch pulley portion 1163b may be formed to be rotatable around the third rotation shaft 1143 that is an end tool pitch rotation shaft. In addition, the wires 303 and 304 may serve to connect the first and second pitch pulley portions 1163a and 1163b of the end tool 1100 and the pulleys 231 and 232 of the manipulation portion 200.

Thus, when the pulleys 231 and 232 of the manipulation portion 200 rotate, the rotation of the pulleys 231 and 232 is transmitted to the end tool hub 1160 of the end tool 1100 through the wires 303 and 304, causing the end tool hub 1160 to rotate as well, and as a result, the end tool 1100 performs a pitch motion while rotating.

That is, the electric cauterization surgical instrument 10 according to the fourth embodiment of the present disclosure includes the first and second pitch pulley portions 1163a and 1163b of the end tool 1100, the pulleys 231 and 232 of the manipulation portion 200, and the wires 303 and 304 of the power transmission portion 300 in order to transmit driving force for a pitch motion, and thus, the driving force for the pitch motion of the manipulation portion 200 is more completely transmitted to the end tool 1100, thereby improving operation reliability.

(Blade Wire and Guide Tube)

Hereinafter, the blade wire 307 and the guide tube 1170 of the present disclosure will be described in more detail.

The guide tube 1170 according to the present disclosure is formed to surround the blade wire 307 in a certain section, and at this time, the blade wire 307 is movable inside the guide tube 1170. In other words, in a state in which in which the blade wire 307 is inserted into the guide tube 1170, the blade wire 307 is movable relative to the guide tube 1170.

Here, the guide tube 1170 serves to guide the path of the blade wire 307 by preventing the blade wire 307 from being curved in an unintended direction when the blade wire 307 is pushed or pulled. A cutting motion may be smoothly performed by the guide tube 1170.

Meanwhile, one end portion of the guide tube 1170 may be fixedly coupled to an actuation hub 1190 to be described later. Here, the actuation hub 1190 may serve as a first coupling portion. In addition, the other end portion of the guide tube 1170 may be fixedly coupled to a second coupling portion (not shown) in the connection portion 400. Since both end portions of the guide tube 1170 are fixedly coupled to certain points (the first coupling portion and the second coupling portion) as described above, respectively, the entire length of the guide tube 1170 may remain constant. Accordingly, the length of the blade wire 307 inserted into the guide tube 1170 may also remain constant.

Meanwhile, the guide tube 1170 according to the present disclosure may be formed of a flexible material and formed to be bendable. Accordingly, when the end tool 1100 performs a yaw motion around the first rotation shaft 1141 or a pitch motion around the third rotation shaft 1143, the guide tube 1170 may be bent while being deformed in shape corresponding thereto. In addition, when the guide tube 1170 is bent, the blade wire 307 placed thereinside is also bent.

Here, although the length of the guide tube 1170 is constant, the relative position and distance of the first coupling portion (i.e., the actuation hub 1190) and the second coupling portion (not shown) may be changed as the end tool 1100 is pitch-rotated or yaw-rotated, and thus a space for the guide tube 1170 to move by the changed distance is required. To this end, a pitch slit 1164 and a yaw slit 1165 may be provided in the end tool hub 1160 to form spaces for movement of the guide tube 1170. Such a configuration of the end tool hub 1160 will be described in detail later.

Meanwhile, as described above, the blade wire 307 is inserted through the guide tube 1170, and the blade wire 307 is relatively movable inside the guide tube 1170 with respect to the guide tube 1170. That is, when the blade wire 307 is pulled in a state in which the guide tube 1170 is fixed, the blade 1175 connected to the blade wire 307 is moved toward the proximal end 1105, and when the blade wire 307 is pushed, the blade 1175 connected to the blade wire 307 is moved toward the distal end 1104.

This will be described below in more detail.

The most reliable way to perform a cutting motion using the blade 1175 is by pushing and pulling the blade 1175 with the blade wire 307. In addition, in order for the blade wire 307 to push and pull the blade 1175, the guide tube 1170 that can guide the path of the blade wire 307 should be provided. When the guide tube 1170 does not guide the path of the blade wire 307 (i.e., does not hold the blade wire 307), a phenomenon may occur in which cutting is not performed and a middle portion of the blade wire 307 is curved even when the blade wire 307 is pushed. Accordingly, in order to reliably perform the cutting motion using the blade 1175, the blade wire 307 and the guide tube 1170 should be essentially included.

However, when the blade wire 307 is used to drive a cutting motion, the cutting should be performed while pushing the blade wire 307, and in this case, in order for the blade wire 307 to receive a force, a relatively stiff (i.e., non-bendable) wire should be used for the blade wire 307. However, the stiff (i.e., non-bendable) wire may have a small bendable range and may be permanently deformed when a force equal to or greater than a certain degree is applied.

In other words, in the case of a stiff (i.e., non-bendable) wire, there is a minimum radius of curvature that may be bent and spread without permanent deformation. In other words, when the wire or the guide tube is curved below a specific radius of curvature, both the wire and the guide tube may undergo permanent deformation while being bent, thereby restricting the capacity to perform cutting while moving backward and forward. Thus, it is necessary to keep the blade wire 307 curved while having a gentle curvature.

Thus, in order to prevent the blade wire 307 from being rapidly bent while passing through the pulleys, a space, in which the blade wire 307 can be gently bent, is required between the jaw 1103 (i.e., the actuation rotation shaft 1145) and the end tool hub 1160 (i.e., the first rotation shaft 1141 that is a yaw shaft).

To this end, according to the present disclosure, the first rotation shaft 1141, which is a yaw rotation shaft, and the actuation rotation shaft 1145 are separately provided, and the first rotation shaft 1141 and the actuation rotation shaft 1145 are spaced apart from each other by a certain distance, thereby forming a space in which the blade wire 307 and the guide tube 1170 can be gently bent.

As described above, since the blade wire 307 and the guide tube 1170 need to be connected to the blade 1175 through the end tool hub 1160, and a space in which the blade wire 307 and the guide tube 1170 can be bent in the end tool hub 1160 is necessary, in the present disclosure, 1) spaces, through which the blade wire 307/the guide tube 1170 can pass and simultaneously are bendable, that is, the pitch slit 1164 and the yaw slit 1165, are formed in the end tool hub 1160, 2) each of the rotation shafts is formed by being divided into two parts, and 3) a pitch round portion 1166 and a yaw round portion 1167 are additionally formed to guide the bending of the blade wire 307 and the guide tube 1170.

In other words, when one end portion of the guide tube 1170 is fixed in the connection portion 400, and the other end portion thereof is moved while performing pitch and yaw motions, the guide tube 1170 is curved in a direction, in which the gentlest curvature (hereinafter, referred to as "maximum gentle curvature") can be achieved in response to a change in a distance between both end portions thereof. As such, by achieving the maximum gentle curvature of the natural state, the motion of the blade wire 307 is smooth and the permanent deformation does not occur.

Thus, in order to secure the maximum gentle curvature, the pitch slit 1164 and the yaw slit 1165 are formed on the path of the guide tube 1170, and furthermore, the pitch round portion 1166 and the yaw round portion 1167 may be additionally formed in the end tool hub 1160. Accordingly, the guide tube 1170 may have such a shape that is the most similar to the maximum gentle curvature (although not having the maximum gentle curvature).

Hereinafter, the end tool hub 1160 will be described in more detail.

(End Tool Hub)

FIG. 147 is a perspective view illustrating the end tool hub of the surgical instrument for electrocautery of FIG. 140. FIGS. 148 and 149 are cut-away perspective views of the end tool hub of FIG. 147. FIGS. 150 and 151 are perspective views illustrating the end tool hub of FIG. 147. FIG. 152 is a side view illustrating the end tool hub of FIG. 147 and the guide tube. FIG. 153 is a plan view illustrating the end tool hub of FIG. 147 and the guide tube.

Referring to FIGS. 147 to 153, the end tool hub 1160 includes a body portion 1161, a first jaw pulley coupling portion 1162*a*, a second jaw pulley coupling portion 1162*b*, the first pitch pulley portion 1163*a*, the second pitch pulley portion 1163*b*, the pitch slit 1164, the yaw slit 1165, the pitch round portion 1166, the yaw round portion 1167, and the wire guide portion 1168. In addition, the wire guide portion 1168 includes the first wire guide portion 1168*a* and the second wire guide portion 1168*b*.

The first jaw pulley coupling portion 1162*a* and the second jaw pulley coupling portion 1162*b* may be formed in the end tool hub 1160 at the distal end side. Here, the first jaw pulley coupling portion 1162*a* and the second jaw pulley coupling portion 1162*b* are formed to face each other, and the pulley 1111 and the pulley 1121 are accommodated therein. Here, the first jaw pulley coupling portion 1162*a* and the second jaw pulley coupling portion 1162*b* may be formed to be approximately parallel to a plane perpendicular to the first rotation shaft 1141 that is a yaw rotation shaft.

The first jaw pulley coupling portion 1162*a* and the second jaw pulley coupling portion 1162*b* are connected by the body portion 1161. That is, the first jaw pulley coupling portion 1162*a* and the second jaw pulley coupling portion 1162*b*, which are parallel to each other, are coupled by the body portion 1161 formed in a direction approximately perpendicular to the first jaw pulley coupling portion 1162*a* and the second jaw pulley coupling portion 1162*b*, so that the first jaw pulley coupling portion 1162*a*, the second jaw pulley coupling portion 1162*b*, and the body portion 1161 form an approximately U-shape, in which the pulley 1111 and the pulley 1121 are accommodated.

In other words, it may be said that the first jaw pulley coupling portion 1162*a* and the second jaw pulley coupling portion 1162*b* are formed to extend in the X-axis direction from the body portion 1161.

Here, the pulley 1111, which is a first jaw pulley, is disposed close to the first jaw pulley coupling portion 1162*a* of the end tool hub 1160, and the pulley 1121, which is a second jaw pulley, is disposed close to the second jaw pulley coupling portion 1162*b* of the end tool hub 1160, and thus the yaw slit 1165 may be formed between the first jaw pulley coupling portion 1162*a* and the second jaw pulley coupling portion 1162*b*. In addition, at least a part of the blade assembly to be described later may be disposed in the yaw slit 1165. In other words, it may be said that at least a part of the guide tube 1170 of the blade assembly may be disposed between the first jaw pulley coupling portion 1162*a* and the second jaw pulley coupling portion 1162*b*. As such, by disposing the blade assembly including the guide tube 1170 between the pulley 1111, which is a first jaw pulley, and the pulley 1121, which is a second jaw pulley, the end tool 1100 is able to perform the cutting motion using the blade 1175 in addition to the pitch and yaw motions. This will be described in more detail later.

Meanwhile, a through hole is formed in the first jaw pulley coupling portion 1162*a* such that the first rotation shaft 1141 passes through the first jaw pulley coupling portion 1162*a* and the pulley 1111 and axially couples the first jaw pulley coupling portion 1162*a* and the pulley 1111. In addition, a through hole is formed in the second jaw pulley coupling portion 1162*b* such that the first rotation shaft 1141 passes through the second jaw pulley coupling portion 1162*b* and the pulley 1121 and axially couples the second jaw pulley coupling portion 1162*b* and the pulley 1121.

Here, as described above, the first rotation shaft 1141, which is a yaw rotation shaft, may be formed by being divided into two parts of the first sub-shaft 1141*a* and the second sub-shaft 1141*b*, and the guide tube 1170 may pass between the first sub-shaft 1141*a* and the second sub-shaft 1141*b* of the first rotation shaft 1141.

In addition, the yaw slit 1165 may be formed between the first jaw pulley coupling portion 1162*a* and the second jaw pulley coupling portion 1162*b*. Since the yaw slit 1165 is formed in the end tool hub 1160 as described above, the guide tube 1170 may pass through the inside of the end tool hub 1160.

In other words, the first rotation shaft 1141 is vertically separated into two parts without passing through the end tool hub 1160, and the yaw slit 1165 may be formed on a plane perpendicular to the first rotation shaft 1141 in the vicinity of the first rotation shaft 1141. Accordingly, the guide tube 1170 is movable (i.e., movable left and right) in the yaw slit 1165 while passing through the vicinity of the first rotation shaft 1141.

Meanwhile, the yaw round portion 1167 may be further formed in the body portion 1161. The yaw round portion 1167 may be formed to be rounded so as to have a predetermined curvature. In detail, when viewed from a plane perpendicular to the first rotation shaft 1141 that is a yaw rotation shaft, the yaw round portion 1167 may be formed to be rounded so as to have a predetermined curvature. For example, the yaw round portion 1167 may be formed in a fan shape, and may be formed along a path in which the guide tube 1170 is bent on an XY plane. The yaw round portion 1167 as described above may serve to guide the path of the guide tube 1170 when the end tool 1100 yaw-rotates.

The wire guide portion 1168, which guides a path of the wire passing through the inside of the end tool hub 1160, is formed at one side of the body portion 1161. Here, the wire guide portion 1168 includes the first wire guide portion 1168a and the second wire guide portion 1168b. Here, the first wire guide portion 1168a may be formed on an inner side surface of the first jaw pulley coupling portion 1162a. In addition, the second wire guide portion 1168b may be formed on an inner side surface of the second jaw pulley coupling portion 1162b.

Here, the wire guide portion 1168 may be formed in a cylindrical shape with a cross section that is approximately semi-circular. In addition, the semi-circular portion may be disposed to protrude toward the pulley 1111 and the pulley 1121. In other words, it may be said that the wire guide portion 1168 is formed to protrude toward a space formed by the first jaw pulley coupling portion 1162a, the second jaw pulley coupling portion 1162b, and the body portion 1161. In other words, it may be said that, in the wire guide portion 1168, a region adjacent to the first jaw pulley coupling portion 1162a and the second jaw pulley coupling portion 1162b is formed to have a cross section that is curved with a predetermined curvature.

Alternatively, in other words, it may be also said that the wire guide portion 1168 functions as a kind of pulley member, which guides the paths of the wire 305 and the wire 302 by winding the wire 305 and the wire 302 around an outer circumferential surface thereof. However, here, the wire guide portion 1168 is not a member that rotates around a certain shaft as the original meaning pulley does, and it may be said that the wire guide portion 1168 is formed to be fixed as a portion of the end tool hub 1160 and performs some similar functions of a pulley by winding a wire therearound.

Here, the wire guide portion 1168 is illustrated in the drawing as being formed in a cylindrical shape with a cross section that is approximately semi-circular. That is, at least a part of the cross section of the wire guide portion 1168 on the XY plane is illustrated as having a certain arc shape. However, the concept of the present disclosure is not limited thereto, and the cross section may have a predetermined curvature like an oval or a parabola, or a corner of a polygonal column is rounded to a certain degree, so that the cross section may have various shapes and sizes suitable for guiding the paths of the wire 305 and the wire 302.

Here, a guide groove for guiding the paths of the wire 305 and the wire 302 well may be further formed in a portion of the wire guide portion 1168, which is in contact with the wire 305 and the wire 302. The guide groove may be formed in the form of a groove recessed to a certain degree from a protruding surface of the wire guide portion 1168.

Here, although the guide groove is illustrated in the drawing as being formed in the entire arc surface of the wire guide portion 1168, the concept of the present disclosure is not limited thereto, and the guide groove may be formed only in a portion of the arc surface of the wire guide portion 1168 as necessary.

As described above, by further forming the guide groove in the wire guide portion 1168, unnecessary friction between the wires is reduced, so that durability of the wires may be improved.

The first pitch pulley portion 1163a and the second pitch pulley portion 1163b, which serve as end tool pitch pulleys, may be formed on the end tool hub 1160 at the proximal end side. Here, the first pitch pulley portion 1163a and the second pitch pulley portion 1163b may be formed to face each other. Here, the first pitch pulley portion 1163a and the second pitch pulley portion 1163b may be formed to be approximately parallel to a plane perpendicular to the third rotation shaft 1143, which is a pitch rotation shaft.

In detail, one end portion of the end tool hub 1160 is formed in a disk shape similar to a pulley, and grooves around which a wire may be wound may be formed on an outer circumferential surface of the one end portion, thereby forming the first pitch pulley portion 1163a and the second pitch pulley portion 1163b The wire 303 and the wire 304 described above are coupled to the first pitch pulley portion 1163a and the second pitch pulley portion 1163b, which serve as end tool pitch pulleys, and a pitch motion is performed while the end tool hub 1160 rotates around the third rotation shaft 1143.

Meanwhile, although not shown in the drawings, the pitch pulley may be formed as a separate member from the end tool hub 1160 and coupled to the end tool hub 1160.

The first pitch pulley portion 1163a and the second pitch pulley portion 1163b may be connected by the body portion 1161. That is, the first pitch pulley portion 1163a and the second pitch pulley portion 1163b, which are parallel to each other, are coupled by the body portion 1161 formed in a direction approximately perpendicular to the first pitch pulley portion 1163a and the second pitch pulley portion 1163b, and thus the first pitch pulley portion 1163a, the second pitch pulley portion 1163b, and the body portion 1161 may form an approximately U-shape.

In other words, it may be said that the first pitch pulley portion 1163a and the second pitch pulley portion 1163b are formed to extend from the body portion 1161 in the X-axis direction.

Meanwhile, a through hole is formed in the first pitch pulley portion 1163a so that the third rotation shaft 1143 may pass through the first pitch pulley portion 1163a. In addition, a through hole is formed in the second pitch pulley portion 1163b so that the third rotation shaft 1143 may pass through the second pitch pulley portion 1163b.

In this case, as described above, the third rotation shaft 1143, which is a pitch rotation shaft, may be formed by being divided into two parts of the first sub-shaft 1143a and the second sub-shaft 1143b, and the guide tube 1170 may pass between the first sub-shaft 1143a and the second sub-shaft 1143b of the third rotation shaft 1143.

The pitch slit 1164 may be formed between the first pitch pulley portion 1163a and the second pitch pulley portion 1163b. Since the pitch slit 1164 is formed in the end tool hub 1160 as described above, the guide tube 1170 may pass through the inside of the end tool hub 1160.

In other words, the third rotation shaft 1143 is horizontally separated into two parts without passing through the end tool hub 1160, and the pitch slit 1164 may be formed on a plane perpendicular to the third rotation shaft 1143 in the vicinity of the third rotation shaft 1143. Accordingly, the guide tube 1170 is movable (movable up and down) in the pitch slit 1164 while passing through the vicinity of the third rotation shaft 1143.

Meanwhile, the pitch round portion 1166 may be further formed in the body portion 1161. The pitch round portion 1166 may be formed to be rounded to have a predetermined curvature. In detail, when viewed from a plane perpendicular to the third rotation shaft 1143, which is a pitch rotation shaft, the pitch round portion 1166 may be formed to be rounded to have a predetermined curvature. For example, the pitch round portion 1166 may be formed in a fan shape, and formed along a path in which the guide tube 1170 is bent on the XZ plane. The pitch round portion 1166 as described above may serve to guide the path of the guide tube 1170 when the end tool 1100 pitch-rotates.

Here, the pitch slit 1164 and the yaw slit 1165 may be formed to be connected to each other. Accordingly, the guide tube 1170 and the blade wire 307 located therein may be disposed to completely pass through the inside of the end tool hub 1160. In addition, the blade 1175 coupled to one end portion of the blade wire 307 may linearly reciprocate inside the first jaw 1101 and the second jaw 1102.

As described above, since the blade wire 307 and the guide tube 1170 need to be connected to the blade 1175 through the end tool hub 1160, and a space in which the blade wire 307 and the guide tube 1170 can be bent in the end tool hub 1160 is necessary, in the present disclosure, 1) spaces, through which the blade wire 307/the guide tube 1170 can pass and simultaneously are bendable, that is, the pitch slit 1164 and the yaw slit 1165, are formed in the end tool hub 1160, 2) the rotation shafts are formed by being divided into two parts, and 3) the pitch round portion 1166 and the yaw round portion 1167 are additionally formed to guide the bending of the blade wire 307/the guide tube 1170.

Hereinafter, the role and function of the wire guide portion 1168 will be described in more detail.

The wire guide portion 1168 may be in contact with the wire 305 and the wire 302 and may change the arrangement path of the wire 305 and the wire 302 to a certain degree to serve to increase a rotation radius of each of the first jaw 1101 and the second jaw 1102.

That is, when the auxiliary pulleys are not disposed, each of the pulley 1111, which is a first jaw pulley, and the pulley 1121, which is a second jaw pulley, may rotate up to a right angle, but in the fourth embodiment of the present disclosure, by additionally providing the wire guide portion 1168 in the end tool hub 1160, the maximum rotation angle of each pulley may be increased.

This enables a motion in which two jaws of the end tool 1100 have to be spread apart for an actuation motion in a state in which the two jaws are yaw-rotated together by 90°. In other words, the range of yaw rotation in which an actuation motion is possible may be increased through the configuration of the wire guide portion 1168 of the end tool hub 1160. In other words, the range of yaw rotation in which an actuation motion is possible may be increased through the configuration of the wire guide portion 1168 of the end tool hub 1160. Furthermore, by forming the wire guide portion 1168 in the end tool hub 1160, which already exists, without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also, the length of the end tool is shortened by as much as the size of the auxiliary pulley, so that the length of the end tool is shortened during a pitch motion. Accordingly, a surgical motion may be more easily performed in a narrow space.

This will be described below in more detail.

In the end tool 1100 of the surgical instrument according to the fourth embodiment of the present disclosure, the arrangement path of the wires may be changed without a separate structure by forming the wire guide portion 1168 capable of changing the path of the wire on an inner side wall of the end tool hub 1160. As described above, as the arrangement path of the wire 305 and the wire 302 is changed to a certain degree by forming the wire guide portion 1168 in the end tool hub 1160, a tangential direction of the wire 305 and the wire 302 is changed, and accordingly, rotation angles of the fastening member 323 and the fastening member 326 that couple respective wires and pulleys may be increased.

That is, the fastening member 326 that couples the wire 302 and the pulley 1121 is rotatable until being located on a common internal tangent of the pulley 1121 and the wire guide portion 1168. Similarly, the fastening member (see 323 of FIG. 6) that couples the wire 305 and the pulley 1111 is rotatable until being located on a common internal tangent of the pulley 1111 and the wire guide portion 1168, so that a rotation angle of the fastening member (see 323 of FIG. 6) may be increased.

In other words, the wire 301 and the wire 305 wound around the pulley 1111 by the wire guide portion 1168 are disposed on one side with respect to a plane perpendicular to the Y-axis and passing through the X-axis. Simultaneously, the wire 302 and the wire 306 wound around the pulley 1121 by the wire guide portion 1168 are disposed on the other side with respect to the plane perpendicular to the Y-axis and passing through the X-axis.

In other words, the pulley 1113 and the pulley 1114 are disposed at one side with respect to the plane perpendicular to the Y-axis and passing through the X-axis, and the pulley 1123 and the pulley 1124 are disposed at the other side with respect to the plane perpendicular to the Y-axis and passing through the X-axis.

In other words, the wire 305 is located on the internal tangent of the pulley 1111 and the wire guide portion 1168, and a rotation angle of the pulley 1111 is increased due to the wire guide portion 1168. In addition, the wire 302 is located on the internal tangent of the pulley 1121 and the wire guide portion 1168, and the rotation angle of the pulley 1121 is increased due to the wire guide portion 1168.

In the present embodiment in which an auxiliary pulley is not formed and the wire guide portion 1168 capable of changing the path of a wire is formed on the inner side wall of the end tool hub 1160, the length of the end tool of the surgical instrument may be shortened as compared to the surgical instrument of the first embodiment in which a separate auxiliary pulley is formed. Since the length of the end tool is shortened as described above, a surgical operator may easily manipulate a surgical instrument, and a side effect of surgery may be reduced when the surgery is performed in a narrow surgical space in the human body.

According to the present disclosure as described above, the rotation radii of the pulley 1111, which is a first jaw pulley, and the pulley 1121, which is a second jaw pulley, increase, so that a yaw motion range in which a normal opening/closing actuation motion and a normal cutting motion can be performed may be increased.

(Actuation Hub)

Figure 154A:
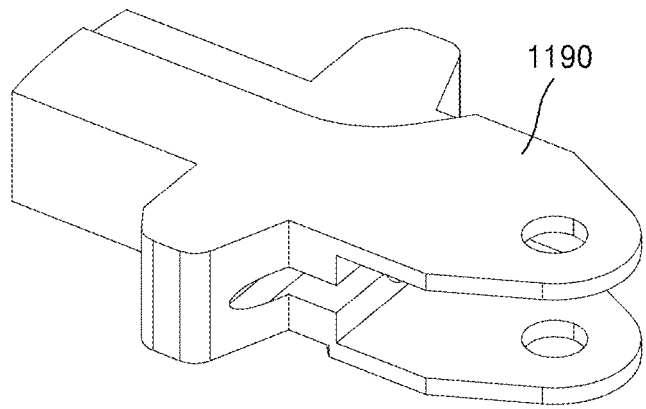
FIGS. 154A and 154B are a perspective view and a cut-away perspective view illustrating an actuation hub of the surgical instrument for electrocautery of FIG. 147 of FIG. 140.
Figure 154B:
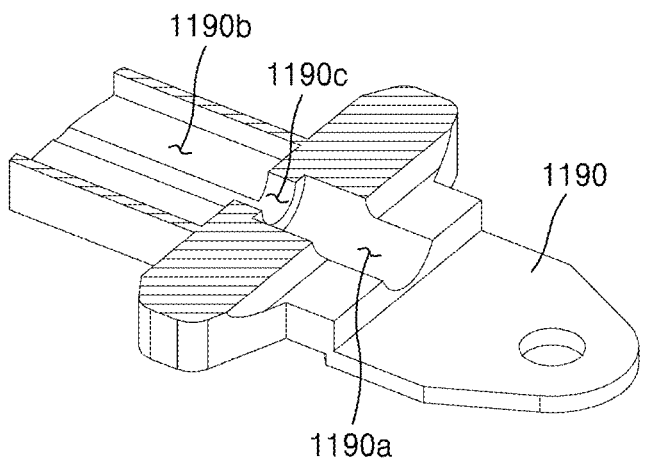

FIGS. 154A and 154B are a perspective view and a cut-away perspective view illustrating an actuation hub of the surgical instrument for electrocautery of FIG. 147 of FIG. 140. FIG. 155 is a view illustrating a state in which the guide tube, the blade wire, and the blade are mounted on the actuation hub illustrated in the cut-away perspective view of FIG. 154. FIG. 156 is an exploded perspective view illustrating the end tool of the surgical instrument for electrocautery of FIG. 140.

Referring to FIGS. 154 to 156, the actuation hub 1190 may be formed in the form of a box having a hollow therein. In addition, the actuation hub 1190 is coupled to each of the first jaw 1101 and the second jaw 1102. In detail, the actuation hub 1190 is axially coupled to the first jaw 1101 by a first actuation rotation shaft 1145*a*. In addition, the actuation hub 1190 is axially coupled to the second jaw 1102 by a second actuation rotation shaft 1145*b*. In this case, the first actuation rotation shaft 1145*a* and the second actuation rotation shaft 1145*b* may be disposed on the same line in a Z-axis direction.

In addition, a tube seating portion 1190*a* may be formed inside the actuation hub 1190, and one end portion of the guide tube 1170 may be fixedly coupled to the tube seating portion 1190*a*.

Meanwhile, a blade accommodation portion 1190*b* may be formed inside the actuation hub 1190, and the blade 1175 may be accommodated in the blade accommodation portion 1190*b*.

In addition, a wire through-hole 1190*c* may be formed between the tube seating portion 1190*a* and the blade accommodation portion 1190*b* inside the actuation hub 1190.

That is, the tube seating portion 1190*a*, the wire through-hole 1190*c*, and the blade accommodation portion 1190*b* are sequentially formed inside the actuation hub 1190, and the blade wire 307 may pass through the inside of the actuation hub 1190 to be connected to the blade 1175.

As described above, by providing the actuation hub 1190 to which the guide tube 1170 is coupled between the first jaw 1101 and the second jaw 1102, the guide tube 1170 may not be curved, or the angle at which the guide tube 1170 is curved may be reduced, even when the first jaw 1101 or the second jaw 1102 rotates around the first rotation shaft 1141 or the actuation rotation shaft 1145.

In detail, in a case in which the guide tube 1170 is directly coupled to the first jaw 1101 or the second jaw 1102, when the first jaw 1101 or the second jaw 1102 rotates, one end portion of the guide tube 1170 also rotates together with the first jaw 1101 or the second jaw 1102, causing the guide tube 1170 to be curved.

On the other hand, in a case in which the guide tube 1170 is coupled to the actuation hub 1190, which is independent of the rotation of the jaw 1103, as in the present embodiment, even when the first jaw 1101 or the second jaw 1102 rotates, the guide tube 1170 may not be curved, or the angle at which the guide tube 1170 is curved may be reduced even when the guide tube 1170 is curved.

That is, by changing the direct connection between the guide tube 1170 and the jaw 1103 by the actuation hub 1190 to an indirect connection, the degree to which the guide tube 1170 is curved by the rotation of the jaw 1103 may be reduced.

(First and Second Jaws and Actuation Motion)

Hereinafter, a coupling structure of the first jaw 1101 and the second jaw 1102 of the end tool 1100 of the surgical instrument 10 of FIG. 140 will be described in more detail.

Referring to FIGS. 157 to 162 and the like, the first jaw 1101 includes a movable coupling hole 1101*c*, a jaw pulley coupling hole 1101*d*, and a shaft pass-through portion 1101*c*.

The first jaw 1101 is formed entirely in an elongated bar shape, and formed to be rotatable together with the pulley 1111 by being coupled to the pulley 1111 at one end portion thereof.

Meanwhile, the movable coupling hole 1101*c*, the jaw pulley coupling hole 1101*d*, and the shaft pass-through portion 1101*e* may be formed in the first jaw 1101 at a side coupled to the pulley 1111, that is, at the proximal end side.

Here, the movable coupling hole 1101*c* may be formed to have a predetermined curvature, and may be formed in an approximately elliptical shape. A shaft coupling portion 1111*a* of the pulley 1111, which will be described later, may be fitted into the movable coupling hole 1101*c*. Here, a short radius of the movable coupling hole 1101*c* may be formed to be substantially the same as or slightly greater than a radius of the shaft coupling portion 1111*a*. Meanwhile, a long radius of the movable coupling hole 1101*c* may be formed to be greater than the radius of the shaft coupling portion 1111*a*. Thus, in a state in which the shaft coupling portion 1111*a* of the pulley 1111 is fitted into the movable coupling hole 1101*c* of the first jaw 1101, the shaft coupling portion 1111*a* is movable to a certain degree in the movable coupling hole 1101*c*. This will be described in more detail below.

Meanwhile, the jaw pulley coupling hole 1101*d* is formed in the form of a cylindrical hole, and a jaw coupling portion 1111*b* of the pulley 1111, which will be described later, may be fitted into the jaw pulley coupling hole 1101*d*. Here, a radius of the jaw pulley coupling hole 1101*d* may be formed to be substantially the same as or slightly greater than a radius of the jaw coupling portion 1111*b*. Thus, the jaw coupling portion 1111*b* of the pulley 1111 may be formed to be rotatably coupled to the jaw pulley coupling hole 1101*d* of the first jaw 1101. This will be described in more detail below.

Meanwhile, the shaft pass-through portion 1101*e* may be formed in the first jaw 1101 at the distal end side relative to the movable coupling hole 1101*c* and the jaw pulley coupling hole 1101*d*. The shaft pass-through portion 1101*e* may be formed in the form of a hole, and the actuation rotation shaft 1145, which is a jaw rotation shaft, may be inserted through the shaft pass-through portion 1101*e*.

The second jaw 1102 includes a movable coupling hole 1102*c*, a jaw pulley coupling hole 1102*d*, and a shaft pass-through portion 1102*e*.

The second jaw 1102 is formed entirely in an elongated bar shape, and formed to be rotatable together with the pulley 1121 by being coupled to the pulley 1121 at one end portion thereof.

Meanwhile, the movable coupling hole 1102*c*, the jaw pulley coupling hole 1102*d*, and the shaft pass-through portion 1102*e* may be formed in the second jaw 1102 at a side coupled to the pulley 1111, that is, at the proximal end side.

Here, the movable coupling hole 1102*c* may be formed to have a predetermined curvature, and may be formed in an approximately elliptical shape. A shaft coupling portion 1121*a* of the pulley 1121, which will be described later, may be fitted into the movable coupling hole 1102*c*. Here, a short radius of the movable coupling hole 1102*c* may be formed to be substantially the same as or slightly greater than a radius of the shaft coupling portion 1121*a*. Meanwhile, a long radius of the movable coupling hole 1102*c* may be formed to be greater than the radius of the shaft coupling portion 1121*a*. Thus, in a state in which the shaft coupling portion 1121*a* of the pulley 1121 is fitted into the movable coupling hole 1102*c* of the second jaw 1102, the shaft coupling portion 1121*a* is movable to a certain degree in the movable coupling hole 1102*c*. This will be described in more detail below.

Meanwhile, the jaw pulley coupling hole 1102*d* is formed in the form of a cylindrical hole, and a jaw coupling portion 1121*b* of the pulley 1121, which will be described later, may be fitted into the jaw pulley coupling hole 1102*d*. Here, a radius of the jaw pulley coupling hole 1102*d* may be formed to be substantially the same as or slightly greater than a radius of the jaw coupling portion 1121*b*. Thus, the jaw coupling portion 1121*b* of the pulley 1121 may be formed to be rotatably coupled to the jaw pulley coupling hole 1102d of the second jaw 1102. This will be described in more detail below.

Meanwhile, the shaft pass-through portion 1102e may be formed in the second jaw 1102 at the distal end side relative to the movable coupling hole 1102c and the jaw pulley coupling hole 1102d. The shaft pass-through portion 1102e may be formed in the form of a hole, and the actuation rotation shaft 1145, which is a jaw rotation shaft, may be inserted through the shaft pass-through portion 1102c.

The pulley 1111, which is a first jaw pulley, may include the shaft coupling portion 1111a and the jaw coupling portion 1111b. The pulley 1111 is formed entirely in the form of a rotatable disk, and the shaft coupling portion 1111a and the jaw coupling portion 1111b may be formed to protrude to a certain degree from one surface of the pulley 1111. As described above, the shaft coupling portion 1111a of the pulley 1111 may be fitted into the movable coupling hole 1101c of the first jaw 1101, and the jaw coupling portion 1111b of the pulley 1111 may be fitted into the jaw pulley coupling hole 1101d of the first jaw 1101. The pulley 1111 may be formed to be rotatable with the first rotation shaft 1141, which is an end tool jaw pulley rotation shaft, as the center of rotation.

Meanwhile, the pulley 1121, which is a second jaw pulley, may include the shaft coupling portion 1121a and the jaw coupling portion 1121b. The pulley 1121 is formed entirely in the form of a rotatable disk, and the shaft coupling portion 1121a and the jaw coupling portion 1121b may be formed to protrude to a certain degree from one surface of the pulley 1121. As described above, the shaft coupling portion 1112a of the pulley 1112 may be inserted into the movable coupling hole 1102c of the second jaw 1102, and the jaw coupling portion 1112b of the pulley 1112 may be inserted into the jaw pulley coupling hole 1102d of the second jaw 1102. The pulley 1121 may be formed to be rotatable with the first rotation shaft 1141, which is an end tool jaw pulley rotation shaft, as the center of rotation.

The coupling relationship between the components described above is as follows.

The first rotation shaft 1141, which is an end tool jaw pulley rotation shaft, is sequentially inserted through the shaft coupling portion 1111a of the pulley 1111, the movable coupling hole 1101c of the first jaw 1101, the movable coupling hole 1102c of the second jaw 1102, and the shaft coupling portion 1121a of the pulley 1121.

The first actuation rotation shaft 1145a is sequentially inserted through the shaft pass-through portion 1101e of the first jaw 1101 and the actuation hub 1190 The second actuation rotation shaft 1145b is sequentially inserted through the shaft pass-through portion 1102e of the second jaw 1102 and the actuation hub 1190.

The shaft coupling portion 1111a of the pulley 1111 is fitted into the movable coupling hole 1101c of the first jaw 1101, and the jaw coupling portion 1111b of the pulley 1111 is fitted into the jaw pulley coupling hole 1101d of the first jaw 1101.

At this time, the jaw pulley coupling hole 1101d of the first jaw 1101 and the jaw coupling portion 1111b of the pulley 1111 are axially coupled to each other so as to be rotatable, and the movable coupling hole 1101c of the first jaw 1101 and the shaft coupling portion 1111a of the pulley 1111 are movably coupled to each other (here, "movably coupled" means that the shaft coupling portion 1111a of the pulley 1111 is coupled so as to be movable to a certain degree in the movable coupling hole 1101c of the first jaw 1101).

The shaft coupling portion 1121a of the pulley 1121 is fitted into the movable coupling hole 1102c of the second jaw 1102, and the jaw coupling portion 1121b of the pulley 1121 is fitted into the jaw pulley coupling hole 1102d of the second jaw 1102.

At this time, the jaw pulley coupling hole 1102d of the second jaw 1101 and the jaw coupling portion 1121b of the pulley 1121 are axially coupled to each other to be rotatable, and the movable coupling hole 1102c of the second jaw 1102 and the shaft coupling portion 1121a of the pulley 1121 are movably coupled to each other.

Here, the pulley 1111 and the pulley 1121 rotate around the first rotation shaft 1141, which is an end tool jaw pulley rotation shaft. Meanwhile, the first jaw 1101 and the second jaw 1102 rotate around the actuation rotation shaft 1145, which is a jaw rotation shaft. That is, the pulley 1111 and the first jaw 1101 have different shafts of rotation. Similarly, the pulley 1121 and the second jaw 1102 have different shafts of rotation.

That is, the rotation angle of the first jaw 1101 is limited to a certain degree by the movable coupling hole 1101c, but the first jaw 1101 essentially rotates around the actuation rotation shaft 1145, which is a jaw rotation shaft. Similarly, the rotation angle of the second jaw 1102 is limited to a certain degree by the movable coupling hole 1102c, but the second jaw 1102 essentially rotates around the actuation rotation shaft 1145, which is a jaw rotation shaft.

Amplification of a grip force due to the coupling relationship between the above-described components will be described.

In the surgical instrument 110 according to an embodiment of the present disclosure, the coupling structure of the first jaw 1101 and the second jaw 1102 forms an X-shaped structure, and thus, when the first jaw 1101 and the second jaw 1102 rotate in a direction of approaching each other (i.e., when the first jaw 1101 and the second jaw 1102 are closed), the grip force is greater in a direction in which the first jaw 1101 and the second jaw 1102 are closed. This will be described below in more detail.

As described above, in motions of the first jaw 1101 and the second jaw 1102 being opened and closed, there are two shafts that serve as the centers of rotation for the first jaw 1101 and the second jaw 1102. That is, the first jaw 1101 and the second jaw 1102 perform the opening and closing motion around two shafts including the first rotation shaft 1141 and the actuation rotation shaft 1145. At this time, the centers of rotation of the first jaw 1101 and the second jaw 1102 become the actuation rotation shaft 1145, and the centers of rotation of rotation of the pulley 1111 and the pulley 1121 become the first rotation shaft 1141. At this time, the first rotation shaft 1141 is a shaft whose position is relatively fixed, and the actuation rotation shaft 1145 is a shaft whose position is relatively moved linearly. In other words, when the pulley 1111 and the pulley 1121 rotate in a state in which the position of the first rotation shaft 1141 is fixed, the first jaw 1101 and the second jaw 1102 are opened/closed while the actuation rotation shaft 1145, which is a rotation shaft of the first jaw 1101 and the second jaw 1102, is moved backward and forward. This will be described below in more detail.

In FIG. 161, r1 is a distance from the jaw coupling portion 1121b of the pulley 1121 to the shaft coupling portion 1121a, and a length thereof is constant. Thus, a distance from the first rotation shaft 1141 inserted into the shaft coupling portion 1121a to the jaw coupling portion 1121b is also constant as r1.

Meanwhile, r2 of FIG. 161 is a distance from the jaw pulley coupling hole 1102d of the second jaw 1102 to the shaft pass-through portion 1102e, and a length thereof is constant. Thus, a distance from the jaw coupling portion 1121b of the pulley 1121 inserted into the jaw pulley coupling hole 1102d to the rotation shaft 1145 inserted into the shaft pass-through portion 1102e is also constant as r2.

That is, the lengths of r1 and r2 remain constant. Accordingly, when the pulley 1111 and the pulley 1121 rotate in the directions of an arrow B1 of FIG. 160 and an arrow B2 of FIG. 161, respectively, around the first rotation shaft 1141 to perform a closing motion, the first jaw 1101 and the second jaw 1102 rotate around the actuation rotation shaft 1145 as the angle between r1 and r2 changes while the lengths of r1 and r2 remain constant, and at this time, the actuation rotation shaft 1145 itself is also linearly moved (i.e., is moved forward/backward) by as much as an arrow C1 of FIG. 160 and an arrow C2 of FIG. 161.

That is, assuming that the position of the first rotation shaft 1141, which is an end tool jaw pulley rotation shaft, is fixed, when the first jaw 1101 and the second jaw 1102 are closed, a force is applied in a direction in which the actuation rotation shaft 1145, which is a jaw rotation shaft, is moved forward (i.e., toward the distal end), and thus the grip force in the direction in which the first jaw 1101 and the second jaw 1102 are closed becomes larger.

In other words, since the lengths of r1 and r2 remain constant when the second jaw 1102 rotates around the actuation rotation shaft 1145, when the pulley 1121 rotates around the first rotation shaft 1141, the angle between r1 and r2 changes while the lengths of r1 and r2 remain constant. That is, 02, which is the angle between r1 and r2 in a state in which the second jaw 1102 is open as shown in FIG. 161A, is greater than 01, which is the angle between r1 and r2 in a state in which the second jaw 1102 is closed as shown in FIG. 161B.

Thus, when the second jaw 1102 rotates from the open state to the close state, the angle between r1 and r2 changes, and a force is applied in a direction in which the actuation rotation shaft 1145 is moved forward.

In this case, since the first rotation shaft 1141 is a shaft whose position is relatively fixed, the actuation rotation shaft 1145 is moved forward in the direction of the arrow C1 of FIG. 160 and the direction of the arrow C2 of FIG. 161, and the grip force is further increased in a direction in which the second jaw 1102 is closed.

In other words, when the pulley 1111 and the pulley 1121 rotate around the first rotation shaft 1141, which is a shaft whose relative position is fixed, the angle θ between r1 and r2 changes while the distance between r1 and r2 remains constant. In addition, when the angle θ changes as described above, the first jaw 1101 and the second jaw 1102 push or pull the actuation rotation shaft 1145, and thus the actuation rotation shaft 1145 is moved forward or backward. In this case, when the first jaw 1101 and the second jaw 1102 are rotated in the direction of closing, the grip force is further increased as the actuation rotation shaft 1145 is moved forward in the directions of the arrow C1 of FIG. 160 and the arrow C2 of FIG. 161. On the contrary, when the first jaw 1101 and the second jaw 1102 are rotated in the direction of opening, the actuation rotation shaft 1145 is moved backward in directions opposite to the arrow C1 of FIG. 160 and the arrow C2 of FIG. 161.

With this configuration, the grip force becomes stronger when the first jaw 1101 and the second jaw 1102 are closed, thereby enabling a surgical operator to perform the actuation motion powerfully even with a small force.

(Components Associated with Cautery and Cutting)

Subsequently, referring to FIGS. 140 to 162 and the like, the end tool 1100 of the fourth embodiment of the present disclosure may include the first jaw 1101, the second jaw 1102, a first electrode 1151, a second electrode 1152, the guide tube 1170, and the blade 1175 in order to perform cauterizing and cutting motions.

Here, components related to the driving of the blade, such as the guide tube 1170 and the blade 1175, may be collectively referred to as a blade assembly. In an embodiment of the present disclosure, by disposing the blade assembly including the guide tube 1170 and the blade 1175 between the pulley 1111, which is a first jaw pulley, and the pulley 1121, which a second jaw pulley, the end tool 1100 is able to perform the cutting motion using the blade 1175 in addition to the pitch and yaw motions. This will be described in more detail.

As described above, the first jaw 1101 is connected to the first jaw pulley 1111 and rotates around the first rotation shaft 1141 together with the first jaw pulley 1111 when the first jaw pulley 1111 rotates around the first rotation shaft 1141.

Meanwhile, the first electrode 1151 may be formed on a surface of the first jaw 1101 facing the second jaw 1102. In addition, the second electrode 1152 may be formed on a surface of the second jaw 1102 facing the first jaw 1101.

At this time, a slit 1151a may be formed in the first electrode 1151, and the blade 1175 may move along the slit 1151a. In addition, a slit 1152a may be formed in the second electrode 1152, and the blade 1175 may move along the slit 1152a.

Meanwhile, although not shown in the drawings, a spacer (not shown) may be formed between the first jaw 1101 and the first electrode 1151, and a spacer (not shown) may be formed between the second jaw 1102 and the second electrode 1152. The spacer (not shown) may include an insulating material such as ceramic. Alternatively, the first jaw 1101 and the second jaw 1102 may themselves be made of a nonconductor such that the first electrode 1151 and the second electrode 1152 may be maintained to be insulated from each other without a separate insulator until the first electrode 1151 and the second electrode 1152 are in contact with each other.

Meanwhile, although not shown in the drawings, one or more sensors (not shown) may be further formed on at least one of the first jaw 1101 or the second jaw 1102. The sensor (not shown) may be formed to measure at least some of current, voltage, resistance, impedance, and temperature during the cautery by locating tissue between the first jaw 1101 and the second jaw 1102 and passing a current through the first electrode 1151 and the second electrode 1152.

Alternatively, instead of providing a separate sensor, monitoring and controlling of at least some of current, voltage, resistance, impedance, and temperature may be directly performed by a generator (not illustrated) which supplies power to the electrodes.

An edge portion formed sharply and configured to cut tissue may be formed in one region of the blade 1175. The tissue disposed between the first jaw 1101 and the second jaw 1102 may be cut as at least a part of the blade 1175 moves between the distal end 1104 and the proximal end 1105 of the end tool 1100.

Here, the guide tube 1170 and the blade 1175 disposed between the pulley 1111 and the pulley 1121 are provided in the end tool 1100 of the electric cauterization surgical instrument 10 according to an embodiment of the present disclosure. In addition, by providing the guide tube 1170 and the blade 1175, a multi-joint/multi-degree-of-freedom surgical instrument capable of pitch/yaw/actuation motions may also perform cauterizing and cutting motions. This will be described below in more detail.

So far, various types of surgical instruments for electrocautery have been developed. Among the various types of surgical instruments for electrocautery, a blood vessel resection device called "Advanced Energy Device" or "Vessel Sealer" has a sensing function added to the existing bipolar cautery method, so that power of different polarities may be supplied to two electrodes, and after denaturing a vessel with the heat generated therefrom for hemostasis, the stanched part may be cut with a blade. At this time, the impedance of the tissue (or blood vessel) while the current is flowing is measured to determine whether the cauterization is completed, and when the cauterization is completed, the current supply is automatically stopped, and the tissue is cut with the blade.

In the case of such a bipolar-type blood vessel resection device, it is essential to have a blade to cut the tissue after cauterization, and the end tool needs to be equipped with a mechanism for facilitating a linear motion of the blade, and thus joint movements such as pitch/yaw movements are not possible in most cases.

Meanwhile, there have been attempts to implement joint movements using fexible joints with multiple nodes connected in the bipolar-type blood vessel resection device, but in this case, a rotation angle is limited and it is difficult to achieve accurate motion control of the end tool.

On the other hand, in the case of a method that utilizes vibration of ultrasonic waves to perform hemostasis and cutting, it is not feasible to provide joints due to the physical properties of ultrasonic waves.

To address these problems, the end tool 1100 of the electric cauterization surgical instrument 10 according to an embodiment of the present disclosure includes the guide tube 1170 disposed between the pulley 1111 and the pulley 1121, and the blade 1175 that moves between a first position and a second position in response to the movement of the blade wire 307 disposed inside the guide tube 1170. In addition, by providing the guide tube 1170 and the blade 1175 as described above, pitch/yaw/actuation motions may also be performed using a pulley/wire in a bipolar-type surgical instrument for cauterizing and cutting tissue.

Figure 163:
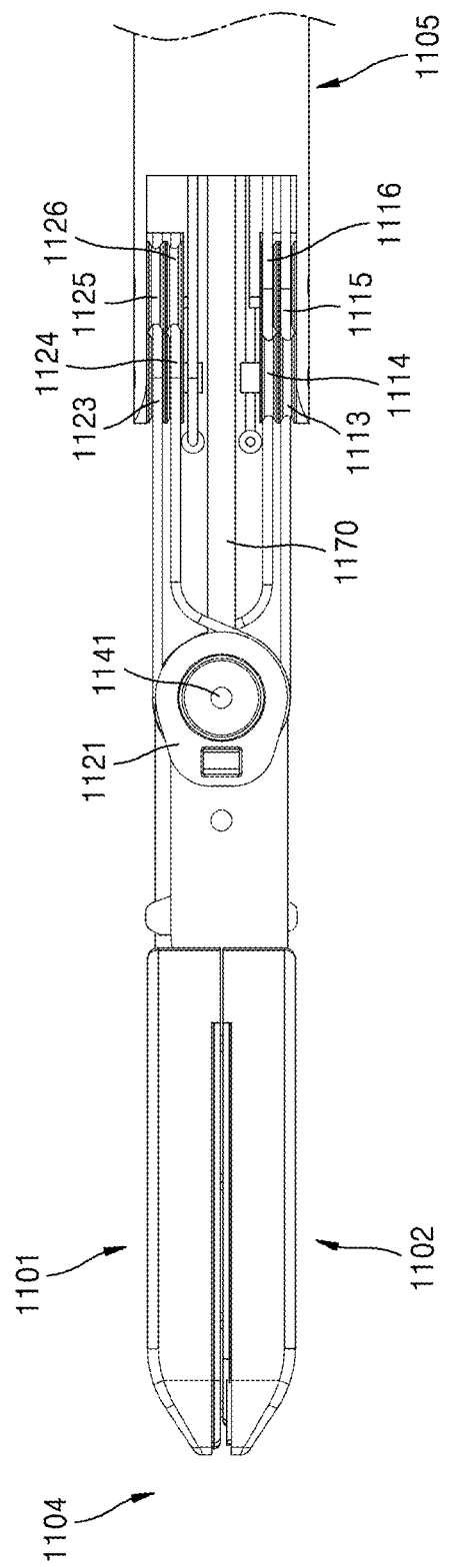
FIGS. 163 and 164 are plan views illustrating an opening and closing motion of the end tool of the surgical instrument for electrocautery of FIG. 140.
Figure 164:
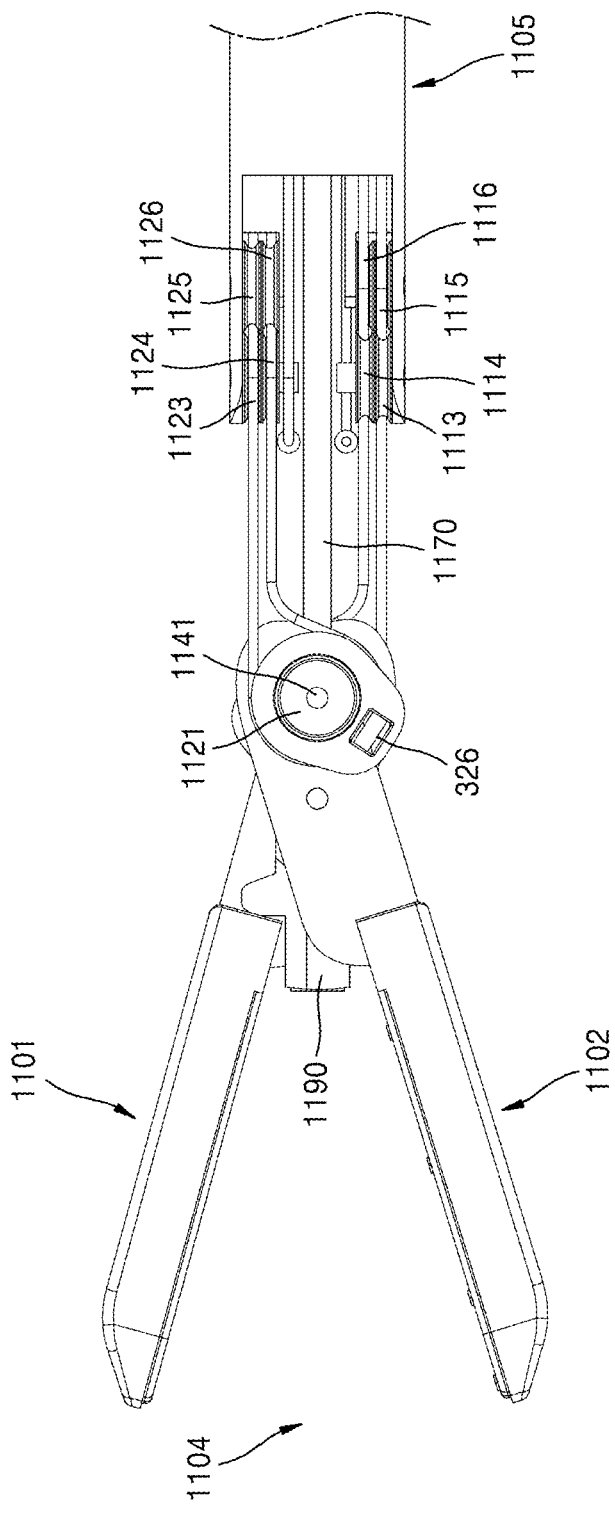

FIG. 163 is a view illustrating a state in which the end tool of the surgical instrument for electrocautery of FIG. 140 is closed, and FIG. 164 is a view illustrating a state in which the end tool of the surgical instrument for electrocautery of FIG. 140 is opened. In addition, FIG. 165 is a view illustrating a state in which the blade wire 307 and the blade 1175 are located at a first position, FIG. 166 is a view illustrating a state in which the blade wire 307 and the blade 1175 are located at a second position, and FIG. 167 is a view illustrating a state in which the blade wire 307 and the blade 1175 are located at a third position.

Figure 165:
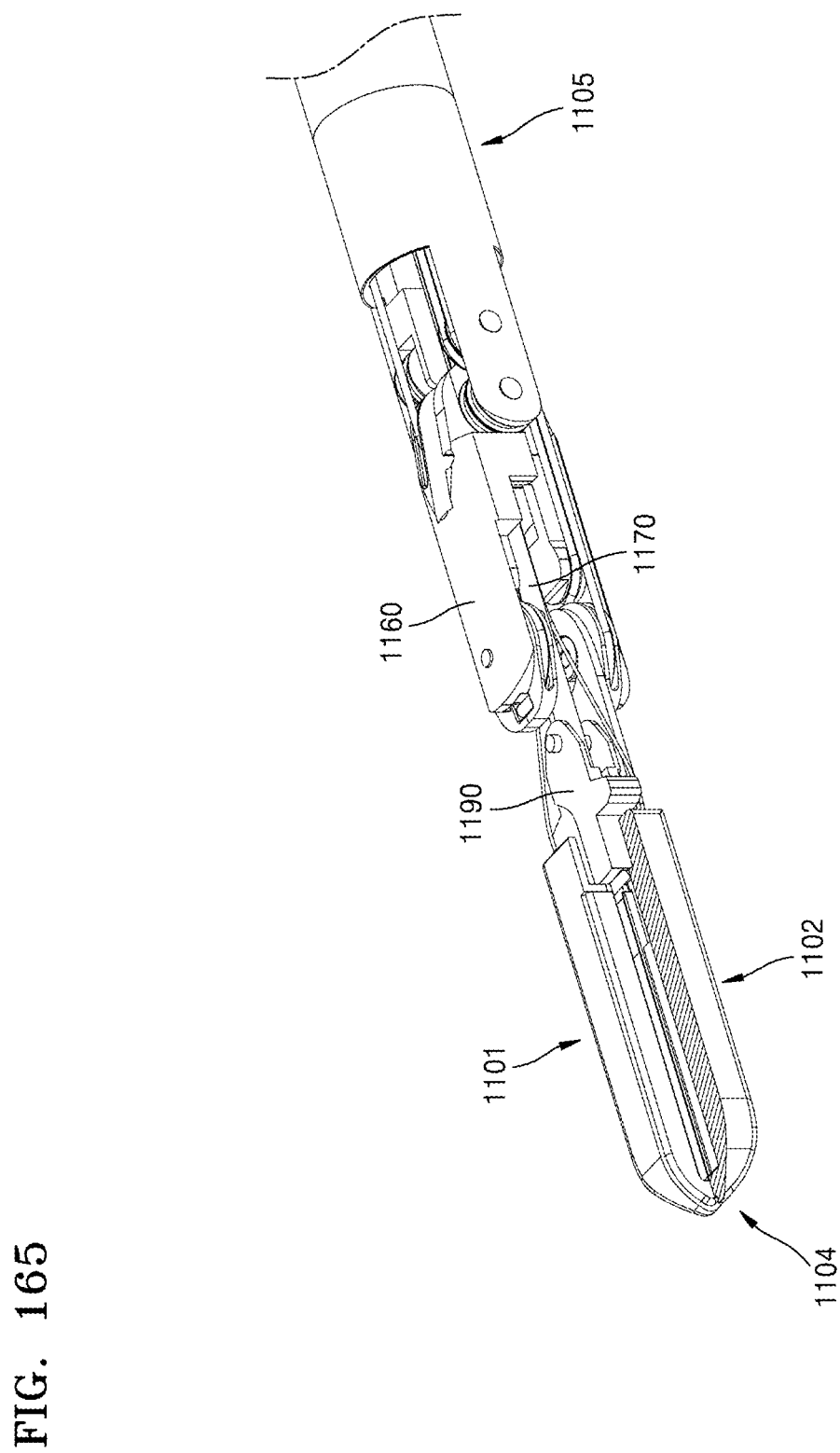
FIGS. 165 to 167 are partial cross-sectional views illustrating an operation of the blade of the end tool of the surgical instrument for electrocautery of FIG. 140.
Figure 166:
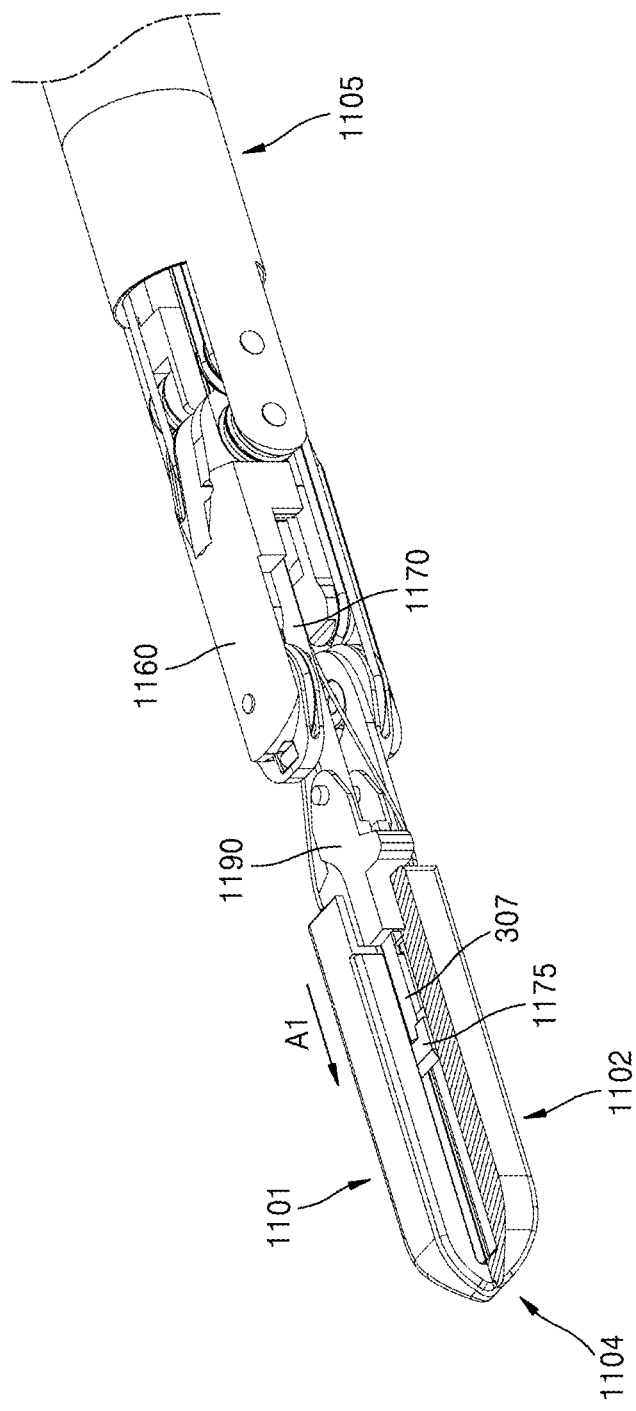
Figure 167:
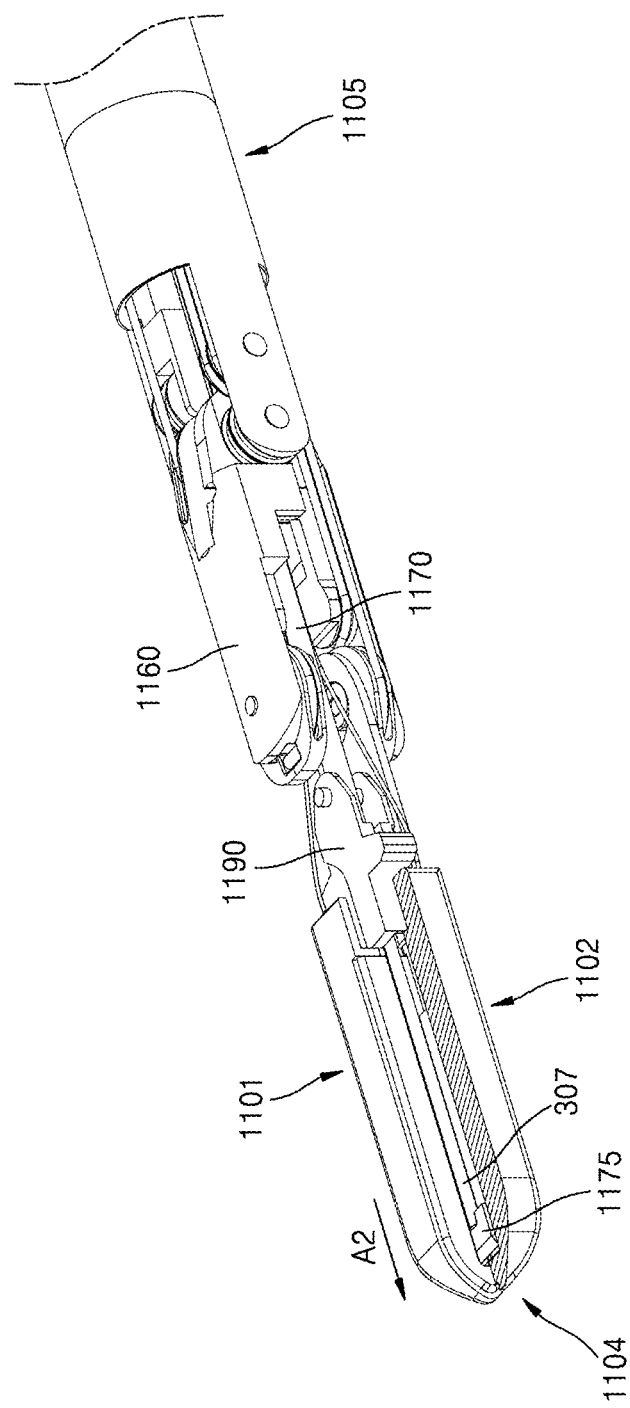

Referring to FIGS. 163 to 167, it may be said that the tissue between the first jaw 1101 and the second jaw 1102 is cut as the cutting motion of FIGS. 165 to 167 is performed in a state in which the first jaw 1101 and the second jaw 1102 are closed as shown in FIG. 163.

Here, the first position illustrated in FIG. 165 may be defined as a state in which the blade 1175 is drawn in toward the proximal end 1105 of the end tool 1100 as much as possible. Alternatively, the first position may be defined as a state in which the blade 1175 is located adjacent to the pulley 1111/pulley 1121.

Meanwhile, the third position illustrated in FIG. 167 may be defined as a state in which the blade 1175 is withdrawn toward the distal end 1104 of the end tool 1100 as much as possible. Alternatively, the third position may be defined as a state in which the blade 1175 is spaced away from the pulley 1111/pulley 1121 as much as possible.

First, as shown in FIG. 164, a tissue to be cut is located between the first jaw 1101 and the second jaw 1102 in a state in which the first jaw 1101 and the second jaw 1102 are opened, and then an actuation motion is performed to close the first jaw 1101 and the second jaw 1102 as shown in FIG. 163.

Next, as shown in FIG. 165, in a state in which the blade wire 307 and the blade 1175 are located at the first position, currents of different polarities are applied to the first electrode 1151 and the second electrode 1152 to cauterize the tissue between the first jaw 1101 and the second jaw 1102. At this time, a generator (not shown) configured to supply power to the electrodes may itself perform monitoring of at least some of current, voltage, resistance, impedance, and temperature, and may stop supplying power when the cauterization is completed.

In the state in which the cautery is completed as described above, when the blade wire 307 moves sequentially in the directions of an arrow A1 of FIG. 155 and an arrow A2 of FIG. 167, the blade 1175 coupled to the blade wire 307 moves from the first position at the proximal end 1105 of the end tool 1100 toward the third position at the distal end 1104 of the end tool 1100, reaching the positions in FIGS. 166 and 167 in turn.

As such, the blade 1175 cuts the tissue between the first jaw 1101 and the second jaw 1102 while moving in the X-axis direction.

However, it is to be understood that the linear motion of the blade 1175 here does not mean a motion in a completely straight line, but rather means a motion of the blade 1175 to the extent that the blade 1175 is able to cut the tissue while achieving a linear motion when viewed as a whole, even though the motion is not in a completely straight line, for example, the middle part of the straight line is bent by a certain angle or there is a section having a gentle curvature in a certain section.

Meanwhile, in this state, when the blade wire 307 is pulled in the opposite direction, the blade 1175 coupled to the blade wire 307 also returns to the first position.

According to the present disclosure, the multi-joint/multi-degree-of-freedom surgical instrument capable of pitch/yaw/actuation motions may also perform cauterizing and cutting motions.

(Manipulation Portion)

Figure 216:
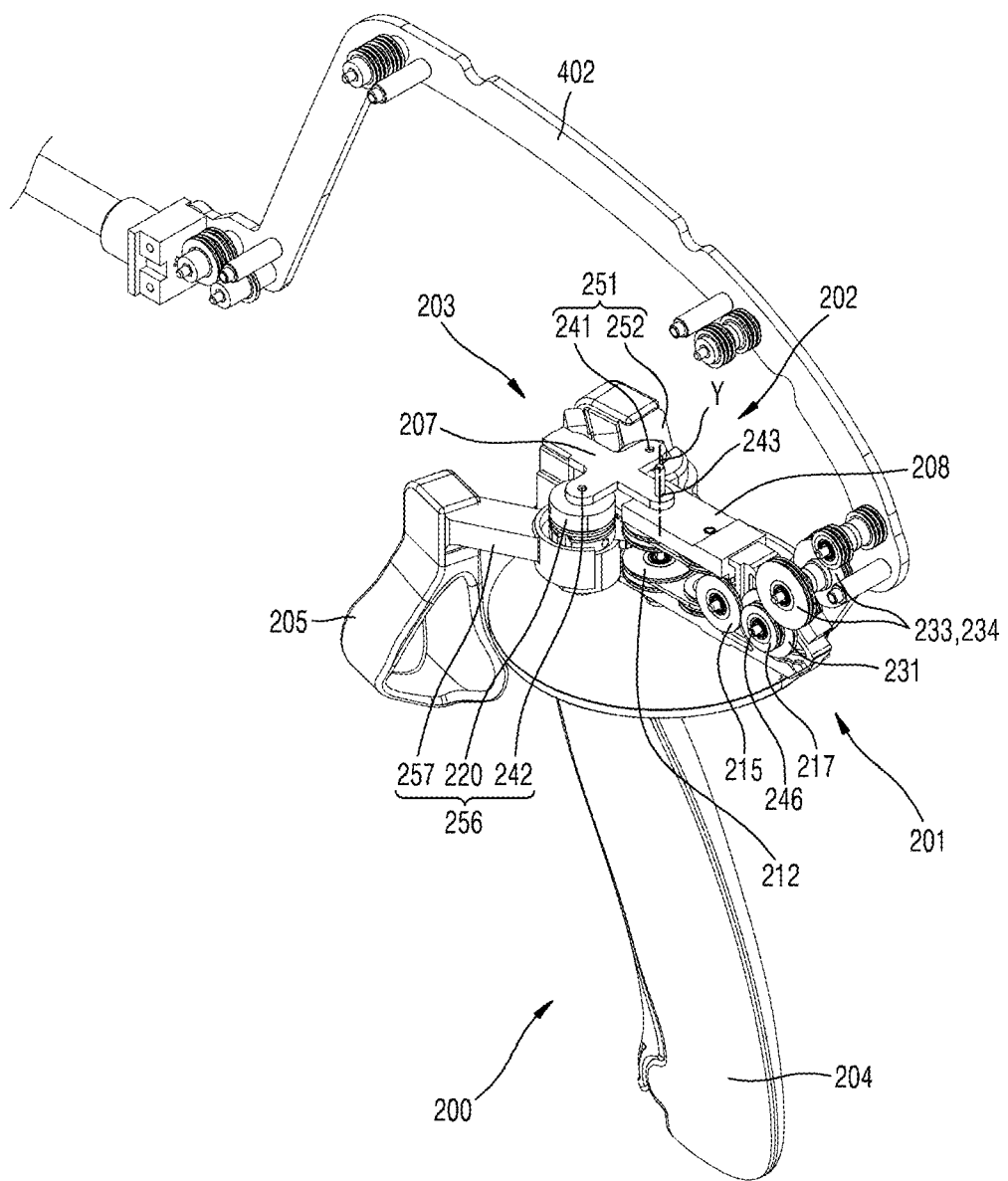
FIGS. 216 and 217 are perspective views illustrating a manipulation portion of the surgical instrument for electrocautery of FIG. 140.
Figure 217:
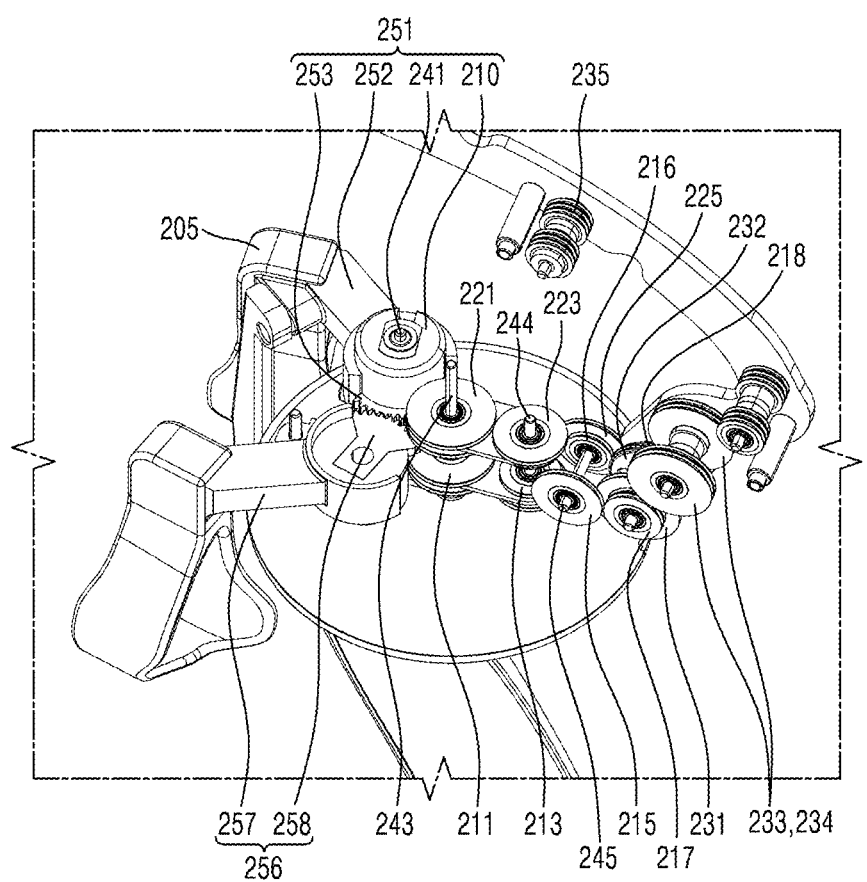
Figure 218:
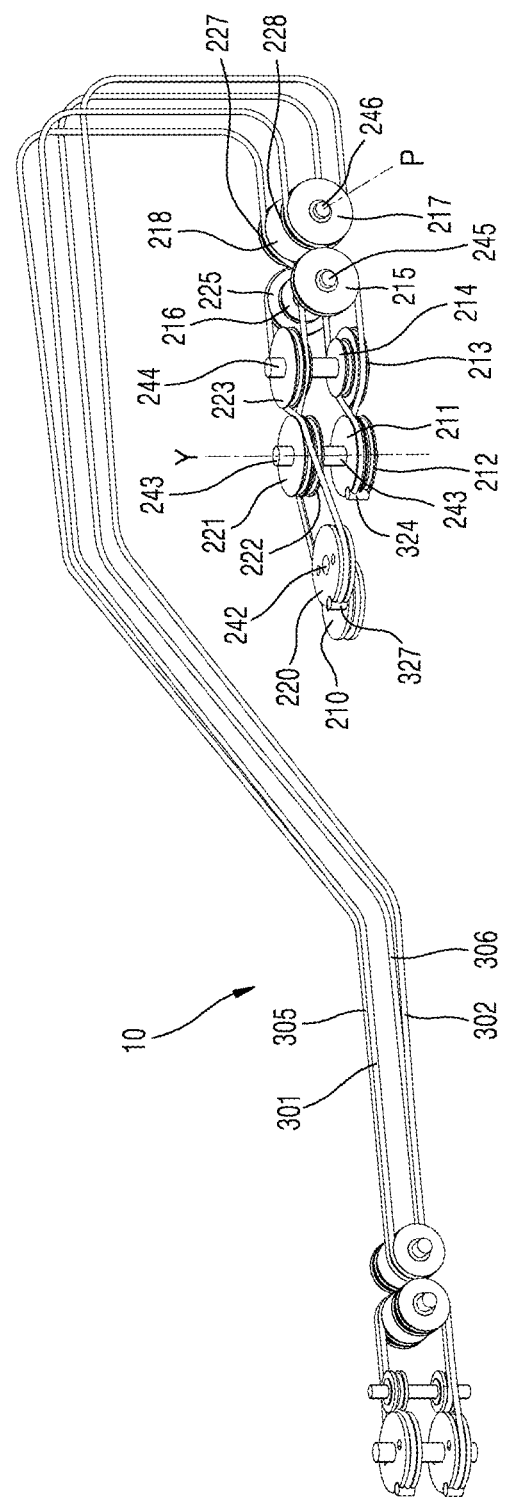
FIG. 218 is a view schematically illustrating only a configuration of pulleys and wires constituting joints of the surgical instrument for electrocautery illustrated in FIG. 140.

FIGS. 216 and 217 are perspective views illustrating the manipulation portion 200 of the surgical instrument of FIG. 140. FIG. 218 is a diagram schematically illustrating only the pulleys and the wires constituting the joint of the surgical instrument for electrocautery of FIG. 140.

With reference to FIGS. 140 to 162 and FIGS. 216 to 218, the manipulation portion 200 of the electric cauterization surgical instrument 10 according to the fourth embodiment may include the first handle 204 which a user may hold, the actuation manipulation portion 203 configured to control the actuation motion of the end tool 1100, the yaw manipulation portion 202 configured to control the yaw motion of the end tool 1100, and the pitch manipulation portion 201 configured to control the pitch motion of the end tool 1100. FIGS. 216 and 217 illustrate components only associated with the pitch/yaw/actuation motions of the electric cauterization surgical instrument 10.

In addition, the manipulation portion 200 of the electric cauterization surgical instrument 10 may further include a blade manipulation portion 260 performing cutting by controlling the movement of the blade 171 of the end tool 1100, and a cautery manipulation portion 270 performing cautery by supplying electrical energy to the first electrode 1151 and the second electrode 1152 of the end tool 1100.

The manipulation portion 200 may include a pulley 210, a pulley 211, a pulley 212, a pulley 213, a pulley 214, a pulley 215, a pulley 216, a pulley 217, and a pulley 218, which are associated with the rotational motion of the first jaw 1101. In addition, the manipulation portion 200 may include a pulley 220, a pulley 221, a pulley 222, a pulley 223, a pulley 224, a pulley 225, a pulley 226, a pulley 227, and a pulley 228, which are associated with the rotational motion of the second jaw 1102. In one embodiment, the manipulation portion 200 may include a pulley 231, a pulley 232, a pulley 233, and a pulley 234, which are associated with the pitch motion. The manipulation portion 200 may include a pulley 235 which is an intermediate pulley arranged in some positions of the bent portion 402 of the connection portion 400.

Here, the drawings illustrate that the pulleys facing each other are arranged in parallel with each other; however, the technical concepts of the present disclosure are not limited thereto, and each pulley may be formed in various positions and sizes suitable for the configuration of the manipulation portion 200.

In addition, the manipulation portion 200 of the fourth embodiment may include a rotation shaft 241, a rotation shaft 242, a rotation shaft 243, a rotation shaft 244, a rotation shaft 245, and a rotation shaft 246. Here, the rotation shaft 241 may function as a manipulation portion first jaw actuation rotation shaft, and the rotation shaft 242 may function as a manipulation portion second jaw actuation rotation shaft. In addition, the rotation shaft 243 may function as a manipulation portion yaw main rotation shaft, and the rotation shaft 244 may function as a manipulation portion yaw subsidiary rotation shaft. The rotation shaft 245 may function as a manipulation portion pitch subsidiary rotation shaft, and the rotation shaft 246 may function as a manipulation portion pitch main rotation shaft.

The rotation shaft 241, the rotation shaft 242, the rotation shaft 243, the rotation shaft 244, the rotation shaft 245, and the rotation shaft 246 may be sequentially arranged in a direction towards a proximal end 206 from a distal end 205.

One or more pulleys may be fit into each of the rotation shafts 241, 242, 243, 244, 245, and 246 which will be described in detail below.

The pulley 210 may function as a manipulation portion first jaw actuation pulley, the pulley 220 may function as a manipulation portion second jaw actuation pulley, and these components may be collectively referred to as a manipulation portion actuation pulley.

The pulley 211 and the pulley 212 may function as a manipulation portion first jaw yaw main pulley, the pulley 221 and the pulley 222 may function as a manipulation portion second jaw yaw main pulley, and these two components may collectively be referred to as a manipulation portion yaw main pulley.

The pulley 213 and the pulley 214 may function as a manipulation portion first jaw yaw subsidiary pulley, the pulley 223 and the pulley 224 may function as a manipulation portion second jaw yaw subsidiary pulley, and these two components may collectively be referred to as a manipulation portion yaw subsidiary pulley.

The pulley 215 and the pulley 216 may function as a manipulation portion first jaw pitch subsidiary pulley, the pulley 225 and the pulley 226 may function as a manipulation portion second jaw pitch subsidiary pulley, and these two components may collectively be referred to as a manipulation portion pitch subsidiary pulley.

The pulley 217 and the pulley 218 may function as a manipulation portion first jaw pitch main pulley, the pulley 227 and the pulley 228 may function as a manipulation portion second jaw pitch main pulley, and these two components may collectively be referred to as a manipulation portion pitch main pulley.

The pulley 231 and the pulley 232 may function as a manipulation portion pitch wire main pulley, and the pulley 233 and the pulley 234 may function as a manipulation portion pitch wire subsidiary pulley.

The components may be classified from the viewpoint of the manipulation portion in connection with each motion (i.e., pitch/yaw/actuation) as follows.

The pitch manipulation portion 201 controlling the pitch motion of the end tool 1100 may include a pulley 215, a pulley 216, a pulley 217, a pulley 218, a pulley 225, a pulley 226, and a pulley 227, a pulley 228, a pulley 231, a pulley 232, and a pulley 234. In addition, the pitch manipulation portion 201 may include the rotation shaft 245 and the rotation shaft 246. In one embodiment, the pitch manipulation portion 201 may further include a pitch frame 208.

The yaw manipulation portion 202 controlling the yaw motion of the end tool 1100 may include a pulley 211, a pulley 212, a pulley 213, a pulley 214, a pulley 221, a pulley 222, a pulley 223, and a pulley 224. In addition, the yaw manipulation portion 202 may include the rotation shaft 243 and the rotation shaft 244. In one embodiment, the yaw manipulation portion 202 may further include a yaw frame 207.

The actuation manipulation portion 203 controlling the actuation motion of the end tool 1100 may include the pulley 210, the pulley 220, the rotation shaft 241, and the rotation shaft 242. In one embodiment, the actuation manipulation portion 203 may further include a first actuation manipulation portion 251 and a second actuation manipulation portion 256.

Hereinafter, each component of the manipulation portion 200 will be described in more detail.

The first handle 204 may be held by a user, and more particularly, a user may hold the first handle 204 by wrapping it with his or her hand. The actuation manipulation portion 203 and the yaw manipulation portion 202 may be formed on the first handle 204, and the pitch manipulation portion 201 may be formed on one side of the yaw manipulation portion 202. In addition, another end of the pitch manipulation portion 201 may be connected to the bent portion 402 of the connection portion 400.

The actuation manipulation portion 203 may include the first actuation manipulation portion 251 and the second actuation manipulation portion 256. The first actuation manipulation portion 251 may include the rotation shaft 241, the pulley 210, a first actuation extension portion 252, and a first actuation gear 253. The second actuation manipulation portion 256 may include the rotation shaft 242, the pulley 220, a second actuation extension portion 257, and a second actuation gear 258. Here, ends of the first actuation extension portion 252 and the second actuation extension portion 257 may be formed in the shape of a hand ring, and may operate as a second handle.

The rotation shaft 241 and the rotation shaft 242, which are the actuation rotation shaft, may be formed to have a certain angle with the XY plane on which the connection portion 400 is formed. For example, the rotation shaft 241 and the rotation shaft 242 may be formed in a direction parallel with the Z-axis, and when the pitch manipulation portion 201 or the yaw manipulation portion 203 rotates, a coordinate system of the actuation manipulation portion 203 may be changed relatively. However, the technical ides of the present disclosure are not limited thereto, and by an ergonomic design, the rotation shaft 241 and the rotation shaft 242 may be formed in various directions suitable for a hand structure of a user holding the actuation manipulation portion 203.

The pulley 210, the first actuation extension portion 252, and the first actuation gear 253 may be fixedly coupled to each other and rotatable together around the rotation shaft 241. Here, the pulley 210 may include one pulley or two pulleys fixedly coupled to each other.

Likewise, the pulley 220, the second actuation extension portion 257, and the second actuation gear 258 may be fixedly coupled to each other and rotatable together around the rotation shaft 242. Here, the pulley 220 may include one pulley or two pulleys fixedly coupled to each other.

The first actuation gear 253 and the second actuation gear 258 may be formed to engage with each other, and when either one of them rotates in one direction, the other one may rotate concurrently in the opposite direction.

The yaw manipulation portion 202 may include the rotation shaft 243, the pulley 211 and the pulley 212, which are the manipulation portion first jaw yaw main pulley, the pulley 211 and the pulley 212, which are the manipulation portion second jaw yaw main pulley, and the yaw frame 207. In addition, the yaw manipulation portion 202 may further include the pulley 213 and the pulley 214, which are the manipulation portion first jaw yaw subsidiary pulley and arranged on one side of the pulley 211 and the pulley 212, and the pulley 223 and the pulley 224, which are the manipulation portion second jaw yaw subsidiary pulley and arranged on one side of the pulley 221 and the pulley 222. Here, the pulley 213, the pulley 214, the pulley 223, and the pulley 224 may be coupled to the pitch frame 208 to be described later.

The drawings illustrate that the yaw manipulation portion 202 includes the pulley 211, the pulley 212, the pulley 221, and the pulley 222, and as the pulley 211 faces the pulley 212 and the pulley 221 faces the pulley 222, two pulleys may be rotatable independently of each other; however the technical concepts of the present disclosure are not limited thereto. That is, one or more pulleys having the same diameter or different diameters may be provided according to the configuration of the yaw manipulation portion 202.

More specifically, on the first handle 204, the rotation shaft 243, which is the manipulation portion yaw main rotation shaft, may be formed on one side of the actuation manipulation portion 203. In this case, the first handle 204 may be formed to be rotatable around the rotation shaft 243.

Here, the rotation shaft 243 may be formed to have a certain angle with the XY plane on which the connection portion 400 is formed. For example, the rotation shaft 243 may be formed in a direction parallel with the Z-axis, and when the pitch manipulation portion 201 rotates, the coordinate system of the rotation shaft 243 may be changed relatively as described above. However, the technical ides of the present disclosure are not limited thereto, and by an ergonomic design, the rotation shaft 243 may be formed in various directions suitable for a hand structure of a user holding the manipulation portion 200.

The pulley 211, the pulley 212, the pulley 221, and the pulley 222 may be coupled to the rotation shaft 243 to be rotatable around the rotation shaft 243. In addition, the wire 301 or the wire 305, which is the first jaw wire, may be wound around the pulley 211 and the pulley 212, and the wire 302 or the wire 306, which is the second jaw wire, may be wound around the pulley 221 and the pulley 222. At this time, as the pulley 211 faces the pulley 212, and the pulley 221 faces the pulley 222, there may be two pulleys which are rotatable independently. Accordingly, as the wire wound inward and the wire wound outward may be respectively wound around separate pulleys, the pulleys may operate without interfering with each other.

The yaw frame 207 may rigidly connect the first handle 204, the rotation shaft 241, the rotation shaft 242, and the rotation shaft 243, and accordingly, the first handle 204, the yaw manipulation portion 202, and the actuation manipulation portion 203 may yaw-rotate around the rotation shaft 243 in an integrated manner.

The pitch manipulation portion 201 may include the rotation shaft 246, the pulley 217 and the pulley 218, which are the manipulation portion first jaw pitch main pulley, the pulley 227 and the pulley 228, which are the manipulation portion second jaw pitch main pulley, and the pitch frame 208. In addition, the pitch manipulation portion 201 may further include the rotation shaft 245, the pulley 215 and the pulley 216, which are the manipulation portion first jaw pitch subsidiary pulley and arranged on one side of the pulley 217 and the pulley 218, and the pulley 225 and the pulley 226, which are the manipulation portion second jaw pitch subsidiary pulley and arranged on one side of the pulley 227 and pulley 228. The pitch manipulation portion 201 may be connected to the bent portion 402 of the connection portion 400 through the rotation shaft 246.

More specifically, the pitch frame 208 may be a base frame of the pitch manipulation portion 201, and one end of the pitch frame 208 may be rotatably coupled to the rotation shaft 243. That is, the yaw frame 207 may be formed to be rotatable around the rotation shaft 243 with respect to the pitch frame 208.

As described above, the yaw frame 207 may connect the first handle 204, the rotation shaft 243, the rotation shaft 241, and the rotation shaft 242, and as the yaw frame 207 is axially coupled to the pitch frame 208, when the pitch frame 208 pitch-rotates around the rotation shaft 246, the yaw frame 207, the first handle 204, the rotation shaft 241, the rotation shaft 242, and the rotation shaft 243, which are connected to the pitch frame 208, may also pitch rotate. That is, when the pitch manipulation portion 201 rotates around the rotation shaft 246, the actuation manipulation portion 203 and the yaw manipulation portion 202 may be rotated together with the pitch manipulation portion 201. In other words, when the user pitch-rotates the first handle 204 around the rotation shaft 246, the actuation manipulation portion 203, the yaw manipulation portion 202, and the pitch manipulation portion 201 may also move together with the first handle 204.

The pulley 217, the pulley 218, the pulley 227, and the pulley 228 may be coupled to the rotation shaft 246 so that they are rotatable around the rotation shaft 246 of the pitch frame 208.

Here, the pulley 217 and the pulley 218 may face each other and rotate independently. Accordingly, as the wire wound inward and the wire wound outward may be respectively wound around separate pulleys, the pulleys may operate without interfering with each other. Likewise, the pulley 227 and the pulley 228 may face each other and rotate independently. Accordingly, as the wire wound inward and the wire wound outward may be respectively wound around separate pulleys, the pulleys may operate without interfering with each other.

Next, the motions of the wire 303 and the wire 304 which are the pitch wire are described below.

In the end tool 1100, the pulley 1131, which is the end tool pitch pulley, may be fixedly coupled to the end tool hub 1180, and in the manipulation portion 200, the pulley 231 and the pulley 232, which are the manipulation portion pitch pulley, may be fixedly coupled to the pitch frame 208. These pulleys may be connected to each other by the wire 303 and the wire 304, which are the pitch wire, to facilitate the pitch motion of the end tool 1100 according to the pitch manipulation of the manipulation portion 200. Here, the wire 303 may be fixedly coupled to the pitch frame 208 via the pulley 231 and the pulley 233, and the wire 304 may be fixedly coupled to the pitch frame 208 via the pulley 232 and the pulley 234. That is, the pitch frame 208, the pulley 231, and the pulley 232 may rotate together around the rotation shaft 246 by the pitch rotation of the manipulation portion 200. As a result, the wire 303 and the wire 304 may also move, and separately from the pitch motion of the end tool 1100 by the wire 301, the wire 302, the wire 305, and the wire 306, which are the jaw wire, additional pitch rotation power may be transmitted.

The connection relation among the first handle 204, the pitch manipulation portion 201, the yaw manipulation portion 202, and the actuation manipulation portion 203 is described below. On the first handle 204, the rotation shaft 241, the rotation shaft 242, the rotation shaft 243, the rotation shaft 244, the rotation shaft 245, and the rotation shaft 246 may be formed. At this time, as the rotation shaft 241 and the rotation shaft 242 are directly formed on the first handle 204, the first handle 204 and the actuation manipulation portion 203 may be directly connected to each other. As the rotation shaft 243 is directly formed on the first handle 204, the first handle 204 and the yaw manipulation portion 202 may be directly connected to each other. As the pitch manipulation portion 201 is arranged on one side of the yaw manipulation portion 202 and connected to the yaw manipulation portion 202, the pitch manipulation portion 201 may not be directly connected to the first handle 204 and the pitch manipulation portion 201 and the first handle 204 may be indirectly connected to each other through the yaw manipulation portion 202.

With reference to the drawings, in the electric cauterization surgical instrument 10 according to the first embodiment, the pitch manipulation portion 201 and the end tool 1100 may be formed on the same or parallel axis (i.e., the X-axis). That is, the rotation shaft 246 of the pitch manipulation portion 201 may be formed at one end of the bent portion 402 of the connection portion 400, and the end tool 1100 may be formed at the other end of the connection portion 400.

In addition, one or more intermediate pulleys 235 changing or guiding a path of the wires may be arranged in some positions of the connection portion 400, in particular, in positions on the bent portion 402. At least a part of the wires may be wound around the intermediate pulleys 235 to guide the path of the wires so that the wires are arranged along the bent shape of the bent portion 402.

Here, the drawings illustrate that the connection portion 400 includes the bent portion 402 and thus is formed in a curved manner with a certain curvature; however, the technical concepts of the present disclosure are not limited thereto, and the connection portion 400 may be formed straightly, if necessary, or curved in one or more points. Even in such cases, the pitch manipulation portion 201 and the end tool 1100 may be formed on the substantially same or parallel axis. In addition, although FIG. 3 illustrates that the pitch manipulation portion 201 and the end tool 1100 are respectively formed on an axis parallel with the X-axis, the technical concepts of the present disclosure are not limited thereto, and the pitch manipulation portion 201 and the end tool 1100 may be formed on different axes.

(Actuation Motion, Yaw Motion, Pitch Motion)

Actuation motion, yaw motion, and pitch motion in this embodiment will be described as follows.

First, the actuation motion is as follows.

When a user puts the index finger in a hand ring formed at the first actuation extension 252, puts the thumb in a hand ring formed at the second actuation extension 257, and rotates the first actuation extension 252 and the second actuation extension 257 using any one of or both the fingers, the pulley 210 and the first actuation gear 253 fixedly coupled to the first actuation extension 252 rotate around the rotation shaft 241, and the pulley 220 and the second actuation gear 258 fixedly coupled to the second actuation extension 257 rotate around the rotation shaft 242. At this time, the pulley 210 and the pulley 220 rotate in opposite directions, and thus the wire 301 and the wire 305 each having one end fixedly coupled to and wound around the pulley 210 and the wire 302 and the wire 306 each having one end fixedly coupled to and wound around the pulley 220 move in opposite directions as well. This rotational force is transmitted to an end tool 1100 through a power transmission portion 300, two jaws 1103 of the end tool 1100 perform the actuation motion.

Here, the actuation motion refers to an action of opening or closing the jaws 1102 while the two jaws 1102 rotate in opposite directions to each other, as described above. In other words, when the actuation extensions 252 and 257 of the actuation manipulation portion 203 are rotated in directions toward each other, the first jaw 1101 rotates counterclockwise and the second jaw 1102 rotates clockwise, and thus the end tool 1100 is closed. Conversely, when the actuation extensions 252 and 257 of the actuation manipulation portion 203 are rotated in directions away from each other, the first jaw 1101 rotates clockwise and the second jaw 1102 rotates counterclockwise, and thus the end tool 1100 is opened.

In this embodiment, for the above-described actuation manipulation, the first actuation extension 252 and the second actuation extension 257 were provided to constitute a second handle, and two fingers were gripped to enable manipulation. However, unlike the above, the actuation manipulation portion 203 for actuation manipulation to open and close the two jaws of the end tool 1100 with each other may be configured differently so that, for example, two actuation pulleys (the pulley 210 and the pulley 220) operate opposite to each other by one actuation rotating portion.

Next, the yaw motion is as follows.

When the user rotates a first handle 204 around a rotation shaft 243 while holding the first handle 204, the actuation manipulation portion 203 and the yaw manipulation portion 202 yaw-rotates around the rotation shaft 243. In other words, when the pulley 210 of the first actuation manipulation portion 251 to which the wire 301 and the wire 305 are fixedly coupled rotates about the rotation shaft 243, the wire 301 and the wire 305 respectively wound around the pulley 211 and the pulley 212 move. Likewise, when the pulley 220 of the second actuation manipulation portion 256 to which the wire 302 and the wire 306 are fixedly coupled rotates about the rotation shaft 243, the wire 302 and the wire 306 respectively wound around the pulley 221 and the pulley 222 move. At this time, the wire 301 and the wire 305 connected to the first jaw 1101 and the wire 302 and the wire 306 connected to the second jaw 1102 are respectively wound around the pulley 211 and the pulley 212 and the pulley 221 and the pulley 222, such that the first jaw 1101 and the second jaw 1102 rotate in the same direction during a yaw rotation. And, this rotational force is transmitted to the end tool 1100 through the power transmission portion 300, the two jaws 1103 of the end tool 1100 performs the yaw motion that rotates in the same direction.

At this time, since the yaw frame 207 connects the first handle 204, the rotation shaft 241, the rotation shaft 242, and the rotation shaft 243, the first handle 204, the yaw manipulation portion 202, and the actuation manipulation portion 203 rotate together around the rotation shaft 243.

Next, the pitch motion is as follows.

When the user rotates a first handle 204 around a rotation shaft 246 while holding the first handle 204, the actuation manipulation portion 203, the yaw manipulation portion 202, and the pitch manipulation portion 201 make pitch rotation around the rotation shaft 243. In other words, when the pulley 210 of the first actuation manipulation portion 251 to which the wire 301 and the wire 305 are fixedly coupled rotates about the rotation shaft 246, the wire 301 and the wire 305 respectively wound around the pulley 217 and the pulley 218 move. Likewise, when the pulley 220 of the second actuation manipulation portion 256 to which the wire 302 and the wire 306 are fixedly coupled rotates about the rotation shaft 246, the wire 302 and the wire 306 respectively wound around the pulley 227 and the pulley 228 move. Here, as described above with reference to FIG. 5, the wire 301, the wire 305, the wire 302, and the wire 306, which are jaw wires, are wound around the pulley 217, the pulley 218, the pulley 227, and the pulley 228, which are manipulation portion pitch main pulleys, such that the wire 301 and wire 305, which are first jaw wires, move in the same direction and the wire 302 and the wire 306, which are second jaw wires, move in the same direction to enable pitch rotation of the first jaw 1101 and the second jaw 1102. And, this rotational force is transmitted to an end tool 1100 through a power transmission portion 300, two jaws 1103 of the end tool 1100 perform the pitch motion.

At this time, the pitch frame 208 is connected to the yaw frame 207 and the yaw frame 207 connects the first handle 204, the rotation shaft 241, the rotation shaft 242, and the rotation shaft 243. Therefore, when the pitch frame 208 rotates around the rotation shaft 246, the yaw frame 207 connected to the pitch frame 208, the first handle 204, the rotation shaft 241, the rotation shaft 242, and the rotation shaft 243 rotate together. That is, when a pitch manipulation portion 201 rotates around the rotation shaft 246, the actuation manipulation portion 203 and the yaw manipulation portion 202 are rotated together with the pitch manipulation portion 201.

In summary, in an electric cauterization surgical instrument 10 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 1100 is induced. Furthermore, auxiliary pulleys may be formed on one side of each pulley, and the wire may not be wound several times on one pulley by these auxiliary pulleys.

FIG. 218 is a schematic view of only the configuration of pulleys and wires constituting joints of the electric cauterization surgical instrument 10 according to an embodiment of the present disclosure shown in FIG. 140. In FIG. 218, intermediate pulleys that are for changing paths of wires and are not associated with joint motions are omitted.

Referring to FIG. 218, the manipulation portion 200 may include the pulley 210, the pulley 211, the pulley 212, the pulley 213, the pulley 214, the pulley 215, the pulley 216, the pulley 217, and the pulley 218 that are associated with the rotational motion of the first jaw 1101.

Also, the manipulation portion 200 may include the pulley 220, the pulley 221, the pulley 222, the pulley 223, the pulley 224, the pulley 225, the pulley 226, the pulley 227, and the pulley 228 associated with the rotational motion of the second jaw 1102. (The arrangement and the configuration of pulleys in the manipulation portion 200 are the same as the arrangement and the configuration of the pulleys in the end tool 1100 in principle, and thus some of the reference numerals thereof will be omitted in the drawings.)

The pulley 211 and the pulley 212 and the pulley 221 and the pulley 222 may be formed to be rotatable independently of each other around the same axis, that is, the rotation shaft 243. At this time, the pulley 211 and the pulley 212 may be formed to face the pulley 221 and the pulley 222, respectively, thereby forming two independently rotatable pulleys.

The pulley 213 and the pulley 214 and the pulley 223 and the pulley 224 may be formed to be rotatable independently of each other around the same axis, that is, the rotation shaft 244. At this time, the pulley 213 and the pulley 214 may be formed to face each other as two independently rotatable pulleys, and, in this case, the two pulleys may be formed to have different diameters. Likewise, the pulley 223 and the pulley 224 may be formed to face each other as two independently rotatable pulleys, and, in this case, the two pulleys may be formed to have different diameters.

The pulley 215 and the pulley 216 and the pulley 225 and the pulley 226 may be formed to be rotatable independently of each other around the same axis, that is, the rotation shaft 245. In this case, the pulley 215 and the pulley 216 may be formed to have different diameters. Also, the pulley 225 and the pulley 226 may be formed to have different diameters.

The pulley 217 and the pulley 218 and the pulley 227 and the pulley 228 may be formed to be rotatable independently of each other around the same axis, that is, the rotation shaft 246.

The wire 301 sequentially passes through the pulley 217, the pulley 215, the pulley 213, and the pulley 211 of the manipulation portion 200, is wound around the pulley 210, and then is coupled to the pulley 210 by a fastening member 324. Meanwhile, the wire 305 sequentially passes through the pulley 218, the pulley 216, the pulley 214, and the pulley 212 of the manipulation portion 200 and is coupled to the pulley 210 by the fastening member 324. Therefore, as the pulley 210 rotates, the wire 301 and the wire 305 are wound around or unwound from the pulley 210, and thus the first jaw 1101 rotates.

The wire 306 sequentially passes through the pulley 227, the pulley 225, the pulley 223, and the pulley 221 of the manipulation portion 200, is wound around the pulley 220, and then is coupled to the pulley 220 by a fastening member 327. Meanwhile, the wire 302 sequentially passes through the pulley 228, the pulley 226, the pulley 224, and the pulley 222 of the manipulation portion 200 and is coupled to the pulley 220 by the fastening member 327. Therefore, as the pulley 220 rotates, the wire 302 and the wire 306 are wound around or unwound from the pulley 220, and thus the second jaw 1102 rotates.

(Conceptual Diagram of Pulleys and Wires)

Figure 219:
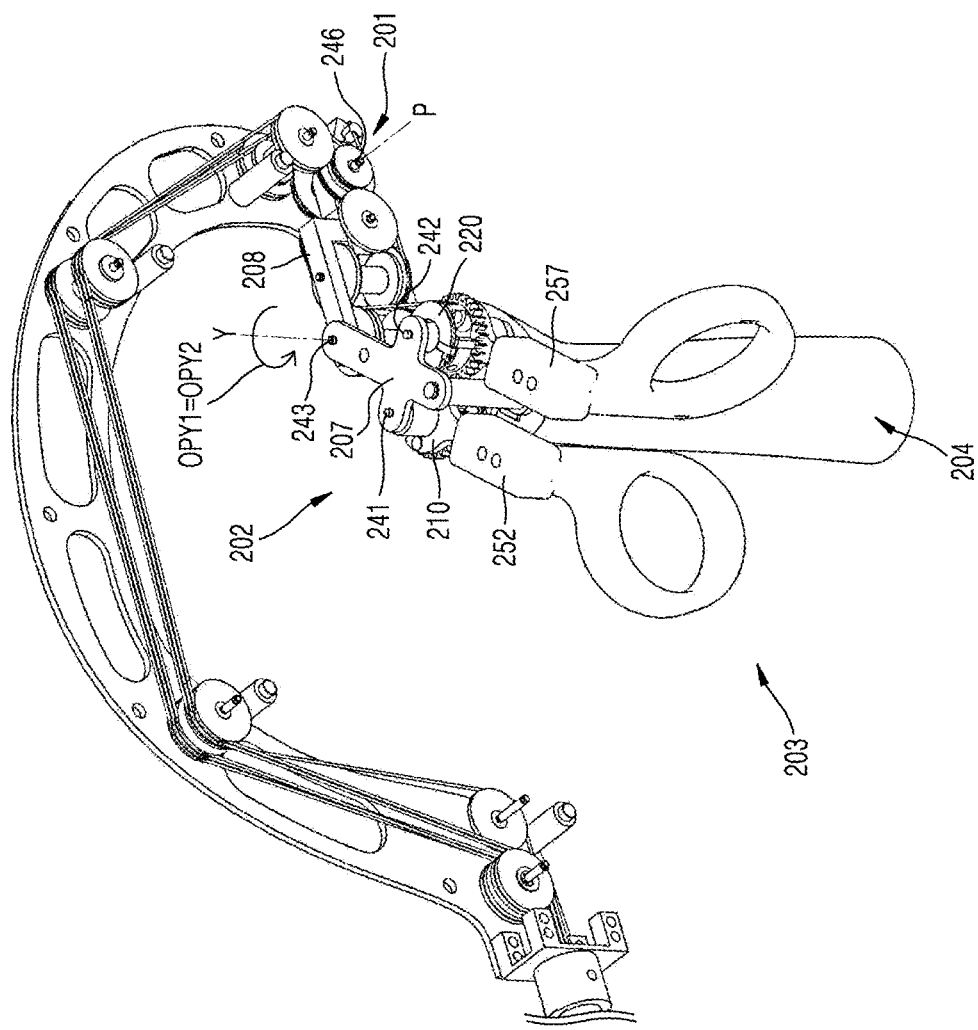
FIG. 219 is a perspective view illustrating a yaw motion of the surgical instrument for electrocautery of FIG. 140.
Figure 219:
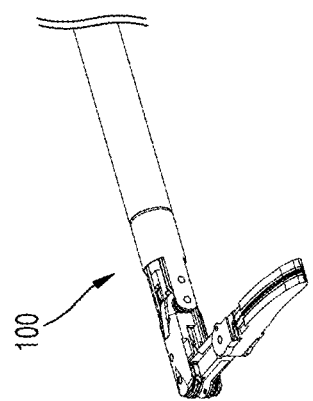
Figure 220:
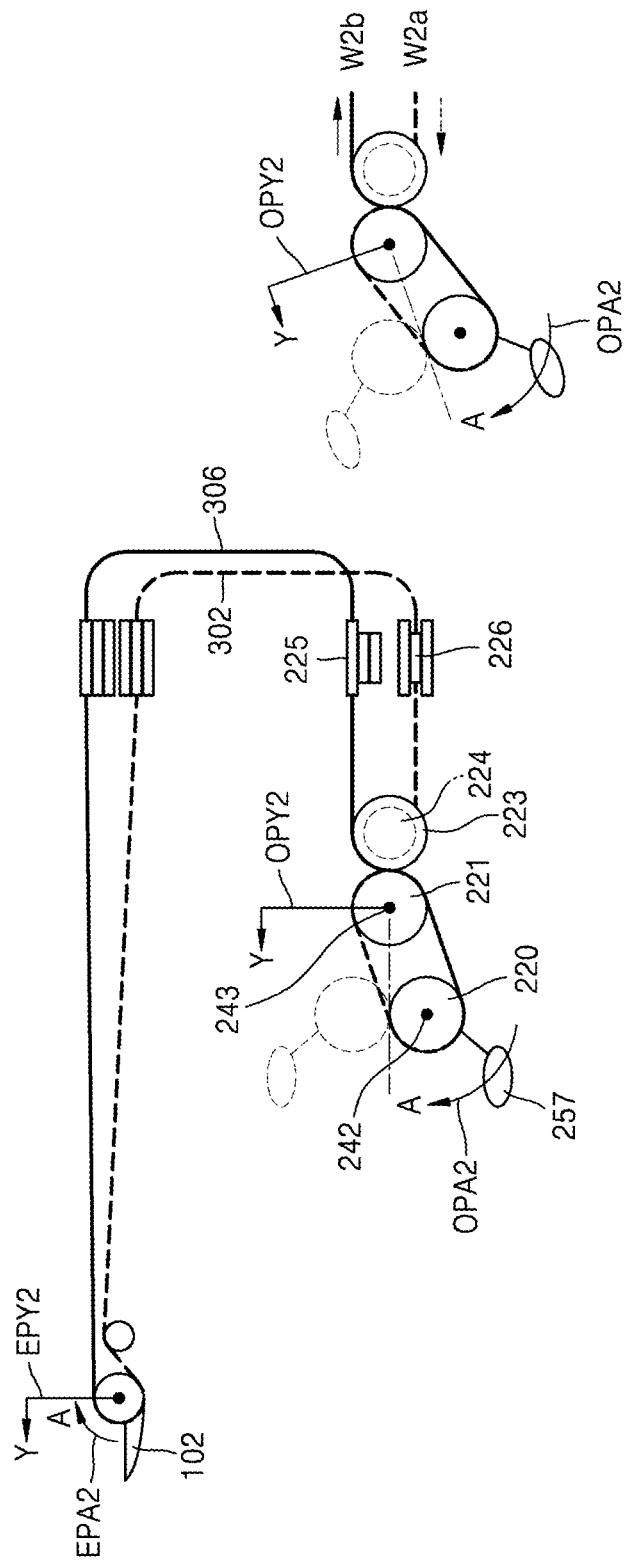
FIGS. 220 and 221 are diagrams illustrating a configuration of pulleys and wires, which are associated with an actuation motion and a yaw motion of the surgical instrument for electrocautery illustrated in FIG. 140, in detail for each of the first jaw and the second jaw.
Figure 221:
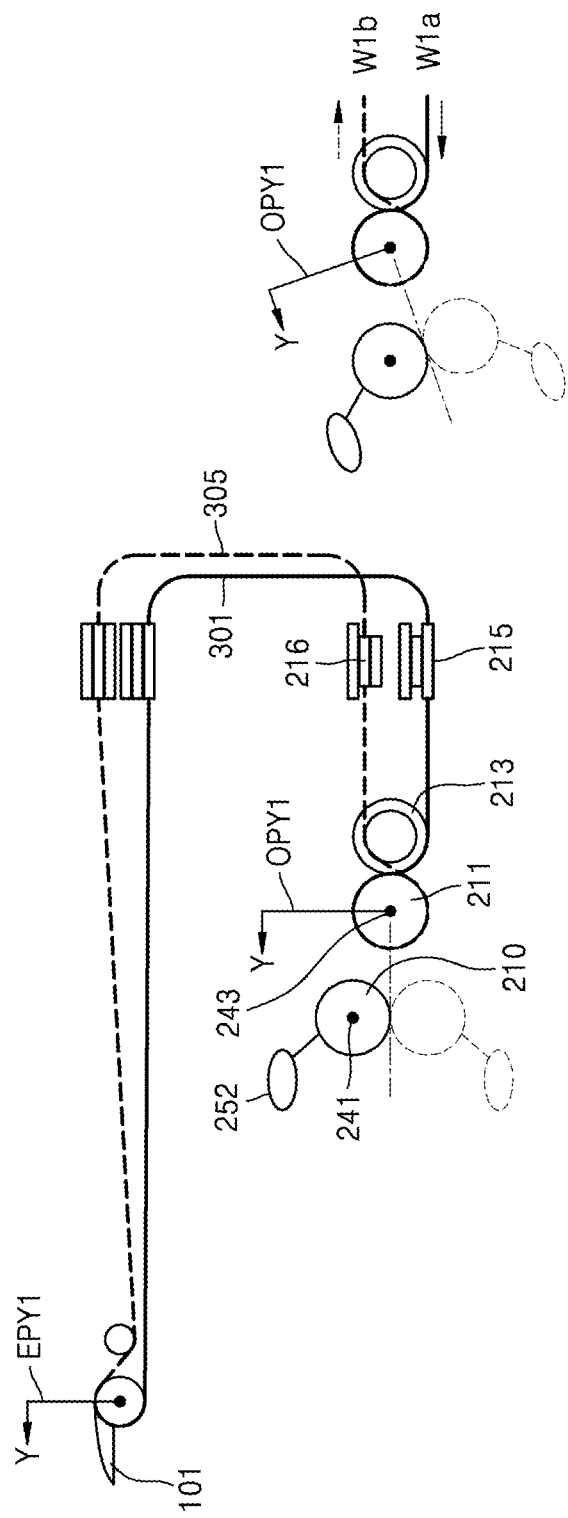

FIGS. 220 and 221 are diagrams illustrating a configuration of pulleys and wires, which are associated with an actuation motion and a yaw motion of the electric cauterization surgical instrument 10 according to an embodiment of the present disclosure illustrated in FIG. 140, in detail for each of the first jaw and the second jaw. FIG. 220 is a diagram illustrating only pulleys and wires related to the second jaw, and FIG. 221 is a diagram illustrating only pulleys and wires related to the first jaw. In addition, FIG. 219 is a perspective view illustrating a yaw motion of the surgical instrument shown in FIG. 140. Here, in FIG. 219, components associated with a cutting motion are omitted.

First, a wire operation in an actuation motion will be described.

Referring to FIG. 221, when the first actuation extension 252 rotates around the rotation shaft 241 in the direction of an arrow OPA1, the pulley 210 connected to the first actuation extension 252 is rotated, and the wire 301 and the wire 305 wound around the pulley 210 are moved in directions W1a and W1b, respectively, and as a result, the first jaw 1101 of the end tool 1100 is rotated in the direction of an arrow EPA1.

Referring to FIG. 220, when the second actuation extension 257 rotates around the rotation shaft 242 in the direction of an arrow OPA2, the pulley 220 connected to the second actuation extension 257 is rotated, and thus both strands of the wires 302 and 306 wound around the pulley 220 are moved in directions W2a and W2b, respectively, and as a result, the second jaw 1102 of the end tool 1100 is rotated in the direction of an arrow EPA2. Accordingly, when a user manipulates the first actuation extension 252 and the second actuation extension 257 in directions close to each other, a motion of the first jaw 1101 and the second jaw 1102 of the end tool being close to each other is performed.

Next, a wire operation in a yaw motion will be described.

First, since the rotation shaft 243 is connected to the rotation shafts 241 and 242 by the yaw frame (see 207 of FIG. 216), the rotation shaft 243 and the rotation shafts 241 and 242 are integrally rotated together.

Referring to FIG. 221, when the first handle 204 rotates around the rotation shaft 243 in the direction of an arrow OPY1, the pulley 210 and the pulleys 211 and 212 and the wires 301 and 305 wound therearound are rotated as a whole around the rotation shaft 243, and as a result, the wires 301 and 305 wound around the pulleys 211 and 212 are moved in the directions W1a and W1b, respectively, which in turn causes the first jaw 1101 of the end tool 1100 to rotate in the direction of an arrow EPY1.

Referring to FIG. 220, when the first handle 204 rotates around the rotation shaft 243 in the direction of an arrow OPY2, the pulley 220 and the pulleys 221 and 222 and the wires 302 and 306 wound therearound are rotated as a whole around the rotation shaft 243, and as a result, the wires 302 and 306 wound around the pulleys 221 and 222 are respectively moved in a direction opposite to the direction W1a and a direction opposite to the direction W1b, which in turn causes the first jaw 1101 of the end tool 1100 to rotate in the direction of an arrow EPY2.

Figure 222:
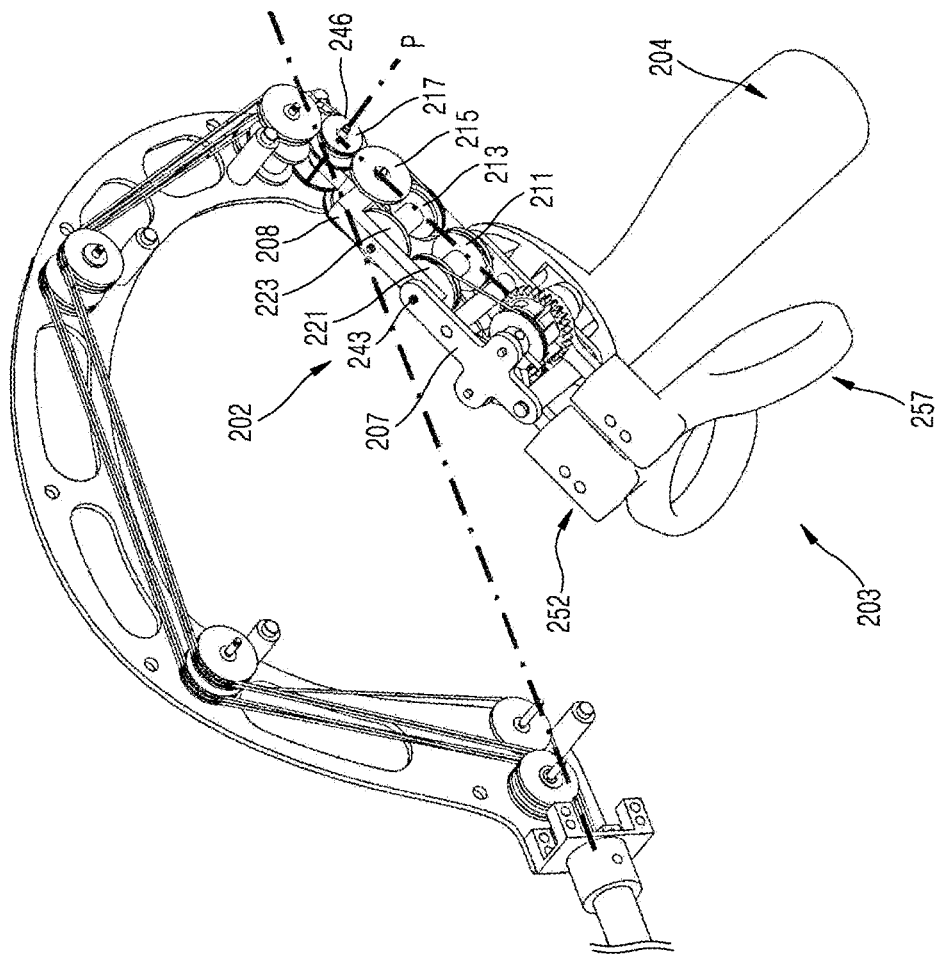
FIG. 222 is a perspective view illustrating a pitch motion of the surgical instrument for electrocautery of FIG. 140.
Figure 222:
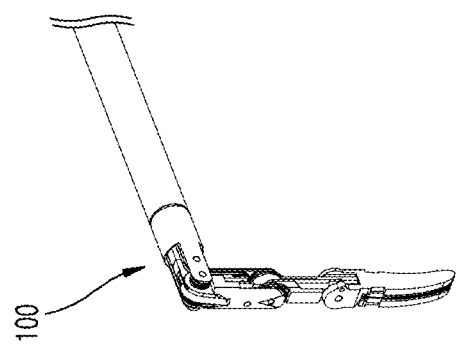
Figure 223:
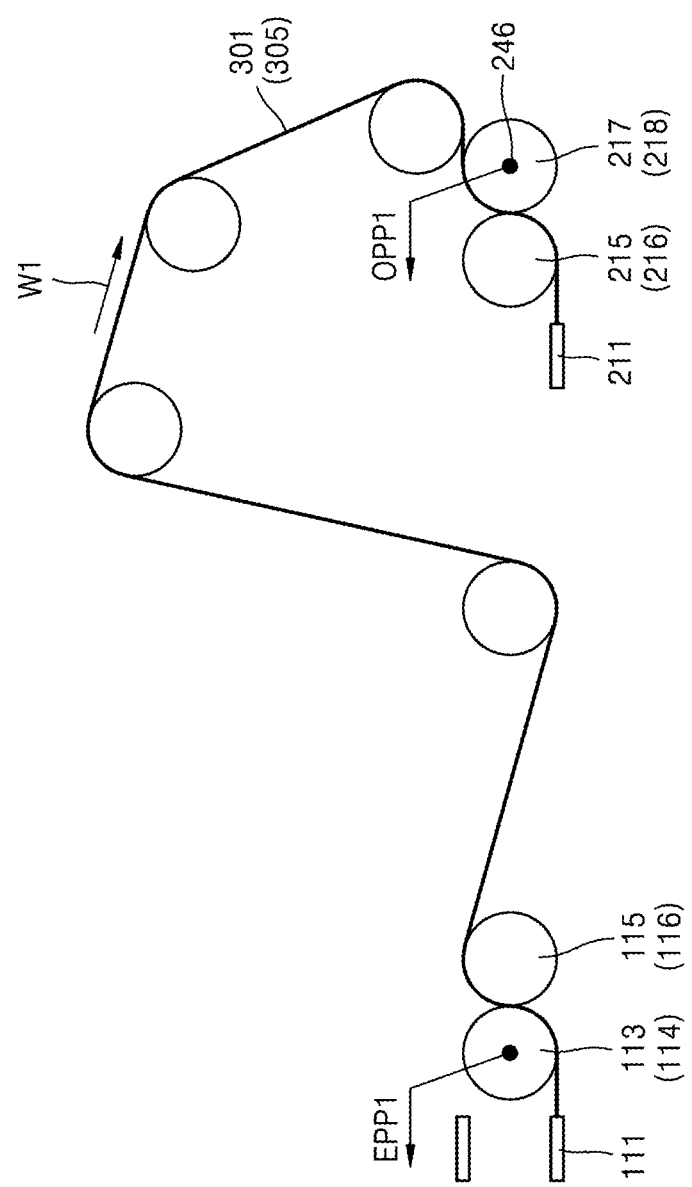
FIGS. 223 and 224 are diagrams illustrating a configuration of pulleys and wires, which are associated with a pitch motion of the surgical instrument for electrocautery illustrated in FIG. 140, in detail for each of the first jaw and the second jaw.
Figure 224:
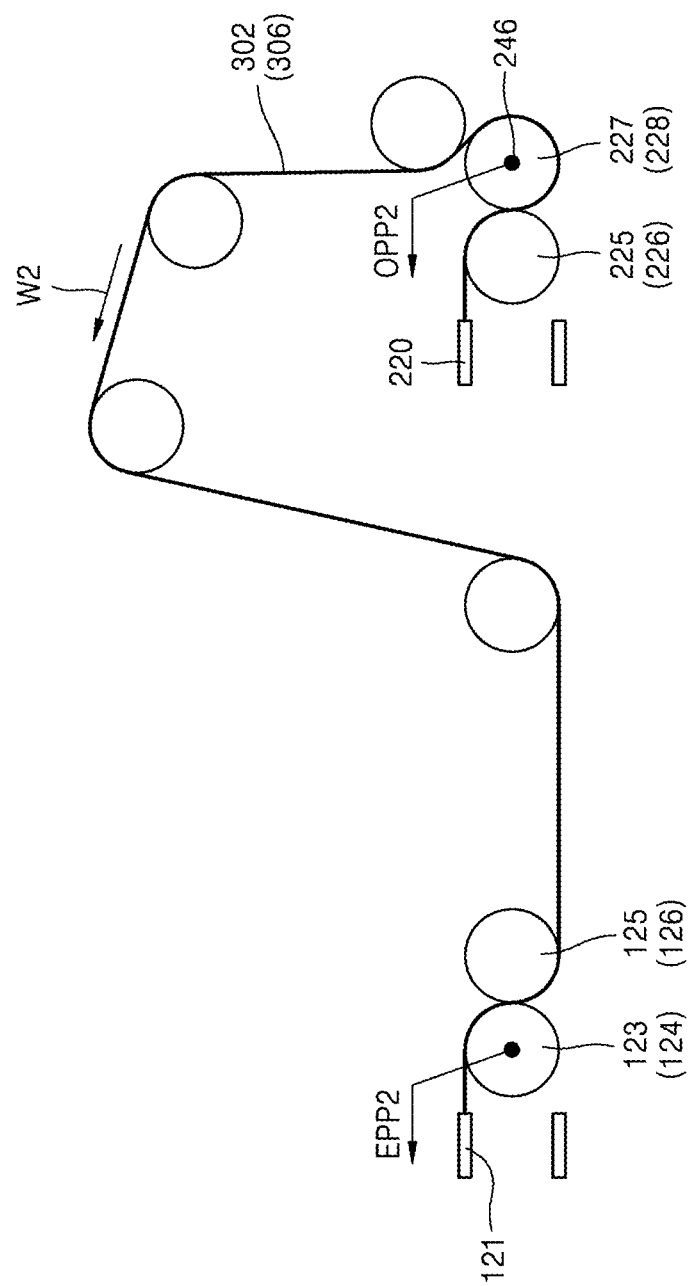

FIGS. 223 and 224 are diagrams illustrating a configuration of pulleys and wires, which are associated with a pitch motion of the electric cauterization surgical instrument 10 according to an embodiment of the present disclosure illustrated in FIG. 140, in detail for each of the first jaw and the second jaw. FIG. 223 is a diagram illustrating only pulleys and wires related to the second jaw, and FIG. 224 is a diagram illustrating only pulleys and wires related to the first jaw. As shown in FIG. 140 and elsewhere herein, there are two pulleys related to the pitch motion, and both strands of each wire are wound in the same path, which is illustrated with one line in FIG. 223. In addition, FIG. 222 is a perspective view illustrating a pitch motion of the surgical instrument of FIG. 140. Here, in FIG. 222, components associated with a cutting motion are omitted.

Referring to FIG. 223, when the first handle 204 rotates around the rotation shaft 246 in the direction of an arrow OPP1, the pulley 210, the pulley 215, the pulley 217, and the like, and the wire 301 and the like wound therearound are rotated as a whole around the rotation shaft 246. At this time, since the wires 301 and 305, which are first jaw wires, are wound around upper portions of the pulley 217 and the pulley 218, the wires 301 and 305 are moved in the direction of an arrow W1. As a result, the first jaw 1101 of the end tool 1100 rotates in the direction of an arrow EPP1.

Referring to FIG. 224, when the first handle 204 rotates around the rotation shaft 246 in the direction of an arrow OPP2, the pulley 220, the pulley 225, the pulley 227, and the like, and the wire 302 and the like wound therearound are rotated as a whole around the rotation shaft 246. At this time, since the wires 302 and 306, which are second jaw wires, are wound around lower portions of the pulley 227 and the pulley 228, the wires 302 and 306 are moved in the direction of an arrow W2. As a result, the second jaw 1102 of the end tool 1100 rotates in the direction of an arrow EPP2.

Thus, the actuation, yaw, and pitch manipulations are manipulatable independent of each other.

As described with reference to FIG. 140, the actuation manipulation portion 203, the yaw manipulation portion 202, and the pitch manipulation portion 201 are configured such that the respective rotation shafts are located at the rear thereof to be identical to the joint configuration of the end tool, so that a user may intuitively perform matching manipulations.

In particular, in the electric cauterization surgical instrument 10 according to an embodiment of the present disclosure, the pulleys are formed on respective joint points (an actuation joint, a yaw joint, and a pitch joint), the wires (the first jaw wire or the second jaw wire) are formed to be wound around the pulleys, the rotational manipulations (actuation rotation, yaw rotation, and pitch rotation) of the manipulation portion cause the movement of each wire, which in turn induces the desired motion of the end tool 1100. Furthermore, the auxiliary pulleys may be formed on one side of the respective pulleys, and these auxiliary pulleys may prevent the wire from being wound around one pulley multiple times, so that the wires wound around the pulley do not come into contact with each other, and paths of the wire being wound around the pulley and the wire being released from the pulley are safely formed, so that safety and efficiency in the transmission of driving force of a wire may be improved.

Meanwhile, as described above, the yaw manipulation portion 202 and the actuation manipulation portion 203 are directly formed on the first handle 204. Thus, when the first handle 204 rotates around the rotation shaft 246, the yaw manipulation portion 202 and the actuation manipulation portion 203 are also rotated together with the first handle 204. Accordingly, the coordinate systems of the yaw manipulation portion 202 and the actuation manipulation portion 203 are not fixed, but are continuously changed relative to the rotation of the first handle 204. That is, in FIG. 140 or the like, the yaw manipulation portion 202 and the actuation manipulation portion 203 are illustrated as being parallel to the Z-axis. However, when the first handle 204 is rotated, the yaw manipulation portion 202 and the actuation manipulation portion 203 are not parallel to the Z-axis any longer. That is, the coordinate systems of the yaw manipulation portion 202 and the actuation manipulation portion 203 arc changed according to the rotation of the first handle 204. However, in the present specification, for convenience of description, unless described otherwise, the coordinate systems of the yaw manipulation portion 202 and the actuation manipulation portion 203 are described on the basis of a state in which the first handle 204 is located perpendicular to the connection portion 400 as illustrated in FIG. 2.

(Pitch, Yaw, and Cutting Motions of End Tool)

Figure 168:
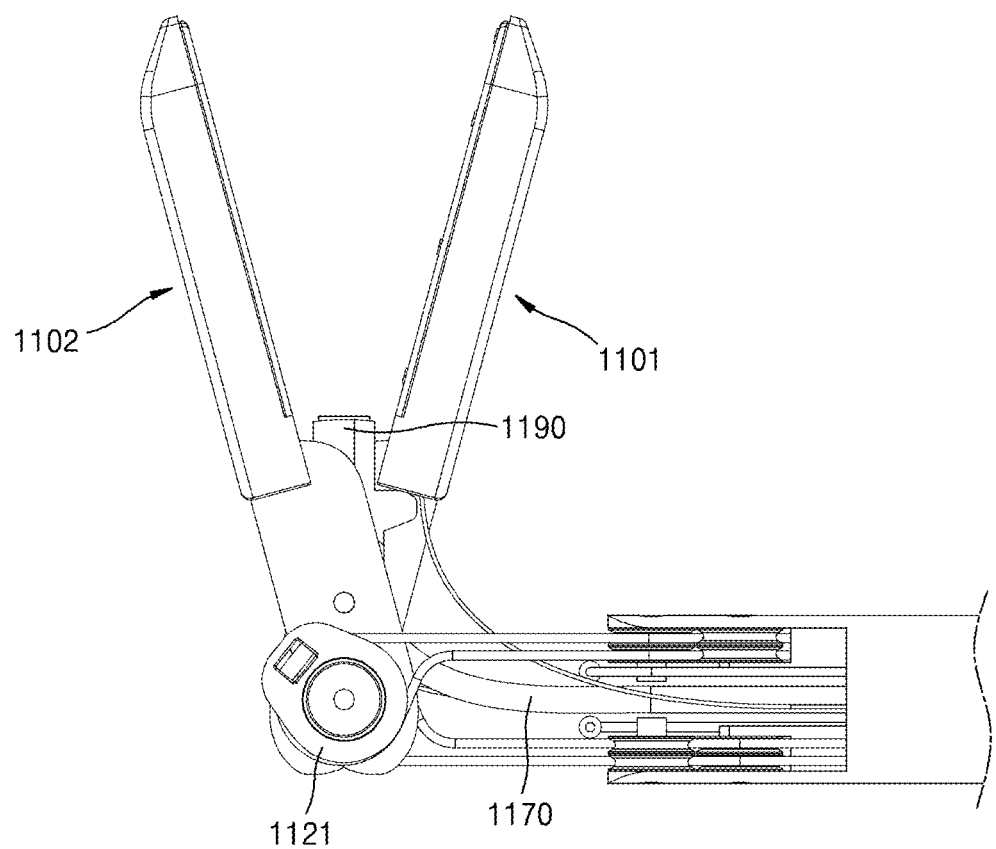
FIGS. 168 and 169 are views illustrating a process of performing an opening and closing motion in a state in which the end tool of the surgical instrument for electrocautery of FIG. 140 is yaw-rotated by −90°.
Figure 169:
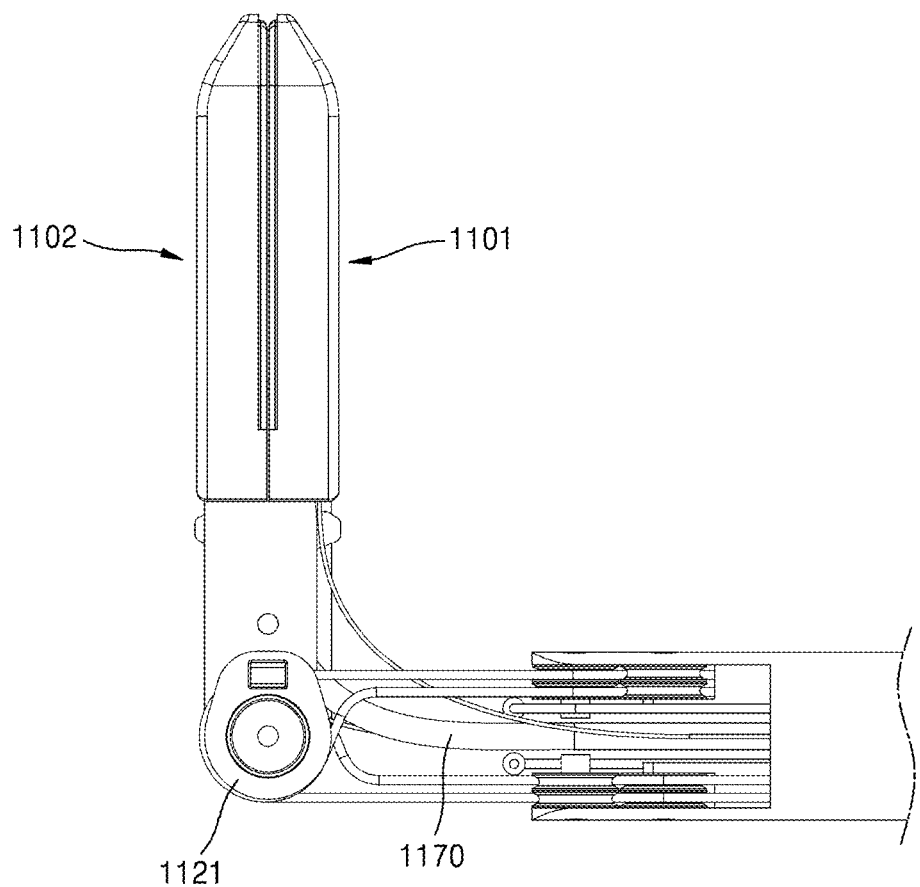
Figure 170:
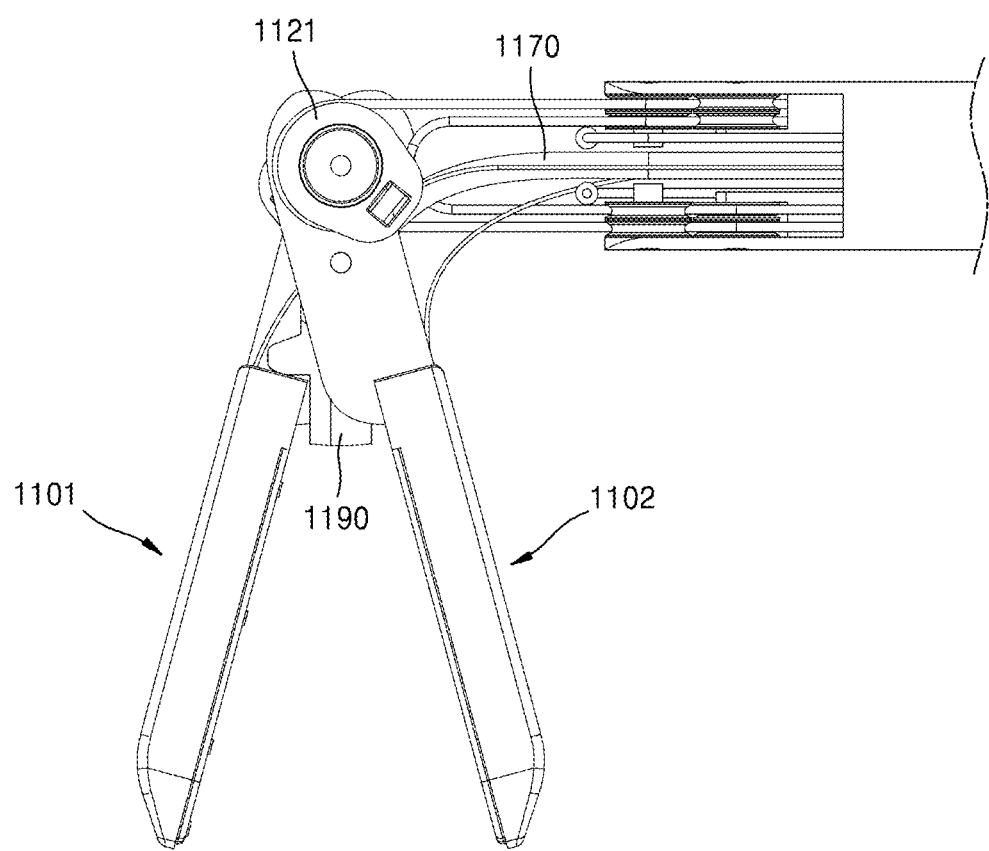
FIGS. 170 and 171 are bottom views illustrating a process of performing an opening and closing motion in a state in which the end tool of the surgical instrument for electrocautery of FIG. 140 is yaw-rotated by +90°.
Figure 171:
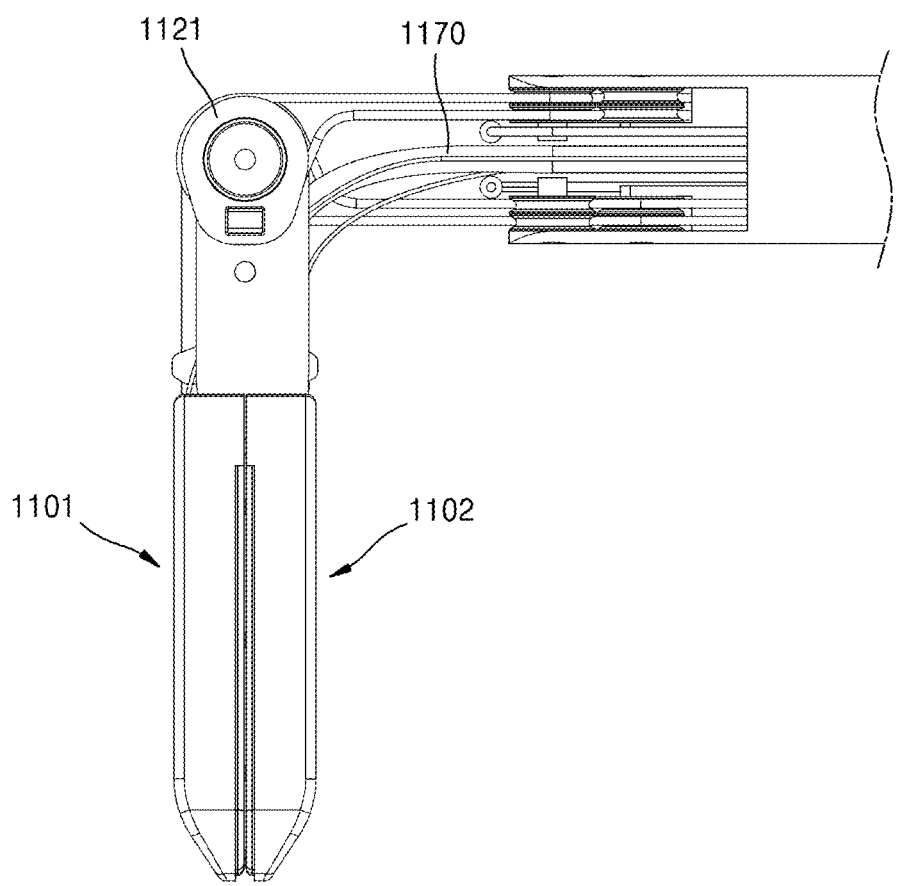

FIGS. 168 and 169 are views illustrating a process of performing an opening and closing motion in a state in which the end tool of the surgical instrument for electrocautery of FIG. 140 is yaw-rotated by +90°. In addition, FIGS. 170 and 171 are views illustrating a process of performing an opening and closing motion in a state in which the end tool of the surgical instrument for electrocautery of FIG. 140 is yaw-rotated by −90°.

As shown in FIGS. 168 to 171, the end tool of the surgical instrument for electrocautery according to the fourth embodiment of the present disclosure is formed to be able to normally perform an opening and closing motion, that is, an actuation motion even in a state in which the jaws are yaw-rotated by +90° or −90°.

Figure 172:
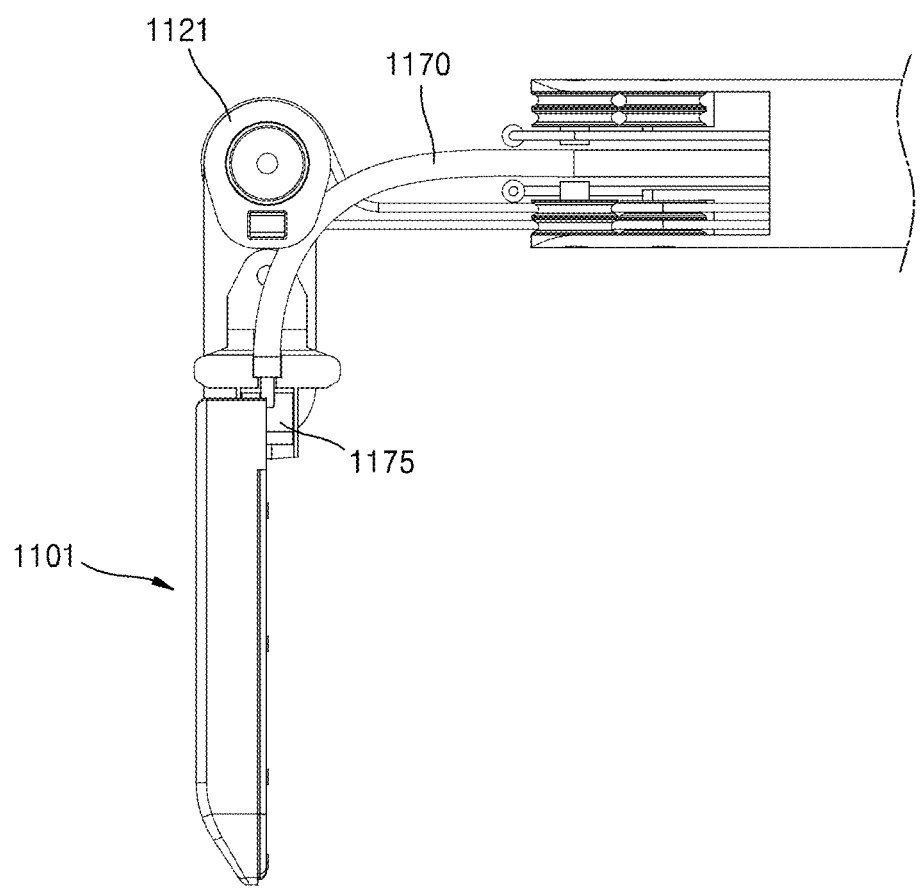
FIGS. 172 and 173 are views illustrating a path of the guide tube and a movement path of a blade during a cutting motion in a state in which the end tool of the surgical instrument for electrocautery of FIG. 140 is yaw-rotated.
Figure 173:
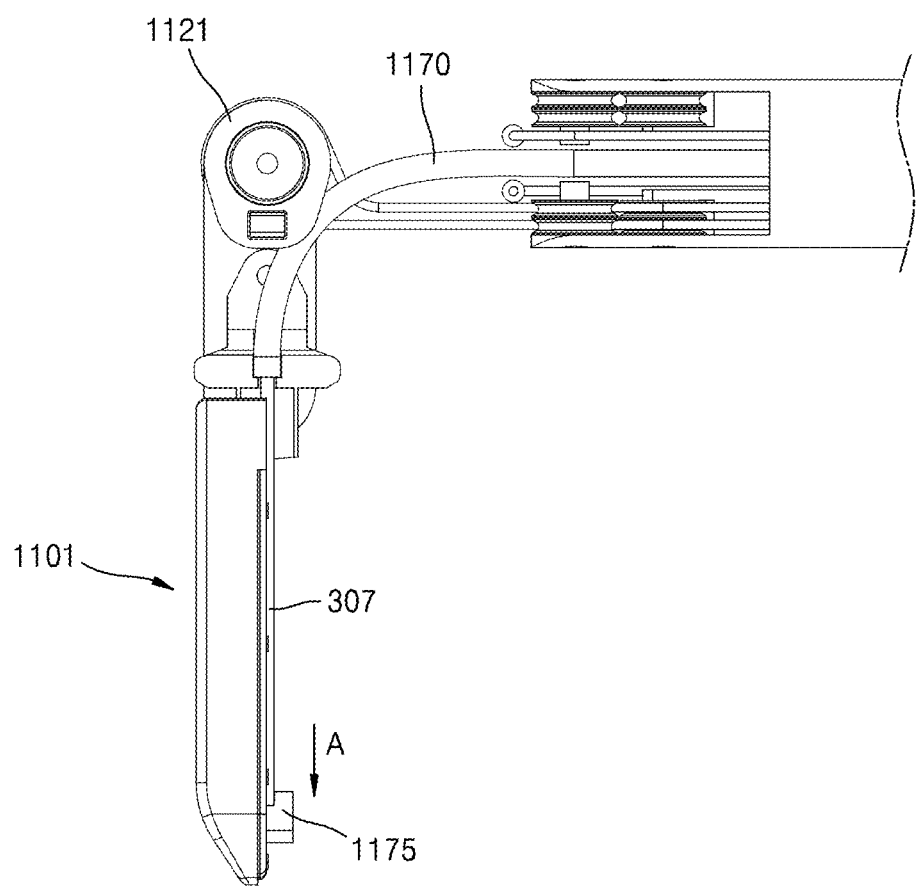

FIGS. 172 and 173 are views illustrating a process of performing a cutting motion in a state in which the end tool of the surgical instrument for electrocautery of FIG. 140 is yaw-rotated by +90°.

As shown in FIGS. 172 and 173, the end tool of the surgical instrument for electrocautery according to the fourth embodiment of the present disclosure is formed to be able to normally perform a cutting motion even in a state in which the jaws are yaw-rotated by +90°.

Figure 174:
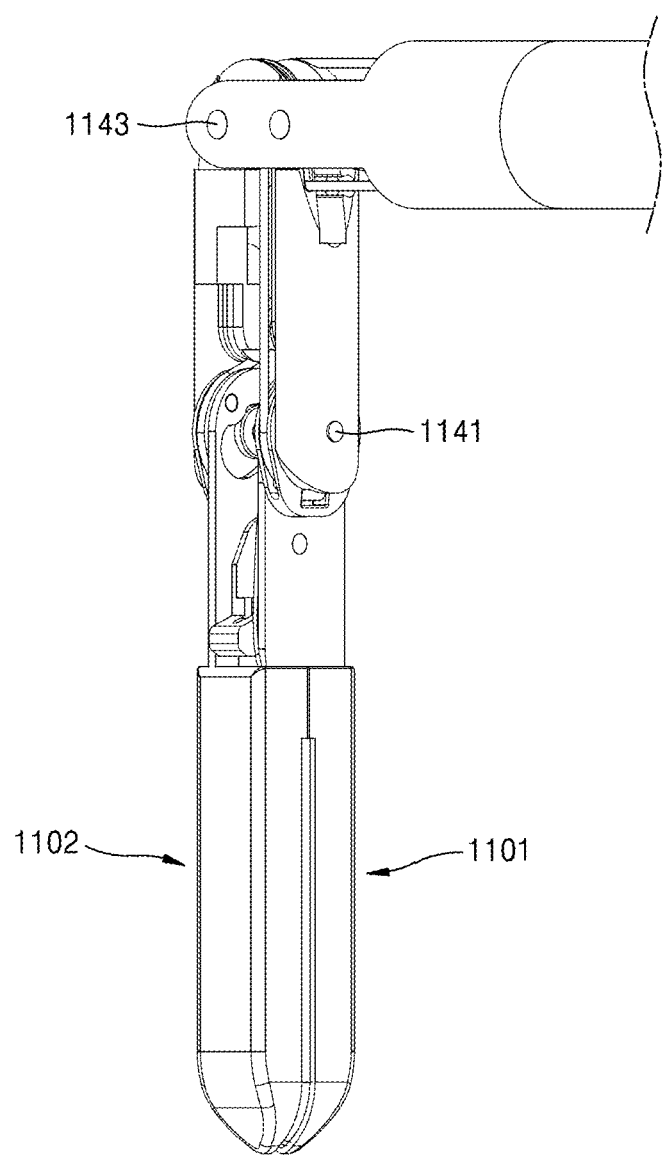
FIGS. 174 and 175 are views illustrating a process of performing an opening and closing motion in a state in which the end tool of the surgical instrument for electrocautery of FIG. 140 is pitch-rotated by +90°.
Figure 175:
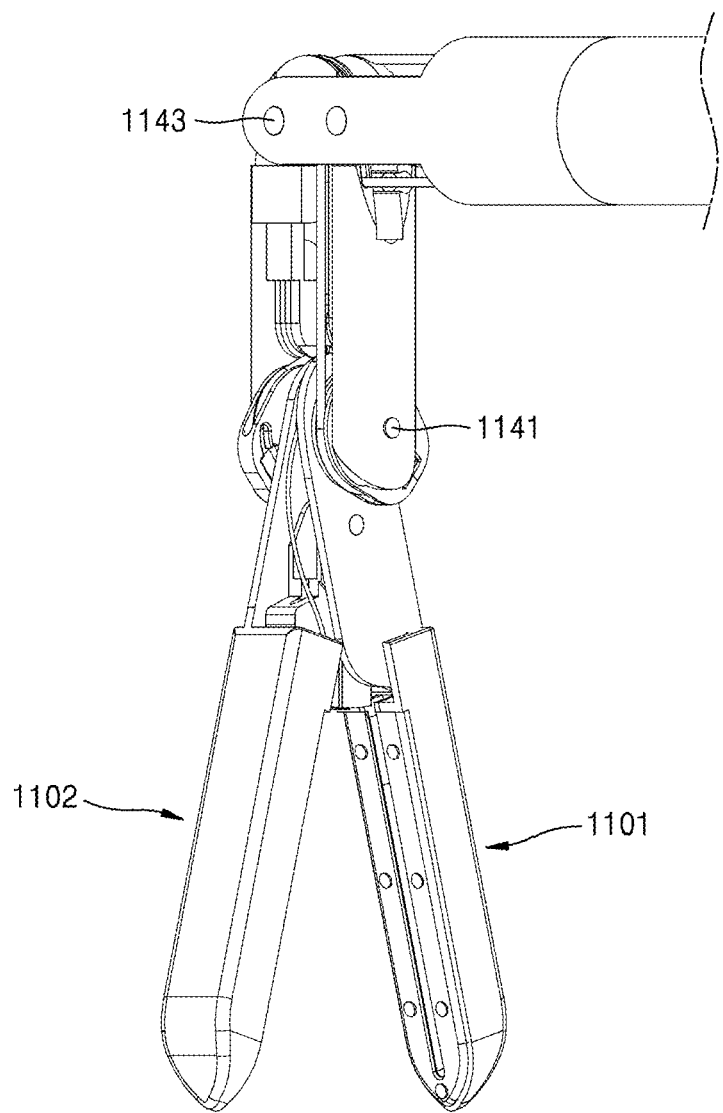
Figure 176:
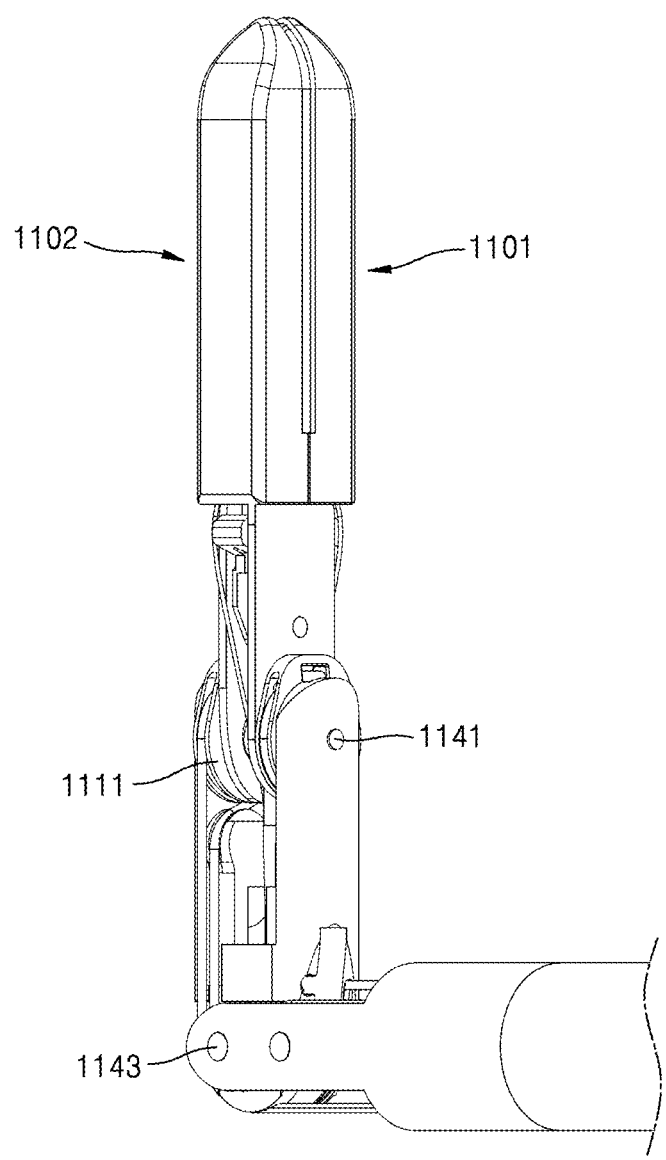
FIGS. 176 and 177 are views illustrating a process of performing an opening and closing motion in a state in which the end tool of the surgical instrument for electrocautery of FIG. 140 is pitch-rotated by −90°.
Figure 177:
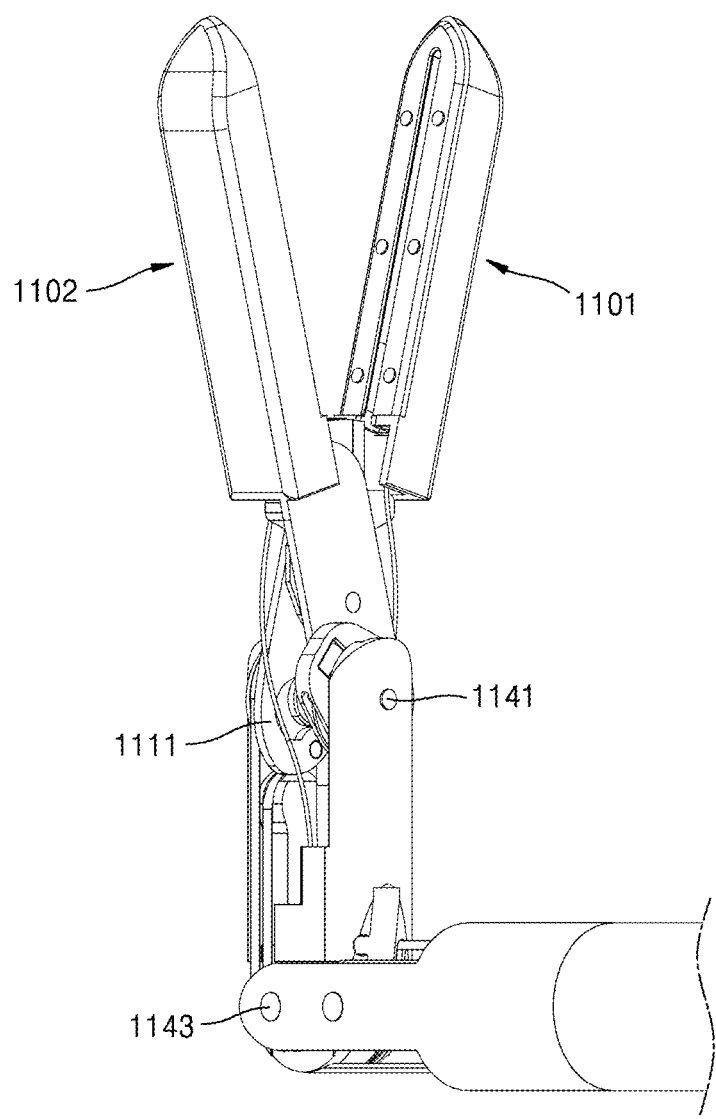
Figure 178:
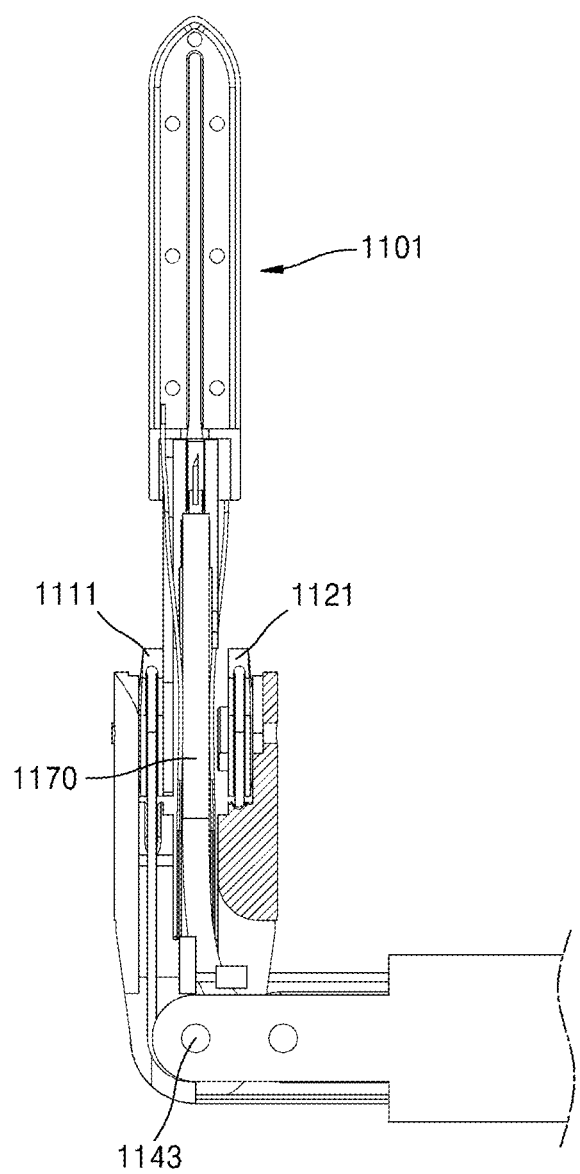
FIG. 178 is a view illustrating a path of the guide tube in a state in which the end tool of the surgical instrument for electrocautery of FIG. 140 is pitch-rotated by −90°.
Figure 179:
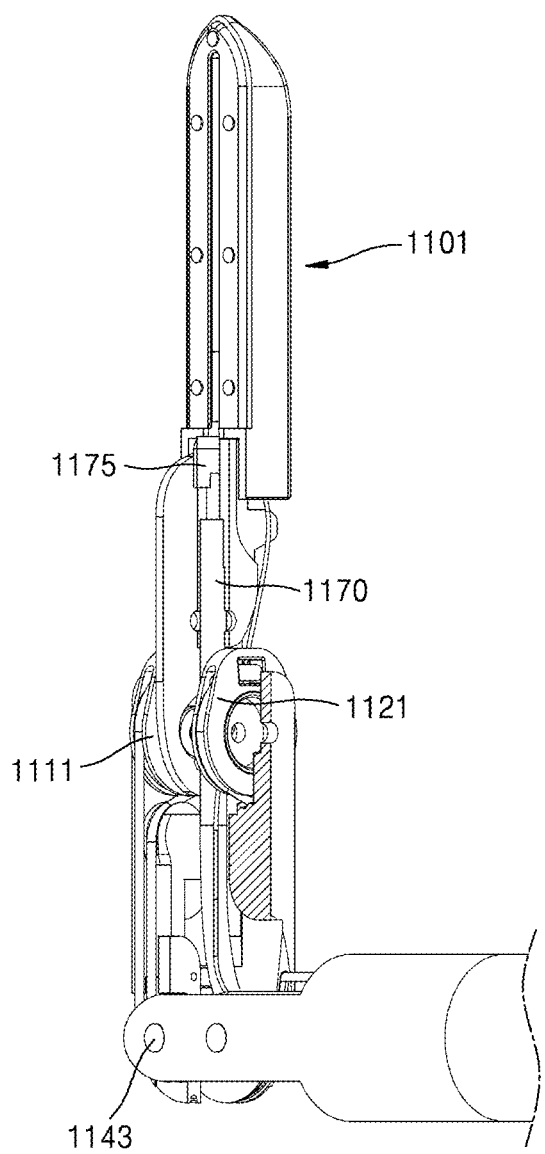
FIGS. 179 and 180 are views illustrating a path of the guide tube and a movement path of the blade during a cutting motion in a state in which the end tool of the surgical instrument for electrocautery of FIG. 140 is pitch-rotated by −90°.
Figure 180:
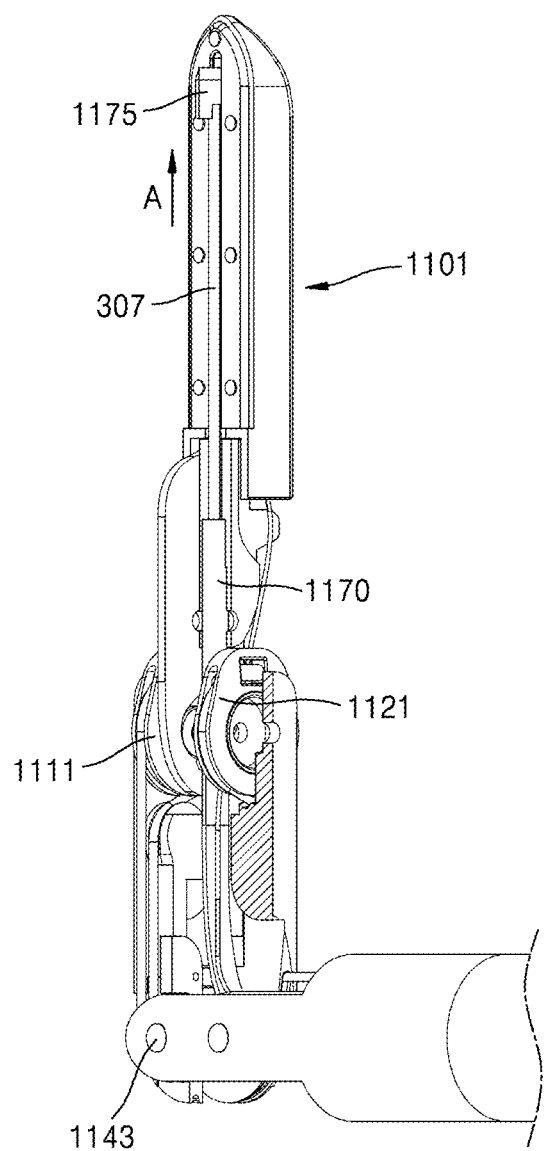

FIGS. 174 and 175 are views illustrating a process of performing an opening and closing motion in a state in which the end tool of the surgical instrument for electrocautery of FIG. 140 is pitch-rotated by +90°. FIGS. 176 and 177 are views illustrating a process of performing an opening and closing motion in a state in which the end tool of the surgical instrument for electrocautery of FIG. 140 is pitch-rotated by −90°. In addition, FIG. 178 is a cut-away perspective view of the end tool of the surgical instrument for electrocautery of FIG. 176. In addition, FIGS. 179 and 180 are views illustrating a process of performing a cutting motion in a state in which the end tool of the surgical instrument for electrocautery of FIG. 140 is pitch-rotated by −90°.

As shown in FIGS. 174 to 180, the end tool of the surgical instrument for electrocautery according to the fourth embodiment of the present disclosure is formed to be able to normally perform a cutting motion even in a state in which the jaws are pitch-rotated by −90°.

Figure 181:
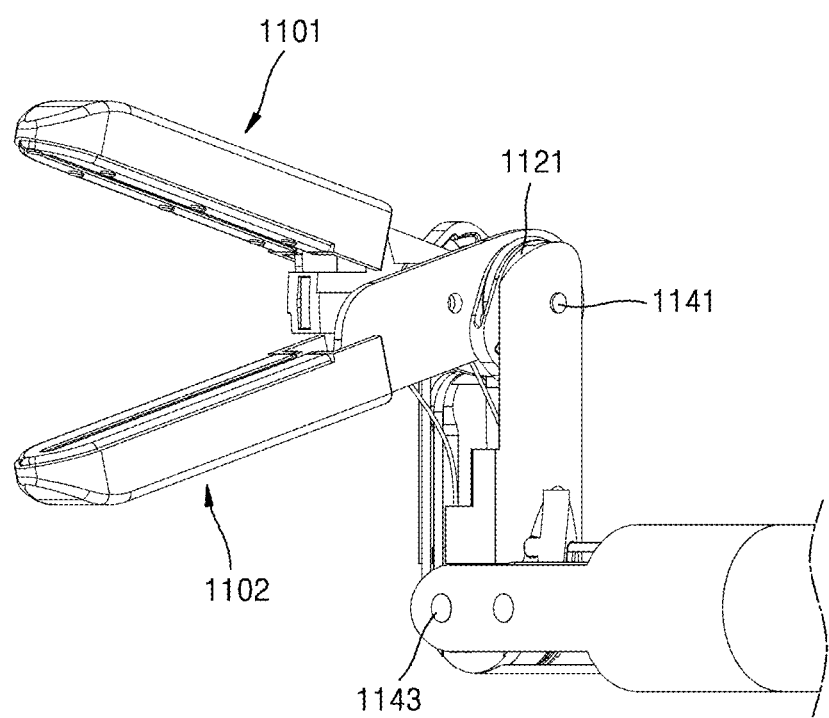
FIG. 181 is a perspective view illustrating the surgical instrument for electrocautery of FIG. 140 in a pitch-rotated and yaw-rotated state.
Figure 182:
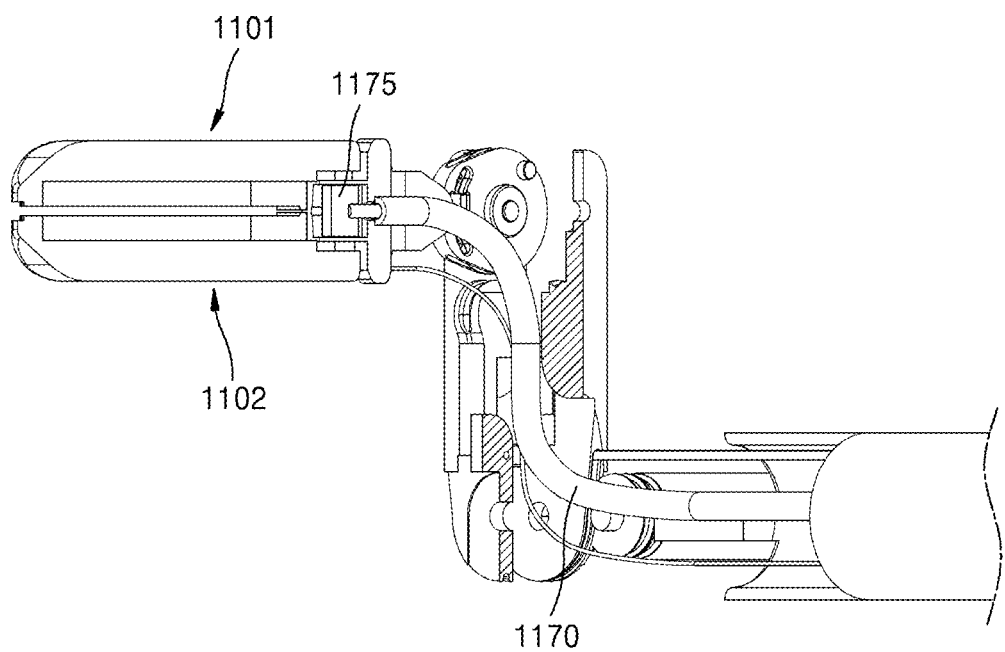
FIGS. 182 to 184 are views illustrating the end tool of the surgical instrument for electrocautery of FIG. 140 performing a cutting motion in a state in which the end tool is pitch-rotated by −90° and simultaneously yaw-rotated by +90°.
Figure 183:
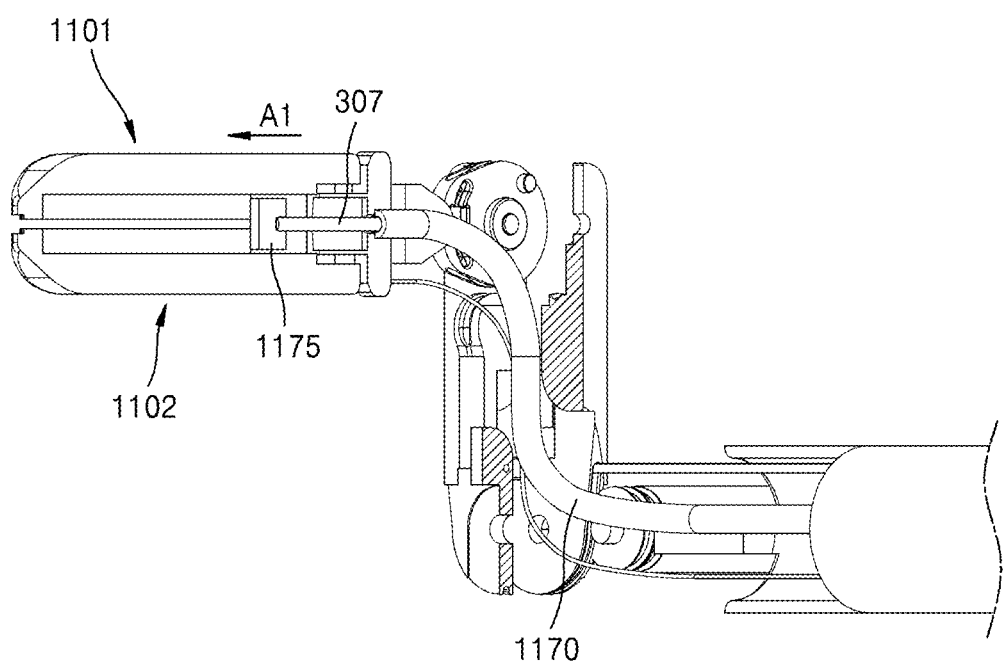
Figure 184:
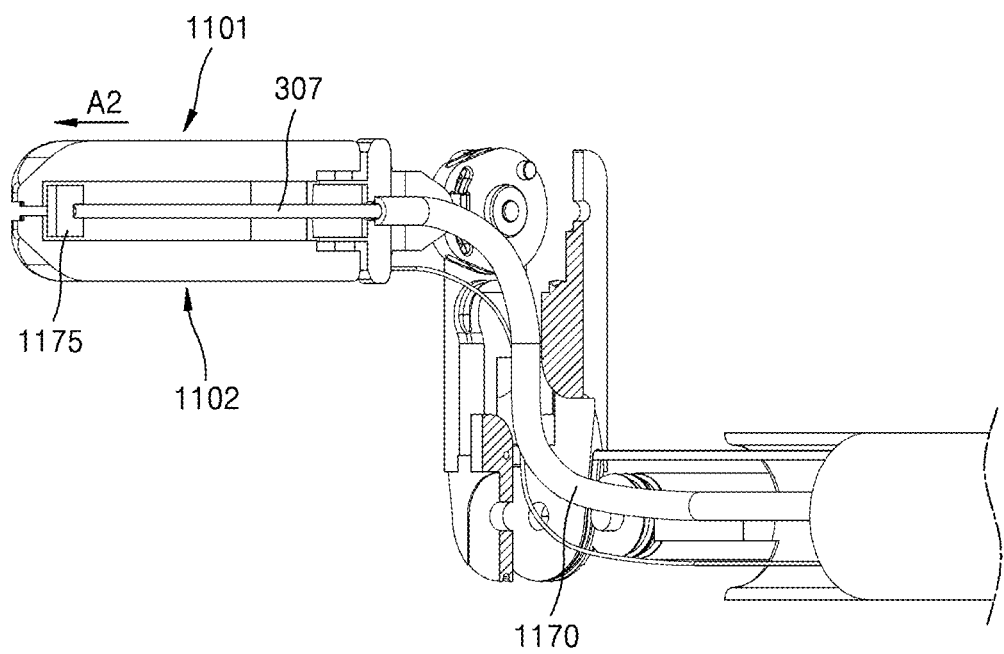

Meanwhile, FIG. 181 is a view illustrating a state in which the jaws are pitch-rotated by −90° and simultaneously yaw-rotated by +90°, and FIGS. 182, 183, and 184 are perspective views illustrating a cutting motion of the end tool of the surgical instrument for electrocautery of FIG. 140 and illustrate a state of performing a cutting motion while the jaws are pitch-rotated by −90° and simultaneously yaw-rotated by +90°.

As shown in FIGS. 181 to 184, the end tool of the surgical instrument for electrocautery according to the fourth embodiment of the present disclosure is formed to be able to normally perform a cutting motion even in a state in which the jaws are pitch-rotated by −90° and simultaneously yaw-rotated by +90°.

First Modified Example of Fourth Embodiment

Hereinafter, an end tool 1200 of a surgical instrument according to a first modified example of the fourth embodiment of the present disclosure will be described. Here, the end tool 1200 of the surgical instrument according to the first modified example of the fourth embodiment of the present disclosure is different from the end tool (see 1100 in FIG. 140 or the like) of the surgical instrument according to the fourth embodiment of the present disclosure described above in that the configuration of an actuation hub 1290 is different. The configuration changed from the fourth embodiment as described above will be described in detail later.

Figure 185:
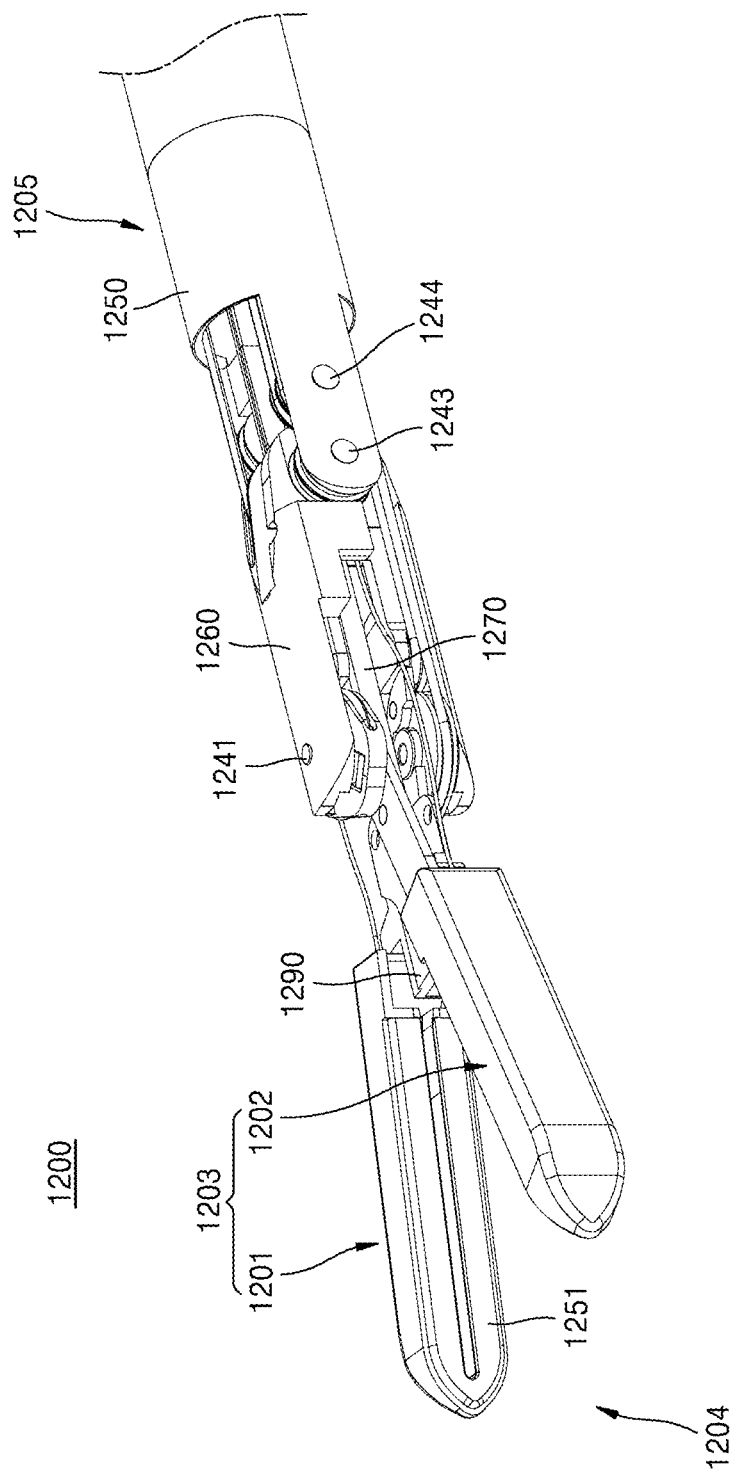
FIGS. 185 and 186 are perspective views illustrating an end tool of a surgical instrument for electrocautery according to a first modified example of the fourth embodiment of the present disclosure.
Figure 186:
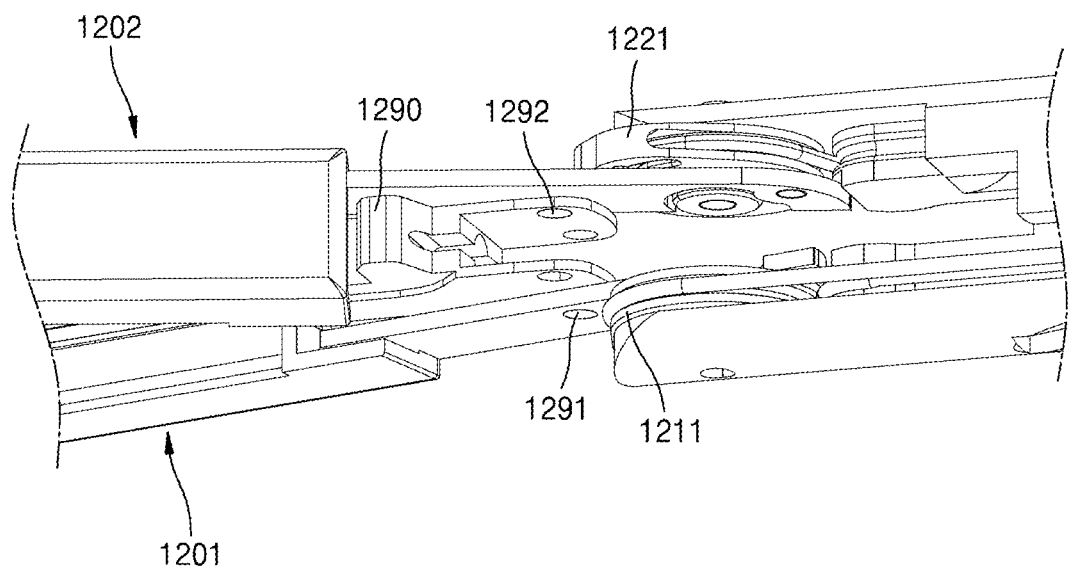
Figure 187:
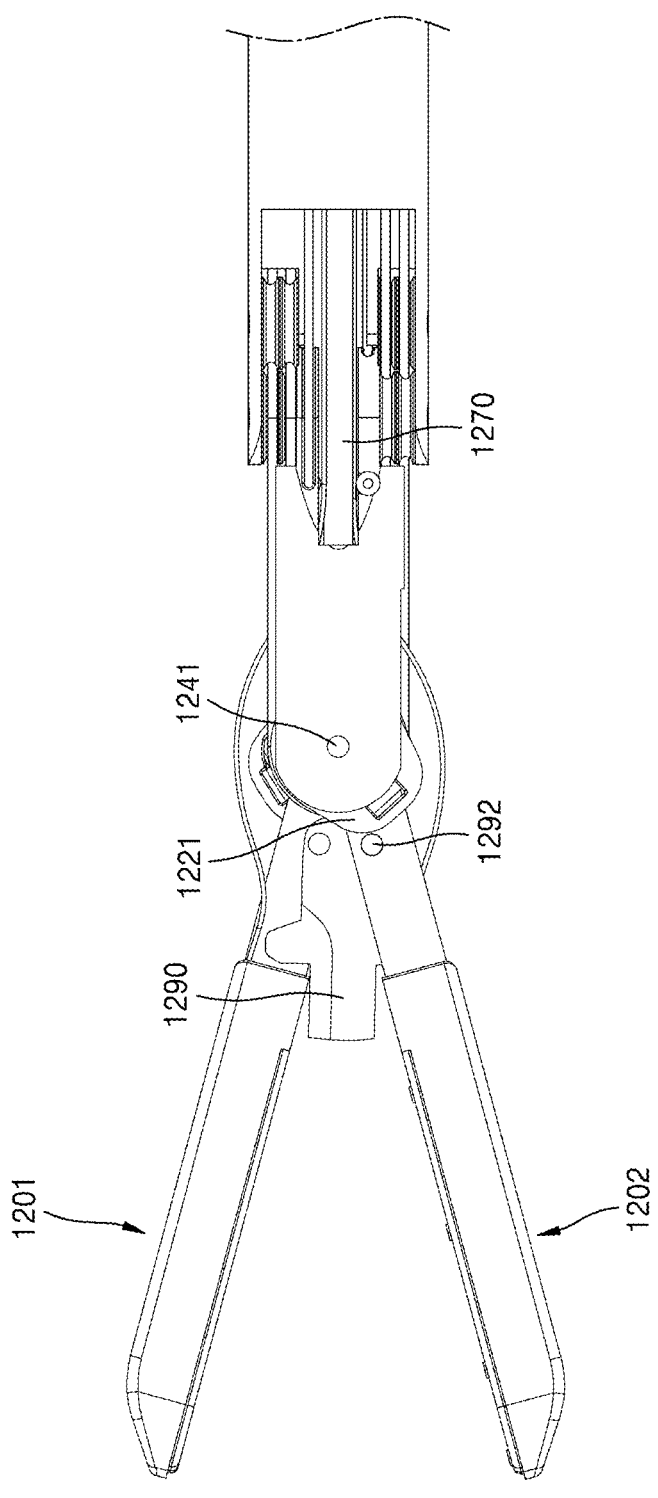
FIGS. 187 and 188 are plan views illustrating the end tool of the surgical instrument for electrocautery according to the first modified example of the fourth embodiment of the present disclosure.
Figure 188:
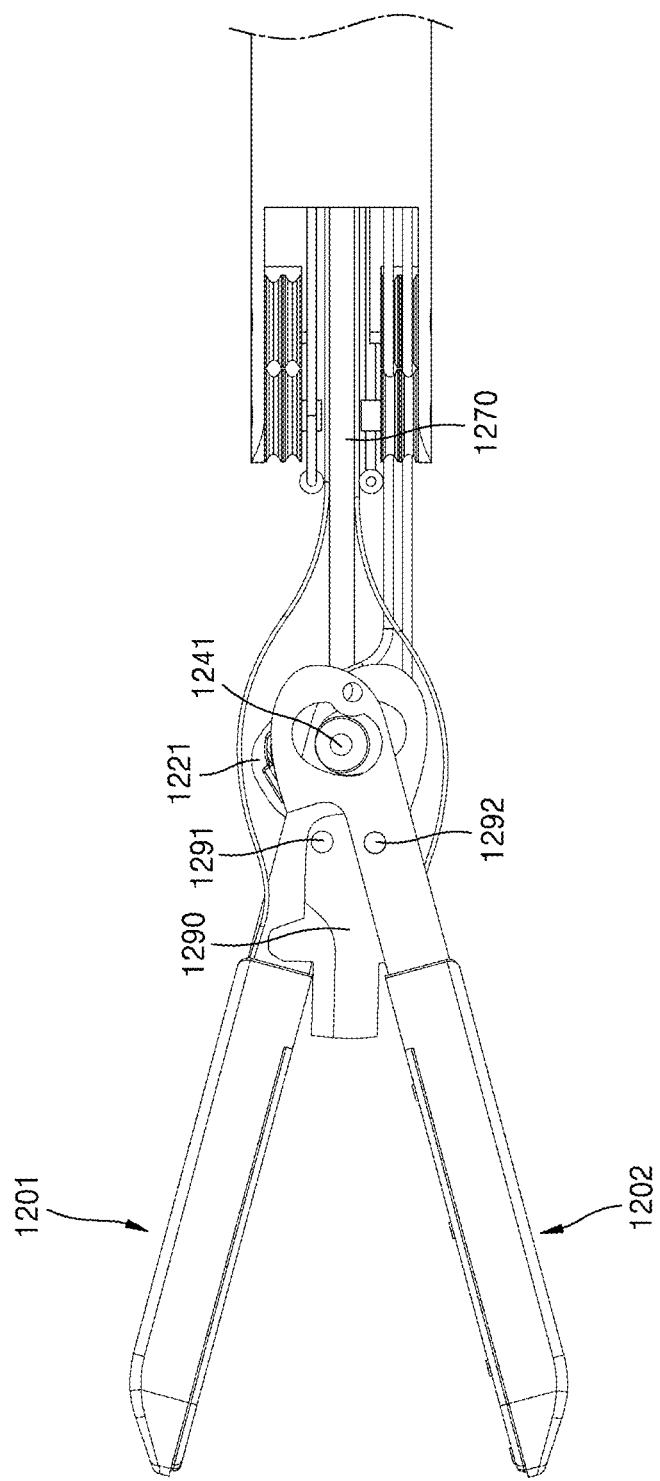
Figure 189:
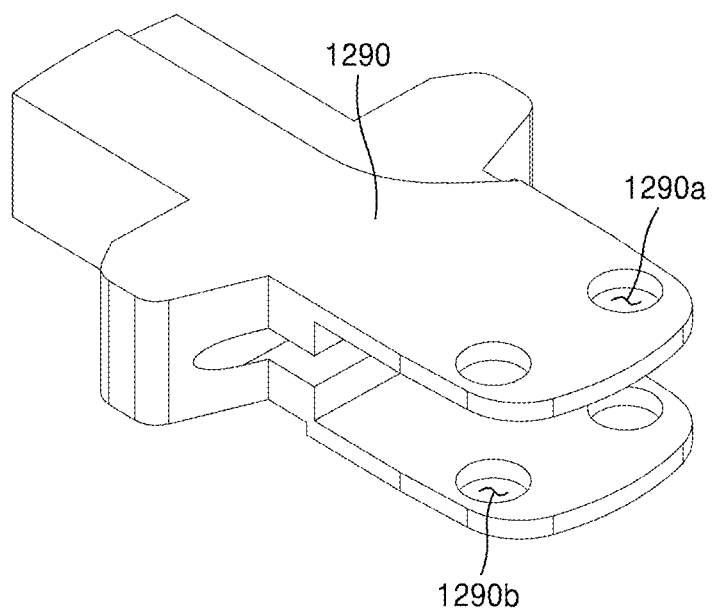
FIGS. 189 and 190 are views illustrating an actuation hub of the surgical instrument for electrocautery according to the first modified example of the fourth embodiment of the present disclosure.
Figure 190:
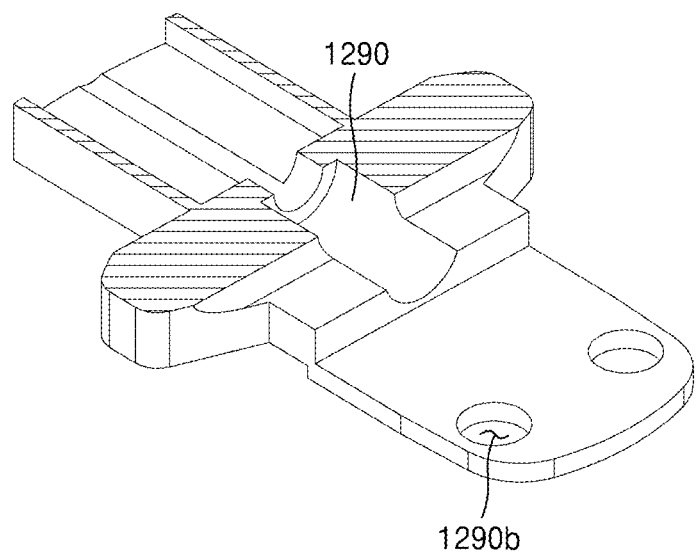
Figure 191:
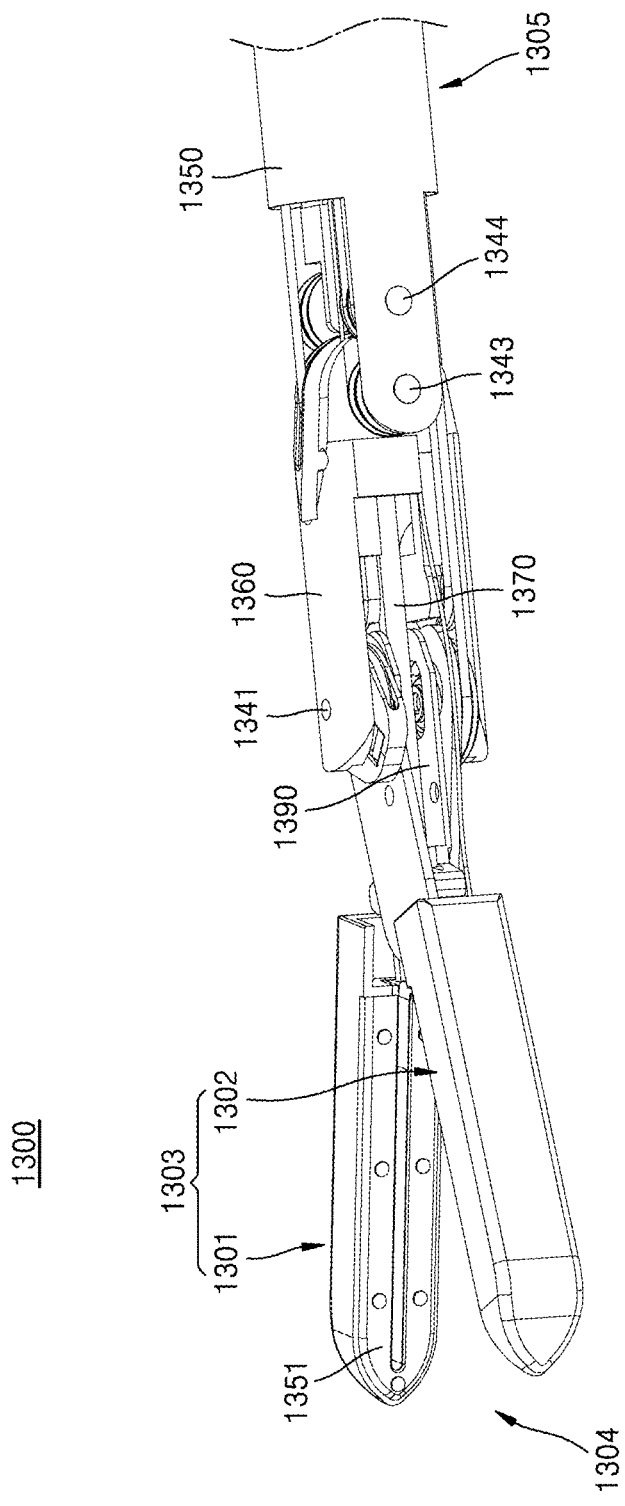
FIGS. 191 to 196 are views illustrating an end tool of a surgical instrument for electrocautery according to a second modified example of the fourth embodiment of the present disclosure.
Figure 192:
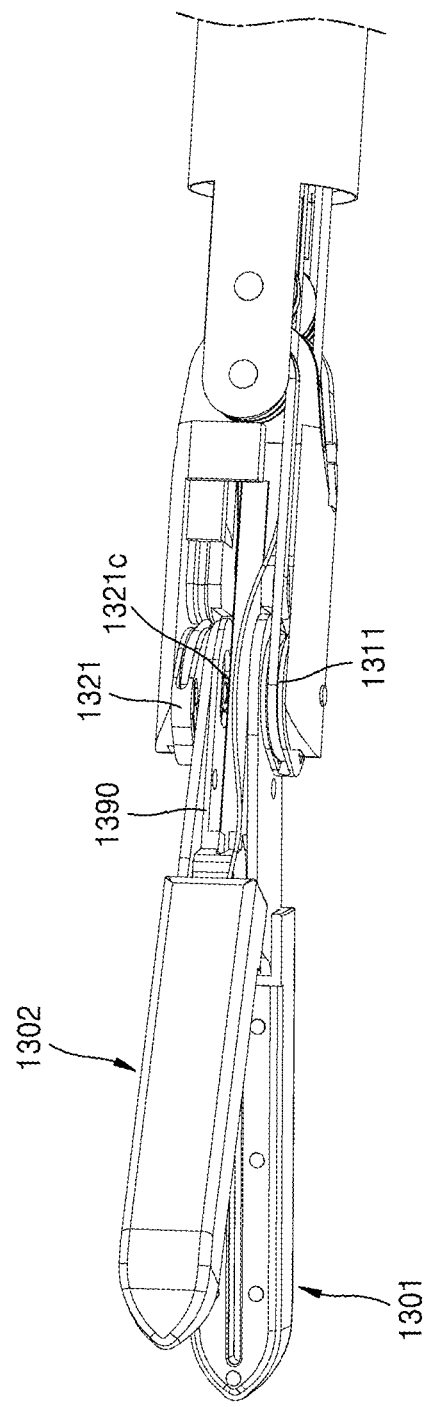
Figure 193:
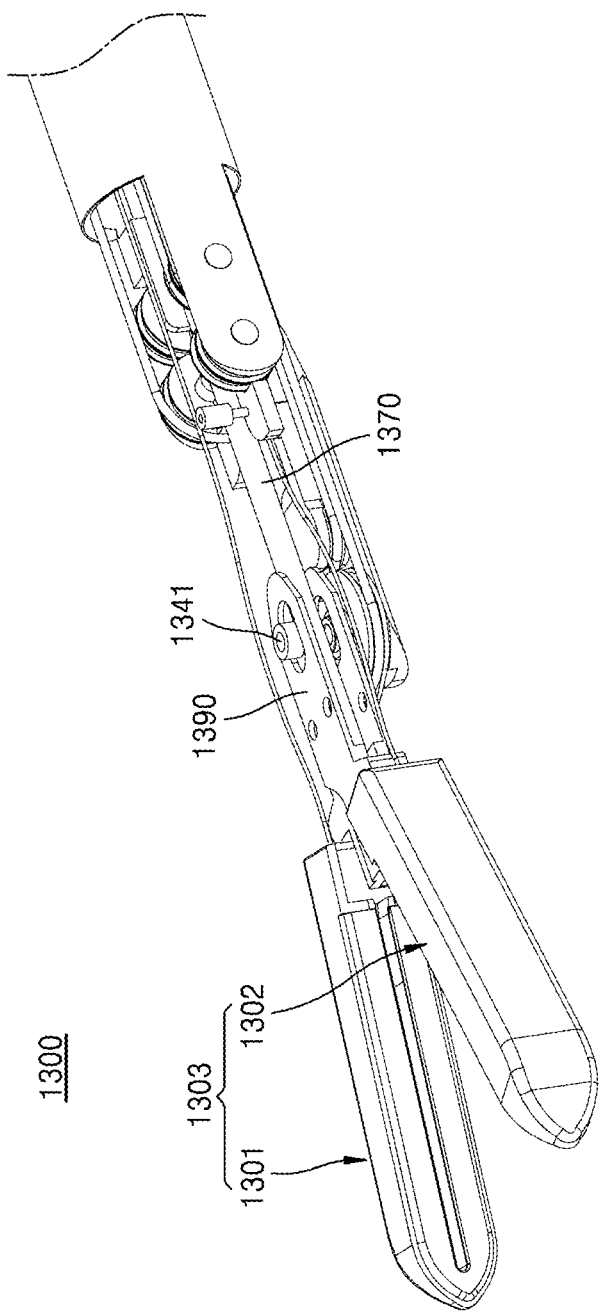
Figure 194:
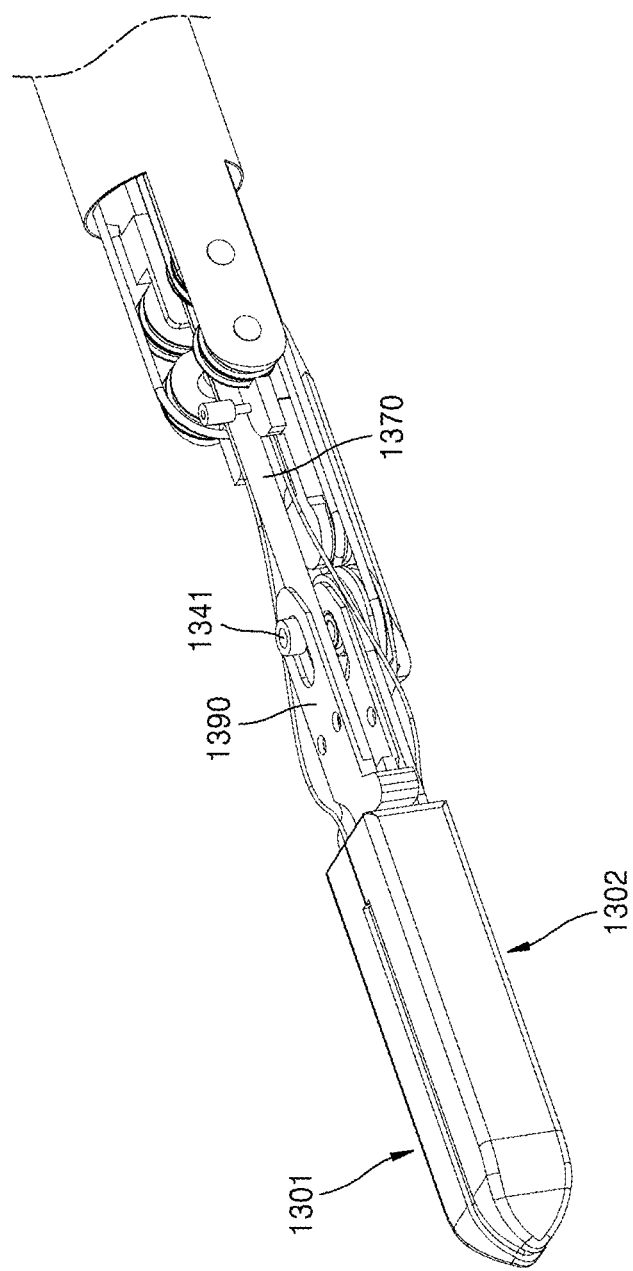
Figure 195:
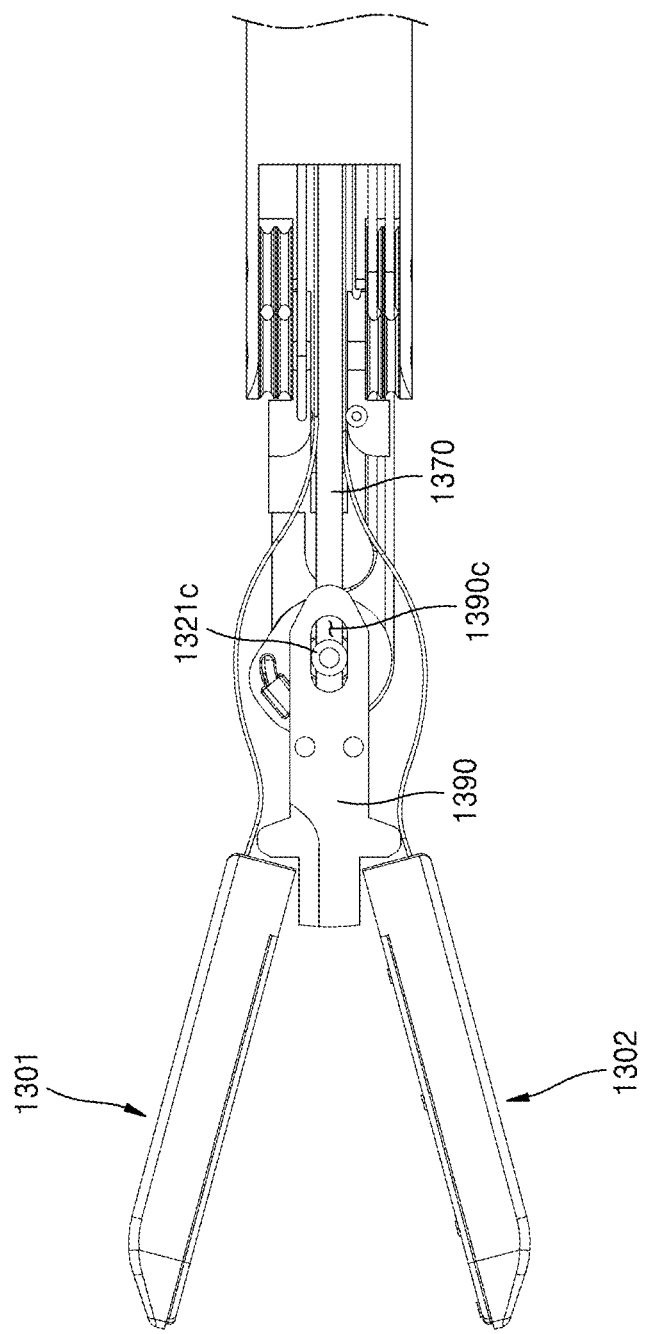
Figure 196:
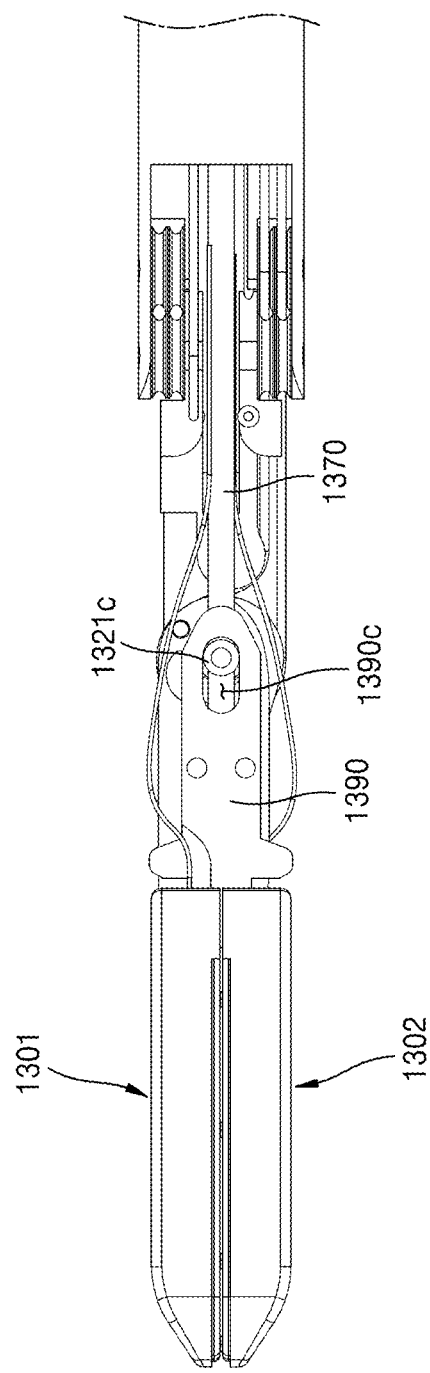

FIGS. 185 and 186 are perspective views illustrating the end tool of the surgical instrument for electrocautery according to the first modified example of the fourth embodiment of the present disclosure. FIGS. 187 and 188 are plan views illustrating the end tool of the surgical instrument for electrocautery according to the first modified example of the fourth embodiment of the present disclosure. FIGS. 189 and 190 are views illustrating an actuation hub of the surgical instrument for electrocautery according to the first modified example of the fourth embodiment of the present disclosure.

Referring to FIGS. 185 to 190, the end tool 1200 of the first modified example of the fourth embodiment of the present disclosure includes a pair of jaws for performing a grip motion, that is, a first jaw 1201 and a second jaw 1202, and herein, each of the first jaw 1201 and the second jaw 1202 or a component encompassing the first jaw 1201 and the second jaw 1202 may be referred to as a jaw 1203.

Meanwhile, the end tool 1200 includes a plurality of pulleys including a pulley 1211, a pulley 1213, and a pulley 1214 that are associated with a rotational motion of the first jaw 1201. Meanwhile, the end tool 1200 includes a plurality of pulleys including a pulley 1221 associated with a rotational motion of the second jaw 1202.

In addition, the end tool 1200 of the first modified example of the fourth embodiment of the present disclosure may include a rotation shaft 1241, a rotation shaft 1243, and a rotation shaft 1244. Here, the rotation shaft 1241 may be inserted through an end tool hub 1260, and the rotation shaft 1243 and the rotation shaft 1244 may be inserted through a pitch hub 1250. The rotation shaft 1241, the rotation shaft 1243, and the rotation shaft 1244 may be arranged sequentially from a distal end 1204 toward a proximal end 1205 of the end tool 1200.

Further, the end tool 1200 of the first modified example of the fourth embodiment of the present disclosure may include the end tool hub 1260 and the pitch hub 1250.

The rotation shaft 1241 is inserted through the end tool hub 1260, and the pulley 1211 and the pulley 1221, which are axially coupled to the rotation shaft 1241, and at least some of the first jaw 1201 and the second jaw 1202 coupled the pulley 1211 and the pulley 1221 may be accommodated inside the end tool hub 1260.

Meanwhile, a first pitch pulley portion 1263a and a second pitch pulley portion 1263b, which serve as end tool pitch pulleys, may be formed at one end portion of the end tool hub 1260. A wire (see 303 of FIG. 146) and a wire 304

(see 304 of FIG. 146) are coupled to the first pitch pulley portion 1263a and the second pitch pulley portion 1263b, which serve as end tool pitch pulleys, and a pitch motion is performed while the end tool hub 1260 rotates around the rotation shaft 1243.

The rotation shaft 1243 and the rotation shaft 1244 may be inserted through the pitch hub 1250, and the pitch hub 1250 may be axially coupled to the end tool hub 1260 by the rotation shaft 1243. Accordingly, the end tool hub 1260 may be formed to be pitch-rotatable around the rotation shaft 1243 with respect to the pitch hub 1250.

Meanwhile, the end tool 1200 of the fourth embodiment of the present disclosure may further include components such as a first electrode 1251, a second electrode 1252, a guide tube 1271, and a blade 1275 in order to perform a cauterizing motion and a cutting motion. Here, components related to the driving of the blade, such as the guide tube 1271 and the blade 1275, may be collectively referred to as a blade assembly. Components for performing a cauterizing motion and a cutting motion in the present embodiment are substantially the same as those described in the fourth embodiment, and thus a detailed description thereof will be omitted herein.

The surgical instrument for electrocautery according to the first modified example of the fourth embodiment of the present disclosure may include a wire 301, a wire 302, a wire 303, a wire 304, a wire 305, a wire 306, and a blade wire 307, as in the fourth embodiment of the present disclosure described with reference to FIG. 140 or the like.

Hereinafter, the actuation hub 1290 of the first modified example of the fourth embodiment of the present disclosure will be described in more detail.

Referring to FIGS. 185 to 190, the actuation hub 1290 may be formed in the form of a box having a hollow therein. Here, a first coupling hole 1290a is formed in any one surface of the actuation hub 1290, specifically, a surface coming into contact with the first jaw 1201, and a second coupling hole 1290b may be formed in the other surface of the actuation hub 1290, specifically, a surface coming into contact with the second jaw 1202.

In this case, the first coupling hole 1290a may be formed to be offset to a certain degree in one direction from the center line in the X-axis direction. In addition, the second coupling hole 1290b may be formed by being offset to a certain degree in another one direction from the center line in the X-axis direction.

In other words, it may be said that the first coupling hole 1290a and the second coupling hole 1290b are not on the same line in the Z-axis direction but are formed to be offset to a certain degree.

In addition, the actuation hub 1290 is coupled to each of the first jaw 1201 and the second jaw 1202. In detail, a first actuation rotation shaft 1291 is inserted through the first jaw 1201 and the first coupling hole 1290a of the actuation hub 1290, so that the actuation hub 1290 and the first jaw 1201 are axially coupled. Further, a second actuation rotation shaft 1292 is inserted through the second jaw 1202 and the second coupling hole 1290B of the actuation hub 1290, so that the actuation hub 1290 and the second jaw 1202 are axially coupled.

Meanwhile, as described with reference to FIG. 154 or the like, a tube seating portion, a wire through-hole, and a blade accommodation portion are sequentially formed inside the actuation hub 1290, and the blade wire 307 may pass through the inside of the actuation hub 1290 to be connected to the blade 1275.

As described above, by providing the actuation hub 1290 to which the guide tube 1270 is coupled between the first jaw 1201 and the second jaw 1202, the guide tube 1270 may not be curved, or the angle at which the guide tube 1270 is curved may be reduced, even when the first jaw 1201 or the second jaw 1202 rotates around the first rotation shaft 1241 or the actuation rotation shaft 1245.

In detail, in a case in which the guide tube 1270 is directly coupled to the first jaw 1201 or the second jaw 1202, when the first jaw 1201 or the second jaw 1202 rotates, one end portion of the guide tube 1270 also rotates together with the first jaw 1201 or the second jaw 1202, causing the guide tube 1270 to be curved.

On the other hand, in a case in which the guide tube 1270 is coupled to the actuation hub 1290, which is independent of the rotation of the jaw 1203, as in the present embodiment, even when the first jaw 1201 or the second jaw 1202 rotates, the guide tube 1270 may not be curved, or the angle at which the guide tube 1270 is curved may be reduced even when the guide tube 1270 is curved.

That is, by changing the direct connection between the guide tube 1270 and the jaw 1203 by the actuation hub 1290 to an indirect connection, the degree to which the guide tube 1270 is curved by the rotation of the jaw 1203 may be reduced.

In particular, in the end tool 1200 of the first modified example of the fourth embodiment of the present disclosure, when the actuation hub 1290 is coupled to the first jaw 1201 and the second jaw 1202, the first actuation rotation shaft 1291 and the second actuation rotation shaft 1292 are not on the same line in the Z-axis direction but are offset from each other to a certain degree. Thus, when the first jaw 1201 and the second jaw 1202 perform an actuation motion, the first actuation rotation shaft 1291 and the second actuation rotation shaft 1292 form a kind of two-point support, thereby obtaining an effect of more stably performing an actuation motion.

Second Modified Example of Fourth Embodiment

Hereinafter, an end tool 1300 of a surgical instrument according to a second modified example of the fourth embodiment of the present disclosure will be described. Here, the end tool 1300 of the surgical instrument according to the second modified example of the fourth embodiment of the present disclosure is different from the end tool (see 1100 in FIG. 140 or the like) of the surgical instrument according to the fourth embodiment of the present disclosure described above in that the configuration of an actuation hub 1390 is different. The configuration changed from the fourth embodiment as described above will be described in detail later.

Figure 197:
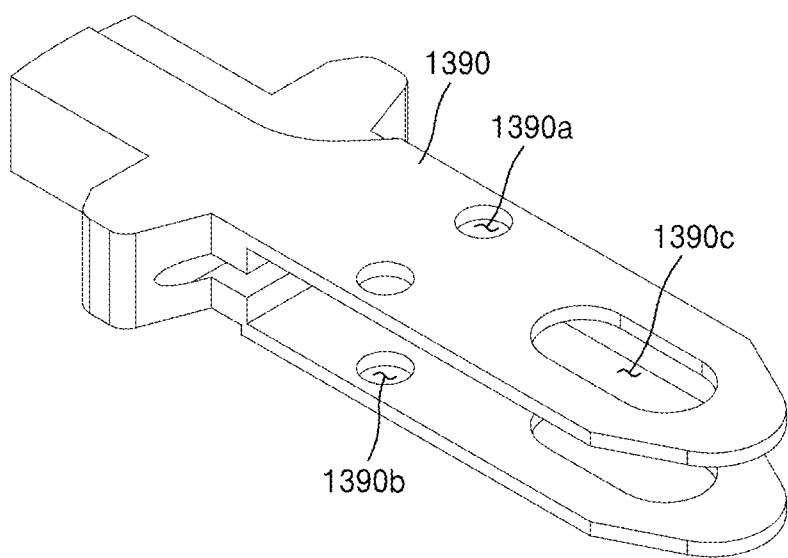
FIGS. 197 and 198 are views illustrating an actuation hub of the end tool of the surgical instrument for electrocautery of FIG. 191.
Figure 198:
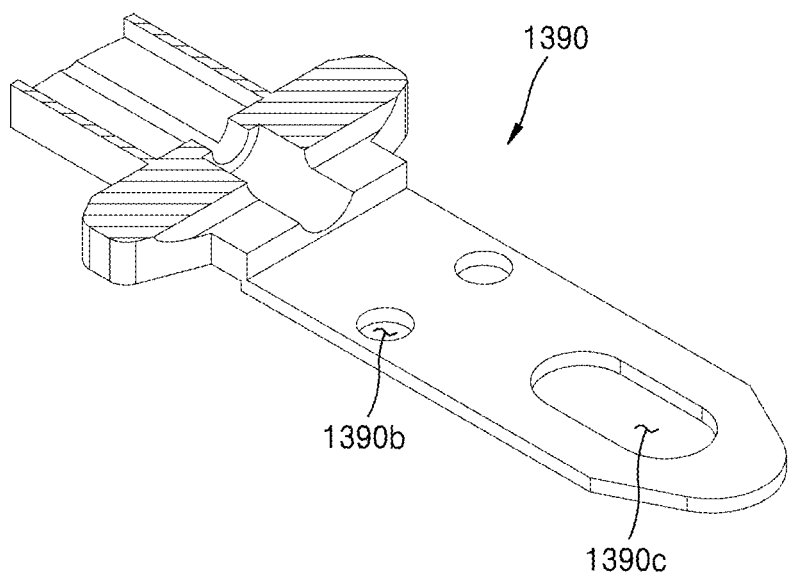
Figure 199:
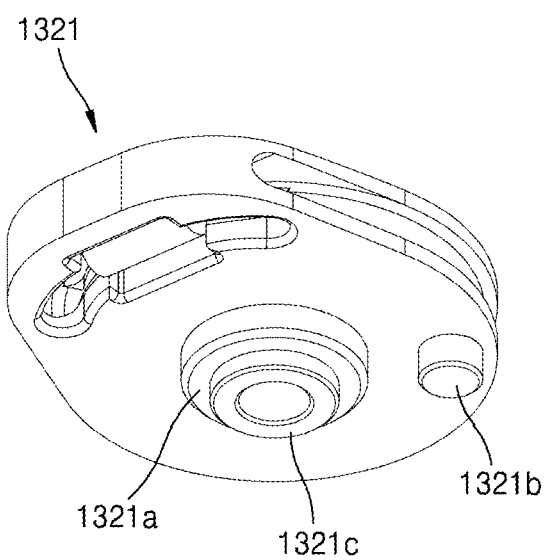
FIG. 199 is a perspective view illustrating a second jaw pulley of the end tool of the surgical instrument for electrocautery of FIG. 191.
Figure 200:
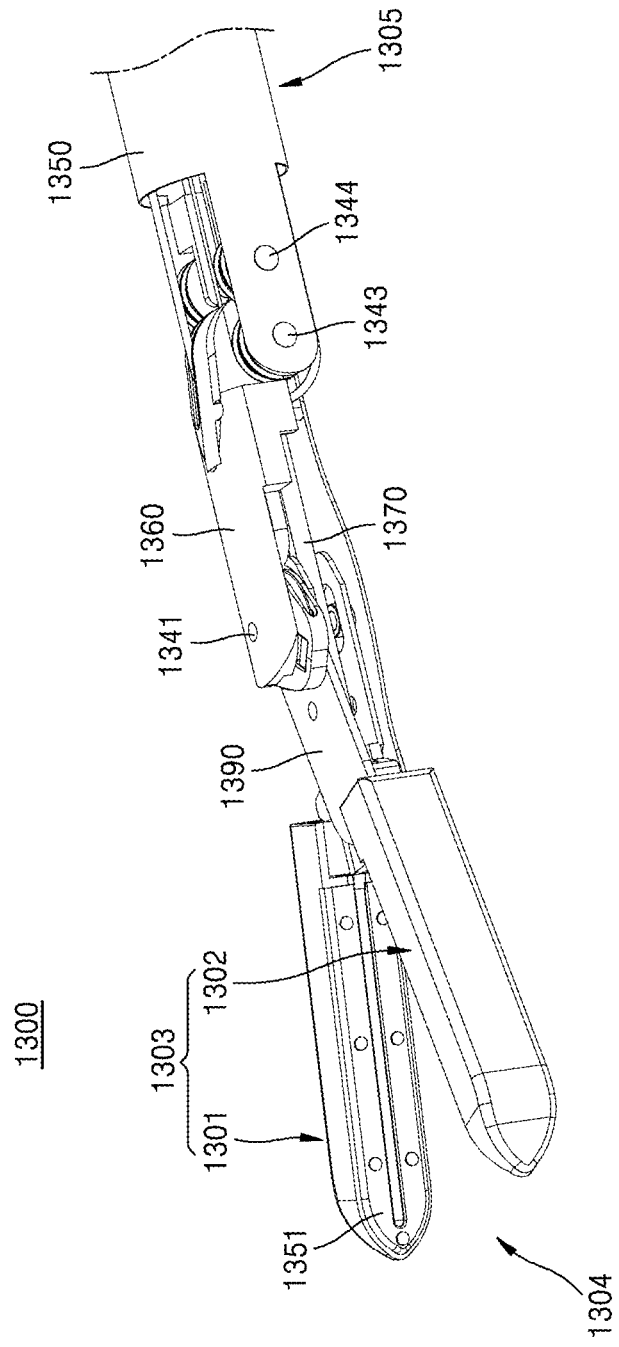
FIGS. 200 and 201 are views illustrating the end tool of the surgical instrument for electrocautery of FIG. 191.
Figure 201:
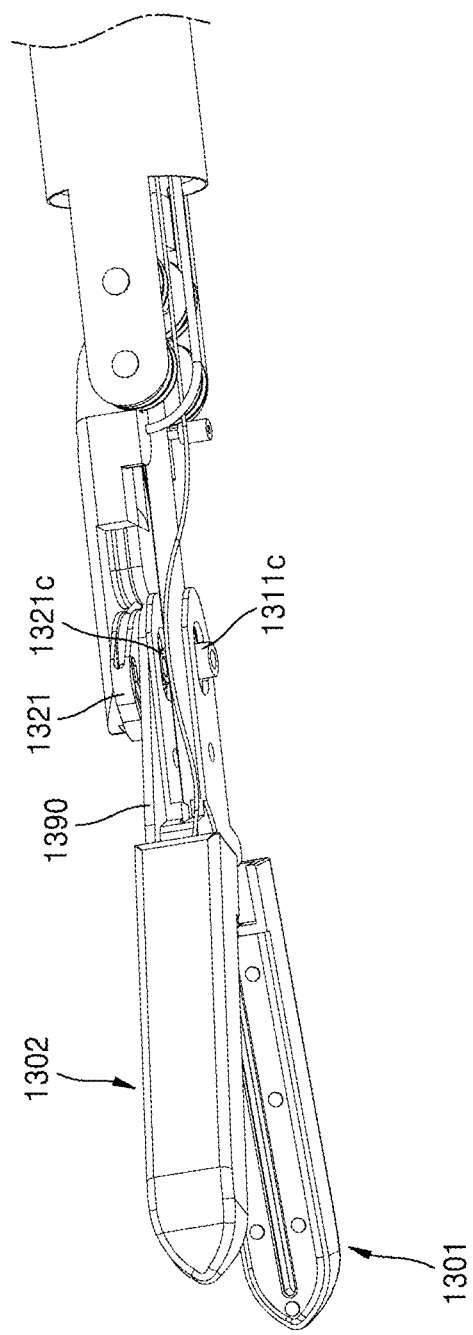
Figure 202:
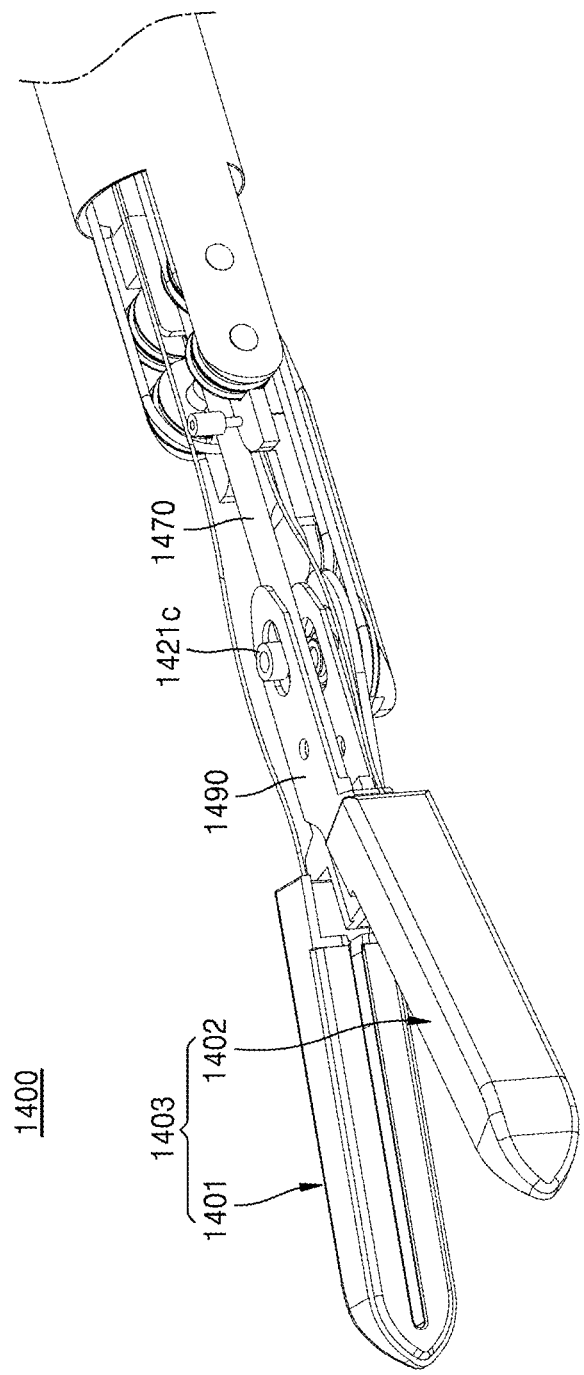
FIGS. 202 to 205 are views illustrating an end tool of a surgical instrument for electrocautery according to a third modified example of the fourth embodiment of the present disclosure.
Figure 203:
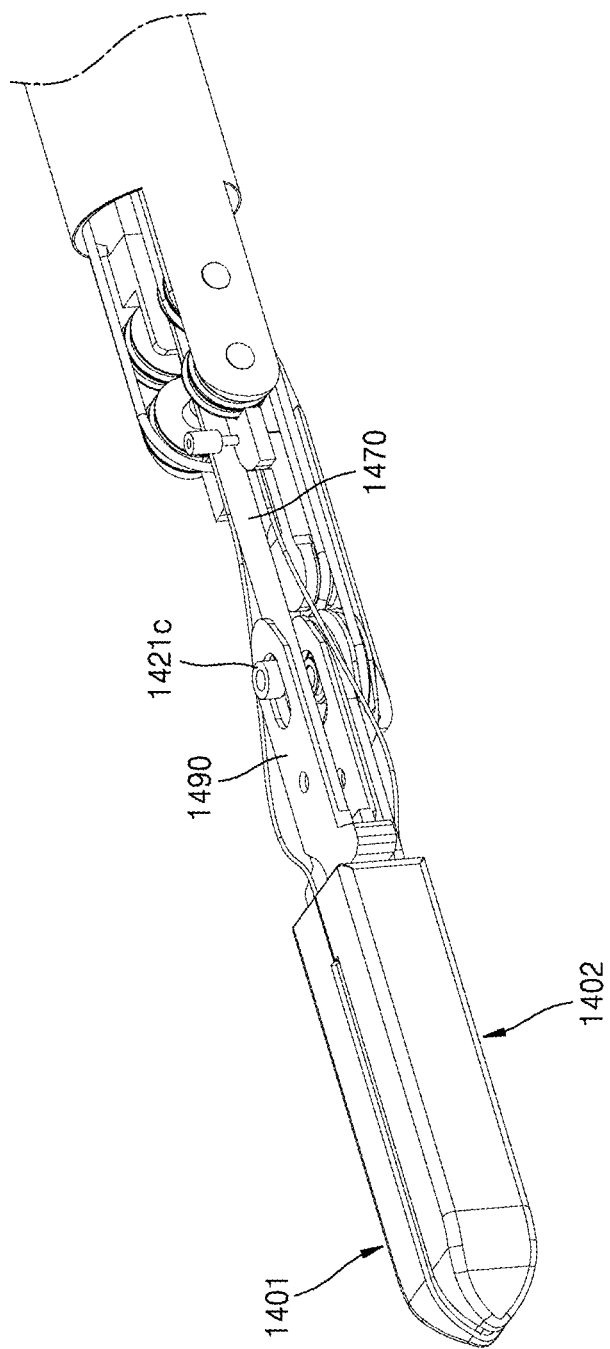
Figure 204:
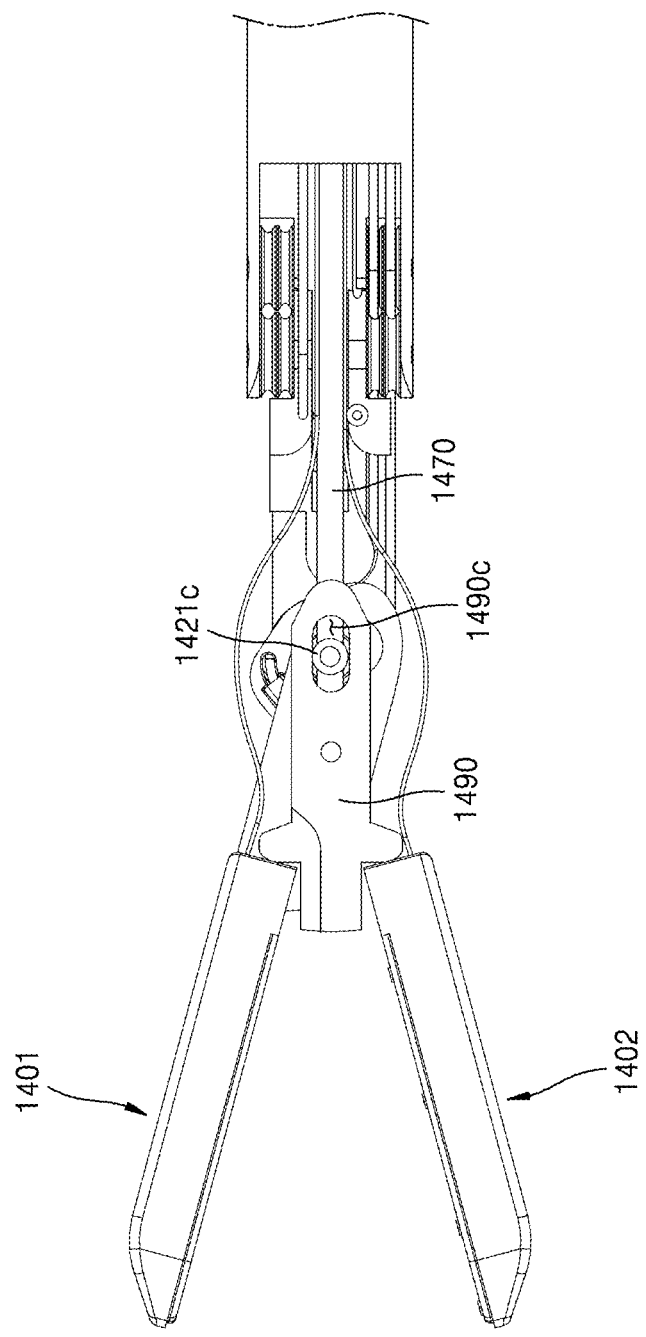
Figure 205:
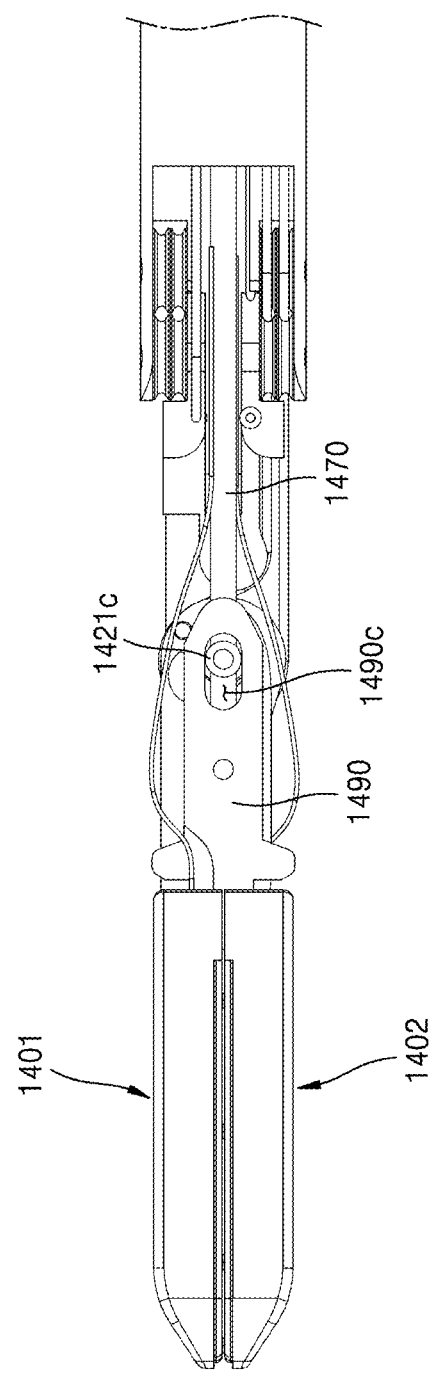

FIGS. 191 to 196 are views illustrating the end tool of the surgical instrument for electrocautery according to the second modified example of the fourth embodiment of the present disclosure. FIGS. 197 and 198 are views illustrating an actuation hub of the end tool of the surgical instrument for electrocautery of FIG. 191. FIG. 199 is a perspective view illustrating a second jaw pulley of the end tool of the surgical instrument for electrocautery of FIG. 191. FIGS. 200 and 201 are views illustrating the end tool of the surgical instrument for electrocautery of FIG. 191.

Referring to FIGS. 191 to 201, the end tool 1300 of the second modified example of the fourth embodiment of the present disclosure includes a pair of jaws for performing a grip motion, that is, a first jaw 1301 and a second jaw 1302, and herein, each of the first jaw 1301 and the second jaw 1302 or a component encompassing the first jaw 1301 and the second jaw 1302 may be referred to as a jaw 1303.

Meanwhile, the end tool 1300 includes a plurality of pulleys including a pulley 1311, a pulley 1313, and a pulley 1314 associated with a rotational motion of a first jaw 1301. Meanwhile, the end tool 1300 includes a plurality of pulleys including a pulley 1321 associated with a rotational motion of the second jaw 1302.

In addition, the end tool 1300 of the second modified example of the fourth embodiment of the present disclosure may include a rotation shaft 1341, a rotation shaft 1343, and a rotation shaft 1344. Here, the rotation shaft 1341 may be inserted through an end tool hub 1360, and the rotation shaft 1343 and the rotation shaft 1344 may be inserted through a pitch hub 1350.

In addition, the end tool 1300 of the second modified example of the fourth embodiment of the present disclosure may include the end tool hub 1360 and the pitch hub 1350.

Meanwhile, the end tool 1300 of the second modified example of the fourth embodiment of the present disclosure may further include components such as a first electrode 1351, a second electrode 1352, a guide tube 1371, and a blade 1375 in order to perform a cauterizing motion and a cutting motion.

The surgical instrument for electrocautery according to the second modified example of the fourth embodiment of the present disclosure may include a wire 301, a wire 302, a wire 303, a wire 304, a wire 305, a wire 306, and a blade wire 307, as in the fourth embodiment of the present disclosure described with reference to FIG. 140 or the like.

Since components of the present modified example described above are substantially the same as the components described in the fourth embodiment, a detailed description thereof will be omitted herein.

Hereinafter, the actuation hub 1390 of the second modified example of the fourth embodiment of the present disclosure will be described in more detail.

Referring to FIGS. 191 to 201, the actuation hub 1390 may be formed in the form of a box having a hollow therein.

Here, a first coupling hole 1390a is formed in any one surface of the actuation hub 1390, specifically, a surface coming into contact with the first jaw 1301, and a second coupling hole 1390b may be formed in the other surface of the actuation hub 1390, specifically, a surface coming into contact with the second jaw 1302.

In this case, the first coupling hole 1390a may be formed to be offset to a certain degree in one direction from the center line in the X-axis direction. In addition, the second coupling hole 1390b may be formed by being offset to a certain degree in another one direction from the center line in the X-axis direction.

In other words, it may be said that the first coupling hole 1390a and the second coupling hole 1390b are not on the same line in the Z-axis direction but are formed to be offset to a certain degree.

In addition, the actuation hub 1390 is coupled to each of the first jaw 1301 and the second jaw 1302. In detail, a first actuation rotation shaft 1391 is inserted through the first jaw 1301 and the first coupling hole 1390a of the actuation hub 1390, so that the actuation hub 1390 and the first jaw 1301 are axially coupled. Further, a second actuation rotation shaft 1392 is inserted through the second jaw 1302 and the second coupling hole 1390b of the actuation hub 1390, so that the actuation hub 1390 and the second jaw 1302 are axially coupled.

Meanwhile, as described with reference to FIG. 154 or the like, a tube seating portion, a wire through-hole, and a blade accommodation portion are sequentially formed inside the actuation hub 1390, and the blade wire 307 may pass through the inside of the actuation hub 1390 to be connected to the blade 1375.

In addition, a guide slit 1390c may be formed in any one surface of the actuation hub 1390 or in both surfaces thereof in a longitudinal direction thereof (i.e., the X-axis direction). In addition, a slit coupling portion 1321c formed on the pulley 1321 may be fitted into the guide slit 1390c, so that a linear movement of the pulley 1321 in the X-axis direction may be guided by the guide slit 1390c.

In detail, a shaft coupling portion 1321a, a jaw coupling portion 1321b, and the slit coupling portion 1321c may be formed on the pulley 1321. Here, the shaft coupling portion 1321a and the jaw coupling portion 1321b may be formed in the same manner as described in the fourth embodiment or the like. The slit coupling portion 1321c may be formed to protrude to a certain degree further from the shaft coupling portion 1321a. The above-described slit coupling portion 1321c is fitted into the guide slit 1390c of the actuation hub 1390.

Meanwhile, although not shown in the drawings, a slit coupling portion (not shown) may also be formed in the pulley 1311.

As described above, by providing the actuation hub 1390 to which the guide tube 1370 is coupled between the first jaw 1301 and the second jaw 1302, the guide tube 1370 may not be curved, or the angle at which the guide tube 1370 is curved may be reduced, even when the first jaw 1301 or the second jaw 1302 rotates around the first rotation shaft 1341 or the actuation rotation shaft 1345.

In detail, in a case in which the guide tube 1370 is directly coupled to the first jaw 1301 or the second jaw 1302, when the first jaw 1301 or the second jaw 1302 rotates, one end portion of the guide tube 1370 also rotates together with the first jaw 1301 or the second jaw 1302, causing the guide tube 1370 to be curved.

On the other hand, in a case in which the guide tube 1370 is coupled to the actuation hub 1390, which is independent of the rotation of the jaw 1303, as in the present embodiment, even when the first jaw 1301 or the second jaw 1302 rotates, the guide tube 1370 may not be curved, or the angle at which the guide tube 1370 is curved may be reduced even when the guide tube 1370 is curved.

That is, by changing the direct connection between the guide tube 1370 and the jaw 1303 by the actuation hub 1390 to an indirect connection, the degree to which the guide tube 1370 is curved by the rotation of the jaw 1303 may be reduced.

In particular, in the end tool 1300 of the second modified example of the fourth embodiment of the present disclosure, when the actuation hub 1390 is coupled to the first jaw 1301 and the second jaw 1302, the first actuation rotation shaft 1391 and the second actuation rotation shaft 1392 are not on the same line in the Z-axis direction but are offset to a certain degree. Thus, when the first jaw 1301 and the second jaw 1302 perform an actuation motion, the first actuation rotation shaft 1391 and the second actuation rotation shaft 1392 form a kind of two point support, thereby obtaining an effect of more stably performing an actuation motion.

In addition, in the end tool 1300 of the second modified example of the fourth embodiment of the present disclosure, the slit coupling portion 1321c formed on the pulley 1321 is fitted into the guide slit 1390c of the actuation hub 1390 so that the linear movement of the pulley 1321 in the X-axis direction may be guided by the guide slit 1390c. That is, when the first jaw 1301 and the second jaw 1302 perform an actuation motion, the first jaw 1301 and the second jaw 1302 move along the guide slit 1390c of the actuation hub 1390, thereby obtaining an effect of more stably performing the actuation motion.

Third Modified Example of Fourth Embodiment

Hereinafter, an end tool 1400 of a surgical instrument according to a third modified example of the fourth embodiment of the present disclosure will be described. Here, the end tool 1400 of the surgical instrument according to the third modified example of the fourth embodiment of the present disclosure is different from the end tool (see 1100 in FIG. 140 or the like) of the surgical instrument according to the fourth embodiment of the present disclosure described above in that the configuration of an actuation hub 1490 is different. The configuration changed from the fourth embodiment as described above will be described in detail later.

Figure 206:
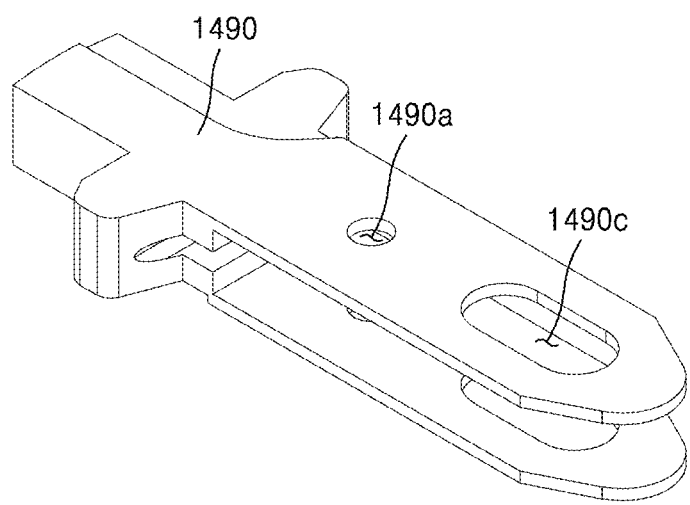
FIGS. 206 and 207 are views illustrating an actuation hub of the end tool of the surgical instrument for electrocautery of FIG. 202.
Figure 207:
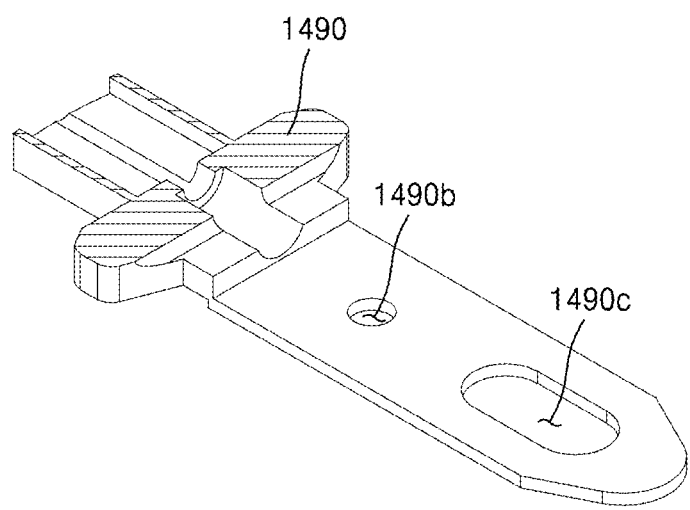
Figure 208:
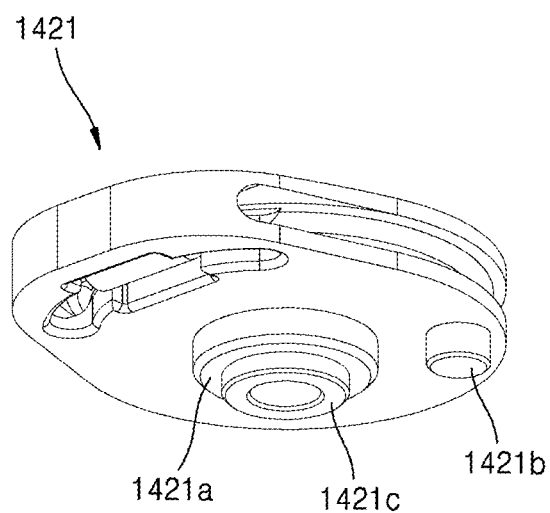
FIG. 208 is a perspective view illustrating a second jaw pulley of the end tool of the surgical instrument for electrocautery of FIG. 202.
Figure 209:
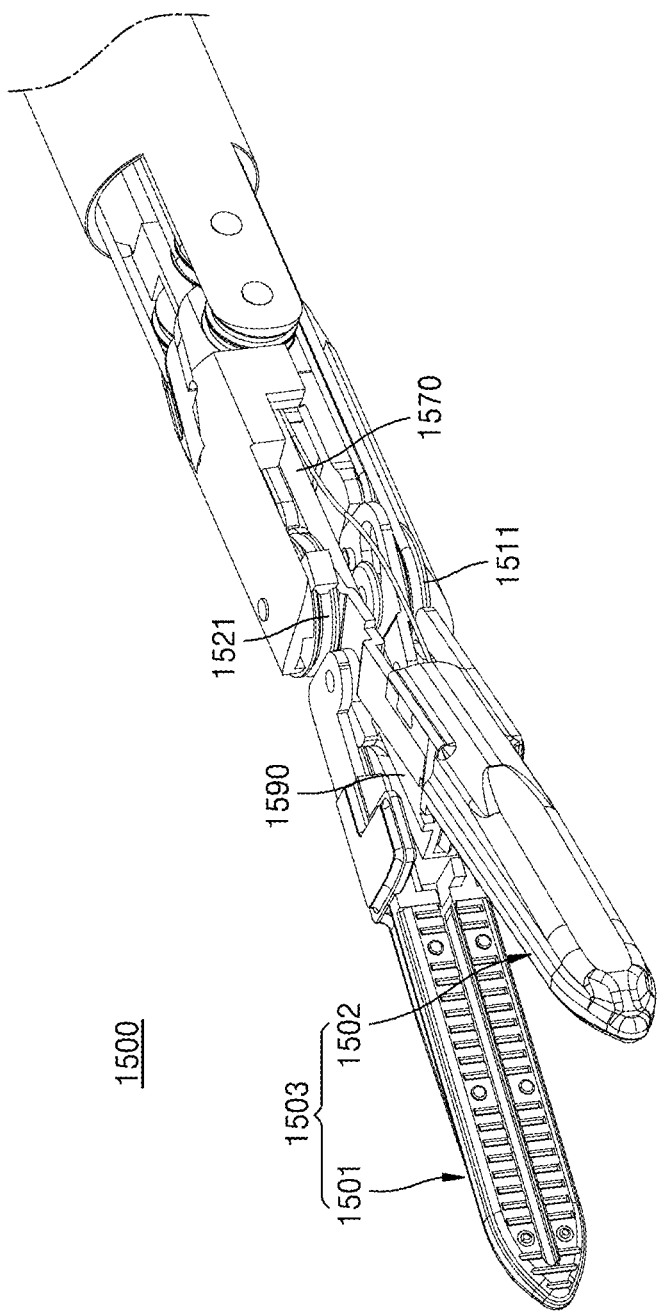
FIGS. 209 to 213 are views illustrating an end tool of a surgical instrument for electrocautery according to a fourth modified example of the fourth embodiment of the present disclosure.
Figure 210:
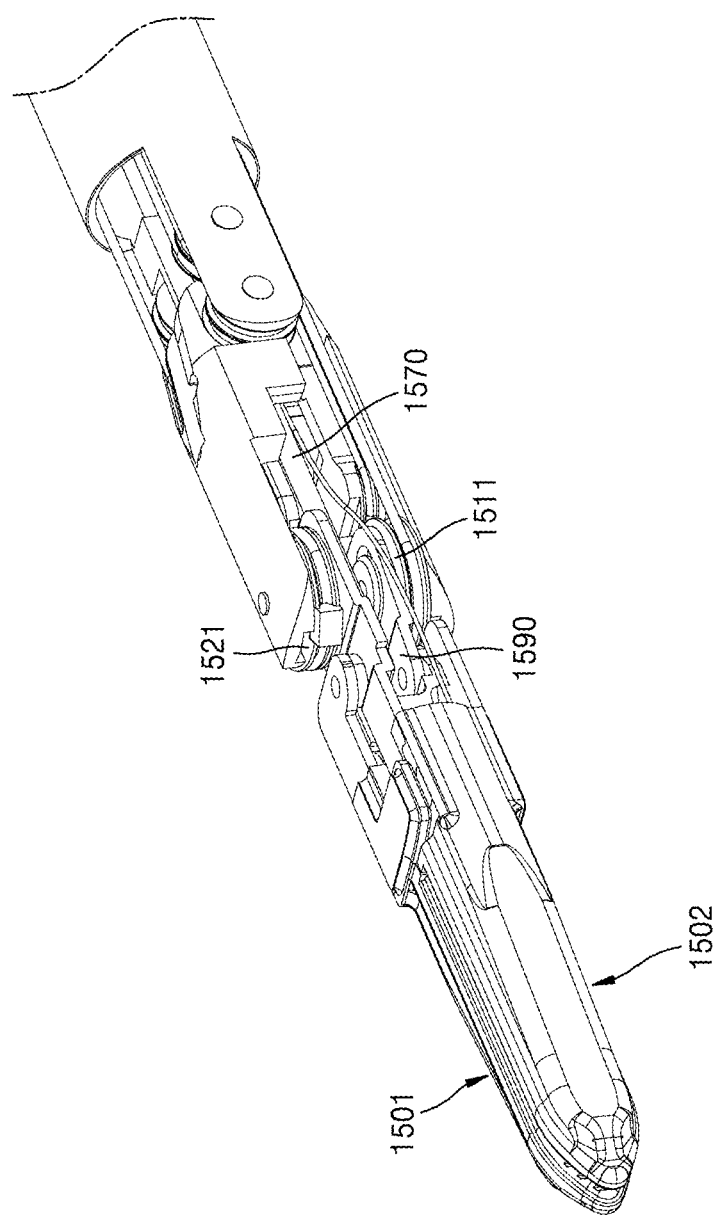
Figure 211:
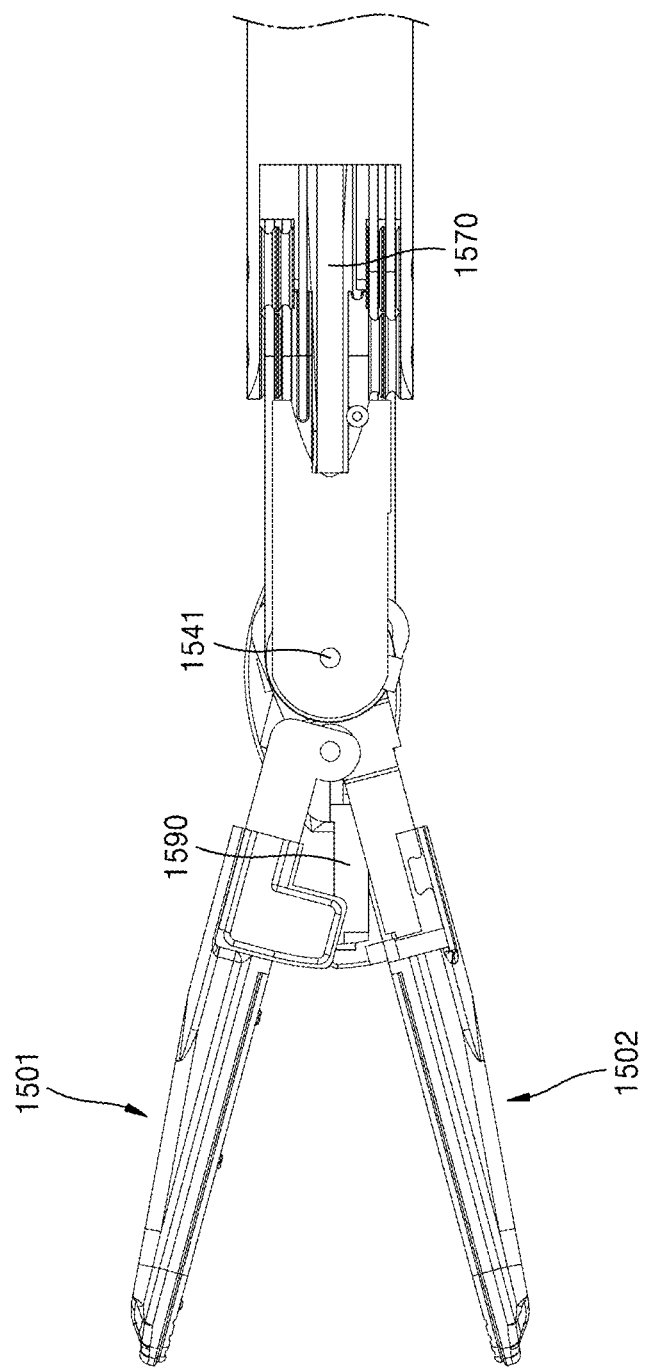
Figure 212:
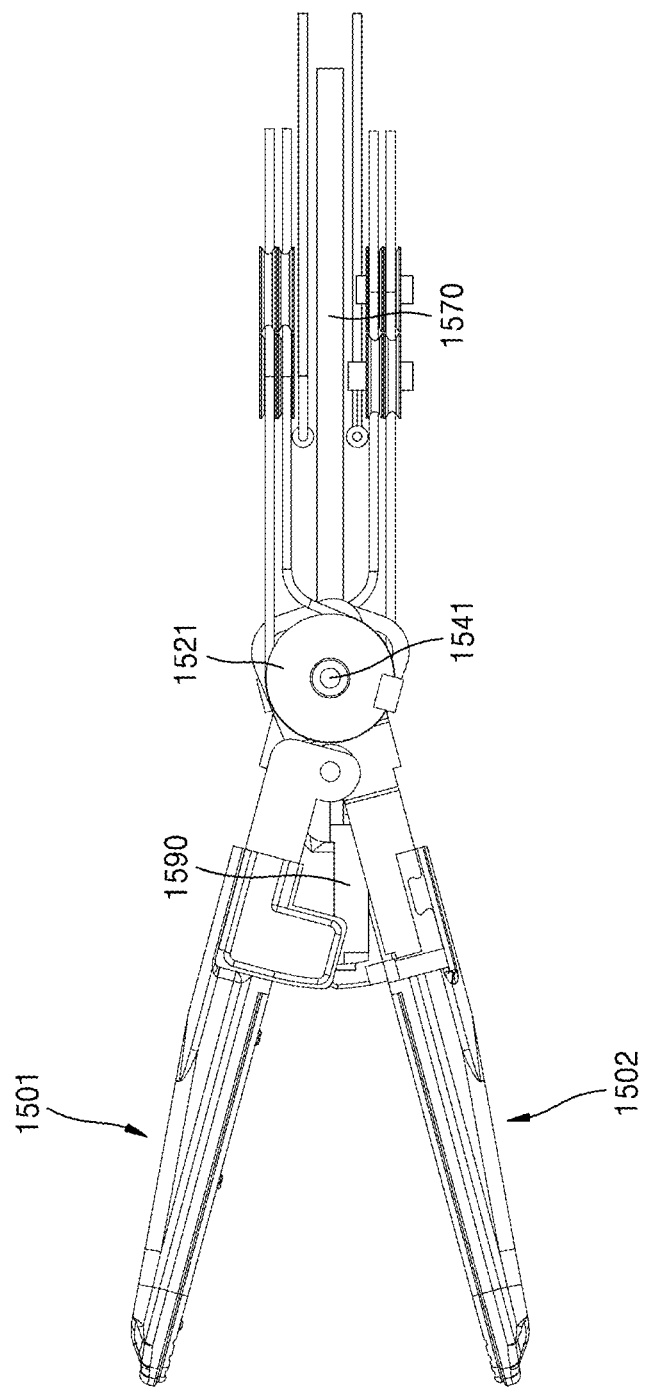
Figure 213:
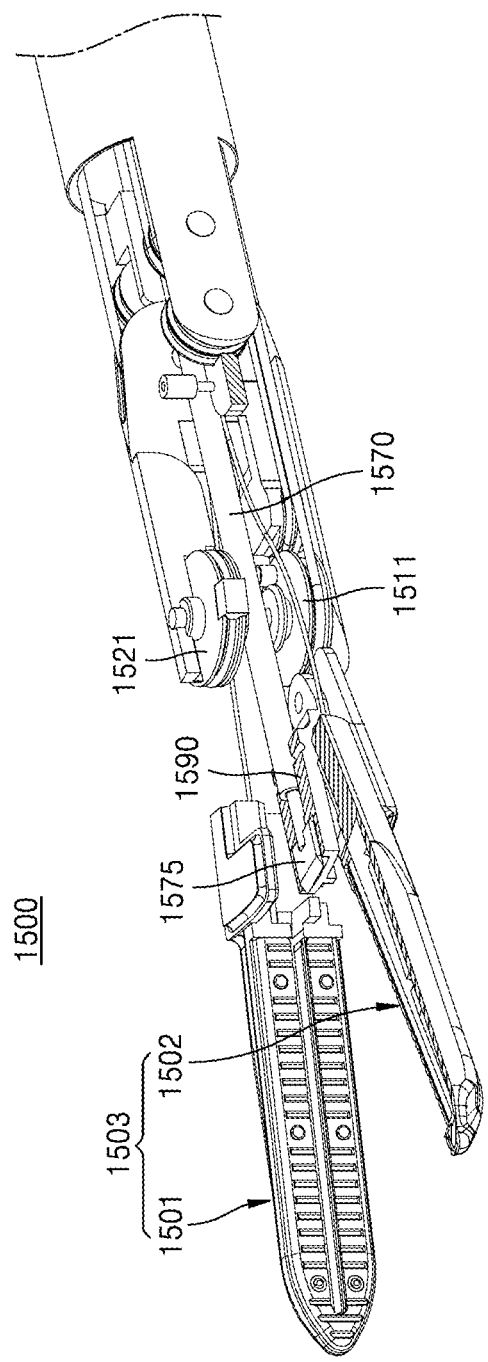

FIGS. 202 to 205 are views illustrating the end tool of the surgical instrument for electrocautery according to the third modified example of the fourth embodiment of the present disclosure. FIGS. 206 and 207 are views illustrating an actuation hub of the end tool of the surgical instrument for electrocautery of FIG. 202. FIG. 208 is a perspective view illustrating a second jaw pulley of the end tool of the surgical instrument for electrocautery of FIG. 202.

Referring to FIGS. 202 to 208, the end tool 1400 of the third modified example of the fourth embodiment of the present disclosure includes a pair of jaws for performing a grip motion, that is, a first jaw 1401 and a second jaw 1402, and herein, each of the first jaw 1401 and the second jaw 1402 or a component encompassing the first jaw 1401 and the second jaw 1402 may be referred to as a jaw 1403.

Meanwhile, the end tool 1400 includes a plurality of pulleys including a pulley 1411, a pulley 1413, and a pulley 1414 that are associated with a rotational motion of the first jaw 1401. Meanwhile, the end tool 1400 includes a plurality of pulleys including a pulley 1421 associated with a rotational motion of the second jaw 1402.

In addition, the end tool 1400 of the third modified example of the fourth embodiment of the present disclosure may include a rotation shaft 1441, a rotation shaft 1443, and a rotation shaft 1444. Here, the rotation shaft 1441 may be inserted through an end tool hub 1460, and the rotation shaft 1443 and the rotation shaft 1444 may be inserted through a pitch hub 1450.

In addition, the end tool 1400 of the third modified example of the fourth embodiment of the present disclosure may include the end tool hub 1460 and the pitch hub 1450.

Meanwhile, the end tool 1400 of the third modified example of the fourth embodiment of the present disclosure may further include components such as a first electrode 1451, a second electrode 1452, a guide tube 1471, and a blade 1475 in order to perform a cauterizing motion and a cutting motion.

The surgical instrument for electrocautery according to the third modified example of the fourth embodiment of the present disclosure may include a wire 301, a wire 302, a wire 303, a wire 304, a wire 305, a wire 306, and a blade wire 307, as in the fourth embodiment of the present disclosure described with reference to FIG. 140 or the like.

Since components of the present modified example described above are substantially the same as the components described in the fourth embodiment, a detailed description thereof will be omitted herein.

Hereinafter, the actuation hub 1490 of the third modified example of the fourth embodiment of the present disclosure will be described in more detail.

Referring to FIGS. 202 to 208, the actuation hub 1490 may be formed in the form of a box having a hollow therein.

Here, a first coupling hole 1490a is formed in any one surface of the actuation hub 1490, specifically, a surface coming into contact with the first jaw 1401, and a second coupling hole 1490b may be formed in the other surface of the actuation hub 1490, specifically, a surface coming into contact with the second jaw 1402.

Here, the first coupling hole 1490a and the second coupling hole 1490b may be located on the same line in the Z-axis direction.

In addition, the actuation hub 1490 is coupled to each of the first jaw 1401 and the second jaw 1402. In detail, a first actuation rotation shaft 1491 is inserted through the first jaw 1401 and the first coupling hole 1490a of the actuation hub 1490, so that the actuation hub 1490 and the first jaw 1401 are axially coupled. Further, a second actuation rotation shaft 1492 is inserted through the second jaw 1402 and the second coupling hole 1490b of the actuation hub 1490, so that the actuation hub 1490 and the second jaw 1402 are axially coupled.

Meanwhile, as described with reference to FIG. 154 or the like, a tube seating portion, a wire through-hole, and a blade accommodation portion are sequentially formed inside the actuation hub 1490, and the blade wire 307 may pass through the inside of the actuation hub 1490 to be connected to the blade 1475.

In addition, a guide slit 1490c may be formed in any one surface of the actuation hub 1490 or in both surfaces thereof in a longitudinal direction thereof (i.e., the X-axis direction). In addition, a slit coupling portion 1421c formed on the pulley 1421 may be fitted into the guide slit 1490c, so that a linear movement of the pulley 1421 in the X-axis direction may be guided by the guide slit 1490c.

In detail, a shaft coupling portion 1421a, a jaw coupling portion 1421b, and the slit coupling portion 1421c may be formed on the pulley 1421. Here, the shaft coupling portion 1421a and the jaw coupling portion 1421b may be formed in the same manner as described in the fourth embodiment or the like. The slit coupling portion 1421c may be formed to protrude to a certain degree further from the shaft coupling portion 1421a. The above-described slit coupling portion 1421c is fitted into the guide slit 1490c of the actuation hub 1490.

Meanwhile, although not shown in the drawings, a slit coupling portion (not shown) may also be formed in the pulley 1411.

As described above, by providing the actuation hub 1490 to which the guide tube 1470 is coupled between the first jaw 1401 and the second jaw 1402, the guide tube 1470 may not be curved, or the angle at which the guide tube 1470 is curved may be reduced, even when the first jaw 1401 or the second jaw 1402 rotates around the first rotation shaft 1441 or the actuation rotation shaft 1445.

In detail, in a case in which the guide tube 1470 is directly coupled to the first jaw 1401 or the second jaw 1402, when the first jaw 1401 or the second jaw 1402 rotates, one end portion of the guide tube 1470 also rotates together with the first jaw 1401 or the second jaw 1402, causing the guide tube 1470 to be curved.

On the other hand, in a case in which the guide tube 1470 is coupled to the actuation hub 1490, which is independent of the rotation of the jaw 1403, as in the present embodiment, even when the first jaw 1401 or the second jaw 1402 rotates, the guide tube 1470 may not be curved, or the angle at which the guide tube 1470 is curved may be reduced even when the guide tube 1470 is curved.

That is, by changing the direct connection between the guide tube 1470 and the jaw 1403 by the actuation hub 1490 to an indirect connection, the degree to which the guide tube 1470 is curved by the rotation of the jaw 1403 may be reduced.

In addition, in the end tool 1400 of the third modified example of the fourth embodiment of the present disclosure, the slit coupling portion 1421*c* formed on the pulley 1421 is fitted into the guide slit 1490*c* of the actuation hub 1490 so that the linear movement of the pulley 1421 in the X-axis direction may be guided by the guide slit 1490*c*. That is, when the first jaw 1401 and the second jaw 1402 perform an actuation motion, the first jaw 1401 and the second jaw 1402 move along the guide slit 1490*c* of the actuation hub 1490, thereby obtaining an effect of more stably performing the actuation motion.

Fourth Modified Example of Fourth Embodiment

Hereinafter, an end tool 1500 of a surgical instrument according to a fourth modified example of the fourth embodiment of the present disclosure will be described. Here, the end tool 1500 of the surgical instrument according to the fourth modified example of the fourth embodiment of the present disclosure is different from the end tool (see 1100 in FIG. 140 or the like) of the surgical instrument according to the fourth embodiment of the present disclosure described above in that the configuration of an actuation hub 1590 is different. The configuration changed from the fourth embodiment as described above will be described in detail later.

Figure 214:
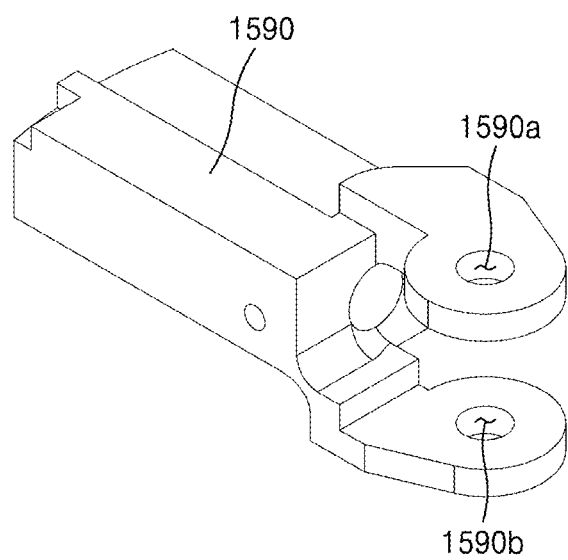
FIGS. 214 and 215 are views illustrating an actuation hub of the end tool of the surgical instrument for electrocautery of FIG. 209.
Figure 215:
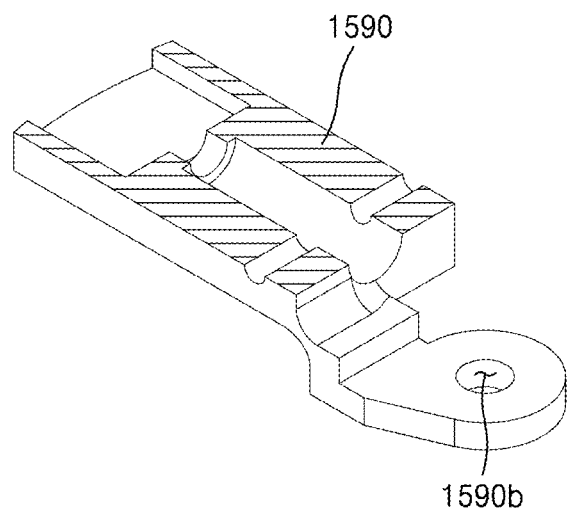

FIGS. 209 to 213 are views illustrating the end tool of the surgical instrument for electrocautery according to the fourth modified example of the fourth embodiment of the present disclosure. FIGS. 214 and 215 are views illustrating an actuation hub of the end tool of the surgical instrument for electrocautery of FIG. 209.

Referring to FIGS. 209 to 215, the end tool 1500 of the fourth modified example of the fourth embodiment of the present disclosure includes a pair of jaws for performing a grip motion, that is, a first jaw 1501 and a second jaw 1502, and herein, each of the first jaw 1501 and the second jaw 1502 or a component encompassing the first jaw 1501 and the second jaw 1502 may be referred to as a jaw 1503.

Meanwhile, the end tool 1500 includes a plurality of pulleys including a pulley 1511 and a pulley 1513, and a pulley 1514 that are associated with a rotational motion of the first jaw 1501. Meanwhile, the end tool 1500 includes a plurality of pulleys including a pulley 1521 associated with a rotational motion of the second jaw 1502.

In addition, the end tool 1500 of the fourth modified example of the fourth embodiment of the present disclosure may include a rotation shaft 1541, a rotation shaft 1543, and a rotation shaft 1544. Here, the rotation shaft 1541 may be inserted through an end tool hub 1560, and the rotation shaft 1543 and the rotation shaft 1544 may be inserted through a pitch hub 1550. The rotation shaft 1541, the rotation shaft 1543, and the rotation shaft 1544 may be arranged sequentially from a distal end 1504 toward a proximal end 1505 of the end tool 1500.

In addition, the end tool 1500 of the fourth modified example of the fourth embodiment of the present disclosure may include the end tool hub 1560 and the pitch hub 1550.

The rotation shaft 1541 is inserted through the end tool hub 1560, and the pulley 1511 and the pulley 1521, which are axially coupled to the rotation shaft 1541, and at least some of the first jaw 1501 and the second jaw 1502 coupled the pulley 1511 and the pulley 1521 may be accommodated inside the end tool hub 1560.

Meanwhile, a first pitch pulley portion 1563*a* and a second pitch pulley portion 1563*b*, which serve as end tool pitch pulleys, may be formed at one end portion of the end tool hub 1560. A wire (see 303 of FIG. 146) and a wire 304 (see 304 of FIG. 146) are coupled to the first pitch pulley portion 1563*a* and the second pitch pulley portion 1563*b*, which serve as end tool pitch pulleys, and a pitch motion is performed while the end tool hub 1560 rotates around the rotation shaft 1543.

The rotation shaft 1543 and the rotation shaft 1544 may be inserted through the pitch hub 1550, and the pitch hub 1550 may be axially coupled to the end tool hub 1560 by the rotation shaft 1543. Accordingly, the end tool hub 1560 may be formed to be pitch-rotatable around the rotation shaft 1543 with respect to the pitch hub 1550.

Meanwhile, the end tool 1500 of the fourth modified example of the fourth embodiment of the present disclosure may further include components such as a first electrode 1551, a second electrode 1552, a guide tube 1571, and a blade 1575 in order to perform a cauterizing motion and a cutting motion. Here, components related to the driving of the blade, such as the guide tube 1571 and the blade 1575, may be collectively referred to as a blade assembly. Components for performing a cauterizing motion and a cutting motion in the present embodiment are substantially the same as those described in the fourth embodiment, and thus a detailed description thereof will be omitted herein.

The surgical instrument for electrocautery according to the fourth modified example of the fourth embodiment of the present disclosure may include a wire 301, a wire 302, a wire 303, a wire 304, a wire 305, a wire 306, and a blade wire 307, as in the fourth embodiment of the present disclosure described with reference to FIG. 140 or the like.

Hereinafter, the actuation hub 1590 of the fourth modified example of the fourth embodiment of the present disclosure will be described in more detail.

Referring to FIGS. 209 to 215, the actuation hub 1590 may be formed in the form of a box having a hollow therein. Here, a first coupling hole 1590*a* is formed in any one surface of the actuation hub 1590, specifically, a surface coming into contact with the first jaw 1501, and a second coupling hole 1590*b* may be formed in the other surface of the actuation hub 1590, specifically, a surface coming into contact with the second jaw 1502. Here, the first coupling hole 1590*a* and the second coupling hole 1590*b* may be disposed on the same line in the Z-axis direction.

In addition, the actuation hub 1590 is coupled to each of the first jaw 1501 and the second jaw 1502. In detail, a first actuation rotation shaft 1591 is inserted through the first jaw 1501 and the first coupling hole 1590*a* of the actuation hub 1590, so that the actuation hub 1590 and the first jaw 1501 are axially coupled. Further, a second actuation rotation shaft 1592 is inserted through the second jaw 1502 and the second coupling hole 1590*b* of the actuation hub 1590, so that the actuation hub 1590 and the second jaw 1502 are axially coupled.

Meanwhile, as described with reference to FIG. 154 or the like, a tube seating portion, a wire through-hole, and a blade accommodation portion are sequentially formed inside the actuation hub 1590, and the blade wire 307 may pass through the inside of the actuation hub 1590 to be connected to the blade 1575.

As described above, by providing the actuation hub 1590 to which the guide tube 1570 is coupled between the first jaw 1501 and the second jaw 1502, the guide tube 1570 may not be curved, or the angle at which the guide tube 1570 is curved may be reduced, even when the first jaw 1501 or the second jaw 1502 rotates around the first rotation shaft 1541 or the actuation rotation shaft 1545.

In detail, in a case in which the guide tube 1570 is directly coupled to the first jaw 1501 or the second jaw 1502, when the first jaw 1501 or the second jaw 1502 rotates, one end portion of the guide tube 1570 also rotates together with the first jaw 1501 or the second jaw 1502, causing the guide tube 1570 to be curved.

On the other hand, in a case in which the guide tube 1570 is coupled to the actuation hub 1590, which is independent of the rotation of the jaw 1503, as in the present embodiment, even when the first jaw 1501 or the second jaw 1502 rotates, the guide tube 1570 may not be curved, or the angle at which the guide tube 1570 is curved may be reduced even when the guide tube 1570 is curved.

That is, by changing the direct connection between the guide tube 1570 and the jaw 1503 by the actuation hub 1590 to an indirect connection, the degree to which the guide tube 1570 is curved by the rotation of the jaw 1503 may be reduced.

As such, the present disclosure has been described with reference to the embodiments described with reference to the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL APPLICABILITY

The present invention relates to a surgical instrument. More specifically, the surgical instrument can be operated manually or automatically for use in laparoscopic surgery or various other surgeries, including a locking device capable of locking and/or unlocking for at least one operation.

The invention claimed is:

1. An end tool of a surgical instrument, the end tool comprising:
a first jaw and a second jaw configured to be rotatable independently of each other;
a first jaw pulley connected to the first jaw and formed to be rotatable around a first rotation shaft;
a second jaw pulley connected to the second jaw, formed to be rotatable around the first rotation shaft, and formed to be spaced a predetermined distance from the first jaw pulley;
a blade assembly configured to receive a driving force and linearly move between a proximal end and a distal end of the first jaw, and having at least a part formed between the first jaw pulley and the second jaw pulley, the blade assembly including a blade and a guide tube;
a blade wire at least partially in contact with the blade assembly and configured to transfer the driving force to the blade assembly and allow the blade to linearly move in a longitudinal direction; and
an end tool hub including a first jaw pulley coupling portion, a second jaw pulley coupling portion, and a guide portion configured to connect the first jaw pulley coupling portion and the second jaw pulley coupling portion, the first jaw pulley coupling portion and the second jaw pulley coupling portion disposed to face each other,
wherein the first jaw pulley and the second jaw pulley perform a yaw motion while rotating around the first rotation shaft, and the first jaw and the second jaw perform an actuation motion while rotating around an actuation rotation shaft spaced apart by a predetermined distance from the first rotation shaft,
wherein the guide tube is configured to internally accommodate at least a part of the blade wire and is disposed to be bent to a predetermined degree, and
wherein the first jaw pulley is disposed adjacent to the first jaw pulley coupling portion of the end tool hub and the second jaw pulley is disposed adjacent to the second jaw pulley coupling portion of the end tool hub, and at least a part of the blade assembly is disposed between the first jaw pulley and the second jaw pulley.

2. The end tool of claim 1, wherein the blade wire passes through an inside of the guide tube and is connected to the blade.

3. The end tool of claim 1, wherein when the guide tube is bent to the predetermined degree, the blade wire inside the guide tube is also bent together with the guide tube.

4. The end tool of claim 1, wherein the blade wire is formed to be movable along the guide tube in the guide tube.

5. The end tool of claim 1, wherein the guide tube is formed to extend toward the blade by passing between central axes of rotation of the first jaw pulley and the second jaw pulley.

6. The end tool of claim 1, wherein the guide tube is formed to extend toward the first jaw or the second jaw by passing through the end tool hub.

7. The end tool of claim 6, wherein a round portion having a predetermined curvature and rounded outward is formed on an inner circumferential surface of the end tool hub, the inner circumferential surface facing the guide tube passing through the end tool hub.

8. The end tool of claim 1, wherein, when the first jaw pulley and the second jaw pulley rotate in a same direction around the first rotation shaft, a yaw motion in which the first jaw and the second jaw rotate in a same direction is performed.

9. The end tool of claim 1, wherein, when the second jaw pulley rotates around the first rotation shaft relative to the first jaw pulley, an actuation motion in which the second jaw rotates relative to the first jaw is performed.

10. The end tool of claim 1, comprising:
a pair of end tool first jaw pitch main pulleys formed at one side of the first jaw pulley, and formed to be rotatable around a third rotation shaft forming a predetermined angle with the first rotation shaft; and
a pair of end tool second jaw pitch main pulleys formed on one side of the second jaw pulley and formed to be rotatable around the third rotation shaft.

11. The end tool of claim 10, wherein the end tool is formed to be yaw-rotatable around the first rotation shaft and simultaneously pitch-rotatable around the third rotation shaft.

12. The end tool of claim 10, further comprising:
a first jaw wire at least a part of which is wound around the first jaw pulley and the pair of end tool first jaw pitch main pulleys; and
a second jaw wire at least a part of which is wound around the second jaw pulley and the pair of end tool second jaw pitch main pulleys.

13. The end tool of claim 1, wherein the blade is configured to move between the proximal end and the distal end of the end tool by the blade wire.

\* \* \* \* \*